(12) United States Patent
Johnson et al.

(10) Patent No.: US 10,173,991 B2
(45) Date of Patent: Jan. 8, 2019

(54) SULFONE AMIDE LINKED BENZOTHIAZOLE INHIBITORS OF ENDOTHELIAL LIPASE

(71) Applicant: BRISTOL-MYERS SQUIBB COMPANY, Princeton, NJ (US)

(72) Inventors: James A. Johnson, Pennington, NJ (US); Zulan Pi, Pennington, NJ (US); Jennifer X. Qiao, Princeton, NJ (US); Soong-Hoon Kim, Titusville, NJ (US); Tammy C. Wang, Lawrenceville, NJ (US); Ji Jiang, West Windsor, NJ (US); Heather Finlay, Skillman, NJ (US); John Lloyd, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/108,584

(22) PCT Filed: Jan. 5, 2015

(86) PCT No.: PCT/US2015/010127
§ 371 (c)(1),
(2) Date: Jun. 28, 2016

(87) PCT Pub. No.: WO2015/105749
PCT Pub. Date: Jul. 16, 2015

(65) Prior Publication Data
US 2016/0326125 A1 Nov. 10, 2016

Related U.S. Application Data

(60) Provisional application No. 61/924,271, filed on Jan. 7, 2014.

(51) Int. Cl.
| C07D 417/04 | (2006.01) |
| C07D 277/64 | (2006.01) |
| C07D 417/10 | (2006.01) |
| C07D 417/12 | (2006.01) |
| C07D 417/14 | (2006.01) |

(52) U.S. Cl.
CPC ......... *C07D 277/64* (2013.01); *C07D 417/04* (2013.01); *C07D 417/10* (2013.01); *C07D 417/12* (2013.01); *C07D 417/14* (2013.01)

(58) Field of Classification Search
CPC .................................................... C07D 417/04
USPC .......................................... 548/159; 514/367
See application file for complete search history.

(56) References Cited

U.S. PATENT DOCUMENTS

| 7,217,727 B2 | 5/2007 | Eacho et al. |
| 7,595,403 B2 | 9/2009 | Eacho et al. |
| 2006/0211766 A1 | 9/2006 | Eacho et al. |
| 2008/0287448 A1 | 11/2008 | Zoller et al. |
| 2009/0054478 A1 | 2/2009 | Zoller et al. |
| 2009/0076068 A1 | 3/2009 | Zoller et al. |
| 2011/0251386 A1 | 10/2011 | Masuda et al. |
| 2012/0253040 A1 | 10/2012 | Masuda et al. |

FOREIGN PATENT DOCUMENTS

| WO | WO1999/32611 A1 | 7/1999 |
| WO | WO2004/093872 A1 | 11/2004 |
| WO | WO2004/094393 A1 | 11/2004 |
| WO | WO2004/094394 A | 11/2004 |
| WO | WO2007/042178 A1 | 4/2007 |
| WO | WO2007/110215 A1 | 10/2007 |
| WO | WO2007/110216 A1 | 10/2007 |
| WO | WO2009/123164 A1 | 10/2009 |
| WO | WO2009/133834 A1 | 11/2009 |
| WO | WO2010/044441 A1 | 4/2010 |
| WO | WO2011/074560 A1 | 6/2011 |
| WO | WO2012/081563 A1 | 6/2012 |
| WO | WO2012/173099 A1 | 12/2012 |
| WO | WO2014/015088 A1 | 1/2014 |

OTHER PUBLICATIONS

Kirk-Othmer Encyclopedia of Chemical Technology, 8, pp. 95-147 (2002).*
Vippagunta et al., "Crystalline Solids", Advanced Drug Delivery Reviews 48 (2001) 3-26.*
Guillory (in Brittain ed.), "Polymorphism in Pharmaceutical Solids.," NY: Marcel Dekker, Inc., 1999, 1-2, 125-181, 183-226.*
Yu et al., "Physical characterization of, etc.," PSTT, vl. 1(3), 118-127 (1998).*
Bernstein, "Polymorphism in . . . " p. 115-118, 272 (2002).*
Davidovich et al., "Detection of polymorphism . . . " Am. Pharm. Rev. v.&(1) p. 10, 12, 14, 16, 100 (2004).*
Dean "Analytical Chem . . . " p. 10.24-10.26 (1995).*
Ivanisevic et al. "Use of X-ray . . . " Pharm. Sci. Encycl. p. 1-42 (2010).*
Seddon "Pseudopolymorph . . . " Crystal Growth & design v.4(6) p. 1087 (2004) (2 pages from internet).*
Jain et al., "Polymorphism in Pharmacy", Indian Drugs, 1986, 23(6) 315-329.*
Braga et al., "Making crystals, etc.," Chem. Commun., 2005, 3635-3645.*

(Continued)

*Primary Examiner* — Patricia L Morris
(74) *Attorney, Agent, or Firm* — Yong Lu

(57) ABSTRACT

The present invention provides compounds of Formula (I) as defined in the specification and compositions comprising any of such novel compounds. These compounds are endothelial lipase inhibitors which may be used medicaments.

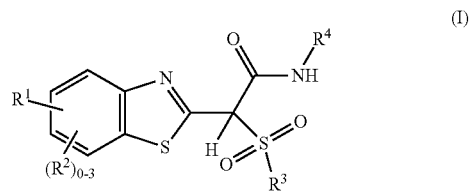

8 Claims, No Drawings

(56) References Cited

OTHER PUBLICATIONS

Bevilacqua, Michal et al., "Selectins", J. Clin. Invest., vol. 91, pp. 379-387 (1993).

Bundgaard, Hans et al., "Glycolamide Esters as Biolabile Prodrugs of Carboxylic Acid Agents: Synthesis, Stability, Bioconversion, and Physicochemical Properties", J of Pharmaceutical Sciences, vol. 77(4), pp. 285-298 (1988).

Bundgaard, Hans, "Means to Enhance Penetration, Prodrugs as a means to improve the delivery of peptide drugs", Advanced Drug Delivery Reviews, vol. 8, pp. 1-38 (1992).

Delemos, Andrew, et al., "Identification of Genetic Variants in Endothelial Lipase in Persons With Elevated High-Density Lipoprotein Cholesterol", Circulation, vol. 106, pp. 1321-1326 (2002).

Folkman Judah et al., "Angiogenesis" J. of Biological Chemistry, vol. 267(16), pp. 10931-10934 (1992).

Folkman, Judah et al., "Angiogenic Factors" Science, vol. 235, pp. 442-447 (1987).

Gordon, David, et al., "High-Density Lipoprotein Cholesterol and Cardiovascular Disease", Circulation, vol. 79, pp. 8-15 (1989).

Gordon, David et al., "High-Density Lipoprotein—The Clinical Implications of Recent Studies", New England J of Medicine, vol. 321(19), pp. 1311-1316 (1989).

Hirata, K. et al., "Cloning of a Unique Lipase from Endothelial Cells Extends the Lipase Gene Family", J. of Biological Chemistry, vol. 274(20), pp. 14170-14175 (1999).

Janssens, Stefan et al., "Cloning and Expression of a cDNA Encoding Human Endothelium-derived Relaxing Factor/Nitric Oxide Synthase", J. of Biological Chemistry, vol. 267(21), pp. 14519-14522 (1992).

Jaye, Michael et al., "A novel endothelial-derived lipase that modulates HDL metabolism", Nature Genetics, vol. 21, pp. 424-428 (1999).

Jin, Weijun et al., "Lipases and HDL metabolism", Trends in Endocrinolgy & Metabolism, vol. 13(4) pp. 174-178 (2002).

Kakeya, Nobuharu et al., "Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid", Chem. Pharm. Bulletin, vol. 32, pp. 692-698 (1984).

Krogsgaard-Larsen, P. et al., A Textbook of Drug Design and Development, pp. 113-191 (1991).

Lamas, Santiago et al., "Endothelial nitric oxide synthase: Molecular cloning and characterization of a distinct constitutive enzyme isoform", PNAS, vol. 89, pp. 6348-6352 (1992).

Lüscher, Thomas et al., "Endothelium-Derived Contracting Factors" Hypertension, vol. 19, pp. 117-130 (1992).

McCoy, Mary G. et al., "Characterization of the lipolytic activity of endothelial lipase", J. of Lipid Research, vol. 43, pp. 921-929 (2002).

Ross, Russell, "The pathogenesis of atherosclerosis: a perspective for the 1990s", Nature, vol. 362(6423) pp. 801-809 (1993).

Strauss, J. et al., "Endothelial cell-derived lipase mediates uptake and binding of high-density lipoprotein (HDL) particles and the selective uptake of HDL-associated cholesterol esters independent of its enzymic activity", Biochem. J. vol. 368, pp. 69-79 (2002).

Widder, Kenneth, Methods in Enzymology, vol. 112, pp. 309-396 (1985).

Williams, T.J. et al., "Adhesion Molecules Involved in the Microvascular Inflammatory Response", Am, Rev Respir. Disease, vol. 146, pp. S45-S50 (1992).

Writing Group Members, "Heart Disease and Stroke Statistics—2012 Update" Circulation, vol. 125, pp. e2-e220 (2012).

Wong, Howard et al., "The lipase gene family" J. Lipid Res. vol. 43, pp. 993-999 (2002).

Yanagisawa, M. et al., "A novel potent vasoconstrictor peptide produced by vascular endothelial cells", Nature, vol. 332, pp. 411-415 (1988).

* cited by examiner

1

SULFONE AMIDE LINKED BENZOTHIAZOLE INHIBITORS OF ENDOTHELIAL LIPASE

CROSS REFERENCE TO RELATED APPLICATIONS

This application is a national phase application under 35 U.S.C. § 371 of International Patent Application No. PCT/US2015/010127, filed Jan. 5, 2015, which claims the benefit of priority to U.S. Provisional Application No. 61/924,271, filed Jan. 7, 2014, the content of which are hereby fully incorporated by reference for all purposes.

FIELD OF THE INVENTION

The present invention provides novel sulfone amide linked benzothiazole compounds and analogues, which are endothelial lipase (EL) inhibitors, compositions containing them, and methods of using them, for example, for the treatment and/or prophylaxis of dyslipidemias and the sequelae thereof.

BACKGROUND OF THE INVENTION

Cardiovascular disease is a major health risk throughout the industrialized world. Atherosclerosis, the most prevalent of cardiovascular diseases, is the principal cause of heart attack, and stroke, and thereby the principal cause of death in the United States.

Atherosclerosis is a complex disease involving many cell types and molecular factors (for a detailed review, see Ross, R., Nature, 362(6423):801-809 (1993)). Results from epidemiologic studies have clearly established an inverse relationship between levels of high density lipoprotein (HDL), which transports endogenous cholesterol from tissues to the liver as well as mediating selective cholesteryl ester delivery to steroidogenic tissues, and the risk for atherosclerosis (Gordon, D. J. et al., N. Engl. J. Med., 321(19):1311-1316 (1989)).

The metabolism of HDL is influenced by several members of the phospholipase and triacylglycerol (TG) lipase family of proteins, which hydrolyze triglycerides, phospholipids (PL), and cholesteryl esters (CE), generating fatty acids to facilitate intestinal absorption, energy production, or storage. Of the TG lipases, lipoprotein lipase (LPL) influences the metabolism of HDL cholesterol by hydrolyzing triglycerides in triglyceride-rich lipoproteins, resulting in the transfer of lipids and apolipoproteins to HDL and is responsible for hydrolyzing chylomicron and very low density lipoprotein (VLDL) in muscle and adipose tissues. Hepatic lipase (HL) hydrolyzes HDL triglyceride and phospholipids, generating smaller, lipid-depleted HDL particles, and plays a role in the uptake of HDL cholesterol (Jin, W. et al., Trends Endocrinol. Metab., 13(4):174-178 (2002); Wong, H. et al., J. Lipid Res., 43:993-999 (2002)). Endothelial lipase (also known as EDL, EL, LIPG, endothelial-derived lipase, and endothelial cell-derived lipase) is synthesized in endothelial cells, a characteristic that distinguishes it from the other members of the family.

Recombinant endothelial lipase protein has substantial phospholipase activity but has been reported to have less hydrolytic activity toward triglyceride lipids (Hirata, K. et al., J. Biol. Chem., 274(20):14170-14175 (1999); Jaye, M. et al., Nat. Genet., 21:424-428 (1999)). However, endothelial lipase does exhibit triglyceride lipase activity ex vivo in addition to its HDL phospholipase activity, and endothelial lipase was found to hydrolyze HDL more efficiently than other lipoproteins (McCoy, M. G. et al., J. Lipid Res., 43:921-929 (2002)). Overexpression of the human endothelial lipase gene in the livers of mice markedly reduces plasma concentrations of HDL cholesterol and its major protein, apolipoprotein A-I (apoA-I) (Jaye, M. et al., Nat. Genet., 21:424-428 (1999)).

Various types of compounds have been reported to modulate the expression of endothelial lipase, for example, 3-oxo-1,3-dihydro-indazole-2-carboxamides (WO 2004/093872, US 2006/0211755 A1), 3-oxo-3-H-benzo[d]isoxazole-2-carboxamides (WO 2004/094393, U.S. Pat. No. 7,217,727), and benzisothiazol-3-one-2-carboxamides (WO 2004/094394, U.S. Pat. No. 7,595,403) by Eli Lilly & Co.; diacylindazole derivatives (WO 2007/042178, US 2008/0287448 A1) and imidazopyridin-2-one derivatives (WO 2007/110215, US 2009/0076068 A1), and azolopyridin-3-one derivatives (WO 2007/110216, US 2009/0054478 A1) by Sanofi-Aventis; heterocyclic derivatives (WO 2009/123164), keto-amide derivatives (WO 2009/133834), acetic acid amide derivatives (WO 2010/44441, US 2011/0251386 A1), oxadiazole derivatives (WO 2011/074560, US 2012/253040 A1), benzothiazole and azabenzothiazole derivatives (WO 2012/081563) and amino derivatives (WO 2012/173099) by Shionogi & Co., Ltd. However, because endothelial lipase is a relatively new member in the lipase gene family, a full understanding of the potential of endothelial lipase inhibitors to human health, as well as the inhibitors of other lipases in general, requires more studies.

Thus, there is a clear need for new types of compounds capable of inhibiting the activity of lipases, particularly endothelial lipase, that would constitute effective treatments to the diseases or disorders associated with the activity of such lipases.

SUMMARY OF THE INVENTION

The present disclosure provides sulfone amide linked benzothiazole compounds and their analogues, including stereoisomers, tautomers, pharmaceutically acceptable salts, or solvates thereof, which are useful as EL inhibitors.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of dyslipidemias and the sequelae thereof.

The compounds of the invention may be used in therapy.

The compounds of the invention may be used for the manufacture of a medicament for the treatment and/or prophylaxis of dyslipidemias and the sequelae thereof.

The compounds of the invention can be used alone, in combination with other compounds of the present invention, or in combination with one or more, preferably one to two other agent(s).

Other features and advantages of the invention will be apparent from the following detailed description and claims.

DETAILED DESCRIPTION OF THE INVENTION

I. Compounds of the Invention

In a first aspect, the present invention provides, inter alia, a compound of Formula (I):

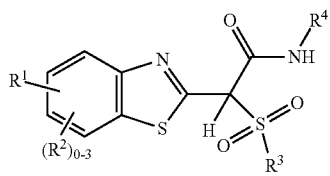

or a stereoisomer, a tautomer, a pharmaceutically acceptable salt, or a solvate thereof, wherein:

$R^1$ is independently selected from: halogen, CN, $CO_2$($C_{1-4}$ alkyl), —CO—$R^j$, —CONR$^g$—$(CH_2)_m$—$R^j$, (phenyl substituted with 0-3 $R^a$), and (a 5- to 10-membered heteroaryl comprising carbon atoms and 1-4 heteroatoms selected from N, NR$^c$, O, and S(O)$_p$; wherein said heteroaryl is substituted with 0-3 $R^a$),

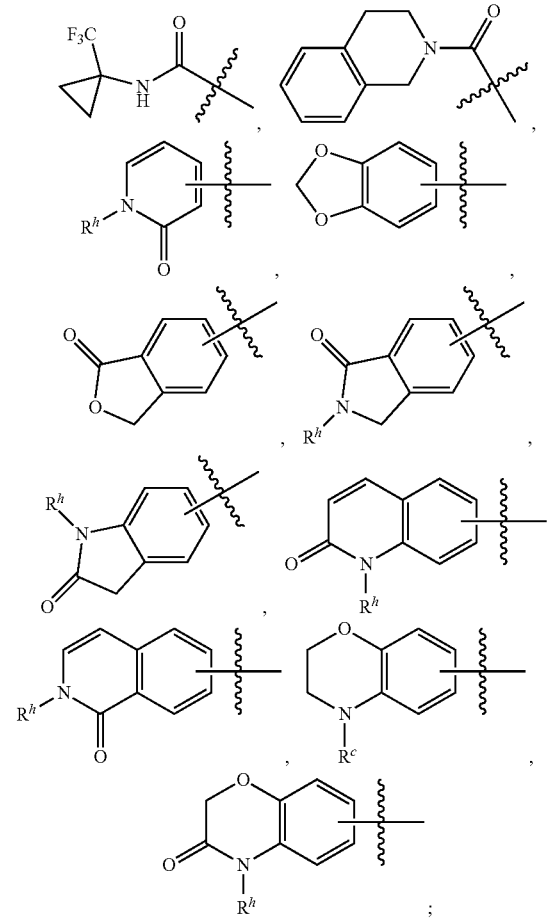

$R^2$ is, independently at each occurrence, selected from: halogen, OH, $C_{1-4}$ alkyl, $C_{1-4}$ alkoxy, $C_{1-4}$ haloalkyl, $C_{1-4}$ haloalkoxy, CN, $NH_2$, $NO_2$, NH($C_{1-4}$ alkyl), N($C_{1-4}$ alkyl)$_2$, $CO_2H$, $CO_2$($C_{1-4}$ alkyl), and $CONH_2$;

$R^3$ is independently selected from: $C_{1-6}$ alkyl substituted with 0-1 $R^7$, $C_{2-6}$ alkenyl, $C_{1-6}$ haloalkyl, N($C_{1-4}$ alkyl)$_2$, —X—($C_{3-6}$ carbocycle substituted with 0-3 $R^b$), —X-(4- to 6-membered heterocycle comprising carbon atoms and 1-4 heteroatoms selected from N, NR$^c$, O, and S(O)$_p$; wherein said heterocycle is substituted with 0-2 $R^b$);

X is —$(CH_2)_m$—, or —$(CH_2)_s$—(O)$_n$—;

$R^4$ independently —$(CH_2)_s$—CONHR$^5$;

$R^5$ is independently selected from: $C_{1-6}$ alkyl substituted with $R^6$, —$(CH_2)_m$—($C_{3-6}$ carbocycle substituted with 0-2 $R^8$), and —$(CH_2)_m$-(4- to 6-membered heterocycle comprising carbon atoms and 1-4 heteroatoms selected from N, NR$^g$, O, and S(O)$_p$; wherein said heterocycle is substituted with 0-2 $R^8$);

$R^6$ is independently selected from: OH, $C_{1-4}$ alkoxy, $C_{1-4}$ haloalkyl, $C_{1-4}$ haloalkoxy, OPh, and OBn;

$R^7$ is independently selected from: OH, halogen, CN, $C_{1-4}$ alkoxy, $C_{1-4}$ haloalkyl, $C_{1-4}$ haloalkoxy, $NH_2$, $CO_2H$, $CO_2$($C_{1-4}$ alkyl), $SO_3H$, CONHR$^d$, NHCONHR$^d$, NHCO$_2$R$^d$,

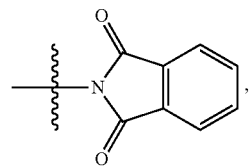 [SMILES: *N1C(=O)c2ccccc2C1=O]

and 5- to 6-membered heterocycle comprising carbon atoms and 1-4 heteroatoms selected from N, NR$^g$, O, and S(O)$_p$;

$R^8$ is, independently at each occurrence, selected from: OH, halogen, $C_{1-6}$ alkyl, $C_{1-4}$ alkoxy, $C_{1-4}$ haloalkyl, $C_{1-4}$ haloalkoxy, $NH_2$, OPh, OBn, Ph, and a 5- to 6-membered heteroaryl comprising carbon atoms and 1-4 heteroatoms selected from N, NR$^g$ and O;

$R^a$ is, independently at each occurrence, selected from: halogen, $C_{1-6}$ alkyl substituted with 0-1 $R^f$, $C_{1-6}$ alkoxy substituted with 0-1 $R^f$, $C_{1-6}$ haloalkyl, $C_{1-6}$ haloalkoxy, OH, CN, $NO_2$, $CO_2H$, $CO_2$($C_{1-4}$ alkyl), NR$^g$R$^h$, CONR$^g$R$^h$, CONR$^g$R$^j$, OCONR$^g$R$^i$, NR$^g$CO$_q$R$^i$, NHCONR$^g$R$^k$, $SO_2$NR$^g$R$^h$, $NHSO_2$($C_{1-4}$ alkyl), N($SO_2$($C_{1-4}$ alkyl))($SO_2$($C_{1-4}$ alkyl substituted with 0-1 $R^f$)), —$(CH_2)_n$—(O)$_n$—$R^j$, —(O)$_n$—$(CH_2)_t$—$R^j$, —CO—$R^j$, —NH(=NCN)NHR$^i$,

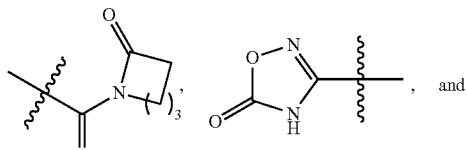

$R^b$ is, independently at each occurrence, selected from: halogen, $C_{1-6}$ alkyl, $C_{1-4}$ alkoxy, $C_{1-4}$ haloalkyl, $C_{1-4}$ haloalkoxy, OH, CN, $NH_2$, $NO_2$, NH($C_{1-4}$ alkyl), N($C_{1-4}$ alkyl)$_2$, $CO_2H$, $CO_2$($C_{1-4}$ alkyl), $SO_2$($C_{1-4}$ alkyl), $CONH_2$, and CONH($C_{1-4}$ alkyl);

$R^c$ is, independently at each occurrence, selected from: H, $C_{1-6}$ alkyl substituted with 0-1 $R^e$, CO$_q$($C_{1-4}$ alkyl), —$(CH_2)_t$—($C_{3-6}$ carbocycle substituted with 0-3 $R^e$), —CO$_q$—(CH$_2$)$_n$—(C$_{3-6}$ carbocycle substituted with 0-2 R$^e$),
—(CH$_2$)$_t$-(5- to 6-membered heterocycle comprising carbon atoms and 1-4 heteroatoms selected from N, NR$^g$ and O), and

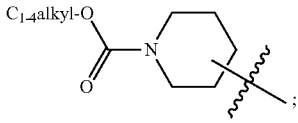

R$^d$ is, independently at each occurrence, selected from: C$_{1-6}$ alkyl and —(CH$_2$)$_r$-(phenyl substituted with 0-2 R$^e$);

R$^e$ and R$^f$ are, independently at each occurrence, selected from: OH, halogen, CN, C$_{1-4}$ alkyl, C$_{1-4}$ haloalkyl, C$_{1-4}$ alkoxy, C$_{1-4}$ haloalkoxy, CO$_2$H, NH$_2$, CONH$_2$, and NHCO(C$_{1-4}$ alkyl);

R$^g$ is, independently at each occurrence, selected from: H and C$_{1-4}$ alkyl;

R$^h$ is, independently at each occurrence, selected from: H, C$_{1-6}$ haloalkyl, C$_{1-6}$ alkyl substituted with 0-1 R$^f$, and —(CH$_2$)$_r$—(C$_{3-6}$ carbocycle substituted with 0-1 R$^f$);

R$^i$ is, independently at each occurrence, selected from: C$_{1-6}$ haloalkyl, C$_{1-6}$ alkyl substituted with 0-1 R$^f$, —(CH$_2$)$_r$—(C$_{3-6}$ carbocycle substituted with 0-1 R$^f$), and —(CH$_2$)$_t$-(5- to 6-membered heterocycle comprising carbon atoms and 1-4 heteroatoms selected from N, NR$^g$ and O);

R$^j$ is, independently at each occurrence: C$_{3-6}$ carbocycle or a 4- to 6-membered heterocycle comprising carbon atoms and 1-4 heteroatoms selected from N, NR$^g$, O, and S(O)$_p$; wherein said carbocycle and heterocycle are substituted with 0-2 R$^f$;

R$^k$ is, independently at each occurrence, selected from: H, C$_{1-6}$ haloalkyl, and C$_{1-6}$ alkyl substituted with 0-1 R$^f$;

m and t are, independently at each occurrence, selected from 0, 1, 2, and 3;

n is, independently at each occurrence, selected from 0 and 1;

p is, independently at each occurrence, selected from 0, 1, and 2;

q is, independently at each occurrence, selected from 0, 1, and 2; and s is, independently at each occurrence, selected from 1, 2, and 3.

In a second aspect, the present invention includes a compound of Formula (IIa) or (IIb):

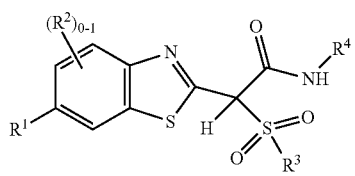
(IIa)

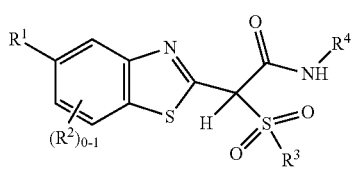
(IIb)

or a stereoisomer, a tautomer, a pharmaceutically acceptable salt, or a solvate thereof, within the scope of the first aspect; wherein:

R$^2$ is, independently at each occurrence, selected from: halogen, C$_{1-4}$ alkyl, C$_{1-4}$ alkoxy, C$_{1-4}$ haloalkyl, and C$_{1-4}$ haloalkoxy.

In a third aspect, the present invention includes a compound of Formula (I), (IIa) or (IIb), or a stereoisomer, a tautomer, a pharmaceutically acceptable salt, or a solvate thereof, within the scope of any of the first and second aspects, wherein:

R$^1$ is independently selected from: halogen, CO$_2$(C$_{1-4}$ alkyl), (phenyl substituted with 0-2 R$^a$), (a 5- to 10-membered heteroaryl comprising carbon atoms and 1-4 heteroatoms selected from N, NR$^c$, O, and S; wherein said heteroaryl is substituted with 0-2 R$^a$), —CO-(4- to 6-membered heterocycle comprising carbon atoms and 1-4 heteroatoms selected from N, NR$^c$, and O; wherein said heterocycle is substituted with 0-2 R$^f$), —CONR$^g$—(CH$_2$)$_{0-2}$-(4- to 6-membered heterocycle comprising carbon atoms and 1-4 heteroatoms selected from N, NR$^c$, and O; wherein said heterocycle is substituted with 0-2 R$^f$),

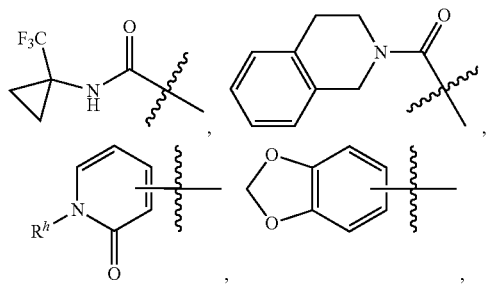

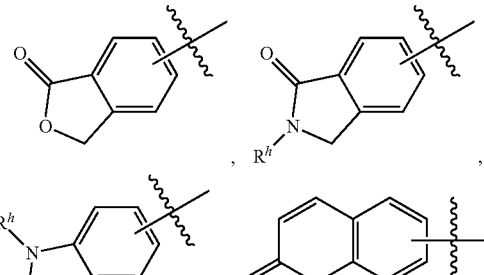

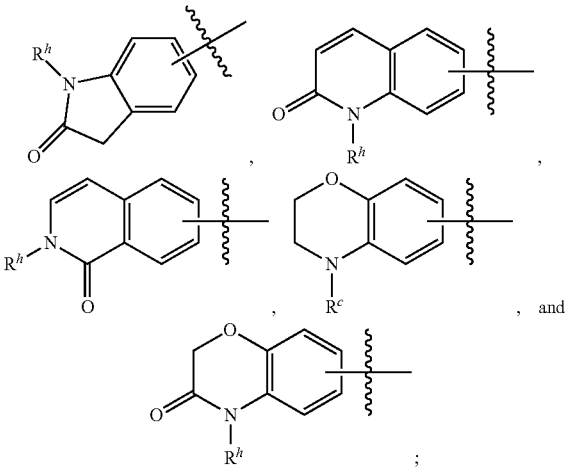

R$^3$ is independently selected from: C$_{1-6}$ alkyl substituted with 0-1 R$^7$, C$_{2-4}$ alkenyl, —X—(C$_{3-6}$ carbocycle substituted with 0-1 R$^b$), —(CH$_2$)$_{0-1}$-(pyridyl substituted with 0-1 R$^b$), —(CH$_2$)$_{0-2}$-morpholinyl, N(C$_{1-4}$ alkyl)$_2$,

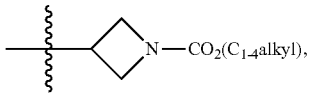

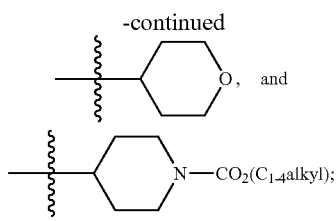 and 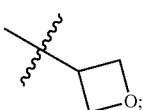

stituted with 0-2 $R^e$), —$CO_q$(benzyl substituted with 0-2 $R^e$), —$(CH_2)_{0-2}$-piperidinyl, —$(CH_2)_{0-2}$-morpholinyl, and

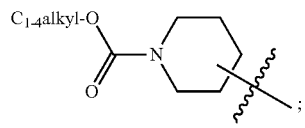

$R^4$ is independently —$CH_2CONHR^5$;

$R^5$ is independently selected from: $C_{1-6}$ alkyl substituted with $R^6$, —$(CH_2)_{0-1}$—($C_{3-6}$ cycloalkyl substituted with 0-1 $R^8$), Ph, and

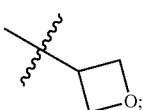

$R^6$ is independently selected from: OH, $C_{1-4}$ alkoxy, $C_{1-4}$ haloalkyl, $C_{1-4}$ haloalkoxy, OPh, and OBn;

$R^7$ is independently selected from: OH, halogen, CN, $C_{1-4}$ alkoxy, $C_{1-4}$ haloalkyl, $C_{1-4}$ haloalkoxy, $NH_2$, and $NHCO_2Bn$;

$R^8$ is independently selected from: $C_{1-4}$ alkyl and 5- to 6-membered heteroaryl comprising carbon atoms and 1-4 heteroatoms selected from N, $NR^g$ and O;

$R^a$ is, independently at each occurrence, selected from: OH, halogen, CN, $C_{1-4}$ alkyl substituted with 0-1 $R^f$, $C_{1-4}$ alkoxy substituted with 0-1 $R^f$, $C_{1-4}$ haloalkyl, $C_{1-4}$ haloalkoxy, $CO_2H$, $CO_2(C_{1-4}$ alkyl), $NH_2$, $NH(C_{1-4}$ alkyl), $N(C_{1-4}$ alkyl)$_2$, $NHCO_q(C_{1-4}$ alkyl substituted with 0-1 $R^f$), $NHCO(C_{1-4}$ haloalkyl), $NHCO_q(CH_2)_{0-2}(C_{3-6}$ carbocycle substituted with 0-1 $R^f$), $N(C_{1-4}$ alkyl)$CO_2(C_{1-4}$ alkyl), $CONH_2$, $CONH(C_{1-4}$ alkyl substituted with 0-1 $R^f$), $CON(C_{1-4}$ alkyl)($C_{1-4}$ alkyl substituted with 0-1 $R^f$), $CONH(C_{1-4}$ haloalkyl), $CONH(CH_2)_{0-2}(C_{3-6}$ carbocycle substituted with 0-1 $R^f$), $CON(C_{1-4}$ alkyl)($C_{3-6}$ carbocycle substituted with 0-1 $R^f$), $NHCONH_2$, $NHCONH(C_{1-4}$ alkyl), $NHCON(C_{1-4}$ alkyl)$_2$, $NHSO_2(C_{1-4}$ alkyl), $N(SO_2(C_{1-4}$ alkyl))($SO_2(C_{1-4}$ alkyl substituted with 0-1 $R^f$)), $SO_2N(C_{1-4}$ alkyl)$_2$, $SO_2NH(C_{1-4}$ alkyl substituted with 0-1 $R^f$), —$(CH_2)_n$—$(O)_n$—$R^j$, —$(O)_n$—$(CH_2)_t$—$R^j$, —CO—$R^j$, —CONH—$R^j$, —$NHCO_2CH_2$-thiazolyl, —$NHCO_2CH_2$-pyridyl, —NH(=NCN)NHBn,

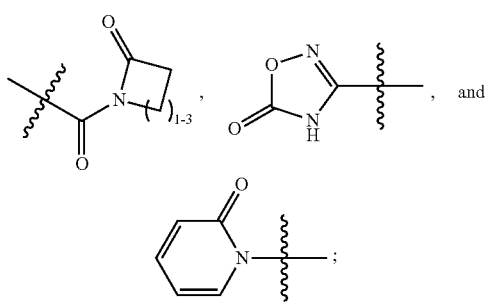

$R^b$ is, independently at each occurrence, selected from: halogen, CN, $C_{1-4}$ alkyl, $C_{1-4}$ alkoxy, $C_{1-4}$ haloalkyl, and $C_{1-4}$ haloalkoxy;

$R^c$ is, independently at each occurrence, selected from: H, $C_{1-4}$ alkyl substituted with 0-1 $R^e$, —$(CH_2)_{0-2}$-(phenyl sub- $R^e$ is, independently at each occurrence, selected from: OH, CN, halogen, $C_{1-4}$ alkyl, and $C_{1-4}$ alkoxy;

$R^f$ is, independently at each occurrence, selected from: OH, halogen, CN, $C_{1-4}$ alkyl, $C_{1-4}$ haloalkyl, $C_{1-4}$ alkoxy, $C_{1-4}$ haloalkoxy, $CO_2H$, $NH_2$, $CONH_2$, and $NHCO(C_{1-4}$ alkyl); and $R^g$ is independently selected from: H and $C_{1-4}$ alkyl.

In a fourth aspect, the present invention includes a compound of Formula (I), (IIa) or (IIb), or a stereoisomer, a tautomer, a pharmaceutically acceptable salt, or a solvate thereof, within the scope of any of the above aspects, wherein:

$R^1$ is independently selected from: halogen, $CO_2(C_{1-4}$ alkyl), (phenyl substituted with 0-2 $R^a$), (a heteroaryl substituted with 0-2 $R^a$ and selected from: isoxazolyl, pyrazolyl, 1-$R^c$-pyrazolyl, 1-$R^c$-imidazolyl, pyridyl, pyrimidinyl and pyridazinyl, 1-$R^c$-indolinyl, 1-$R^c$-indazolyl, and benzothiazolyl), —CO-(morpholinyl substituted with 0-2 $R^f$), —CO-(1-$C_{1-4}$ alkyl-piperazinyl), —$CONHCH_2$-(isoxazolyl substituted with 0-1 $R^f$), —CON(Me)$CH_2$-(isoxazolyl substituted with 0-1 $R^f$), —$CONH(CH_2)_2$-(imidazolyl substituted with 0-1 $R^f$),

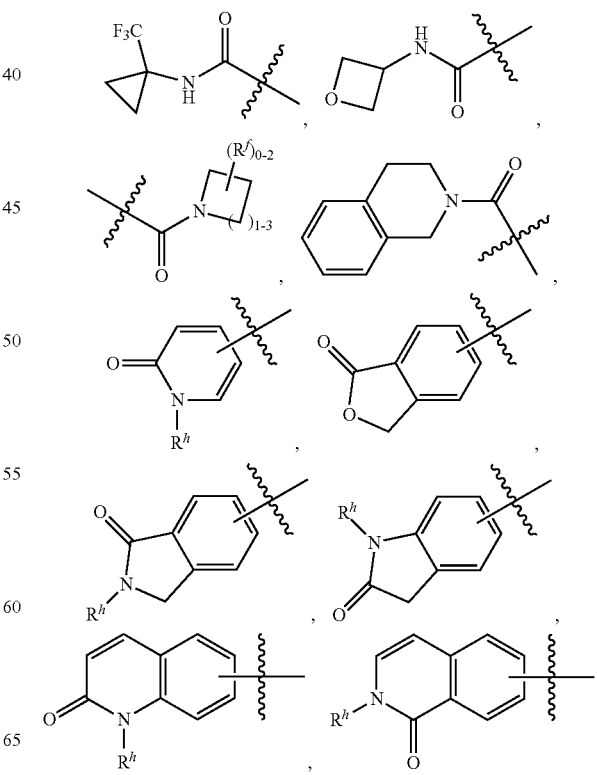

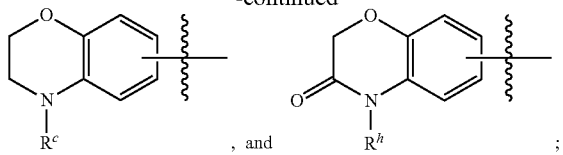

, and

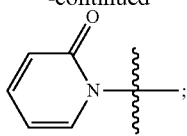

;

$R^3$ is independently selected from: $C_{1-6}$ alkyl substituted with 0-1 $R^7$, $C_{2-4}$ alkenyl, —(CH$_2$)$_{0-3}$—(O)$_{0-1}$—($C_{3-6}$ carbocycle substituted with 0-1 $R^b$), —(CH$_2$)$_{0-1}$-(pyridyl substituted with 0-1 $R^b$), —(CH$_2$)$_{0-2}$-morpholinyl, N(C$_{1-4}$ alkyl)$_2$,

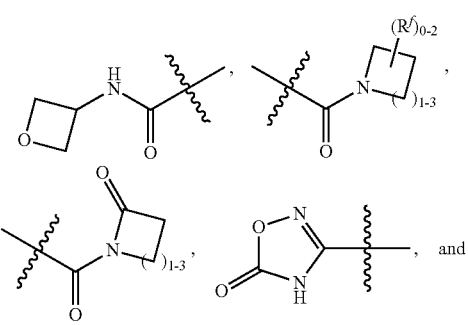

$R^6$ is independently selected from: OH, $C_{1-4}$ alkoxy, $C_{1-4}$ haloalkyl, OPh, and OBn;

$R^8$ is independently selected from: $C_{1-4}$ alkyl, oxadiazolyl, pyridyl and pyrimidinyl;

$R^a$ is, independently at each occurrence, selected from: OH, halogen, $C_{1-4}$ alkyl substituted with 0-1 $R^f$, $C_{1-4}$ alkoxy substituted with 0-1 $R^f$, $C_{1-4}$ haloalkyl, $C_{1-4}$ haloalkoxy, CO$_2$H, CO$_2$(C$_{1-4}$ alkyl), NH$_2$, NH(C$_{1-4}$ alkyl), N(C$_{1-4}$ alkyl)$_2$, NHCO$_q$(C$_{1-4}$ alkyl substituted with 0-1 $R^f$), NHCO$_q$(CH$_2$)$_{0-2}$(C$_{3-6}$ carbocycle substituted with 0-1 $R^f$), N(C$_{1-4}$ alkyl)CO$_2$(C$_{1-4}$ alkyl), CONH$_2$, CONH(C$_{1-4}$ alkyl substituted with 0-1 $R^f$), CON(C$_{1-4}$ alkyl)(C$_{1-4}$ alkyl substituted with 0-1 $R^f$), CONH(C$_{1-4}$ haloalkyl), CONH(CH$_2$)$_{0-2}$(C$_{3-6}$ carbocycle substituted with 0-1 $R^f$), CON(C$_{1-4}$ alkyl)(C$_{3-6}$ carbocycle substituted with 0-1 $R^f$), NHCONH$_2$, NHCONH(C$_{1-4}$ alkyl), NHCON(C$_{1-4}$ alkyl)$_2$, NHSO$_2$(C$_{1-4}$ alkyl), N(SO$_2$(C$_{1-4}$ alkyl))(SO$_2$(C$_{1-4}$ alkyl substituted with 0-1 $R^f$)), —(CH$_2$)$_{0-1}$—(O)$_{0-1}$—(C$_{3-6}$ carbocycle substituted with 0-1 $R^f$), pyrrolidinyl, oxazolyl, oxadiazolyl substituted with 0-1 $C_{1-4}$ alkyl, pyrazolyl substituted with 0-3 $R^f$, imidazolyl, tetrazolyl, 1-C$_{1-4}$ alkyl-tetrazolyl, pyridyl, —NHCO$_2$CH$_2$-thiazolyl, —(CH$_2$)$_{0-2}$-morpholinyl, —CO-(morpholinyl substituted with 0-2 $R^f$), piperazinyl, —CO-(1-C$_{1-4}$ alkyl-piperazinyl), —NHCO$_2$CH$_2$-pyridyl, —NH(=NCN)NHBn, $R^f$ is, independently at each occurrence, selected from: OH, halogen, CN, $C_{1-4}$ alkyl, $C_{1-4}$ alkoxy, $C_{1-4}$ haloalkyl, CO$_2$H, NH$_2$, CONH$_2$, and NHCO(C$_{1-4}$ alkyl); and $R^h$ is, independently at each occurrence, selected from: H, $C_{1-4}$ alkyl, and —(CH$_2$)$_{0-1}$—C$_{3-6}$ carbocycle.

In a fifth aspect, the present invention includes a compound of Formula (I), (IIa) or (IIb), or a stereoisomer, a tautomer, a pharmaceutically acceptable salt, or a solvate thereof, within the scope of any of the above aspects, wherein:

$R^1$ is independently selected from: CO$_2$(C$_{1-4}$ alkyl), (phenyl substituted with 0-2 $R^a$), (1-$R^c$-pyrazolyl substituted with 0-1 $R^a$), (1-$R^c$-imidazolyl substituted with 0-1 $R^a$), (pyridyl substituted with 0-2 $R^a$), (pyrimidinyl substituted with 0-1 $R^a$), (pyridazinyl substituted with 0-1 $R^a$), (benzothiazolyl substituted with 0-1 $R^a$), —CO-(morpholinyl substituted with 0-2 $R^f$), —CO-(1-C$_{1-4}$ alkyl-piperazinyl), —CONHCH$_2$-(isoxazolyl substituted with 0-1 $R^f$), —CON(Me)CH$_2$-(isoxazolyl substituted with 0-1 $R^f$), —CONH(CH$_2$)$_2$-(imidazolyl substituted with 0-1 $R^f$),

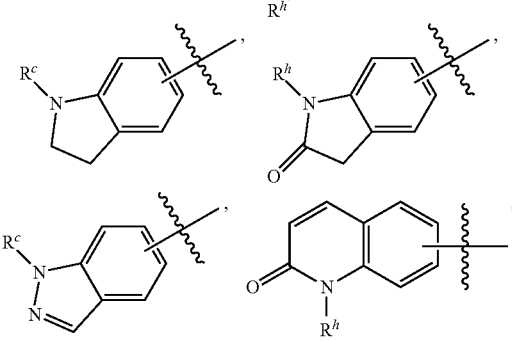

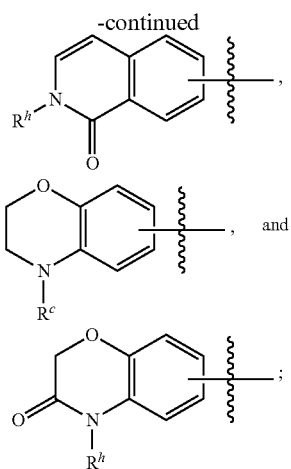

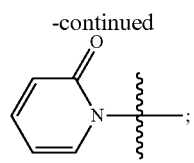

$R^c$ is, independently at each occurrence, selected from: H, $CO_q(C_{1-4}$ alkyl), $C_{1-4}$ alkyl substituted with 0-1 OH, $CO_q$ (benzyl substituted with 0-2 $R^e$);

$R^e$ is, independently at each occurrence, selected from: halogen and $C_{1-4}$ alkyl; and $R^f$ is, independently at each occurrence, selected from: OH, halogen, CN, $C_{1-4}$ alkyl, $C_{1-4}$ alkoxy, $C_{1-4}$ haloalkyl, $CO_2H$, $NH_2$, and $CONH_2$.

In a sixth aspect, the present invention includes a compound of Formula (I), (IIa) or (IIb), or a stereoisomer, a tautomer, a pharmaceutically acceptable salt, or a solvate thereof, within the scope of any of the above aspects, wherein:

$R^1$ is independently selected from: $CO_2$(t-Bu), 4-$CH_2$OMe-Ph, 4-$CH_2$NHCOMe-Ph, 3-$CO_2$(t-Bu)-Ph, 2-$NHCO_2$Me-Ph, 3-$NHCO_2$Me-Ph, 4-$NHCO_2$Me-Ph, 4-$NHCO_2$(i-Pr)-Ph, 4-$NHCO_2(CH_2)_2$OMe-Ph, 4-$NHCO_2CH_2CF_3$-Ph, 4-$NHCO_2$(cyclopropylmethyl)-Ph, 3-$NHCO_2$Bn-Ph, 4-$NHCO_2$Bn-Ph, 4-$NHCO_2$(3-CN-Bn)-Ph, 4-N(Me)$CO_2$(t-Bu)-Ph, 3-CON(Me)$_2$-Ph, 4-CON(Me)$_2$-Ph, 3-CONH(CH$_2$)$_2$OH-Ph, 3-CONH(CH$_2$)$_2$OMe-Ph, 4-CONH(CH$_2$)$_2$OMe-Ph, 4-CONH(CH$_2$)$_2$CN-Ph, 4-CONHC(Me)$_2$CH$_2$OMe-Ph, 4-CONHCH$_2$C(Me)$_2$OH-Ph, 4-CONHCH$_2$C(Me)$_2$OMe-Ph, 4-CONHCH$_2$C(Me)$_2$CH$_2$OMe-Ph, 3-CONHCH$_2$CF$_3$-Ph, 4-CONHCH$_2$CF$_3$-Ph, 3-F-4-CON(Me)(CH$_2$)$_2$OMe-Ph, 4-NHCONH$_2$-Ph, 4-NHCON(Me)$_2$-Ph, 3-OMe-4-NHCO$_2$Me-Ph, 3-OMe-4-CONH(CH$_2$)$_2$OMe-Ph, 1-Me-pyrazol-3-yl, 1-Me-pyrazol-5-yl, 2,3-diMe-pyrazol-5-yl, 1-Me-2-Cl-imidazol-5-yl, 2-Me-pyrid-3-yl, 6-Me-pyrid-3-yl, 2-OH-pyrid-3-yl, 2-OMe-pyrid-3-yl, 5-OMe-pyrid-3-yl, 6-OMe-pyrid-3-yl, 2-OEt-pyrid-3-yl, 6-OEt-pyrid-3-yl, 4-O(i-Pr)-pyrid-3-yl, 6-O(i-Pr)-pyrid-3-yl, 6-N(Me)$_2$-pyrid-3-yl, 6-Ph-pyrid-3-yl, 2-Me-pyrid-4-yl, 2-OH-pyrid-4-yl, 2-OMe-pyrid-4-yl, 2,6-diF-pyrid-3-yl, 2-F-4-Me-pyrid-3-yl, 2-Me-6-F-pyrid-3-yl, 4-Me-6-F-pyrid-3-yl, 5-Me-6-F-pyrid-3-yl, 5-F-6-OMe-pyrid-3-yl, 5-NH$_2$-6-OMe-pyrid-3-yl, 2-OH-3-F-pyrid-4-yl, 2-OMe-3-F-pyrid-4-yl, 2-Me-pyrimidin-5-yl, 4-(i-Pr)-pyrimidin-5-yl, 2-CF$_3$-pyrimidin-5-yl, 2-Ph-pyrimidin-5-yl, 6-Me-pyridazin-4-yl,

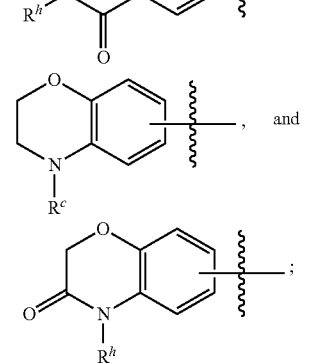

$R^2$ is, independently at each occurrence, selected from: halogen, $C_{1-4}$ alkyl, $C_{1-4}$ alkoxy, $C_{1-4}$ haloalkyl, and $C_{1-4}$ haloalkoxy;

$R^3$ is independently selected from: $C_{1-6}$ alkyl substituted with 0-1 $R^7$, —(CH$_2$)$_{0-1}$—(C$_{3-6}$ carbocycle substituted with 0-1 $R^b$), —(CH$_2$)$_{0-2}$-(morpholinyl), and N(C$_{1-4}$ alkyl)$_2$;

$R^4$ is independently —CH$_2$CONH(C$_{3-6}$ cycloalkyl substituted with 0-1 $R^8$);

$R^7$ is independently selected from: halogen, CN, $C_{1-4}$ alkoxy, $C_{1-4}$ haloalkyl, and $C_{1-4}$ haloalkoxy;

$R^a$ is, independently at each occurrence, selected from: halogen, OH, $C_{1-4}$ alkyl, $C_{1-4}$ alkoxy, $C_{1-4}$ haloalkyl, $C_{1-4}$ haloalkoxy, CH$_2$O(C$_{1-4}$ alkyl), CH$_2$NHCO(C$_{1-4}$ alkyl), CO$_2$H, CO$_2$(C$_{1-4}$ alkyl), NH$_2$, NH(C$_{1-4}$ alkyl), N(C$_{1-4}$ alkyl)$_2$, NHCO(C$_{1-4}$ alkyl), NHCO(CH$_2$)$_{0-2}$(C$_{3-6}$ carbocycle), NHCO$_2$(C$_{1-4}$ alkyl substituted with 0-1 $R^f$), NHCO$_2$(CH$_2$)$_{0-2}$(C$_{3-6}$ carbocycle substituted with 0-1 $R^f$), N(C$_{1-4}$ alkyl)CO$_2$(C$_{1-4}$ alkyl), CONH(C$_{1-4}$ alkyl substituted with 0-1 $R^f$), CON(C$_{1-4}$ alkyl)(C$_{1-4}$ alkyl substituted with 0-1 $R^f$), CONH(C$_{1-4}$ haloalkyl), CONH(CH$_2$)$_{0-2}$(C$_{3-6}$ carbocycle substituted with 0-1 $R^f$), CON(C$_{1-4}$ alkyl)(C$_{3-6}$ cycloalkyl substituted with 0-1 $R^f$), NHCONH$_2$, NHCONH(C$_{1-4}$ alkyl), NHCON(C$_{1-4}$ alkyl)$_2$, N(SO$_2$(C$_{1-4}$ alkyl))(SO$_2$(C$_{1-4}$ alkyl substituted with 0-1 $R^f$)), —(CH$_2$)$_{0-1}$—(O)$_{0-1}$—(C$_{3-6}$ carbocycle substituted with 0-1 $R^f$), pyrrolidinyl, oxazolyl, oxadiazolyl substituted with 0-1 $C_{1-4}$ alkyl, pyrazolyl substituted with 0-3 $R^f$, imidazolyl, tetrazolyl, 1-$C_{1-4}$ alkyl-tetrazolyl, pyridyl, —NHCO$_2$CH$_2$-thiazolyl, —CO-(morpholinyl substituted with 0-2 $R^f$), —CO-(1-$C_{1-4}$ alkyl-piperazinyl), —NHCO$_2$CH$_2$-pyridyl, —NH(=NCN)NHBn,

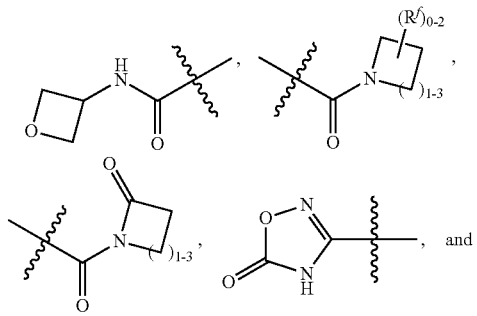

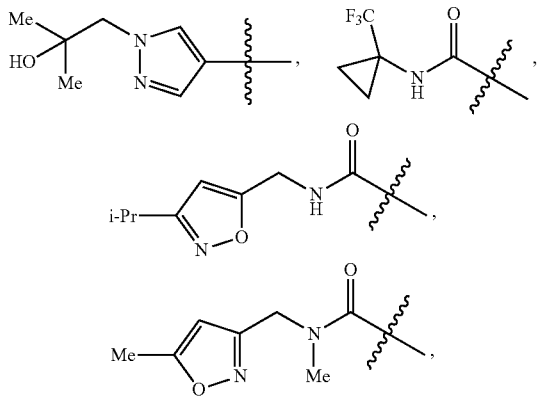

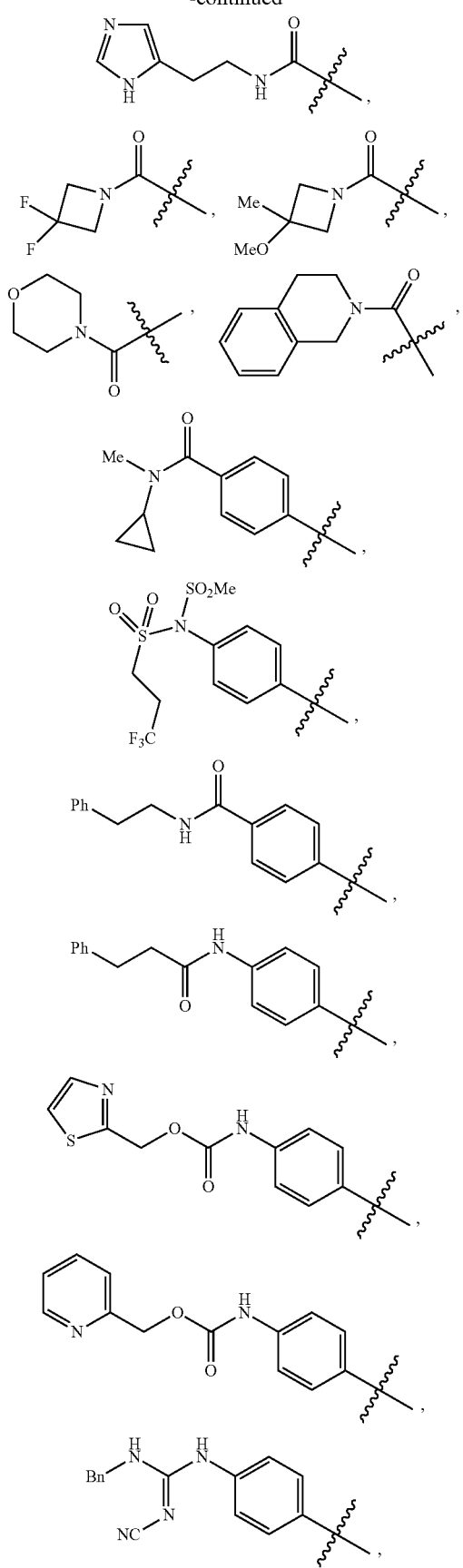
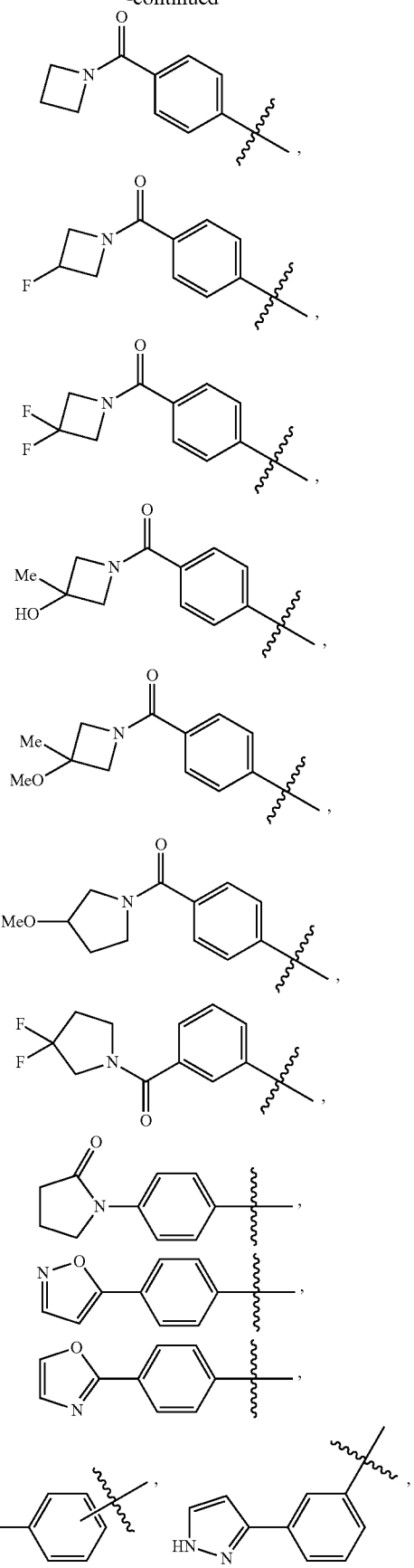

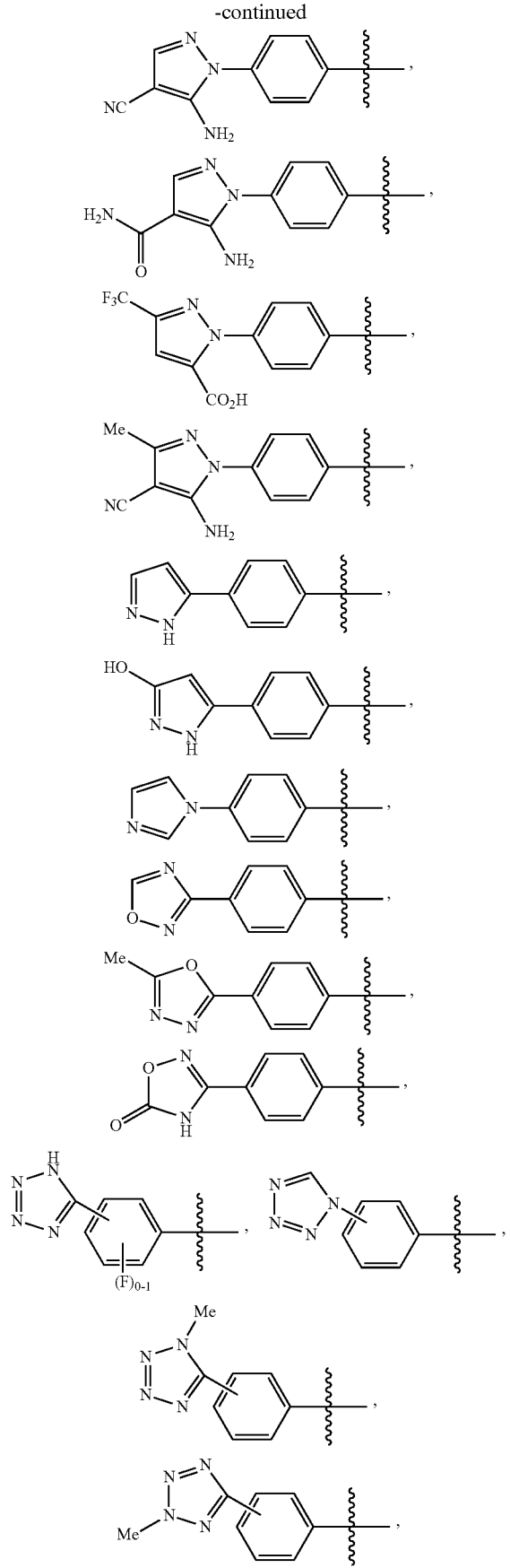
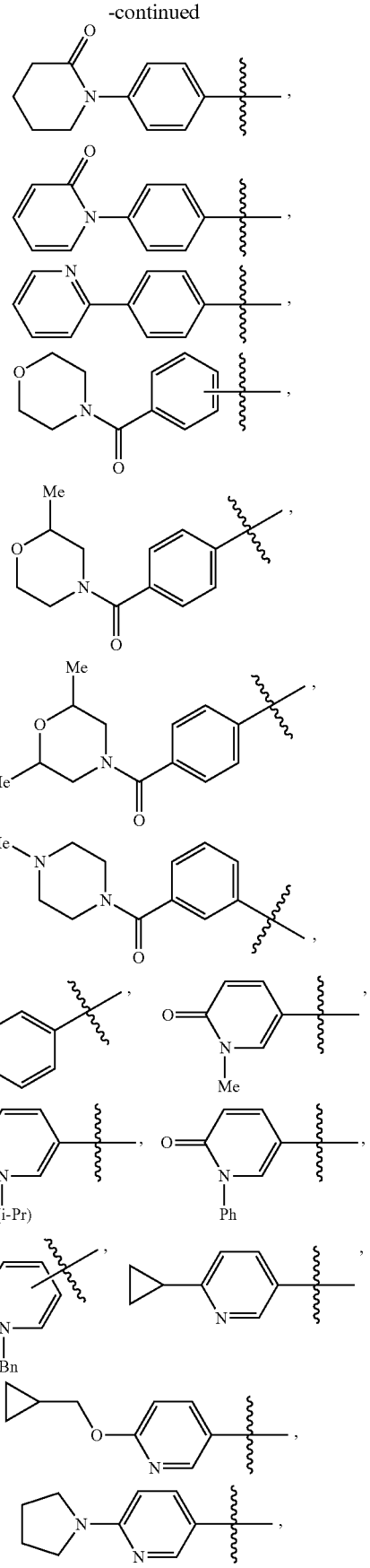

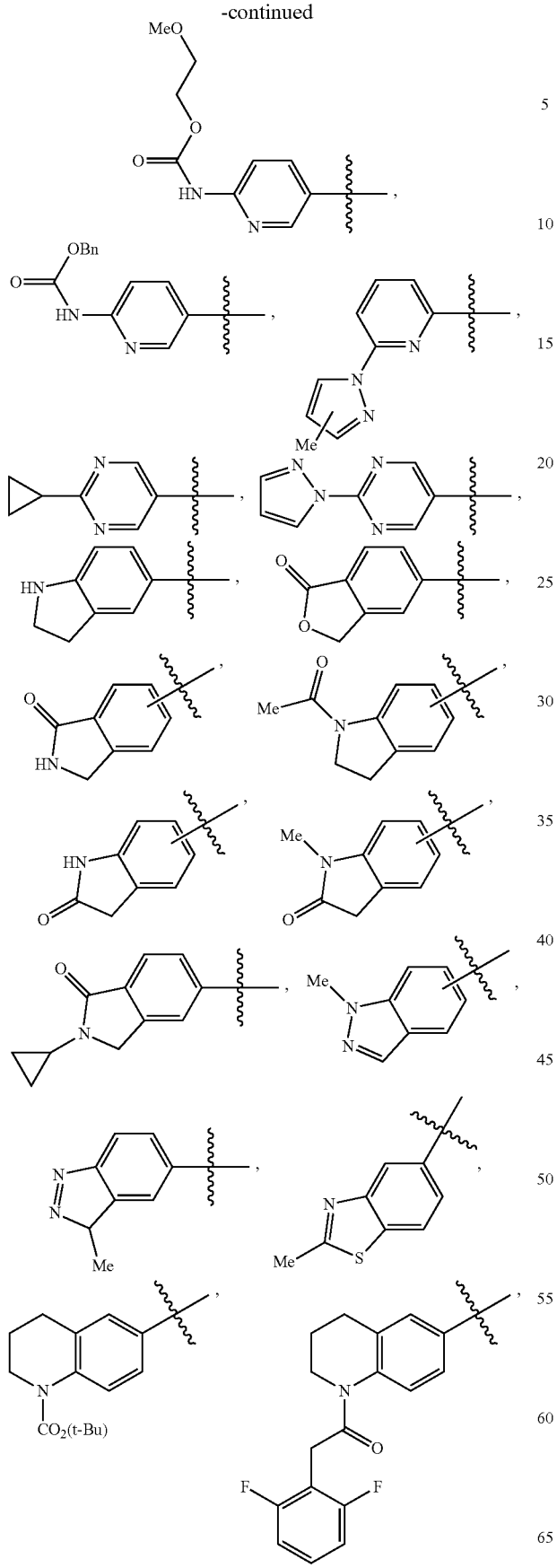

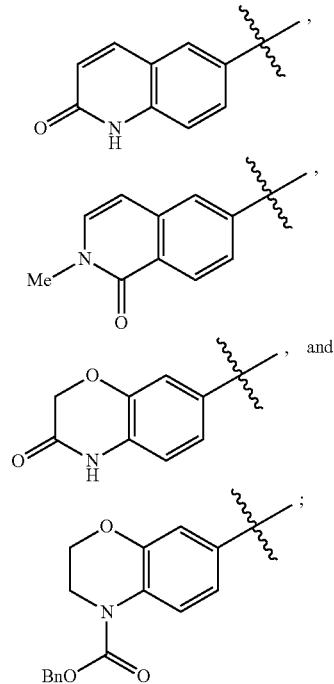

$R^2$ is independently selected from: F, Cl, Me, OMe, OCF$_2$, and CF$_3$;

$R^3$ is independently selected from: Me, Et, Pr, i-Pr, n-Bu, i-Bu, —CH$_2$CN, —(CH$_2$)$_2$OMe, —(CH$_2$)$_2$CF$_3$, —(CH$_2$)$_{0-1}$-(cyclopropyl), —CH$_2$-(cyclohexyl), —(CH$_2$)$_{0-2}$-(morpholinyl), N(Me)$_2$, Ph, 4-F-Ph, 4-F-Bn, and 3-CN-Bn; and $R^4$ is independently selected from: —CH$_2$CONH(cyclopropyl) and

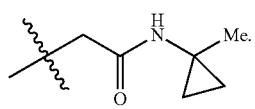 [SMILES: *CC(=O)NC1(C)CC1]

In a seventh aspect, the present invention includes a compound of Formula (I), (IIa) or (IIb), or a stereoisomer, a tautomer, a pharmaceutically acceptable salt, or a solvate thereof, within the scope of any of the first to fourth aspects, wherein:

$R^1$ is independently selected from: halogen, phenyl substituted with 0-2 $R^a$, 1-C$_{1-4}$ alkyl-pyrazol-5-yl, pyridyl substituted with 0-1 $R^a$, and pyrimidinyl;

$R^2$ is, independently at each occurrence, selected from: halogen, C$_{1-4}$ alkyl, C$_{1-4}$ alkoxy, and C$_{1-4}$ haloalkyl;

$R^3$ is independently selected from: N(C$_{1-4}$ alkyl)$_2$, C$_{1-4}$ alkyl substituted with 0-1 $R^7$, C$_{2-4}$ alkenyl, —CH$_2$(C$_{3-6}$ cycloalkyl), —(CH$_2$)$_{0-1}$-(phenyl substituted with 0-1 $R^b$), —(CH$_2$)$_3$—O-(phenyl substituted with 0-1 $R^b$), —(CH$_2$)$_{0-1}$-(pyridyl substituted with 0-1 $R^b$),

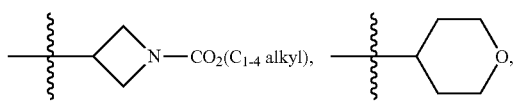

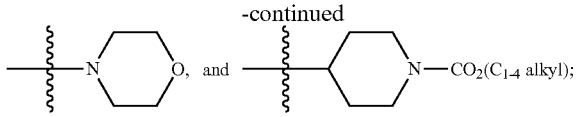

$R^4$ is independently —CH$_2$CONHR$^5$;

$R^5$ is independently selected from: C$_{1-6}$ alkyl substituted with R$^6$, —(CH$_2$)$_{0-1}$—(C$_{3-6}$ cycloalkyl substituted with 0-1 R$^8$), Ph, and

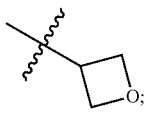 [SMILES: *C1COC1]

$R^6$ is independently selected from: OH, C$_{1-4}$ alkoxy, C$_{1-4}$ haloalkyl, OPh, and OBn;

$R^7$ is independently selected from: OH, halogen, C$_{1-4}$ alkoxy, C$_{1-4}$ haloalkyl, and C$_{1-4}$ haloalkoxy;

$R^8$ is independently selected from: C$_{1-4}$ alkyl, oxadiazolyl, pyridyl and pyrimidinyl;

$R^a$ is independently selected from: halogen, OH, CO$_2$H, C$_{1-4}$ alkyl, C$_{1-4}$ haloalkyl, C$_{1-4}$ haloalkoxy, C$_{1-4}$ alkoxy substituted with 0-1 C$_{1-4}$ alkoxy, NHCO(C$_{1-4}$ alkyl), CONH(C$_{1-4}$ alkyl substituted with 0-1 C$_{1-4}$ alkoxy), NHCONH$_2$, CON(C$_{1-4}$ alkyl)$_2$, NHSO$_2$(C$_{1-4}$ alkyl), C$_{3-6}$ cycloalkyl, and —CO-morpholinyl; and $R^b$ is, independently at each occurrence, selected from: halogen, CN, C$_{1-4}$ alkyl, C$_{1-4}$ alkoxy, C$_{1-4}$ haloalkyl, and C$_{1-4}$ haloalkoxy.

In an eighth aspect, the present invention includes a compound of Formula (I), (IIa) or (IIb), or a stereoisomer, a tautomer, a pharmaceutically acceptable salt, or a solvate thereof, within the scope of any of the first to fourth and seventh aspects, wherein:

$R^1$ is independently selected from: Br, Ph, 3-Cl-Ph, 4-F-Ph, 6-F-Ph, 3-OMe-Ph, 4-OCH$_2$OMe-Ph, 4-CO$_2$H-Ph, 3-NHCO(Me)-Ph, 4-NHCO(Me)-Ph, 3-CONH(Me)-Ph, 3-CON(Me)$_2$-Ph, 4-CONH(CH$_2$)$_2$OMe-Ph, 4-NHCONH$_2$-Ph, 4-NHSO$_2$Me-Ph, 1-Me-pyrazol-5-yl, 5-F-pyrid-2-yl, 6-F-pyrid-2-yl, 4-Cl-pyrid-2-yl, 5-Cl-pyrid-2-yl, 6-Cl-pyrid-2-yl, pyrid-3-yl, 2-F-pyrid-3-yl, 2-Cl-pyrid-3-yl, 5-F-pyrid-3-yl, 6-F-pyrid-3-yl, 5-Cl-pyrid-3-yl, 6-Cl-pyrid-3-yl, 2-CF$_3$-pyrid-3-yl, 6-CF$_3$-pyrid-3-yl, 6-cyclopropyl-pyrid-3-yl, pyrid-4-yl, 2-F-pyrid-4-yl, 3-F-pyrid-4-yl, 3-Cl-pyrid-4-yl, 2-OH-pyrid-4-yl, 2-CF$_3$-pyrid-4-yl, pyrimidin-5-yl, and

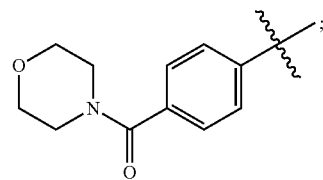 [SMILES: *c1ccc(C(=O)N2CCOCC2)cc1]

$R^2$ is, independently at each occurrence, selected from: F, Cl, Me, OMe, and CF$_3$;

$R^3$ is independently selected from: Me, i-Pr, i-Bu, —CH$_2$CH=CH$_2$, —(CH$_2$)$_2$OH, —(CH$_2$)$_2$OMe, —(CH$_2$)$_2$CF$_3$, —(CH$_2$)$_3$O(4-OMe-Ph), N(Me)$_2$, —CH$_2$(cyclopropyl), Ph, 3-Me-Ph, 4-F-Ph, Bn, 2-F-Bn, 3-F-Bn, 3-CN-Bn, 4-F-Bn, 4-CF$_3$—Bn, 4-OCF$_3$—Bn, N(Me)$_2$,

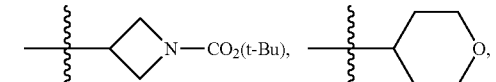
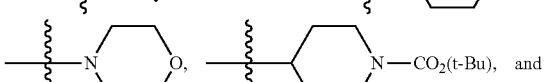
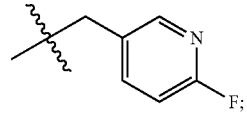

and $R^4$ is independently selected from: —CH$_2$CONH(CH$_2$)$_2$OH, —CH$_2$CONHCH$_2$C(Me)$_2$OH, —CH$_2$CONH(CH$_2$)$_2$OMe, —CH$_2$CONH(CH$_2$)$_2$O(i-Pr), —CH$_2$CONH(CH$_2$)$_2$OPh, —CH$_2$CONH(CH$_2$)$_2$OBn, —CH$_2$CONHCH$_2$CF$_3$, —CH$_2$CONH(cyclopropyl), —CH$_2$CONH(cyclobutyl), —CH$_2$CONHPh,

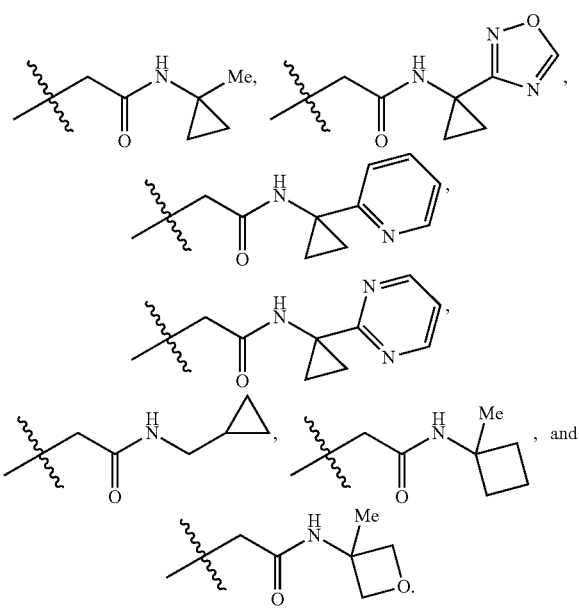

In a ninth aspect, the present invention includes a compound of Formula (I), (IIa) or (IIb), or a stereoisomer, a tautomer, a pharmaceutically acceptable salt, or a solvate thereof, within the scope of any of the first to fourth aspects, wherein:

$R^1$ is independently selected from:

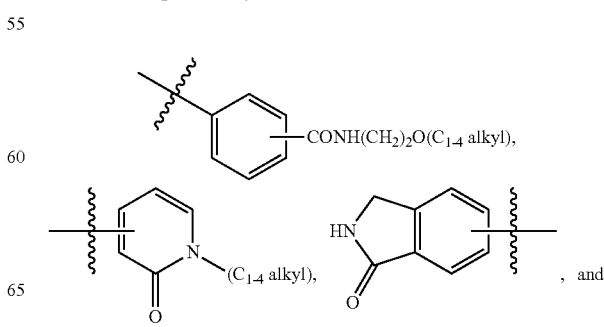

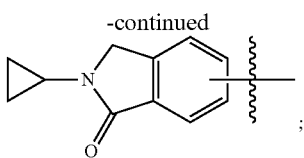

$R^2$ is, independently at each occurrence, selected from: F and $CF_3$;

$R^3$ is independently selected from: $C_{1-4}$ alkyl and phenyl substituted with 0-1 halogen; and $R^4$ is independently $-CH_2CONH(CH_2)_2O(C_{1-4}$ alkyl).

In a tenth aspect, the present invention provides a compound selected from the exemplified examples or a stereoisomer, a tautomer, a pharmaceutically acceptable salt, or a solvate thereof.

In another aspect, the present invention provides a compound selected from any subset list of compounds within the scope of the tenth aspect.

In another embodiment, the compounds of the present invention have EL $IC_{50}$ values ≤500 nM.

In another embodiment, the compounds of the present invention have EL $IC_{50}$ values ≤100 nM.

In another embodiment, the compounds of the present invention have EL $IC_{50}$ values ≤50 nM.

In another embodiment, the compounds of the present invention have EL $IC_{50}$ values ≤25 nM.

In another embodiment, the compounds of the present invention have EL $IC_{50}$ values ≤10 nM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising additional therapeutic agent(s).

In another embodiment, the present invention provides a method for the treatment and/or prophylaxis of dyslipidemias and the sequelae thereof comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Examples of diseases or disorders associated with the activity of endothelial lipase that can be prevented, modulated, or treated according to the present invention include, but are not limited to, atherosclerosis, coronary heart disease, coronary artery disease, coronary vascular disease, cerebrovascular disorders, Alzheimer's disease, venous thrombosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia.

In one embodiment, the present invention provides a method for the treatment and/or prophylaxis of atherosclerosis, coronary heart disease, cerebrovascular disorders and dyslipidemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment and/or prophylaxis of dyslipidemias and the sequelae thereof.

In another embodiment, the present invention also provides the use of a compound of the present invention for the manufacture of a medicament for the treatment and/or prophylaxis of dyslipidemias and the sequelae thereof.

In another embodiment, the present invention provides a method for the treatment and/or prophylaxis of dyslipidemias and the sequelae thereof, comprising administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of dyslipidemias and the sequelae thereof.

The compounds of the present invention may be employed in combination with additional therapeutic agent(s) selected from one or more, preferably one to three, of the following therapeutic agents: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease, treatment for malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), acyl-coenzyme A:cholesterol acyltransferase (ACAT) inhibitors, LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

In another embodiment, additional therapeutic agent(s) used in combined pharmaceutical compositions or combined methods or combined uses, are selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rivastatin.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl". A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl", "$C_{6-10}$ aryl", or "aromatic residue" may be unsubstituted or substituted with 1 to 5 groups, preferably 1 to 3 groups, selected from —OH, —OCH$_3$, —Cl, —F, —Br, —I, —CN, —NO$_2$, —NH$_2$, —N(CH$_3$)H, —N(CH$_3$)$_2$, —CF$_3$, —OCF$_3$, —C(O)CH$_3$, —SCH$_3$, —S(O)CH$_3$, —S(O)$_2$CH$_3$, —CH$_3$, —CH$_2$CH$_3$, —CO$_2$H, and —CO$_2$CH$_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, OCH$_3$, Cl, F, Br, I, CN, NO$_2$, NH$_2$, N(CH$_3$)H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R.

Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

As a person of ordinary skill in the art would be able to understand that imine and carbonyl groups in a molecule may tautomerize to their enamine and enol forms, and the double bond can exist as geometrical (E and Z) isomers as shown in the following equation, wherein $R^1$, $R^2$, $R^3$ and $R^4$ are as defined above:

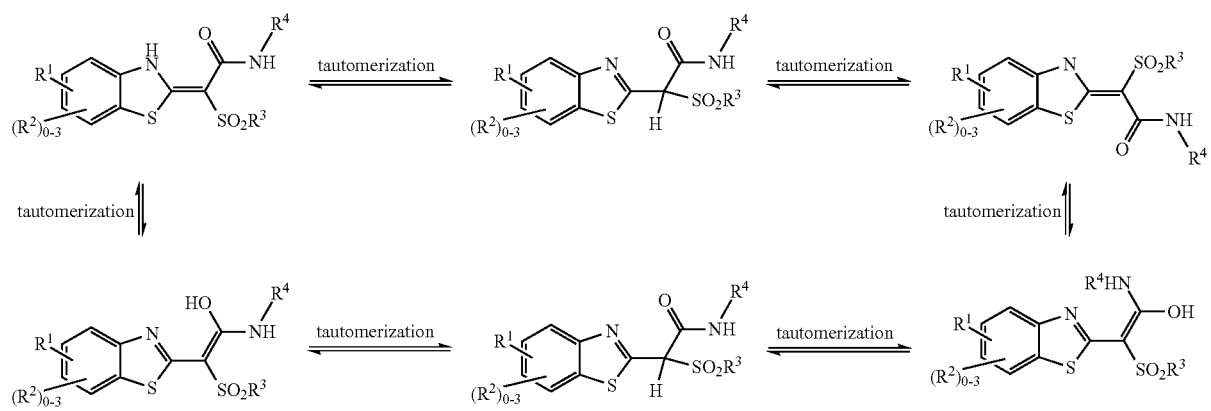

Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr. et al., eds., Remington: The Science and Practice of Pharmacy, 22nd Edition, Pharmaceutical Press, London, UK (2012), the disclosure of which is hereby incorporated by reference.

In addition, compounds of Formula (I), Formula (II), or Formula (III) may have prodrug forms. Any compound that will be converted in vivo to provide the bioactive agent (i.e., a compound of Formula (I), Formula (II) or Formula (III)) is a prodrug within the scope and spirit of the invention. Various forms of prodrugs are well known in the art. For examples of such prodrug derivatives, see:

a) Bundgaard, H., ed., Design of Prodrugs, Elsevier (1985), and Widder, K. et al., eds., Methods in Enzymology, 112:309-396, Academic Press (1985);

b) Bundgaard, H., Chapter 5, "Design and Application of Prodrugs", Krosgaard-Larsen, P. et al., eds., A Textbook of Drug Design and Development, pp. 113-191, Harwood Academic Publishers (1991);

c) Bundgaard, H., Adv. Drug Deliv. Rev., 8:1-38 (1992);

d) Bundgaard, H. et al., J. Pharm. Sci., 77:285 (1988);

e) Kakeya, N. et al., Chem. Pharm. Bull., 32:692 (1984); and f) Rautio, J., ed., Prodrugs and Targeted Delivery (Methods and Principles in Medicinal Chemistry), Vol. 47, Wiley-VCH (2011).

Compounds containing a carboxy group can form physiologically hydrolyzable esters that serve as prodrugs by being hydrolyzed in the body to yield Formula (I), (IIa), (IIb), (IIIa) or (IIIb) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of the present invention include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., Medicinal Chemistry: Principles and Practice, The Royal Society of Chemistry, Cambridge, UK, 2nd Edition (reproduced 2006); Testa, B. et al., Hydrolysis in Drug and Prodrug Metabolism. Chemistry, Biochemistry and Enzymology, VCHA an Wiley-VCH, Zurich, Switzerland (2003); Wermuth, C. G., ed., The Practice of Medicinal Chemistry, 3rd Edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

AcOH or HOAc acetic acid
$AlCl_3$ aluminum chloride
Alk alkyl
$BBr_3$ boron tribromide
$BCl_3$ boron trichloride
Bn benzyl
Boc tert-butyloxycarbonyl
BOP reagent benzotriazol-1-yloxytris(dimethylamino)phosphonium hexafluorophosphate
Bu butyl
i-Bu isobutyl
t-Bu tert-butyl
t-BuOH tert-butanol
Cbz carbobenzyloxy
$CDCl_3$ deutero-chloroform
$CD_3OD$ deutero-methanol
$CH_2Cl_2$ dichloromethane
$CH_3CN$ or ACN acetonitrile
$CHCl_3$ chloroform
$CO_2$ carbon dioxide
mCPBA or m-CPBA meta-chloroperbenzoic acid
$Cs_2CO_3$ cesium carbonate
$Cu(OAc)_2$ copper (II) acetate
DBU 1,8-diazabicyclo[5.4.0]undec-7-ene
DCE 1,2-dichloroethane
DCM dichloromethane
DEA diethylamine
DIC or DIPCDI diisopropylcarbodiimide
DIEA, DIPEA or diisopropylethylamine
Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
EDC N-(3-dimethylaminopropyl)-N'-ethylcarbodiimide
EDTA ethylenediaminetetraacetic acid
Et ethyl
$Et_3N$ or TEA triethylamine
$Et_2O$ diethyl ether
EtOAc ethyl acetate
EtOH ethanol
HATU (2-(7-aza-1H-benzotriazole-1-yl)-1,1,3,3-tetramethyluronium hexafluorophosphate)
HCl hydrochloric acid
HOBt or HOBT 1-hydroxybenzotriazole
HPLC high-performance liquid chromatography
$H_3PO_4$ phosphoric acid
$H_2SO_4$ sulfuric acid
$K_2CO_3$ potassium carbonate
KOAc potassium acetate
$K_3PO_4$ potassium phosphate
LAH lithium aluminum hydride
LDA lithium diisopropylamide
LG leaving group
LiOH lithium hydroxide
Me methyl
MeOH methanol
$MgSO_4$ magnesium sulfate
MsOH or MSA methylsulfonic acid
NaCl sodium chloride
$Na_2CO_3$ sodium carbonate
NaH sodium hydride
$NaHB(OAc)_3$ sodium triacetoxyborohydride
$NaHCO_3$ sodium bicarbonate
NaHMDS sodium hexamethyldisilazane
NaOH sodium hydroxide
NaOMe sodium methoxide
$Na_2SO_3$ sodium sulfite
$Na_2SO_4$ sodium sulfate
NBS N-bromosuccinimide
$NH_3$ ammonia
$NH_4Cl$ ammonium chloride
$NH_4OAc$ ammonium acetate
$NH_4OH$ ammonium hydroxide OTf triflate or trifluoromethanesulfonate
Pd$_2$(dba)$_3$ tris(dibenzylideneacetone)dipalladium(0)
Pd(OAc)$_2$ palladium(II) acetate
Pd/C palladium on carbon
Pd(dppf)Cl$_2$ [1,1'-bis(diphenylphosphino)-ferrocene]dichloropalladium(II)
Ph$_3$PCl$_2$ triphenylphosphine dichloride
PG protecting group
Ph phenyl
PMB p-methoxybenzyl
POCl$_3$ phosphorus oxychloride
Pr propyl
i-Pr isopropyl
i-PrOH or IPA isopropanol
PS polystyrene
PS-Pd(Ph$_3$)$_4$ tetrakis(triphenylphosphine)palladium (0) on polystyrene support
PyBOP or PYPOP (benzotriazol-1-yloxy)tripyrrolidinophosphonium hexafluorophosphate
SiO$_2$ silica oxide
SnCl$_2$ tin(II) chloride
TBAF tetra-n-butylammonium fluoride
TBAI tetra-n-butylammonium iodide
TEA triethylamine
TFA trifluoroacetic acid
THF tetrahydrofuran
TMSCHN$_2$ trimethylsilyldiazomethane
T3P 1-propanephosphonic acid cyclic anhydride
Xantphos or X-Phos 4,5-bis(diphenylphosphino)-9,9-dimethylxanthene
X-Phos pre-catalyst chloro(2-dicyclohexylphosphino-2',4',6'-triisopropyl-1,1'-biphenyl)[2-(2'-amino-1,1'-biphenyl)]palladium(II)

SYNTHESIS

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C., Comprehensive Organic Transformations, VCH, New York (1989). Preferred methods include, but are not limited to, those described below. All references cited herein are hereby incorporated in their entirety herein by reference.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al., (Protective Groups in Organic Synthesis, Wiley and Sons (1991)).

General Schemes

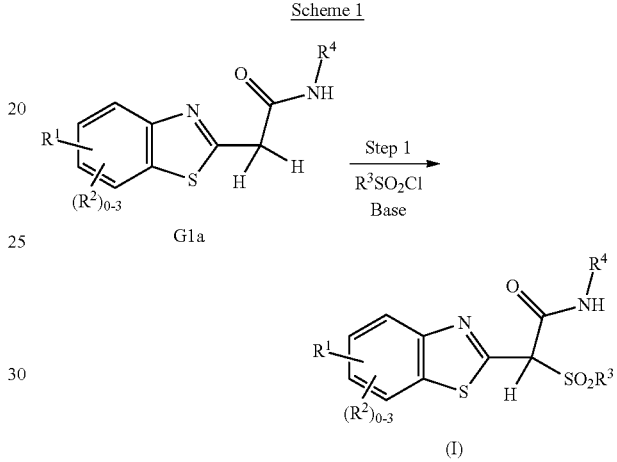

Scheme 1

Step 1
Step 1 describes the preparation of compounds of Formula (I) by reacting a compound of Formula (G1a) with a sulfonylating reagent R$^3$—SO$_2$Cl. Preferred solvents are polar aprotic solvents (such as N,N-dimethylformamide) and ethers (such as tetrahydrofuran, dioxane and the like). Preferred bases include metal hydrides (such as sodium hydride and the like) and metal amides (such as sodium bis(trimethylsilyl)amide and lithium diisopropylamide and the like).

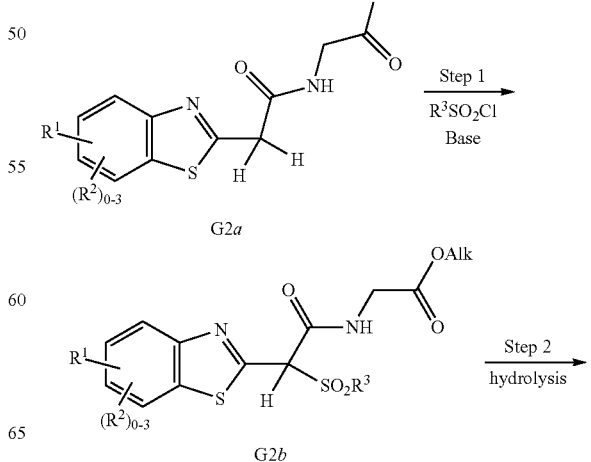

Scheme 2

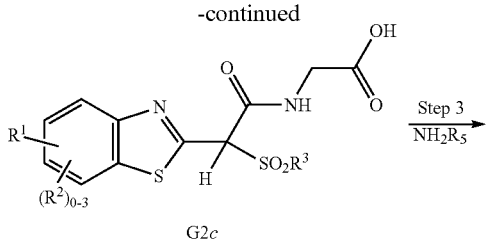

G2c

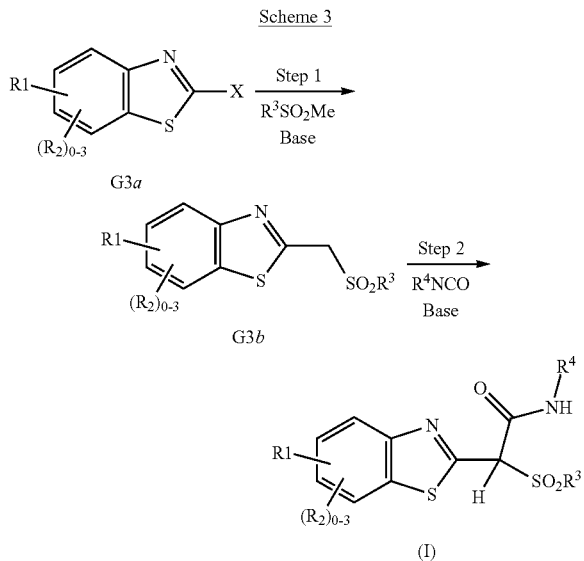

(I)

Step 1

Step 1 describes the preparation of a compound of Formula (G2b) from a compound of Formula (G2a) and is analogous to Step 1 in Scheme 1.

Step 2

Step 2 describes the conversion of an ester of Formula (G2b) to an acid of Formula (G2c). Preferred solvents are halogenated solvents (such as DCM and the like) and water. Preferred reagents are acids (such as TFA, HCl and the like) or metal hydroxides (such as sodium hydroxide and the like).

Step 3

Step 3 describes the conversion of an acid of Formula (G2c) to an amide of Formula (I). Preferred solvents are polar aprotic solvents (such as N,N-dimethylformamide) and ethers (such as tetrahydrofuran, dioxane and the like). Preferred reagent are amide bond coupling reagents (such as HATU, PyBOP, T3P and the like).

Step 1

Step 1 describes the preparation of compounds of Formula (G3b) by displacement of a leaving group X (such as Cl, Br and the like) on a compound of Formula G3a with a methyl sulfone $R^3$—$SO_2Me$ in the presence of base. Preferred solvents are non-polar aprotic solvents (such as toluene, benzene and the like). Preferred bases include metal amides (such as sodium bis(trimethylsilyl)amide and the like) and metal hydrides (such as sodium hydride and the like).

Step 2

Step 2 describes the preparation of a compound of Formula (I) from a compound of Formula (G3b) with an isocyanate in the presence of base. Preferred solvent are polar aprotic solvents (such as DMF) and ethers (such as THF, dioxane and the like). Preferred base include metal hydrides (such as sodium hydride and the like) and metal amides (such as sodium bis(trimethylsilyl)amide and lithium diisopropylamide and the like).

General Methods

The following methods were used in the exemplified Examples, except where noted otherwise.

Products were analyzed by reverse phase analytical HPLC carried out on a Shimadzu Analytical HPLC system running Discovery VP software using Method A: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% TFA; B: 10% water, 89.9% methanol, 0.1% TFA, UV 220 nm), or Method B: PHENOMENEX® Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 nm) or Method C: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% $H_3PO_4$; B: 10% water, 89.9% methanol, 0.1% $H_3PO_4$, UV 220 nm) or Method D: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% $NH_4OAc$; B: 10% water, 89.9% methanol, 0.1% $NH_4OAc$, UV 220 nm).

Purification of intermediates and final products was carried out via either normal or reverse phase chromatography. Normal phase chromatography was carried out using prepacked $SiO_2$ cartridges eluted with gradients of hexane and ethyl acetate or methylene chloride and methanol. Reverse phase preparative HPLC was carried out using a Shimadzu Preparative HPLC system running Discovery VP software using Method A: YMC SunFire 5 nm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm), Method B: PHENOMENEX® Axia Luna 5 nm C18 30×100 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), Method C: PHENOMENEX® Luna 5 nm C18 30×100 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), or Method D: PHENOMENEX® Luna 5 nm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm).

Alternatively, reverse phase preparative HPLC was carried out using a VARIAN® ProStar Preparative HPLC System running Star 6.2 Chromatography Workstation software using Method E: Dynamax 10 nm C18 41.4×250 mm column with a 30 min gradient at 30 mL/min from 10% B to 100% B (A 98% water, 2% acetonitrile, 0.05% TFA; B: 98% acetonitrile, 2% water, 0.05% TFA, UV 254 nm).

LCMS chromatograms were obtained on a Shimadzu HPLC system running Discovery VP software, coupled with a Waters ZQ mass spectrometer running MassLynx version 3.5 software and using the following respective methods. Unless specified otherwise, for each method, the LC column was maintained at room temperature and UV detection was set to 220 nm.

Method A: A linear gradient using solvent A (10% methanol, 90% water, 0.1% of TFA) and solvent B (90% methanol, 10% water, 0.1% of TFA); 0-100% of solvent B over 4 min and then 100% of solvent B over 1 min. Column: PHENOMENEX® Luna 5 μm C18 (4.5×50 mm). Flow rate was 4 mL/min.

Method B: A linear gradient using solvent A (10% methanol, 90% water, 0.1% of TFA) and solvent B (90% methanol, 10% water, 0.1% of TFA); 0-100% of solvent B over 2 min and then 100% of solvent B over 1 min. Column: PHENOMENEX® Luna 5 μm C18 (2.0×30 mm). Flow rate was 1 mL/min.

Method C: A linear gradient using solvent A (10% acetonitrile, 90% water, 10 mM $NH_4OAc$) and solvent B (90% acetonitrile, 10% water, 10 mM $NH_4OAc$); 0-100% of solvent B over 4 min and then 100% of solvent B over 1 min. Column: PHENOMENEX® Luna 5 μm C18 (4.5×50 mm). Flow rate was 4 mL/min.

Method D: A linear gradient using solvent A (10% acetonitrile, 90% water, 0.05% of TFA) and solvent B (90% acetonitrile, 10% water, 0.05% of TFA); 0-100% of solvent B over 2 min and then 100% of solvent B over 1 min. Column: PHENOMENEX® Luna 5 μm C18 (4.5×30 mm). Flow rate was 1 mL/min.

Method E: A linear gradient using solvent A (10% MeOH, 90% water, 10 mM $NH_4OAc$) and solvent B (90% MeOH, 10% water, 10 mM $NH_4OAc$); 0-100% of solvent B over 4 min and then 100% of solvent B over 1 min. Column: PHENOMENEX® Luna 5 μm C18 (4.5×50 mm). Flow rate was 4 mL/min.

Method F: A linear gradient using solvent A (10 mM $NH_4OAc$, 95% water, 5% ACN) and solvent B (10 mM $NH_4OAc$, 95% ACN, 5% water); 0-100% of solvent B over 4 min and then 100% of solvent B over 1 min. Column: Mac-Mod Halo (C18, 4.6×50 mm). Flow rate was 4 mL/min.

Method G: A linear gradient using solvent A (10% acetonitrile, 90% water, 0.1% TFA) and solvent B (90% acetonitrile, 10% water, 0.1% TFA); 0-100% of solvent B over 4 min and then 100% of solvent B over 1 min. Column: PHENOMENEX® Luna 3 μm C18 (2.0×50 mm). Flow rate was 4 mL/min.

Method H: A linear gradient using solvent A (10% methanol, 90% water, 0.1% of formic acid) and solvent B (90% methanol, 10% water, 0.1% of formic acid); 0-100% of solvent B over 2 min and then 100% of solvent B over 1 min. Column: PHENOMENEX® Luna 3 μm C18 (2.0×30 mm). Flow rate was 1 mL/min.

Method I: A linear gradient using solvent A (10% MeOH, 90% water, 10 mM $NH_4OAc$) and solvent B (90% MeOH, 10% water, 10 mM $NH_4OAc$); 0-100% of solvent B over 2 min and then 100% of solvent B over 1 min. Column: PHENOMENEX® Luna 3 μm C18 (2.0×30 mm). Flow rate was 1 mL/min.

Method J: A linear gradient using solvent A (10% methanol, 90% water, 0.1% of formic acid) and solvent B (90% methanol, 10% water, 0.1% of TFA); 0-100% of solvent B over 4 min and then 100% of solvent B over 1 min. Column: PHENOMENEX® Luna 5 μm C18 (4.5×50 mm). Flow rate was 4 mL/min.

Method K: A linear gradient using solvent A (10 mM $NH_4OAc$, 95% water, 5% ACN) and solvent B (10 mM $NH_4OAc$, 95% ACN, 5% water); 0-100% of solvent B over 5.5 min and then 100% of solvent B over 1.5 min. Column: SUPELCO® Ascentis 4.6×50 mm 2.7 μm C18. Flow rate was 4 mL/min.

Method L: A linear gradient using solvent A (5% methanol, 95% water, 0.05% of TFA) and solvent B (95% methanol, 5% water, 0.05% of TFA); 0-100% of solvent B over 4 min and then 100% of solvent B over 1 min. Column: Waters XBridge C18 (4.6×50 mm, 5 μm). Flow rate was 4 mL/min. The LC column was maintained at 35° C.

Method M: A linear gradient using of Solvent A (0.05% TFA, 100% water) and Solvent B (0.05% TFA, 100% ACN); 2 to 98% B over 1 min, with 0.5 min hold time at 98% B. Column: Waters BEH C18 (2.1×50 mm). Flow rate: 0.8 mL/min.

Method N: A linear gradient using solvent A (5% ACN, 95% water, 10 mM $NH_4OAc$) and solvent B (95% ACN, 5% water, 10 mM $NH_4OAc$); 0-100% of solvent B over 3 min and then 100% of solvent B over 1 min. Column: Waters BEH C18 (2.1×50 mm). Flow rate: 1.1 mL/min.

Method O: A linear gradient using solvent A (5% ACN, 95% water, 0.05% of TFA) and solvent B (95% ACN, 5% water, 0.05% of TFA); 0-100% of solvent B over 3 min and then 100% of solvent B over 1 min. Column: Waters BEH C18 (2.1×50 mm). Flow rate: 1.1 mL/min.

Method P: A linear gradient using solvent A (5% ACN, 95% water, 10 mM $NH_4OAc$) and solvent B (95% ACN, 5% water, 10 mM $NH_4OAc$); 0-100% of solvent B over 4 min and then 100% of solvent B over 1 min. Column: Waters XBridge C18 (4.6×50 mm, 5 μm). Flow rate was 4 mL/min.

Method Q: A linear gradient using solvent A (10% MeOH, 90% water, 0.1% TFA) and solvent B (90% MeOH, 10% water, 0.1% TFA); 0-100% of solvent B over 2 min and then 100% of solvent B over 1 min. Column: PHENOMENEX® Luna 3 μm C18 (2.0×50 mm). Flow rate was 1 mL/min.

Method R: A linear gradient using solvent A (10% MeOH, 90% water, 0.1% TFA) and solvent B (90% MeOH, 10% water, 0.1% TFA); 0-100% of solvent B over 4 min and then 100% of solvent B over 1 min. Column: PHENOMENEX® Luna 3 μm C18 (2.0×50 mm). Flow rate was 0.8 mL/min.

Method S: A linear gradient using solvent A (5% ACN, 95% water, 10 μM $NH_4OAc$) and solvent B (95% ACN, 5% water, 10 μM $NH_4OAc$); 0-100% of solvent B over 3 min and then 100% of solvent B over 0.5 min. Column: Waters BEH C18 (2.0×50 mm). Flow rate: 1.0 mL/min.

Method T: A linear gradient using solvent A (5% MeOH, 95% water, 10 μM $NH_4OAc$) and solvent B (95% ACN, 5% water, 10 μM $NH_4OAc$); 0-100% of solvent B over 3 min and then 100% of solvent B over 0.5 min. Column: Waters BEH C18 (2.0×50 mm). Flow rate: 0.5 mL/min.

Method U: A linear gradient using solvent A (water, 0.05% TFA) and solvent B (ACN, 0.05% TFA); 2-98% of solvent B over 1.6 min and then 98% of solvent B over 0.26 min. Column: Acquity BEH C18 (2.1×50 mm, 1.7 μM). Flow rate: 0.8 mL/min.

Preparative HPLC methods employed in the purification of products:

Method A: Linear gradient of 0 to 100% B over 10 min, with 5 min hold time at 100% B; Shimadzu LC-8A binary pumps Waters ZQ mass spectrometer using Waters Masslynx 4.0 SP4 MS software UV visualization at 220 nm Column: Waters XBridge 19×150 mm 5 μm C18

Flow rate: 20 mL/min

Peak collection triggered by mass spectrometry

Solvent A: 0.1% TFA, 10% ACN, 90% water

Solvent B: 0.1% TFA, 90% ACN, 10% water

NMR Employed in Characterization of Examples $^1$H NMR spectra were obtained with Bruker or JEOL® Fourier transform spectrometers operating at frequencies as follows: $^1$H NMR: 400 MHz (Bruker or JEOL®) or 500 MHz (JEOL®). $^{13}$C NMR: 100 MHz (Bruker or JEOL®). Spectra data are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled.

IV. Biology

The endothelium occupies a pivotal position at the interface between the circulating humoral and cellular elements of the blood, and the solid tissues which constitute the various organs. In this unique position, endothelial cells regulate a large number of critical processes, including leukocyte adherence and transit through the blood vessel wall, local control of blood vessel tone, modulation of the immune response, the balance between thrombosis and thrombolysis, and new blood vessel development. Thus, endothelial cell dysfunction has been postulated as a central feature of vascular diseases such as hypertension and atherosclerosis. (WO 1999/032611 and references cited therein, e.g., Folkman, J. et al., *Science*, 235:442-447 (1987); Yanagisawa, M. et al., *Nature*, 332(6163):411-415 (1988); Folkman, J. et al., *J. Biol. Chem.*, 267(16):10931-10934 (1992); Janssens, S. P. et al., *J. Biol. Chem.*, 267(21):14519-14522 (1992); Lamas, S. et al., *Proc. Natl. Acad. Sci. USA*, 89(14):6348-6352 (1992); Luscher, T. F. et al., *Hypertension*, 19(2):117-130 (1992); Williams et al., *Am. Rev. Respir. Dis.*, 146:S45-S50 (1992); and Bevilacqua, M. P. et al., *J. Clin. Invest.*, 91(2):379-387 (1993)).

Atherosclerosis and its associated coronary artery disease (CAD) is the leading cause of mortality in the industrialized world. Despite attempts to modify secondary risk factors (smoking, obesity, lack of exercise) and treatment of dyslipidemia with dietary modification and drug therapy, coronary heart disease (CHD) remains the most common cause of death in the U.S. In 2008, cardiovascular disease accounted for 33% of all deaths in the U.S., and ~1 of every 6 deaths were specifically caused by atherosclerotic coronary heart disease (*Circulation* 125:e2-e220 (2012)).

Risk for development of atherosclerosis has been shown to be strongly correlated with certain plasma lipid levels. While elevated low density lipoprotein-cholesterol (LDL-C) may be the most recognized form of dyslipidemia, it is by no means the only significant lipid associated contributor to CHD. A low level of high density lipoprotein-cholesterol (HDL-C) is also a known risk factor for CHD (Gordon, D. J. et al., *Circulation*, 79(1):8-15 (1989)).

High LDL-C and triglyceride levels are positively correlated, while high levels of HDL-C are negatively correlated with the risk for developing cardiovascular diseases. Thus, dyslipidemia is not a unitary risk profile for CHD but may be comprised of one or more, preferably one to three, lipid aberrations.

At least 50% of the variation in HDL cholesterol levels is genetically determined. The phenotype of elevated HDL cholesterol is often dominantly inherited, but homozygous deficiency of HL or of the cholesteryl ester transfer protein (CETP), which result in elevated HDL cholesterol, are recessive conditions. Recently, several genetic variations in the human endothelial lipase gene have been identified, six of which potentially produce functional variants of the protein, and the frequencies of these variants were found to be associated with elevated levels of HDL cholesterol in human subjects (deLemos, A. S. et al., *Circulation*, 106(11): 1321-1326 (2002)). Notably, the endothelial lipase-mediated binding and uptake of HDL particles and the selective uptake of HDL-derived cholesterol esters have been reported to be independent of its enzymatic lipolytic activity (Strauss, J. G. et al., *Biochem. J.*, 368:69-79 (2002)).

Because of the beneficial effects widely associated with elevated HDL levels, an agent which inhibits EL activity in humans, by virtue of its HDL increasing ability, are expected to be useful for the treatment, prevention, the arrestment and/or regression of atherosclerosis, coronary heart disease, cerebrovascular disorders etc., especially those (but not restricted thereto) which are characterized by one or more of the following factors: (a) high plasma triglyceride concentrations, high postprandial plasma triglyceride concentrations; (b) low HDL cholesterol concentration; (c) low apoA1 lipoprotein concentrations; (d) high LDL cholesterol concentrations; (e) high levels of small dense LDL cholesterol particles; and (f) high apoB lipoprotein concentrations.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, receptor internalization, and/or may be manifest only in particular cell types.

It is also desirable and preferable to find compounds with advantageous and improved characteristics compared with known anti-atherosclerosis agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index.

As used herein, the term "patient" encompasses all mammalian species.

As used herein, the term "subject" refers to any human or non-human organism that could potentially benefit from treatment with an anti-atherosclerosis agent, e.g., an endothelial lipase inhibitor. Exemplary subjects include human beings of any age with risk factors for atherosclerosis and its associated coronary artery disease. Common risk factors include, but are not limited to, age, sex, weight, and family history.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit endothelial lipase and/or to prevent or treat the disorders listed herein. When applied to a combination, the term refers to combined amounts of the active ingredients that result in the preventive or therapeutic effect, whether administered in combination, serially, or simultaneously.

Biological Activity

Endothelial lipase (EL) and hepatic lipase (HL) activities were measured using a fluorescent substrate, A10070, (Invitrogen, CA) doped into an artificial vesicle containing DMPG (Avanti Polar Lipids) as the excipient. Vesicles were prepared by combining 571 µL of 29 mM DMPG in a 1:1 mixture of MeOH and CHCl$_3$ with 2000 µL of 1 mM A10070 in a 1:1 mixture of MeOH and CHCl$_3$. The mixture was dried under nitrogen in multiple vials then resuspended in 20 mL total volume of 50 mM HEPES pH 8.0 buffer containing 50 mM NaCl and 0.2 mM EDTA. The sample was allowed to sit at room temperature for 15 min and then was sonicated 3×4 mins on ice with a Branson Sonicator using duty cycle 1. This preparation provides vesicles with a mole fraction of 0.11 for the FRET substrate.

The enzymatic assay was measured using 384-well white Optiplates. Each well contained 20 µL of assay buffer (50 mM HEPES pH 8.0, 50 mM NaCl and 1 mM CaCl$_2$) and 0.25 µL of a DMSO solution containing a compound of interest. EL or HL (10 µL) was added and allowed to incubate with the compound for 30 min at 37° C. The source of EL was conditioned media obtained from HT-1080 cells that were transformed using RAGE technology (Athersys) to overexpress endogenous EL, and HL was partially purified from conditioned media obtained from COS cells overexpressing HL. The reaction was started by the addition of 10 µL of a 1:10 dilution of vesicles. The final total reaction volume was 20.25 µL. The reaction rates were measured on a Gemini plate reader with an excitation wavelength of 490 nm and an emission wavelength of 530 nm. Readings were taken over a period of 60 minutes, and the slope between 300 and 900 secs of the readout was used to calculate the rate of the reaction.

Reference Compounds

The following reference compounds and their preparations are described below. The EL IC$_{50}$ values were measured using the EL assay described above.

| Compound No. | Structure | EL IC$_{50}$ (nM) |
|---|---|---|
| Reference 1 | 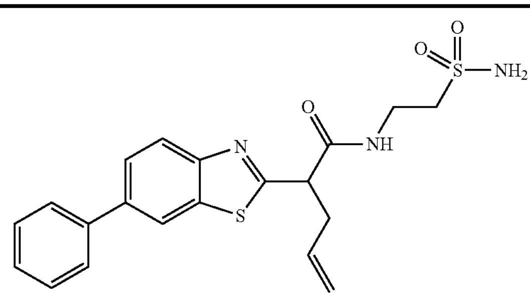 | 9400 |
| Reference 2 | 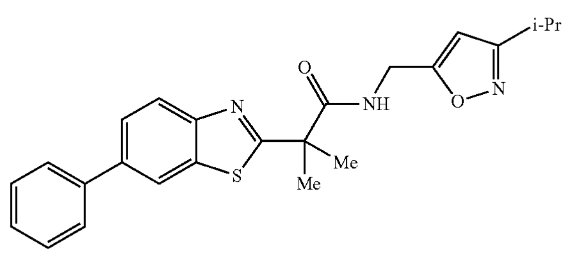 [SMILES: CC(C)c1cc(CNC(=O)C(C)(C)c2nc3ccc(-c4ccccc4)cc3s2)on1] | >62000 |
| Reference 3 | 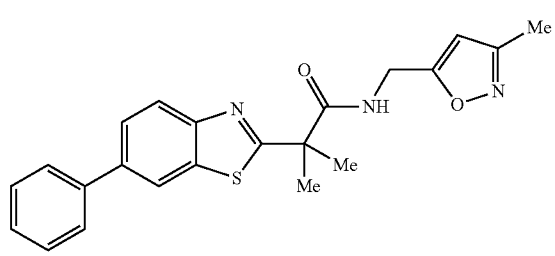 [SMILES: Cc1cc(CNC(=O)C(C)(C)c2nc3ccc(-c4ccccc4)cc3s2)on1] | >62000 |

The exemplified compounds, Example to Example, disclosed in the present invention were tested in the EL assay described above. Surprisingly, Examples were found having a range of EL $IC_{50}$ values of ≤0.3 μM (300 nM), as shown below.

Accordingly, the compounds of the present invention can be administered to mammals, preferably humans, for the treatment of a variety of conditions and disorders, including, but not limited to, atherosclerosis, coronary heart disease, coronary artery disease, coronary vascular disease, cerebrovascular disorders, Alzheimer's disease, venous thrombosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia.

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions, (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., eds., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., HMG-CoA reductase inhibitors or other pharmaceutically active material.

The compounds of the present invention may be employed in combination with other EL inhibitors or one or more, preferably one to three, other suitable therapeutic agents useful in the treatment of the aforementioned disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease, treatment for malignant tumors, and anti-inflammatory agents.

The compounds of the present invention may be employed in combination with additional therapeutic agent(s) selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), acyl-coenzyme A:cholesterol acyltransferase (ACAT) inhibitors, LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

The compounds of the present invention may be employed in combination with additional therapeutic agent(s) selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rivastatin.

The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art.

The compounds of the invention may be used in combination with one or more, preferably one to three, of the following anti-diabetic agents depending on the desired target therapy. Studies indicate that diabetes and hyperlipidemia modulation can be further improved by the addition of a second agent to therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-$SO_4$); anti-glucocorticoids; TNFα inhibitors; α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as therapeutic agents discussed above for treating atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, phentiramine, $\beta_3$-adrenoreceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the endothelial lipase. Such compounds may be provided in a commercial kit, for example, for use in pharmaceutical research involving endothelial lipase or HDL activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving endothelial lipase.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof; and, (c) a package insert stating that the pharmaceutical composition can be used for the treatment and/or prophylaxis of dyslipidemias and the sequelae thereof. In another embodiment, the package insert states that the pharmaceutical composition can be used in combination (as defined previously) with a second therapeutic agent for the treatment and/or prophylaxis of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention should become apparent in the course of the above descriptions of exemplary embodiments that are given for illustration of the invention and are not intended to be limiting thereof.

VI. Examples

The following Examples have been prepared, isolated and characterized using the methods disclosed herein. The following examples demonstrate a partial scope of the invention and are not meant to be limiting of the scope of the invention.

Example 1

Benzyl N-{4-[2-({[(cyclopropylcarbamoyl)methyl]carbamoyl}(methanesulfonyl)methyl)-5-fluoro-1,3-benzothiazol-6-yl]phenyl}carbamate

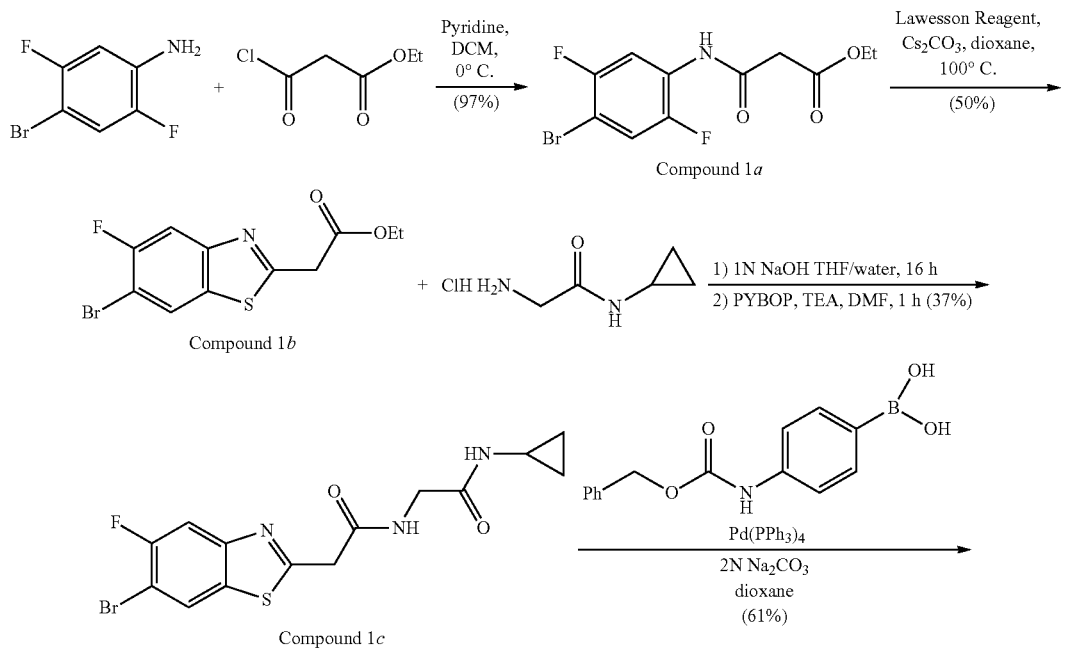

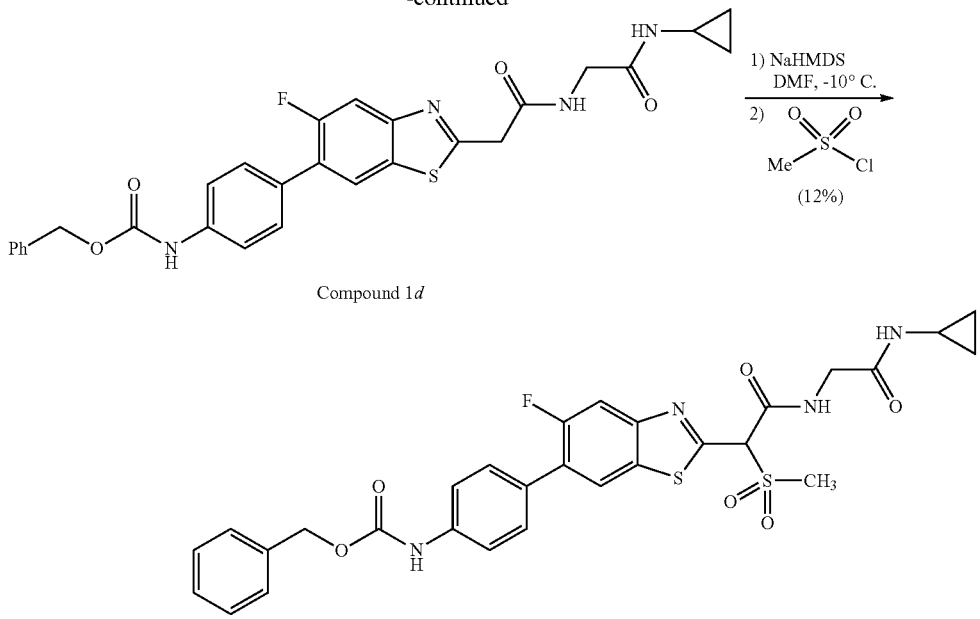

Example 1

Compound 1a. Ethyl 3-((4-bromo-2,5-difluorophenyl)amino)-3-oxopropanoate

To a solution of 4-bromo-2,5-difluoroaniline 11 g, 24 mmol) in DCM (30 mL) were added pyridine (6.4 mL, 36 mmol) and ethyl 3-chloro-3-oxopropanoate (6.9 mL, 24 mmol) at 0° C. After 1 h, the reaction mixture was concentrated under reduced pressure, diluted with EtOAc, washed with 1 M HCl and brine. The organic phase was dried over sodium sulfate, filtered and concentrated under reduced pressure. The residue was purified by flash column chromatography (ISCO, silica gel, 80 g column, eluting with ethyl acetate/hexane 0% to 50% gradient) to give Compound 1a (17 g, 97%). HPLC RT=1.78 min (LCMS Method B). MS(ES): m/z=323.9 [M+H]$^+$. $^1$H NMR (400 MHz, chloroform-d) δ 8.60 (m, 1H), 6.97 (dd, J=10.6, 7.9 Hz, 1H), 4.28 (m, 2H), 3.50 (m, 2H), 1.33 (t, J=7.2 Hz, 3H).

Compound 1b. Ethyl 2-(6-bromo-5-fluorobenzo[d]thiazol-2-yl)acetate

To a solution of Compound 1b (10 g, 31 mmol) in 1,4-dioxane (20 mL) was added Lawesson's reagent (7.5 g, 19 mmol). The reaction was stirred under argon at 100° C. After 16 h, the reaction mixture was allowed to cool to rt. $Cs_2CO_3$ (12 g, 37 mmol) was added, and the reaction mixture was heated at 100° C. After 18 h, the reaction mixture was filtered and concentrated. The residue was dissolved in water and extracted with DCM (2×). The combined organic layers were dried over sodium sulfate, filtered and concentrated. The residue was purified by flash column chromatography (ISCO, silica gel, 80 g column, eluting with ethyl acetate/hexane 0% to 30% gradient) to give Compound 1b (4.9 g, 50% yield) as a pale yellow solid. HPLC RT=2.0 min (LCMS Method B). MS(ES): m/z=319.9 [M+H]. $^1$H NMR (400 MHz, chloroform-d) δ 8.19 (d, J=6.2 Hz, 1H), 7.62 (d, J=7.7 Hz, 1H), 4.26 (m, 2H), 4.15 (m, 2H), 1.31 (t, J=7.2 Hz, 3H).

Compound 1c. 2-(6-Bromo-5-fluorobenzo[d]thiazol-2-yl)-N-(2-(cyclopropylamino)-2-oxoethyl)acetamide Compound 1b (2.0 g, 6.3 mmol) was dissolved in THF (20 mL) and treated with 1N NaOH (7.3 mL, 7.3 mmol). After 1 h, the reaction mixture was concentrated under reduced pressure. The reaction mixture was co-evaporated with toluene (4 mL), dissolved in DMF (20 mL) and treated with TEA (2.4 mL, 13 mmol), 2-amino-N-cyclopropylacetamide, HCl (1.2 g, 7.9 mmol), and PYBOP (3.5 g, 9.2 mmol). After 30 min, the reaction mixture was concentrated and suspended in water (50 mL) and stirred at rt. After 16 h, the reaction mixture was filtered, the solid washed with ether (2×2 mL), and Compound 1c (830 mg, 37% yield) was isolated as a yellow solid. HPLC RT=0.8 min (LCMS Method M). MS(ES): m/z=387.6 [M+H]. $^1$H NMR (500 MHz, DMSO-$d_6$) δ 8.58 (s, 1H), 8.51 (d, J=6.9 Hz, 1H), 8.08-7.82 (m, 2H), 4.15 (s, 2H), 3.70 (d, J=5.8 Hz, 2H), 2.61 (dd, J=7.4, 3.6 Hz, 1H), 0.71-0.56 (m, 2H), 0.45-0.29 (m, 2H).

Compound 1d. Benzyl (4-(2-(2-((2-(cyclopropylamino)-2-oxoethyl)amino)-2-oxoethyl)-5-fluorobenzo[d]thiazol-6-yl)phenyl)carbamate Compound 1c (100 mg, 0.26 mmol), and (4-(((benzyloxy)carbonyl)amino)phenyl)boronic acid (88 mg, 0.32 mmol) in dioxane (4 mL)/2M $Na_2CO_3$ (2 mL) was purged with argon and heated at 100° C. for 1 h. The reaction mixture was filtered through CELITE®, concentrated under reduced pressure and purified using reverse phase HPLC (PHENOMENEX® Luna Axia 5μ C18, 21.2×100, UV at 220 nm, 10 to 70% B over 30 min with 10 min hold time, solvent A: 90% water/ACN/0.1% TFA, solvent B:90% ACN/water/ 0.1% TFA, Flow rate 20 mL/min; detector at 254) to isolate Compound 1d (84 mg, 61% yield) as an off-white solid. HPLC RT=0.95 min (LCMS Method M). MS(ES): m/z=533.3 [M+H]. $^1$H NMR (500 MHz, DMSO-$d_6$) δ 10.07-9.76 (m, 1H), 8.79-8.50 (m, 1H), 8.27-8.13 (m, 1H), 8.09-7.96 (m, 1H), 7.93-7.80 (m, 1H), 7.59 (s, 4H), 7.43 (d, J=17.6 Hz, 5H), 5.18 (s, 2H), 4.15 (s, 2H), 3.70 (d, J=5.5 Hz, 2H), 2.69-2.59 (m, 1H), 0.79-0.55 (m, 2H), 0.51-0.26 (m, 2H).

Example 1

1 M NaHMDS in THF (0.075 mL, 0.075 mmol) was added to DMF (2 mL) solution of Compound 1d (20 mg, 0.038 mmol) cooled to −10° C. After 5 min, methanesulfonyl chloride (5.1 µL, 0.066 mmol) was added. The solution was quenched with 0.2 mL acetic acid, diluted with 0.5 mL methanol and purified using HPLC (Column: Waters XBridge shield rp18, 19×200 mm, 5-µm particles; Mobile Phase A: 5:95 acetonitrile: water with 0.1% trifluoroacetic acid; Mobile Phase B: 95:5 acetonitrile: water with 0.1% trifluoroacetic acid; Gradient: 20-60% B over 20 minutes, then a 5-minute hold at 100% B; Flow: 20 mL/min) to isolate Example 1 (2.9 mg, 12% yield). HPLC RT=1.8 min (LCMS Method N). MS(ES): m/z=611.14 [M+H]. $^1$H NMR (500 MHz, DMSO-$d_6$) δ 9.92 (br. s., 1H), 9.00 (br. s., 1H), 8.26 (d, J=7.3 Hz, 1H), 8.08-7.91 (m, 2H), 7.66-7.47 (m, 4H), 7.47-7.19 (m, 5H), 6.15 (br. s., 1H), 5.14 (br. s., 2H), 3.79 (br. s., 2H), 3.42 (br. s., 2H), 3.23 (br. s., 3H), 2.60 (br. s., 1H), 0.59 (d, J=5.8 Hz, 2H), 0.36 (br. s., 2H). EL $IC_{50}$=3 nM.

Example 2 to Example 54 were prepared by the general procedures described for Example 1.

Example 55

N-[(Cyclopropylcarbamoyl)methyl]-2-[6-(6-fluoro-pyridin-3-yl)-1,3-benzothiazol-2-yl]-2-phenylmethanesulfonylacetamide

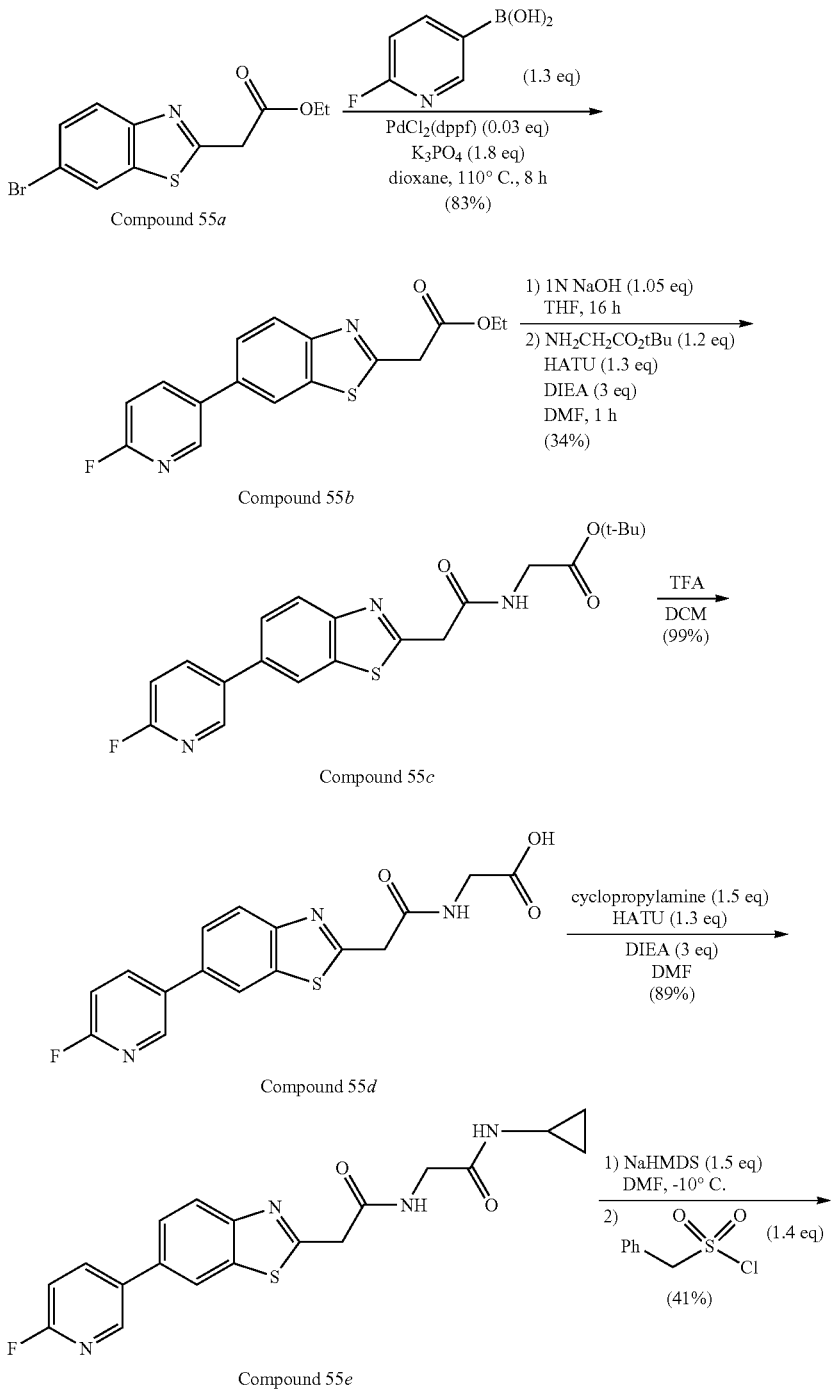

-continued

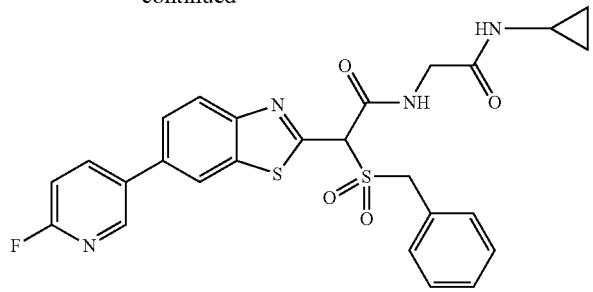

Example 55

Compound 55a. Ethyl 2-(6-bromobenzo[d]thiazol-2-yl)acetate

The preparation of Compound 55a is described in described in WO 2010/044441.

Compound 55b. Ethyl 2-(6-(6-fluoropyridin-3-yl)benzo[d]thiazol-2-yl)acetate

To a heavy-wall reaction flask was added Compound 55a (1.0 g, 3.3 mmol), (6-fluoropyridin-3-yl)boronic acid (0.56 g, 4.0 mmol), and potassium phosphate tribasic (1.3 g, 6.0 mmol). The reaction mixture was suspended in dioxane (10 mL) and degassed with argon using vacuum (3×). $PdCl_2$(dppf) (0.054 g, 0.073 mmol) was added and the reaction mixture degassed again then sealed and stirred at 110° C. 8 h. The reaction mixture was allowed to cool to rt then passed through a pad of silica gel and the filter cake rinsed with 5% MeOH/DCM. The filtrate was evaporated onto CELITE® and the residue purified using silica gel chromatography eluting with 5 to 70% EtOAc/hexane to give Compound 55b (880 mg, 83% yield) as a pale yellow solid. HPLC RT=1.86 min (LCMS Method B). MS(ES): m/z=317.0 [M+H]$^+$. $^1$H NMR (400 MHz, $CDCl_3$) δ 8.40 (br. s., 1H), 8.02 (d, J=8.5 Hz, 1H), 7.99-7.89 (m, 2H), 7.56 (dd, J=8.5, 1.8 Hz, 1H), 6.97 (dd, J=8.3, 3.0 Hz, 1H), 4.20 (q, J=7.3 Hz, 2H), 4.13 (s, 2H), 1.25 (t, J=7.2 Hz, 3H).

Compound 55c. tert-Butyl 2-(2-(6-(6-fluoropyridin-3-yl)benzo[d]thiazol-2-yl)acetamido)acetate To a solution of Compound 55b (430 mg, 1.4 mmol) in THF (10 mL) at 0° C. was added 1N NaOH (1.5 mL, 1.5 mmol). The ice bath was removed and the mixture stirred for 2.5 h then the solvent was removed under reduced pressure. The residue was evaporated from toluene (3×). The residue was suspended in DMF (5 mL) and cooled to 0° C. then DIPEA (0.52 mL, 3.0 mmol) and glycine tert-butyl ester hydrochloride (200 mg, 1.2 mmol) were added followed by HATU (490 mg, 1.3 mmol), and the reaction mixture stirred for 1 h. The reaction mixture was poured into saturated $NH_4Cl$ and extracted with 1:1 EtOAc/hexane (3×). The combined organic extracts were washed with brine, dried ($Na_2SO_4$) filtered and concentrated under reduced pressure. The residue was purified by silica gel chromatography eluting with 10 to 75% EtOAc/DCM to give Compound 55c (210 mg, 52% yield) as a yellow solid. HPLC RT=1.85 min (LCMS Method B). MS(ES): m/z=402.1 [M+H]$^+$. $^1$H NMR (400 MHz, $CDCl_3$) δ 8.48 (d, J=2.0 Hz, 1H), 8.12 (d, J=8.6 Hz, 1H), 8.07-7.97 (m, 2H), 7.65 (dd, J=8.5, 1.7 Hz, 1H), 7.45 (br. s., 1H), 7.05 (dd, J=8.5, 3.0 Hz, 1H), 4.14 (s, 2H), 4.01 (d, J=5.1 Hz, 2H), 1.47 (s, 9H).

Compound 55d. 2-(2-(6-(6-Fluoropyridin-3-yl)benzo[d]thiazol-2-yl)acetamido)acetic acid To a flask charged with Compound 55c (170 mg, 0.42 mmol) was added 50% TFA in DCM (2 mL) and the reaction mixture stirred for 1.5 h. The reaction mixture was evaporated to dryness under reduced pressure then evaporated from toluene (2×) under reduced pressure to yield Compound 55d (140 mg, 99% yield) as a white solid. HPLC RT=1.49 min (LCMS Method B). MS(ES): m/z=346.1 [M+H]$^+$. $^1$H NMR (400 MHz, DMSO-$d_6$) δ 8.72 (t, J=5.8 Hz, 1H), 8.65 (d, J=2.6 Hz, 1H), 8.47 (d, J=1.3 Hz, 1H), 8.38 (td, J=8.3, 2.6 Hz, 1H), 8.06 (d, J=8.4 Hz, 1H), 7.85 (dd, J=8.5, 1.9 Hz, 1H), 7.33 (dd, J=8.6, 2.4 Hz, 1H), 4.17 (s, 2H), 3.86 (d, J=5.7 Hz, 2H).

Compound 55e. N-Cyclopropyl-2-(2-(6-(6-fluoropyridin-3-yl)benzo[d]thiazol-2-yl)acetamido)acetamide To a solution of Compound 55d (140 mg, 0.42 mmol) and cyclopropanamine (0.043 mL, 0.63 mmol) in DMF (5 mL) was added DIEA (0.22 mL, 1.3 mmol) followed by HATU (210 mg, 0.54 mmol) and the reaction mixture stirred for 0.5 h. The reaction mixture was poured into saturated $NH_4Cl$ and extracted with 1:1 EtOAc/hexane (3×). The combined organic extracts were washed with brine, dried ($Na_2SO_4$) filtered and concentrated under reduced pressure. The residue was purified by silica gel chromatography eluting with 0.2 to 7% MeOH/DCM to give Compound 55e (140 mg, 89% yield) as a yellow solid. HPLC RT=1.57 min (LCMS Method B). MS(ES): m/z=385.1 [M+H]$^+$. $^1$H NMR (400 MHz, DMSO-$d_6$) δ 8.65 (s, 1H), 8.59 (t, J=5.3 Hz, 1H), 8.47 (s, 1H), 8.42-8.33 (m, 1H), 8.05 (d, J=8.6 Hz, 1H), 8.01 (br. s., 1H), 7.85 (dd, J=8.4, 1.8 Hz, 1H), 7.33 (dd, J=8.6, 2.6 Hz, 1H), 4.17 (s, 2H), 3.72 (d, J=5.7 Hz, 2H), 2.66-2.60 (m, 1H), 0.68-0.60 (m, 2H), 0.45-0.38 (m, 2H).

Example 55

Example 55 (11 mg, 41% yield) was prepared from Compound 55e as described in the general procedure given for Example 1. HPLC RT=1.74 min (LCMS Method O). MS(ES): m/z=539.2 [M+H]$^+$. $^1$H NMR (500 MHz, DMSO-$d_6$) δ 9.13 (br. s., 1H), 8.68 (br. s., 1H), 8.59 (br. s., 1H), 8.42 (t, J=8.0 Hz, 1H), 8.25 (d, J=8.5 Hz, 1H), 8.09 (br. s., 1H), 7.97-7.93 (m, 1H), 7.42 (s, 4H), 7.39-7.35 (m, 1H), 6.31 (s, 1H), 4.81 (s, 2H), 3.85 (br. s., 2H), 2.71-2.62 (m, 1H), 0.70-0.60 (m, 2H), 0.47-0.36 (m, 2H). EL $IC_{50}$=26 nM.

Example 56 to Example 59 were prepared as described in the general procedure given for Example 55.

Example 60 tert-Butyl N-{4-[2-({[(cyclopropylcarbamoyl)methyl]carbamoyl}(2-methoxyethanesulfonyl)methyl)-1,3-benzothiazol-6-yl]phenyl}-N-methylcarbamate

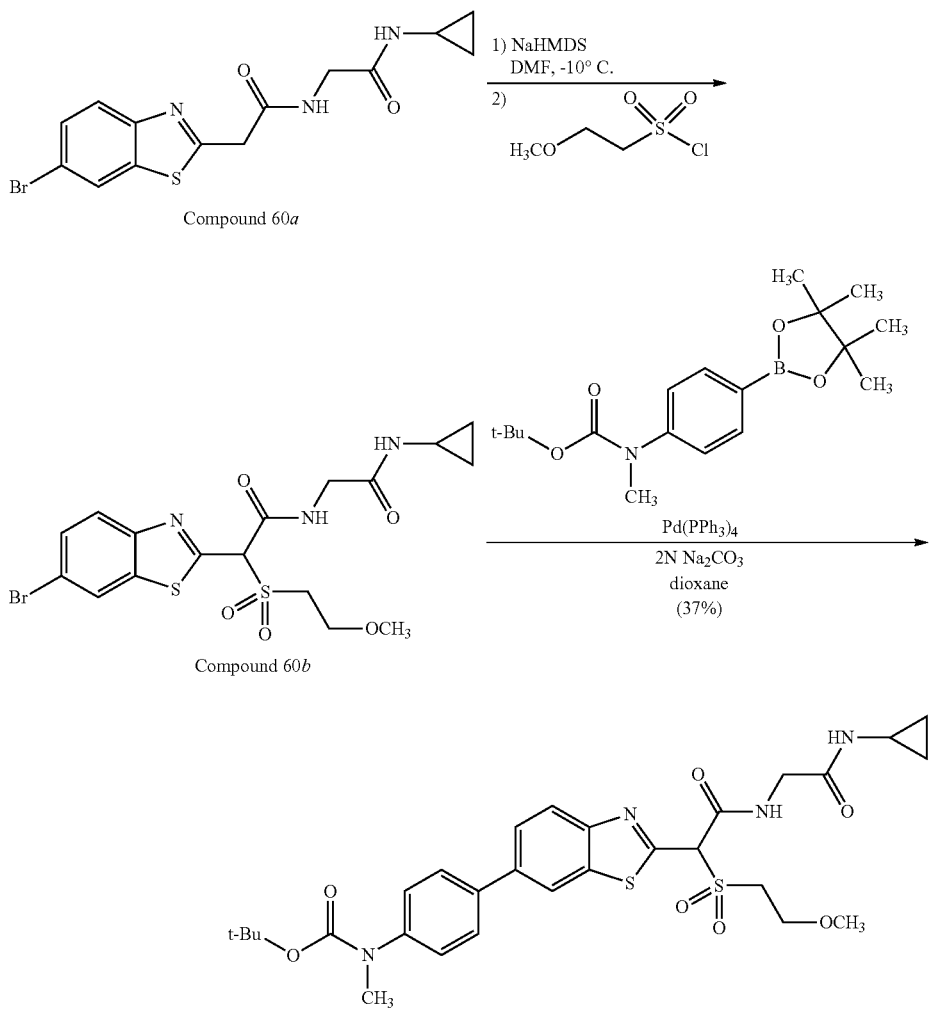

Compound 60a. 2-(6-Bromobenzo[d]thiazol-2-yl)-N-(2-(cyclopropylamino)-2-oxoethyl)acetamide Compound 60a was prepared by the general procedure described in Example 1.

Compound 60b. 2-(6-Bromobenzo[d]thiazol-2-yl)-N-(2-(cyclopropylamino)-2-oxoethyl)-2-((2-methoxyethyl)sulfonyl)acetamide Compound 60b (11 mg, 41% yield) was prepared from Compound 60a as described in the general procedure given for Example 1. HPLC RT=3.39 min (LCMS Method Q). MS(ES): m/z=492.0 [M+H]$^+$. $^1$H NMR (500 MHz, DMSO-d$_6$) δ 9.06-8.93 (m, 1H), 8.47 (d, J=1.9 Hz, 1H), 8.02 (d, J=8.8 Hz, 2H), 7.77-7.69 (m, 1H), 6.17 (s, 1H), 3.85-3.62 (m, 4H), 3.36-3.23 (m, 3H), 3.19-3.11 (m, 2H), 2.68-2.60 (m, 1H), 0.62 (dd, J=7.2, 1.9 Hz, 2H), 0.49-0.30 (m, 2H).

Example 60

Example 60 (6.9 mg, 37% yield) was prepared from Compound 60b as described in the general procedure given for Compound 1d. HPLC RT=1.91 min (LCMS Method N). MS(ES): m/z=617.2 [M+H]$^+$. $^1$H NMR (500 MHz, DMSO-d$_6$) δ 8.99 (s, 1H), 8.48 (d, J=1.9 Hz, 1H), 8.15 (d, J=8.5 Hz, 1H), 8.02 (d, J=4.1 Hz, 1H), 7.87 (dd, J=8.5, 1.9 Hz, 1H), 7.79-7.70 (m, 2H), 7.47-7.39 (m, J=8.5 Hz, 2H), 6.20 (s, 1H), 3.85-3.68 (m, 6H), 3.28 (s, 3H), 3.26-3.21 (m, 3H), 2.64 (d, J=3.9 Hz, 1H), 1.47-1.38 (m, 9H), 0.69-0.57 (m, 2H), 0.46-0.36 (m, 2H). EL IC$_{50}$=3 nM.

Example 61 to Example 286 were prepared as described in the general procedure given for Example 60.

Example 287

N-(2-((2-Isopropoxyethyl)amino)-2-oxoethyl)-2-(methylsulfonyl)-2-(6-(1-oxoisoindolin-5-yl)benzo[d]thiazol-2-yl)acetamide

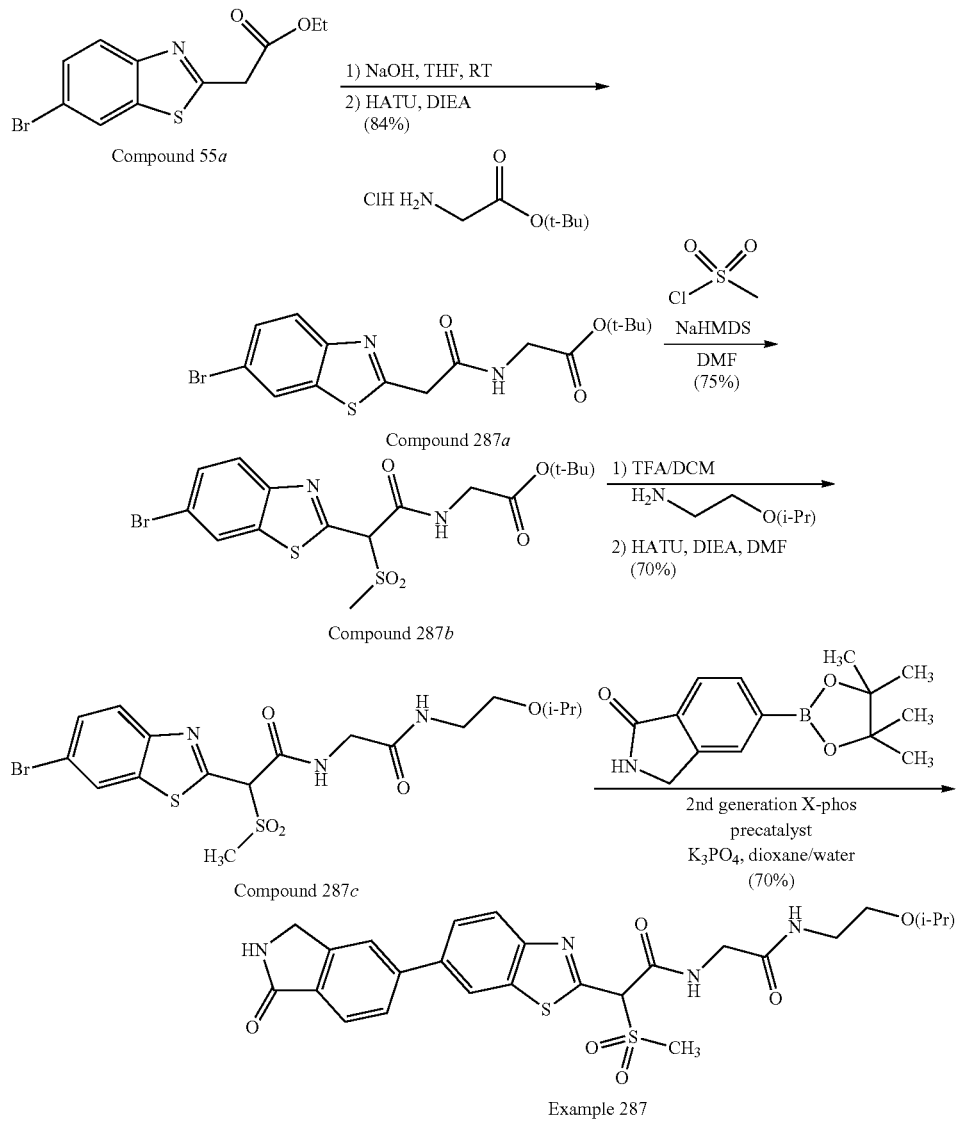

Example 287

Compound 287a. tert-Butyl 2-(2-(6-bromobenzo[d]thiazol-2-yl)acetamido)acetate To a solution of Compound 55a (1.5 g, 5.1 mmol prepared by the general methods described for Example 1b) in THF (40 mL) was added 1N NaOH (5.6 mL, 5.6 mmol) and the mixture stirred for 2 h. The reaction mixture was concentrated under reduced pressure then co-evaporated from toluene (3×). The residue was dissolved in DMF (10 mL) then tert-butyl 2-aminoacetate hydrochloride (1.0 g, 6.1 mmol), and DIEA (2.3 mL, 13 mmol) were added followed by HATU (2.52 g, 6.63 mmol). After 16 h, the reaction mixture was diluted with EtOAc, washed with water, brine, and dried over sodium sulfate, filtered and concentrated under reduced pressure. The residue was purified by silica gel chromatography eluting with 0-100% EtOAc/hexane) to isolate Compound 287a (1.6 g, 84% yield). HPLC RT=0.92 min (LCMS Method O). MS(ES): m/z=386.9 [M+H]$^+$. $^1$H NMR (400 MHz, chloroform-d) δ 8.02 (d, J=2.0 Hz, 1H), 7.89 (d, J=8.8 Hz, 1H), 7.60 (dd, J=8.7, 1.9 Hz, 1H), 4.10 (s, 2H), 4.00 (d, J=5.1 Hz, 2H), 2.81 (s, 1H), 1.47 (s, 9H).

Compound 287b. tert-Butyl 2-(2-(6-bromobenzo[d]thiazol-2-yl)-2-(methylsulfonyl)acetamido)acetate Compound 287b (690 mg, 75% yield) was prepared from Compound 287a as described in the general procedure given for Example 1. HPLC RT=0.99 min (LCMS Method O). MS(ES): m/z=464.6 [M+H]$^+$. $^1$H NMR (400 MHz, DMSO-d$_6$) δ 9.10 (t, J=5.6 Hz, 1H), 8.49 (d, J=1.8 Hz, 1H), 8.04 (d, J=8.6 Hz, 1H), 7.73 (dd, J=8.7, 2.1 Hz, 1H), 6.13 (s, 1H), 3.97-3.88 (m, 2H), 3.27 (s, 3H), 1.39 (s, 9H).

Compound 287c. 2-(6-Bromobenzo[d]thiazol-2-yl)-N-(2-((2-isopropoxyethyl)amino)-2-oxoethyl)-2-(methylsulfonyl)acetamide To a solution of Compound 287b (690 mg, 1.5 mmol) in DCM (6 mL) was added TFA (5 mL, 65 mmol). The reaction mixture was stirred at rt for 1 h and concentrated under reduced pressure. The residue was dissolved in DMF (1.0 mL) and was treated with 2-isopropoxyethanamine (69 mg, 0.67 mmol), DIEA (0.23 mL, 1.3 mmol), HATU (220 mg, 0.58 mmol) at room temperature. After 14 h, the reaction mixture was diluted with saturated NH$_4$Cl and extracted with EtOAc. The organic phase was washed with 1N HCl, brine, dried over sodium sulfate, filtered and concentrated under reduced pressure. The residue was purified by silica gel chromatography eluting with 0-10% MeOH/DCM to give Compound 287c (160 mg, 70% yield) as an off-white solid. HPLC RT=0.87 min (LCMS Method O). MS(ES): m/z=494.1 [M+H]$^+$. $^1$H NMR (400 MHz, DMSO-d$_6$) δ 9.18-8.97 (m, 1H), 8.52-8.43 (m, 1H), 8.10-7.99 (m, 2H), 7.73 (dd, J=8.7, 2.1 Hz, 1H), 6.19 (s, 1H), 3.89 (d, J=5.5 Hz, 2H), 3.57-3.49 (m, 1H), 3.26 (s, 3H), 3.24-3.18 (m, 4H), 1.08 (s, 3H), 1.06 (s, 3H).

Example 287

To a mixture of Compound 287c (22 mg, 0.045 mmol), 5-(4,4,5,5-tetramethyl-1,3,2-dioxaborolan-2-yl)isoindolin-1-one (12 mg, 0.045 mmol), K$_3$PO$_4$ (23 mg, 0.11 mmol) and second generation X-Phos precatalyst (3.5 mg, 4.5 mmol) was added dioxane (1.0 mL) and water (0.25 mL). The reaction mixture was degassed and heated at 85° C. for 1 h. The resulting reaction mixture was allowed to cool to rt, diluted with DMF, filtered and purified via preparative LC/MS with the following conditions: Column: Waters XBridge c-18, 19×200 mm, 5-μm particles; Mobile Phase A: 5:95 acetonitrile: water with 0.1% formic acid; Mobile Phase B: 95:5 acetonitrile: water with 0.1% formic acid; Gradient: 5-50% B over 18 min, then a 5-min hold at 100% B; Flow: 20 mL/min. Fractions containing the desired product were combined and dried via centrifugal evaporation to give Example 287 (17 mg, 70% yield). HPLC RT=1.15 min (LCMS Method O). MS(ES): m/z=544.6 [M+H]$^+$. $^1$H NMR (500 MHz, DMSO-d$_6$) δ 9.08-9.01 (m, 1H), 8.65-8.58 (m, 1H), 8.57-8.52 (m, 1H), 8.19 (d, J=8.5 Hz, 1H), 8.04 (t, J=5.5 Hz, 1H), 7.96 (s, 1H), 7.93 (dd, J=8.7, 1.8 Hz, 1H), 7.87 (d, J=7.7 Hz, 1H), 7.79 (d, J=8.0 Hz, 1H), 6.21 (s, 1H), 4.47 (s, 2H), 3.90 (dd, J=5.2, 3.6 Hz, 2H), 3.53 (dt, J=12.1, 6.1 Hz, 1H), 3.39-3.35 (m, 2H), 3.28 (s, 3H), 3.21 (q, J=5.7 Hz, 2H), 1.07 (s, 3H), 1.06 (s, 3H). EL IC$_{50}$=2.90 nM.

Example 288 to Example 375 were prepared as described in the general procedure given for Example 287.

Example 376

N-[(Cyclopropylcarbamoyl)methyl]-2-[6-(6-fluoropyridin-3-yl)-1,3-benzothiazol-2-yl]-2-(2-methoxyethanesulfonyl)acetamide

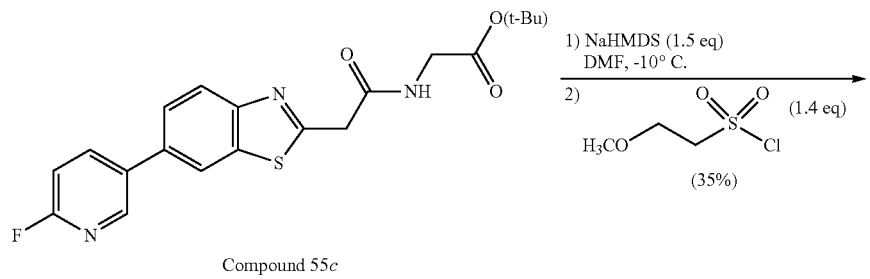

Compound 55c

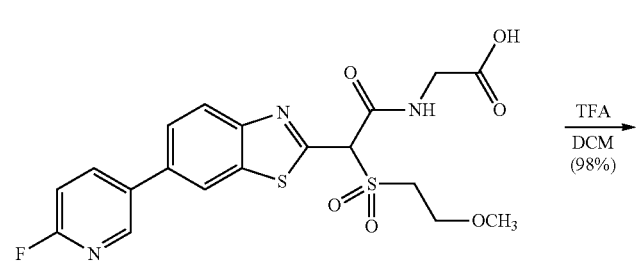

Compound 376a

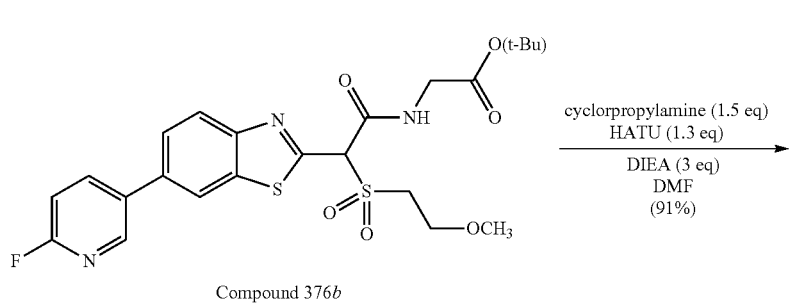

Compound 376b

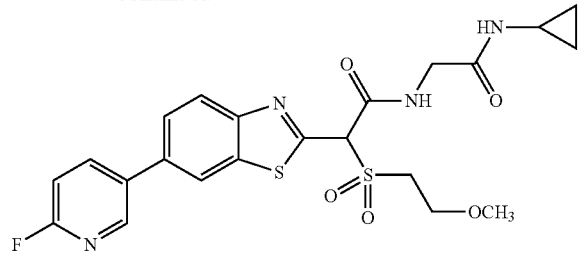

Example 376

Compound 376a. tert-Butyl 2-(2-(6-(6-fluoropyridin-3-yl)benzo[d]thiazol-2-yl)-2-((2-methoxyethyl)sulfonyl)acetamido)acetate Compound 376a (95 mg, 35% yield) was prepared from Compound 55c as described in the general procedure given for Example 1. HPLC RT=1.95 min (LCMS Method B). MS(ES): m/z=524.1 [M+H]+. 1H NMR of major tautomer (400 MHz, CDCl3) δ 14.41 (s, 1H), 8.42 (d, J=2.6 Hz, 1H), 8.13 (t, J=5.3 Hz, 1H), 8.00-7.90 (m, 1H), 7.78-7.71 (m, 1H), 7.57-7.49 (m, 1H), 7.44-7.36 (m, 1H), 7.03 (dd, J=8.8, 2.9 Hz, 1H), 4.09-3.96 (m, 2H), 3.84 (t, J=6.2 Hz, 2H), 3.55-3.47 (m, 2H), 3.28 (s, 3H), 1.50 (s, 9H).

Compound 376b. 2-(2-(6-(6-Fluoropyridin-3-yl)benzo[d]thiazol-2-yl)-2-((2-methoxyethyl)sulfonyl)acetamido)acetic acid To a flask charged with Compound 376a (100 mg, 0.19 mmol) was added 50% TFA in DCM (1 mL) and the reaction mixture stirred for 1 h. The reaction mixture was evaporated under reduced pressure and the residue evaporated from toluene (2×) to Compound 376b (89 mg, 98% yield) as a pale brown solid. HPLC RT=1.40 min (LCMS Method B). MS(ES): m/z=468.0 [M+H]+. 1H NMR of major tautomer (500 MHz, DMSO-d6) δ 9.07 (br. s., 1H), 8.72-8.50 (m, 2H), 8.46-8.26 (m, 1H), 8.22-8.14 (m, 1H), 7.96-7.85 (m, 1H), 7.42-7.22 (m, 1H), 6.18 (br. s., 1H), 4.09-3.85 (m, 2H), 3.81-3.57 (m, 4H), 3.13 (br. s., 3H).

Example 376

Example 376 (17 mg, 91% yield) was prepared from Compound 376b as described in the general procedure given for Compound 55e. HPLC RT=1.66 min (LCMS Method B). MS(ES): m/z=507.1 [M+H]+. 1H NMR (400 MHz, DMSO-d6) δ 9.00 (t, J=5.5 Hz, 1H), 8.66 (d, J=2.6 Hz, 1H), 8.58-8.54 (m, 1H), 8.45-8.36 (m, 1H), 8.20 (dd, J=8.6, 0.4 Hz, 1H), 8.02 (d, J=4.0 Hz, 1H), 7.93 (dd, J=8.6, 2.0 Hz, 1H), 7.35 (dd, J=8.6, 2.4 Hz, 1H), 6.22 (s, 1H), 3.86-3.81 (m, 2H), 3.81-3.75 (m, 2H), 3.75-3.69 (m, 2H), 3.28 (s, 3H), 2.68-2.61 (m, 1H), 0.69-0.58 (m, 2H), 0.44-0.36 (m, 2H). EL IC50=4 nM.

Example 377 to Example 392 were prepared as described in the general procedure given for Example 376.

Example 393

N-Cyclopropyl-4-(2-(2-((2-(cyclopropylamino)-2-oxoethyl)amino)-1-((2-methoxyethyl)sulfonyl)-2-oxoethyl)benzo[d]thiazol-6-yl)-N-methylbenzamide

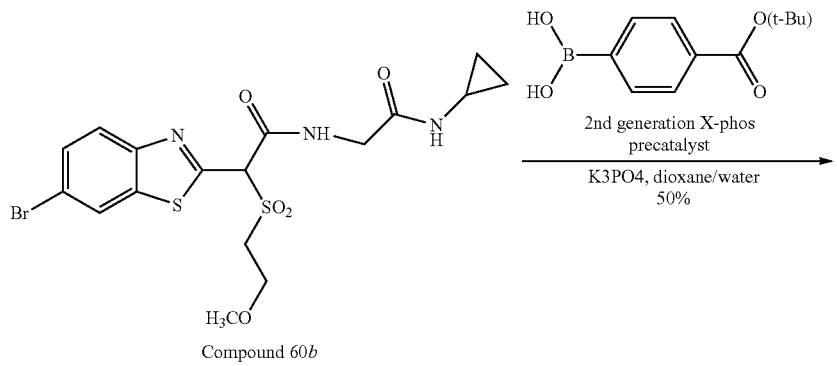

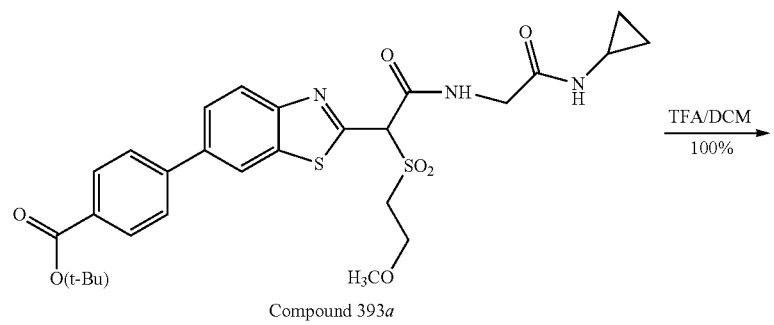

-continued

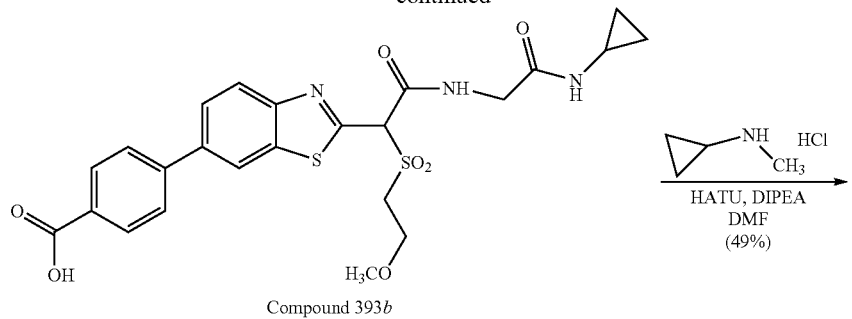

Compound 393b

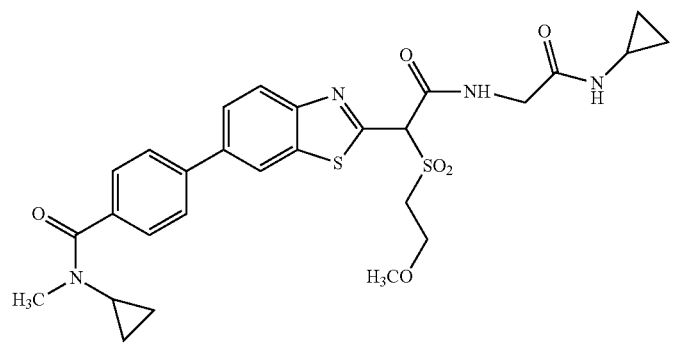

Example 393

Compound 393a. tert-Butyl 4-(2-(2-((2-(cyclopropylamino)-2-oxoethyl)amino)-1-((2-methoxyethyl)sulfonyl)-2-oxoethyl)benzo[d]thiazol-6-yl)benzoate Compound 393a (110 mg, 50% yield) was prepared from Compound 60a as described in the general procedure given for Example 287. HPLC RT=1.03 min (LCMS Method O). MS(ES): m/z=588.3 [M+H]$^+$. $^1$H NMR (400 MHz, DMSO-$d_6$) δ 9.13-8.94 (m, 1H), 8.62-8.52 (m, 1H), 8.30-8.16 (m, 2H), 8.07-7.81 (m, 8H), 6.22 (s, 1H), 3.87-3.68 (m, 5H), 2.72-2.58 (m, 1H), 0.66-0.59 (m, 2H), 0.46-0.36 (m, 2H).

Compound 393b. 4-(2-(2-((2-(Cyclopropylamino)-2-oxoethyl)amino)-1-((2-methoxyethyl)sulfonyl)-2-oxoethyl)benzo[d]thiazol-6-yl)benzoic acid Compound 393b (97 mg, 100% yield) was prepared from Compound 393a as described in the general procedure given for Example 393b. HPLC RT=1.27 min (LCMS Method M). MS(ES): m/z=532.2 [M+H]$^+$. $^1$H NMR (500 MHz, DMSO-$d_6$) δ 13.01 (br. s., 1H), 9.09-8.96 (m, 1H), 8.59 (d, J=1.7 Hz, 1H), 8.22-8.17 (m, 1H), 8.07 (s, 2H), 8.05-8.01 (m, 1H), 7.97-7.91 (m, 3H), 7.88-7.75 (m, 1H), 6.23 (s, 1H), 3.88-3.69 (m, 5H), 3.29 (s, 3H), 2.69-2.62 (m, 1H), 0.69-0.60 (m, 2H), 0.47-0.32 (m, 2H).

Example 393

Example 393 (8 mg, 49% yield) was prepared from Compound 393b as described in the general procedure given for Example 55e. HPLC RT=1.43 min (LCMS Method S). MS(ES): m/z=585.2 [M+H]$^+$. $^1$H NMR (500 MHz, DMSO-$d_6$) δ 9.07-8.98 (m, 1H), 8.61-8.53 (m, 1H), 8.22-8.14 (m, 1H), 8.06-8.01 (m, 1H), 7.96-7.92 (m, 1H), 7.87-7.81 (m, 2H), 7.68-7.63 (m, 2H), 6.28-6.05 (m, 1H), 3.92 (s, 2H), 3.86-3.71 (m, 5H), 3.29 (s, 3H), 3.04-2.98 (m, 3H), 2.69-2.61 (m, 1H), 0.70-0.55 (m, 4H), 0.51-0.32 (m, 4H). EL IC$_{50}$=33 nM.

Example 394 to Example 410, were prepared as described in the general procedure given for Example 393.

Example 411

2-(6-(4-(1,2,4-Oxadiazol-3-yl)phenyl)-5-fluorobenzo[d]thiazol-2-yl)-N-(2-(cyclopropylamino)-2-oxoethyl)-2-((2-methoxyethyl)sulfonyl)acetamide

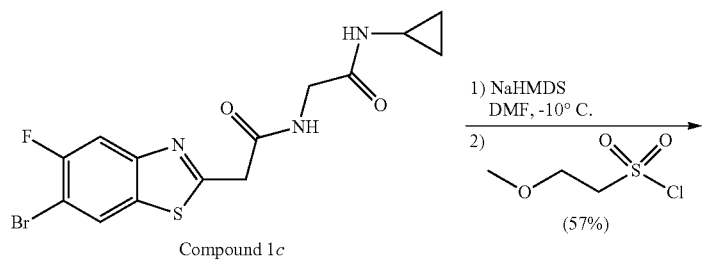

Compound 1c

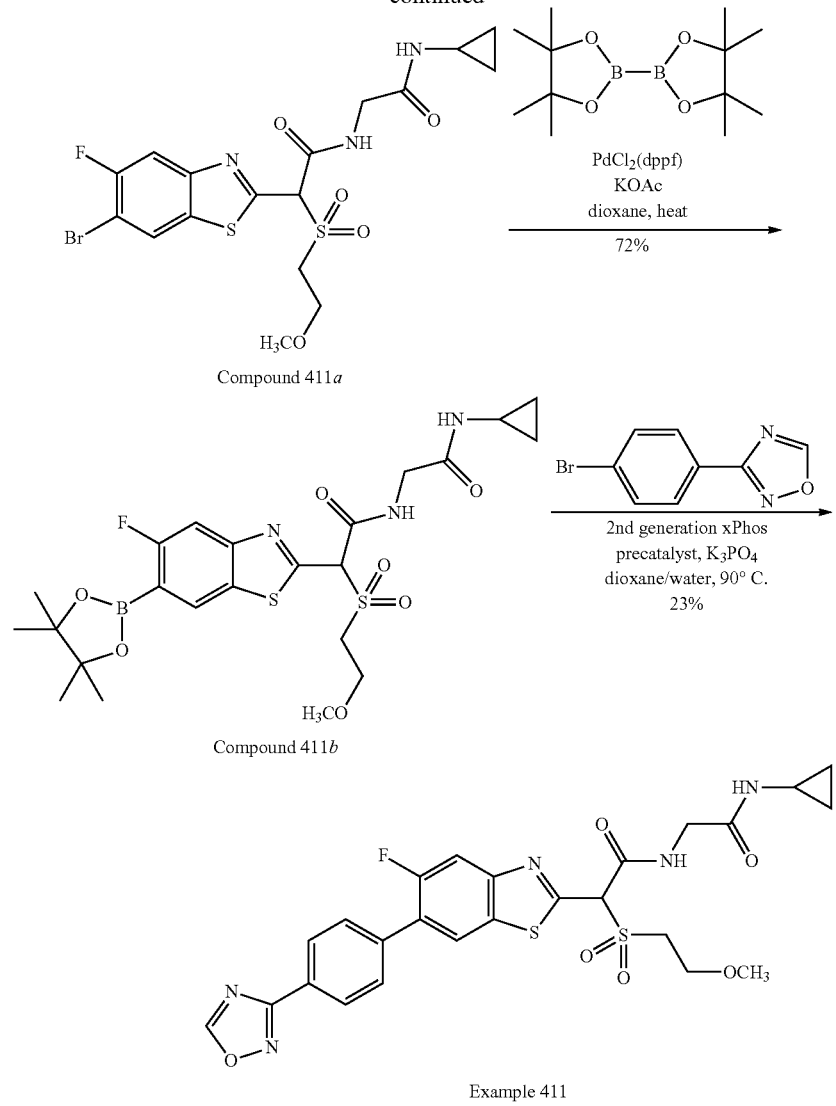

Example 411

Compound 411a. 2-(6-Bromo-5-fluorobenzo[d]thiazol-2-yl)-N-(2-(cyclopropylamino)-2-oxoethyl)-2-(2-methoxyethylsulfonyl)acetamide Compound 411a was prepared from Compound 1c as described in the general procedure given for Example 1. HPLC RT=0.88 min (LCMS Method O). MS(ES): m/z=510.0 [M+H]⁺. ¹H NMR (500 MHz, DMSO-d₆) d 8.98 (t, J=5.5 Hz, 1H), 8.61 (d, J=6.9 Hz, 1H), 8.14 (d, J=9.4 Hz, 1H), 8.00 (d, J=4.1 Hz, 1H), 7.96-7.88 (m, 1H), 6.18 (s, 1H), 5.78-5.70 (m, 1H), 3.82-3.66 (m, 4H), 3.25 (s, 3H), 2.62 (tq, J=7.4, 3.9 Hz, 1H), 0.65-0.58 (m, 2H), 0.41-0.34 (m, 2H).

Compound 411b. N-(2-(Cyclopropylamino)-2-oxoethyl)-2-(5-fluoro-6-(4,4,5,5-tetramethyl-1,3,2-dioxaborolan-2-yl)benzo[d]thiazol-2-yl)-2-((2-methoxyethyl)sulfonyl)acetamide Compound 411a (270 mg, 0.52 mmol), bis(pinacolato)diboron (270 mg, 1.0 mmol), [1,1'-bis(diphenylphosphino)ferrocene]dichloropalladium(II) (38 mg, 0.05 mmol) and potassium acetate (154 mg, 1.57 mmol) in dioxane (4 mL) were purged with argon and heated at 100° C. for 2 hours. The reaction mixture was concentrated under reduced pressure and was purified by silica gel chromatography eluting with 0-10% MeOH/DCM to give Compound 411b (210 mg, 72% yield). HPLC RT=0.98 min (LCMS Method U). MS(ES): m/z=556.2 [M+H]⁺. ¹H NMR (400 MHz, chloroform-d) δ 8.18 (t, J=5.7 Hz, 1H), 7.95 (d, J=4.8 Hz, 1H), 7.07 (d, J=9.0 Hz, 1H), 6.43 (br. s., 1H), 4.05-3.97 (m, 2H), 3.84 (d, J=4.0 Hz, 2H), 3.54 (s, 2H), 3.52-3.45 (m, 2H), 3.29-3.24 (m, 2H), 2.81-2.69 (m, 1H), 1.39 (s, 12H), 0.83-0.76 (m, 2H), 0.56-0.50 (m, 2H).

Example 411

Example 411 (3.6 mg, 23% yield) was prepared from Compound 411b as described in the general procedure given for Example 287. HPLC RT=1.63 min (LCMS Method U). MS(ES): m/z=574.1 [M+H]⁺. ¹H NMR (500 MHz, DMSO-d₆) δ 9.75-9.66 (m, 1H), 9.01 (br. s., 1H), 8.42 (d, J=7.3 Hz, 1H), 8.24-7.99 (m, 4H), 7.84 (d, J=7.9 Hz, 2H), 6.20 (s, 1H), 3.85-3.67 (m, 5H), 3.47 (br. s., 2H), 3.27 (s, 2H), 2.67-2.57 (m, 1H), 0.62 (d, J=6.7 Hz, 2H), 0.39 (br. s., 2H). EL IC₅₀=2.1 nM.

Example 412 to Example 420 were prepared as described in the general procedure given for Example 411.

Example 421

N-[(Cyclopropylcarbamoyl)methyl]-2-[5-fluoro-6-(6-fluoropyridin-3-yl)-1,3-benzothiazol-2-yl]-2-[2-(morpholin-4-yl)ethanesulfonyl]acetamide

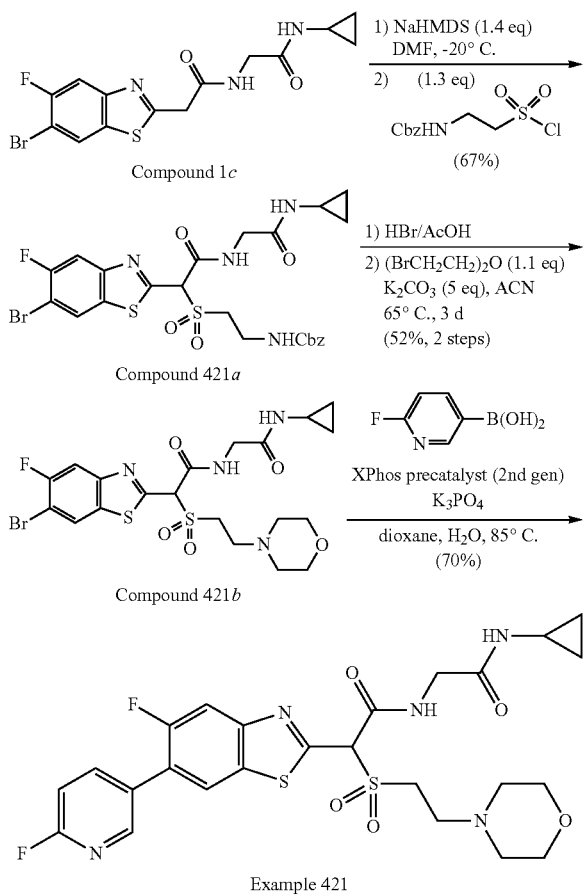

Compound 421a. Benzyl (2-((1-(6-bromo-5-fluorobenzo[d]thiazol-2-yl)-2-((2-(cyclopropylamino)-2-oxoethyl)amino)-2-oxoethyl)sulfonyl)ethyl)carbamate Compound 421a (61 mg, 67% yield) was prepared from Compound 1c as described in the general procedure given for Example 1. HPLC RT=2.12 min (LCMS Method B). MS(ES): m/z=629.1 [M+H]$^+$. $^1$H NMR (400 MHz, DMSO-d$_6$) δ 9.03 (t, J=5.3 Hz, 1H), 8.63 (d, J=6.8 Hz, 1H), 8.13 (d, J=9.5 Hz, 1H), 8.05 (d, J=3.7 Hz, 1H), 7.54-7.44 (m, 1H), 7.42-7.26 (m, 5H), 6.27 (s, 1H), 5.04 (s, 2H), 3.93-3.75 (m, 2H), 3.68-3.37 (m, 4H), 2.64 (td, J=7.3, 3.6 Hz, 1H), 0.67-0.58 (m, 2H), 0.44-0.35 (m, 2H).

Compound 421b. 2-(6-Bromo-5-fluorobenzo[d]thiazol-2-yl)-N-(2-(cyclopropylamino)-2-oxoethyl)-2-((2-morpholinoethyl)sulfonyl)acetamide To a flask charged with Compound 421a (60 mg, 0.096 mmol) was added 33% HBr in AcOH (1 mL) and the reaction mixture stirred for 2 h. The reaction mixture was diluted with ether and the organic liquid decanted (3×) and the solvent removed under reduced pressure give the hydrobromide salt of the corresponding debenzylated amine (64 mg) as a brown solid. HPLC RT=0.67 min (LCMS Method M). MS(ES): m/z=495.1 [M+H]$^+$. $^1$H NMR (400 MHz, DMSO-d$_6$) δ 9.07 (t, J=5.2 Hz, 1H), 8.67 (d, J=6.8 Hz, 1H), 8.15 (d, J=9.2 Hz, 1H), 7.92 (br. s., 3H), 6.41 (s, 1H), 3.89-3.82 (m, 2H), 3.72 (dd, J=14.5, 7.5 Hz, 2H), 3.32-3.21 (m, 2H), 2.64 (td, J=7.3, 3.7 Hz, 1H), 0.68-0.59 (m, 2H), 0.45-0.36 (m, 2H). The hydrobromide salt was suspended in ACN (3.5 mL) then 2,2'-dibromodiethyl ether (0.015 mL, 0.11 mmol) was added followed by K$_2$CO$_3$ (66 mg, 0.48 mmol) and the reaction mixture heated at 65° C. for 3 days. The reaction mixture was allowed to cool to rt, diluted with DCM and evaporated onto CELITE®. The residue was purified by silica gel chromatography eluting with 0.2 to 7% MeOH/DCM to give Compound 421b (28 mg, 52% yield) as a yellow solid. HPLC RT=1.56 min (LCMS Method B). MS(ES): m/z=565.1 [M+H]$^+$. $^1$H NMR (400 MHz, DMSO-d$_6$) δ 8.86 (br. s., 1H), 8.53 (br. s., 1H), 8.04 (br. s., 2H), 3.82 (br. s., 2H), 3.61 (t, J=6.9 Hz, 2H), 3.56-3.48 (m, 4H), 2.81 (br. s., 2H), 2.63 (td, J=7.2, 3.9 Hz, 1H), 2.48-2.37 (m, 4H), 0.72-0.59 (m, 2H), 0.46-0.35 (m, 2H).

Example 421

Example 421 (3.9 mg, 70% yield) was prepared from Compound 421b as described in the general procedure given for Example 287. HPLC RT=1.52 min (LCMS Method B). MS(ES): m/z=580.2 [M+H]$^+$. $^1$H NMR (400 MHz, DMSO-d$_6$) δ 8.85 (br. s., 1H), 8.49 (br. s., 1H), 8.36 (br. s., 1H), 8.24 (br. s., 1H), 8.04 (br. s., 2H), 7.36 (br. s., 1H), 3.83 (br. s., 2H), 3.62 (t, J=7.0 Hz, 2H), 3.53 (br. s., 4H), 3.23-3.12 (m, 1H), 2.81 (br. s., 2H), 2.64 (dt, J=7.5, 3.5 Hz, 1H), 2.43 (br. s., 4H), 0.70-0.57 (m, 2H), 0.45-0.36 (m, 2H). EL IC$_{50}$=22 nM.

Example 422 to Example 424 were prepared as described in the general procedure given for Example 421.

Example 425

N-(2-(Cyclopropylamino)-2-oxoethyl)-2-(6-fluoro-5-(morpholine-4-carbonyl)benzo[d]thiazol-2-yl)-2-((2-methoxyethyl)sulfonyl)acetamide

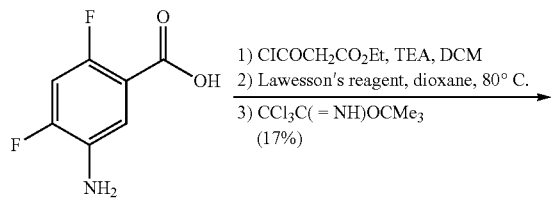

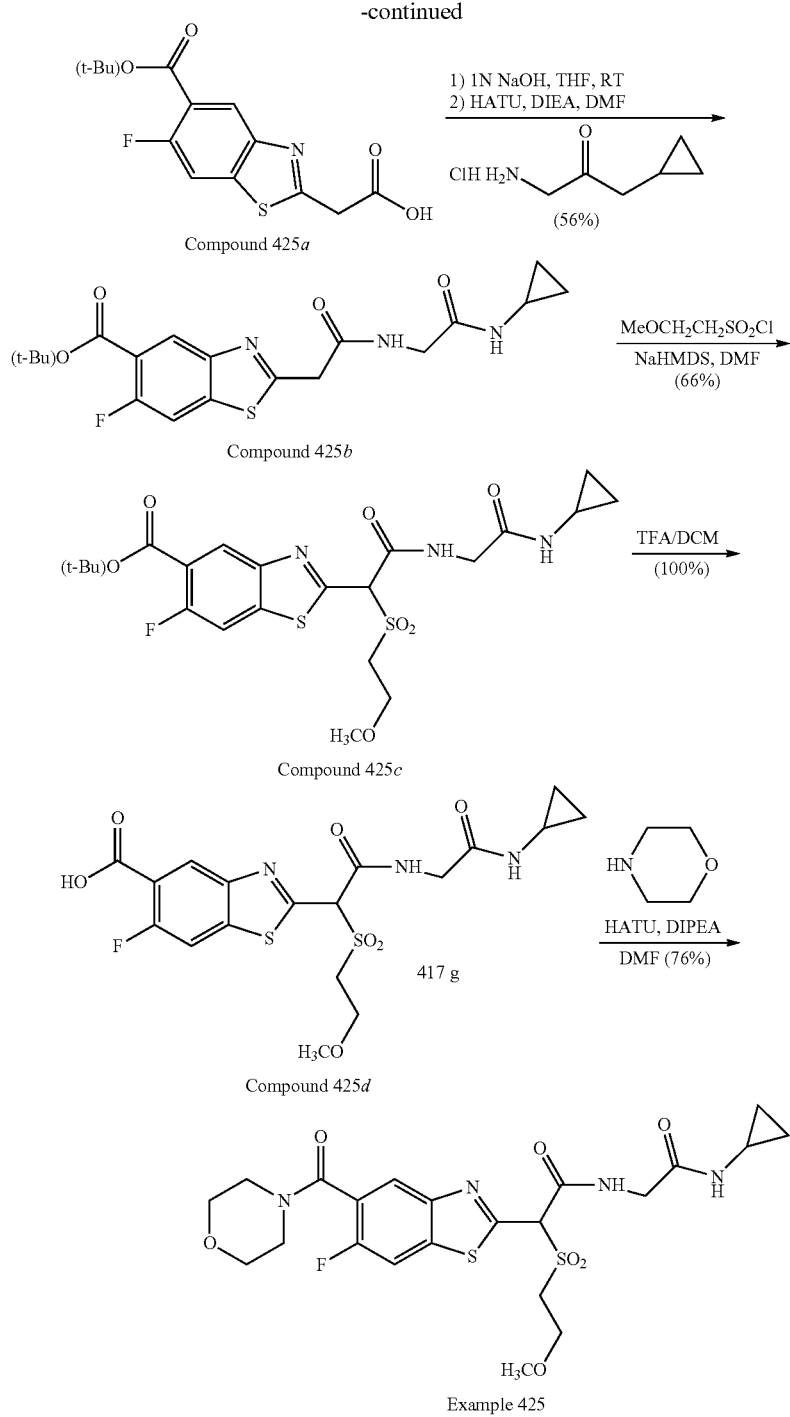

Example 425

Compound 425a. tert-Butyl 2-(2-ethoxy-2-oxo-ethyl)-6-fluorobenzo[d]thiazole-5-carboxylate Compound 425a (770 mg, 17% yield) was prepared from 5-amino-2,4-difluorobenzoic acid (2.3 g, 13 mmol) as described in the general procedure given for Compound 1a. HPLC RT=1.04 min (LCMS Method O). MS(ES): m/z=340.2 [M+H]+. $^1$H NMR (400 MHz, DMSO-$d_6$) δ 8.34 (d, J=6.6 Hz, 1H), 8.14 (d, J=10.8 Hz, 1H), 4.36 (s, 2H), 4.18 (q, J=7.0 Hz, 2H), 1.64-1.51 (m, 9H), 1.23 (t, J=7.2 Hz, 3H).

Compound 425b. tert-Butyl 2-(2-((2-(cyclopropylamino)-2-oxoethyl)amino)-2-oxoethyl)-6-fluorobenzo[d]thiazole-5-carboxylate Compound 425b (520 mg, 56% yield) was prepared from Compound 425a as described in the general procedure given for Compound 1c. HPLC RT=0.86 min (LCMS Method O). MS(ES): m/z=408.2 [M+H]+. $^1$H NMR (400 MHz, DMSO-$d_6$) δ 8.60 (t, J=5.6 Hz, 1H), 8.32 (d, J=6.4 Hz, 1H), 8.11 (d, J=10.6 Hz, 1H), 8.01 (d, J=3.3 Hz, 1H), 4.17 (s, 2H), 3.71 (d, J=5.7 Hz, 2H), 2.63 (tq, J=7.4, 3.8 Hz, 1H), 1.58 (s, 9H), 0.67-0.60 (m, 2H), 0.45-0.37 (m, 2H).

Compound 425c. tert-Butyl 2-(2-((2-(cyclopropylamino)-2-oxoethyl)amino)-1-((2-methoxyethyl)sulfonyl)-2-oxoethyl)-6-fluorobenzo[d]thiazole-5-carboxylate Compound 425c (190 mg, 66% yield) was prepared from Compound 425b as described in the general procedure given for Example 1. HPLC RT=0.92 min (LCMS Method O). MS(ES): m/z=530.2 [M+H]$^+$. $^1$H NMR (400 MHz, DMSO-$d_6$) δ 9.06-8.94 (m, 1H), 8.51-8.44 (m, 1H), 8.23-8.15 (m, 1H), 8.07-7.94 (m, 1H), 6.21 (s, 1H), 3.85-3.67 (m, 5H), 3.28-3.25 (m, 3H), 2.90-2.89 (m, 1H), 2.67-2.58 (m, 1H), 1.61-1.53 (m, 9H), 0.66-0.59 (m, 2H), 0.44-0.28 (m, 2H).

Compound 425d. 2-(2-((2-(Cyclopropylamino)-2-oxoethyl)amino)-1-((2-methoxyethyl)sulfonyl)-2-oxoethyl)-6-fluorobenzo[d]thiazole-5-carboxylic acid To a solution of Compound 425c (180 mg, 0.34 mmol) in DCM (1 mL) was added TFA (1 mL). The reaction mixture was stirred at rt for 1 h. The reaction mixture was concentrated under reduced pressure to give Compound 425d (160 mg, 100% yield) as a yellow solid. HPLC RT=0.67 min (LCMS Method O). MS(ES): m/z=474.1 [M+H]$^+$. $^1$H NMR (400 MHz, DMSO-$d_6$) δ 9.01 (t, J=5.5 Hz, 1H), 8.50 (d, J=6.6 Hz, 1H), 8.20 (d, J=10.3 Hz, 1H), 8.05-7.98 (m, 1H), 6.21 (s, 1H), 3.85-3.66 (m, 7H), 2.67-2.58 (m, 1H), 0.68-0.57 (m, 3H), 0.47-0.33 (m, 3H).

Example 425

Example 425 (15 mg, 76% yield) was prepared from Compound 425d as described in the general procedure given for Compound 55e. HPLC RT=1.13 min (LCMS Method O). MS(ES): m/z=543.1 [M+H]$^+$. $^1$H NMR (500 MHz, DMSO-$d_6$) δ 9.09-8.96 (m, 1H), 8.23-8.18 (m, 1H), 8.17-8.11 (m, 1H), 8.06-7.99 (m, 1H), 6.26-6.16 (m, 1H), 3.86-3.65 (m, 9H), 3.59-3.49 (m, 2H), 3.31-3.25 (m, 6H), 2.69-2.59 (m, 1H), 0.67-0.60 (m, 2H), 0.47-0.38 (m, 2H). EL IC$_{50}$=204 nM.

Example 426 to Example 429 were prepared as described in the general procedure given for Example 425.

Example 430

2-(Benzenesulfonyl)-N-[(cyclopropylcarbamoyl)methyl]-2-(6-phenyl-1,3-benzothiazol-2-yl)acetamide

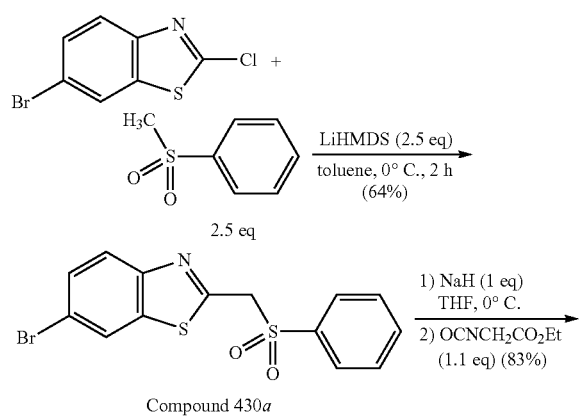

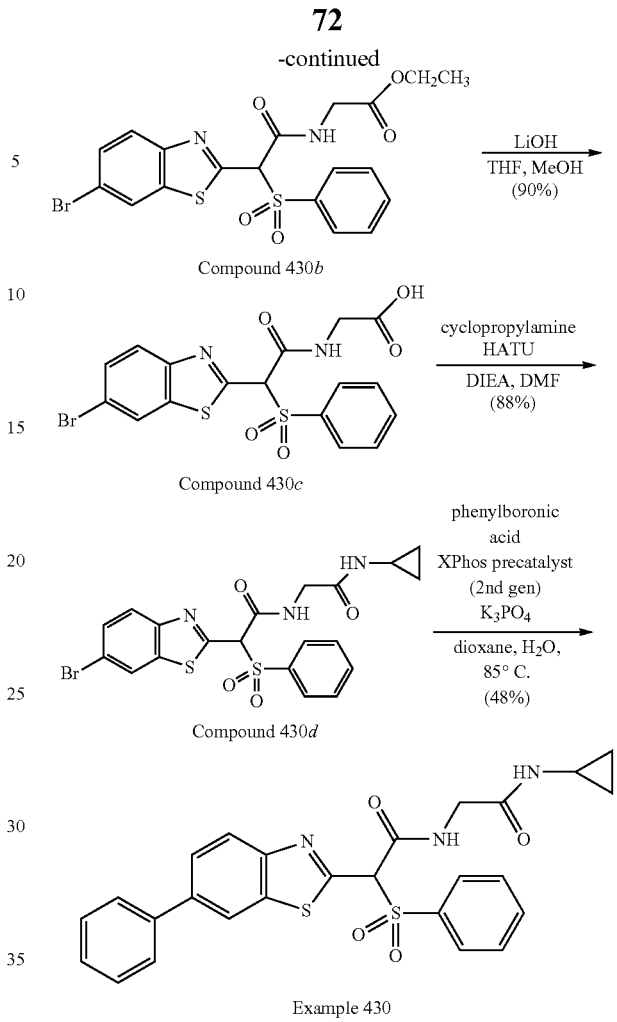

Compound 430a. 6-Bromo-2-((phenylsulfonyl)methyl)benzo[d]thiazole

To a solution of 6-bromo-2-chlorobenzo[d]thiazole (990 mg, 4.00 mmol) and (methylsulfonyl)benzene (1.56 g, 10.0 mmol) in degassed toluene (16 mL) at 0° C. was slowly added 1.0 M lithium bis(trimethylsilyl)amide in toluene (10.0 mL, 10.0 mmol). After 2 h, the reaction mixture was quenched by the addition of saturated NH$_4$Cl (50 mL) and the aqueous portion extracted with EtOAc (40 mL×2). The combined organic extracts were dried (Na$_2$SO$_4$), filtered and concentrated under reduced pressure. The residue was purified by silica gel chromatography eluting with 20-40% ethyl acetate in hexane to give Compound 430a (1.1 g, 64% yield) as a white solid. HPLC RT=1.87 min (LCMS Method B). MS(ES): m/z=369.9 [M+H]$^+$. $^1$H NMR (400 MHz, DMSO-$d_6$) δ 8.43 (d, J=2.0 Hz, 1H), 7.90-7.81 (m, 3H), 7.80-7.72 (m, 1H), 7.70-7.57 (m, 3H), 5.43 (s, 2H).

Compound 430b. Ethyl 2-(2-(6-bromobenzo[d]thiazol-2-yl)-2-(phenylsulfonyl)acetamido)acetate To a suspension of Compound 430a (50 mg, 0.14 mmol) in THF (1.4 mL) at 0° C. was added 60% sodium hydride in mineral oil (5.4 mg, 0.14 mmol). The reaction mixture was allowed to warm to rt then stirred for 15 min, turning homogeneous. Ethyl 2-isocyanatoacetate (0.017 mL, 0.15 mmol) was then added, and the reaction mixture stirred for 15 min. The reaction mixture was quenched by the addition of saturated NH₄Cl and extracted with DCM (3×). The combined extracts were dried (Na₂SO₄), filtered and concentrated under reduced pressure. The residue was purified by silica gel chromatography eluting with 5 to 40% EtOAc/hexane to give Compound 430b (56 mg, 83% yield) as a white solid. HPLC RT=2.00 min (LCMS Method B). MS(ES): m/z=498.9 [M+H]⁺. ¹H NMR (400 MHz, DMSO-d₆) δ 9.18 (t, J=5.7 Hz, 1H), 8.43 (d, J=2.0 Hz, 1H), 7.91 (d, J=8.8 Hz, 1H), 7.79-7.72 (m, 1H), 7.70-7.63 (m, 3H), 7.61-7.53 (m, 2H), 6.31 (s, 1H), 4.26-3.84 (m, 4H), 1.22-1.13 (m, 3H).

Compound 430c. 2-(2-(6-Bromobenzo[d]thiazol-2-yl)-2-(phenylsulfonyl)acetamido)acetic acid To a suspension of Compound 430b (27 mg, 0.054 mmol) in THF (0.25 mL) and MeOH (0.25 mL) was added 2M LiOH (0.14 mL, 0.28 mmol) and the reaction mixture stirred for 0.5 h. The organic solvents were removed under reduced pressure and the residue dissolved in H₂O (~1 mL) then acidified to pH 2 by addition of 1N HCl (~250 µL). The solid was filtered and rinsed with ether then dried under vacuum to give Compound 430c (23 mg, 0.049 mmol, 90% yield) as a white solid. HPLC RT=1.83 min (LCMS Method B). MS(ES): m/z=470.9 [M+H]⁺. ¹H NMR (400 MHz, DMSO-d₆) δ 12.79 (br. s., 1H), 9.08 (t, J=5.4 Hz, 1H), 8.43 (d, J=2.0 Hz, 1H), 7.90 (d, J=8.6 Hz, 1H), 7.80-7.73 (m, 1H), 7.70-7.64 (m, 3H), 7.61-7.55 (m, 2H), 6.33 (s, 1H), 4.01-3.93 (m, 1H), 3.88-3.79 (m, 1H).

Compound 430d. 2-(6-Bromobenzo[d]thiazol-2-yl)-N-(2-(cyclopropylamino)-2-oxoethyl)-2-(phenylsulfonyl)acetamide Compound 430d (21 mg, 88% yield) was prepared from Compound 430c as described in the general procedure given for Compound 55e. HPLC RT=1.93 min (LCMS Method B). MS(ES): m/z=510.0 [M+H]⁺. ¹H NMR (400 MHz, DMSO-d₆) δ 9.06 (t, J=5.3 Hz, 1H), 8.42 (d, J=1.8 Hz, 1H), 8.02 (d, J=4.0 Hz, 1H), 7.89 (d, J=8.6 Hz, 1H), 7.79-7.71 (m, 1H), 7.68-7.62 (m, 3H), 7.61-7.54 (m, 2H), 6.36 (s, 1H), 3.92-3.77 (m, 1H), 3.72-3.62 (m, 1H), 2.63 (td, J=7.4, 3.9 Hz, 1H), 0.66-0.57 (m, 2H), 0.46-0.34 (m, 2H).

Example 430

2-(Benzenesulfonyl)-N-[(cyclopropylcarbamoyl)methyl]-2-(6-phenyl-1,3-benzothiazol-2-yl)acetamide Example 430 (9 mg, 48% yield) was prepared from Compound 430d as described in the general procedure given for Example 287. HPLC RT=2.04 min (LCMS Method B). MS(ES): m/z=506.1 [M+H]⁺. ¹H NMR (400 MHz, DMSO-d₆) δ 9.06 (br. s., 1H), 8.43 (s, 1H), 8.01 (d, J=8.4 Hz, 2H), 7.88-7.36 (m, 11H), 6.40 (s, 1H), 3.94-3.62 (m, 2H), 2.70-2.59 (m, 1H), 0.68-0.58 (m, 2H), 0.41 (br. s., 2H). EL IC₅₀=6.6 nM.

Example 431 to Example 479 were prepared as described in the general procedure given for Example 430.

Example 480

4-[2-({[(Cyclopropylcarbamoyl)methyl]carbamoyl}(morpholine-4-sulfonyl)methyl)-1,3-benzothiazol-6-yl]-N-(2-methoxyethyl)benzamide

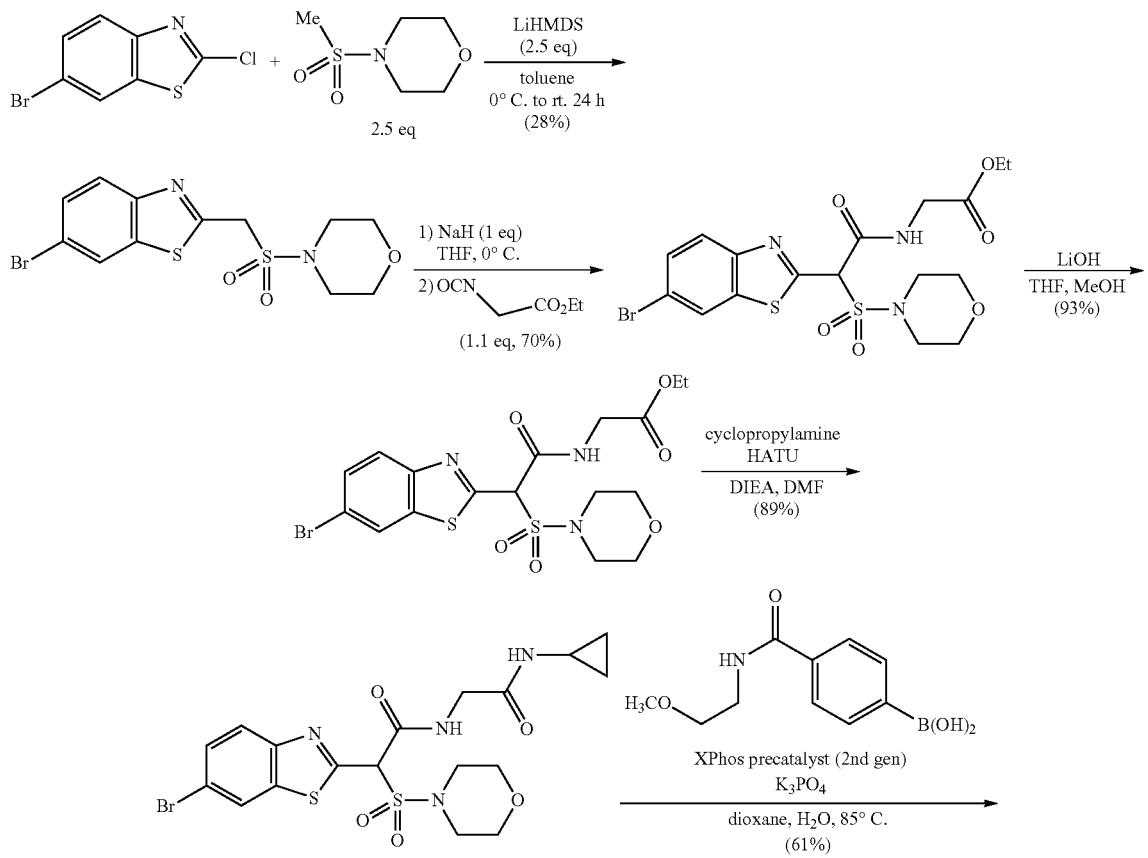

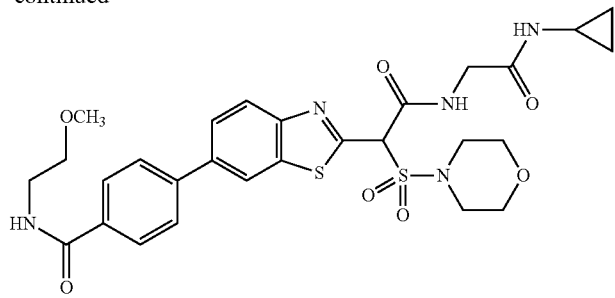

Example 480

Example 480

4-[2-({[(Cyclopropylcarbamoyl)methyl]carbamoyl} (morpholine-4-sulfonyl)methyl)-1,3-benzothiazol-6-yl]-N-(2-methoxyethyl)benzamide Example 480 was prepared from 2-chloro-6-bromobenzothiazole as described in the general procedure given for Example 430. HPLC RT=1.26 min (LCMS Method O). MS(ES): m/z=616.3 [M+H]$^+$. $^1$H NMR (500 MHz, DMSO-d$_6$) d 9.07 (t, J=5.4 Hz, 1H), 8.61 (t, J=5.1 Hz, 1H), 8.57 (d, J=1.1 Hz, 1H), 8.19 (d, J=8.5 Hz, 1H), 8.04 (d, J=4.1 Hz, 1H), 8.00 (d, J=8.3 Hz, 2H), 7.94 (dd, J=8.5, 1.7 Hz, 1H), 7.89 (d, J=8.3 Hz, 2H), 6.32 (s, 1H), 3.90-3.84 (m, 1H), 3.83-3.76 (m, 1H), 3.60-3.54 (m, 4H), 3.52-3.45 (m, 4H), 3.30 (s, 3H), 3.25-3.10 (m, 4H), 2.64 (tq, J=7.3, 3.8 Hz, 1H), 0.67-0.61 (m, 2H), 0.43-0.38 (m, 2H). EL IC$_{50}$=4 nM.

Example 481 to Example 508 were prepared as described in the general procedure given for Example 480.

Example 509

N-[(Cyclopropylcarbamoyl)methyl]-2-[6-(6-fluoropyridin-3-yl)-1,3-benzothiazol-2-yl]-2-(2-hydroxyethanesulfonyl)acetamide

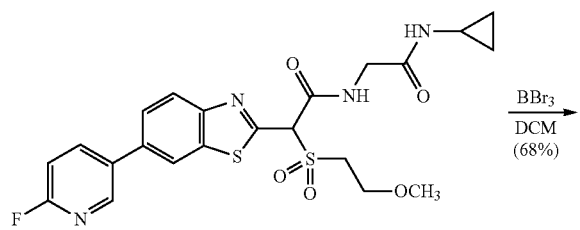

To a solution of Example 376 (40 mg, 0.079 mmol) at 0° C. was added 1.0 M BBr$_3$ in heptane (0.40 mL, 0.40 mmol) and the reaction mixture stirred for 1 h. The reaction mixture was allowed to warm to room temperature and stirred for 1 h then poured into ice water and extracted with DCM (3×). The combined extracts were dried (Na$_2$SO$_4$), filtered and concentrated under reduced pressure. The residue was purified by silica gel chromatography eluting with 0.3 to 8% MeOH/DCM to give Example 509 (28 mg, 68% yield) as a white solid. HPLC RT=1.63 min (LCMS Method B). MS(ES): m/z=493.1 [M+H]$^+$. $^1$H NMR (400 MHz, DMSO-d$_6$) δ 8.99 (t, J=5.6 Hz, 1H), 8.67 (d, J=2.6 Hz, 1H), 8.57 (d, J=1.5 Hz, 1H), 8.40 (td, J=8.2, 2.8 Hz, 1H), 8.20 (d, J=8.4 Hz, 1H), 8.03 (d, J=3.7 Hz, 1H), 7.93 (dd, J=8.6, 1.8 Hz, 1H), 7.35 (dd, J=8.5, 2.8 Hz, 1H), 6.23 (s, 1H), 5.24 (t, J=5.5 Hz, 1H), 3.93-3.79 (m, 4H), 3.72-3.50 (m, 2H), 2.65 (ddd, J=11.1, 7.4, 4.0 Hz, 1H), 0.64 (dd, J=7.0, 2.0 Hz, 2H), 0.47-0.36 (m, 2H). EL IC$_{50}$=280 nM.

Example 510

Pyridin-2-ylmethyl (4-(2-(2-((2-(cyclopropylamino)-2-oxoethyl)amino)-1-(methylsulfonyl)-2-oxoethyl)-5-fluorobenzo[d]thiazol-6-yl)phenyl)carbamate

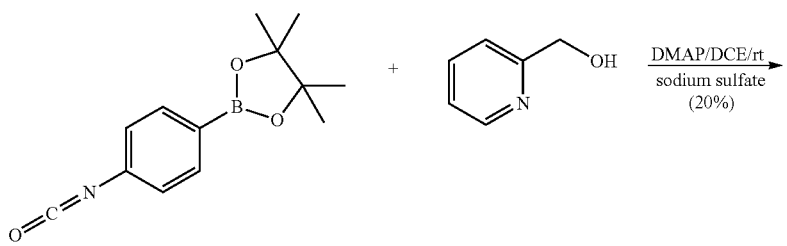

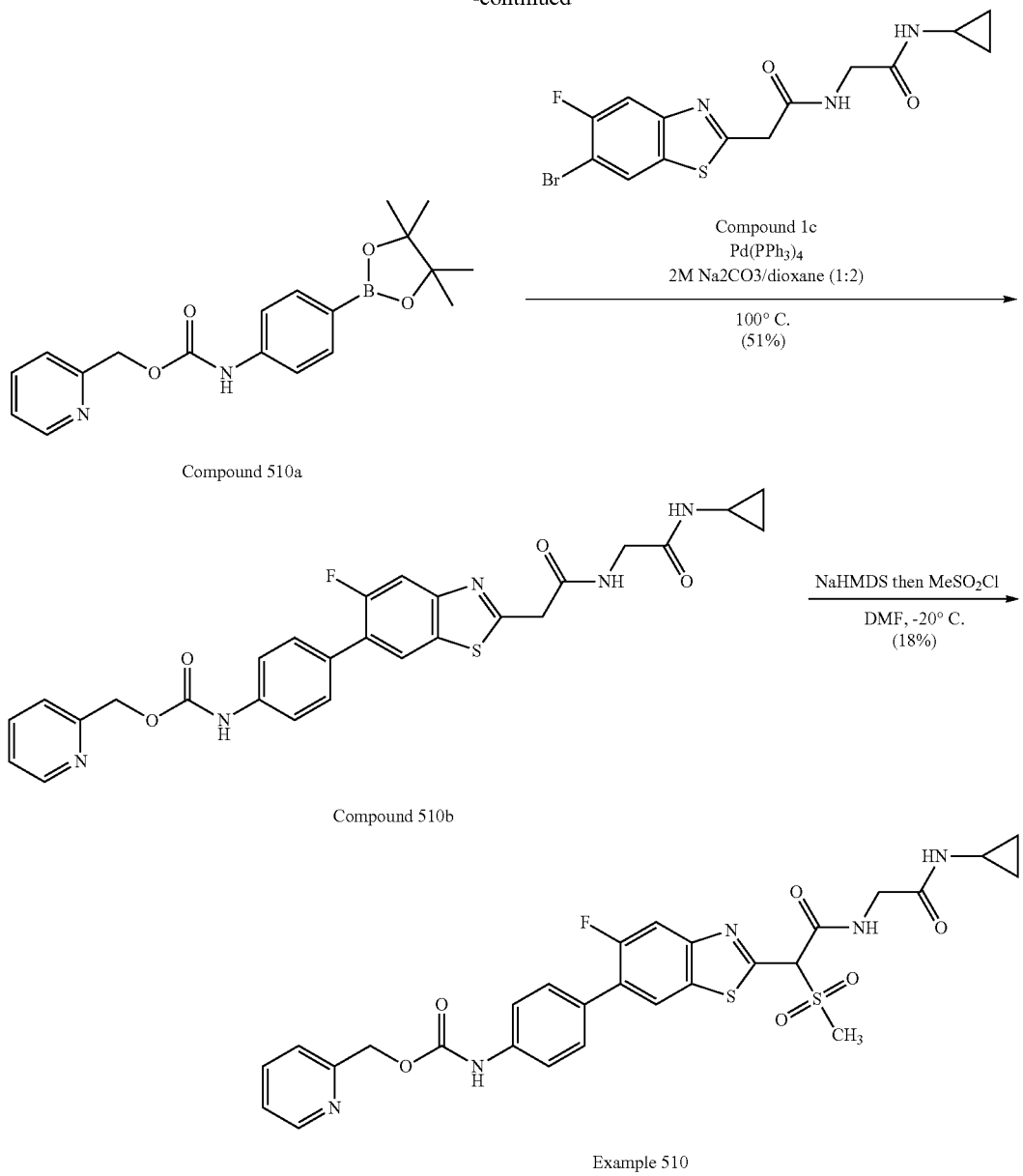

Example 510

Compound 510a. Pyridin-2-ylmethyl (4-(4,4,5,5-tetramethyl-1,3,2-dioxaborolan-2-yl)phenyl)carbamate N,N-Dimethylpyridin-4-amine (20 mg, 0.16 mmol) was added to pyridin-2-ylmethanol (0.12 mL, 1.2 mmol), 2-(4-isocyanatophenyl)-4,4,5,5-tetramethyl-1,3,2-dioxaborolane (200 mg, 0.82 mmol) and anhydrous sodium sulfate (0.5 g) in DCE (4 mL). After 3 days, the reaction mixture was filtered through CELITE®, concentrated and purified using silica gel chromatography (50% ethyl acetate/hexanes to 100% ethyl acetate) to isolate Compound 510a (70 mg, 0.2 mmol, 20% yield) as a clear film. HPLC RT=0.83 min (LCMS Method M). MS(ES): m/z=355.3 [M+H]$^+$. $^1$H NMR (500 MHz, chloroform-d) δ 8.66-8.55 (m, 1H), 7.79-7.73 (m, 2H), 7.71 (d, J=1.9 Hz, 1H), 7.44-7.38 (m, 3H), 7.26-7.21 (m, 1H), 7.05-6.99 (m, 1H), 5.32 (s, 2H), 1.28-1.19 (m, 12H).

Example 510

Example 510 was prepared from Compound 510a as described in the general procedure given for Example 1. HPLC RT=1.44 min (LCMS Method N). MS(ES): m/z=612.14 [M+H]$^+$. $^1$H NMR (500 MHz, DMSO-d$_6$) δ 10.07 (br. s., 1H), 9.04 (br. s., 1H), 8.60 (d, J=4.0 Hz, 1H), 8.29 (d, J=7.3 Hz, 1H), 8.01 (d, J=11.6 Hz, 2H), 8.01-7.85 (m, 1H), 7.67-7.49 (m, 5H), 7.45-7.37 (m, 1H), 6.18 (s, 1H), 5.26 (s, 2H), 3.93-3.75 (m, 2H), 3.26 (s, 3H), 2.62 (d, J=3.7 Hz, 1H), 0.62 (d, J=6.4 Hz, 2H), 0.39 (br. s., 2H). EL IC$_{50}$=1.3 nM.

Example 511 to Example 524 were prepared as described in the general procedure given for Example 510.

Example 525

Cyclopropylmethyl N-{4-[2-({[(cyclopropylcarbamoyl)methyl]carbamoyl}(2-methoxyethanesulfonyl)methyl)-5-fluoro-1,3-benzothiazol-6-yl]phenyl}carbamate

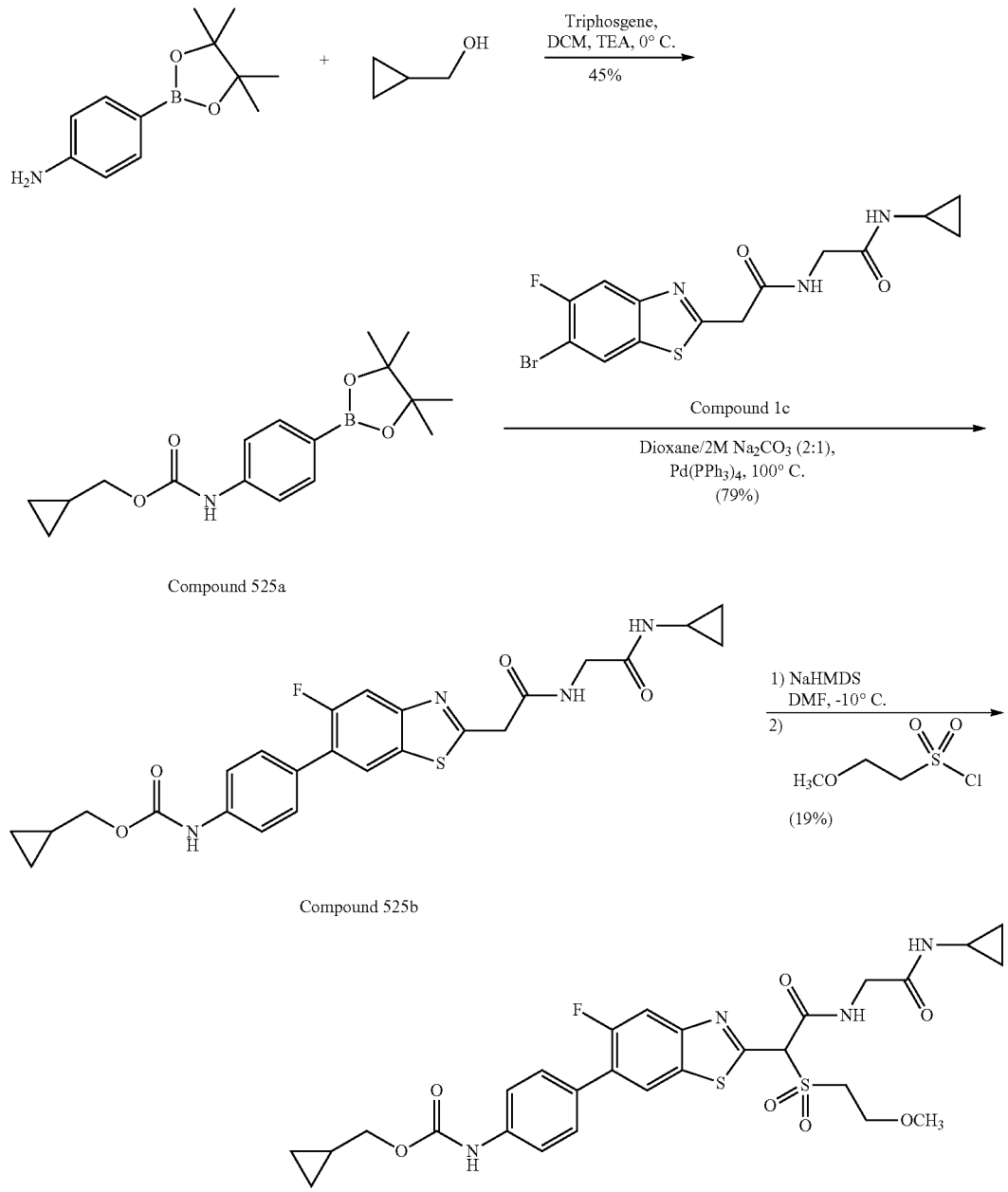

Example 525

Compound 525a. Cyclopropylmethyl (4-(4,4,5,5-tetramethyl-1,3,2-dioxaborolan-2-yl)phenyl)carbamate Triphosgene (135 mg, 0.46 mmol) in DCM (2 mL) was added to TEA (0.509 mL, 3.65 mmol) and 4-(4,4,5,5-tetramethyl-1,3,2-dioxaborolan-2-yl)aniline (200 mg, 0.91 mmol) in DCM (2 mL) cooled in ice/water bath. After 5 min, cyclopropylmethanol (260 mg, 3.7 mmol) was added, and the reaction mixture was allowed to warm to rt. After 16 h, the reaction mixture was concentrated, and the residue was purified using silica gel chromatography (hexanes to 30% ethyl acetate/hexanes) to isolate Compound 525a as a clear oil (130 mg, 45% yield). HPLC RT=1.05 min (LCMS Method M). MS(ES): m/z=318.5 [M+H]$^+$. $^1$H NMR (500 MHz, chloroform-d) δ 7.90-7.66 (m, 2H), 7.45-7.37 (m, 2H), 6.76-6.61 (m, 1H), 4.01 (d, J=7.2 Hz, 2H), 1.34 (s, 12H), 1.24-1.09 (m, 1H), 0.74-0.56 (m, 2H), 0.40-0.26 (m, 2H).

Example 525

Example 525 was prepared from Compound 525b as described in the general procedure given for Example 1. HPLC RT=1.71 min (LCMS Method N). MS(ES): m/z=619.2 [M+H]$^+$. $^1$H NMR (500 MHz, DMSO-d$_6$) δ 9.85 (br. s., 1H), 8.99 (br. s., 1H), 8.29 (d, J=7.6 Hz, 1H), 8.09-7.90 (m, 2H), 7.72-7.56 (m, 2H), 7.53 (d, J=7.3 Hz, 2H), 7.46 (d, J=7.6 Hz, 1H), 3.94 (d, J=7.0 Hz, 2H), 3.81 (br. s., 2H), 3.76 (d, J=5.5 Hz, 1H), 3.70 (d, J=4.9 Hz, 2H), 3.41 (br. s., 2H), 3.12 (br. s., 2H), 2.62 (br. s., 1H), 1.15 (br. s., 1H), 0.62 (d, J=6.7 Hz, 2H), 0.55 (d, J=7.0 Hz, 2H), 0.39 (br. s., 2H), 0.34-0.20 (m, 2H). EL IC$_{50}$=0.5 nM.

Example 526 to Example 531 were prepared as described in the general procedure given for Example 525.

Example 532

Methyl N-{2-[2-({[(cyclopropylcarbamoyl)methyl]carbamoyl}(methanesulfonyl)methyl)-5-fluoro-1,3-benzothiazol-6-yl]phenyl}carbamate

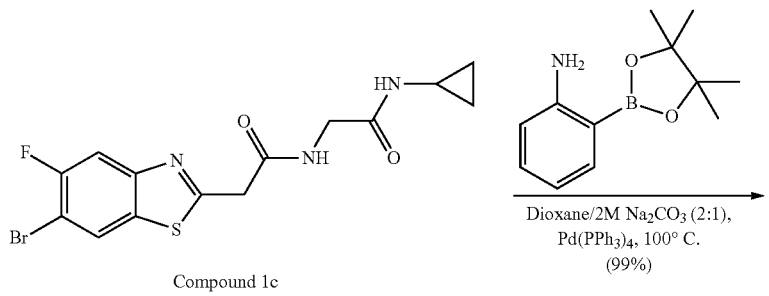

Compound 1c

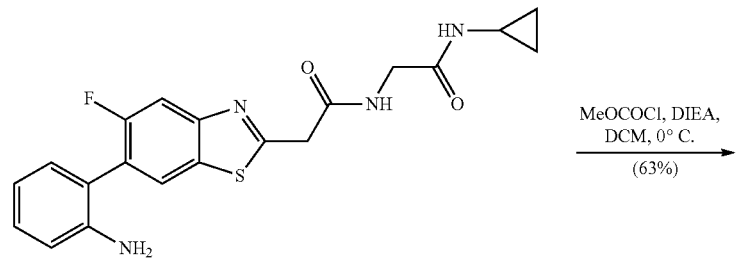

Compound 532a

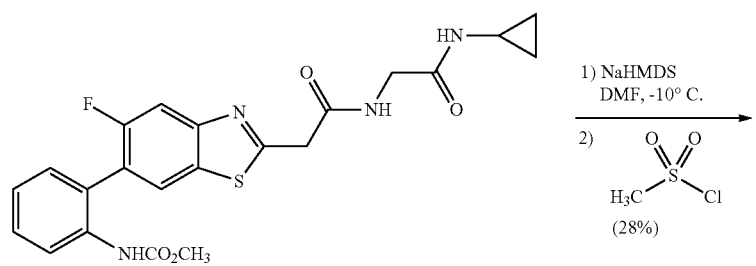

Compound 532b

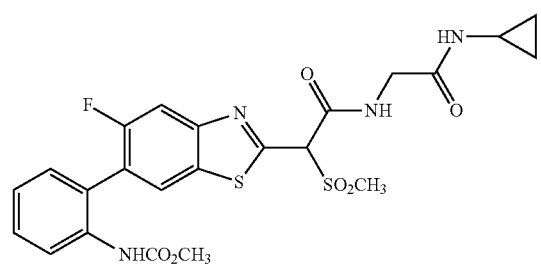

Example 532

Compound 532a. 2-(6-(2-Aminophenyl)-5-fluorobenzo[d]thiazol-2-yl)-N-(2-(cyclopropylamino)-2-oxoethyl)acetamide Compound 532a (51 mg, 99%) was prepared from Compound 1c as described in the general procedure given for Compound 1d. HPLC RT=0.70 min (LCMS Method M). MS(ES): m/z=399.2 [M+H]+. 1H NMR (500 MHz, chloroform-d) δ 7.94-7.79 (m, 3H), 7.20-7.13 (m, 1H), 6.99-6.84 (m, 3H), 6.65-6.35 (m, 1H), 4.18 (s, 2H), 4.06-3.93 (m, 2H), 2.25-2.17 (m, 1H), 1.38-1.21 (m, 2H), 0.91-0.76 (m, 2H), 0.63-0.46 (m, 2H).

Compound 532b. Methyl (2-(2-(2-((2-(cyclopropylamino)-2-oxoethyl)amino)-2-oxoethyl)-5-fluorobenzo[d]thiazol-6-yl)phenyl)carbamate Methyl chloroformate (0.012 mL, 0.16 mmol) was added to DCM (2 mL) solution of Compound 532a (51 mg, 0.13 mmol) and DIEA (0.045 mL, 0.26 mmol) at 0° C. The reaction mixture was allowed to warm to rt. After 30 min, additional DIEA (0.045 mL, 0.26 mmol) and methyl chloroformate (0.012 mL, 0.16 mmol) were added. After 30 min, the reaction mixture was concentrated and purified using reverse phase HPLC (PHENOMENEX® Luna Axia 5μ C18, 21.2×100, UV at 220 nm, 10 to 70% B over 30 min with 10 min hold time, solvent A: 90% water/ACN/0.1% TFA, solvent B:90% ACN/water/0.1% TFA, Flow rate 20 mL/min; detector at 254) to isolate Compound 532b (37 mg, 63% yield) as an off-white solid. HPLC RT=0.80 min (LCMS Method M). MS(ES): m/z=457.1 [M+H]+. 1H NMR (500 MHz, chloroform-d) δ 7.86-7.75 (m, 3H), 7.51-7.41 (m, 1H), 7.25-7.12 (m, 3H), 6.46 (br. s., 1H), 4.19 (s, 2H), 3.99 (d, J=5.5 Hz, 2H), 3.70 (s, 3H), 2.74 (dt, J=7.1, 3.5 Hz, 1H), 0.85-0.77 (m, 2H), 0.59-0.50 (m, 2H).

Example 532

Example 532 (5.5 mg, 28%) was prepared from Compound 532b as described in the general procedure given for Example 1. HPLC RT=1.39 min (LCMS Method N). MS(ES): m/z=535.1 [M+H]+. 1H NMR (500 MHz, DMSO-d6) δ 9.05 (br. s., 1H), 8.74 (s, 1H), 8.15-7.89 (m, 3H), 7.62-7.22 (m, 5H), 3.81 (d, J=5.5 Hz, 2H), 3.65-3.40 (m, 3H), 3.31-3.08 (m, 3H), 2.62 (td, J=7.2, 3.7 Hz, 1H), 0.62 (d, J=6.7 Hz, 2H), 0.38 (br. s., 2H). EL IC50=110 nM.

Example 533 to Example 537 were prepared as described in the general procedure given for Example 532.

Example 538

Methyl N-{4-[2({[(cyclopropylcarbamoyl)methyl]carbamoyl}(methanesulfonyl)methyl)-5-fluoro-1,3-benzothiazol-6-yl]-2-methoxyphenyl}carbamate

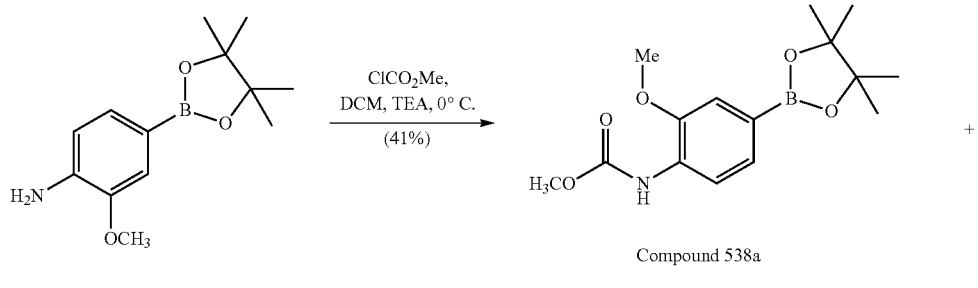

Compound 538a

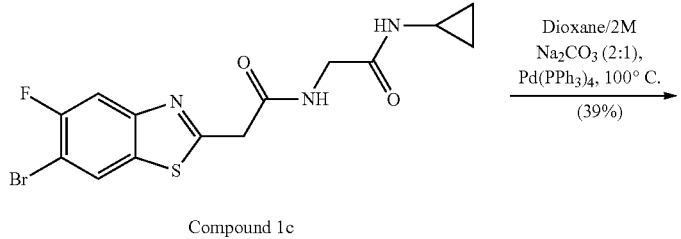

Compound 1c

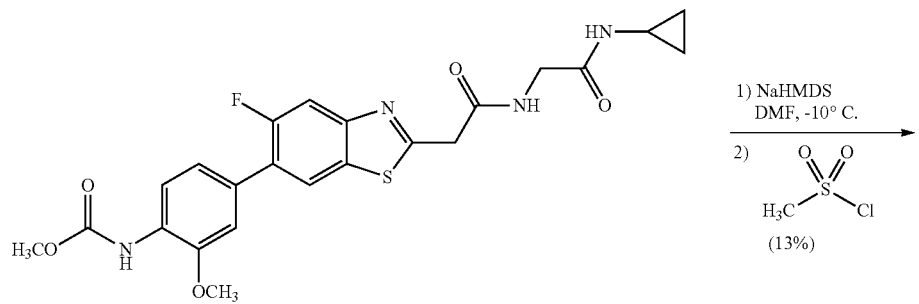

Compound 538b

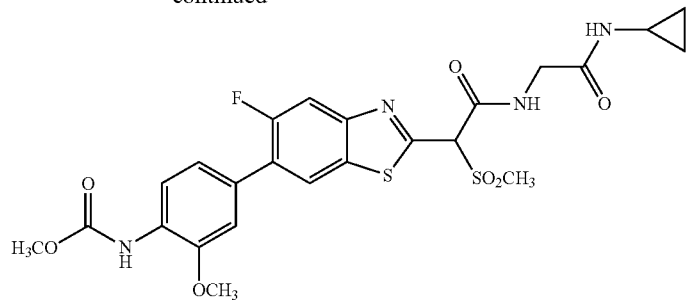

Example 538

Compound 538a. Methyl (2-methoxy-4-(4,4,5,5-tetramethyl-1,3,2-dioxaborolan-2-yl)phenyl)carbamate Methyl chloroformate (0.068 mL, 0.88 mmol) was added to 2-methoxy-4-(4,4,5,5-tetramethyl-1,3,2-dioxaborolan-2-yl)aniline (200 mg, 0.80 mmol) and TEA (0.22 mL, 1.6 mmol) in DCM (1 mL) at 0° C. The reaction mixture was allowed to warm to rt. After 18 h, the reaction mixture was concentrated under reduced pressure, and the residue was purified by silica gel chromatography (hexanes to 30% ethyl acetate/hexanes) to give Compound 538a (100 mg, 41% yield) as a clear oil. HPLC RT=1.39 min (LCMS Method M). MS(ES): m/z=307.9 [M+H]$^+$. $^1$H NMR (500 MHz, chloroform-d) δ 8.10 (d, J=7.2 Hz, 1H), 7.44 (dd, J=8.0, 0.8 Hz, 1H), 7.38 (br. s., 1H), 7.26 (d, J=0.8 Hz, 1H), 3.96-3.84 (m, 3H), 3.78 (s, 3H), 1.43-1.29 (m, 12H).

Example 538

Example 538 was prepared from Compound 538a as described in the general procedure given for Example 1.

HPLC RT=1.63 min (LCMS Method N). MS(ES): m/z=561.1 [M+H]$^+$. $^1$H NMR (500 MHz, DMSO-d$_6$) δ 8.82 (br. s., 1H), 8.40 (s, 1H), 8.12 (d, J=7.4 Hz, 1H), 7.79 (s, 1H), 7.81 (s, 1H), 7.55 (d, J=7.7 Hz, 1H), 6.99 (s, 1H), 6.93 (d, J=8.4 Hz, 1H), 5.95 (s, 1H), 3.59 (d, J=5.0 Hz, 3H), 3.43 (s, 3H), 3.03 (s, 3H), 2.39 (d, J=3.7 Hz, 1H), 0.39 (d, J=6.4 Hz, 2H), 0.15 (br. s., 2H). EL IC$_{50}$=4.5 nM.

Example 539 to Example 557, were prepared as described in the general procedure given for Example 538.

Example 558

(E)-2-(6-(4-(3-Benzyl-2-cyanoguanidino)phenyl)-5-fluorobenzo[d]thiazol-2-yl)-N-(2-(cyclopropylamino)-2-oxoethyl)-2-((2-methoxyethyl)sulfonyl)acetamide

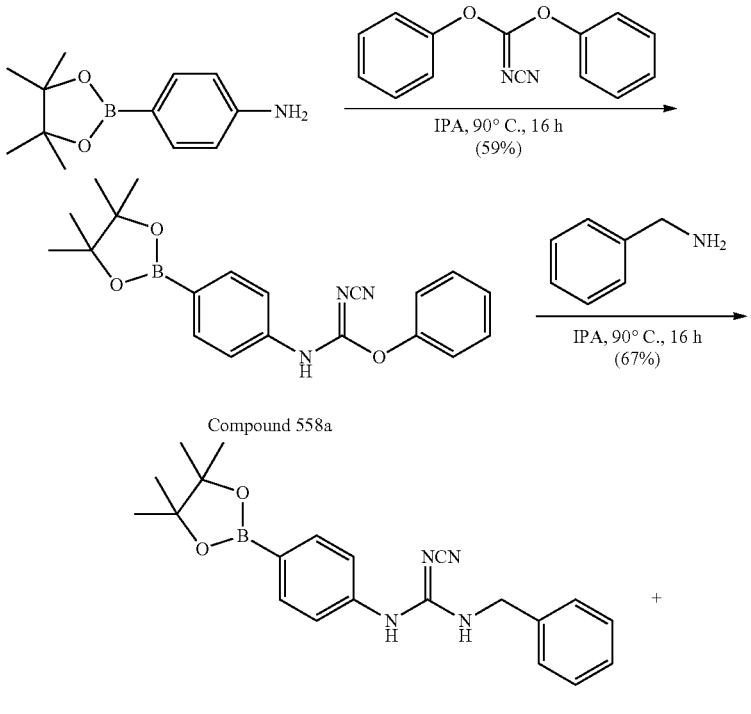

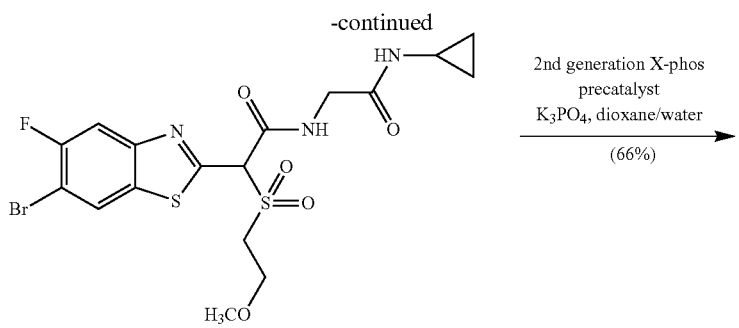

Compound 411a

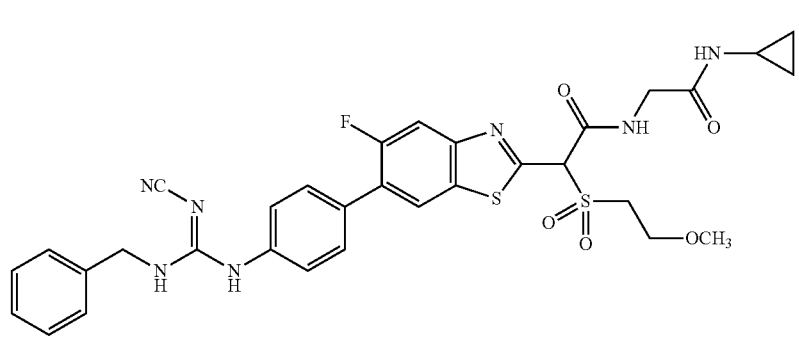

Example 558

Compound 558a. N'-Cyano-N-(4-(4,4,5,5-tetramethyl-1,3,2-dioxaborolan-2-yl)phenyl)carbamimidate A mixture of diphenyl cyanocarbonimidate (300 mg, 1.3 mmol) and 4-(4,4,5,5-tetramethyl-1,3,2-dioxaborolan-2-yl)aniline (280 mg, 1.3 mmol) in 2-propanol (10 mL) was stirred at rt overnight. The solid was collected by filtration and washed with isopropanol and hexanes, dried in vacuo to give Compound 558a (280 mg, 59% yield). HPLC RT=1.10 min (LCMS Method O). MS(ES): m/z=364.3 [M+H]$^+$. $^1$H NMR (400 MHz, chloroform-d) δ 7.85 (d, J=8.4 Hz, 2H), 7.49-7.42 (m, 2H), 7.40-7.31 (m, 3H), 7.17 (d, J=7.7 Hz, 2H), 1.35 (s, 12H).

Compound 558b. 1-Benzyl-2-cyano-3-(4-(4,4,5,5-tetramethyl-1,3,2-dioxaborolan-2-yl)phenyl)guanidine A mixture of Compound 558a (70 mg, 0.19 mmol) and phenylmethanamine (52 mg, 0.48 mmol) in 2-propanol (2 mL) was heated at 90° C. overnight. The mixture was filtered and the solid was washed with 2-propanol and hexanes to give Compound 558b (49 mg, 68% yield) as a white solid. HPLC RT=0.97 min (LCMS Method O). MS(ES): m/z=377.0 [M+H]$^+$. $^1$H NMR (400 MHz, DMSO-d$_6$) δ 9.24 (br. s., 1H), 7.87 (t, J=5.5 Hz, 1H), 7.68-7.58 (m, 2H), 7.46-7.21 (m, 7H), 4.45 (d, J=5.9 Hz, 2H), 1.29 (s, 12H).

Example 558

Example 558 (13 mg, 66% yield) was prepared from Compound 558b and Compound 411a as described in the general procedure given for Example 287. HPLC RT=1.61 min (LCMS Method U). MS(ES): m/z=678.1 [M+H]$^+$. $^1$H NMR (500 MHz, DMSO-d$_6$) δ 9.29-9.20 (m, 1H), 9.00 (t, J=5.5 Hz, 1H), 8.26 (d, J=7.3 Hz, 1H), 8.04-7.95 (m, 2H), 7.92-7.74 (m, 1H), 7.59 (d, J=7.6 Hz, 2H), 7.40-7.20 (m, 7H), 6.11 (s, 1H), 4.43 (d, J=5.5 Hz, 2H), 3.86 (s, 4H), 3.80-3.65 (m, 3H), 3.25 (s, 2H), 2.64-2.54 (m, 1H), 0.62 (d, J=5.5 Hz, 2H), 0.37 (br. s., 2H).

Example 559

4-(2-(2-((2-(Cyclopropylamino)-2-oxoethyl)amino)-1-((2-methoxyethyl)sulfonyl)-2-oxoethyl)benzo[d]thiazol-6-yl)-N-(3-methoxy-2,2-dimethylpropyl)benzamide

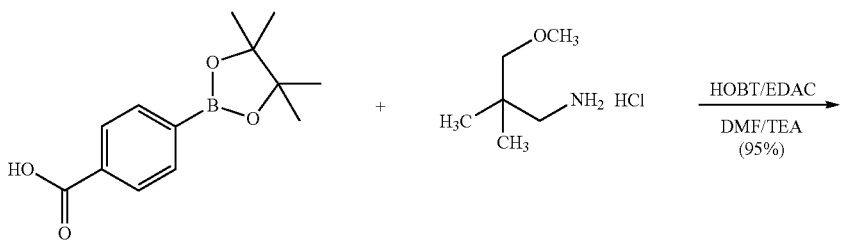

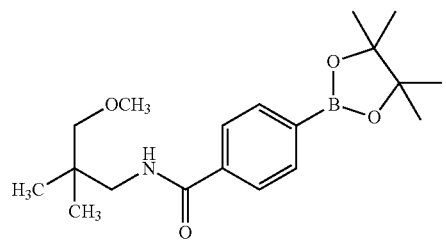

Compound 559a

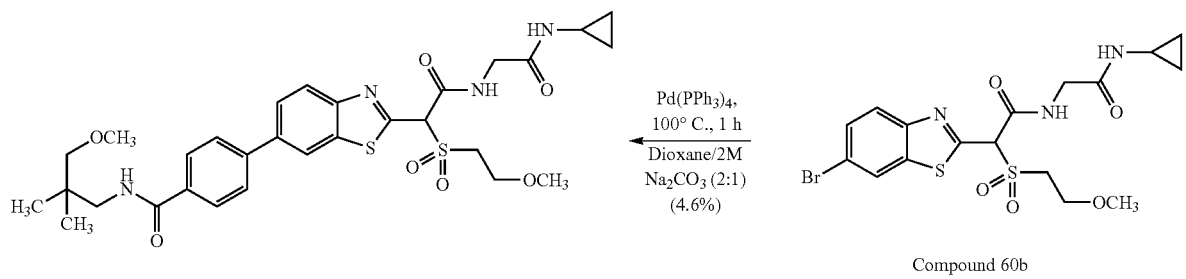

Example 559

Compound 559a. N-(3-Methoxy-2,2-dimethylpropyl)-4-(4,4,5,5-tetramethyl-1,3,2-dioxaborolan-2-yl)benzamide EDC (0.85 g, 4.4 mmol) was added to DMF (6 mL) solution of 4-(4,4,5,5-tetramethyl-1,3,2-dioxaborolan-2-yl)benzoic acid (0.55 g, 2.2 mmol), 3-methoxy-2,2-dimethylpropan-1-amine hydrochloride (0.51 g, 3.3 mmol), HOBT hydrate (0.68 g, 4.4 mmol) and TEA (0.80 mL, 4.4 mmol) at room temperature. After 16 h, the reaction mixture was diluted with water (50 mL), extracted with DCM (2×50 mL), dried over $Na_2SO_4$, filtered and concentrated under reduced pressure. The residue was purified using silica gel chromatography (50% ethyl acetate/hexanes) to isolate Compound 559a (730 mg, 95% yield) as a clear oil. HPLC RT=1.11 min (LCMS Method M). MS(ES): m/z=347.9 [M+H]$^+$. $^1$H NMR (500 MHz, chloroform-d) δ 7.87 (d, J=8.0 Hz, 2H), 7.80-7.69 (m, 2H), 7.36-7.29 (m, 1H), 3.45-3.37 (m, 5H), 3.28 (s, 2H), 1.36 (s, 12H), 1.00 (s, 6H).

Example 559

Example 559 (1.8 mg, 4.6% yield) was prepared from Compound 559a and Compound 60b as described in the general procedure given for Example 60. HPLC RT=2.24 min (LCMS Method N). MS(ES): m/z=631.23 [M+H]$^+$. $^1$H NMR (500 MHz, DMSO-$d_6$) δ 9.14-8.91 (m, 1H), 8.67-8.49 (m, 1H), 8.38-8.27 (m, 1H), 8.22-8.11 (m, 1H), 8.08-7.72 (m, 7H), 3.90 (s, 2H), 3.87-3.65 (m, 6H), 3.29-3.26 (m, 3H), 3.25-3.20 (m, 2H), 3.12 (s, 3H), 2.70-2.59 (m, 1H), 0.99-0.85 (m, 6H), 0.70-0.56 (m, 2H), 0.48-0.34 (m, 2H). EL $IC_{50}$=5.5 nM.

Example 560 to Example 571, were prepared as described in the general procedure given for Example 559.

Example 572

4-[2-({[(Cyclopropylcarbamoyl)methyl]carbamoyl}(3,3,3-trifluoropropanesulfonyl)methyl)-5-fluoro-1,3-benzothiazol-6-yl]-N-(2-phenylethyl)benzamide

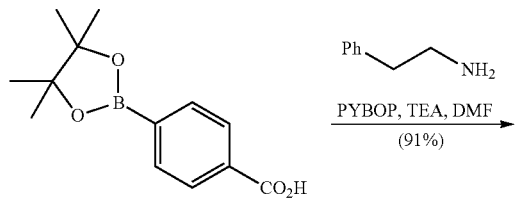

-continued

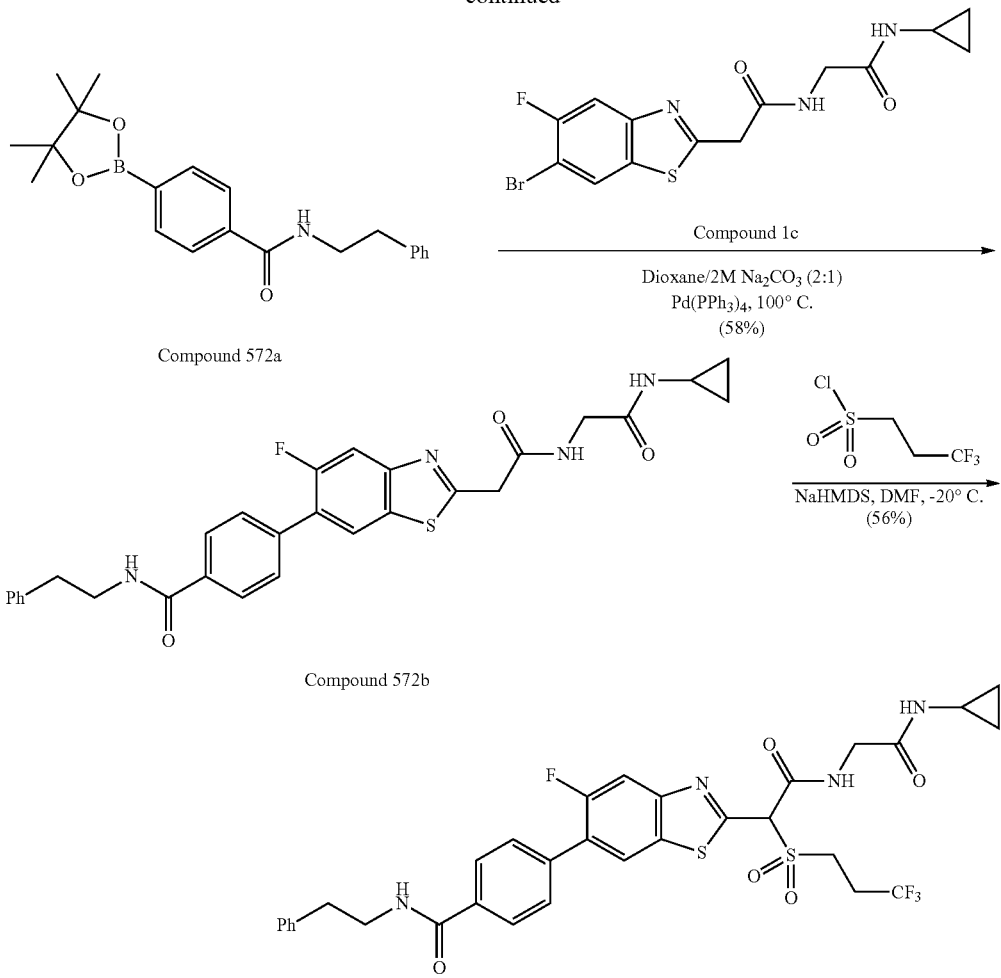

Compound 572a

Compound 572b

Example 572

Compound 572a. N-Phenethyl-4-(4,4,5,5-tetramethyl-1,3,2-dioxaborolan-2-yl)benzamide 4-(4,4,5,5-Tetramethyl-1,3,2-dioxaborolan-2-yl)benzoic acid (200 mg, 0.81 mmol), 2-phenylethanamine (120 mg, 1.0 mmol) and TEA (0.29 mL, 1.6 mmol) in DMF (4 mL) was treated with PYBOP (380 mg, 1.0 mmol). After 2 hours, the reaction mixture was concentrated under reduced pressure, suspended in water (25 mL) and stirred at room temperature. After 16 hours, the reaction mixture was filtered and the solid washed with ether (2×2 mL). Compound 572a (260 mg, 91% yield) was isolated as a yellow solid. HPLC RT=1.06 min (LCMS Method M). MS(ES): m/z=352.3 [M+H]$^+$. $^1$H NMR (500 MHz, DMSO-d$_6$) δ 8.63 (s, 1H), 7.96-7.79 (m, 2H), 7.73 (d, J=8.3 Hz, 2H), 7.37-7.16 (m, 5H), 3.59-3.41 (m, 2H), 2.85 (t, J=7.4 Hz, 2H), 1.31 (s, 12H).

Example 572

Example 572 was prepared from Compound 572a as described in the general procedure given for Example 1.

HPLC RT=1.02 min (LCMS Method N). MS(ES): m/z=691.8 [M+H]$^+$. $^1$H NMR (500 MHz, DMSO-d$_6$) δ 9.04 (t, J=5.2 Hz, 1H), 8.76-8.57 (m, 1H), 8.39 (d, J=7.6 Hz, 1H), 8.16-8.01 (m, 2H), 7.99-7.84 (m, 2H), 7.77-7.56 (m, 2H), 7.41-7.12 (m, 6H), 3.97-3.67 (m, 4H), 3.60-3.39 (m, 1H), 2.93-2.80 (m, 4H), 2.72 (br. s., 1H), 2.62 (dd, J=7.2, 3.5 Hz, 1H), 0.62 (d, J=6.7 Hz, 2H), 0.39 (d, J=2.4 Hz, 2H). EL IC$_{50}$=2.8 nM.

Example 573 to Example 574 were prepared as described in the general procedure given for Example 572.

Example 575

N-{4-[2-({[(Cyclopropylcarbamoyl)methyl]carbamoyl}(3,3,3-trifluoropropanesulfonyl)methyl)-5-fluoro-1,3-benzothiazol-6-yl]phenyl}-3-phenylpropanamide

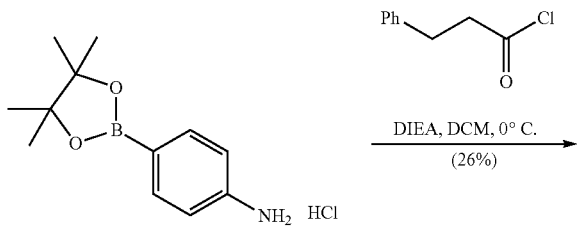

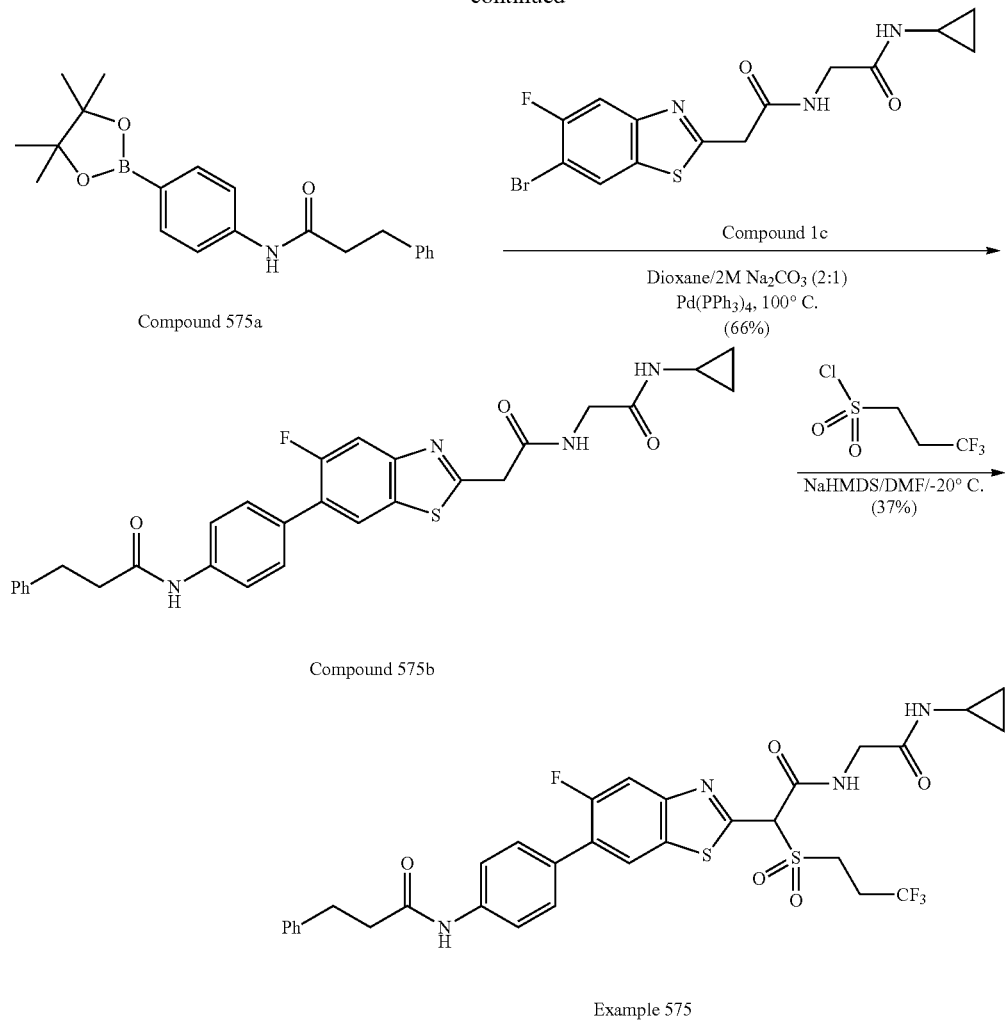

Example 575

Compound 575a. 3-Phenyl-N-(4-(4,4,5,5-tetramethyl-1,3,2-dioxaborolan-2-yl)phenyl)propanamide 3-Phenylpropanoyl chloride (0.15 mL, 0.98 mmol) was added to 4-(4,4,5,5-tetramethyl-1,3,2-dioxaborolan-2-yl)aniline hydrochloride (200 mg, 0.78 mmol) and DIEA (0.41 mL, 2.3 mmol) in DCM (4 mL) at 0° C. After 15 min, the reaction mixture was diluted with 1N HCl (50 mL), extracted with DCM (3×15 mL), dried over $Na_2SO_4$, and concentrated to isolate Compound 575a (70 mg, 0.2 mmol, 26% yield) as an off-white solid. HPLC RT=1.1 min (LCMS Method M). MS(ES): m/z=352.3 $[M+H]^+$. $^1H$ NMR (500 MHz, chloroform-d) δ 7.75 (d, J=8.5 Hz, 2H), 7.46 (br. s., 2H), 7.27 (s, 5H), 7.06-6.95 (m, 1H), 3.07 (t, J=7.7 Hz, 2H), 2.68 (t, J=7.6 Hz, 2H), 1.34 (s, 12H).

Example 575

Example 575 was prepared from Compound 575a as described in the general procedure given for Example 1. HPLC RT=1.91 min (LCMS Method N). MS(ES): m/z=691.1 $[M+H]^+$. $^1H$ NMR (500 MHz, DMSO-$d_6$) δ 10.28-9.93 (m, 1H), 9.04 (br. s., 1H), 8.28 (d, J=7.6 Hz, 1H), 8.11-7.86 (m, 2H), 7.74-7.62 (m, 2H), 7.57-7.45 (m, 2H), 7.29-7.08 (m, 5H), 6.32 (s, 1H), 3.81 (t, J=5.0 Hz, 1H), 3.74-3.63 (m, 3H), 2.99-2.81 (m, 4H), 2.68-2.59 (m, 3H), 0.61 (d, J=6.1 Hz, 2H), 0.38 (d, J=2.4 Hz, 2H). EL $IC_{50}$=0.9 nM.

Example 576 to Example 578 were prepared as described in the general procedure given for Example 575.

Example 579

N-[(Cyclopropylcarbamoyl)methyl]-2-{5-fluoro-6-[4-(1H-imidazol-1-yl)phenyl]-1,3-benzothiazol-2-yl}-2-methanesulfonylacetamide

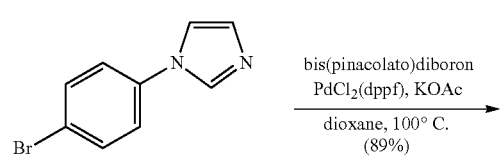

-continued

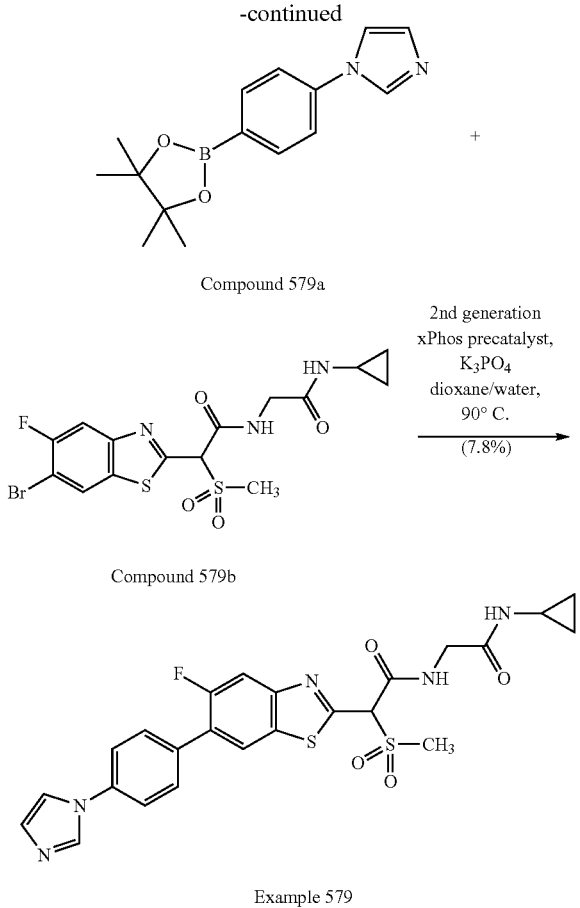

Compound 579a

Compound 579b

Example 579

Compound 579a. 1-(4-(4,4,5,5-Tetramethyl-1,3,2-dioxaborolan-2-yl)phenyl)-1H-imidazole A mixture of 1-(4-bromophenyl)-1H-imidazole (450 mg, 2.0 mmol), bis(pinacolato)diboron (1.0 g, 4.0 mmol), [1,1'-bis(diphenylphosphino)ferrocene]dichloropalladium(II) (150 mg, 0.2 mmol) and potassium acetate (990 mg, 10 mmol) in dioxane (8 mL) was stirred at 100° C. for 2 h. The crude reaction mixture was concentrated under reduced pressure. The residue was purified by silica gel chromatography eluting with 0-100% EtOAc/DCM to give Compound 579a (490 mg, 89% yield). HPLC RT=0.73 min (LCMS Method O). MS(ES): m/z=271.2 [M+H]+. $^1$H NMR (400 MHz, chloroform-d) δ 8.01-7.85 (m, 3H), 7.42-7.35 (m, 2H), 7.32-7.29 (m, 1H), 7.19 (d, J=0.9 Hz, 1H), 1.35 (s, 12H).

Example 579

Example 579 was prepared from Compound 579a and Compound 579b (prepared using the general procedure given for Compound 411a) as described in the general procedure given for Example 287. HPLC RT=1.01 min (LCMS Method U). MS(ES): m/z=528.1 [M+H]+. $^1$H NMR (500 MHz, DMSO-$d_6$) δ 8.91-8.81 (m, 1H), 8.41-8.28 (m, 2H), 7.82 (d, J=14.0 Hz, 10H), 7.44 (br. s., 1H), 3.90-3.67 (m, 1H), 3.57 (br. s., 2H), 2.65-2.57 (m, 1H), 0.64 (d, J=7.0 Hz, 2H), 0.38 (br. s., 2H). EL $IC_{50}$=6 nM.

Example 580 to Example 590 were prepared as described in the general procedure given for Example 579.

Example 591

2-[6-(1-Benzyl-2-oxo-1,2-dihydropyridin-3-yl)-5-fluoro-1,3-benzothiazol-2-yl]-N-[(cyclopropylcarbamoyl)methyl]-2-(3,3,3-trifluoropropanesulfonyl)acetamide

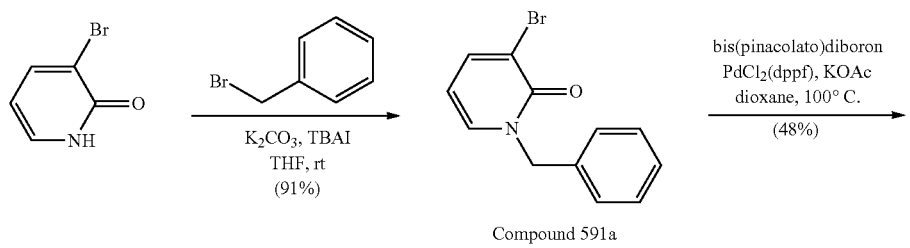

Compound 591a

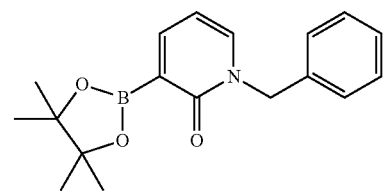

Compound 591b

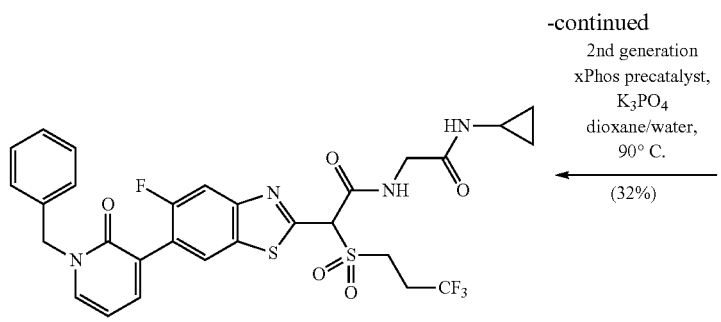

Example 591

Compound 591a.
1-Benzyl-3-bromopyridin-2(1H)-one

To a solution of 3-bromopyridin-2(1H)-one (620 mg, 3.5 mmol) in THF was added potassium carbonate (1.5 g 11 mmol), benzyl bromide (910 mg, 5.3 mmol), TBAI (1.96 g, 5.3 mmol). The resulting mixture stirred at rt overnight. The mixture was partitioned between EtOAc and water. The organic layer was separated, washed with brine, dried over sodium sulfate and concentrated under reduced pressure. The residue was purified by silica gel chromatography eluting with 0-100% EtOAc/hexane to give Compound 591a (860 mg, 91% yield). HPLC RT=0.82 min (LCMS Method O). MS(ES): m/z=266.1 [M+H]$^+$. $^1$H NMR (400 MHz, chloroform-d) δ 7.73 (dd, J=7.3, 1.8 Hz, 1H), 7.37-7.29 (m, 6H), 6.07 (t, J=7.0 Hz, 1H), 5.19 (s, 2H).

Example 591

Example 591 was prepared from Compound 591b and Compound 591c (prepared using the general procedure given for Compound 411a) as described in the general procedure given for Example 287. HPLC RT=1.8 min (LCMS Method U). MS(ES): m/z=651.1 [M+H]$^+$. $^1$H NMR (500 MHz, DMSO-d$_6$) δ 9.02 (br. s., 1H), 8.23 (d, J=7.0 Hz, 1H), 8.09-8.03 (m, 1H), 7.99-7.90 (m, 2H), 7.63-7.50 (m, 1H), 7.39-7.21 (m, 5H), 6.45-6.33 (m, 2H), 5.22-5.13 (m, 2H), 3.82 (br. s., 3H), 3.45 (br. s., 2H), 2.89-2.79 (m, 1H), 2.68-2.58 (m, 1H), 0.62 (d, J=7.0 Hz, 2H), 0.39 (br. s., 2H). EL IC$_{50}$=268 nM.

Example 592 to Example 594 were prepared as described in the general procedure given for Example 591.

Example 595

2-(6-(2-Cyclopropyl-1-oxoisoindolin-5-yl)benzo[d]thiazol-2-yl)-2-((4-fluorophenyl)sulfonyl)-N-(2-((2-methoxyethyl)amino)-2-oxoethyl)

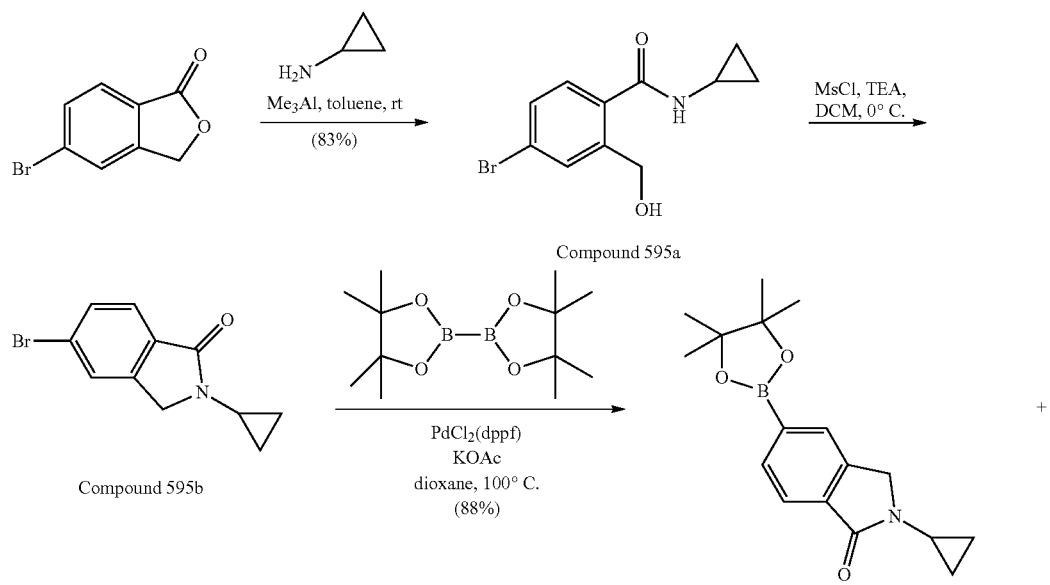

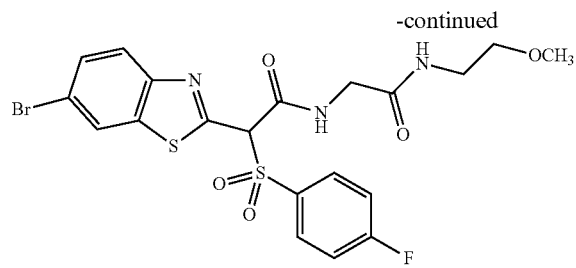

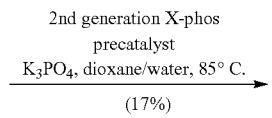

Compound 595d

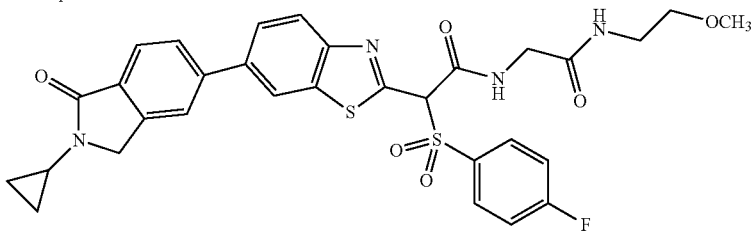

Example 595

Compound 595a.
4-Bromo-N-cyclopropyl-2-(hydroxymethyl)benzamide

To a solution of cyclopropanamine (160 mg, 2.8 mmol) in toluene (8 mL) at 0° C. was added AlMe$_3$ (1.3 mL, 2.6 mmol). After 5 min, 5-bromoisobenzofuran-1(3H)-one (0.5 g, 2.4 mmol) was added. The reaction mixture was allowed to warm to rt over a period of 10 min. After 16 h, the reaction mixture was quenched with the addition of 1N NaOH (10 mL). The resulting reaction mixture was diluted with EtOAc, washed with water and brine. The organic phase was dried over sodium sulfate, filtered and concentrated under reduced pressure. The residue was purified silica gel chromatography eluting with 0-10% MeOH/DCM to give Compound 595a (0.53 g, 83% yield) as a yellow solid. HPLC RT=0.70 min (LCMS Method O). MS(ES): m/z=272.2 [M+H]$^+$. $^1$H NMR (400 MHz, CD$_3$OD) δ 7.76-7.68 (m, 1H), 7.53-7.47 (m, 1H), 7.36 (s, 1H), 4.68 (s, 2H), 2.84 (tt, J=7.4, 3.7 Hz, 1H), 0.84-0.77 (m, 2H), 0.65-0.57 (m, 2H).

Compound 595b.
5-Bromo-2-cyclopropylisoindolin-1-one

To a solution of Compound 595a (530 mg, 2.0 mmol) in DCM (15 mL) at 0° C. were added TEA (0.81 mL, 5.8 mmol) and MeSO$_2$Cl (0.23 mL, 2.9 mmol). The reaction mixture was allowed to warm to rt. After 2 days, the solvent was removed under reduced pressure. The residue was purified by silica gel chromatography eluting with 0-100% EtOAc/hexanes gradient to Compound 595b (390 mg, 79% yield) as a white solid. HPLC RT=0.56 min (LCMS Method O). MS(ES): m/z=254.1 [M+H]$^+$. $^1$H NMR (400 MHz, chloroform-d) δ 7.62 (s, 1H), 7.56-7.54 (m, 1H), 7.52 (s, 1H), 5.33 (s, 2H), 3.35 (tt, J=7.1, 3.7 Hz, 1H), 0.86-0.79 (m, 2H), 0.78-0.72 (m, 2H).

Compound 595c. 2-Cyclopropyl-5-(4,4,5,5-tetramethyl-1,3,2-dioxaborolan-2-yl)isoindolin-1-one Compound 595c (400 mg, 88% yield) was prepared from Compound 595b as described in the general procedure given for Compound 579a. HPLC RT=0.82 min (LCMS Method O). MS(ES): m/z=300.0[M+H]$^+$. $^1$H NMR (400 MHz, DMSO-d$_6$) δ 7.84-7.79 (m, 1H), 7.75-7.67 (m, 1H), 7.65-7.58 (m, 1H), 5.51-5.34 (m, 2H), 3.34-3.24 (m, 1H), 1.32 (s, 6H), 1.18 (s, 6H), 0.82-0.75 (m, 2H), 0.65-0.57 (m, 2H).

Example 595

Example 595 was prepared from Compound 595c and Compound 595d (prepared using the general procedure given for Compound 430d) as described in the general procedure given for Example 287. HPLC RT=1.91 min (LCMS Method O). MS(ES): m/z=637.1 [M+H]$^+$. $^1$H NMR (500 MHz, DMSO-d$_6$) δ 9.10-9.03 (m, 1H), 8.56-8.46 (m, 1H), 8.10-8.04 (m, 2H), 7.95-7.80 (m, 3H), 7.78-7.68 (m, 3H), 7.52-7.41 (m, 2H), 6.46-6.36 (m, 1H), 5.55-5.32 (m, 2H), 3.95-3.70 (m, 2H), 3.39-3.29 (m, 2H), 3.27-3.16 (m, 5H), 0.83-0.75 (m, 2H), 0.68-0.56 (m, 2H). EL IC$_{50}$=24 nM.

Example 596 to Example 597 were prepared as described in the general procedure given for Example 595.

Example 598

N-(2-(Cyclopropylamino)-2-oxoethyl)-2-(6-(3-fluoro-2-hydroxypyridin-4-yl)benzo[d]thiazol-2-yl)-2-((2-methoxyethyl)sulfonyl)acetamide

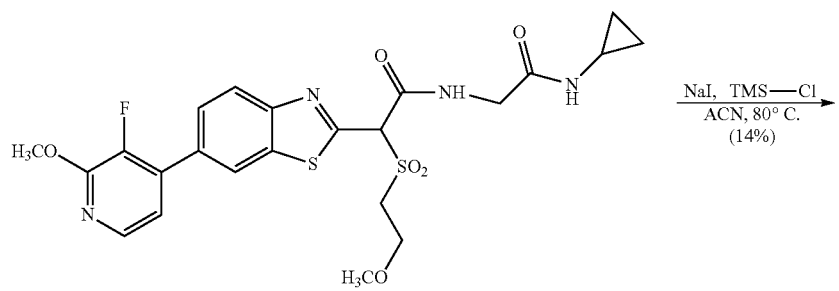

Example 343

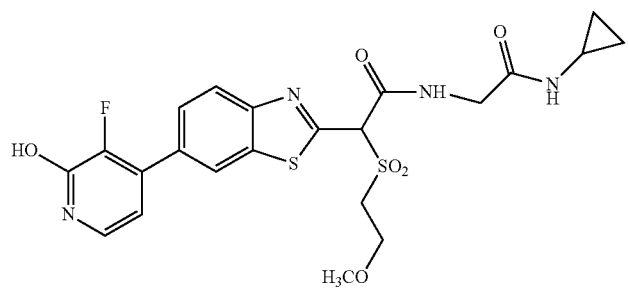

Example 598

A mixture of Example 343 (67 mg, 0.13 mmol), NaI (110 mg, 0.75 mmol) and TMS-Cl (0.16 mL, 1.3 mmol) in ACN (2 mL) was stirred at 80° C. After 1 h, the reaction mixture was concentrated, and the residue was purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 0-35% B over 20 minutes, then a 5-minute hold at 100% B; Flow: 20 mL/min. Fractions containing the desired product were combined and dried via centrifugal evaporation to give Example 598 (9 mg, 14% yield). HPLC RT=1.03 min (LCMS Method O). MS(ES): m/z=523.1 [M+H]$^+$. $^1$H NMR (500 MHz, DMSO-d$_6$) δ 12.51-12.04 (m, 1H), 9.33-8.99 (m, 1H), 8.57-8.38 (m, 1H), 8.27-8.17 (m, 1H), 8.06-7.98 (m, 1H), 7.81-7.69 (m, 1H), 7.40-7.35 (m, 1H), 6.46-6.38 (m, 1H), 6.23 (s, 1H), 3.85-3.71 (m, 5H), 3.29 (s, 4H), 2.69-2.60 (m, 1H), 0.70-0.61 (m, 2H), 0.46-0.38 (m, 2H). EL IC$_{50}$=101 nM.

Example 599 to Example 600 were prepared as described in the general procedure given for Example 598.

Example 601

N-[(Cyclopropylcarbamoyl)methyl]-2-[5-(difluoromethoxy)-6-(2-methylpyrimidin-5-yl)-1,3-benzothiazol-2-yl]-2-methanesulfonylacetamide

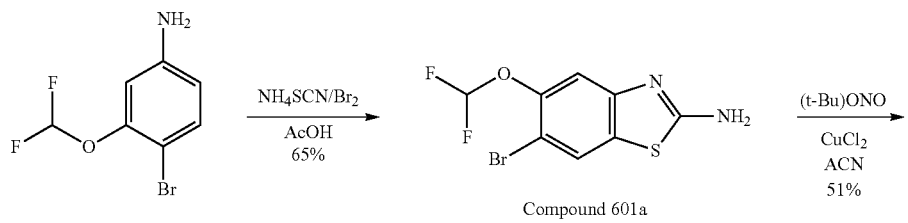

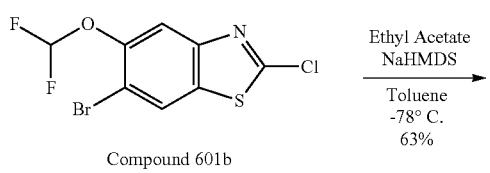
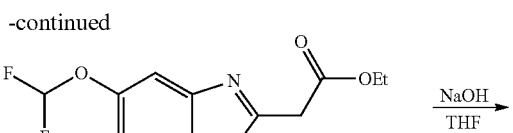
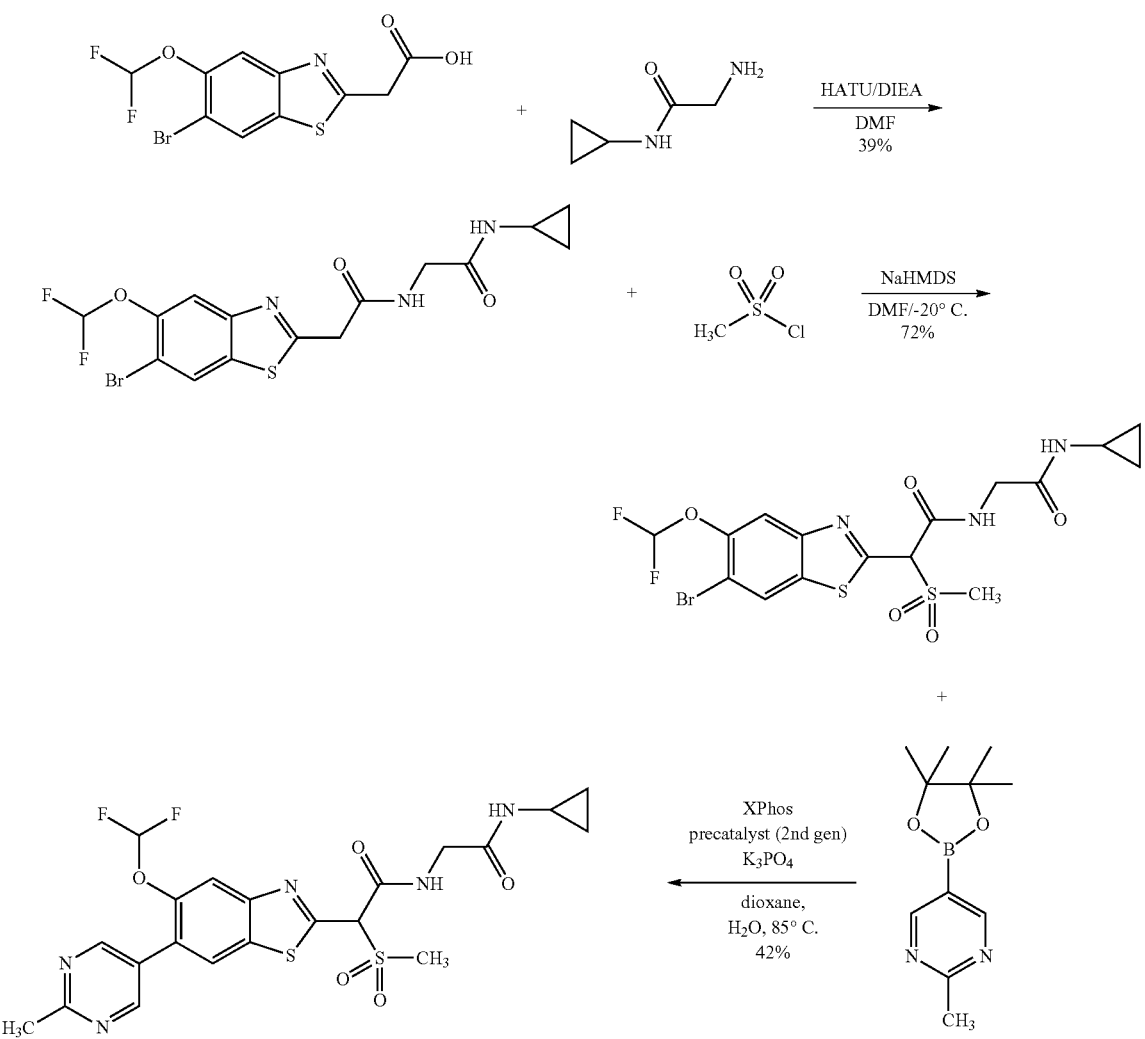

Example 601

Compound 601a. 6-Bromo-5-(difluoromethoxy)benzo[d]thiazol-2-amine

To a solution of 4-bromo-3-(difluoromethoxy)aniline (2.8 g, 12 mmol) and ammonium thiocyanate (1.8 g, 24 mmol) in AcOH (10 mL) at ice bath temperature was added dropwise a solution of bromine (0.61 mL, 12 mmol) in AcOH (5 mL) over a 10 min period, generating a precipitate. The mixture was allowed to warm to rt then stirred for 16 h. The mixture was concentrated under reduced pressure then diluted with 1N KOH (100 mL) and extracted with EtOAc (3×). The organic extracts were dried (Na$_2$SO$_4$) filtered and concentrated onto CELITE®. The residue was purified by silica gel chromatography eluting with 15 to 60% EtOAc/hexane to give Compound 601a (2.3 g, 65%) as a white solid. HPLC RT=1.78 min (LCMS Method B). MS(ES): m/z=296.9 [M+H]$^+$. $^1$H NMR (400 MHz, DMSO-d$_6$) δ 7.65 (s, 1H), 7.38-6.91 (m, 1H), 6.75 (s, 1H).

Compound 601b. 6-Bromo-2-chloro-5-(difluoromethoxy)benzo[d]thiazole

To a suspension of copper (II) chloride (450 mg, 3.4 mmol) in acetonitrile (8 mL) was added tert-butyl nitrite (0.52 mL, 3.9 mmol). The reaction mixture was stirred for 5 min then a solution of 601a (830 mg, 2.8 mmol) in acetonitrile (8 mL) was added dropwise. The reaction mixture was stirred at 60° C. for 1 h. After allowing to cool to room temperature, the reaction mixture was concentrated on silica and purified by silica gel chromatography eluting with 0-40% EtOAc/hexane to afford Compound 601b (450 mg, 51%) as a light brown powder. HPLC RT=2.03 min (LCMS Method B). MS(ES): m/z=315.8 [M+H]+. ¹H NMR (400 MHz, chloroform-d) δ 8.04 (s, 1H), 7.82 (s, 1H), 6.82-6.36 (m, 1H).

Compound 601c. Ethyl 2-(6-bromo-5-(difluoromethoxy)benzo[d]thiazol-2-yl)acetate

To a solution of 1N NaHMDS in THF (1.54 mL, 1.54 mmol) in toluene (10 mL) at −78° C. was added ethyl acetate (82 μL, 0.84 mmol) and the reaction mixture stirred for 1 h. A solution of Compound 601b (220 mg, 0.70 mmol) in toluene (3 mL) was added over a 7 min period. The resulting reaction mixture was maintained at −78° C. for 1 h and then allowed to warm to 0° C. over a period of 1.5 h. The reaction mixture was poured in to a 1N HCl solution and extracted with EtOAc (2×). The combined organic extracts were washed with brine (2×), dried over sodium sulfate, filtered and concentrated. The residue was purified by silica gel chromatography eluting with 0-100%, EtOAc/hexane to give Compound 601c (160 mg, 63%) as a white solid. HPLC RT=2.08 min (LCMS Method B). MS(ES): m/z=367.9 [M+H]+. ¹H NMR (400 MHz, chloroform-d) δ 8.12 (s, 1H), 7.86 (s, 1H), 6.82-6.39 (m, 1H), 4.27 (m, 2H), 4.16 (s, 2H), 1.34-1.27 (m, 3H).

Example 601

Example 601 was prepared from Compound 601c as described in the general procedure given for Example 60. HPLC RT=1.19 min (LCMS Method N). MS(ES): m/z=526.1. ¹H NMR (500 MHz, DMSO-$d_6$) δ 9.13 (m, 1H), 8.96 (m, 2H), 8.47 (s, 1H), 8.12 (m, 2H), 7.56-7.10 (m, 2H), 6.29 (s, 1H), 3.90 (m, 2H), 3.61 (s, 3H), 2.77 (s, 3H), 2.70 (m, 1H), 0.70 (m, 2H), 0.47 (m, 2H). EL IC$_{50}$=19 nM.

Example 602 to Example 607 were prepared as described in the general procedure given for Example 601. Example 608 to Example 612 were prepared as described in the general procedure given for Example 1.

Reference 1

2-(6-Phenyl-1,3-benzothiazol-2-yl)-N-(2-sulfamoylethyl)-4-pentenamide

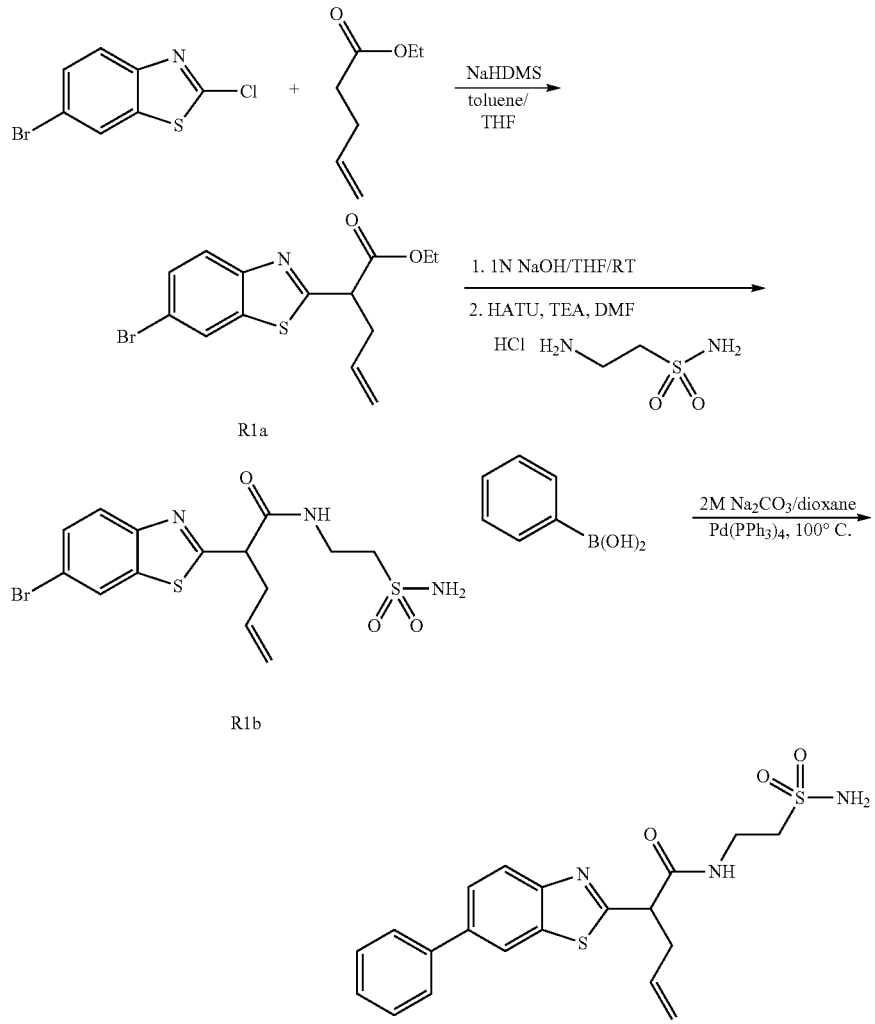

Reference 1

Compound R1a. Ethyl 2-(6-bromobenzo[d]thiazol-2-yl)pent-4-enoate

Compound R1a (2.4 g, 35% yield) was prepared from ethyl 6-bromo-2-chlorobenzo[d]thiazole as described in the general procedure given for Compound 601c. HPLC: RT=1.15 (LCMS Method M). MS(ES): m/z=341.7 [M+H]$^+$. $^1$H NMR (500 MHz, chloroform-d) δ 8.01 (d, J=1.9 Hz, 1H), 7.94-7.79 (m, 1H), 7.58 (dd, J=8.5, 1.9 Hz, 1H), 5.80 (ddt, J=17.1, 10.2, 6.9 Hz, 1H), 5.15 (dq, J=17.1, 1.5 Hz, 1H), 5.08 (dd, J=10.2, 1.4 Hz, 1H), 4.34-4.18 (m, 3H), 3.03-2.90 (m, 1H), 2.90-2.73 (m, 1H), 1.35-1.22 (m, 3H).

Compound R1b. Ethyl 2-(6-phenylbenzo[d]thiazol-2-yl)pent-4-enoate

Compound R1b (120 mg, 29%) was prepared from Compound R1a as described in the general procedure given for Compound 55c. HPLC: RT=0.86 (LCMS Method M). MS(ES): m/z=419.7 [M+H]$^+$. $^1$H NMR (500 MHz, DMSO-d$_6$) δ 8.70-8.54 (m, 1H), 8.36 (d, J=1.9 Hz, 1H), 7.89 (d, J=8.8 Hz, 1H), 7.68-7.59 (m, 1H), 6.89 (s, 2H), 5.82-5.66 (m, 1H), 5.08 (dd, J=17.1, 1.7 Hz, 1H), 5.04-4.94 (m, 1H), 4.18 (dd, J=8.0, 7.2 Hz, 1H), 3.55-3.37 (m, 2H), 3.16-3.04 (m, 2H), 2.76 (d, J=1.1 Hz, 1H), 2.66 (d, J=7.2 Hz, 1H).

Reference 1

Reference 1 (14 mg, 46%) was prepared from Compound R1b as described in the general procedure given for Compound 1d. HPLC: RT=0.93 (LCMS Method M). MS(ES): m/z=416.0 [M+H]$^+$. $^1$H NMR (500 MHz, DMSO-d$_6$) δ 8.63 (t, J=5.8 Hz, 1H), 8.38 (d, J=1.4 Hz, 1H), 8.03 (d, J=8.5 Hz, 1H), 7.80 (dd, J=8.4, 1.8 Hz, 1H), 7.78-7.70 (m, 2H), 7.56-7.46 (m, 2H), 7.44-7.33 (m, 1H), 6.91 (s, 2H), 5.87-5.70 (m, 1H), 5.12 (dd, J=17.2, 1.8 Hz, 1H), 5.07-4.97 (m, 1H), 4.28-4.16 (m, 1H), 3.49 (td, J=13.9, 7.4 Hz, 2H), 3.18 (d, J=5.0 Hz, 1H), 3.13 (t, J=7.3 Hz, 2H), 2.87-2.76 (m, 1H), 2.77-2.65 (m, 1H).

Reference 2

N-((3-Isopropylisoxazol-5-yl)methyl)-2-methyl-2-(6-phenylbenzo[d]thiazol-2-yl)propanamide

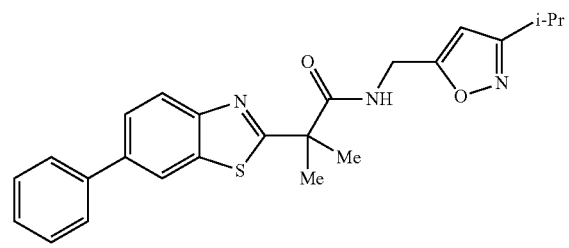 [SMILES: CC(C)c1cc(CNC(=O)C(C)(C)c2nc3ccc(-c4ccccc4)cc3s2)on1]

Reference 2 was prepared as described in the general procedure given for Reference 1. HPLC: RT=2.16 (LCMS Method B). MS(ES): m/z=420.1 [M+H]$^+$. $^1$H NMR (400 MHz, chloroform-d) δ 8.11-8.05 (m, 2H), 7.90 (m, 1H), 7.75 (dd, J=8.5, 1.8 Hz, 1H), 7.68-7.62 (m, 2H), 7.52-7.46 (m, 2H), 7.44-7.37 (m, 1H), 5.93 (s, 1H), 4.55 (dd, J=5.9, 0.6 Hz, 2H), 3.07-2.95 (m, 1H), 1.84 (s, 6H), 1.24 (s, 3H), 1.22 (s, 3H).

Reference 3

N-((3-Isopropylisoxazol-5-yl)methyl)-2-methyl-2-(6-phenylbenzo[d]thiazol-2-yl)propanamide

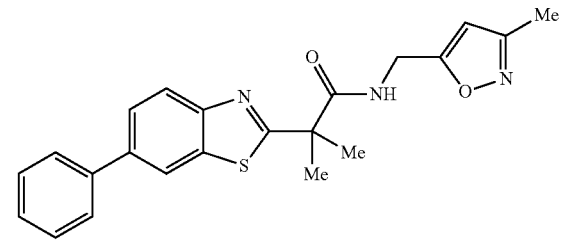 [SMILES: Cc1cc(CNC(=O)C(C)(C)c2nc3ccc(-c4ccccc4)cc3s2)on1]

Reference 3 was prepared as described in the general procedure given for Reference 1. HPLC: RT=1.97 (LCMS Method B). MS(ES): m/z=393.1 [M+H]$^+$. $^1$H NMR (400 MHz, chloroform-d) δ 8.12-8.06 (m, 2H), 7.77 (dd, J=8.5, 1.8 Hz, 1H), 7.67-7.62 (m, 2H), 7.53-7.46 (m, 2H), 7.44-7.38 (m, 1H), 4.70 (d, J=6.0 Hz, 2H), 2.55 (s, 3H), 1.86 (s, 6H).

| Ex. No. | Structure | Name | $^1$H NMR δ (500 MHz, DMSO-d$_6$, unless otherwise indicated) | LC/MS RT (min) Method M + H | EL IC$_{50}$ (nM) |
|---|---|---|---|---|---|
| 2 | 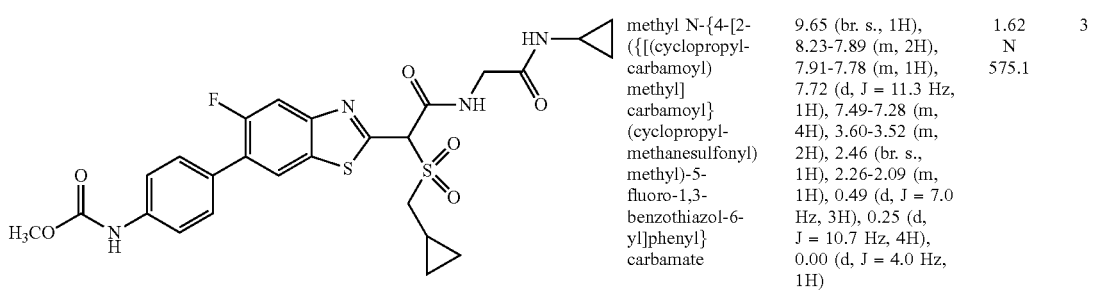 | methyl N-{4-[2-({[(cyclopropyl-carbamoyl)methyl]carbamoyl}(cyclopropyl-methanesulfonyl)methyl)-5-fluoro-1,3-benzothiazol-6-yl]phenyl}carbamate | 9.65 (br. s., 1H), 8.23-7.89 (m, 2H), 7.91-7.78 (m, 1H), 7.72 (d, J = 11.3 Hz, 1H), 7.49-7.28 (m, 4H), 3.60-3.52 (m, 2H), 2.46 (br. s., 1H), 2.26-2.09 (m, 1H), 0.49 (d, J = 7.0 Hz, 3H), 0.25 (d, J = 10.7 Hz, 4H), 0.00 (d, J = 4.0 Hz, 1H) | 1.62 N 575.1 | 3 |

-continued

| Ex. No. | Structure | Name | $^1$H NMR δ (500 MHz, DMSO-$d_6$, unless otherwise indicated) | LC/MS RT (min) EL ethod M + H | IC$_{50}$ (nM) |
|---|---|---|---|---|---|
| 3 | 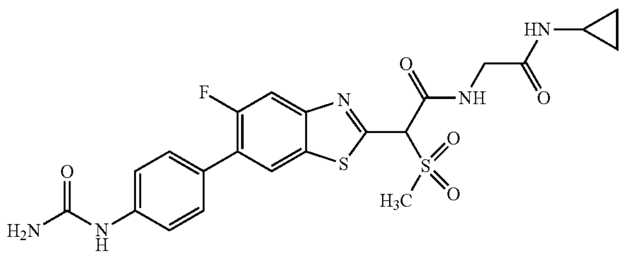 [SMILES: CS(=O)(=O)C(C(=O)NCC(=O)NC1CC1)c1nc2cc(F)c(-c3ccc(NC(N)=O)cc3)cc2s1] | 2-{6-[4-(carbamoyl-amino)phenyl]-5-fluoro-1,3-benzothiazol-2-yl}-N-[(cyclopropyl-carbamoyl)methyl]-2-methanesulfonyl-acetamide | 9.03 (br. s., 1H), 8.73 (s, 1H), 8.28 (d, J = 7.6 Hz, 1H), 8.09-7.99 (m, 2H), 7.94 (s,1H), 7.64-7.42 (m, 4H), 6.19 (s, 1H), 5.91 (br. s., 2H), 3.82 (d, J = 5.5 Hz, 2H), 2.63 (br. s., 1H), 0.62 (d, J = 5.5 Hz, 2H), 0.48-0.32 (m, 2H) | 1.1 N 520.1 | 3 |
| 4 | 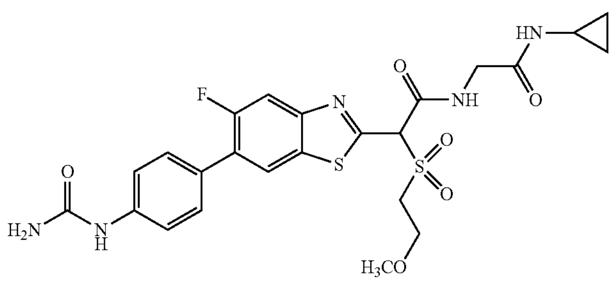 | 2-{6-[4-(carbamoyl-amino)phenyl]-5-fluoro-1,3-benzothiazol-2-yl}-N-[(cyclopropyl-carbamoyl)methyl]-2-(2-methoxy-ethanesulfonyl)acetamide | 8.99 (br. s., 1H), 8.75 (s, 1H), 8.26 (d, J = 7.6 Hz, 1H), 8.04-7.93 (m, 2H), 7.60-7.43 (m, 4H), 6.14 (s, 1H), 3.88-3.71 (m, 3H), 3.69 (d, J = 5.5 Hz, 1H), 3.62 (br. s., 2H), 3.25 (s, 3H), 2.61 (d, J = 3.7 Hz, 1H), 0.62 (d, J = 5.8 Hz, 2H), 0.38 (br. s., 2H) | 1.17 N 564.6 | 9 |
| 5 | 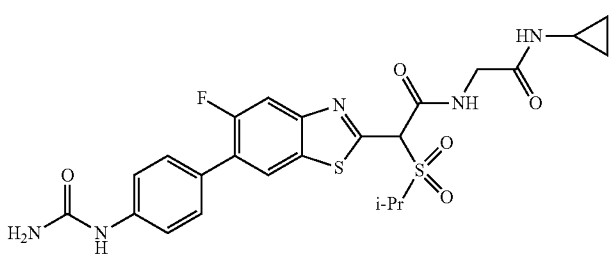 | 2-{6-[4-(carbamoyl-amino)phenyl]-5-fluoro-1,3-benzothiazol-2-yl}-N-[(cyclopropyl-carbamoyl)methyl]-2-(propane-2-sulfonyl)acetamide | 9.11 (br. s., 1H), 8.77-8.67 (m, 1H), 8.26 (d, J = 7.6 Hz, 1H), 8.05-7.81 (m, 3H), 7.63-7.44 (m, 3H), 7.40 (br. s., 1H), 6.32 (s, 1H), 3.91-3.73 (m, 2H), 3.61-3.46 (m, 1H), 2.62 (d, J = 4.0 Hz, 1H), 1.36 (d, J = 6.7 Hz, 2H), 1.26 (d, J = 6.7 Hz, 4H), 0.62 (d, J = 5.8 Hz, 2H), 0.39 (br. s., 2H) | 1.25 N 548.2 | 9 |
| 6 | 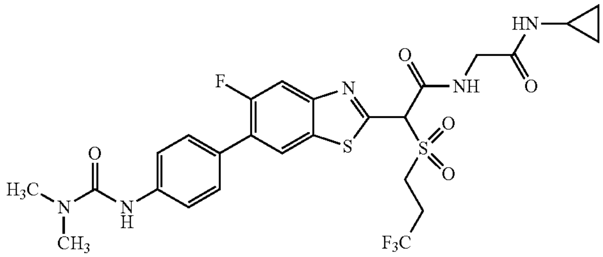 [SMILES: CN(C)C(=O)Nc1ccc(-c2cc3sc(C(C(=O)NCC(=O)NC4CC4)S(=O)(=O)CCC(F)(F)F)nc3cc2F)cc1] | N-[(cyclopropyl-carbamoyl)methyl]-2-(6-{4-[(dimethyl-carbamoyl)amino]phenyl}-5-fluoro-1,3-benzothiazol-2-yl)-2-(3,3,3-trifluoropropane-sulfonyl)acetamide | 9.17 (br. s., 1H), 8.63-8.43 (m, 1H), 8.37 (d, J = 7.3 Hz, 1H), 8.14 (br. s., 1H), 8.08 (d, J = 11.3 Hz, 1H), 8.00 (br. s., 1H), 7.70-7.55 (m, 4H), 3.99 (br. s., 6H), 3.03 (s, 6H), 2.70 (br. s., 1H), 0.73 (d, J = 6.4 Hz, 2H), 0.48 (br. s., 2H) | 1.53 N 630.2 | 3 |

-continued

| Ex. No. | Structure | Name | $^1$H NMR δ (500 MHz, DMSO-$d_6$, unless otherwise indicated) | LC/MS RT (min) ethod M + H | EL IC$_{50}$ (nM) |
|---|---|---|---|---|---|
| 7 | 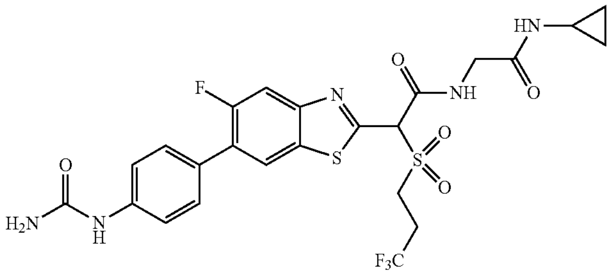 [SMILES: NC(=O)Nc1ccc(-c2cc3sc(C(C(=O)NCC(=O)NC4CC4)S(=O)(=O)CCC(F)(F)F)nc3cc2F)cc1] | 2-{6-[4-(carbamoyl-amino)phenyl]-5-fluoro-1,3-benzothiazol-2-yl}-N-[(cyclopropyl-carbamoyl)methyl]-2-(3,3,3-trifluoropropane-sulfonyl)acetamide | 8.75 (s, 1H), 8.27 (d, J = 7.6 Hz, 1H), 8.06 (d, J = 3.4 Hz, 1H), 7.98 (d, J = 11.3 Hz, 1H), 7.92 (s, 1H), 7.59-7.43 (m, 4H), 7.43-7.33 (m, 1H), 5.99-5.80 (m, 2H), 3.88-3.66 (m, 2H), 3.66-3.49 (m, 2H), 2.85-2.77 (m, 1H), 2.61 (d, J = 3.4 Hz, 2H), 0.61 (d, J = 6.7 Hz, 2H), 0.38 (br. s., 2H) | 1.32 N 602.1 | 5 |
| 8 | 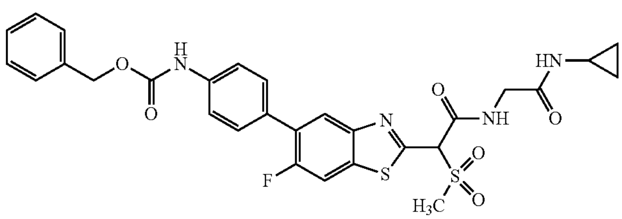 [SMILES: CS(=O)(=O)C(C(=O)NCC(=O)NC1CC1)c1nc2cc(-c3ccc(NC(=O)OCc4ccccc4)cc3)c(F)cc2s1] | benzyl N-{4-[2-({[(cyclopropyl-carbamoyl)methyl]carbamoyl}(methane-sulfonyl)methyl)-6-fluoro-1,3-benzothiazol-5-yl]phenyl}carbamate | 9.96 (br. s., 1H), 9.05 (br. s., 1H), 8.26-8.09 (m, 2H), 8.05 (br. s., 1H), 7.96 (s, 1H), 7.70-7.54 (m, 4H), 7.50-7.27 (m, 5H), 5.20 (s, 2H), 3.84 (d, J = 5.5 Hz, 2H), 3.28 (s, 3H), 2.65 (d, J = 3.7 Hz, 1H), 0.64 (d, J = 6.7 Hz, 2H), 0.41 (br. s., 2H) | 1.85 N 611.1 | 1 |
| 9 | 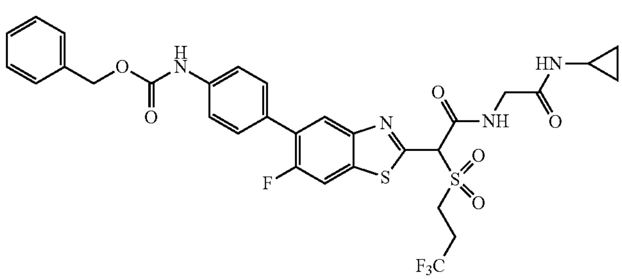 [SMILES: O=C(CNC(=O)C(c1nc2cc(-c3ccc(NC(=O)OCc4ccccc4)cc3)c(F)cc2s1)S(=O)(=O)CCC(F)(F)F)NC1CC1] | benzyl N-{4-[2-({[(cyclopropyl-carbamoyl)methyl]carbamoyl}(3,3,3-trifluoro-propanesulfonyl)methyl)-6-fluoro-1,3-benzothiazol-5-yl]phenyl}carbamate | 9.92 (br. s., 1H), 9.07-8.97 (m, 1H), 8.23-8.08 (m, 2H), 8.06 (d, J = 4.0Hz, 1H), 7.91 (s, 1H), 7.65-7.45 (m, 4H), 7.45-7.21 (m, 5H), 6.32 (s, 1H), 5.16 (s, 2H), 3.81 (t, J = 5.2 Hz, 1H), 3.76 (s, 1H), 2.86-2.76 (m, 2H), 2.61 (d, J = 4.0 Hz, 1H), 2.53 (t, J = 5.6 Hz, 2H), 0.61 (d, J = 6.7 Hz, 2H), 0.48-0.24 (m, 2H) | 2.05 N 693.2 | 1 |
| 10 | 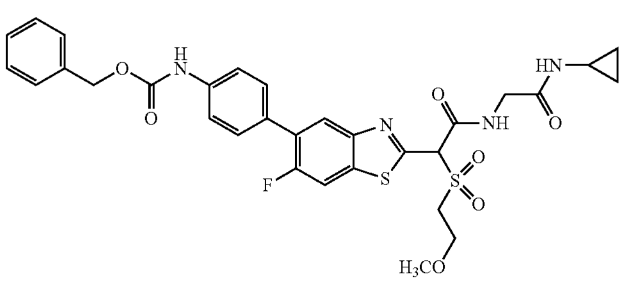 [SMILES: COCCS(=O)(=O)C(C(=O)NCC(=O)NC1CC1)c1nc2cc(-c3ccc(NC(=O)OCc4ccccc4)cc3)c(F)cc2s1] | benzyl N-{4-[2-({[(cyclopropyl-carbamoyl)methyl]carbamoyl}(2-methoxyethane-sulfonyl)methyl)-6-fluoro-1,3-benzothiazol-5-yl]phenyl}carbamate | 9.94 (br. s., 1H), 9.02-8.95 (m, 1H), 8.23-8.05 (m, 2H), 8.01 (d, J = 3.4 Hz, 1H), 7.68-7.52 (m, 4H), 7.52-7.31 (m, 5H), 6.16 (s, 1H), 5.17 (s, 2H), 3.89-3.65 (m, 5H), 3.47 (s, 1H), 3.22-2.99 (m, 3H), 2.67-2.52 (m, 1H), 0.62 (d, J = 5.8 Hz, 2H), 0.38 (br. s., 2H) | 1.89 N 655.2 | 1 |

-continued

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 11 | 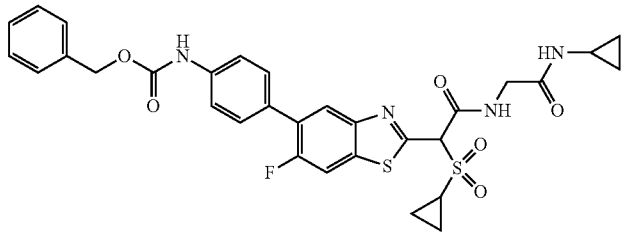 [SMILES: O=C(CNC(=O)C(c1nc2cc(-c3ccc(NC(=O)OCc4ccccc4)cc3)c(F)cc2s1)S(=O)(=O)C1CC1)NC1CC1] | benzyl N-(4-{2-[(cyclopropane-sulfonyl)({[(cyclopropyl-carbamoyl)methyl]carbamoyl})methyl]6-fluoro-1,3-benzothiazol-5-yl}phenyl)carbamate | 9.94 (br. s., 1H), 9.10 (br. s., 1H), 8.28-8.05 (m, 2H), 8.02 (br. s., 1H), 7.67-7.52 (m, 4H), 7.50-7.28 (m, 5H), 6.23 (s, 1H), 5.17 (s, 2H), 3.89-3.74 (m, 2H), 3.53-3.31 (m, 1H), 2.62 (d, J = 3.7 Hz, 1H), 1.08 (d, J = 7.3 Hz, 2H), 0.97 (br. s., 1H), 0.93 (br. s., 1H), 0.62 (d, J = 6.7 Hz, 2H), 0.38 (br. s., 2H) | 1.88 N 637.2 | 1 |
| 12 | 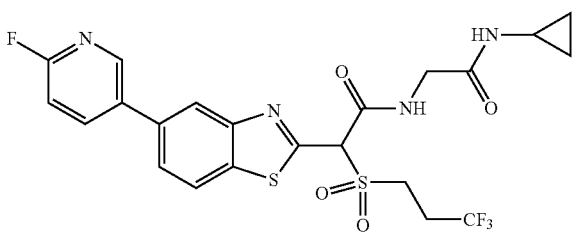 [SMILES: O=C(CNC(=O)C(c1nc2cc(-c3ccc(F)nc3)ccc2s1)S(=O)(=O)CCC(F)(F)F)NC1CC1] | N-[(cyclopropyl-carbamoyl)methyl]-2-[5-(6-fluoropyridin-3-yl)-1,3-benzothiazol-2-yl]-2-(3,3,3-trifluoropropane-sulfonyl)acetamide | 9.01 (t, J = 5.4 Hz, 1H), 8.69 (d, J = 2.2 Hz, 1H), 8.49-8.39 (m, 2H), 8.30 (d, J = 8.5 Hz, 1H), 8.07 (d, J = 3.9 Hz, 1H), 7.89 (d, J = 8.3 Hz, 1H), 7.32 (dd, J = 8.5, 2.8 Hz, 1H), 6.40 (s, 1H), 3.92-3.70 (m, 4H), 2.90-2.80 (m, 2H), 2.64-2.58 (m, 1H), 0.66-0.57 (m, 2H), 0.40 (d, J = 2.2 Hz, 2H) | 2.08 B 545.1 | 7 |
| 13 | 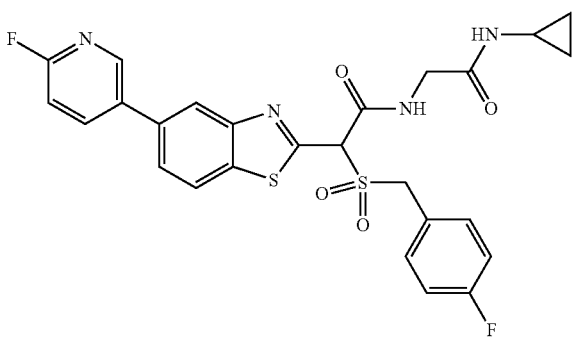 [SMILES: O=C(CNC(=O)C(c1nc2cc(-c3ccc(F)nc3)ccc2s1)S(=O)(=O)Cc1ccc(F)cc1)NC1CC1] | N-[(cyclopropyl-carbamoyl)methyl]-2-[(4-fluorophenyl)methanesulfonyl]-2-[5-(6-fluoropyridin-3-yl)-1,3-benzothiazol-2-yl]acetamide | 8.70 (d, J = 2.2 Hz, 1H), 8.55-8.38 (m, 2H), 8.29 (d, J = 8.3 Hz, 1H), 8.12-8.02 (m, 1H), 7.87 (dd, J = 13.3, 8.4 Hz, 1H), 7.61-7.45 (m, 2H), 7.23 (t, J = 8.8 Hz, 3H), 7.12-6.99 (m, 1H), 6.26 (s, 1H), 4.85-4.61 (m, 2H), 3.88-3.73 (m, 2H), 2.64 (tt, J = 7.3, 3.7 Hz, 1H), 0.66-0.58 (m, 2H), 0.42-0.35 (m, 2H) | 2.07 B 557.2 | 15 |
| 14 | 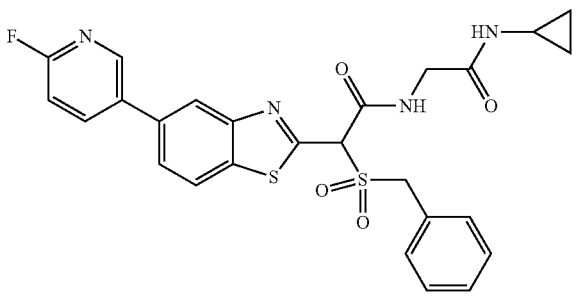 [SMILES: O=C(CNC(=O)C(c1nc2cc(-c3ccc(F)nc3)ccc2s1)S(=O)(=O)Cc1ccccc1)NC1CC1] | N-[(cyclopropyl-carbamoyl)methyl]-2-[5-(6-fluoropyridin-3-yl)-1,3-benzothiazol-2-yl]-2-phenylmethane-sulfonylacetamide | 9.08 (t, J = 5.4 Hz, 1H), 8.70 (s, 1H), 8.54-8.39 (m, 2H), 8.29 (d, J = 8.3 Hz, 1H), 8.17-8.00 (m, 1H), 7.93-7.81 (m, 1H), 7.44-7.13 (m, 6H), 6.29 (s, 1H), 4.84-4.58 (m, 2H), 3.85-3.72 (m, 2H), 2.64 (dt, J = 7.2, 3.6 Hz, 1H), 0.67-0.56 (m, 2H), 0.46-0.32 (m, 2H) | 1.79 O 539 | 23 |

-continued

| Ex. No. | Structure | Name | $^1$H NMR δ (500 MHz, DMSO-$d_6$, unless otherwise indicated) | LC/MS RT (min) ethod M + H | EL IC$_{50}$ (nM) |
|---|---|---|---|---|---|
| 15 | 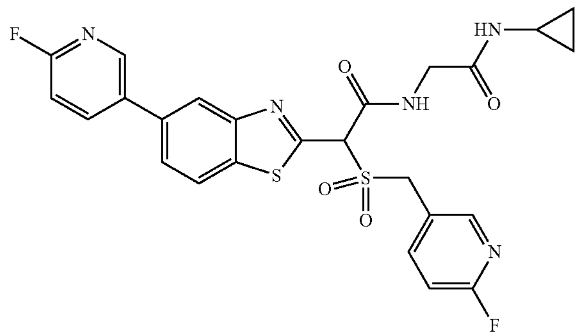 | N-[(cyclopropylcarbamoyl)methyl]-2-[5-(6-fluoropyridin-3-yl)-1,3-benzothiazol-2-yl]-2-[(6-fluoropyridin-3-yl)methanesulfonyl]acetamide | 9.09 (t, J = 5.2 Hz, 1H), 8.72 (s, 1H), 8.59-8.41 (m, 2H), 8.36-8.28 (m, 1H), 8.22-8.07 (m, 2H), 8.00-7.89 (m, 2H), 7.42-7.08 (m, 2H), 6.29 (s, 1H), 5.00-4.77 (m, 2H), 3.96-3.75 (m, 2H), 2.76-2.62 (m, 1H), 0.70-0.59 (m, 2H), 0.48-0.36 (m, 2H) | 1.81 B 558.2 | 29 |
| 16 | 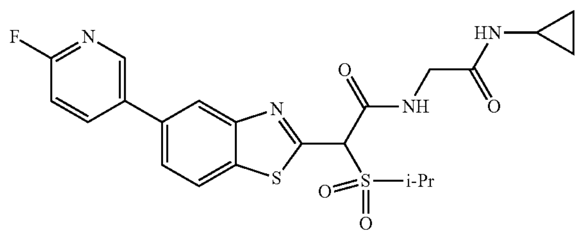 [SMILES: CC(C)S(=O)(=O)C(C(=O)NCC(=O)NC1CC1)c1nc2cc(-c3ccc(F)nc3)ccc2s1] | N-[(cyclopropylcarbamoyl)methyl]-2-[5-(6-fluoropyridin-3-yl)-1,3-benzothiazol-2-yl]-2-(propane-2-sulfonyl)acetamide | 9.10 (t, J = 5.5 Hz, 1H), 8.68 (d, J = 2.2 Hz, 1H), 8.48-8.38 (m, 2H), 8.28 (d, J = 8.3 Hz, 1H), 7.91-7.82 (m, 1H), 7.32 (dd, J = 8.5, 3.0 Hz, 1H), 6.38 (s, 1H), 3.93-3.75 (m, 2H), 3.59 (dt, J = 13.6, 6.9 Hz, 1H), 2.63 (td, J = 7.2, 3.7 Hz, 1H), 1.38 (d, J = 6.6 Hz, 2H), 1.33-1.24 (m, 4H), 0.62 (d, J = 5.5 Hz, 2H), 0.40 (br. s., 2H) | 1.96 B 491.1 | 39 |
| 17 | 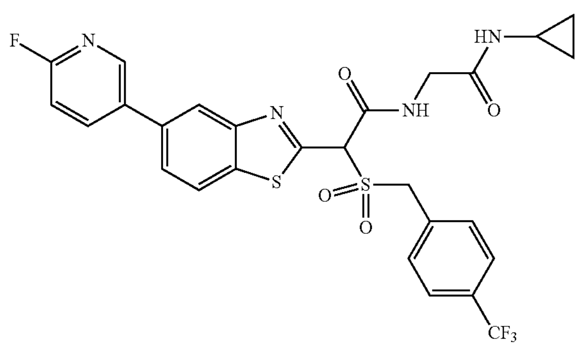 [SMILES: O=C(CNC(=O)C(c1nc2cc(-c3ccc(F)nc3)ccc2s1)S(=O)(=O)Cc1ccc(C(F)(F)F)cc1)NC1CC1] | N-[(cyclopropylcarbamoyl)methyl]-2-[5-(6-fluoropyridin-3-yl)-1,3-benzothiazol-2-yl]-2-{[4-(trifluoromethyl)phenyl]methanesulfonyl}acetamide | 9.09 (t, J = 5.2 Hz, 1H), 8.71 (s, 1H), 8.50-8.43 (m, 1H), 8.30 (d, J = 8.3 Hz, 1H), 8.07 (d, J = 3.3 Hz, 1H), 7.90 (d, J = 8.5 Hz, 1H), 7.77 (d, J = 8.0 Hz, 1H), 7.67 (d, J = 8.0 Hz, 2H), 7.62-7.55 (m, 2H), 7.35 (d, J = 6.6 Hz, 1H), 6.32 (s, 1H), 5.00-4.75 (m, 2H), 3.89-3.74 (m, 2H), 2.69-2.61 (m, 1H), 0.64 (d, J = 6.3 Hz, 2H), 0.47-0.35 (m, 2H) | 1.81 O 604.9 (M − H) | 46 |
| 18 | 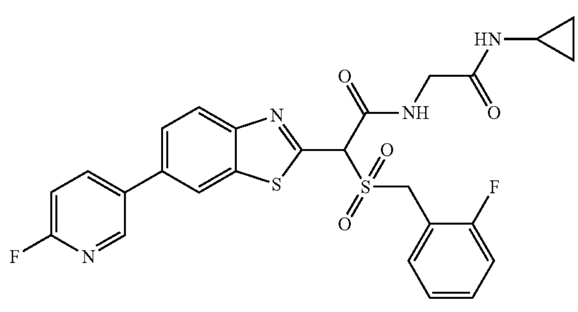 [SMILES: O=C(CNC(=O)C(c1nc2ccc(-c3ccc(F)nc3)cc2s1)S(=O)(=O)Cc1ccccc1F)NC1CC1] | N-[(cyclopropylcarbamoyl)methyl]-2-[(2-fluorophenyl)methanesulfonyl]-2-[6-(6-fluoropyridin-3-yl)-1,3-benzothiazol-2-yl]acetamide | 9.11 (t, J = 5.50 Hz, 1H), 8.52-8.69 (m, 2H), 8.36-8.43 (m, 1H), 8.22 (d, J = 8.53 Hz, 1H), 8.05 (d, J = 3.85 Hz, 1H), 7.93 (d, J = 8.53 Hz, 1H), 7.38-7.49 (m, 2H), 7.20-7.30 (m, 2H), 7.00 (s, 1H), 6.40 (s, 1H), 4.83-4.99 (m, 1H), 4.65-4.78 (m, 1H), 3.85 (d, J = 5.23 Hz, 1H), 3.68-3.83 (m, 1H), 2.61-2.67 (m, 1H), 0.62 (d, J = 6.60 Hz, 2H), 0.37-0.45 (m, 2H) | 0.89 O 557.2 | 253 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 19 | 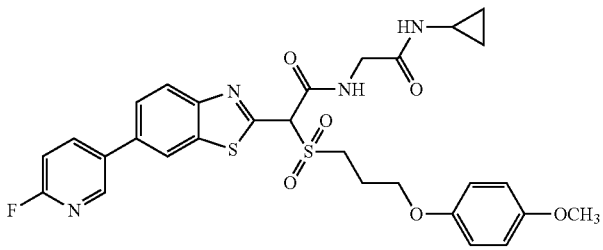 [SMILES: COc1ccc(OCCCS(=O)(=O)C(C(=O)NCC(=O)NC2CC2)c2nc3ccc(-c4ccc(F)nc4)cc3s2)cc1] | N-[(cyclopropylcarbamoyl)methyl]-2-[6-(6-fluoropyridin-3-yl)-1,3-benzothiazol-2-yl]-2-[3-(4-methoxyphenoxy)propanesulfonyl]acetamide | 9.07 (t, J = 5.36 Hz, 1H), 8.65 (s, 1H), 8.55 (s, 1H), 8.39 (t, J = 7.29 Hz, 1H), 8.17 (d, J = 8.53 Hz, 1H), 8.03 (d, J = 3.85 Hz, 1H), 7.92 (d, J = 8.53 Hz, 1H), 7.34 (dd, J = 2.06, 8.67 Hz, 1H), 6.82-6.87 (m, 4H), 6.32 (s, 1H), 4.02 (t, J = 5.91 Hz, 2H), 3.84 (t, J = 6.33 Hz, 2H), 3.68 (s, 3H), 3.57 (dd, J = 7.29, 14.44 Hz, 2H), 2.63 (dt, J = 3.71, 7.22 Hz, 1H), 2.13-2.18 (m, 2H), 0.62 (d, J = 7.15 Hz, 2H), 0.39 (br. s., 2H) | 0.91 O 613.2 | 7 |
| 20 | 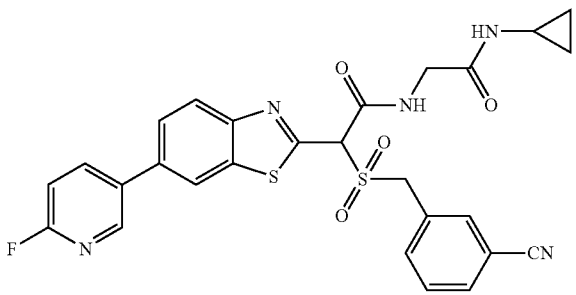 [SMILES: N#Cc1cccc(CS(=O)(=O)C(C(=O)NCC(=O)NC2CC2)c2nc3ccc(-c4ccc(F)nc4)cc3s2)c1] | 2-[(3-cyanophenyl)methanesulfonyl]-N-[(cyclopropylcarbamoyl)methyl]-2-[6-(6-fluoropyridin-3-yl)-1,3-benzothiazol-2-yl]acetamide | 9.08 (t, J = 5.23 Hz, 1H), 8.52-8.68 (m, 1H), 8.39 (t, J = 7.84 Hz, 1H), 8.21 (d, J = 8.53 Hz, 1H), 8.03-8.16 (m, 2H), 7.93 (d, J = 8.53 Hz, 1H), 7.84-7.88 (m, 1H), 7.75-7.82 (m, 1H), 7.61 (t, J = 7.70 Hz, 1H), 7.27-7.38 (m, 1H), 6.29 (s, 1H), 4.90 (d, J = 6.88 Hz, 1H), 4.76-4.85 (m, 1H), 3.81-3.85 (m, 1H), 3.73-3.81 (m, 1H), 2.64 (dd, J = 3.58, 7.15 Hz, 1H), 0.63 (t, J = 6.19 Hz, 2H), 0.38-0.44 (m, 2H) | 0.87 O 564.2 | 46 |
| 21 | 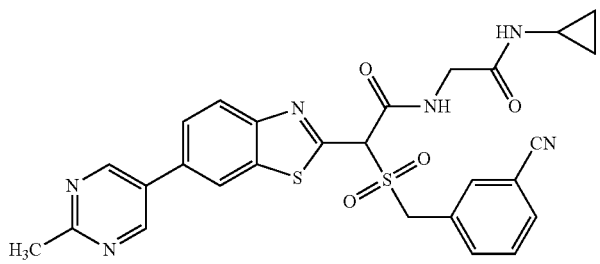 [SMILES: Cc1ncc(-c2ccc3nc(C(C(=O)NCC(=O)NC4CC4)S(=O)(=O)Cc4cccc(C#N)c4)sc3c2)cn1] | 2-[(3-cyanophenyl)methanesulfonyl]-N-[(cyclopropylcarbamoyl)methyl]-2-[6-(2-methylpyrimidin-5-yl)-1,3-benzothiazol-2-yl]acetamide | 9.12 (s, 2H), 8.98-9.11 (m, 1H), 8.62 (s, 1H), 8.17-8.26 (m, 1H), 7.98-8.08 (m, 1H), 7.85-7.89 (m, 1H), 7.74-7.84 (m, 1H), 7.59-7.65 (m, 1H), 6.29 (s, 1H), 4.90 (d, J = 6.33 Hz, 1H), 4.81-4.87 (m, 1H), 3.81-3.86 (m, 1H), 3.78 (d, J = 15.96 Hz, 1H), 2.69 (s, 1H), 2.63-2.67 (m, 3H), 0.63 (t, J = 5.36 Hz, 2H), 0.38-0.46 (m, 2H) | 0.75 O 561.1 | 145 |

-continued

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 22 | 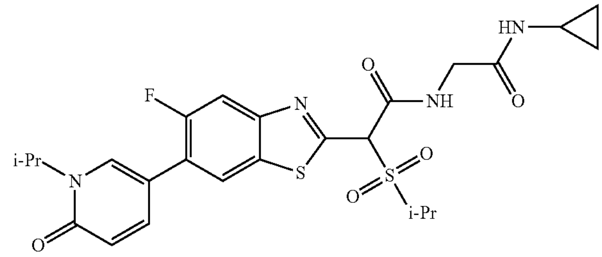 [SMILES: CC(C)n1cc(-c2cc3sc(C(C(=O)NCC(=O)NC4CC4)S(=O)(=O)C(C)C)nc3cc2F)ccc1=O] | N-[(cyclopropyl-carbamoyl)methyl]-2-{5-fluoro-6-[6-oxo-1-(propan-2-yl)-1,6-dihydropyridin-3-yl]-1,3-benzothiazol-2-yl}-2-(propane-2-sulfonyl)acetamide | 9.11 (br. s., 1H), 8.30 (d, J = 7.63 Hz, 1H), 8.01 (d, J = 10.68 Hz, 1H), 7.84-7.99 (m, 1H), 7.64-7.79 (m, 1H), 6.45-6.54 (m, 1H), 6.33 (s, 1H), 5.03-5.19 (m, 1H), 3.77-3.92 (m, 1H), 3.56 (d, J = 10.38 Hz, 2H), 2.62 (br. s., 1H), 1.23-1.37 (m, 12H), 0.62 (d, J = 6.71 Hz, 2H), 0.39 (br. s., 2H) | 0.76 O 549.3 | 37 |
| 23 | 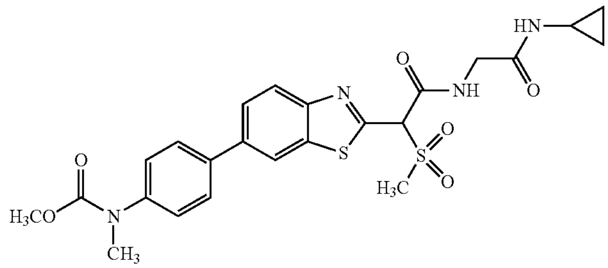 [SMILES: COC(=O)N(C)c1ccc(-c2ccc3nc(C(C(=O)NCC(=O)NC4CC4)S(C)(=O)=O)sc3c2)cc1] | methyl N-{4-[2-({[(cyclopropyl-carbamoyl)methyl]carbamoyl}(methanesulfonyl)methyl)-1,3-benzothiazol-6-yl]phenyl}-N-methylcarbamate | 9.33 (d, J = 9.8 Hz, 1H), 9.01 (br. s., 1H), 8.58-8.26 (m, 1H), 8.14-7.87 (m, 2H), 7.85-7.65 (m, 3H), 7.47-7.29 (m, 2H), 3.95-3.76 1H), 3.69-3.57 (m, 1H), 3.21 (br. s., 3H), 2.59 (d, J = 14.3 Hz, 1H), 2.46 (br. s., 3H), 2.32 (s, 3H), 0.66-0.54 (m, 2H), 0.43-0.30 (m, 2H). | 1.42 N 531.1 | 14 |
| 24 | 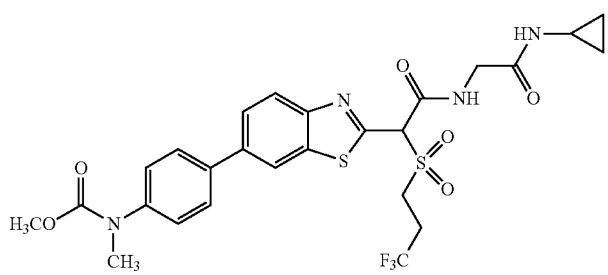 [SMILES: COC(=O)N(C)c1ccc(-c2ccc3nc(C(C(=O)NCC(=O)NC4CC4)S(=O)(=O)CCC(F)(F)F)sc3c2)cc1] | methyl N-{4-[2-({[(cyclopropyl-carbamoyl)methyl]carbamoyl}(3,3,3-trifluoropropane-sulfonyl)methyl)-1,3-benzothiazol-6-yl]phenyl}-N-methylcarbamate | 8.48-8.28 (m, 1H), 8.23-7.91 (m, 2H), 7.90-7.63 (m, 4H), 7.53-7.34 (m, 3H), 3.73-3.51 (m, 2H), 3.32-3.19 (m, 3H), 2.94-2.82 (m, 1H), 2.78-2.70 (m, 1H), 2.67-2.58 (m, 3H), 2.54 (br. s., 3H), 0.65 (d, J = 6.4 Hz, 2H), 0.47-0.30 (m, 2H) | 1.71 N 613.1 | 6 |
| 25 | 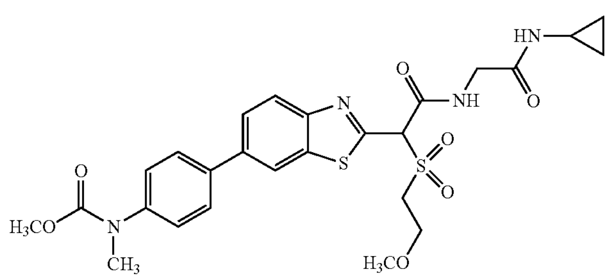 [SMILES: COCCS(=O)(=O)C(C(=O)NCC(=O)NC1CC1)c1nc2ccc(-c3ccc(N(C)C(=O)OC)cc3)cc2s1] | methyl N-{4-[2-({[(cyclopropyl-carbamoyl)methyl]carbamoyl}(2-methoxyethane-sulfonyl)methyl)-1,3-benzothiazol-6-yl]phenyl}-N-methylcarbamate | 8.50-8.26 (m, 2H), 8.18-8.07 (m, 1H), 8.06-7.94 (m, 1H), 7.91-7.64 (m, 4H), 7.52-7.33 (m, 2H), 3.78-3.67 (m, 2H), 3.61 (s, 1H), 3.59-3.49 (m, 1H), 3.34-3.21 (m, 6H), 3.21-3.15 (m, 3H), 2.79-2.55 (m, 3H), 0.72-0.57 (m, 2H), 0.45-0.29 (m, 2H) | 1.49 N 575.2 | 7 |
| 26 | 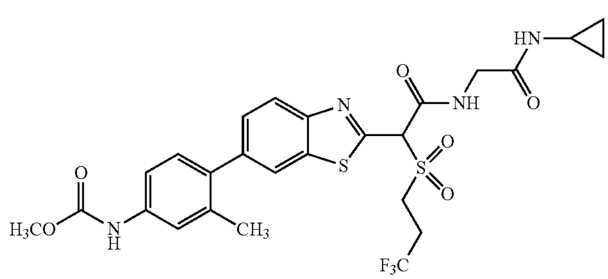 [SMILES: COC(=O)Nc1ccc(-c2ccc3nc(C(C(=O)NCC(=O)NC4CC4)S(=O)(=O)CCC(F)(F)F)sc3c2)c(C)c1] | methyl N-{4-[2-({[(cyclopropyl-carbamoyl)methyl]carbamoyl}(3,3,3-trifluoropropane-sulfonyl)methyl)-1,3-benzothiazol-6-yl]-3-ethylphenyl}carbamate | 9.62-9.36 (m, 1H), 8.92-8.75 (m, 1H), 7.95-7.81 (m, 2H), 7.71 (s, 1H), 7.29 (d, J = 8.4 Hz, 1H), 7.22-7.08 (m, 2H), 7.03-6.89 (m, 1H), 3.71-3.51 (m, 3H), 3.45 (br. s., 1H), 2.75-2.60 (m, 3H), 2.43-2.34 (m, 1H), 2.28 (br. s., 3H), 2.10-1.79 (m, 2H), 0.56-0.36 (m, 2H), 0.17 (br. s., 2H) | 1.73 N 613.1 | 7 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 27 | 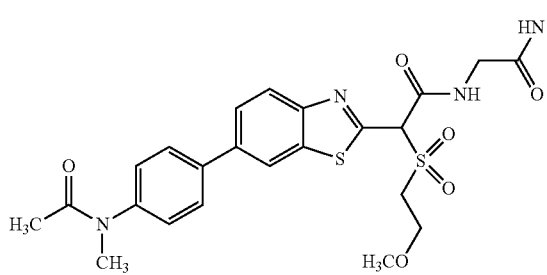 | N-[(cyclopropyl-carbamoyl)methyl]-2-(2-methoxy-ethanesulfonyl)-2-{6-[4-(N-methylacetamido)phenyl]-1,3-benzothiazol-2-yl}acetamide | 9.01 (br. s., 1H), 8.50 (br. s., 1H), 8.31-7.70 (m, 5H), 7.46 (br. s., 2H), 4.00-3.67 (m, 11H), 3.39-3.14 (m, 3H), 2.63 (br. s., 1H), 1.85 (br. s., 3H), 0.62 (d, J = 6.7 Hz, 2H), 0.39 (br. s., 2H) | 1.36 N 559.2 | 58 |
| 28 | 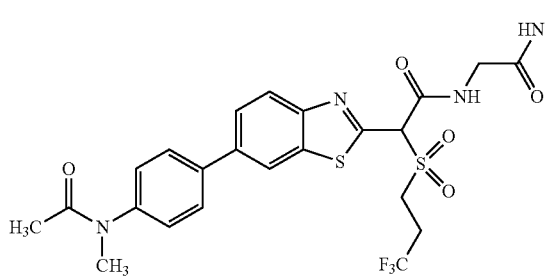 | N-[(cyclopropyl-carbamoyl)methyl]-2-{6-[4-(N-methylacetamido)phenyl]-1,3-benzothiazol-2-yl}-2-(3,3,3-trifluoropropane-sulfonyl)acetamide | 9.04 (br. s., 1H), 8.59-8.43 (m, 1H), 8.23-7.66 (m, 5H), 7.46 (d, J = 7.4 Hz, 2H), 3.98-3.70 (m, 3H), 3.47 (d, J = 8.4 Hz, 3H), 3.19 (br. s., 1H), 2.95-2.83 (m, 2H), 2.69-2.57 (m, 1H), 2.11-1.71 (m, 3H), 0.69-0.56 (m, 2H), 0.38 (br. s., 2H) | 1.58 N 5.97.1 | 54 |
| 29 | 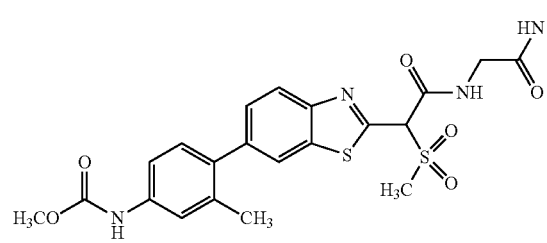 | methyl N-{4-[2-({[(cyclopropyl-carbamoyl)methyl]carbamoyl}(methanesulfonyl)methyl)-1,3-benzothiazol-6-yl]-3-methylphenyl}carbamate | 9.70 (br. s., 1H), 9.04 (br. s., 1H), 8.18-7.92 (m, 3H), 7.50 (d, J = 8.4 Hz, 1H), 7.46-7.34 (m, 2H), 7.20 (d, J = 8.1 Hz, 1H), 6.19 (s, 1H), 3.93-3.77 (m, 2H), 3.68 (s, 3H), 3.28 (s, 3H), 2.63 (d, J = 3.7 Hz, 1H), 2.30-2.14 (m, 3H), 0.62 (d, J = 6.1 Hz, 2H), 0.39 (br. s., 2H) | 1.49 N 531.1 | 20 |
| 30 | 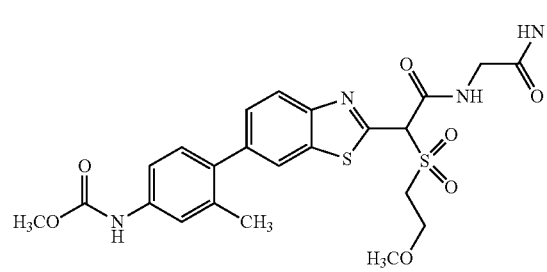 | methyl N-{4-[2-({[(cyclopropylcarbamoyl)methyl]carbamoyl}(2-methoxyethane-sulfonyl)methyl)-1,3-benzothiazol-6-yl]-3-methylphenyl}carbamate | 9.93-9.55 (m, 1H), 9.00 (t, J = 5.2 Hz, 1H), 8.17-7.98 (m, 3H), 7.50 (d, J = 8.4 Hz, 1H), 7.45-7.28 (m, 2H), 7.29-7.02 (m, 1H), 6.17 (s, 1H), 3.97-3.58 (m, 8H), 3.50 (d, J = 7.1 Hz, 1H), 3.33-3.18 (m, 3H), 2.66-2.57 (m, 1H), 2.35-2.04 (m, 3H), 0.62 (d, J = 5.7 Hz, 2H), 0.38 (br. s., 2H) | 1.52 N 575.2 | 21 |

-continued

| Ex. No. | Structure | Name | $^1$H NMR δ (500 MHz, DMSO-$d_6$, unless otherwise indicated) | LC/MS RT (min) ethod M + H | EL IC$_{50}$ (nM) |
|---|---|---|---|---|---|
| 31 | 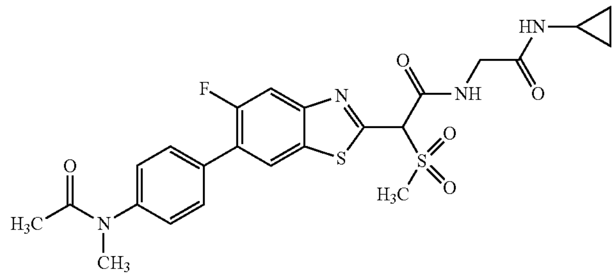 [SMILES: CC(=O)N(C)c1ccc(-c2cc3sc(C(C(=O)NCC(=O)NC4CC4)S(C)(=O)=O)nc3cc2F)cc1] | N-[(cyclopropyl-carbamoyl)methyl]-2-{5-fluoro-6-[4-(N-methylacetamido)phenyl]-1,3-benzothiazol-2-yl}-2-methanesulfonyl-acetamide | 9.13-8.64 (m, 1H), 8.21-8.04 (m, 1H), 7.95-7.77 (m, 2H), 7.72 (s, 1H), 7.45 (br. s., 2H), 7.26 (d, J = 7.1 Hz, 2H), 5.98 (s, 1H), 3.60 (d, J = 5.4 Hz, 2H), 3.05 (s, 2H), 2.45-2.34 (m, 1H), 2.33-2.19 (m, 3H), 1.63 (br. s., 3H), 0.40 (d, J = 6.1 Hz, 2H), 0.16 (br. s., 2H) | 1.23 N 533.1 | 11 |
| 32 | 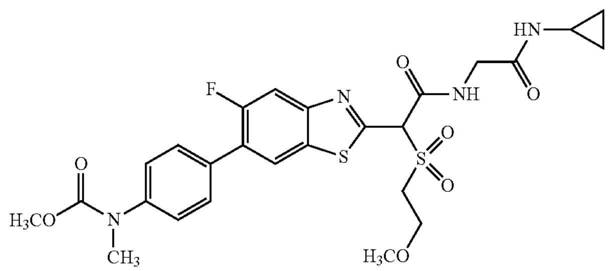 | methyl N-{4-[2-({[(cyclopropyl-carbamoyl)methyl]carbamoyl}(2-methoxyethane-sulfonyl)methyl)-5-fluoro-1,3-benzothiazol-6-yl]phenyl}-N-methylcarbamate | 8.79 (t, J = 5.2 Hz, 1H), 8.12 (d, J = 7.4 Hz, 1H), 7.93-7.79 (m, 2H), 7.75-7.68 (m, 1H), 7.38 (d, J = 7.7 Hz, 2H), 7.27-7.11 (m, 2H), 5.98 (s, 1H), 3.76-3.45 (m, 6H), 3.41 (s, 3H), 3.10-3.02 (m, 3H), 2.40 (dd, J = 7.2, 3.5 Hz, 1H), 2.28 (br. s., 3H), 0.40 (d, J = 5.7 Hz, 2H), 0.17 (d, J = 2.4 Hz, 2H) | 1.5 N 593.2 | 6 |
| 33 | 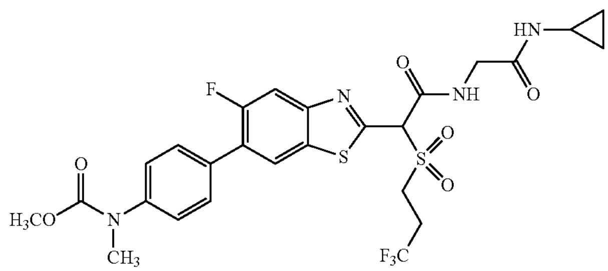 [SMILES: COC(=O)N(C)c1ccc(-c2cc3sc(C(C(=O)NCC(=O)NC4CC4)S(=O)(=O)CCC(F)(F)F)nc3cc2F)cc1] | methyl N-{4-[2-({[(cyclopropyl-carbamoyl)methyl]carbamoyl}(3,3,3-trifluoropropane-sulfonyl)methyl)-5-fluoro-1,3-benzothiazol-6-yl]phenyl}-N-methylcarbamate | 8.22-8.03 (m, 1H), 7.94-7.76 (m, 2H), 7.74-7.66 (m, 1H), 7.44-7.27 (m, 2H), 7.26-7.07 (m, 2H), 6.16 (s, 1H), 3.89-3.46 (m, 3H), 3.41 (s, 3H), 3.34-3.18 (m, 1H), 2.44-2.37 (m, 1H), 2.36-2.14 (m, 4H), 0.66-0.31 (m, 2H), 0.17 (d, J = 2.0 Hz, 2H) | 1.66 N 631.1 | 4 |
| 34 | 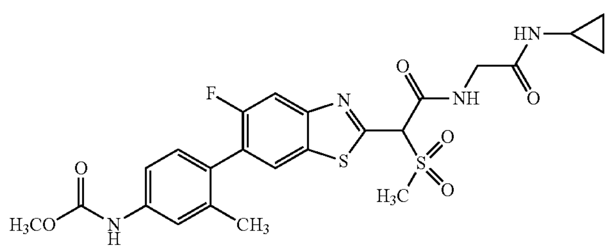 [SMILES: COC(=O)Nc1ccc(-c2cc3sc(C(C(=O)NCC(=O)NC4CC4)S(C)(=O)=O)nc3cc2F)c(C)c1] | methyl N-{4-[2-({[(cyclopropyl-carbamoyl)methyl]carbamoyl}(methanesulfonyl)methyl)-5-fluoro-1,3-benzothiazol-6-yl]-3-methylphenyl}carbamate | 9.51 (br. s., 1H), 8.83 (br. s., 1H), 8.01-7.63(m, 3H), 7.42-7.11 (m, 2H), 7.08-6.85 (m, 1H), 5.97 (s, 1H), 3.45 (s, 2H), 3.13-2.89 (m, 3H), 2.40 (d, J = 3.4 Hz, 1H), 2.28 (br. s., 3H), 1.98-1.72 (m, 3H), 0.40 (d, J = 6.1 Hz, 2H), 0.16 (br. s., 2H) | 1.39 N 549.1 | 4 |
| 35 | 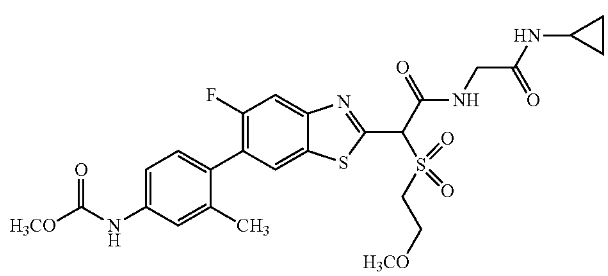 [SMILES: COCCS(=O)(=O)C(C(=O)NCC(=O)NC1CC1)c1nc2cc(F)c(-c3ccc(NC(=O)OC)cc3C)cc2s1] | methyl N-{4-[2-({[(cyclopropyl-carbamoyl)methyl]carbamoyl}(2-methoxyethane-sulfonyl)methyl)-5-fluoro-1,3-benzothiazol-6-yl]-3-methylphenyl}carbamate | 9.62-9.41 (m, 1H), 8.79 (br. s., 1H), 8.01-7.68 (m, 3H), 7.31-7.12 (m, 2H), 7.03-6.85 (m, 1H), 5.97 (s, 1H), 3.96-3.38 (m, 9H), 2.40 (d, J = 3.7Hz, 1H), 2.28 (br. s., 3H), 2.01-1.73 (m, 3H), 0.40 (d, J = 5.7 Hz, 2H), 0.16 (br. s., 2H) | 1.46 N 593.2 | 8 |

-continued

| Ex. No. | Structure | Name | ¹H NMR δ (500 MHz, DMSO-d₆, unless otherwise indicated) | LC/MS RT (min) Method M+H | EL IC$_{50}$ (nM) |
|---|---|---|---|---|---|
| 36 | 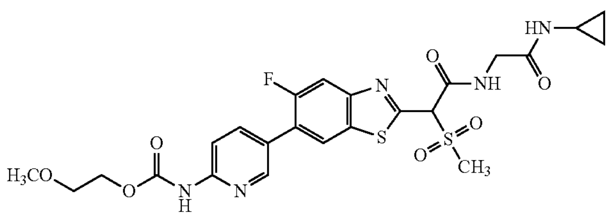 [SMILES: COCCOC(=O)Nc1ccc(-c2cc3sc(C(C(=O)NCC(=O)NC4CC4)S(C)(=O)=O)nc3cc2F)cn1] | 2-methoxyethyl N-{5-[2-({[(cyclopropyl-carbamoyl)methyl] carbamoyl} (methanesulfonyl) methyl)-5-fluoro-1,3-benzothiazol-6-yl]pyridin-2-yl}carbamate | 10.34 (s, 1H), 9.05 (t, J = 5.3 Hz, 1H), 8.49 (s, 1H), 8.37 (d, J = 7.3 Hz, 1H), 8.16-7.86 (m, 4H), 4.43-4.17 (m, 2H), 3.81 (d, J = 5.5 Hz, 2H), 3.63-3.48 (m, 2H), 3.36-3.19 (m, 6H), 2.62 (td, J = 7.3, 3.7 Hz, 1H), 0.79-0.55 (m, 2H), 0.38 (d, J = 2.1 Hz, 2H) | 1.31 N 580.1 | 11 |
| 37 | 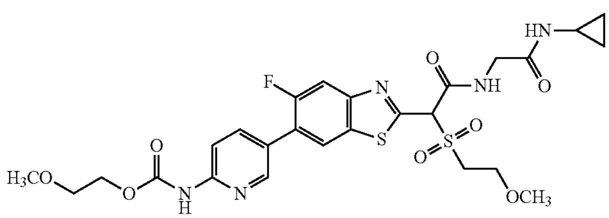 [SMILES: COCCOC(=O)Nc1ccc(-c2cc3sc(C(C(=O)NCC(=O)NC4CC4)S(=O)(=O)CCOC)nc3cc2F)cn1] | 2-methoxyethyl N-{5-[2-({[(cyclopropyl-carbamoyl)methyl] carbamoyl}(2-methoxyethane-sulfonyl)methyl)-5-fluoro-1,3-benzothiazol-6-yl] pyridin-2-yl} carbamate | 10.51-10.22 (m, 1H), 9.00 (t, J = 5.5 Hz, 1H), 8.50 (s, 1H), 8.37 (d, J = 7.3 Hz, 1H), 8.12-7.91 (m, 4H), 6.17 (s, 1H), 4.29-4.21 (m, 2H), 3.93-3.65 (m, 4H), 3.61-3.49 (m, 2H), 3.33-3.24 (m, 6H), 3.09 (d, J = 13.1 Hz, 1H), 2.76-2.70 (m, 1H), 2.62 (dd, J = 7.2, 3.5 Hz, 1H), 0.71-0.56 (m, 2H), 0.38 (d, J = 2.7 Hz, 2H) | 1.34 N 624.2 | 5 |
| 38 | 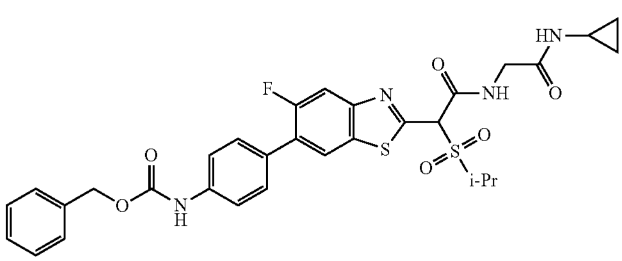 [SMILES: CC(C)S(=O)(=O)C(C(=O)NCC(=O)NC1CC1)c1nc2cc(F)c(-c3ccc(NC(=O)OCc4ccccc4)cc3)cc2s1] | benzyl N-{4-[2-({[(cyclopropyl-carbamoyl) methyl] carbamoyl} (propane-2-sulfonyl)methyl)-5-fluoro-1,3-benzothiazol-6-yl]phenyl} carbamate | 10.20-9.51 (m, 1H), 9.12 (t, J = 5.5 Hz, 1H), 8.26 (d, J = 7.6 Hz, 1H), 8.03-7.85 (m, 2H), 7.63-7.16 (m, 9H), 6.31 (s, 1H), 5.26-5.07 (m, 2H), 3.88-3.74 (m, 1H), 3.67-3.50 (m, 2H), 2.61 (td, J = 7.3, 3.7 Hz, 1H), 1.41-1.19 (m, 6H), 0.69-0.56 (m, 2H), 0.38 (d, J = 2.1 Hz, 2H) | 1.94 N 639.2 | 2 |
| 39 | 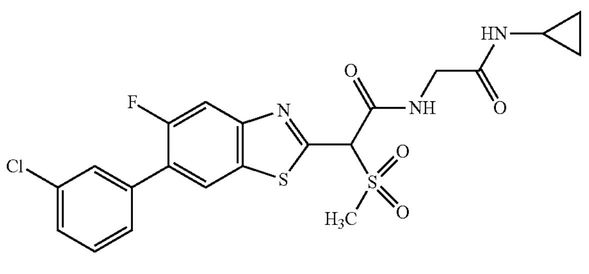 [SMILES: CS(=O)(=O)C(C(=O)NCC(=O)NC1CC1)c1nc2cc(F)c(-c3cccc(Cl)c3)cc2s1] | 2-[6-(3-chlorophenyl)-5-fluoro-1,3-benzothiazol-2-yl]-N-[(cyclopropyl-carbamoyl) methyl]-2-methanesulfonyl-acetamide | 9.05 (t, J = 5.5 Hz, 1H), 8.44-8.27 (m, 1H), 8.18-7.96 (m, 2H), 7.88-7.42 (m, 4H), 6.17 (s, 1H), 3.81 (d, J = 5.5 Hz, 2H), 3.39-3.16 (m, 3H), 2.61 (td, J = 7.3, 3.7 Hz, 1H), 0.74-0.56 (m, 2H), 0.38 (d, J = 2.1 Hz, 2H) | 1.79 N 496.1 | 3 |

-continued

| Ex. No. | Structure | Name | ¹H NMR δ (500 MHz, DMSO-d₆, unless otherwise indicated) | LC/MS RT (min) EL ethod M + H | IC₅₀ (nM) |
|---|---|---|---|---|---|
| 40 | 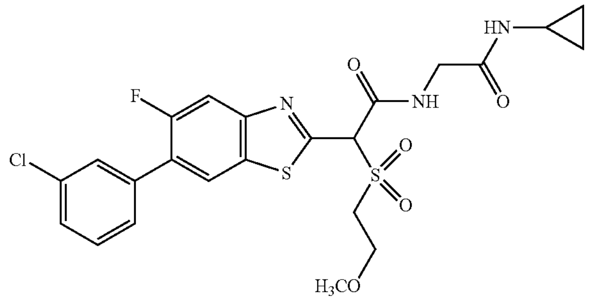 [SMILES: COCCS(=O)(=O)C(C(=O)NCC(=O)NC1CC1)c1nc2cc(F)c(-c3cccc(Cl)c3)cc2s1] | 2-[6-(3-chlorophenyl)-5-fluoro-1,3-benzothiazol-2-yl]-N-[(cyclopropyl-carbamoyl)methyl]-2-(2-methoxyethane-sulfonyl)acetamide | 9.00 (t, J = 5.3 Hz, 1H), 8.38 (d, J = 7.3 Hz, 1H), 8.14-7.88 (m, 3H), 7.71-7.46 (m, 4H), 3.93-3.60 (m, 6H), 3.33-3.05 (m, 3H), 2.68-2.58 (m, 1H), 0.62 (d, J = 5.8 Hz, 2H), 0.39 (d, J = 2.4 Hz, 2H) | 1.85 N 540.1 | 3 |
| 41 | 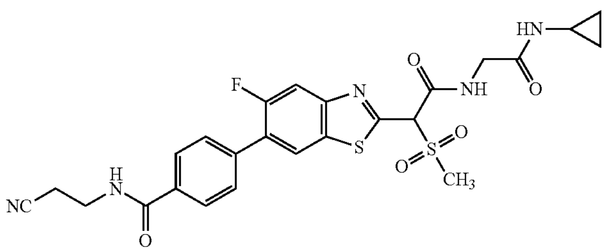 [SMILES: CS(=O)(=O)C(C(=O)NCC(=O)NC1CC1)c1nc2cc(F)c(-c3ccc(C(=O)NCCC#N)cc3)cc2s1] | N-(2-cyanoethyl)-4-[2-({[(cyclopropyl-carbamoyl)methyl] carbamoyl}(methanesulfonyl)methyl)-5-fluoro-1,3-benzothiazol-6-yl]benzamide | 9.14-8.82 (m, 2H), 8.40 (d, J = 7.6 Hz, 1H), 8.18-7.89 (m, 5H), 7.82-7.65 (m, 2H), 3.83 (d, J = 5.5 Hz, 2H), 3.59-3.36 (m, 2H), 3.31-3.15 (m, 2H), 2.80 (t, J = 6.3 Hz, 2H), 2.68-2.59 (m, 1H), 0.62 (d, J = 7.0 Hz, 2H), 0.39 (br. s., 2H) | 1.19 N 558.1 | 5 |
| 42 | 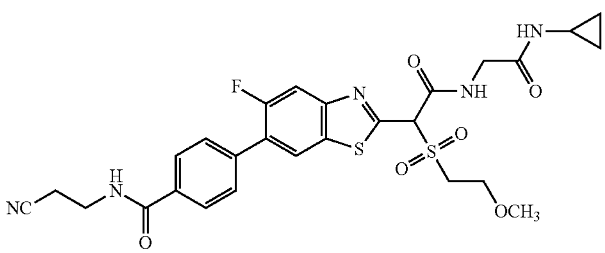 [SMILES: COCCS(=O)(=O)C(C(=O)NCC(=O)NC1CC1)c1nc2cc(F)c(-c3ccc(C(=O)NCCC#N)cc3)cc2s1] | N-(2-cyanoethyl)-4-[2-({[(cyclopropyl-carbamoyl)methyl] carbamoyl}(2-methoxyethane-sulfonyl)methyl)-5-fluoro-1,3-benzothiazol-6-yl]benzamide | 9.22-8.81 (m, 2H), 8.36 (d, J = 7.3 Hz, 1H), 8.19-7.90 (m, 4H), 7.77-7.56 (m, 2H), 6.15 (s, 1H), 3.76-3.66 (m, 6H), 3.57-3.43 (m, 2H), 3.25 (s, 3H), 2.78 (t, J = 6.3 Hz, 2H), 2.61 (d, J =4.0 Hz, 1H), 0.62 (d, J = 5.8 Hz, 2H), 0.37 (br. s., 2H) | 1.23 N 602.1 | 7 |
| 43 | 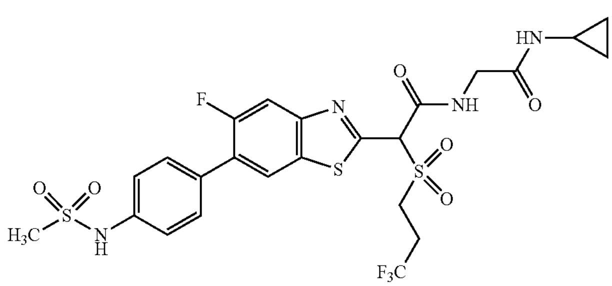 [SMILES: CS(=O)(=O)Nc1ccc(-c2cc3sc(C(C(=O)NCC(=O)NC4CC4)S(=O)(=O)CCC(F)(F)F)nc3cc2F)cc1] | N-[(cyclopropyl-carbamoyl)methyl]-2-[5-fluoro-6-(4-methanesulfon-amidophenyl)-1,3-benzothiazol-2-yl]-2-(3,3,3-trifluoropropane-sulfonyl)acetamide | 10.18-9.72 (m, 1H), 9.34-8.91 (m, 1H), 8.67-8.28 (m, 1H), 8.14-7.93 (m, 2H), 7.75-7.48 (m, 2H), 7.45-6.97 (m, 2H), 6.48-6.21 (m, 1H), 3.98-3.70 (m, 4H), 3.11-2.98 (m, 3H), 2.96-2.77 (m, 2H), 2.74-2.57 (m, 1H), 0.77-0.56 (m, 2H), 0.52-0.23 (m, 2H) | 1.48 N 637.1 | 37 |
| 44 | 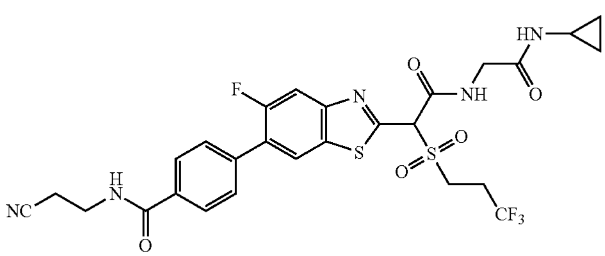 [SMILES: N#CCCNC(=O)c1ccc(-c2cc3sc(C(C(=O)NCC(=O)NC4CC4)S(=O)(=O)CCC(F)(F)F)nc3cc2F)cc1] | N-(2-cyanoethyl)-4-[2-({[(cyclopropyl-carbamoyl)methyl] carbamoyl}(3,3,3-trifluoropropane-sulfonyl)methyl)-5-fluoro-1,3-benzothiazol-6-yl]benzamide | 9.20-8.87 (m, 2H), 8.47-8.29 (m, 1H), 8.17-7.85 (m, 5H), 7.78-7.63 (m, 2H), 3.90-3.74 (m, 2H), 3.65-3.49 (m, 4H), 2.91-2.72 (m, 4H), 2.68-2.56 (m, 1H), 0.62 (d, J = 5.8 Hz, 2H), 0.38 (d, J = 3.1 Hz, 2H) | 1.42 N 640.1 | 3 |

| Ex. No. | Structure | Name | $^1$H NMR δ (500 MHz, DMSO-d$_6$, unless otherwise indicated) | LC/MS RT (min) Method M + H | EL IC$_{50}$ (nM) |
|---|---|---|---|---|---|
| 45 | 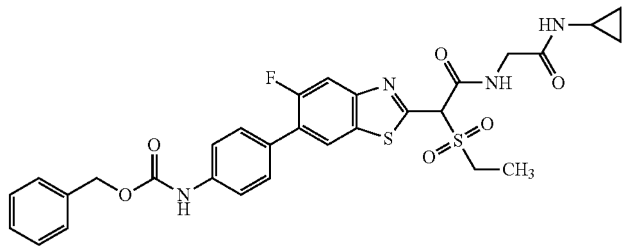 [SMILES: CCS(=O)(=O)C(C(=O)NCC(=O)NC1CC1)c1nc2cc(F)c(-c3ccc(NC(=O)OCc4ccccc4)cc3)cc2s1] | benzyl N-{4-[2-({[(cyclopropyl-carbamoyl)methyl]carbamoyl}(ethanesulfonyl)methyl)-5-fluoro-1,3-benzothiazol-6-yl]phenyl}carbamate | 10.10-9.75 (m, 1H), 9.08 (t, J = 5.3 Hz, 1H), 8.27 (d, J = 7.3 Hz, 1H), 8.08-7.90 (m, 2H), 7.64-7.30 (m, 9H), 6.20 (s, 1H), 5.16 (s, 2H), 4.07-3.72 (m, 2H), 3.48-3.25 (m, 2H), 2.61 (dt, J = 7.3, 3.7 Hz, 1H), 1.31-1.17 (m, 3H), 0.62 (d, J = 7.0 Hz, 2H), 0.38 (d, J = 2.4 Hz, 2H) | 1.89 N 625.2 | 3 |
| 46 | 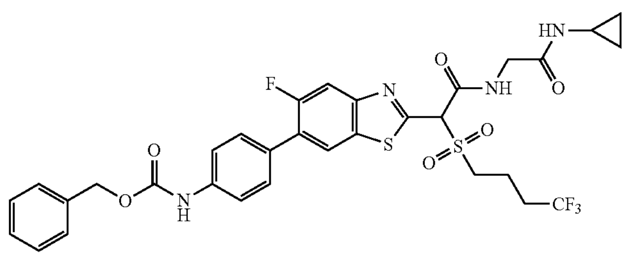 [SMILES: O=C(CNC(=O)C(c1nc2cc(F)c(-c3ccc(NC(=O)OCc4ccccc4)cc3)cc2s1)S(=O)(=O)CCCC(F)(F)F)NC1CC1] | benzyl N-{4-[2-({[(cyclopropyl-carbamoyl)methyl]carbamoyl}(4,4,4-trifluorobutane-sulfonyl)methyl)-5-fluoro-1,3-benzothiazol-6-yl]phenyl}carbamate | 10.04-9.78 (m, 1H), 9.08 (t, J = 5.3 Hz, 1H), 8.36-8.23 (m, 1H), 8.02-7.82 (m, 2H), 7.66-7.51 (m, 4H), 7.47-7.23 (m, 6H), 5.16 (s, 2H), 3.87-3.78 (m, 1H), 3.61 (br. s.,2H), 3.56-3.40 (m, 1H), 2.67-2.56 (m, 1H), 2.50 (br. s.,2H), 2.04-1.61 (m, 2H), 0.73-0.58 (m, 2H), 0.42-0.30 (m, 2H) | 2.03 N 707.2 | 2 |
| 47 | 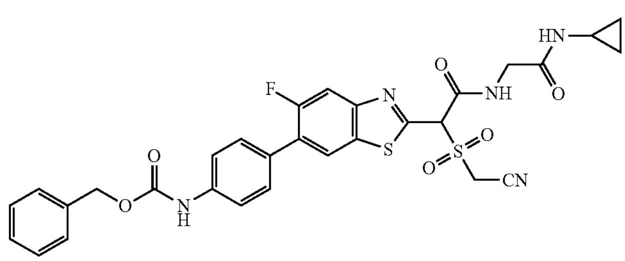 | benzyl N-(4-{2-[(cyanomethane-sulfonyl)({[(cyclopropyl-carbamoyl)methyl]carbamoyl}methyl]-5-fluoro-1,3-benzothiazol-6-yl}phenyl)carbamate | 10.05-9.79 (m, 1H), 8.12-8.02 (m, 1H), 7.67-7.30 (m, 10H), 5.21-5.13 (m, 2H), 5.09-4.96 (m, 2H), 3.84 (d, J = 5.8 Hz, 2H), 2.71-2.60 (m, 1H), 0.70-0.56 (m, 2H), 0.46-0.36 (m, 2H) | 1.75 N 636.1 | 2 |
| 48 | 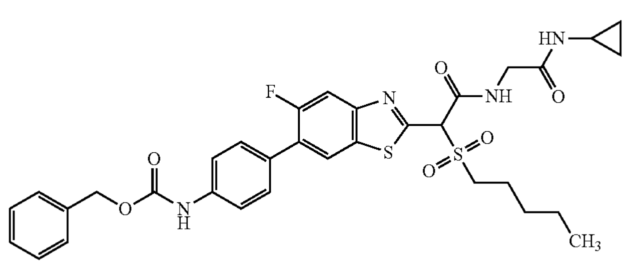 [SMILES: CCCCCS(=O)(=O)C(C(=O)NCC(=O)NC1CC1)c1nc2cc(F)c(-c3ccc(NC(=O)OCc4ccccc4)cc3)cc2s1] | benzyl N-{4-[2-({[(cyclopropyl-carbamoyl)methyl]carbamoyl}(pentane-1-sulfonyl)methyl)-5-fluoro-1,3-benzothiazol-6-yl]phenyl}carbamate | 10.10-9.78 (m, 1H), 9.06 (t, J = 5.3 Hz, 1H), 8.28 (d, J = 7.6 Hz, 1H), 8.08-7.96 (m, 2H), 7.72-7.52 (m, 4H), 7.49-7.23 (m, 6H), 5.17 (s, 2H), 3.88-3.73 (m, 2H), 3.44-3.22 (m, 2H), 2.63 (td, J = 7.2, 3.5 Hz, 1H), 1.72 (quin, J = 7.6 Hz, 2H), 1.43-1.21 (m, 4H), 1.00-0.77 (m, 3H), 0.70-0.56 (m, 2H), 0.39 (d, J = 2.1 Hz, 2H) | 2.17 N 667.1 | 1 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 49 | 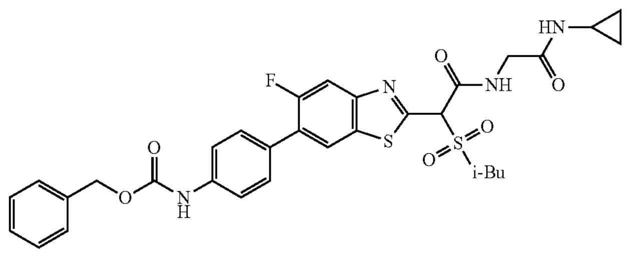 | benzyl N-{4-[2-({[(cyclopropyl-carbamoyl)methyl]carbamoyl}(2-methylpropane-sulfonyl)methyl)-5-fluoro-1,3-benzothiazol-6-yl]phenyl}carbamate | 9.94 (br. s., 1H), 9.05 (t, J = 5.2 Hz, 1H), 8.28 (d, J = 7.6 Hz, 1H), 8.07-7.95 (m, 2H), 7.65-7.51 (m, 4H), 7.48-7.29 (m, 5H), 6.17 (s, 1H), 5.17 (s, 2H), 3.81 (d, J = 5.5 Hz, 2H), 3.41-3.22 (m, 2H), 2.66-2.59 (m, 1H), 2.24 (dt, J = 13.3, 6.5 Hz, 1H), 1.02 (d, J = 6.4 Hz, 6H), 0.62 (d, J = 7.0 Hz, 2H), 0.39 (br. s., 2H) | 2.07 N 653.2 | 3 |
| 50 | 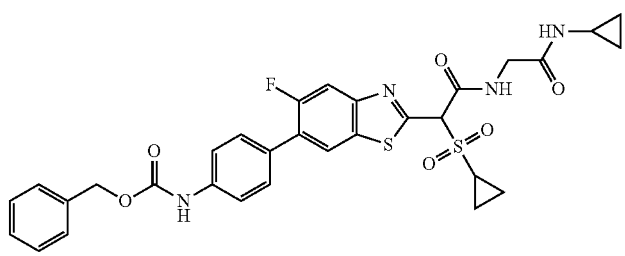 [SMILES: O=C(CNC(=O)C(c1nc2cc(F)c(-c3ccc(NC(=O)OCc4ccccc4)cc3)cc2s1)S(=O)(=O)C1CC1)NC1CC1] | benzyl N-(4-{2-[(cyclopropane-sulfonyl)({[(cyclopropyl-carbamoyl)methyl]carbamoyl}methyl]-5-fluoro-1,3-benzothiazol-6-yl}phenyl)carbamate | 9.94 (s, 1H), 9.11 (t, J = 5.3 Hz, 1H), 8.28 (d, J = 7.6 Hz, 1H), 8.08-7.95 (m, 2H), 7.72-7.26 (m, 7H), 6.28-6.22 (m, 1H), 5.17 (s, 2H), 3.88-3.75 (m, 2H), 2.87-2.80 (m, 1H), 2.62 (td, J = 7.2, 3.7 Hz, 1H), 1.26-0.89 (m, 4H), 0.62 (d, J = 5.5 Hz, 2H), 0.38 (br. s., 2H) | 1.89 N 637.2 | 3 |
| 51 | 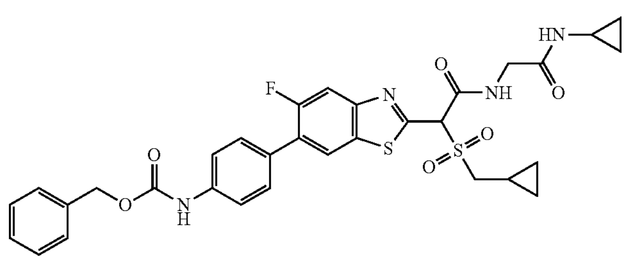 [SMILES: O=C(CNC(=O)C(c1nc2cc(F)c(-c3ccc(NC(=O)OCc4ccccc4)cc3)cc2s1)S(=O)(=O)CC1CC1)NC1CC1] | benzyl N-{4-[2-({[(cyclopropyl-carbamoyl)methyl]carbamoyl}(cyclopropyl-methanesulfonyl)methyl)-5-fluoro-1,3-benzothiazol-6-yl]phenyl}carbamate | 9.91-9.64 (m, 1H), 9.28-8.89 (m, 1H), 8.40-8.26 (m, 1H), 8.19-8.07 (m, 1H), 8.09-7.91 (m, 1H), 7.93-7.79 (m, 1H), 7.75-7.29 (m,9H), 5.17 (s, 2H), 3.85-3.66 (m, 2H), 3.51-3.33 (m, 2H), 2.72-2.57 (m, 1H), 1.00-0.83 (m, 1H), 0.78-0.52 (m, 3H), 0.49-0.32 (m, 4H), 0.27-0.08 (m, 1H) | 2.01 N 651.2 | 3 |
| 52 | 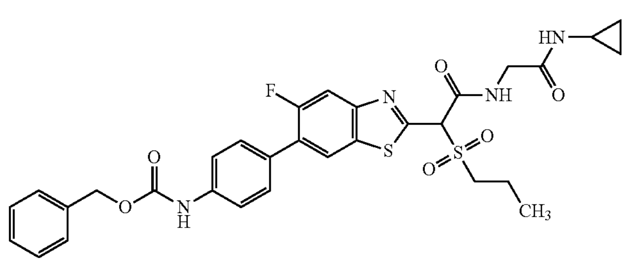 [SMILES: CCCS(=O)(=O)C(C(=O)NCC(=O)NC1CC1)c1nc2cc(F)c(-c3ccc(NC(=O)OCc4ccccc4)cc3)cc2s1] | benzyl N-{4-[2-({[(cyclopropyl-carbamoyl)methyl]carbamoyl}(propane-1-sulfonyl)methyl)-5-fluoro-1,3-benzothiazol-6-yl]phenyl}carbamate | 9.95 (br. s., 1H), 9.06 (br. s., 1H), 8.29 (d, J = 7.6 Hz, 1H), 8.07-7.88 (m, 3H), 7.65-7.31 (m, 9H), 5.25-5.03 (m, 2H), 3.81 (d, J = 5.2 Hz, 2H), 3.46 (s, 2H), 1.81-1.69 (m, 1H), 1.66-1.53 (m, 1H), 0.99 (t, J = 7.3 Hz, 3H), 0.92-0.81 (m, 1H), 0.62 (d, J = 5.5 Hz, 2H), 0.39 (br. s., 2H) | 1.95 N 639.2 | 1 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 53 | 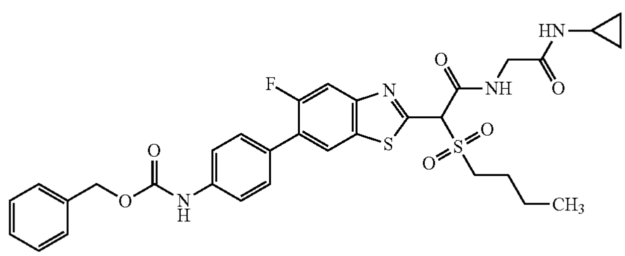 | benzyl N-(4-{2-[(butane-1-sulfonyl)({[(cyclopropyl-carbamoyl)methyl]carbamoyl})methyl]-5-fluoro-1,3-benzothiazol-6-yl}phenyl)carbamate | 9.94 (br. s., 1H), 9.06 (br. s., 1H), 8.28 (d, J = 7.3 Hz, 1H), 8.08-7.85 (m, 3H), 7.66-7.17 (m, 10H), 5.17 (s, 2H), 3.81 (d, J = 5.5 Hz, 2H)), 3.46-3.32 (m, 2H), 1.80-1.59 (m, 1H), 1.90-1.54 (m, 2H), 1.48-1.19 (m, 2H), 0.96-0.77 (m, 3H), 0.62 (d, J = 5.5 Hz, 2H), 0.39 (br. s., 2H) | 2.04 N 653.2 | 2 |
| 54 | 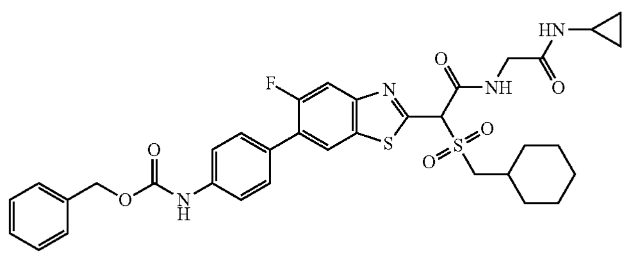 [SMILES: O=C(CNC(=O)C(c1nc2cc(F)c(-c3ccc(NC(=O)OCc4ccccc4)cc3)cc2s1)S(=O)(=O)CC1CCCCC1)NC1CC1] | benzyl N-(4-{2-[cyclohexyl-methanesulfonyl({[(cyclopropyl-carbamoyl)methyl]carbamoyl})methyl]-5-fluoro-1,3-benzothiazol-6-yl}phenyl)carbamate | 9.94 (br. s., 1H), 9.05 (t, J = 5.3 Hz, 1H), 8.28 (d, J = 7.3 Hz, 1H), 8.12-7.89 (m, 3H), 7.68-7.23 (m, 9H), 5.17 (s, 2H), 3.94-3.68 (m, 2H), 3.42-3.20 (m, 2H), 2.62 (dd, J = 7.0, 3.4 Hz, 1H), 1.94 (br. s., 1H), 1.79 (d, J = 11.0 Hz, 2H), 1.68-1.42 (m, 3H), 1.33-0.97 (m, 5H), 0.62 (d, J = 7.0 Hz, 2H), 0.38 (br. s., 2H) | 2.24 N 693.2 | 1 |
| 56 | 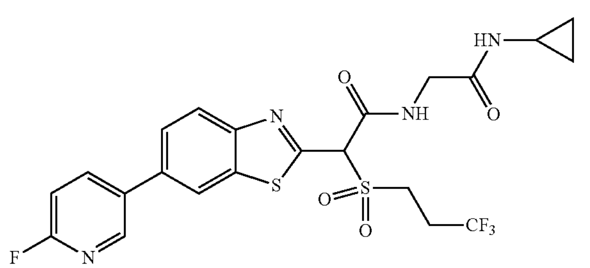 [SMILES: O=C(CNC(=O)C(c1nc2ccc(-c3ccc(F)nc3)cc2s1)S(=O)(=O)CCC(F)(F)F)NC1CC1] | N-[(cyclopropyl-carbamoyl)methyl]-2-[6-(6-fluoropyridin-3-yl)-1,3-benzothiazol-2-yl]-2-(3,3,3-trifluoropropane-sulfonyl)acetamide | 9.04 (br. s., 1H), 8.67 (br. s., 1H), 8.59 (br. s., 1H), 8.44-8.37 (m, 1H), 8.21 (d, J = 8.5 Hz, 1H), 8.09 (br. s., 1H), 7.95 (d, J = 8.3 Hz, 1H), 7.36 (d, J = 8.0 Hz, 1H), 6.42 (s, 1H), 3.90-3.84 (m, 2H), 3.80 (dd, J = 14.7, 6.5 Hz, 2H), 2.95-2.83 (m, 2H), 2.70-2.61 (m, 1H), 0.69-0.60 (m, 2H), 0.47-0.37 (m, 2H) | 1.66 O 545.2 | 29 |
| 57 | 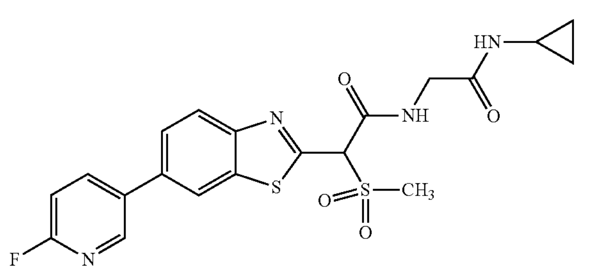 [SMILES: CS(=O)(=O)C(C(=O)NCC(=O)NC1CC1)c1nc2ccc(-c3ccc(F)nc3)cc2s1] | N-[(cyclopropyl-carbamoyl)methyl]-2-[6-(6-fluoropyridin-3-yl)-1,3-benzothiazol-2-yl]-2-methanesulfonyl-acetamide | (400 MHz, DMSO-d₆) 9.04 (t, J = 5.6 Hz, 1H), 8.66 (d, J = 2.6 Hz, 1H), 8.57 (d, J = 1.8 Hz, 1H), 8.40 (td, J = 8.1, 2.6 Hz, 1H), 8.20 (d, J = 8.6 Hz, 1H), 8.05 (d, J = 3.7 Hz, 1H), 7.93 (dd, J = 8.6, 2.0 Hz, 1H), 7.35 (dd, J = 8.5, 2.8 Hz, 1H), 6.22 (s, 1H), 3.84 (d, J = 5.5 Hz, 2H), 3.28 (s, 3H), 2.64 (dt, J = 7.3, 3.6 Hz, 1H), 0.64 (dd, J = 7.3, 2.0 Hz, 2H), 0.42-0.39 (m, 2H) | 1.74 B 463 | 47 |

-continued

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 58 | 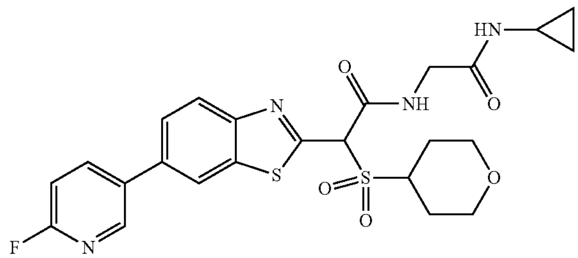 [SMILES: O=C(CNC(=O)C(c1nc2ccc(-c3ccc(F)nc3)cc2s1)S(=O)(=O)C1CCOCC1)NC1CC1] | N-[(cyclopropylcarbamoyl)methyl]-2-[6-(6-fluoropyridin-3-yl)-1,3-benzothiazol-2-yl]-2-(oxane-4-sulfonyl)acetamide | 9.15 (m, 1H), 8.67 (br. s., 1H), 8.57 (br. s., 1H), 8.41 (t, J = 7.7 Hz, 1H), 8.20 (d, J = 6.3 Hz, 1H), 8.09 (br. s., 1H), 7.93 (d, J = 8.3 Hz, 1H), 7.36 (d, J = 8.5 Hz, 1H), 6.37 (s, 1H), 4.04-3.90 (m, 3H), 3.89-3.82 (m, 2H), 3.35-3.27 (m, 2H), 2.66 (m, 1H), 2.17-1.62 (m, 4H), 0.65 (d, J = 6.1 Hz, 2H), 0.42 (m, 2H) | 1.74 B 463 | 47 |
| 59 | 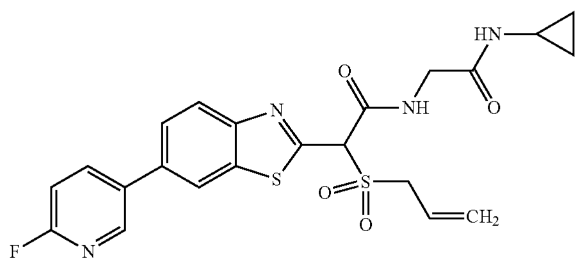 [SMILES: C=CCS(=O)(=O)C(C(=O)NCC(=O)NC1CC1)c1nc2ccc(-c3ccc(F)nc3)cc2s1] | N-[(cyclopropylcarbamoyl)methyl]-2-[6-(6-fluoropyridin-3-yl)-1,3-benzothiazol-2-yl]-2-(prop-2-ene-1-sulfonyl)acetamide | (400 MHz, DMSO-d₆) 9.09 (t, J = 5.4 Hz, 1H), 8.66 (d, J = 2.6 Hz, 1H), 8.57 (d, J = 1.5 Hz, 1H), 8.44-8.35 (m, 1H), 8.20 (d, J = 8.8 Hz, 1H), 8.03 (d, J = 3.1 Hz, 1H), 7.93 (dd, J = 8.6, 1.8 Hz, 1H), 7.35 (dd, J = 8.7, 2.8 Hz, 1H), 6.26 (s, 1H), 5.95-5.75 (m, 1H), 5.60-5.45 (m, 2H), 4.23 (d, J = 7.0 Hz, 2H), 3.83 (dd, J = 5.4, 2.1 Hz, 2H), 2.65 (dd, J = 7.4, 3.6 Hz, 1H), 0.64 (dd, J = 7.0, 1.8 Hz, 2H), 0.47-0.36 (m, 2H) | 0.82 M 489.2 | 20 |
| 61 | 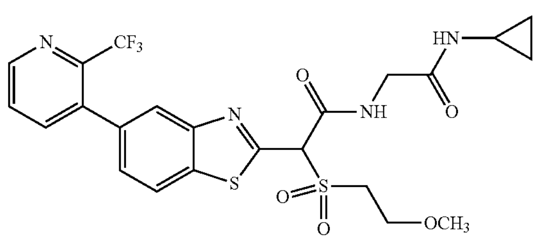 [SMILES: COCCS(=O)(=O)C(C(=O)NCC(=O)NC1CC1)c1nc2cc(-c3cccnc3C(F)(F)F)ccc2s1] | N-[(cyclopropylcarbamoyl)methyl]-2-(2-methoxyethanesulfonyl)-2-{5-[2-(trifluoromethyl)pyridin-3-yl]-1,3-benzothiazol-2-yl}acetamide | 9.02 (br. s., 1H), 8.79 (s, 1H), 8.42 (d, J = 7.9 Hz, 1H), 8.32-8.23 (m, 3H), 8.20 (t, J = 7.6 Hz, 1H), 8.01 (br. s., 1H), 7.87 (d, J = 7.6 Hz, 1H), 6.18 (s, 1H), 3.83-3.74 (m, 6H), 3.25 (s, 3H), 2.61 (d, J = 3.1 Hz, 1H), 0.62 (d, J = 7.0 Hz, 2H), 0.38 (br. s., 2H) | 2.55 T 557.4 | 5 |
| 62 | 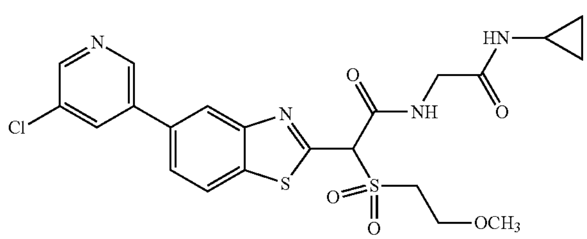 [SMILES: COCCS(=O)(=O)C(C(=O)NCC(=O)NC1CC1)c1nc2cc(-c3cncc(Cl)c3)ccc2s1] | 2-[5-(5-chloropyridin-3-yl)-1,3-benzothiazol-2-yl]-N-(cyclopropylcarbamoyl)methyl]-2-(2-methoxyethanesulfonyl)acetamide | 9.00 (br. s., 2H), 8.66 (br. s., 1H), 8.53 (br. s., 1H), 8.40 (br. s., 1H), 8.34-8.23 (m, 1H), 8.03 (br. s., 1H), 7.94 (d, J = 8.5 Hz, 1H), 6.22 (s, 1H), 3.84-3.71 (m, 6H), 3.27 (d, J = 1.2 Hz, 3H), 2.63 (br. s., 1H), 0.62 (d, J = 4.6 Hz, 2H), 0.39 (br. s., 2H) | 1.74 S 523.3 | 5 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 63 | 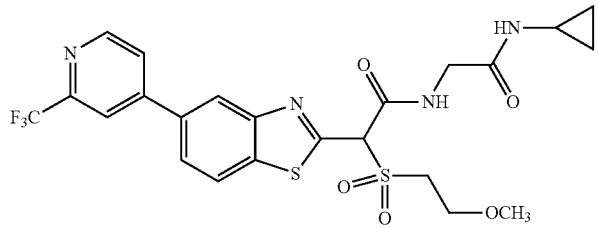 [SMILES: COCCS(=O)(=O)C(C(=O)NCC(=O)NC1CC1)c1nc2cc(-c3ccnc(C(F)(F)F)c3)ccc2s1] | N-[(cyclopropylcarbamoyl)methyl]-2-(2-methoxyethanesulfonyl)-2-{5-[2-(trifluoromethyl)pyridin-4-yl]-1,3-benzothiazol-2-yl}acetamide | 9.03 (br. s., 1H), 8.79 (br. s., 1H), 8.64 (br. s., 1H), 8.41-7.82 (m, 5H), 7.54 (br. s., 1H), 3.26 (br. s., 6H), 3.16 (d, J = 14.3 Hz, 3H), 2.63 (d, J = 3.7 Hz, 1H), 0.63 (d, J = 6.7 Hz, 2H), 0.40 (br. s., 2H) | 2.51 T 557.3 | 5 |
| 64 | 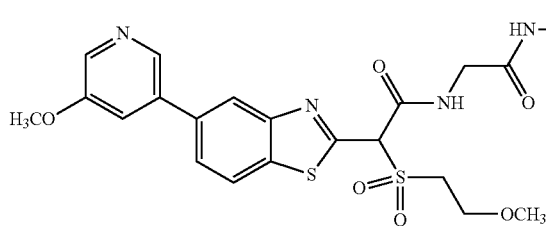 | N-[(cyclopropylcarbamoyl)methyl]-2-(2-methoxyethanesulfonyl)-2-[5-(5-methoxypyridin-3-yl)-1,3-benzothiazol-2-yl]acetamide | 9.00 (br. s., 1H), 8.61 (br. s., 1H), 8.50 (br. s., 1H), 8.34-8.24 (m, 1H), 8.03 (br. s., 1H), 7.92 (d, J = 8.5 Hz, 1H), 7.78 (br. s., 1H), 7.64 (br. s., 1H), 6.22 (br. s., 1H), 3.93 (d, J = 7.9 Hz, 2H), 3.84-3.56 (m, 4H), 3.27 (br. s., 3H), 2.63 (d, J = 3.7 Hz, 1H), 1.91 (s, 3H), 0.62 (br. s., 2H), 0.40 (br. s., 2H) | 1.28 S 519.3 | 11 |
| 65 | 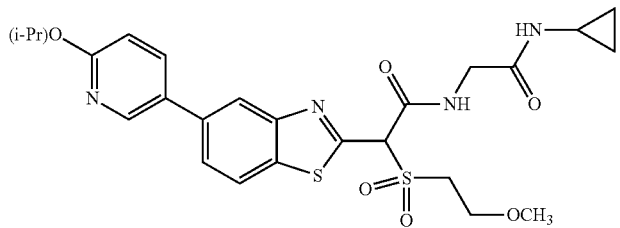 | N-[(cyclopropylcarbamoyl)methyl]-2-(2-methoxyethanesulfonyl)-2-{5-[6-(propan-2-yloxy)pyridin-3-yl]-1,3-benzothiazol-2-yl}acetamide | (400 MHz, METHANOL-$d_4$) 8.46 (d, J = 2.2 Hz, 1H), 8.40 (d, J = 2.2 Hz, 1H), 8.29 (s, 1H), 8.12 (d, J = 8.3 Hz, 1H), 8.05-8.00 (m, 1H), 7.99-7.94 (m, 1H), 7.81 (s, 1H), 7.78-7.70 (m, 1H), 6.83 (dd, J = 13.2, 8.6 Hz, 1H), 4.08-3.59 (m, 6H), 3.41 (s, 3H), 2.73-2.58 (m, 1H), 1.36 (dd, J = 6.0, 3.8 Hz, 6H), 0.78-0.64 (m, 2H), 0.53 (d, J = 2.2 Hz, 2H) | 2.77 T 545.4 | 11 |
| 66 | 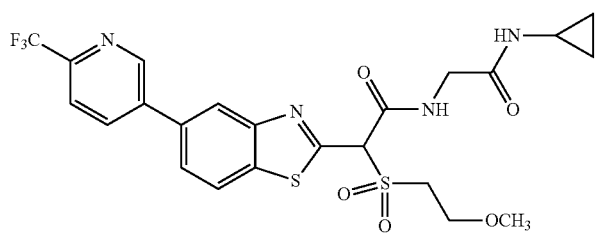 [SMILES: COCCS(=O)(=O)C(C(=O)NCC(=O)NC1CC1)c1nc2cc(-c3ccc(C(F)(F)F)nc3)ccc2s1] | N-[(cyclopropylcarbamoyl)methyl]-2-(2-ethoxyethanesulfonyl)-2-{5-[6-(trifluoromethyl)pyridin-3-yl]-1,3-benzothiazol-2-yl}acetamide | 9.20 (br. s., 1H), 9.11-8.98 (m, 1H), 8.54 (s, 2H), 8.39-8.30 (m, 1H), 8.05-7.93 (m, 3H), 6.19 (s, 1H), 3.83-3.69 (m, 6H), 3.26 (d, J = 1.2 Hz, 3H), 2.62 (br. s., 1H), 0.62 (d, J = 6.1 Hz, 2H), 0.38 (br. s., 2H) | 2.4 T 557.3 | 12 |

-continued

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 67 | 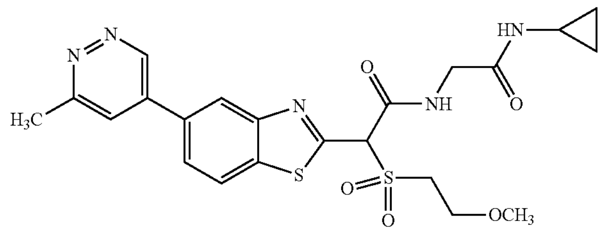 [SMILES: COCCS(=O)(=O)C(C(=O)NCC(=O)NC1CC1)c1nc2cc(-c3cnnc(C)c3)ccc2s1] | N-[(cyclopropyl-carbamoyl)methyl]-2-(2-methoxyethane-sulfonyl)-2-[5-(6-methylpyridazin-4-yl)-1,3-benzothiazol-2-yl]acetamide | 9.62-9.43 (m, 1H), 9.04 (br. s., 1H), 8.64 (br. s., 1H), 8.34 (d, J = 8.5 Hz, 1H), 8.09-7.90 (m, 3H), 6.20 (s, 1H), 3.27 (s, 2H), 3.15 (s, 2H), 2.71 (s, 3H), 2.68 (s, 2H), 2.63 (br. s., 1H), 2.52 (br. s., 3H), 0.63 (d, J = 6.7 Hz, 2H), 0.40 (br. s., 2H) | 2.11 T 504.1 | 16 |
| 68 | 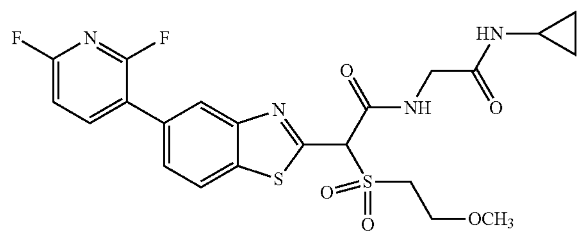 [SMILES: COCCS(=O)(=O)C(C(=O)NCC(=O)NC1CC1)c1nc2cc(-c3ccc(F)nc3F)ccc2s1] | N-[(cyclopropyl-carbamoyl)methyl]-2-[5-(2,6-difluoropyridin-3-yl)-1,3-benzothiazol-2-yl]-2-(2-methoxy-ethane-sulfonyl)acetamide | 9.02 (br. s., 1H), 8.50-8.43 (m, 1H), 8.39-8.28 (m, 2H), 8.04 (br. s., 1H), 7.75 (d, J = 8.5 Hz, 1H), 7.39-7.27 (m, 1H), 6.23 (s, 1H), 3.86-3.65 (m, 6H), 2.65 (d, J = 3.4 Hz, 1H), 2.52 (br. s., 3H), 0.64 (d, J = 5.8 Hz, 2H), 0.41 (br. s., 2H) | 2.44 T 525.1 | 19 |
| 69 | 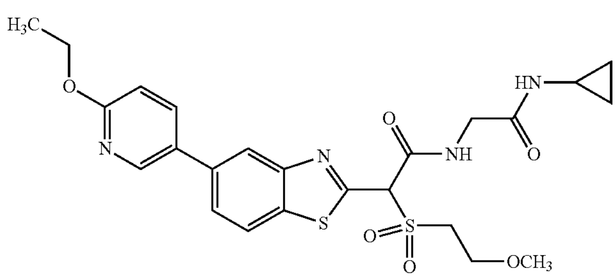 [SMILES: CCOc1ccc(-c2ccc3sc(C(C(=O)NCC(=O)NC4CC4)S(=O)(=O)CCOC)nc3c2)cn1] | N-[(cyclopropyl-carbamoyl)methyl]-2-[5-(6-ethoxypyridin-3-yl)-1,3-benzothiazol-2-yl]-2-(2-methoxyethane-sulfonyl)acetamide | 9.02 (br. s., 1H), 8.61 (s, 1H), 8.38 (s, 1H), 8.25 (d, J = 8.5 Hz, 1H), 8.16 (d, J = 8.5 Hz, 1H), 8.07-8.01 (m, 1H), 7.84 (d, J = 8.2 Hz, 1H), 6.93 (d, J = 8.9 Hz, 1H), 6.22 (s, 1H), 4.42-4.32 (m, 2H), 3.84-3.64 (m, 6H), 3.28 (s, 3H), 2.65 (br. s., 1H), 1.41-1.30 (m, 3H), 0.64 (d, J = 6.4 Hz, 2H), 0.41 (br. s., 2H) | 1.77 S 533.4 | 23 |
| 70 | 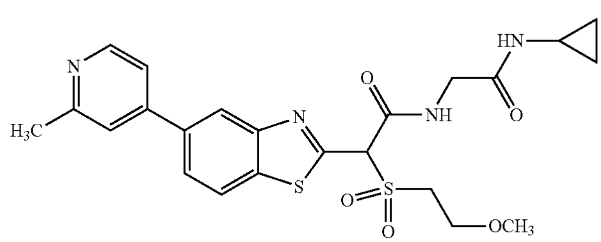 [SMILES: COCCS(=O)(=O)C(C(=O)NCC(=O)NC1CC1)c1nc2cc(-c3ccnc(C)c3)ccc2s1] | N-[(cyclopropyl-carbamoyl)methyl]-2-(2-methoxyethane-sulfonyl)-2-[5-(2-methylpyridin-4-yl)-1,3-benzothiazol-2-yl]acetamide | 9.03 (br. s., 1H), 8.58-8.45 (m, 1H), 8.31 (d, J = 7.6 Hz, 1H), 8.07-7.81 (m, 2H), 7.76 (br. s., 1H), 7.68-7.62 (m, 1H), 7.54 (br. s., 1H), 7.40 (d, J = 4.6 Hz, 1H), 6.24 (br. s., 1H), 3.90-3.58 (m, 6H), 3.18 (br. s., 3H), 2.64 (br. s., 1H), 2.59-2.52 (m, 3H), 0.63 (br. s., 2H), 0.42 (br. s., 2H) | 2.12 T 503.3 | 24 |

-continued

| Ex. No. | Structure | Name | ¹H NMR δ (500 MHz, DMSO-d₆, unless otherwise indicated) | LC/MS RT (min) ethod M + H | EL IC₅₀ (nM) |
|---|---|---|---|---|---|
| 71 | 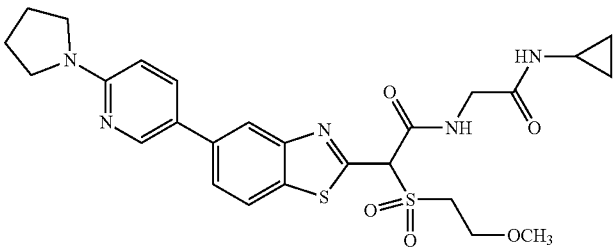 [SMILES: COCCS(=O)(=O)C(C(=O)NCC(=O)NC1CC1)c1nc2cc(-c3ccc(N4CCCC4)nc3)ccc2s1] | N-[(cyclopropyl-carbamoyl)methyl]-2-(2-methoxyethane-sulfonyl)-2-{5-[6-(pyaolidin-1-yl)pyridin-3-yl]-1,3-benzothiazol-2-yl}acetamide | 8.55 (br. s., 1H), 8.43 (br. s., 1H), 8.29 (br. s., 1H), 8.19 (d, J = 7.6 Hz, 1H), 8.04 (br. s., 1H), 7.96 (d, J = 7.3 Hz, 1H), 7.87-7.78 (m, 1H), 6.61-6.48 (m, 1H), 6.20 (br. s., 1H), 3.88-3.50 (m, 10H), 3.28 (br. s., 3H), 2.65 (br. s., 1H), 1.26 (d, J = 12.8 Hz, 2H), 1.05 (br. s., 1H), 0.86 (br. s., 1H), 0.63 (br. s., 2H), 0.41 (br. s., 2H) | 1.82 S 558.4 | 25 |
| 72 | 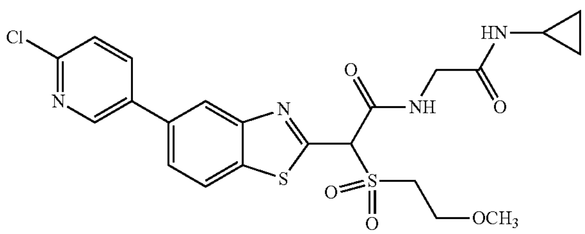 [SMILES: COCCS(=O)(=O)C(C(=O)NCC(=O)NC1CC1)c1nc2cc(-c3ccc(Cl)nc3)ccc2s1] | 2-[5-(6-chloropyridin-3-yl)-1,3-benzothiazol-2-yl]-N-[(cyclopropyl-carbamoyl)methyl]-2-(2-methoxyethane-sulfonyl)acetamide | 8.77 (br. s., 1H), 8.23-8.18 (m, 1H), 7.87 (br. s., 1H), 7.78-7.70 (m, 2H), 7.58 (d, J = 8.2 Hz, 1H), 7.30 (d, J = 7.3 Hz, 1H), 3.79-3.67 (m, 4H), 3.60 (d, J = 7.0 Hz, 2H), 3.18 (s, 3H), 2.65 (br. s., 1H), 0.62 (d, J = 5.8 Hz, 2H), 0.42 (br. s., 2H) | 1.62 S 523.3 | 25 |
| 73 | 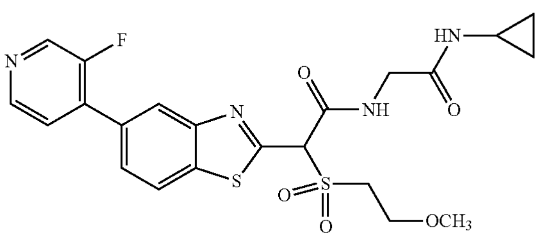 | N-[(cyclopropyl-carbamoyl)methyl]-2-[5-(3-fluoropyridin-4-yl)-1,3-benzothiazol-2-yl]-2-(2-methoxyethane-sulfonyl)acetamide | 9.03 (br. s., 1H), 8.76-8.65 (m, 1H), 8.61-8.48 (m, 1H), 8.43-8.28 (m, 1H), 8.04 (br. s., 1H), 7.87-7.76 (m, 2H), 7.69 (br. s., 1H), 6.24 (s, 1H), 3.87-3.59 (m, 6H), 3.28 (s, 3H), 2.65 (d, J = 2.4 Hz, 1H), 0.64 (d, J = 6.1 Hz, 2H), 0.41 (br. s., 2H) | 2.11 T 507.3 | 28 |
| 74 | 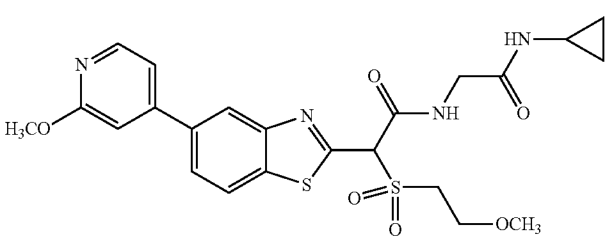 [SMILES: COCCS(=O)(=O)C(C(=O)NCC(=O)NC1CC1)c1nc2cc(-c3ccnc(OC)c3)ccc2s1] | N-[(cyclopropyl-carbamoyl)methyl]-2-(2-methoxyethane-sulfonyl)-2-[5-(2-methoxypyridin-4-yl)-1,3-benzothiazol-2-yl]acetamide | 9.03 (br. s., 1H), 8.76-8.65 (m, 1H), 8.61-8.48 (m, 2H), 8.43-8.28 (m, 1H), 8.04 (br. s., 1H), 7.87-7.76 (m, 1H), 7.69 (br. s., 1H), 6.24 (s, 1H), 3.87-3.59 (m, 6H), 3.28 (s, 3H), 2.65 (d, J = 2.4 Hz, 1H), 0.64 (d, J = 6.1 Hz, 2H), 0.41 (br. s., 2H) CH₃ buried in water peak | 1.62 S 519.3 | 31 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 75 | 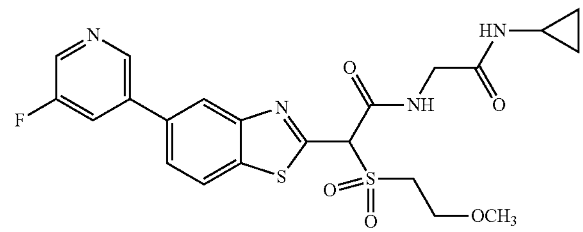 [SMILES: COCCS(=O)(=O)C(C(=O)NCC(=O)NC1CC1)c1nc2cc(-c3cncc(F)c3)ccc2s1] | N-[(cyclopropyl-carbamoyl)methyl]-2-[5-(5-fluoropyridin-3-yl)-1,3-benzothiazol-2-yl]-2-(2-methoxyethane-sulfonyl)acetamide | 9.03 (br. s., 1H), 8.89 (br. s., 1H), 8.61-8.46 (m, 2H), 8.28 (d, J = 8.2 Hz, 1H), 8.17 (d, J = 9.8 Hz, 1H), 8.06-8.00 (m, 2H), 7.91 (d, J = 8.5 Hz, 2H), 6.17 (s, 1H), 3.27 (s, 3H), 2.62 (br. s., 1H), 0.62 (br. s., 2H), 0.39 (br. s., 2H) methylenes buried in water peak | 2.32 T 507.3 | 31 |
| 76 | 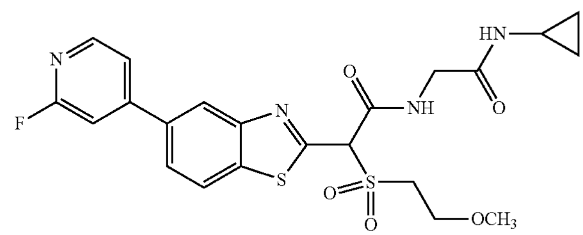 [SMILES: COCCS(=O)(=O)C(C(=O)NCC(=O)NC1CC1)c1nc2cc(-c3ccnc(F)c3)ccc2s1] | N-[(cyclopropyl-carbamoyl)methyl]-2-[5-(2-fluoropyridin-4-yl)-1,3-benzothiazol-2-yl]-2-(2-methoxyethane-sulfonyl)acetamide | 9.03 (br. s., 1H), 8.64 (s, 1H), 8.38-8.31 (m, 2H), 8.07-8.00 (m, 2H), 7.88 (d, J = 4.9 Hz, 1H), 7.77-7.69 (m, 1H), 7.55 (s, 1H), 6.25 (s, 1H), 3.93-3.60 (m, 6H), 2.65 (d, J = 3.7 Hz, 1H), 0.63 (br. s., 2H), 0.41 (br. s., 2H) | 1.51 S 507.3 | 32 |
| 77 | 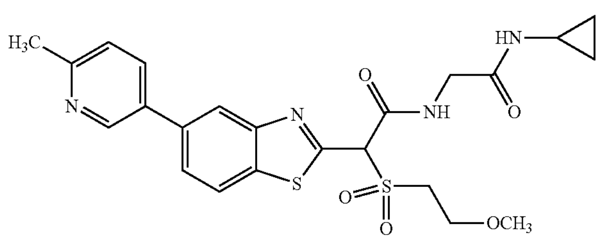 [SMILES: COCCS(=O)(=O)C(C(=O)NCC(=O)NC1CC1)c1nc2cc(-c3ccc(C)nc3)ccc2s1] | N-[(cyclopropyl-carbamoyl)methyl]-2-(2-methoxyethane-sulfonyl)-2-[5-(6-methylpyridin-3-yl)-1,3-benzothiazol-2-yl]acetamide | 9.02 (br. s., 1H), 8.93-8.72 (m, 1H), 8.48-8.22 (m, 1H), 8.12 (d, J = 6.7 Hz, 1H), 8.06-7.97 (m, 1H), 7.94-7.85 (m, 1H), 7.77 (br. s., 1H), 7.42-7.28 (m, 1H), 6.22 (s, 1H), 3.87-3.58 (m, 6H), 2.65 (d, J = 3.7 Hz, 1H), 2.54 (br. s., 3H), 0.63 (br. s., 2H), 0.41 (br. s., 2H). CH$_3$ buried in water peak | 1.48 S 501.3 | 34 |
| 78 | 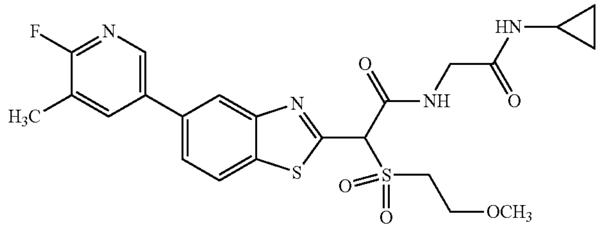 | N-[(cyclopropyl-carbamoyl)methyl]-2-[5-(6-fluoro-5-methylpyridin-3-yl)-1,3-benzothiazol-2-yl]-2-(2-methoxyethane-sulfonyl)acetamide | 9.02 (br. s., 1H), 8.55-8.44 (m, 2H), 8.40-8.25 (m, 2H), 8.05 (br. s., 1H), 7.89 (d, J = 8.9 Hz, 1H), 6.23 (s, 1H), 3.86-3.63 (m, 6H), 2.65 (br. s., 1H), 2.37-2.32 (m, 3H), 0.64 (d, J = 6.4 Hz, 2H), 0.41 (br. s., 2H) CH$_3$ buried in water peak | 1.65 S 521.3 | 38 |
| 79 | 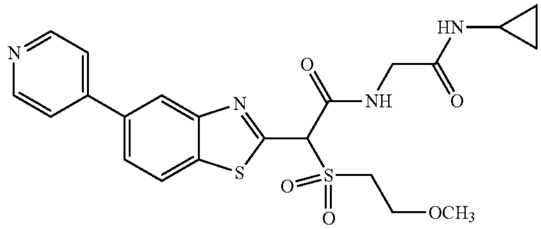 [SMILES: COCCS(=O)(=O)C(C(=O)NCC(=O)NC1CC1)c1nc2cc(-c3ccncc3)ccc2s1] | N-[(cyclopropyl-carbamoyl)methyl]-2-(2-methoxyethane-sulfonyl)-2-[5-(pyridin-4-yl)-1,3-benzothiazol-2-yl]acetamide | 9.03 (br. s., 1H), 8.73-8.50 (m, 2H), 8.33 (d, J = 8.5 Hz, 1H), 7.94-7.84 (m, 2H), 7.82-7.73 (m, 2H), 7.43 (br. s., 1H), 6.24 (br. s., 1H), 3.94-3.57 (m, 6H), 2.65 (d, J = 3.7 Hz, 1H), 0.64 (br. s., 2H), 0.42 (br. s., 2H) CH$_3$ buried in water peak | 2.02 T 489.3 | 40 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 80 | 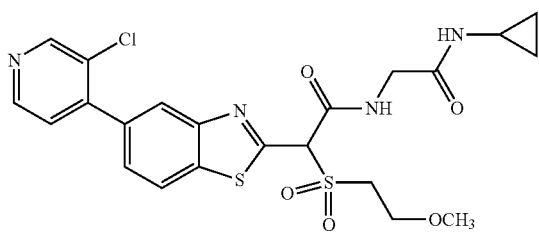 [SMILES: COCCS(=O)(=O)C(C(=O)NCC(=O)NC1CC1)c1nc2cc(-c3ccncc3Cl)ccc2s1] | 2-[5-(3-chloropyridin-4-yl)-1,3-benzothiazol-2-yl]-N-[(cyclopropylcarbamoyl)methyl]-2-(2-methoxyethanesulfonyl)acetamide | 9.03 (br. s., 1H), 8.80 (s, 1H), 8.65 (d, J = 4.9 Hz, 1H), 8.33 (d, J = 8.2 Hz, 1H), 8.25 (s, 1H), 8.04 (d, J = 3.4 Hz, 1H), 7.67 (d, J = 8.5 Hz, 1H), 7.62 (d, J = 4.6 Hz, 1H), 6.24 (s, 1H), 3.88-3.66 (m, 6H), 3.28 (s, 3H), 2.65 (d, J = 3.7 Hz, 1H), 0.64 (d, J = 6.4 Hz, 2H), 0.41 (br. s., 2H) | 2.38 T 523.3 | 49 |
| 81 | 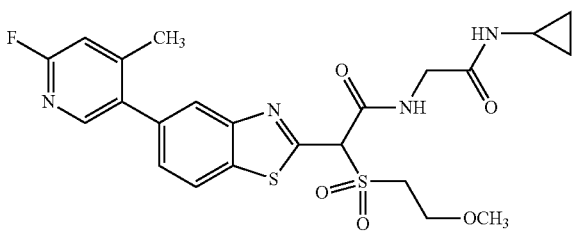 [SMILES: COCCS(=O)(=O)C(C(=O)NCC(=O)NC1CC1)c1nc2cc(-c3cnc(F)cc3C)ccc2s1] | N-[(cyclopropylcarbamoyl)methyl]-2-[5-(6-fluoro-4-methylpyridin-3-yl)-1,3-benzothiazol-2-yl]-2-(2-methoxyethanesulfonyl)acetamide | 9.01 (br. s., 1H), 8.23 (d, J = 8.2 Hz, 1H), 8.08 (d, J = 12.5 Hz, 3H), 7.51 (d, J = 7.9 Hz, 1H), 7.20-7.08 (m, 1H), 6.14 (s, 1H), 3.25 (s, 3H), 2.60 (d, J = 3.7 Hz, 1H), 2.30 (s, 3H), 0.61 (d, J = 6.4 Hz, 2H), 0.37 (br. s., 2H) other methylenes buried under water peak | 2.27 T 521.5 | 58 |
| 82 | 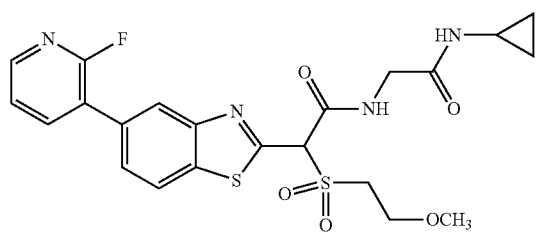 [SMILES: COCCS(=O)(=O)C(C(=O)NCC(=O)NC1CC1)c1nc2cc(-c3cccnc3F)ccc2s1] | N-[(cyclopropylcarbamoyl)methyl]-2-[5-(2-fluoropyridin-3-yl)-1,3-benzothiazol-2-yl]-2-(2-methoxyethanesulfonyl)acetamide | 9.03 (br. s., 1H), 8.36-8.14 (m, 3H), 8.07-7.89 (m, 1H), 7.80-7.66 (m, 1H), 7.56-7.43 (m, 1H), 7.22 (br. s., 1H), 6.24 (s, 1H), 3.86-3.58 (m, 6H), 3.28 (s, 3H), 2.65 (br. s., 1H), 0.63 (s, 2H), 0.41 (br. s., 2H) | 1.3 S 507.3 | 61 |
| 83 | 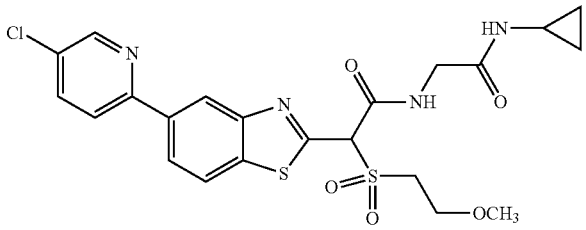 [SMILES: COCCS(=O)(=O)C(C(=O)NCC(=O)NC1CC1)c1nc2cc(-c3ccc(Cl)cn3)ccc2s1] | 2-[5-(5-chloropyridin-2-yl)-1,3-benzothiazol-2-yl]-N-[(cyclopropylcarbamoyl)methyl]-2-(2-methoxyethanesulfonyl)acetamide | 9.03 (br. s., 1H), 8.83-8.71 (m, 2H), 8.35-8.18 (m, 2H), 8.10-8.00 (m, 2H), 6.24 (s, 1H), 3.85-3.65 (m, 6H), 3.29 (s, 3H), 2.65 (br. s., 1H), 0.64 (s, 2H), 0.41 (br. s., 2H) | 2.48 T 523.3 | 71 |
| 84 | 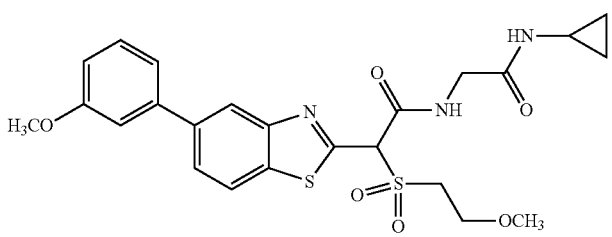 [SMILES: COCCS(=O)(=O)C(C(=O)NCC(=O)NC1CC1)c1nc2cc(-c3cccc(OC)c3)ccc2s1] | N-[(cyclopropylcarbamoyl)methyl]-2-(2-methoxyethanesulfonyl)-2-[5-(3-methoxyphenyl)-1,3-benzothiazol-2-yl]acetamide | 9.02 (br. s., 1H), 8.38 (s, 1H), 8.24 (d, J = 7.9 Hz, 1H), 8.04 (br. s., 1H), 7.85 (d, J = 8.2 Hz, 1H), 7.48-7.30 (m, 2H), 7.29-7.19 (m, 1H), 7.02-6.92 (m, 1H), 6.22 (s, 1H), 3.92-3.62 (m, 9H), 3.29 (s, 3H), 2.65 (br. s., 1H), 0.63 (br. s., 2H), 0.41 (br. s., 2H) | 2.67 T 518.3 | 82 |

-continued

| Ex. No. | Structure | Name | ¹H NMR δ (500 MHz, DMSO-d₆, unless otherwise indicated) | LC/MS RT (min) ethod M + H | EL IC₅₀ (nM) |
|---|---|---|---|---|---|
| 85 | 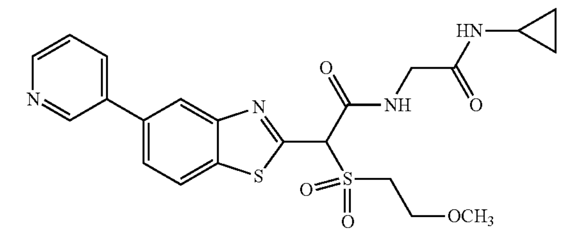 [SMILES: COCCS(=O)(=O)C(C(=O)NCC(=O)NC1CC1)c1nc2cc(-c3cccnc3)ccc2s1] | N-[(cyclopropyl-carbamoyl)methyl]-2-(2-methoxyethane-sulfonyl)-2-[5-(pyridin-3-yl)-1,3-benzothiazol-2-yl]acetamide | 9.10-8.85 (m, 2H), 8.68-8.41 (m, 1H), 8.36-8.19 (m, 1H), 8.16-8.02 (m, 1H), 7.90 (br. s., 1H), 7.76 (br. s., 1H), 7.58-7.43 (m, 1H), 7.33 (br. s., 1H), 6.24 (br. s., 1H), 3.89-3.59 (m, 6H), 3.18 (br. s., 3H), 2.65 (d, J = 3.4 Hz, 1H), 0.63 (s, 2H), 0.42 (br. s., 2H) | 1.11 S 489.3 | 85 |
| 86 | 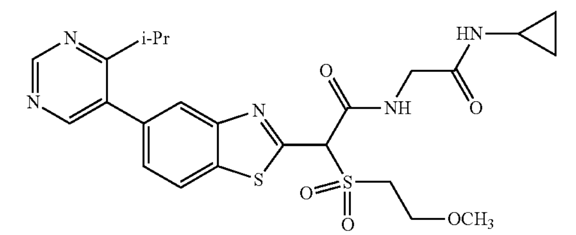 [SMILES: COCCS(=O)(=O)C(C(=O)NCC(=O)NC1CC1)c1nc2cc(-c3cncnc3C(C)C)ccc2s1] | N-[(cyclopropyl-carbamoyl)methyl]-2-(2-methoxyethane-sulfonyl)-2-{5-[4-(propan-2-yl)pyrimidin-5-yl]-1,3-benzothiazol-2-yl}acetamide | ¹H NMR (400 MHz, METHANOL-(d₄) 9.18-9.05 (m, 1H), 8.68-8.58 (m, 1H), 8.27-8.07 (m, 1H), 7.80 (d, J = 7.8 Hz, 1H), 7.61 (s, 1H), 7.53 (d, J = 5.9 Hz, 1H), 7.40 (d, J = 3.2 Hz, 1H), 4.05-3.69 (m, 6H), 2.74-2.65 (m, 1H), 1.78 (d, J = 3.4 Hz, 1H), 1.30-1.22 (m, 6H), 0.77-0.68 (m, 2H), 0.56 (br. s., 2H) | 2.26 T 532.3 | 293 |
| 87 | 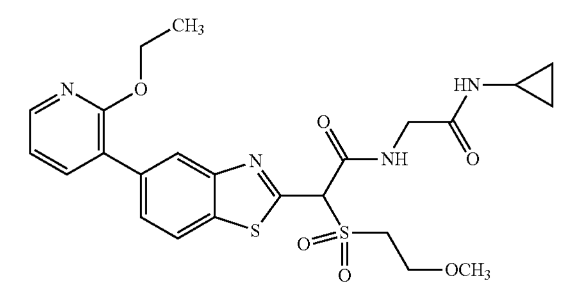 [SMILES: CCOc1ncccc1-c1ccc2sc(C(C(=O)NCC(=O)NC3CC3)S(=O)(=O)CCOC)nc2c1] | N-[(cyclopropyl-carbamoyl)methyl]-2-[5-(2-ethoxypyridin-3-yl)-1,3-benzothiazol-2-yl]-2-(2-methoxyethane-sulfonyl)acetamide | 9.02 (d, J = 4.9 Hz, 1H), 8.29-8.18 (m, 3H), 8.04 (br. s., 1H), 7.88 (d, J = 5.5 Hz, 1H), 7.81-7.70 (m, 1H), 7.17-7.11 (m, 1H), 6.21 (s, 1H), 4.41 6H), 3.31-3.26 (m, 3H), 2.64 (d, J = 4.0 Hz, 1H), 1.35-1.27 (m, 3H), 0.64 (br. s, 2H), 0.41 (br. s., 2H) | 1.62 S 533.3 | 346 |
| 88 | 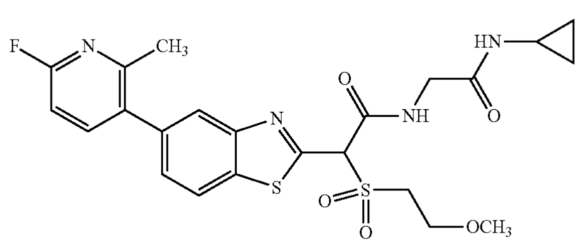 [SMILES: COCCS(=O)(=O)C(C(=O)NCC(=O)NC1CC1)c1nc2cc(-c3ccc(F)nc3C)ccc2s1] | N-[(cyclopropyl-carbamoyl)methyl]-2-[5-(6-fluoro-2-methylpyridin-3-yl)-1,3-benzothiazol-2-yl]-2-(2-methoxyethane-sulfonyl)acetamide | 9.02 (br. s., 1H), 8.27 (d, J = 8.2 Hz, 1H), 8.14-8.01 (m, 1H), 7.92 (t, J = 8.2 Hz, 2H), 7.56 (d, J = 8.2 Hz, 1H), 7.17-7.06 (m, 1H), 6.22 (s, 1H), 3.89-3.60 (m, 6H), 3.28 (s, 3H), 2.64 (br. s., 1H), 2.42 (d, J = 3.7 Hz, 3H), 0.64 (d, J = 5.2 Hz, 2H), 0.41 (br. s., 2H) | 2.39 T 521.3 | 82 |
| 89 | 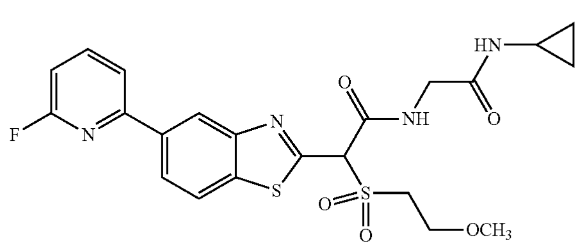 [SMILES: COCCS(=O)(=O)C(C(=O)NCC(=O)NC1CC1)c1nc2cc(-c3cccc(F)n3)ccc2s1] | N-[(cyclopropyl-carbamoyl)methyl]-2-[5-(6-fluoropyridin-2-yl)-1,3-benzothiazol-2-yl]-2-(2-methoxyethane-sulfonyl)acetamide | 9.03 (t, J = 5.3 Hz, 1H), 8.75 (s, 1H), 8.32-8.20 (m, 2H), 8.16-8.00 (m, 3H), 7.18 (d, J = 5.2 Hz, 1H), 1H), 3.85-3.71 (m, 6H), 3.28 (s, 3H), 2.64 (dd, J = 7.2, 3.5 Hz, 1H), 0.64 (s, 2H), 0.40 (br. s., 2H) | 1.41 S 507.5 | 171 |

-continued

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 90 | 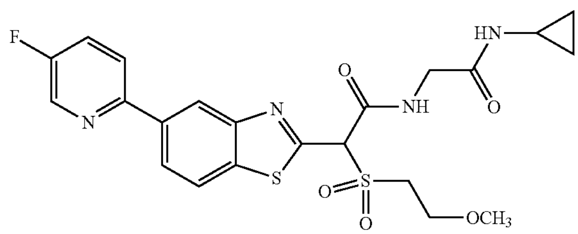 [SMILES: COCCS(=O)(=O)C(C(=O)NCC(=O)NC1CC1)c1nc2cc(-c3ccc(F)cn3)ccc2s1] | N-[(cyclopropyl-carbamoyl)methyl]-2-[5-(5-fluoropyridin-2-yl)-1,3-benzothiazol-2-yl]-2-(2-methoxyethane-sulfonyl)acetamide | 9.03 (br. s., 1H), 8.73 (d, J = 13.7 Hz, 1H), 8.65 (br. s., 1H), 8.32-8.19 (m, 2H), 8.04 (br. s., 1H), 7.97-7.73 (m, 2H), 6.22 (s, 1H), 3.86-3. (m, 6H), 3.28 (s, 3H), 2.64 (br. s., 1H), 0.64 (br. s, 2H), 0.41 (br. s., 2H) | 1.36 S 507.5 | 274 |
| 91 | 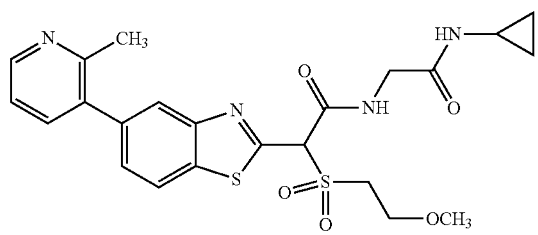 [SMILES: COCCS(=O)(=O)C(C(=O)NCC(=O)NC1CC1)c1nc2cc(-c3cccnc3C)ccc2s1] | N-[(cyclopropyl-carbamoyl)methyl]-2-(2-methoxyethane-sulfonyl)-2-[5-(2-methylpyridin-3-yl)-1,3-benzothiazol-2-yl]acetamide | 9.02 (br. s., 1H), 8.56-8.42 (m, 1H), 8.26 (d, J = 6.4 Hz, 1H), 8.14-7.88 (m, 1H), 7.80-7.54 (m, 2H), 7.39-7.20 (m, 1H), 6.99 (br. s., 1H), 6.22 (br. s., 1H), 3.85-3.59 (m, 6H), 2.64 (br. s., 1H), 2.48 (s, 3H), 1.92 (s, 3H), 0.63 (br. s., 2H), 0.41 (br. s., 2H) | 1.41 S 503.3 | 18 |
| 92 | 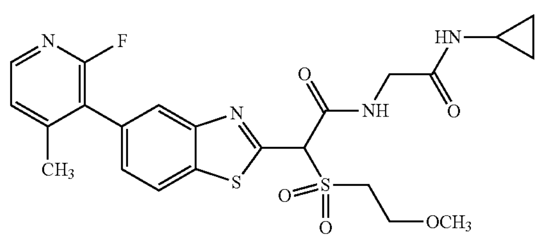 [SMILES: COCCS(=O)(=O)C(C(=O)NCC(=O)NC1CC1)c1nc2cc(-c3c(C)ccnc3F)ccc2s1] | N-[(cyclopropyl-carbamoyl)methyl]-2-[5-(2-fluoro-4-methylpyridin-3-yl)-1,3-benzothiazol-2-yl]-2-(2-methoxyethane-sulfonyl)acetamide | 9.02 (br. s., 1H), 8.27 (d, J = 8.2 Hz, 1H), 8.17-7.94 (m, 3H), 7.50-7.31 (m, 2H), 6.17 (s, 1H), 3.81 (br. s., 6H), 3.30-3.22 (m, 3H), 2.65-2.59 (m, 1H), 2.22 (s, 3H), 0.63 (br. s, 2H), 0.39 (br. s., 2H) | 2.14 T 521.5 | 77 |
| 93 | 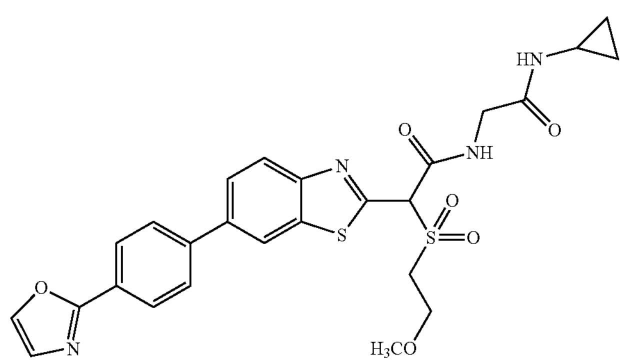 [SMILES: COCCS(=O)(=O)C(C(=O)NCC(=O)NC1CC1)c1nc2ccc(-c3ccc(-c4ncco4)cc3)cc2s1] | N-[(cyclopropyl-carbamoyl)methyl]-2-(2-methoxyethane-sulfonyl)-2-{6[4-(1,3-oxazol-2-yl)phenyl]-1,3-benzothiazol-2-yl}acetamide | 9.01 (t, J = 5.4 Hz, 1H), 8.60 (s, 1H), 8.30-8.25 (m, 1H), 8.20 (d, J = 8.5 Hz, 1H), 8.13 (d, J = 8.0 Hz, 2H), 8.09 (d, J = 7.7 Hz, 1H), 8.03 (d, J = 3.3 Hz, 1H), 8.01-7.94 (m, 3H), 7.48-7.39 (m, 1H), 6.22 (s, 1H), 3.88-3.68 (m, 6H), 3.29 (s, 3H), 2.65 (dd, J = 7.0, 3.4 Hz,1H), 0.64 (d, J = 6.9 Hz, 2H), 0.46-0.38 (m, 2H) | 1.57 N 555.2 | 1 |
| 94 | 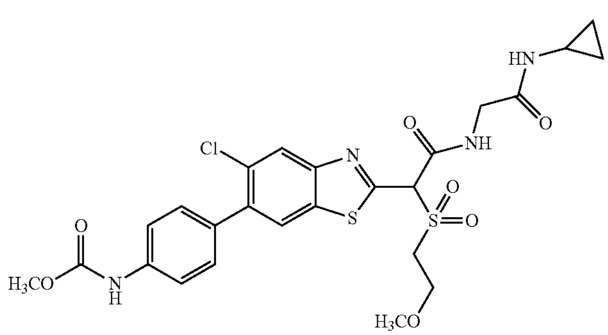 [SMILES: COCCS(=O)(=O)C(C(=O)NCC(=O)NC1CC1)c1nc2cc(Cl)c(-c3ccc(NC(=O)OC)cc3)cc2s1] | methyl N-{4-[5-chloro-2-({[(cyclopropyl-carbamoyl)methyl]carbamoyl}(2-methoxyethane-sulfonyl)methyl)-1,3-benzothiazol-6-yl]phenyl}carbamate | 9.83 (s, 1H), 9.01 (br. s., 1H), 8.31 (s, 1H), 8.23 (s, 1H), 8.03 (br. s., 1H), 7.64-7.51 (m, J = 7.7 Hz, 2H), 7.48-7.34 (m, J = 7.7 Hz, 2H), 6.22 (s, 1H), 3.93-3.75 (m, 4H), 3.74-3.67 (m, 5H), 3.29 (s, 3H), 2.70-2.60 (m, 1H), 0.64 (d, J = 6.6 Hz, 2H), 0.41 (br. s., 2H) | 1.52 N 595.1 | 2 |

| Ex. No. | Structure | Name | $^1$H NMR δ (500 MHz, DMSO-$d_6$, unless otherwise indicated) | LC/MS RT (min) EL ethod M + H | IC$_{50}$ (nM) |
|---|---|---|---|---|---|
| 95 | 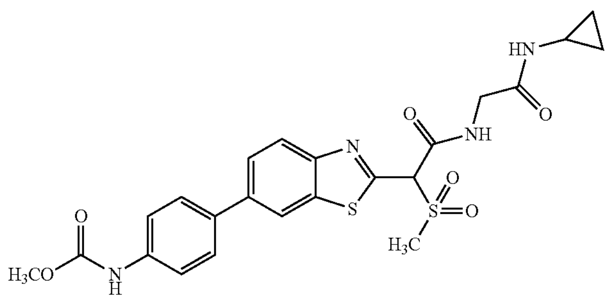 [SMILES: COC(=O)Nc1ccc(-c2ccc3nc(C(C(=O)NCC(=O)NC4CC4)S(C)(=O)=O)sc3c2)cc1] | methyl N-{4-[2-({[(cyclopropyl-carbamoyl)methyl]carbamoyl}(methanesulfonyl)methyl)-1,3-benzothiazol-6-yl]phenyl}carbamate | 9.81 (s, 1H), 9.03 (s, 1H), 8.44 (d, J = 1.7 Hz, 1H), 8.13 (d, J = 8.8 Hz, 1H), 8.05 (d, J = 3.9 Hz, 1H), 7.85 (dd, J = 8.5, 1.9 Hz, 1H), 7.77-7.69 (m, J = 8.8 Hz, 2H), 7.65-7.53 (m, J = 8.5 Hz, 2H), 6.20 (s, 1H), 3.84 (d, J = 5.5 Hz, 2H), 3.74-3.68 (m, 3H), 3.28 (s, 3H), 2.65 (d, J = 3.9 Hz, 1H), 0.64 (dd, J = 7.3, 1.8 Hz, 2H), 0.46-0.37 (m, 2H) | 1.33 N 517.2 | 2 |
| 96 | 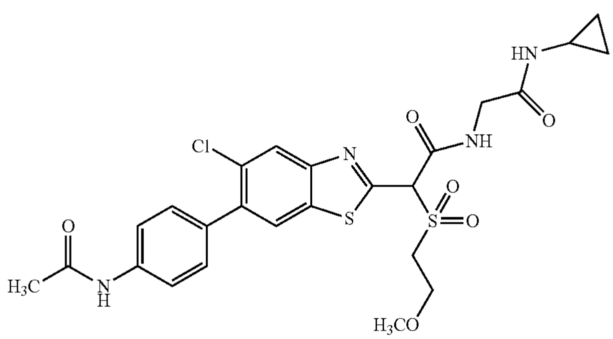 [SMILES: COCCS(=O)(=O)C(C(=O)NCC(=O)NC1CC1)c1nc2cc(Cl)c(-c3ccc(NC(C)=O)cc3)cc2s1] | 2-[5-chloro-6-(4-acetamidophenyl)-1,3-benzothiazol-2-yl]-N-[(cyclopropyl-carbamoyl)methyl]-2-(2-methoxyethane-sulfonyl)acetamide | 10.10 (s, 1H), 9.01 (br. s., 1H), 8.31 (s, 1H), 8.24 (s, 1H), 8.11-7.99 (m, 1H), 7.78-7.59 (m, 2H), 7.51-7.40 (m, J = 8.0 Hz, 2H), 6.23 (s, 1H), 3.88-3.67 (m, 6H), 3.29 (s, 3H), 2.65 (br. s., 1H), 2.10 (s, 3H), 0.64 (d, J = 6.6 Hz, 2H), 0.42 (br. s., 2H) | 1.34 N 517.2 | 2 |
| 97 | 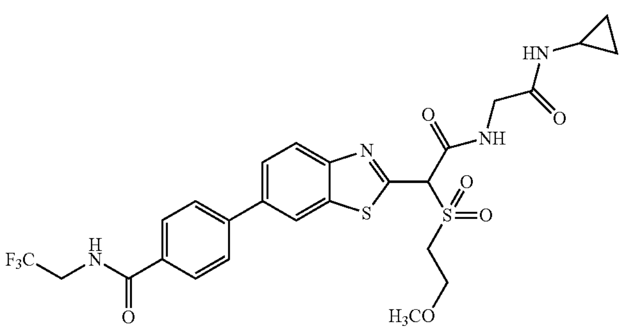 [SMILES: COCCS(=O)(=O)C(C(=O)NCC(=O)NC1CC1)c1nc2ccc(-c3ccc(C(=O)NCC(F)(F)F)cc3)cc2s1] | 4-[2-({[(cyclopropyl-carbamoyl)methyl]carbamoyl}(2-methoxyethane-sulfonyl)methyl)-1,3-benzothiazol-6-yl]-N-(2,2,2-trifluoroethyl)benzamide | 9.12 (t, J = 6.2 Hz, 1H), 8.95 (t, J = 5.4 Hz, 1H), 8.54 (s, 1H), 8.14 (d, J = 8.5 Hz, 1H), 8.03-7.93 (m, 3H), 7.93-7.83 (m, 3H), 6.16 (s, 1H), 4.08 (dd, J = 9.5, 6.2 Hz, 2H), 3.86-3.63 (m, 6H), 3.23 (s, 3H), 2.59 (dd, J = 7.0, 3.4 Hz, 1H), 0.58 (d, J = 6.9 Hz, 2H), 0.44-0.22 (m, 2H) | 1.48 N 613.2 | 4 |
| 98 | 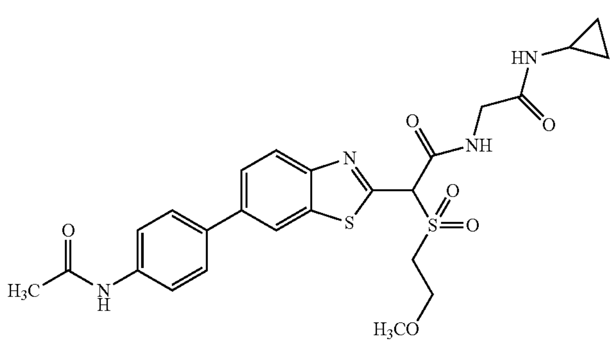 [SMILES: COCCS(=O)(=O)C(C(=O)NCC(=O)NC1CC1)c1nc2ccc(-c3ccc(NC(C)=O)cc3)cc2s1] | N-[(cyclopropyl-carbamoyl)methyl]-2-[6-(4-acetamidophenyl)-1,3-benzothiazol-2-yl]-2-(2-methoxyethane-sulfonyl)acetamide | 10.08 (s, 1H), 9.00 (t, J = 5.4 Hz, 1H), 8.45 (s, 1H), 8.13 (d, J = 8.8 Hz, 1H), 8.02 (d, J = 3.6 Hz, 1H), 7.97 (s, 1H), 7.86 (d, J = 8.5 Hz, 1H), 7.73 (s, 3H), 6.20 (s, 1H), 3.90-3.68 (m, 6H), 3.29 (s, 3H), 2.65 (dd, J = 7.2, 3.6 Hz, 1H), 2.14-2.04 (m, 3H), 0.64 (d, J = 6.9 Hz, 2H), 0.50-0.33 (m, 2H) | 1.26 N 545.3 | 8 |

-continued

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 99 | 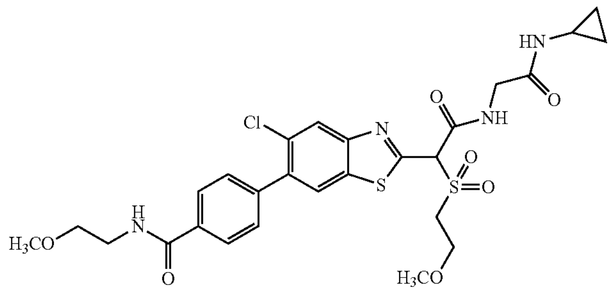 [SMILES: COCCNC(=O)c1ccc(-c2cc3sc(C(C(=O)NCC(=O)NC4CC4)S(=O)(=O)CCOC)nc3cc2Cl)cc1] | 4-[5-chloro-2-({[(cyclopropyl-carbamoyl)methyl]carbamoyl}(2-methoxyethane-sulfonyl)methyl)-1,3-benzothiazol-6-yl]-N-(2-methoxyethyl)benzamide | 9.02 (br. s., 1H), 8.63 (br. s., 1H), 8.36 (s, 1H), 8.30 (s, 1H), 8.03 (br. s., 1H), 8.01-7.88 (m, 2H), 7.60 (d, J = 7.4 Hz, 1H), 6.24 (s, 1H), 3.90-3.66 (m, 6H), 3.49 (d, J = 4.7 Hz, 4H), 3.31-3.22 (m, 6H), 2.65 (br. s., 1H), 0.64 (d, J = 6.6 Hz, 2H), 0.42 (br. s., 2H) | 1.35 N 620.9 | 8 |
| 100 | 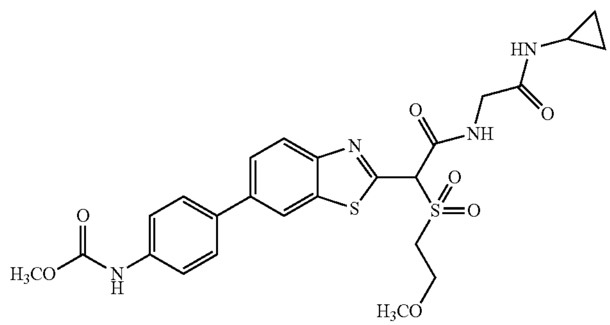 [SMILES: COCCS(=O)(=O)C(C(=O)NCC(=O)NC1CC1)c1nc2ccc(-c3ccc(NC(=O)OC)cc3)cc2s1] | methyl N-{4-[2-({[(cyclopropyl-carbamoyl)methyl]carbamoyl}(2-methoxyethane-sulfonyl)methyl)-1,3-benzothiazol-6-yl]phenyl}carbamate | 9.81 (s, 1H), 9.08-8.95 (m, 1H), 8.44 (s, 1H), 8.13 (d, J = 8.5 Hz, 1H), 8.02 (br. s., 1H), 7.97 (s, 1H), 7.85 (d, J = 8.8 Hz, 1H), 7.73 (d, J = 8.0 Hz, 2H), 7.67-7.57 (m, 2H), 6.20 (s, 1H), 3.89-3.65 (m, 9H), 3.29 (s, 3H), 2.65 (br. s., 1H), 0.64 (d, J = 6.9 Hz, 2H), 0.42 (br. s., 2H) | 1.41 N 561.3 | 8 |
| 101 | 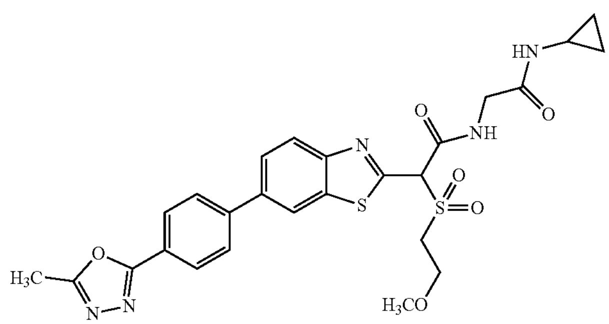 [SMILES: COCCS(=O)(=O)C(C(=O)NCC(=O)NC1CC1)c1nc2ccc(-c3ccc(-c4nnc(C)o4)cc3)cc2s1] | N-[(cyclopropyl-carbamoyl)methyl]-2-(2-methoxyethane-sulfonyl)-2-{6-[4-(5-methyl-1,3,4-oxadiazol-2-yl)phenyl]-1,3-benzothiazol-2-yl}acetamide | 9.02 (t, J = 5.2 Hz, 1H), 8.62 (s, 1H), 8.21 (d, J = 8.5 Hz, 1H), 8.15-8.05 (m, 2H), 8.05-8.00 (m, 2H), 8.00-7.90 (m, 2H), 6.23 (s, 1H), 3.92-3.69 (m, 6H), 3.30-3.25 (m, 3H), 2.71-2.59 (m, 4H), 0.64 (d, J = 7.2 Hz, 2H), 0.42 (br. s., 2H) | 1.40 N 570.2 | 9 |
| 102 | 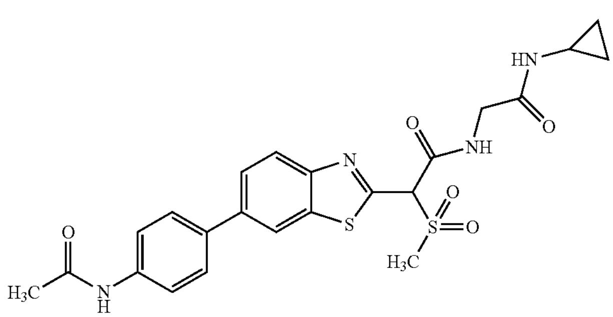 [SMILES: CC(=O)Nc1ccc(-c2ccc3nc(C(C(=O)NCC(=O)NC4CC4)S(C)(=O)=O)sc3c2)cc1] | N-[(cyclopropyl-carbamoyl)methyl]-2-[6-(4-acetamidophenyl)-1,3-benzothiazol-2-yl]-2-methanesulfonyl-acetamide | 10.08 (s, 1H), 9.03 (t, J = 5.5 Hz, 1H), 8.49-8.41 (m, 1H), 8.13 (d, J = 8.5 Hz, 1H), 8.05 (d, J = 3.9 Hz, 1H), 7.86 (dd, J = 8.7, 1.8 Hz, 1H), 7.73 (s, 4H), 6.20 (s, 1H), 3.84 (d, J = 5.2 Hz, 2H), 3.28 (s, 3H), 2.65 (dd, J = 7.2, 3.6 Hz, 1H), 2.17-2.01 (m, 3H), 0.72-0.55 (m, 2H), 0.47-0.28 (m, 2H) | 1.17 N 501.2 | 14 |

-continued

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 103 | 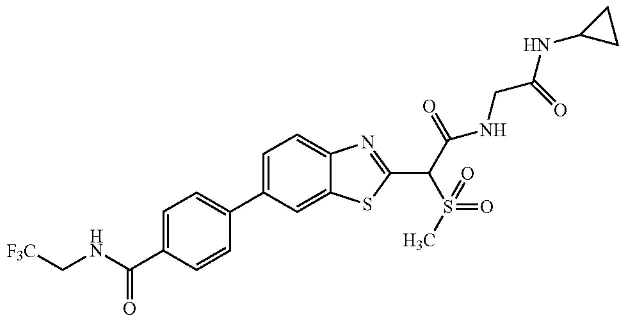 [SMILES: CS(=O)(=O)C(C(=O)NCC(=O)NC1CC1)c1nc2ccc(-c3ccc(C(=O)NCC(F)(F)F)cc3)cc2s1] | 4-[2-({[(cyclopropyl-carbamoyl)methyl]carbamoyl}(methanesulfonyl)methyl)-1,3-benzothiazol-6-yl]-N-(2,2,2-trifluoroethyl)benzamide | 9.18 (s, 1H), 9.05 (s, 1H), 8.60 (s, 1H), 8.20 (d, J = 8.8 Hz, 1H), 8.05 (d, J = 8.0 Hz, 3H), 7.99-7.82 (m, 3H), 6.23 (s, 1H), 4.14 (dd, J = 9.5, 6.5 Hz, 2H), 3.85 (d, J = 5.2 Hz, 2H), 3.30 (s, 3H), 2.65 (d, J = 3.3 Hz, 1H), 0.64 (d, J = 6.9 Hz, 2H), 0.42 (br. s., 2H) | 1.45 N 569.2 | 20 |
| 104 | 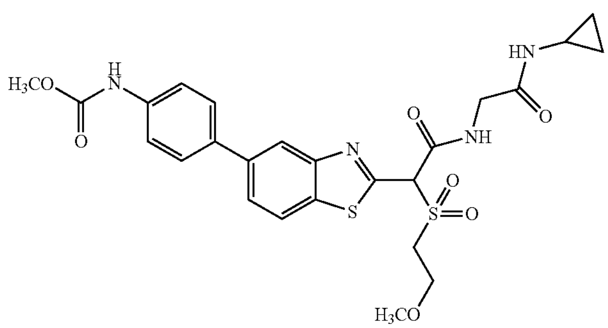 [SMILES: COCCS(=O)(=O)C(C(=O)NCC(=O)NC1CC1)c1nc2cc(-c3ccc(NC(=O)OC)cc3)ccc2s1] | methyl N-{4-[2-({[(cyclopropyl-carbamoyl)methyl]carbamoyl}(2-methoxyethane-sulfonyl)methyl)-1,3-benzothiazol-5-yl]phenyl} carbamate | 9.79 (s, 1H), 9.00 (s, 1H), 8.32 (d, J = 1.4 Hz, 1H), 8.20 (d, J = 8.5 Hz, 1H), 8.01 (d, J = 3.9 Hz, 1H), 7.81 (dd, J = 8.5, 1.7 Hz, 1H), 7.75 (d, J = 8.8 Hz, 2H), 7.59 (d, J = 8.8 Hz, 2H), 6.20 (s, 1H), 3.92-3.72 (m, 6H), 3.72-3.63 (m, 4H), 3.28 (s, 4H), 2.64 (d, J = 3.9 Hz, 1H), 0.63 (dd, J = 7.0, 1.8 Hz, 2H), 0.47-0.33 (m, 2H) | 1.46 N 561.1 | 28 |
| 105 | 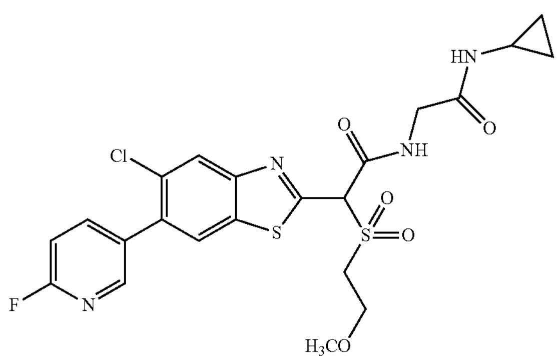 [SMILES: COCCS(=O)(=O)C(C(=O)NCC(=O)NC1CC1)c1nc2cc(Cl)c(-c3ccc(F)nc3)cc2s1] | 2-[5-chloro-6-(6-fluoropyridin-3-yl)-1,3-benzothiazol-2-yl]-N-[(cyclopropyl-carbamoyl)methyl]-2-(2-methoxyethane-sulfonyl)acetamide | 9.02 (t, J = 5.2 Hz, 1H), 8.45-8.30 (m, 3H), 8.18 (t, J = 8.3 Hz, 1H), 8.04 (d, J = 3.3 Hz, 1H), 7.37 (d, J = 8.3 Hz, 1H), 6.25 (s, 1H), 3.88-3.69 (m, 6H), 3.29 (s, 3H), 2.71-2.60 (m, 1H), 0.64 (d, J = 7.2 Hz, 2H), 0.46-0.34 (m, 2H) | 1.52 N 540.8 | 28 |
| 106 | 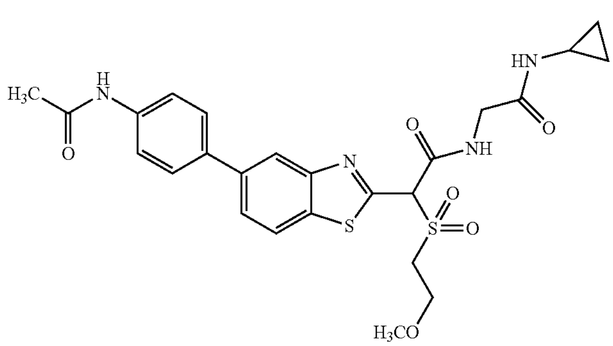 [SMILES: COCCS(=O)(=O)C(C(=O)NCC(=O)NC1CC1)c1nc2cc(-c3ccc(NC(C)=O)cc3)ccc2s1] | N-[(cyclopropyl-carbamoyl)methyl]-2-[5-(4-acetamidophenyl)-1,3-benzothiazol-2-yl]-2-(2-methoxyethane-sulfonyl)acetamide | 10.07 (s, 1H), 9.00 (br. s., 1H), 8.34 (s, 1H), 8.22 (d, J = 9.1 Hz, 1H), 8.03 (br. s., 1H), 7.83 (d, J = 8.3 Hz, 1H), 7.80-7.69 (m, 3H), 7.65 (br. s., 1H), 6.21 (s, 1H), 3.83 (br. s., 2H), 3.77 (d, J = 14.9 Hz, 4H), 3.29 (s, 3H), 2.65 (br. s., 2H), 2.10 (s, 3H), 0.64 (d, J = 7.4 Hz, 2H), 0.42 (br. s., 2H) | 1.20 N 545.2 | 30 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 107 | 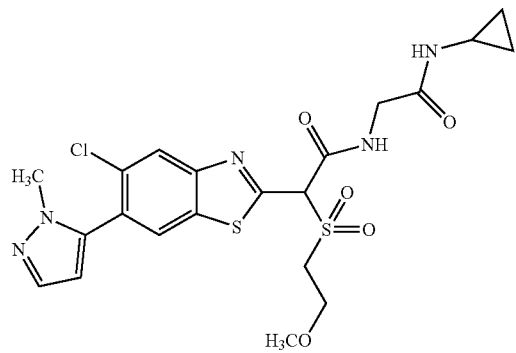 [SMILES: COCCS(=O)(=O)C(C(=O)NCC(=O)NC1CC1)c1nc2cc(Cl)c(-c3ccnn3C)cc2s1] | 2-[5-chloro-6-(1-methyl-1H-pyrazol-5-yl)-1,3-benzothiazol-2-3[1]-N-[(cyclopropyl-carbamoyl)methyl]-2-(2-methoxyethane-sulfonyl)acetamide | 9.02 (br. s., 1H), 8.41 (s, 1H), 8.35 (s, 1H), 8.04 (br. s., 1H), 7.59-7.45 (m, 1H), 6.42 (s, 1H), 6.25 (s, 1H), 3.88-3.70 (m, 6H), 3.70-3.60 (m, 3H), 3.29 (s, 3H), 2.70-2.59 (m, 1H), 0.64 (d, J = 6.9 Hz, 2H), 0.41 (br. s., 2H) | 1.29 N 526.1 | 34 |
| 108 | 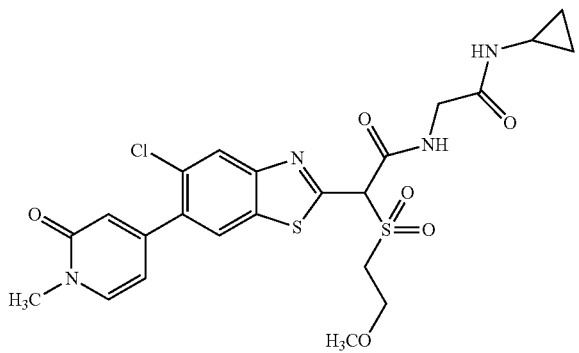 [SMILES: COCCS(=O)(=O)C(C(=O)NCC(=O)NC1CC1)c1nc2cc(Cl)c(-c3ccn(C)c(=O)c3)cc2s1] | 2-[5-chloro-6-(1-methyl-2-oxo-1,2-dihydropyridin-4-yl)-1,3-benzothiazol-2-yl]-N-[(cyclopropyl-carbamoyl)methyl]-2-(2-methoxyethane-sulfonyl)acetamide | 9.01 (s, 1H), 8.34 (s, 1H), 8.30 (s, 1H), 8.13-7.89 (m, 2H), 7.81 (d, J = 6.9 Hz, 1H), 6.47 (s, 1H), 6.35 (d, J = 6.9 Hz, 1H), 6.24 (s, 1H), 3.90-3.67 (m, 6H), 3.53-3.48 (m, 3H), 3.29 (s, 3H), 2.65 (d, J = 3.9 Hz, 1H), 0.64 (d, J = 6.9 Hz, 2H), 0.41 (br. s., 2H) | 1.14 N 552.8 | 51 |
| 109 | 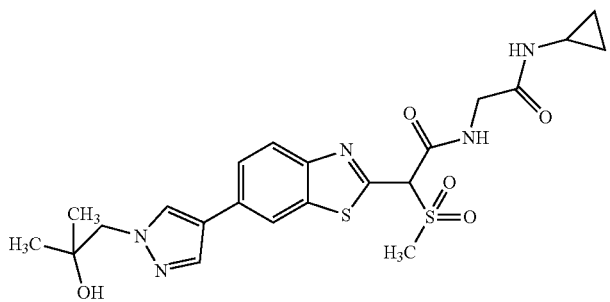 [SMILES: CC(C)(O)Cn1cc(-c2ccc3nc(C(C(=O)NCC(=O)NC4CC4)S(C)(=O)=O)sc3c2)cn1] | N-[(cyclopropyl-carbamoyl)methyl]-2-{6-[1-(2-hydroxy-2-methylpropyl)-1H-pyrazol-4-yl]-1,3-benzothiazol-2-yl}-2-methanesulfonyl-acetamide | 9.02 (t, J = 5.5 Hz, 1H), 8.38 (d, J = 1.4 Hz, 1H), 8.21 (s, 1H), 8.09-8.01 (m, 2H), 7.99 (s, 1H), 7.81 (dd, J = 8.5, 1.7 Hz, 1H), 6.17 (s, 1H), 4.07 (s, 2H), 3.83 (d, J = 5.5 Hz, 2H), 3.27 (s, 3H), 2.68-2.60 (m, 1H), 1.19-1.05 (m, 6H), 0.69-0.57 (m, 2H), 0.46-0.33 (m, 2H) | 1.11 N 506.2 | 14 |
| 110 | 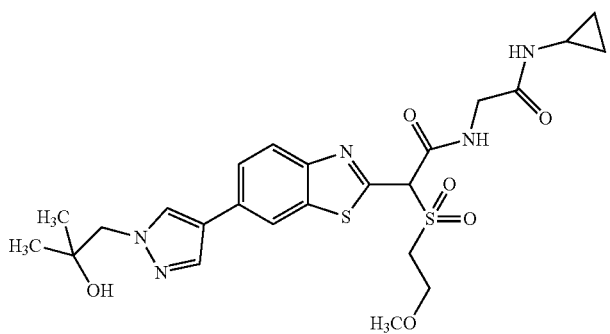 [SMILES: COCCS(=O)(=O)C(C(=O)NCC(=O)NC1CC1)c1nc2ccc(-c3cnn(CC(C)(C)O)c3)cc2s1] | N-[(cyclopropyl-carbamoyl)methyl]-2-{6-[1-(2-hydroxy-2-methylpropyl)-1H-pyrazol-4-yl]-1,3-enzothiazol-2-yl}-2-(2-methoxyethane-sulfonyl)acetamide | 8.99 (s, 1H), 8.38 (s, 1H), 8.21 (s, 1H), 8.14-7.93 (m, 3H), 7.81 (d, J = 8.5 Hz, 1H), 6.17 (s, 1H), 4.15-3.98 (m, 2H), 3.89-3.67 (m, 6H), 3.28 (s, 3H), 2.65 (d, J = 3.6 Hz, 1H), 1.21-1.03 (m, 6H), 0.64 (d, J = 6.9 Hz, 2H), 0.41 (br. s., 2H) | 1.18 N 550.1 | 31 |

| Ex. No. | Structure | Name | $^{1}$H NMR δ (500 MHz, DMSO-$d_6$, unless otherwise indicated) | LC/MS RT (min) Method M + H | EL IC$_{50}$ (nM) |
|---|---|---|---|---|---|
| 111 | 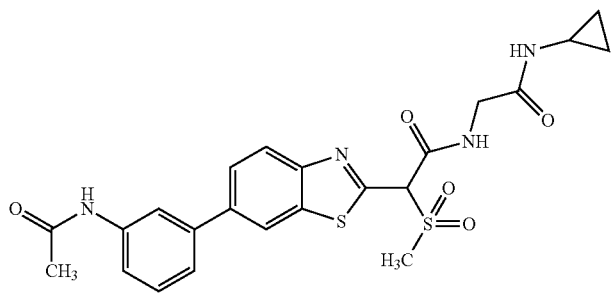 [SMILES: CC(=O)Nc1cccc(-c2ccc3nc(C(C(=O)NCC(=O)NC4CC4)S(C)(=O)=O)sc3c2)c1] | N-[(cyclopropyl-carbamoyl)methyl]-2-[6-(3-acetamidophenyl)-1,3-benzothiazol-2-yl]-2-methanesulfonyl-acetamide | 10.06 (s, 1H), 9.03 (s, 1H), 8.30-8.21 (m, 2H), 8.02 (s, 2H), 7.76 (dd, J = 8.5, 1.7 Hz, 1H), 7.49-7.37 (m, 2H), 6.23 (s, 1H), 3.84 (d, J = 5.5 Hz, 2H), 3.29 (s, 3H), 2.65 (m, 1H), 2.09 (s, 3H), 0.64 (dd, J = 7.3, 2.1 Hz, 2H), 0.41 (dt, J = 3.7, 1.7 Hz, 2H) | 0.81 M 500.9 | 23 |
| 112 | 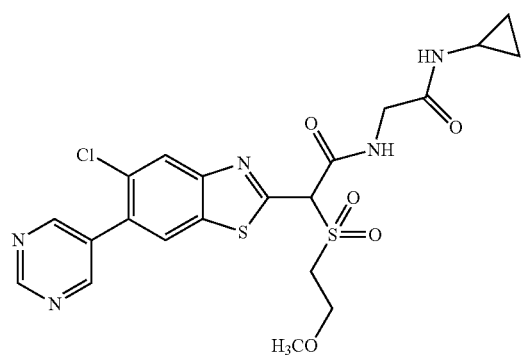 [SMILES: COCCS(=O)(=O)C(C(=O)NCC(=O)NC1CC1)c1nc2cc(Cl)c(-c3cncnc3)cc2s1] | 2-[5-chloro-6-(pyrimidin-5-yl)-1,3-benzothiazol-2-yl]-N-[(cyclopropyl-carbamoyl)methyl]-2-(2-methoxyethane-sulfonyl)acetamide | 9.34-9.22 (m, 1H), 9.07-8.99 (m, 2H), 8.96 (s, 1H), 8.43 (br. s., 1H), 8.04 (br. s., 1H), 6.26 (s, 1H), 3.91-3.70 (m, 6H), 3.30 (s, 3H), 2.72-2.57 (m, 1H), 0.64 (d, J = 6.9 Hz, 2H), 0.42 (br. s., 2H) | 1.19 N 524.1 | 97 |
| 113 | 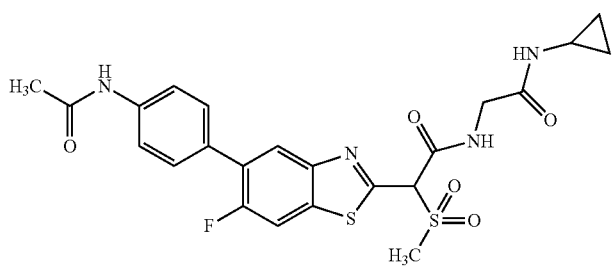 [SMILES: CC(=O)Nc1ccc(-c2cc3nc(C(C(=O)NCC(=O)NC4CC4)S(C)(=O)=O)sc3cc2F)cc1] | N-[(cyclopropyl-carbamoyl)methyl]-2-[5-(4-acetamidophenyl)-6-fluoro-1,3-benzothiazol-2-yl]-2-methanesulfonyl-acetamide | 10.12 (s, 1H), 9.14-8.92 (m, 1H), 8.26-8.10 (m, 2H), 8.10-8.00 (m, 1H), 7.81-7.65 (m, J = 8.5 Hz, 2H), 7.65-7.47 (m, J = 7.9 Hz, 2H), 6.20 (s, 1H), 3.84 (d, J = 5.5 Hz, 2H), 3.21 (s, 3H), 2.65 (d, J = 3.7 Hz, 1H), 2.10 (s, 3H), 0.64 (d, J = 6.1 Hz, 2H), 0.41 (br. s., 2H) | 1.30 N 518.8 | 9 |
| 114 | 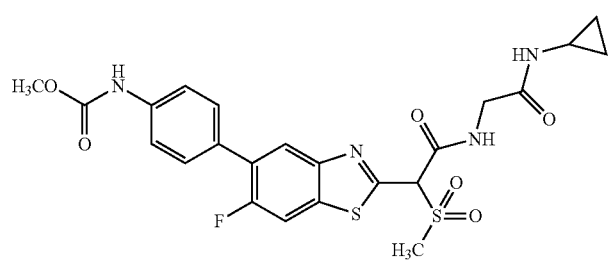 [SMILES: COC(=O)Nc1ccc(-c2cc3nc(C(C(=O)NCC(=O)NC4CC4)S(C)(=O)=O)sc3cc2F)cc1] | methyl N-{4-[2-({[(cyclopropyl-carbamoyl)methyl]caramoyl}(methanesulfonyl)methyl)-6-fluoro-1,3-benzothiazol-5-yl]phenyl} carbamate | 9.76 (br. s., 1H), 9.07-8.86 (m, 1H), 8.20-8.02 (m, 2H), 7.98 (br. s., 1H), 7.61-7.44 (m, 5H), 6.13 (s, 1H), 3.77 (d, J = 5.2 Hz, 2H), 3.21 (s, 3H), 2.5 (d, J = 3.7 Hz, 1H), 0.57 (d, J = 6.7 Hz, 2H), 0.34 (br. s., 2H) | 1.46 N 535.1 | 4 |

| Ex. No. | Structure | Name | ¹H NMR δ (500 MHz, DMSO-d₆, unless otherwise indicated) | LC/MS RT (min) ethod M + H | EL IC$_{50}$ (nM) |
|---|---|---|---|---|---|
| 115 | 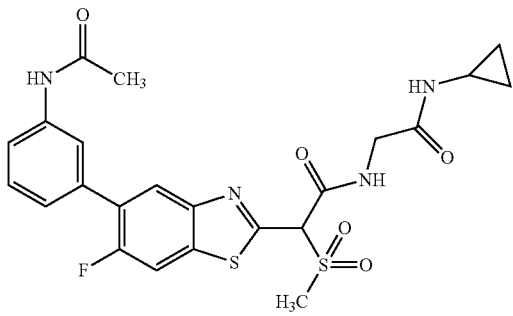 [SMILES: CC(=O)Nc1cccc(-c2cc3nc(C(C(=O)NCC(=O)NC4CC4)S(C)(=O)=O)sc3cc2F)c1] | N-[(cyclopropyl-carbamoyl)methyl]-2-[5-(3-acetamidophenyl)-6-fluoro-1,3-benzothiazol-2-yl]-2-methanesulfonyl-acetamide | 10.03 (br. s., 1H), 8.98 (br. s., 1H), 8.20-8.03 (m, 2H), 8.03-7.93 (m, 1H), 7.89 (s, 1H), 7.81 (br. s., 1H), 7.59 (d, J = 7.9 Hz, 1H), 7.38 (t, J = 7.9 Hz, 1H), 7.23 (d, J = 7.0 Hz, 1H), 6.14 (s, 1H), 3.77 (d, J = 5.2 Hz, 2H), 3.21(s, 2H), 2.58 (d, J = 3.4 Hz, 1H), 2.01 (s, 3H), 0.57 (d, J = 5.8 Hz, 2H), 0.34 (br. s., 2H) | 1.33 N 519.2 | 12 |
| 116 | 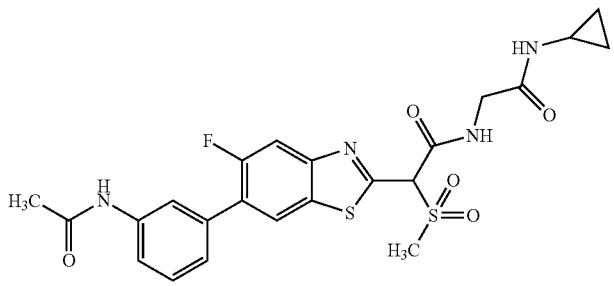 [SMILES: CC(=O)Nc1cccc(-c2cc3sc(C(C(=O)NCC(=O)NC4CC4)S(C)(=O)=O)nc3cc2F)c1] | N-[(cyclopropyl-carbamoyl)methyl]-2-[6-(3-acetamidophenyl)-5-fluoro-1,3-benzothiazol-2-yl]-2-methanesulfonyl-acetamide | 10.14 (br. s., 1H), 9.07 (br. s., 1H), 8.29 (d, J = 7.0 Hz, 1H), 8.05 (d, J = 9.5 Hz, 2H), 7.94 (s, 1H), 7.84 (br. s., 1H), 7.63 (d, J = 7.6 Hz, 1H), 7.45 (t, J = 7.8 Hz, 1H), 7.27 (d, J = 6.7 Hz, 1H), 6.18 (s, 1H), 3.83 (d, J = 4.6 Hz, 1H), 3.65 (s, 1H), 3.27 (s, 3H), 2.63 (br. s., 1H), 2.07 (s, 3H), 0.64 (d, J = 7.0 Hz, 2H), 0.40 (br. s., 2H) | 1.30 N 519.1 | 17 |
| 117 | 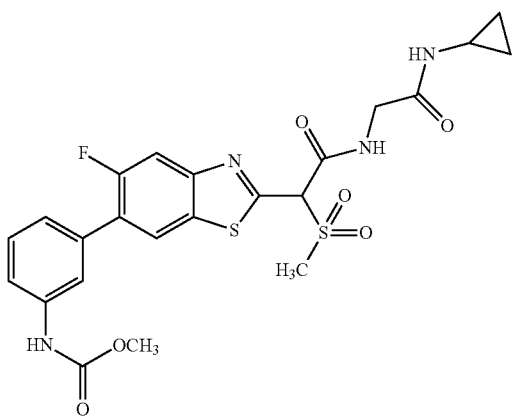 [SMILES: COC(=O)Nc1cccc(-c2cc3sc(C(C(=O)NCC(=O)NC4CC4)S(C)(=O)=O)nc3cc2F)c1] | methyl N-{3-[2-({[(cyclopropyl-carbamoyl)methyl]carbamoyl}(methanesulfonyl)methyl)-5-fluoro-1,3-benzothiazol-6-yl]phenyl}carbamate | 9.83 (br. s., 1H), 9.06 (br. s., 1H), 8.30 (d, J = 7.3 Hz, 1H), 8.10-7.97 (m, 2H), 7.67-7.51 (m, 4H), 6.18 (s, 1H), 3.83 (d, J = 4.9 Hz, 2H), 3.70 (s, 3H), 3.64-3.50 (m, 3H), 2.64 (br. s., 1H), 0.64 (d, J = 7.0 Hz, 2H), 0.40 (br. s., 2H) | 1.44 N 534.6 | 4 |
| 118 | 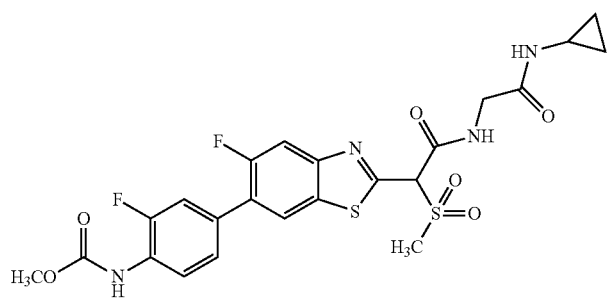 [SMILES: COC(=O)Nc1ccc(-c2cc3sc(C(C(=O)NCC(=O)NC4CC4)S(C)(=O)=O)nc3cc2F)cc1F] | methyl N-{4-[2-({[(cyclopropyl-carbamoyl)methyl]carbamoyl}(methanesulfonyl)methyl)-5-fluoro-1,3-benzothiazol-6-yl]-2-fluorophenyl}carbamate | 9.54 (br. s., 1H), 9.07 (br. s., 1H), 8.36 (d, J = 7.3 Hz, 1H), 8.14-7.98 (m, 2H), 7.81 (br. s., 1H), 7.51 (d, J = 11.9 Hz, 1H), 7.44 (d, J = 8.5 Hz, 1H), 6.19 (s, 1H), 3.83 (d, J = 4.9 Hz, 2H), 3.70 (s, 3H), 3.58 (s, 3H), 2.63 (br. s., 1H), 0.64 (d, J = 6.7 Hz, 2H), 0.40 (br. s., 2H) | 1.49 N 553.1 | 11 |

| Ex. No. | Structure | Name | $^1$H NMR δ (500 MHz, DMSO-$d_6$, unless otherwise indicated) | LC/MS RT (min) EL ethod M + H | IC$_{50}$ (nM) |
|---|---|---|---|---|---|
| 119 | 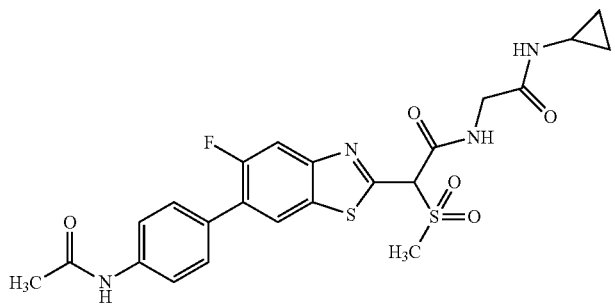 [SMILES: CC(=O)Nc1ccc(-c2cc3sc(C(C(=O)NCC(=O)NC4CC4)S(C)(=O)=O)nc3cc2F)cc1] | N-[(cyclopropylcarbamoyl)methyl]-2-[6-(4-acetamidophenyl)-5-fluoro-1,3-benzothiazol-2-yl]-2-methanesulfonylacetamide | 10.14 (s, 1H), 9.06 (t, J = 5.2 Hz, 1H), 8.31 (d, J = 7.3 Hz, 1H), 8.12-7.99 (m, 2H), 7.81-7.64 (m, J = 8.2 Hz, 2H), 7.64-7.45 (m, J = 7.9 Hz, 2H), 6.20 (s, 1H), 3.84 (d, J = 5.2 Hz, 2H), 3.46 (br. s., 3H), 2.65 (d, J = 3.7 Hz, 1H), 2.09 (s, 3H), 0.64 (d, J = 7.0 Hz, 2H), 0.41 (br. s., 2H) | 1.25 N 518.2 | 9 |
| 120 | 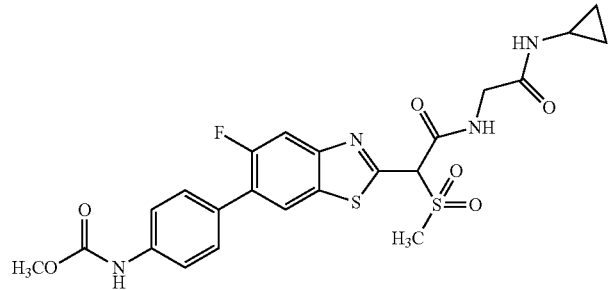 [SMILES: COC(=O)Nc1ccc(-c2cc3sc(C(C(=O)NCC(=O)NC4CC4)S(C)(=O)=O)nc3cc2F)cc1] | methyl N-{4-[2-({[(cyclopropylcarbamoyl)methyl]carbamoyl}(methanesulfonyl)methyl)-5-fluoro-1,3-benzothiazol-6-yl]phenyl} carbamate | 9.81 (br. s., 1H), 9.07 (br. s., 1H), 8.28 (d, J = 7.6 Hz, 1H), 8.09-7.96 (m, 2H), 7.66-7.48 (m, 4H), 6.16 (s, 1H), 3.82 (d, J = 5.2 Hz, 2H), 3.75-3.59 (m, 3H), 3.26 (s, 3H), 2.63 (d, J = 3.7 Hz, 1H), 0.64 (d, J = 6.7 Hz, 2H), 0.39 (br. s., 2H) | 1.43 N 534.4 | 4 |
| 121 | 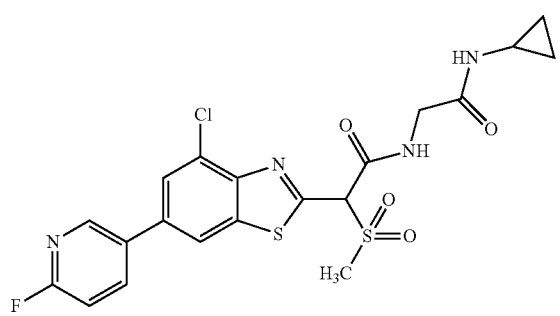 [SMILES: CS(=O)(=O)C(C(=O)NCC(=O)NC1CC1)c1nc2c(Cl)cc(-c3ccc(F)nc3)cc2s1] | 2-[4-chloro-6-(6-fluoropyridin-3-yl)-1,3-benzothiazol-2-yl]-N-[(cyclopropylcarbamoyl)methyl]-2-methanesulfonylacetamide | 9.05 (s, 1H), 8.70 (d, J = 2.5 Hz, 1H), 8.56 (d, J = 1.7 Hz, 1H), 8.44 (d, J = 2.8 Hz, 1H), 8.10 (d, J = 1.7 Hz, 1H), 8.07 (br. s., 1H), 7.39-7.33 (m, 1H), 6.29 (s, 1H), 3.85 (d, J = 5.5 Hz, 2H), 1.16 (s, 1H), 0.64 (dd, J = 7.3, 1.8 Hz, 2H), 0.45-0.36 (m, 2H) | 0.87 M 496.6 | 14 |
| 122 | 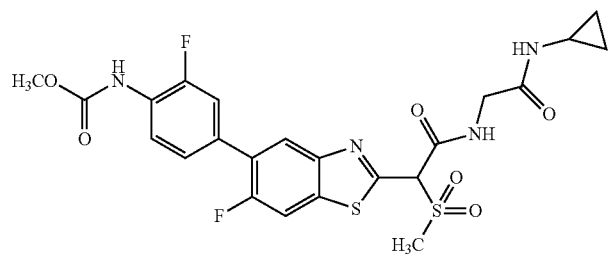 [SMILES: COC(=O)Nc1ccc(-c2cc3nc(C(C(=O)NCC(=O)NC4CC4)S(C)(=O)=O)sc3cc2F)cc1F] | methyl N-{4-[2-({[(cyclopropylcarbamoyl)methyl]carbamoyl}(methanesulfonyl)methyl)-6-fluoro-1,3-benzothiazol-5-yl]-2-fluorophenyl} carbamate | 9.59 (br. s., 1H), 9.13 (br. s., 1H), 8.30 (d, J = 6.7 Hz, 1H), 8.24 (d, J = 10.4 Hz, 1H), 8.11 (br. s., 1H), 7.87 (t, J = 7.8 Hz, 1H), 7.60 (d, J = 11.9 Hz, 1H), 7.52 (d, J = 8.2 Hz, 1H), 6.25 (s, 1H), 3.89 (d, J = 5.2 Hz, 2H), 3.77 (s, 3H), 3.34 (s, 3H), 2.70 (br. s., 1H), 0.70 (d, J = 7.0 Hz, 2H), 0.47 (br. s., 2H) | 1.46 N 553.1 | 7 |

| Ex. No. | Structure | Name | $^1$H NMR δ (500 MHz, DMSO-$d_6$, unless otherwise indicated) | LC/MS RT (min) EL ethod M + H | IC$_{50}$ (nM) |
|---|---|---|---|---|---|
| 123 | 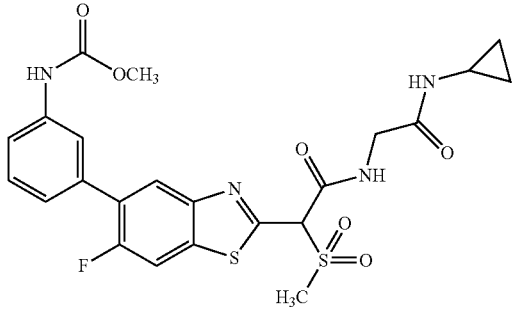 [SMILES: COC(=O)Nc1cccc(-c2cc3nc(C(C(=O)NCC(=O)NC4CC4)S(C)(=O)=O)sc3cc2F)c1] | methyl N-{3-[2-({[(cyclopropyl-carbamoyl)methyl]carbamoyl}(methanesulfonyl)methyl)-6-fluoro-1,3-benzothiazol-5-yl]phenyl} carbamate | 9.76 (s, 1H), 8.96 (s, 1H), 8.16-8.05 (m, 2H), 7.97 (d, J = 3.9 Hz, 1H), 7.59-7.44 (m, 4H), 6.12 (s, 1H), 3.76 (d, J = 5.8 Hz, 2H), 3.63 (s, 3H), 3.20 (s, 3H), 2.57 (d, J = 3.9 Hz, 1H), 0.63-0.48 (m, 2H), 0.33 (dd, J = 4.0, 2.1 Hz, 2H) | 1.49 N 535.1 | 5 |
| 124 | 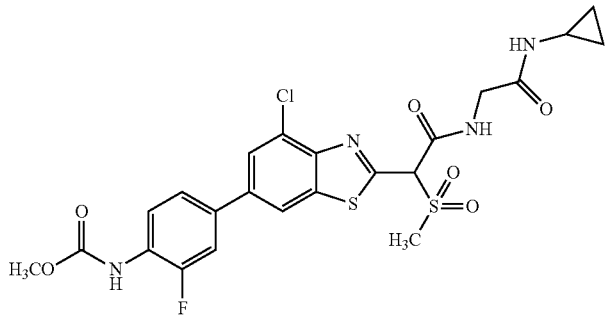 [SMILES: COC(=O)Nc1ccc(-c2cc(Cl)c3nc(C(C(=O)NCC(=O)NC4CC4)S(C)(=O)=O)sc3c2)cc1F] | methyl N-{4-[4-chloro-2-({[(cyclopropyl-carbamoyl)methyl]carbamoyl}(methanesulfonyl)methyl)-1,3-benzothiazol-6-yl]-2-fluorophenyl} carbamate | 9.30 (br. s., 1H), 8.83 (t, J = 5.4 Hz, 1H), 8.25 (s, 1H), 7.83 (d, J = 3.7 Hz, 1H), 7.78 (s, 1H), 7.57 (br. s., 1H), 7.48 (d, J = 12.1 Hz, 1H), 7.38 (d, J = 7.7 Hz, 2H), 6.01 (s, 1H), 3.59 (d, J = 5.4 Hz, 2H), 3.27 (d, J = 9.8 Hz, 2H), 3.07 (s, 2H), 2.38 (dd, J = 7.2, 3.5 Hz, 1H), 0.38 (d, J = 6.1 Hz, 2H), 0.15 (br. s., 2H) | 1.58 N 568.5 | 2 |
| 125 | 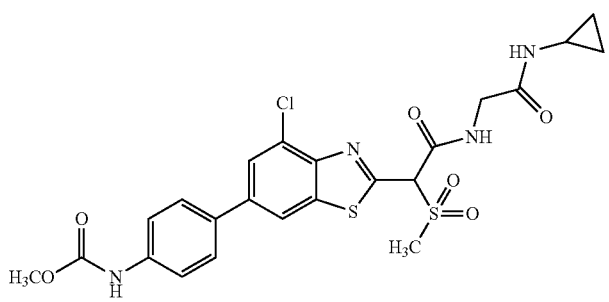 [SMILES: COC(=O)Nc1ccc(-c2cc(Cl)c3nc(C(C(=O)NCC(=O)NC4CC4)S(C)(=O)=O)sc3c2)cc1] | methyl N-{4-[4-chloro-2-({[(cyclopropyl-carbamoyl)methyl]carbamoyl}(methanesulfonyl)methyl)-1,3-benzothiazol-6-yl]phenyl} carbamate | 9.60 (s, 1H), 8.83 (t, J = 5.4 Hz, 1H), 8.18 (s, 1H), 7.83 (d, J = 3.4 Hz, 1H), 7.70 (s, 2H), 7.55-7.43 (m, J = 8.8 Hz, 2H), 7.41-7.25 (m, J = 8.4 Hz, 2H), 5.99 (s, 1H), 3.58 (d, J = 5.4 Hz, 2H), 3.44 (s, 3H), 3.06 (s, 3H), 2.38 (dd, J = 7.2, 3.5 Hz, 1H), 0.38 (d, J = 6.1 Hz, 2H), 0.14 (br. s., 2H) | 1.46 N 573.0 | 2 |
| 126 | 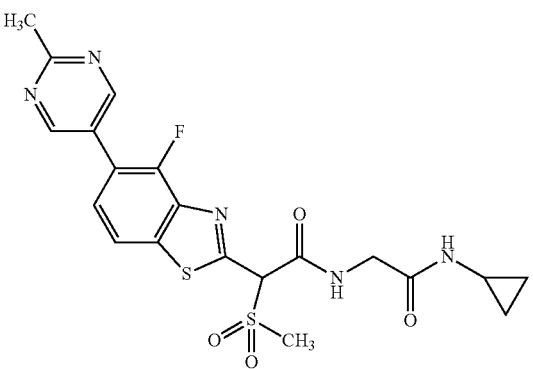 [SMILES: Cc1ncc(-c2ccc3sc(C(C(=O)NCC(=O)NC4CC4)S(C)(=O)=O)nc3c2F)cn1] | N-[(cyclopropyl-carbamoyl)methyl]-2-[4-fluoro-5-(2-methylpyrimidin-5-yl)-1,3-benzothiazol-2-yl]-2-methanesulfonyl-acetamide | 8.85 (br. s., 1H), 8.75 (s, 2H), 7.90 (d, J = 8.4 Hz, 1H), 7.83 (br. s., 1H), 7.53 (t, J = 7.4 Hz, 1H), 6.02 (s, 1H), 3.59 (d, J = 5.4 Hz, 2H), 3.05 (s, 3H), 2.39 (d, J = 3.7 Hz, 1H), 2.27 (br. s., 3H), 0.39 (d, J = 6.7 Hz, 2H), 0.15 (br. s., 2H) | 1.13 N 478 | 137 |

-continued

| Ex. No. | Structure | Name | $^1$H NMR δ (500 MHz, DMSO-$d_6$, unless otherwise indicated) | LC/MS RT (min) EL ethod M + H | IC$_{50}$ (nM) |
|---|---|---|---|---|---|
| 127 | 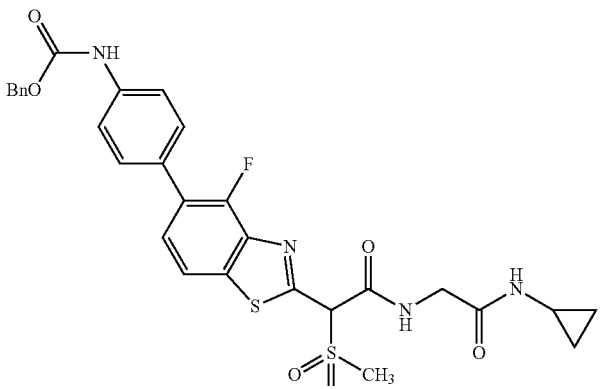 | benzyl N-{4-[2-({[(cyclopropyl-carbamoyl)methyl] carbamoyl} (methanesulfonyl) methyl)-4-fluoro-1,3-benzothiazol-5-yl]phenyl} carbamate | 9.06 (s, 1H), 8.01 (d, J = 8.2 Hz, 3H), 7.69-7.49 (m, 5H), 7.47-7.26 (m, 6H), 5.17 (s, 2H), 3.81 (d, J = 5.5 Hz, 2H), 2.67-2.56 (m, 1H), 2.50 (br. s., 3H), 0.62 (d, J = 7.0 Hz, 2H), 0.38 (br. s., 2H) | 1.86 N 611 | 3 |
| 128 | 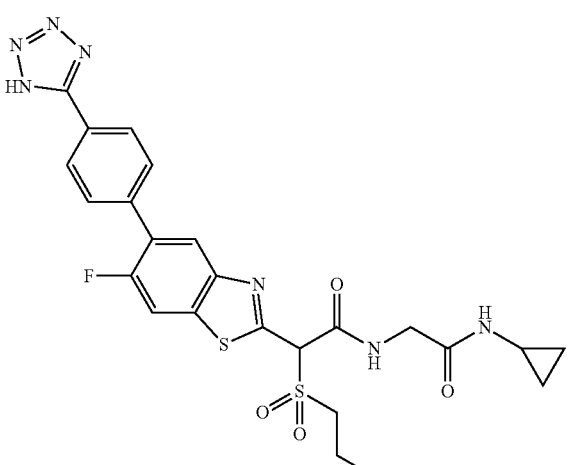 | N-[(cyclopropyl-carbamoyl) methyl]-2-{6-fluoro-5-[4-(1H-1,2,3,4-tetrazol-5-yl) phenyl]-1,3-benzothiazol-2-yl}-2-(2-methoxyethane-sulfonyl) acetamide | 9.01 (t, J = 5.5 Hz, 1H), 8.24 (d, J = 7.0 Hz, 1H), 8.13 (d, J = 7.9 Hz, 3H), 7.98 (d, J = 3.7 Hz, 1H), 7.83 (d, J = 7.6 Hz, 2H), 6.10 (s, 1H), 3.84-3.62 (m, 6H), 3.25 (s, 3H), 2.59 (d, J = 3.7 Hz, 1H), 0.62 (d, J = 5.8 Hz, 2H), 0.37 (br. s., 2H) | 1.08 N 574 | 97 |
| 129 | 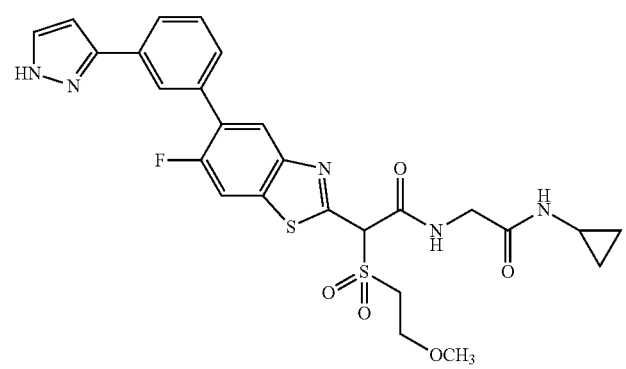 [SMILES: COCCS(=O)(=O)C(C(=O)NCC(=O)NC1CC1)c1nc2cc(-c3cccc(-c4cc[nH]n4)c3)c(F)cc2s1] | N-[(cyclopropyl-carbamoyl) methyl]-2-{6-fluoro-5-[3-(1H-pyrazol-3-yl) phenyl]-1,3-benzothiazol-2-yl}-2-(2-methoxyethane-sulfonyl) acetamide | 9.00 (t, J = 5.2 Hz, 1H), 8.28-7.81 (m, 5H), 7.55 (d, J = 4.3 Hz, 2H), 6.83-6.75 (m, 1H), 6.19 (s, 1H), 3.90-3.62 (m, 5H), 3.49-3.39 (m, 1H), 3.27 (s, 3H), 2.63 (d, J = 3.7 Hz, 1H), 0.62 (d, J = 6.4 Hz, 2H), 0.39 (br. s., 2H) | 1.54 N 572 | 12 |

-continued

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 130 | 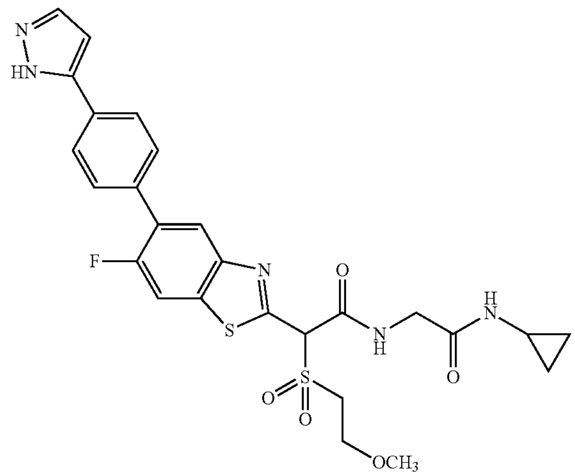 [SMILES: COCCS(=O)(=O)C(C(=O)NCC(=O)NC1CC1)c1nc2cc(-c3ccc(-c4ccn[nH]4)cc3)c(F)cc2s1] | N-[(cyclopropylcarbamoyl)methyl]-2-{6-fluoro-5-[4-(1H-pyrazol-5-yl)phenyl]-1,3-benzothiazol-2-yl}-2-(2-methoxyethanesulfonyl)acetamide | 9.07 (t, J = 5.2 Hz, 1H), 8.34-8.21 (m, 2H), 8.12-7.63 (m, 7H), 6.88-6.81 (m, 1H), 3.98-3.68 (m, 5H), 3.55-3.47 (m, 1H), 3.34 (s, 3H), 2.70 (d, J = 3.7 Hz, 1H), 0.70 (d, J = 6.1 Hz, 2H), 0.46 (br. s., 2H) | 1.5 N 572 | 18 |
| 131 | 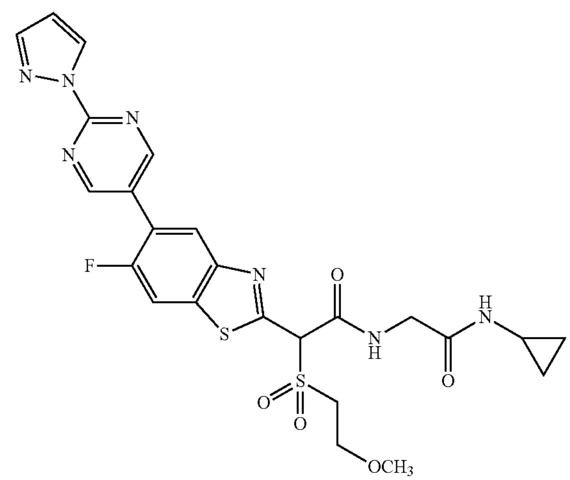 [SMILES: COCCS(=O)(=O)C(C(=O)NCC(=O)NC1CC1)c1nc2cc(-c3cnc(-n4cccn4)nc3)c(F)cc2s1] | N-[(cyclopropylcarbamoyl)methyl]-2-{6-fluoro-5-[2-(1H-pyrazol-1-yl)pyrimidin-5-yl]-1,3-benzothiazol-2-yl}-2-(2-methoxyethanesulfonyl)acetamide | 9.23 (s, 2H), 9.08 (t, J = 5.5 Hz, 1H), 8.80 (d, J = 2.4 Hz, 1H), 8.56 (d, J = 6.7 Hz, 1H), 8.35 (d, J = 10.4 Hz, 1H), 8.09 (d, J = 4.0 Hz, 1H), 8.03-7.96 (m, 2H), 6.72 (br. s., 1H), 6.28 (s, 1H), 3.97-3.75 (m, 4H), 3.49 (s, 2H), 3.34 (s, 3H), 2.70 (dt, J = 7.2, 3.5 Hz, 1H), 0.74-0.66 (m, 2H), 0.46 (br. s., 2H) | 1.4 N 574 | 131 |
| 132 | 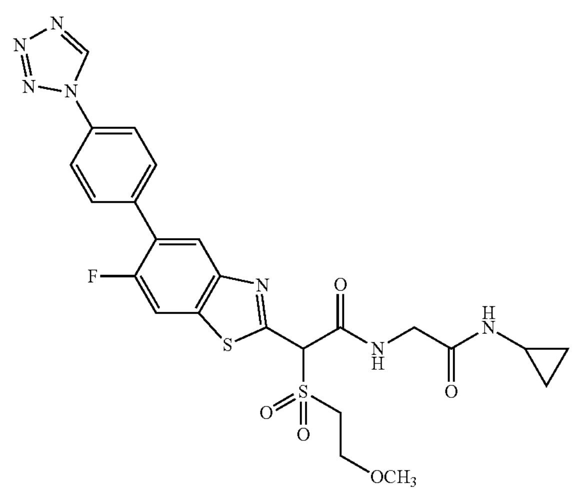 [SMILES: COCCS(=O)(=O)C(C(=O)NCC(=O)NC1CC1)c1nc2cc(-c3ccc(-n4cnnn4)cc3)c(F)cc2s1] | N-[(cyclopropylcarbamoyl)methyl]-2-{6-fluoro-5-[4-(1H-1,2,3,4-tetrazol-1-yl)phenyl]-1,3-benzothiazol-2-yl}-2-(2-methoxyethanesulfonyl)acetamide | 9.00 (t, J = 5.2 Hz, 1H), 8.37-8.16 (m, 2H), 8.11-7.79 (m, 6H), 6.19 (s, 1H), 3.95-3.62 (m, 5H), 3.49-3.36 (m, 1H), 3.27 (s, 3H), 2.63 (d, J = 3.7 Hz, 1H), 0.62 (d, J = 5.5 Hz, 2H), 0.39 (br. s., 2H) | 1.35 N 571.6 (M − H) | 52 |

-continued

| Ex. No. | Structure | Name | ¹H NMR δ (500 MHz, DMSO-d₆, unless otherwise indicated) | LC/MS RT (min) ethod M + H | EL IC₅₀ (nM) |
|---|---|---|---|---|---|
| 133 | 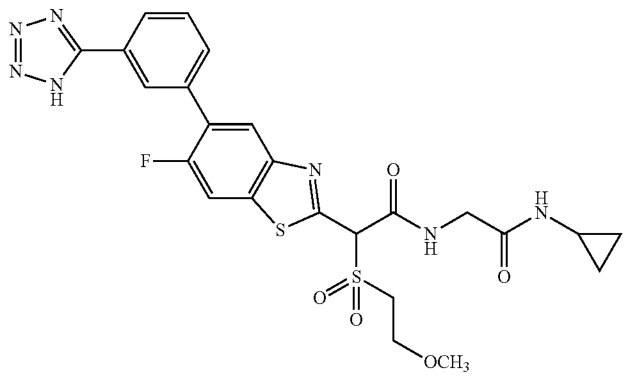 [SMILES: COCCS(=O)(=O)C(C(=O)NCC(=O)NC1CC1)c1nc2cc(-c3cccc(-c4nnn[nH]4)c3)c(F)cc2s1] | N-[(cyclopropyl-carbamoyl)methyl]-2-{6-fluoro-5-[3-(1H-1,2,3,4-tetrazol-5-yl)phenyl]-1,3-benzothiazol-2-yl}-2-(2-methoxyethane-sulfonyl)acetamide | 9.01 (t, J = 5.5 Hz, 1H), 8.28-8.22 (m, 2H), 8.16 (d, J = 10.4 Hz, 1H), 8.08 (d, J = 7.9 Hz, 1H), 7.99 (d, J = 3.7 Hz, 1H), 7.83 (d, J = 7.6 Hz, 1H), 7.78-7.69 (m, 1H), 6.11 (s, 1H), 3.83-3.64 (m, 6H), 3.25 (s, 3H), 2.59 (dt, J = 7.1, 3.6 Hz, 1H), 0.62 (d, J = 5.8 Hz, 2H), 0.37 (d, J = 2.1 Hz, 2H) | 1.15 N 574 | 145 |
| 134 | 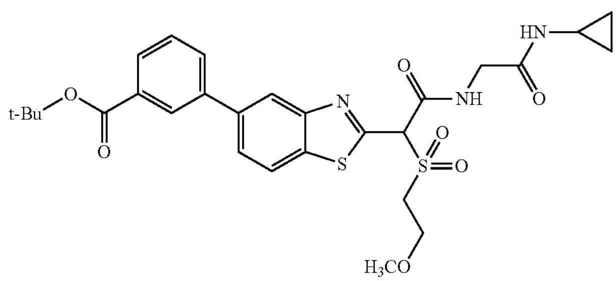 [SMILES: COCCS(=O)(=O)C(C(=O)NCC(=O)NC1CC1)c1nc2cc(-c3cccc(C(=O)OC(C)(C)C)c3)ccc2s1] | tert-butyl 3-[2-({[(cyclopropyl-carbamoyl)methyl]carbamoyl}(2-methoxyethane-sulfonyl)methyl)-1,3-benzothiazol-5-yl]benzoate | 9.00 (t, J = 5.2 Hz, NH), 8.38 (s, 1H), 8.32-8.18 (m, 2H), 8.11-7.81 (m, 4H), 7.68-7.56 (m, 1H), 6.22 (s, 1H), 3.95-3.67 (m, 7H), 3.27 (s, 3H), 2.63 (d, J = 3.3 Hz, 1H), 0.62 (d, J = 6.9 Hz, 2H), 0.40 (br. s., 2H) | 2.2 B 588.3 | 2 |
| 135 | 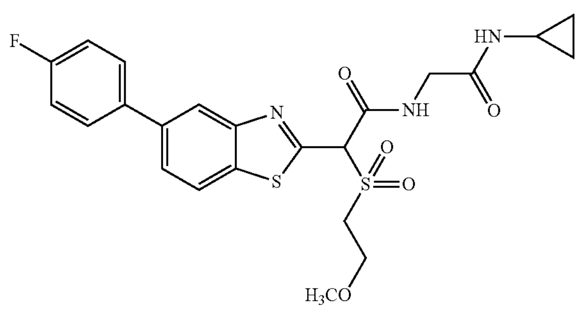 [SMILES: COCCS(=O)(=O)C(C(=O)NCC(=O)NC1CC1)c1nc2cc(-c3ccc(F)cc3)ccc2s1] | N-[(cyclopropyl-carbamoyl)methyl]-2-[5-(4-fluorophenyl)-1,3-benzothiazol-2-yl]-2-(2-methoxyethane-sulfonyl)acetamide | 9.01 (t, J = 5.4 Hz, 1H), 8.35 (d, J = 1.1 Hz, 1H), 8.25 (d, J = 8.5 Hz, 1H), 8.02 (d, J = 3.9 Hz, 1H), 7.90-7.78 (m, 2H), 7.35 (t, J = 8.8 Hz, 2H), 6.21 (s, 1H), 3.95-3.69 (m, 6H), 3.29 (s, 3H), 2.65 (td, J = 7.3, 3.9 Hz, 1H), 0.64 (dd, J = 7.0, 1.5 Hz, 2H), 0.45-0.37 (m, 2H) | 1.68 N 506.2 | 49 |
| 136 | 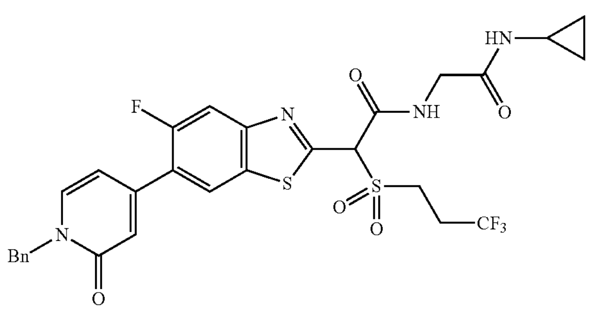 [SMILES: O=C(CNC(=O)C(c1nc2cc(F)c(-c3ccn(Cc4ccccc4)c(=O)c3)cc2s1)S(=O)(=O)CCC(F)(F)F)NC1CC1] | 2-[6-(1-benzyl-2-oxo-1,2-dihydropyridin-4-yl)-5-fluoro-1,3-benzothiazol-2-yl]-N-[(cyclopropyl-carbamoyl)methyl]-2-(3,3,3-trifluoropropane-sulfonyl)acetamide | 9.11-9.02 (m, 1H), 8.45-8.38 (m, 1H), 8.13-8.03 (m, 2H), 7.89 (d, J = 7.0 Hz, 1H), 7.45-7.19 (m, 5H), 6.71-6.32 (m, 2H), 5.25-4.98 (m, 2H), 3.88-3.54 (m, 3H), 2.90-2.68 (m, 3H), 2.65-2.57 (m, 1H), 0.61 (d, J = 6.4 Hz, 2H), 0.38 (br. s., 2H) | 1.74 U 651.1 | 6 |

-continued

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 137 | 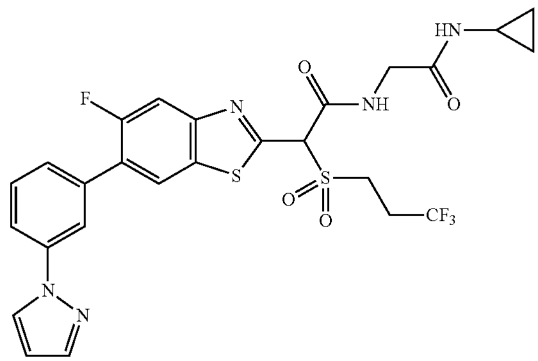 [SMILES: O=C(CNC(=O)C(c1nc2cc(F)c(-c3cccc(-n4cccn4)c3)cc2s1)S(=O)(=O)CCC(F)(F)F)NC1CC1] | N-[(cyclopropyl-carbamoyl)methyl]-2-{5-fluoro-6-[3-(1H-pyrazol-1-yl)phenyl]-1,3-benzothiazol-2-yl}-2-(3,3,3-trifluoropropane-sulfonyl)acetamide | 9.15-9.09 (m, 1H), 8.69-8.57 (m, 1H), 8.52-8.44 (m, 1H), 8.04 (s, 4H), 7.90-7.70 (m, 3H), 6.65 (br. s., 1H), 6.45 (s, 1H), 3.93-3.76 (m, 3H), 3.64-3.55 (m, 1H), 2.99-2.87 (m, 1H), 2.74-2.62 (m, 1H), 0.74-0.67 (m, 2H), 0.51-0.42 (m, 2H) | 1.92 U 610.1 | 1 |
| 138 | 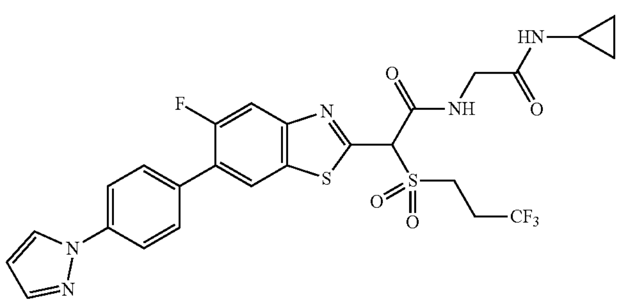 [SMILES: O=C(CNC(=O)C(c1nc2cc(F)c(-c3ccc(-n4cccn4)cc3)cc2s1)S(=O)(=O)CCC(F)(F)F)NC1CC1] | N-[(cyclopropyl-carbamoyl)methyl]-2-{5-fluoro-6-[4-(1H-pyrazol-1-yl)phenyl]-1,3-benzothiazol-2-yl}-2-(3,3,3-trifluoropropane-sulfonyl)acetamide | 9.05 (t, J = 5.2 Hz, 1H), 8.60-8.53 (m, 1H), 8.44 (d, J = 7.6 Hz, 1H), 8.13-8.04 (m, 2H), 7.94-7.82 (m, 1H), 7.77 (br. s., 1H), 7.70-7.42 (m, 2H), 6.57 (br. s., 1H), 6.37 (s, 1H), 3.91-3.71 (m, 3H), 3.52 (br. s., 3H), 2.90-2.81 (m, 1H), 2.66-2.57 (m, 1H), 0.62 (d, J = 6.1 Hz, 2H), 0.39 (br. s., 2H) | 1.84 S 610.1 | 6 |
| 139 | 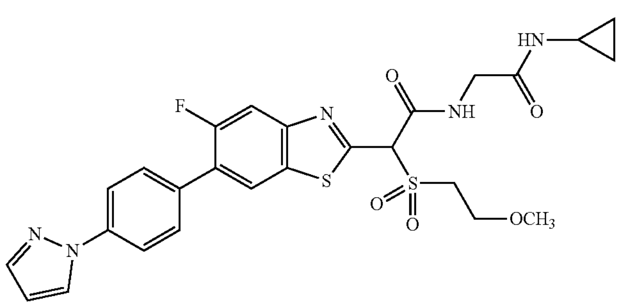 [SMILES: COCCS(=O)(=O)C(C(=O)NCC(=O)NC1CC1)c1nc2cc(F)c(-c3ccc(-n4cccn4)cc3)cc2s1] | N-[(cyclopropyl-carbamoyl)methyl]-2-{5-fluoro-6-[4-(1H-pyrazol-1-yl)phenyl]-1,3-benzothiazol-2-yl}-2-(2-methoxyethane-sulfonyl)acetamide | 9.05-8.94 (m, 1H), 8.60-8.53 (m, 1H), 8.43-8.36 (m, 1H), 8.10-7.91 (m, 4H), 7.81-7.66 (m, 3H), 6.62-6.55 (m, 1H), 6.23-6.11 (m, 1H), 3.81 (br. s., 5H), 3.41-3.35 (m, 1H), 3.27 (s, 3H), 2.67-2.57 (m, 1H), 0.67-0.58 (m, 2H), 0.42-0.34 (m, 2H) | 1.7 U 572.1 | 2 |
| 140 | 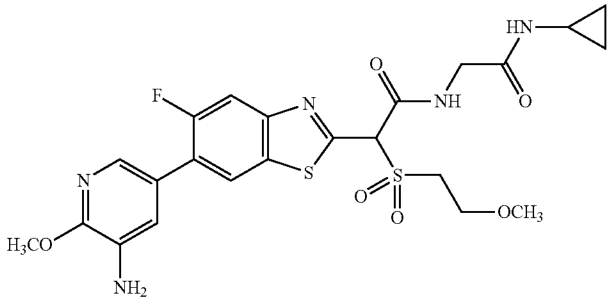 [SMILES: COCCS(=O)(=O)C(C(=O)NCC(=O)NC1CC1)c1nc2cc(F)c(-c3cnc(OC)c(N)c3)cc2s1] | 2-[6-(5-amino-6-methoxypyridin-3-yl)-5-fluoro-1,3-benzothiazol-2-3[1]-N-[(cyclopropyl-carbamoyl)methyl]-2-(2-methoxyethane-sulfonyl)acetamide | 8.99 (br. s., 1H), 8.27 (d, J = 7.6 Hz, 1H), 8.09-7.92 (m, 2H), 7.64-7.47 (m, 1H), 7.19-7.03 (m, 1H), 6.27-5.04 (m, 1H), 3.97-3.88 (m, 3H), 3.85-3.60 (m, 5H), 3.38 (br. s., 1H), 3.26 (s, 2H), 3.14 (s, 1H), 2.69-2.58 (m, 1H), 0.62 (d, J = 5.2 Hz, 2H), 0.39 (br. s., 2H) | 1.27 U 552.1 | 12 |

-continued

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 141 | 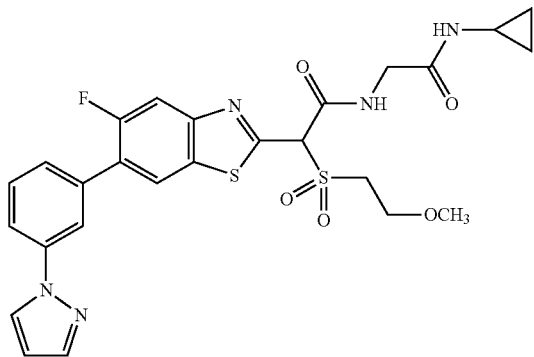 [SMILES: COCCS(=O)(=O)C(C(=O)NCC(=O)NC1CC1)c1nc2cc(F)c(-c3cccc(-n4cccn4)c3)cc2s1] | N-[(cyclopropyl-carbamoyl)methyl]-2-{5-fluoro-6-[3-(1H-pyrazol-1-yl)phenyl]-1,3-benzothiazol-2-yl}-2-(2-methoxyethane-sulfonyl)acetamide | 9.06-8.96 (m, 1H), 8.64-8.54 (m, 1H), 8.47-8.41 (m, 1H), 8.13-8.05 (m, 2H), 8.04-7.98 (m, 1H), 7.95-7.89 (m, 1H), 7.80-7.74 (m, 1H), 7.69-7.60 (m, 1H), 7.56-7.52 (m, 1H), 6.62-6.50 (m, 1H), 6.26-6.14 (m, 1H), 3.82 (br. s., 4H), 3.42-3.35 (m, 3H), 3.27 (s, 2H), 2.66-2.58 (m, 1H), 0.66-0.59 (m, 2H), 0.42-0.35 (m, 2H) | 1.69 U 572.1 | 2 |
| 142 | 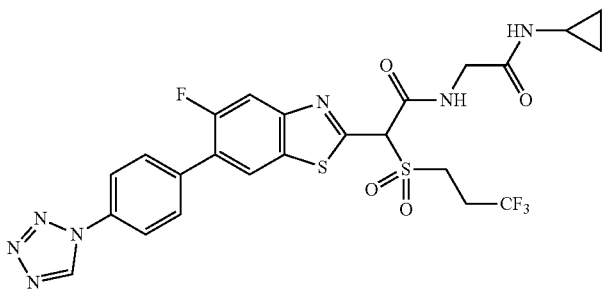 [SMILES: O=C(CNC(=O)C(c1nc2cc(F)c(-c3ccc(-n4cnnn4)cc3)cc2s1)S(=O)(=O)CCC(F)(F)F)NC1CC1] | N-[(cyclopropyl-carbamoyl)methyl]-2-{5-fluoro-6-[4-(1H-1,2,3,4-tetrazol-1-yl)phenyl]-1,3-benzothiazol-2-yl}-2-(3,3,3-trifluoropropane-sulfonyl)acetamide | 10.14-10.04 (m, 1H), 9.12-9.01 (m, 1H), 8.51-8.40 (m, 1H), 8.15-7.98 (m, 4H), 7.94-7.78 (m, 2H), 6.43-6.28 (m, 1H), 3.88-3.50 (m, 4H), 2.91-2.82 (m, 2H), 2.67-2.57 (m, 1H), 0.67-0.59 (m, 2H), 0.40 (br. s., 2H) | 1.62 U 612.1 | 5 |
| 143 | 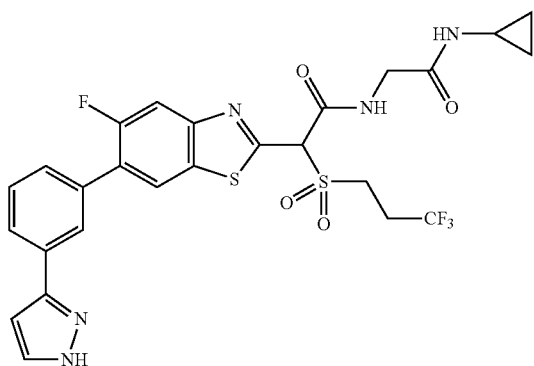 [SMILES: O=C(CNC(=O)C(c1nc2cc(F)c(-c3cccc(-c4cc[nH]n4)c3)cc2s1)S(=O)(=O)CCC(F)(F)F)NC1CC1] | N-[(cyclopropyl-carbamoyl)methyl]-2-{5-fluoro-6-[3-(1H-pyrazol-3-yl)phenyl]-1,3-benzothiazol-2-yl}-2-(3,3,3-trifluoropropane-sulfonyl)acetamide | 9.12-9.01 (m, 1H), 8.41 (d, J = 7.3 Hz, 1H), 8.12-7.68 (m, 6H), 7.60-7.41 (m, 2H), 6.80-6.71 (m, 1H), 6.38 (s, 1H), 3.92-3.69 (m, 3H), 2.91-2.81 (m, 2H), 2.62 (d, J = 3.7 Hz, 1H), 0.62 (d, J = 6.7 Hz, 2H), 0.39 (br. s., 2H) | 1.59 U 610.1 | 3 |
| 144 | 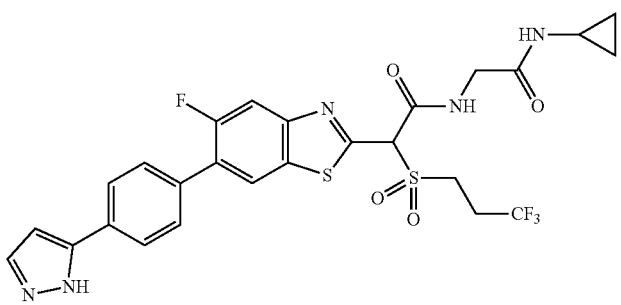 [SMILES: O=C(CNC(=O)C(c1nc2cc(F)c(-c3ccc(-c4ccn[nH]4)cc3)cc2s1)S(=O)(=O)CCC(F)(F)F)NC1CC1] | N-[(cyclopropyl-carbamoyl)methyl]-2-{5-fluoro-6-[4-(1H-pyrazol-5-yl)phenyl]-1,3-benzothiazol-2-yl}-2-(3,3,3-trifluoropropane-sulfonyl)acetamide | 9.13-8.95 (m, 1H), 8.39 (d, J = 7.3 Hz, 1H), 8.15-8.01 (m, 2H), 7.98-7.86 (m, 2H), 7.84-7.54 (m, 4H), 6.84-6.71 (m, 1H), 6.37 (s, 1H), 3.86-3.71 (m, 3H), 3.51-3.43 (m, 1H), 2.93-2.80 (m, 2H), 2.67-2.58 (m, 1H), 1.29 (s, 1H), 0.62 (d, J = 6.4 Hz, 2H), 0.39 (br. s., 2H) | 1.55 U 610 | 1 |

| Ex. No. | Structure | Name | $^1$H NMR δ (500 MHz, DMSO-$d_6$, unless otherwise indicated) | LC/MS RT (min) ethod M + H | EL IC$_{50}$ (nM) |
|---|---|---|---|---|---|
| 145 | 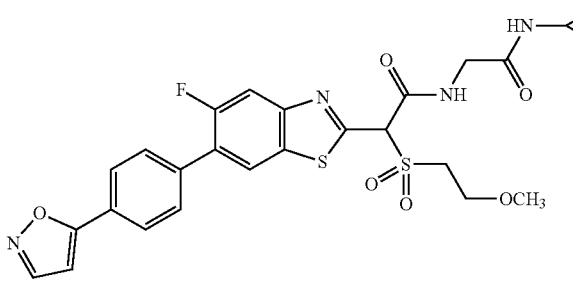 | N-[(cyclopropyl-carbamoyl)methyl]-2-{5-fluoro-6-[4-(1,2-oxazol-5-yl)phenyl]-1,3-benzothiazol-2-yl}-2-(2-methoxyethane-sulfonyl)acetamide | 9.03-8.99 (m, 1H), 8.67 (s, 1H), 8.41 (d, J = 7.6 Hz, 1H), 8.17-7.95 (m, 5H), 7.82-7.69 (m, 2H), 7.16-7.03 (m, 1H), 6.19 (s, 1H), 3.84-3.67 (m, 5H), 3.27 (s, 3H), 2.62 (d, J = 3.7 Hz, 1H), 0.62 (d, J = 6.1 Hz, 2H), 0.39 (br. s., 2H) | 1.57 U 573 | 3 |
| 146 | 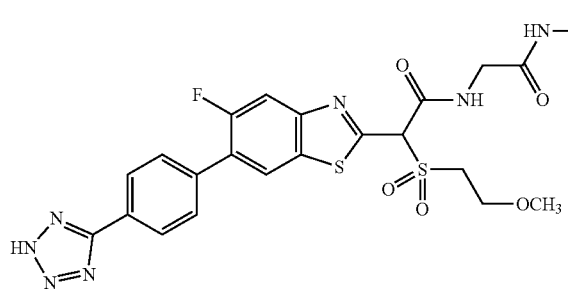 | N-[(cyclopropyl-carbamoyl)methyl]-2-{5-fluoro-6-[4-(2H-1,2,3,4-tetrazol-5-yl)phenyl]-1,3-benzothiazol-2-yl}-2-(2-methoxyethane-sulfonyl)acetamide | 9.09 (t, J = 5.3 Hz, 1H), 8.50 (d, J = 7.3 Hz, 1H), 8.29-8.06 (m, 5H), 7.97-7.83 (m, 3H), 6.28 (s, 1H), 3.93-3.75 (m, 5H), 3.35 (s, 3H), 2.75-2.66 (m, 1H), 0.70 (d, J = 5.8 Hz, 2H), 0.47 (br. s., 2H) | 1.26 U 574 | 6 |
| 147 | 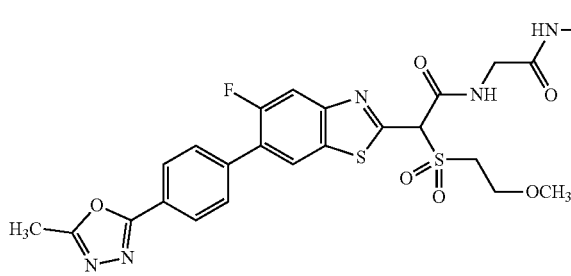 | N-[(cyclopropyl-carbamoyl)methyl]-2-{5-fluoro-6-[4-(5-methyl-1,3,4-oxadiazol-2-yl)phenyl]-1,3-benzothiazol-2-yl}-2-(2-methoxyethane-sulfonyl)acetamide | 9.01 (br. s., 1H), 8.42 (d, J = 7.3 Hz, 1H), 8.14-8.00 (m, 3H), 7.87-7.82 (m, 2H), 6.19 (s, 1H), 3.84-3.68 (m, 7H), 3.27 (s, 3H), 2.60 (s, 4H), 0.62 (d, J = 6.4 Hz, 2H), 0.39 (br. s., 2H) | 1.47 U 588.1 | 4 |
| 148 | 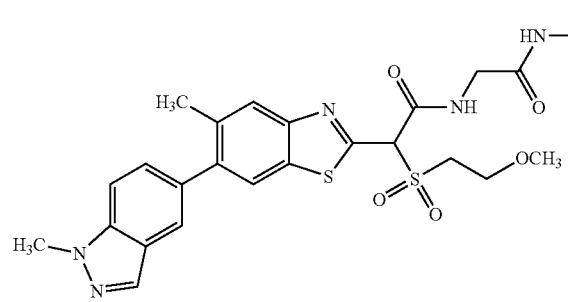 | N-[(cyclopropyl-carbamoyl)methyl]-2-(2-methoxyethane-sulfonyl)-2-[5-methyl-6-(1-methyl-1H-indazol-5-yl)-1,3-benzothiazol-2-yl]acetamide | 8.99 (t, J = 5.5 Hz, 1H), 8.06-8.12 (m, 1H), 7.63-8.05 (m, 5H), 7.43 (dd, J = 8.7, 1.5 Hz, 1H), 6.19 (s, 1H), 4.00-4.19 (m, 3H), 3.61-3.89 (m, 6H), 3.29 (s, 3H), 2.64 (td, J = 7.2, 3.7 Hz, 1H), 2.37 (s, 3H), 0.57-0.76 (m, 2H), 0.16-0.48 (m, 2H) | 0.96 M 556.3 | 2 |
| 149 | 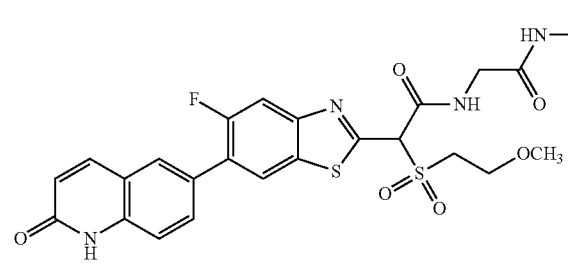 | N-[(cyclopropyl-carbamoyl)methyl]-2-[5-fluoro-6-(2-oxo-1,2-dihydroquinolin-6-yl)-1,3-benzothiazol-2-yl]-2-(2-methoxyethane-sulfonyl)acetamide | 11.89 (s, 1H), 9.01 (t, J = 5.5 Hz, 1H), 8.38 (d, J = 7.7 Hz, 1H), 7.89-8.22 (m, 4H), 7.67-7.84 (m, 1H), 7.44 (d, J = 8.5 Hz, 1H), 6.57 (dd, J = 9.6, 1.9 Hz, 1H), 6.22 (s, 1H), 3.62-4.04 (m, 6H), 3.28 (s, 3H), 2.64 (td, J = 7.4, 3.7 Hz, 1H), 0.56-0.75 (m, 2H), 0.31-0.47 (m, 2H) | 0.69 M 573.2 | 2 |

-continued

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 150 | 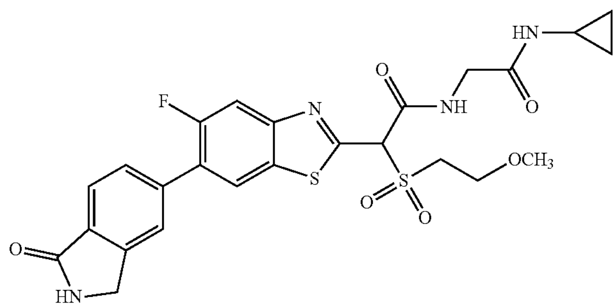 [SMILES: COCCS(=O)(=O)C(C(=O)NCC(=O)NC1CC1)c1nc2cc(F)c(-c3ccc4c(c3)CNC4=O)cc2s1] | N-[(cyclopropyl-carbamoyl)methyl]-2-[5-fluoro-6-(1-oxo-2,3-dihydro-1H-isoindol-5-yl)-1,3-benzothiazol-2-yl]-2-(2-methoxyethane-sulfonyl)acetamide | 9.01 (t, J = 5.5 Hz, 1H), 8.56-8.71 (m, 1H), 8.40 (d, J = 7.7 Hz, 1H), 8.12 (s, 1H), 7.53-8.05 (m, 4H), 6.22 (s, 1H), 4.25-4.57 (m, 2H), 3.65-3.88 (m, 6H), 3.28 (s, 3H), 2.64 (td, J = 7.2, 3.7 Hz, 1H), 0.59-0.76 (m, 2H), 0.30-0.47 (m, 2H) | 0.68 M 561.2 | 2 |
| 151 | 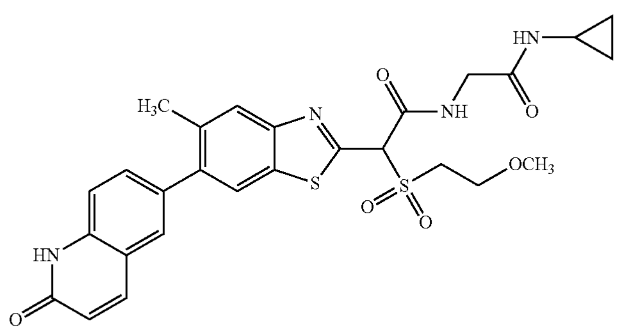 [SMILES: COCCS(=O)(=O)C(C(=O)NCC(=O)NC1CC1)c1nc2cc(C)c(-c3ccc4[nH]c(=O)ccc4c3)cc2s1] | N-[(cyclopropyl-carbamoyl)methyl]-2-(2-methoxyethane-sulfonyl)-2-[5-methyl-6-(2-oxo-1,2-dihydroquinolin-6-yl)-1,3-benzothiazol-2-yl]acetamide | 11.72-11.92 (m, 1H), 8.99 (t, J = 5.5 Hz, 1H), 7.88-8.12 (m, 4H), 7.72 (d, J = 1.7 Hz, 1H), 7.56 (dd, J = 8.5, 1.9 Hz, 1H), 7.32-7.45 (m, 1H), 6.56 (dd, J = 9.5, 1.5 Hz, 1H), 6.19 (s, 1H), 3.61-3.88 (m, 6H), 3.28 (s, 3H), 2.64 (td, J = 7.2, 4.0 Hz, 1H), 2.39 (s, 3H), 0.50-0.71 (m, 2H), 0.30-0.46 (m, 2H) | 0.71 M 569.2 | 2 |
| 152 | 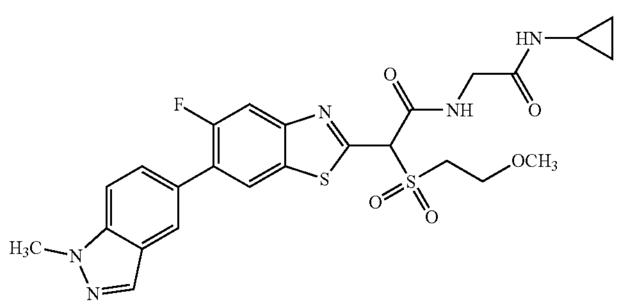 [SMILES: COCCS(=O)(=O)C(C(=O)NCC(=O)NC1CC1)c1nc2cc(F)c(-c3ccc4c(cnn4C)c3)cc2s1] | N-[(cyclopropyl-carbamoyl)methyl]-2-[5-fluoro-6-(1-methyl-1H-indazol-5-yl)-1,3-benzothiazol-2-yl]-2-(2-methoxyethane-sulfonyl)acetamide | 9.02 (t, J = 5.5 Hz, 1H), 8.40 (d, J = 7.7 Hz, 1H), 8.17 (s, 1H), 7.99-8.12 (m, 3H), 7.79 (d, J = 8.8 Hz, 1H), 7.62-7.69 (m, 1H), 6.23 (s, 1H), 4.06-4.15 (m, 3H), 3.68-3.90 (m, 6H), 3.29 (s, 3H), 2.65 (td, J = 7.2, 3.7 Hz, 1H), 0.61-0.68 (m, 2H), 0.33-0.47 (m, 2H) | 0.85 M 559.8 | 3 |
| 153 | 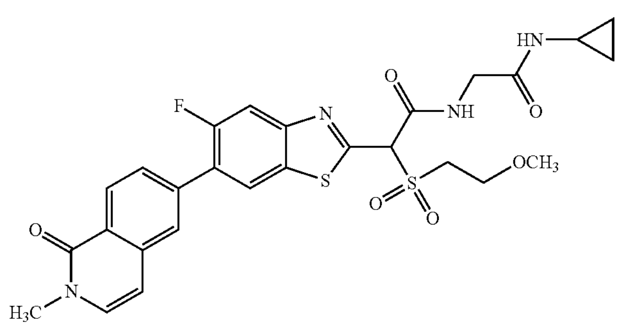 [SMILES: COCCS(=O)(=O)C(C(=O)NCC(=O)NC1CC1)c1nc2cc(F)c(-c3ccc4c(=O)n(C)ccc4c3)cc2s1] | N-[(cyclopropyl-carbamoyl)methyl]-2-[5-fluoro-6-(2-methyl-1-oxo-1,2-dihydro-isoquinolin-6-yl)-1,3-benzothiazol-2-yl]-2-(2-methoxyethane-sulfonyl)acetamide | 9.01 (t, J = 5.5 Hz, 1H), 8.48 (d, J = 11.6 Hz, 1H), 8.33 (d, J = 8.5 Hz, 1H), 8.13 (d, J = 11.3 Hz, 1H), 8.03 (br. s., 1H), 7.92 (s, 1H), 7.73 (d, J = 8.3 Hz, 1H), 7.40-7.61 (m, 1H), 6.58-6.82 (m, 1H), 6.23 (s, 1H), 3.65-3.88 (m, 6H), 3.49-3.60 (m, 3H), 3.28 (s, 3H), 2.64 (td, J = 7.3, 3.9 Hz, 1H), 0.57-0.69 (m, 2H), 0.29-0.50 (m, 2H) | 0.77 M 587.2 | 3 |

-continued

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 154 | 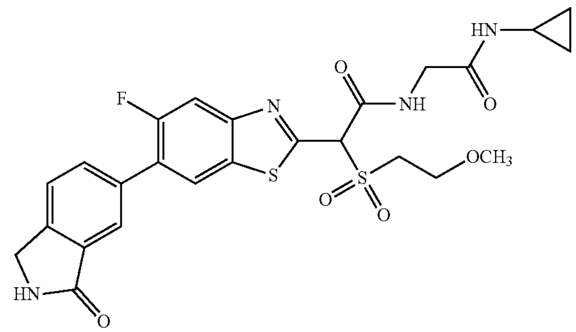 [SMILES: COCCS(=O)(=O)C(C(=O)NCC(=O)NC1CC1)c1nc2cc(F)c(-c3ccc4c(c3)C(=O)NC4)cc2s1] | N-[(cyclopropyl-carbamoyl)methyl]-2-[5-fluoro-6-(3-oxo-2,3-dihydro-1H-isoindol-5-yl)-1,3-benzothiazol-2-yl]-2-(2-methoxyethane-sulfonyl)acetamide | 9.01 (t, J = 5.4 Hz, 1H), 8.60-8.75 (m, 1H), 8.44 (d, J = 7.4 Hz, 1H), 8.10 (d, J = 11.3 Hz, 1H), 8.02 (d, J = 3.9 Hz, 1H), 7.79-7.91 (m, 2H), 7.74 (d, J = 8.0 Hz, 1H), 6.22 (s, 1H), 4.29-4.62 (m, 2H), 3.63-3.97 (m, 6H), 3.28 (s, 3H), 2.64 (td, J = 7.3, 3.6 Hz, 1H), 0.59-0.69 (m, 2H), 0.30-0.48 (m, 2H) | 0.7 M 561.2 | 5 |
| 155 | 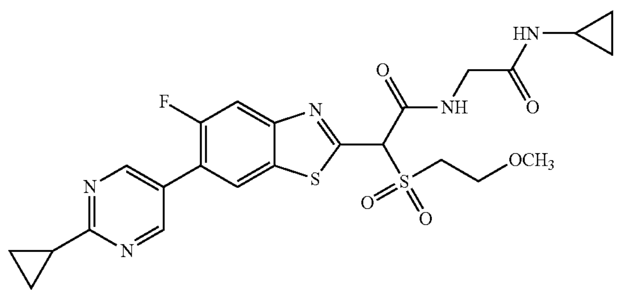 [SMILES: COCCS(=O)(=O)C(C(=O)NCC(=O)NC1CC1)c1nc2cc(F)c(-c3cnc(C4CC4)nc3)cc2s1] | N-[(cyclopropyl-carbamoyl)methyl]-2-[6-(2-cyclopropyl-pyrimidin-5-yl)-5-fluoro-1,3-benzothiazol-2-yl]-2-(2-methoxyethane-sulfonyl)acetamide | 5.96-9.17 (m, 7H), 3.62-3.89 (m, 6H), 3.27 (s, 3H), 2.64 (td, J = 7.3, 3.6 Hz, 1H), 2.29 (td, J = 8.3, 4.0 Hz, 1H), 0.86-1.23 (m, 4H), 0.53-0.80 (m, 2H), 0.28-0.48 (m, 2H) | 0.82 M 548.2 | 7 |
| 156 | 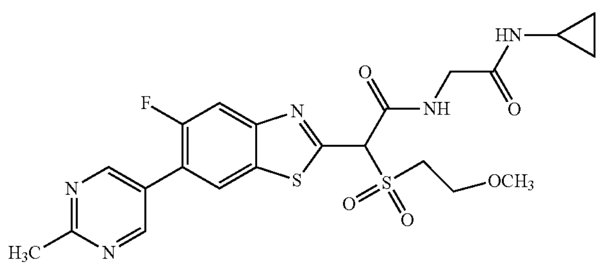 [SMILES: COCCS(=O)(=O)C(C(=O)NCC(=O)NC1CC1)c1nc2cc(F)c(-c3cnc(C)nc3)cc2s1] | N-[(cyclopropyl-carbamoyl)methyl]-2-[5-fluoro-6-(2-methylpyrimidin-5-yl)-1,3-benzothiazol-2-yl]-2-(2-methoxyethane-sulfonyl)acetamide | 9.01 (t, J = 5.5 Hz, 1H), 8.81-8.99 (m, 2H), 8.50 (d, J = 7.4 Hz, 1H), 8.16 (d, J = 11.3 Hz, 1H), 8.03 (d, J = 3.9 Hz, 1H), 6.23 (s, 1H), 3.66-3.90 (m, 6H), 3.28 (s, 3H), 3.17 (s, 3H), 2.64 (td, J = 7.2, 3.7 Hz, 1H), 0.56-0.67 (m, 2H), 0.28-0.48 (m, 2H) | 0.7 M 522.2 | 11 |
| 157 | 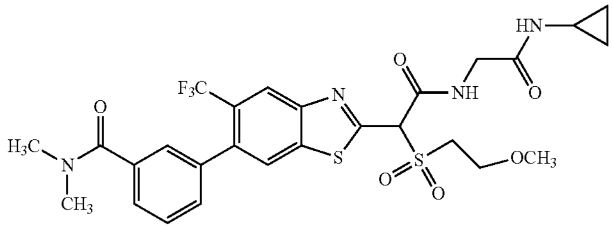 [SMILES: COCCS(=O)(=O)C(C(=O)NCC(=O)NC1CC1)c1nc2cc(C(F)(F)F)c(-c3cccc(C(=O)N(C)C)c3)cc2s1] | 3-[2-({[(cyclopropyl-carbamoyl)methyl]carbamoyl}(2-methoxyethane-sulfonyl)methyl)-5-(trifluoromethyl)-1,3-benzothiazol-6-yl]-N,N-dimethylbenzamide | 9.04 (m, 1H), 8.56 (br. s., 1H), 8.32 (br. s., 1H), 8.04 (br. s., 1H), 7.21-7.72 (m, 4H), 6.30 (br. s., 1H), 3.62-3.90 (m, 6H), 3.30 (br. s., 3H), 2.86-3.08 (m, 6H), 2.65 (br. s., 1H), 0.64 (br. s., 2H), 0.42 (br. s., 2H) | 0.85 M 626.9 | 11 |
| 158 | 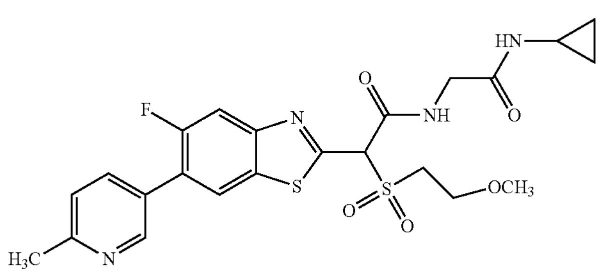 | N-[(cyclopropyl-carbamoyl)methyl]-2-[5-fluoro-6-(6-methylpyridin-3-yl)-1,3-benzothiazol-2-yl]-2-(2-methoxyethane-sulfonyl)acetamide | 9.02 (m, 1H), 8.71 (br. s., 1H), 8.42 (br. s., 1H), 7.84-8.16 (m, 3H), 7.46 (m, 1H), 6.23 (br. s., 1H), 3.65-3.99 (m, 6H), 3.29 (br. s., 3H), 2.65 (m, 1H), 2.57 (br. s., 3H), 0.64 (br. s., 2H), 0.41 (br. s., 2H) | 0.61 M 520.9 | 11 |

| Ex. No. | Structure | Name | $^1$H NMR δ (500 MHz, DMSO-d$_6$, unless otherwise indicated) | LC/MS RT (min) ethod M + H | EL IC$_{50}$ (nM) |
|---|---|---|---|---|---|
| 159 | 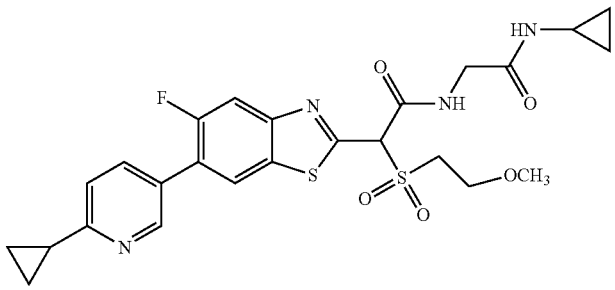 [SMILES: COCCS(=O)(=O)C(C(=O)NCC(=O)NC1CC1)c1nc2cc(F)c(-c3ccc(C4CC4)nc3)cc2s1] | N-[(cyclopropylcarbamoyl)methyl]-2-[6-(6-cyclopropylpyridin-3-yl)-5-fluoro-1,3-benzothiazol-2-yl]-2-(2-methoxyethanesulfonyl)acetamide | 9.02 (t, J = 5.5 Hz, 1H), 8.68 (s, 1H), 8.41 (d, J = 7.7 Hz, 1H), 8.13 (s, 1H), 7.92-8.06 (m, 2H), 7.43-7.59 (m, 1H), 6.23 (s, 1H), 3.77-3.90 (m, 6H), 3.29 (s, 3H), 2.65 (tt, J = 7.4, 3.8 Hz, 1H), 2.13-2.31 (m, 1H), 0.96-1.15 (m, 4H), 0.59-0.72 (m, 2H), 0.31-0.51 (m, 2H) | 0.68 M 546.9 | 12 |
| 160 | 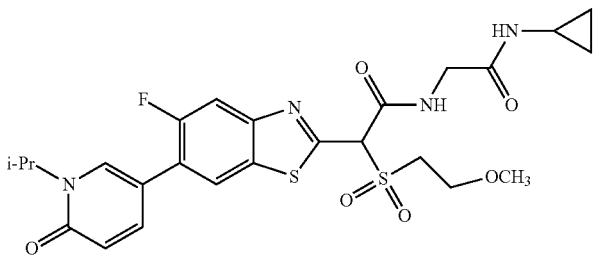 [SMILES: COCCS(=O)(=O)C(C(=O)NCC(=O)NC1CC1)c1nc2cc(F)c(-c3ccc(=O)n(C(C)C)c3)cc2s1] | N-[(cyclopropylcarbamoyl)methyl]-2-{5-fluoro-6-[6-oxo-1-(propan-2-yl)-1,6-dihydropyridin-3-yl]-1,3-benzothiazol-2-yl}-2-(2-methoxyethanesulfonyl)acetamide | 9.00 (t, J = 5.5 Hz, 1H), 8.33 (d, J = 7.7 Hz, 1H), 7.89-8.15 (m, 3H), 7.67 (dt, J = 9.4, 2.3 Hz, 1H), 6.52 (d, J = 9.4 Hz, 1H), 6.20 (s, 1H), 4.90-5.19 (m, 1H), 3.63-3.92 (m, 6H), 3.28 (s, 3H), 2.58-2.70 (m, 1H), 1.25-1.42 (m, 6H), 0.57-0.68 (m, 2H), 0.30-0.47 (m, 2H) | 0.73 M 565.2 | 12 |
| 161 | 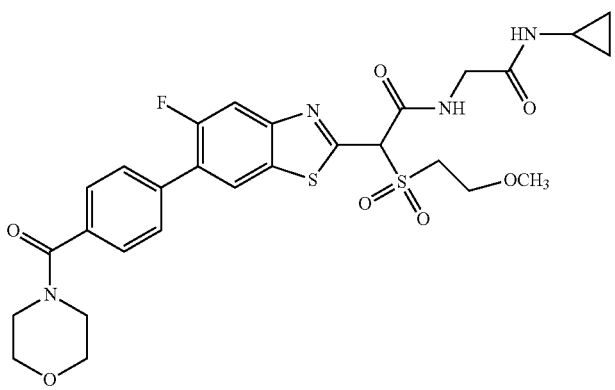 [SMILES: COCCS(=O)(=O)C(C(=O)NCC(=O)NC1CC1)c1nc2cc(F)c(-c3ccc(C(=O)N4CCOCC4)cc3)cc2s1] | N-[(cyclopropylcarbamoyl)methyl]-2-{5-fluoro-6-[4-(morpholine-4-carbonyl)phenyl]-1,3-benzothiazol-2-yl}-2-(2-methoxyethanesulfonyl)acetamide | 9.02 (t, J = 5.4 Hz, 1H), 8.40 (d, J = 7.4 Hz, 1H), 8.11 (d, J = 11.0 Hz, 1H), 7.93-8.06 (m, 1H), 7.44-7.80 (m, 4H), 6.23 (s, 1H), 3.70-3.90 (m, 6H), 3.54-3.69 (m, 8H), 3.29 (s, 3H), 2.65 (td, J = 7.4, 3.7 Hz, 1H), 0.56-0.72 (m, 2H), 0.32-0.50 (m, 2H) | 0.78 M 618.9 | 14 |
| 162 | 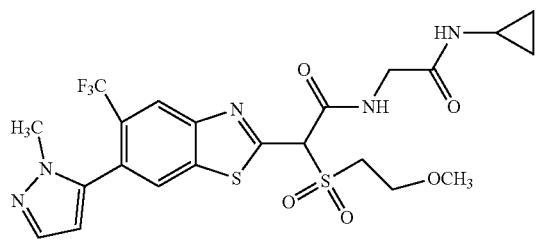 [SMILES: COCCS(=O)(=O)C(C(=O)NCC(=O)NC1CC1)c1nc2cc(C(F)(F)F)c(-c3ccnn3C)cc2s1] | N-[(cyclopropylcarbamoyl)methyl]-2-(2-methoxyethanesulfonyl)-2-[6-(1-methyl-1H-pyrazol-5-yl)-5-(trifluoromethyl)-1,3-benzothiazol-2-yl]acetamide | 9.05 (m, 1H), 8.62 (br. s., 1H), 8.44 (br. s., 1H), 8.04 (br. s., 1H), 7.43-7.65 (m, 1H), 6.35-6.61 (m, 1H), 6.31 (br. s., 1H), 3.66-4.06 (m, 6H), 3.54-3.64 (m, 3H), 3.30 (br. s., 3H), 2.65 (br. s., 1H), 0.64 (m, 2H), 0.41 (m, 2H) | 0.82 M 559.8 | 16 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 163 | 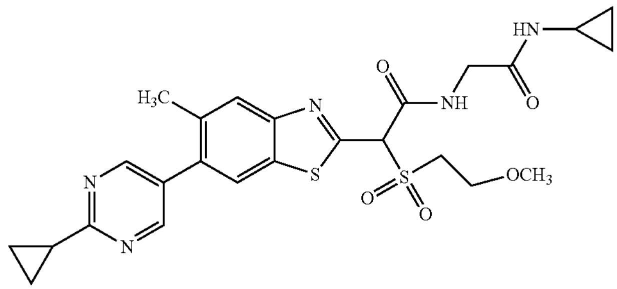 [SMILES: COCCS(=O)(=O)C(C(=O)NCC(=O)NC1CC1)c1nc2cc(C)c(-c3cnc(C4CC4)nc3)cc2s1] | N-[(cyclopropylcarbamoyl)methyl]-2-[6-(2-cyclopropylpyrimidin-5-yl)-5-methyl-1,3-benzothiazol-2-yl]-2-(2-methoxyethanesulfonyl)acetamide | 8.99 (t, J = 5.5 Hz, 1H), 8.54-8.84 (m, 2H), 7.56-8.26 (m, 3H), 6.20 (s, 1H), 3.63-3.89 (m, 6H), 3.28 (s, 3H), 2.64 (td, J = 7.3, 3.9 Hz, 1H), 2.39 (s, 3H), 2.22-2.33 (m, 1H), 1.03-1.15 (m, 4H), 0.59-0.68 (m, 2H), 0.17-0.50 (m, 2H) | 0.82 M 544.3 | 16 |
| 164 | 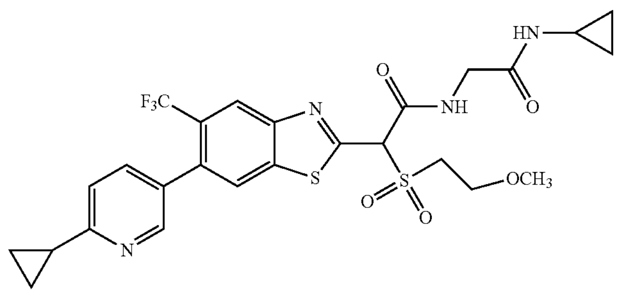 | N-[(cyclopropylcarbamoyl)methyl]-2-[6-(6-cyclopropylpyridin-3-yl)-5-(trifluoromethyl)-1,3-benzothiazol-2-yl]-2-(2-methoxyethanesulfonyl)acetamide | 9.05 (m, 1H), 8.57 (br. s., 1H), 8.26-8.49 (m, 2H), 7.90-8.15 (m, 1H), 7.73 (d, J = 7.4 Hz, 1H), 7.44 (d, J = 7.4 Hz, 1H), 6.29 (br. s., 1H), 3.68-3.89 (m, 6H), 3.30 (br. s., 3H), 2.65 (br. s., 1H), 2.21 (br. s., 1H), 1.03 (m, 4H), 0.64 (m., 2H), 0.41 (m, 2H) | 0.95 M 596.8 | 17 |
| 165 | 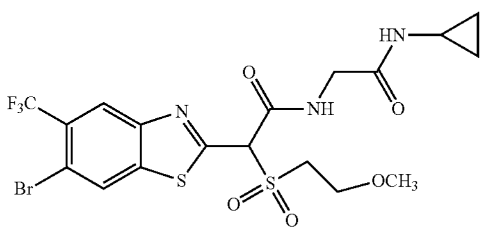 [SMILES: COCCS(=O)(=O)C(C(=O)NCC(=O)NC1CC1)c1nc2cc(C(F)(F)F)c(Br)cc2s1] | 2-[6-bromo-5-(trifluoromethyl)-1,3-benzothiazol-2-yl]-N-[(cyclopropylcarbamoyl)methyl]-2-(2-methoxyethanesulfonyl)acetamide | 9.04 (t, J = 5.5 Hz, 1H), 8.82 (s, 1H), 8.56 (s, 1H), 8.03 (d, J = 3.9 Hz, 1H), 6.26 (s, 1H), 3.67-3.89 (m, 6H), 3.27 (s, 3H), 2.60-2.75 (m, 1H), 0.58-0.69 (m, 2H), 0.34-0.51 (m, 2H) | 0.94 M 559.7 | 18 |
| 166 | 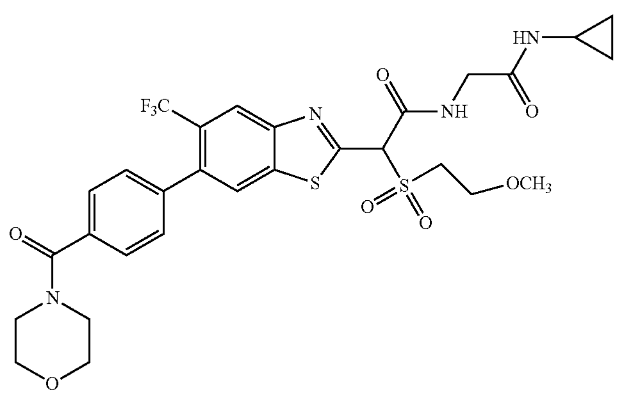 [SMILES: COCCS(=O)(=O)C(C(=O)NCC(=O)NC1CC1)c1nc2cc(C(F)(F)F)c(-c3ccc(C(=O)N4CCOCC4)cc3)cc2s1] | N-[(cyclopropylcarbamoyl)methyl]-2-(2-methoxyethanesulfonyl)-2-{6-[4-(morpholine-4-carbonyl)phenyl]-5-(trifluoromethyl)-1,3-benzothiazol-2-yl}acetamide | 9.04 (t, J = 5.5 Hz, 1H), 8.56 (s, 1H), 8.29 (s, 1H), 7.92-8.15 (m, 1H), 7.33-7.58 (m, 4H), 6.29 (s, 1H), 3.72-3.89 (m, 6H), 3.64 (br. s., 7H), 3.38-3.45 (m, 1H), 2.64 (td, J = 7.3, 3.9 Hz, 1H), 0.55-0.67 (m, 2H), 0.33-0.48 (m, 2H) | 0.83 M 668.8 | 20 |
| 167 | 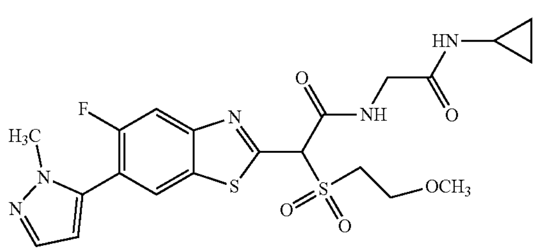 [SMILES: COCCS(=O)(=O)C(C(=O)NCC(=O)NC1CC1)c1nc2cc(F)c(-c3ccnn3C)cc2s1] | N-[(cyclopropylcarbamoyl)methyl]-2-[5-fluoro-6-(1-methyl-1H-pyrazol-5-yl)-1,3-benzothiazol-2-yl]-2-(2-methoxyethanesulfonyl)acetamide | 9.01 (t, J = 5.5 Hz, 1H), 8.36 (d, J = 7.2 Hz, 1H), 7.93-8.22 (m, 1H), 7.47-7.65 (m, 1H), 6.34-6.56 (m, 1H), 6.24 (s, 1H), 3.65-3.90 (m, 9H), 3.29 (s, 3H), 2.64 (td, J = 7.3, 3.9 Hz, 1H), 0.57-0.70 (m, 2H), 0.34-0.48 (m, 2H) | 0.76 M 509.8 | 23 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 168 | 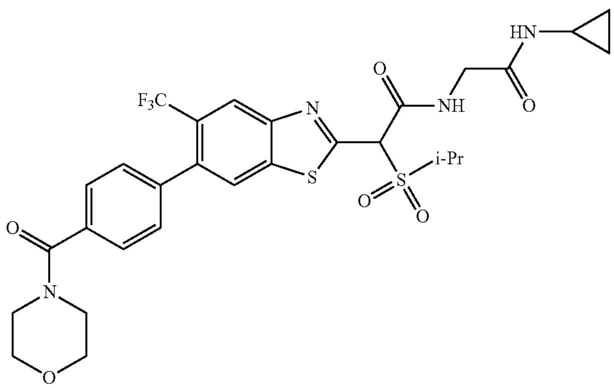 [SMILES: CC(C)S(=O)(=O)C(C(=O)NCC(=O)NC1CC1)c1nc2cc(C(F)(F)F)c(-c3ccc(C(=O)N4CCOCC4)cc3)cc2s1] | N-[(cyclopropyl-carbamoyl)methyl]-2-{6-[4-(morpholine-4-carbonyl)phenyl]-5-(trifluoromethyl)-1,3-benzothiazol-2-yl}-2-(propane-2-sulfonyl)acetamide | 5.56-9.65 (m, 9H), 3.63-3.95 (m, 11H), 2.56-2.68 (m, 1H), 1.12-1.63 (m, 6H), 0.58-0.73 (m, 2H), 0.41 (br. s., 2H) | 1.69 O 653.2 | 24 |
| 169 | 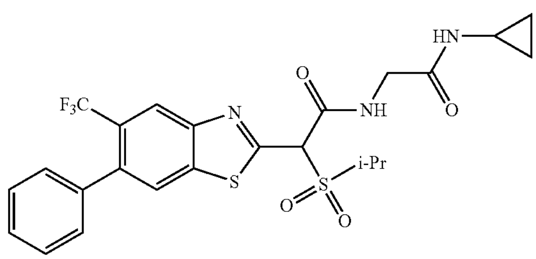 [SMILES: CC(C)S(=O)(=O)C(C(=O)NCC(=O)NC1CC1)c1nc2cc(C(F)(F)F)c(-c3ccccc3)cc2s1] | N-[(cyclopropyl-carbamoyl)methyl]-2-[6-phenyl-5-(trifluoromethyl)-1,3-benzothiazol-2-yl]-2-(propane-2-sulfonyl)acetamide | 9.21 (br. s., 1H), 8.53 (br. s., 1H), 8.26 (br. s., 1H), 7.99-8.14 (m, 1H), 6.97-7.63 (m, 5H), 6.46 (br. s., 1H), 3.56-4.31 (m, 3H), 2.64 (br. s., 1H), 1.43 (m, 2H), 1.19-1.36 (m, 4H), 0.64 (d, J = 5.5 Hz, 2H), 0.41 (br. s., 2H) | 0.98 M 540.2 | 26 |
| 170 | 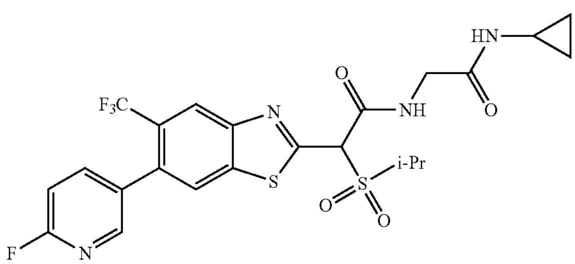 [SMILES: CC(C)S(=O)(=O)C(C(=O)NCC(=O)NC1CC1)c1nc2cc(C(F)(F)F)c(-c3ccc(F)nc3)cc2s1] | N-[(cyclopropyl-carbamoyl)methyl]-2-[6-(6-fluoropyridin-3-yl)-5-(trifluoromethyl)-1,3-benzothiazol-2-yl]-2-(propane-2-sulfonyl)acetamide | 6.08-9.41 (m, 8H), 3.46-4.04 (m, 3H), 2.65 (m, 1H), 1.93 (m, 1H), 1.12-1.58 (m, 5H), 0.56-0.74 (m, 2H), 0.41 (br. s., 2H) | 0.87 M 559.1 | 27 |
| 171 | 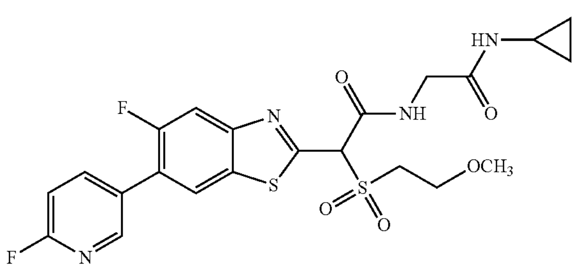 [SMILES: COCCS(=O)(=O)C(C(=O)NCC(=O)NC1CC1)c1nc2cc(F)c(-c3ccc(F)nc3)cc2s1] | N-[(cyclopropyl-carbamoyl)methyl]-2-[5-fluoro-6-(6-fluoropyridin-3-yl)-1,3-benzothiazol-2-yl]-2-(2-methoxyethane-sulfonyl)acetamide | 9.05 (br. s., 1H), 8.38-8.68 (m, 2H), 8.28 (t, J = 7.7 Hz, 1H), 7.74-8.22 (m, 2H), 7.30-7.49 (m, 1H), 6.24 (s, 1H), 3.51-3.90 (m, 6H), 3.29 (br. s., 3H), 2.64 (br. s., 1H), 0.64 (d, J = 6.1 Hz, 2H), 0.41 (br. s., 2H) | 1.48 O 525.3 | 27 |
| 172 | 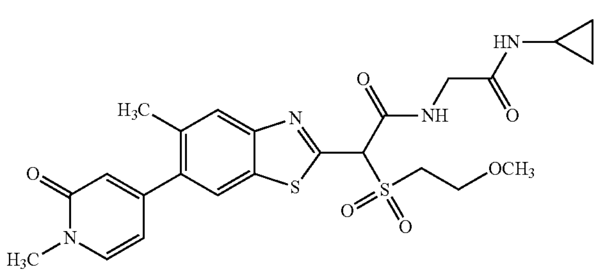 [SMILES: COCCS(=O)(=O)C(C(=O)NCC(=O)NC1CC1)c1nc2cc(C)c(-c3ccn(C)c(=O)c3)cc2s1] | N-[(cyclopropyl-carbamoyl)methyl]-2-(2-methoxyethane-sulfonyl)-2-[5-methyl-6-(1-methyl-2-oxo-1,2-dihydropyridin-4-yl)-1,3-benzothiazol-2-yl]acetamide | 8.98 (t, J = 5.6 Hz, 1H), 7.95-8.16 (m, 3H), 7.59-7.87 (m, 2H), 6.23-6.44 (m, 2H), 6.19 (s, 1H), 3.64-3.88 (m, 6H), 3.46-3.53 (m, 3H), 3.24-3.29 (m, 3H), 2.63 (td, J = 7.3, 3.9 Hz, 1H), 2.41 (s, 3H), 0.61-0.68 (m, 2H), 0.29-0.45 (m, 2H) | 0.66 M 533.2 | 27 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 173 | 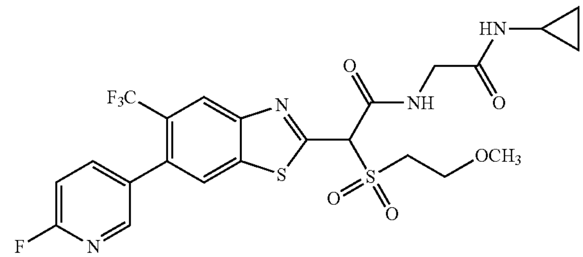 [SMILES: COCCS(=O)(=O)C(C(=O)NCC(=O)NC1CC1)c1nc2cc(C(F)(F)F)c(-c3ccc(F)nc3)cc2s1] | N-[(cyclopropyl-carbamoyl)methyl]-2-[6-(6-fluoropyridin-3-yl)-5-(trifluoromethyl)-1,3-benzothiazol-2-yl]-2-(2-methoxyethane-sulfonyl)acetamide | 9.05 (br. s., 1H), 8.60 (br. s., 1H), 8.16-8.48 (m, 2H), 7.87-8.13 (m, 2H), 7.21-7.49 (m, 1H), 6.21-6.67 (m, 1H), 3.57-4.00 (m, 6H), 3.30 (br. s., 3H), 2.56-2.69 (m, 1H), 0.64 (br. s., 2H), 0.41 (br. s., 2H) | 0.91 M 574.8 | 32 |
| 174 | 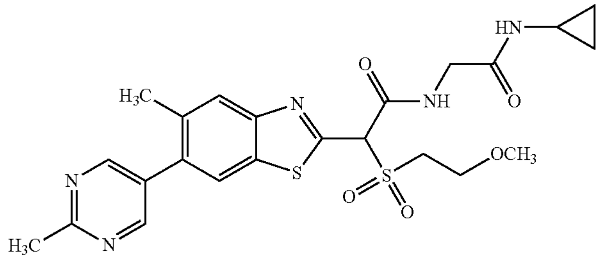 | N-[(cyclopropyl-carbamoyl)methyl]-2-(2-methoxyethane-sulfonyl)-2-[5-methyl-6-(2-methylpyrimidin-5-yl)-1,3-benzothiazol-2-yl]acetamide | 5.95-9.11 (m, 7H), 3.63-3.97 (m, 6H), 3.28 (s, 3H), 2.66-2.74 (m, 3H), 2.64 (td, J = 7.2, 3.7 Hz, 1H), 2.35-2.42 (m, 3H), 0.58-0.67 (m, 2H), 0.35-0.44 (m, 2H) | 0.7 M 518.3 | 35 |
| 175 | 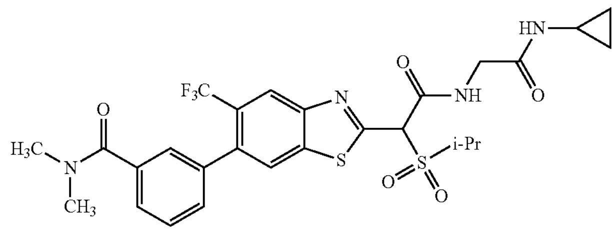 [SMILES: CC(C)S(=O)(=O)C(C(=O)NCC(=O)NC1CC1)c1nc2cc(C(F)(F)F)c(-c3cccc(C(=O)N(C)C)c3)cc2s1] | 3-[2-({[(cyclopropyl-carbamoyl)methyl]carbamoyl}(propane-2-sulfonyl)methyl)-5-(trifluoromethyl)-1,3-benzothiazol-6-yl]-N,N-dimethyl-benzamide | 6.09-9.46 (m, 9H), 3.55-4.09 (m, 3H), 2.84-3.09 (m, 6H), 2.65 (br. s., 1H), 1.42 (d, J = 6.3 Hz, 2H), 1.29 (d, J = 6.9 Hz, 4H), 0.65 (br. s., 2H), 0.41 (br. s., 2H) | 0.84 M 611.2 | 37 |
| 176 | 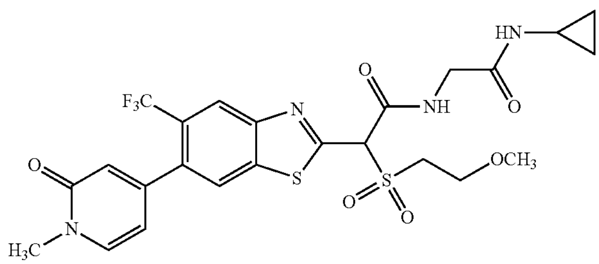 [SMILES: COCCS(=O)(=O)C(C(=O)NCC(=O)NC1CC1)c1nc2cc(C(F)(F)F)c(-c3ccn(C)c(=O)c3)cc2s1] | N-[(cyclopropyl-carbamoyl)methyl]-2-(2-methoxyethane-sulfonyl)-2-[6-(1-methyl-2-oxo-1,2-dihydropyridin-4-yl)-5-(trifluoromethyl)-1,3-benzothiazol-2-yl]acetamide | 9.03 (t, J = 5.5 Hz, 1H), 8.55 (s, 1H), 8.21-8.38 (m, 1H), 8.03 (d, J = 4.1 Hz, 1H), 7.65-7.84 (m, 1H), 6.12-6.49 (m, 3H), 3.64-3.91 (m, 6H), 3.45-3.56 (m, 3H), 3.29 (s, 3H), 2.64 (td, J = 7.3, 3.6 Hz, 1H), 0.57-0.69 (m, 2H), 0.33-0.48 (m, 2H) | 0.75 M 586.9 | 37 |
| 177 | 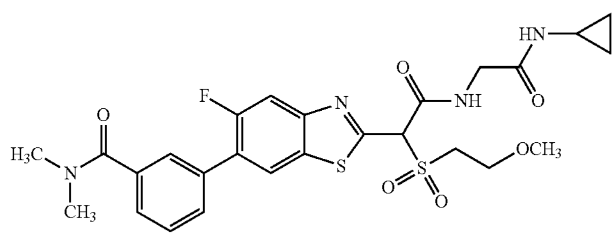 [SMILES: COCCS(=O)(=O)C(C(=O)NCC(=O)NC1CC1)c1nc2cc(F)c(-c3cccc(C(=O)N(C)C)c3)cc2s1] | 3-[2-({[(cyclopropyl-carbamoyl)methyl]carbamoyl}(2-methoxyethane-sulfonyl)methyl)-5-fluoro-1,3-benzothiazol-6-yl]-N,N-dimethyl-benzamide | 9.01 (t, J = 5.5 Hz, 1H), 8.41 (d, J = 7.7 Hz, 1H), 7.96-8.20 (m, 4H), 7.43-7.82 (m, 4H), 6.23 (s, 1H), 3.59-4.02 (m, 6H), 3.28 (br.s., 3H), 2.87-3.10 (m, 6H), 2.60-2.68 (m, 1H), 0.64 (dd, J = 7.2, 1.9 Hz, 2H), 0.30-0.49 (m, 2H) | 0.8 M 576.9 | 51 |

| Ex. No. | Structure | Name | $^1$H NMR δ (500 MHz, DMSO-d$_6$, unless otherwise indicated) | LC/MS RT (min) Method M + H | EL IC$_{50}$ (nM) |
|---|---|---|---|---|---|
| 178 | 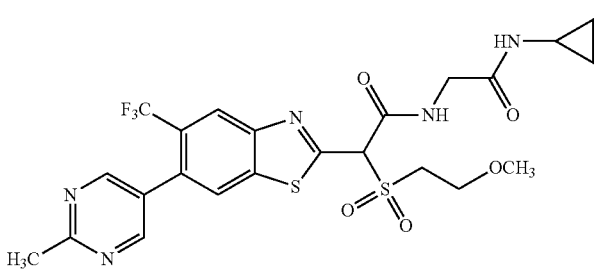 | N-[(cyclopropyl-carbamoyl)methyl]-2-(2-methoxyethane-sulfonyl)-2-[6-(2-methylpyrimidin-5-yl)-5-(trifluoromethyl)-1,3-benzothiazol-2-yl]acetamide | 7.65-8.86 (m, 4H), 3.62-4.02 (m, 6H), 3.44 (s, 2H), 2.76-2.85 (m, 3H), 2.62-2.76 (m, 1H), 0.75 (d, J = 6.6 Hz, 2H), 0.44-0.62 (m, 2H) | 0.8 M 571.9 | 56 |
| 179 | 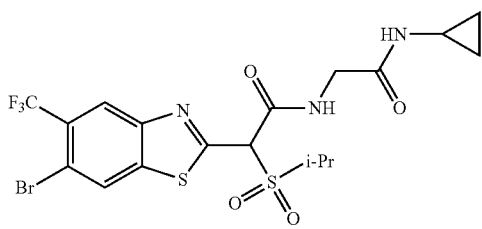 [SMILES: CC(C)S(=O)(=O)C(C(=O)NCC(=O)NC1CC1)c1nc2cc(C(F)(F)F)c(Br)cc2s1] | 2-[6-bromo-5-(trifluoromethyl)-1,3-benzothiazol-2-yl]-N-[(cyclopropyl-carbamoyl)methyl]-2-(propane-2-sulfonyl)acetamide | 9.18 (br. s., 1H), 8.83 (s, 1H), 7.93-8.65 (m, 2H), 6.22-6.71 (m, 1H), 3.71-3.98 (m, 2H), 3.49-3.66 (m, 1H), 2.64 (br. s., 1H), 1.13-1.51 (m, 6H), 0.64 (d, J = 6.1 Hz, 2H), 0.41 (br. s., 2H) | 0.93 M 544 | 82 |
| 180 | 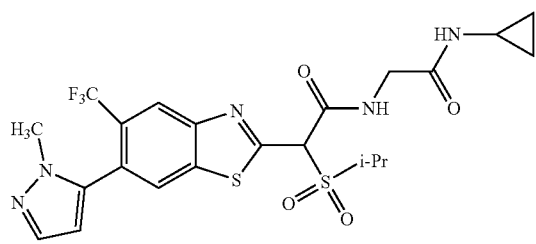 [SMILES: CC(C)S(=O)(=O)C(C(=O)NCC(=O)NC1CC1)c1nc2cc(C(F)(F)F)c(-c3ccnn3C)cc2s1] | N-[(cyclopropyl-carbamoyl)methyl]-2-[6-(1-methyl-1H-pyrazol-5-yl)-5-(trifluoromethyl)-1,3-benzothiazol-2-yl]-2-(propane-2-sulfonyl)acetamide | 5.20-9.68 (m, 7H), 3.76-3.99 (m, 2H), 3.58-3.65 (m, 3H), 2.65 (m, 1H), 1.04-1.60 (m, 6H), 0.64 (d, J = 6.6 Hz, 2H), 0.41 (br. s., 2H) | 0.81 M 544.1 | 88 |
| 181 | 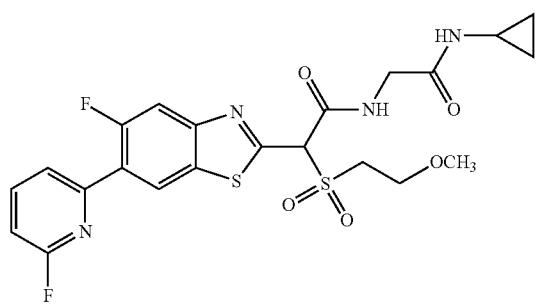 [SMILES: COCCS(=O)(=O)C(C(=O)NCC(=O)NC1CC1)c1nc2cc(F)c(-c3cccc(F)n3)cc2s1] | N-[(cyclopropyl-carbamoyl)methyl]-2-[5-fluoro-6-(6-fluoropyridin-2-yl)-1,3-benzothiazol-2-yl]-2-(2-methoxyethane-sulfonyl)acetamide | 9.02 (t, J = 5.5 Hz, 1H), 7.67-8.80 (m, 5H), 7.28 (dd, J = 8.3, 2.5 Hz, 1H), 6.24 (s, 1H), 3.66-4.00 (m, 6H), 3.28 (s, 3H), 2.60-2.71 (m, 1H), 0.59-0.70 (m, 2H), 0.30-0.50 (m, 2H) | 0.88 M 524.8 | 143 |
| 182 | 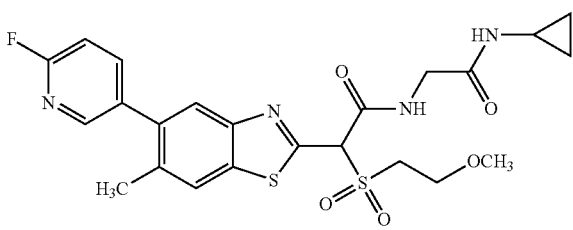 [SMILES: COCCS(=O)(=O)C(C(=O)NCC(=O)NC1CC1)c1nc2cc(-c3ccc(F)nc3)c(C)cc2s1] | N-[(cyclopropyl-carbamoyl)methyl]-2-[5-(6-fluoropyridin-3-yl)-6-methyl-1,3-benzothiazol-2-yl]-2-(2-methoxy-ethane-sulfonyl)acetamide | 9.00 (t, J = 5.5 Hz, 1H), 8.32 (d, J = 2.2 Hz, 1H), 8.07-8.17 (m, 2H), 8.02 (d, J = 4.1 Hz, 1H), 7.97 (s, 1H), 7.32 (dd, J = 8.4, 2.6 Hz, 1H), 6.18 (s, 1H), 3.65-3.90 (m, 6H), 3.28 (s, 3H), 2.64 (td, J = 7.3, 3.6 Hz, 1H), 2.36 (s, 3H), 0.58-0.69 (m, 2H), 0.37-0.46 (m, 2H) | 0.86 M 520.9 | 21 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 183 | 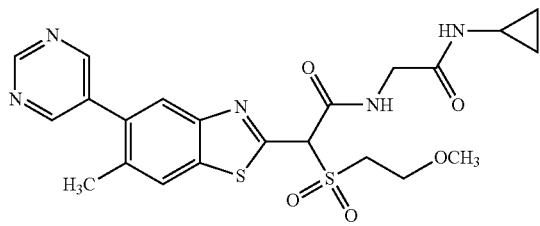 [SMILES: COCCS(=O)(=O)C(C(=O)NCC(=O)NC1CC1)c1nc2cc(-c3cncnc3)c(C)cc2s1] | N-[(cyclopropyl-carbamoyl)methyl]-2-(2-methoxyethane-sulfonyl)-2-[6-methyl-5-(pyrimidin-5-yl)-1,3-benzothiazol-2-yl]acetamide | 9.19-9.36 (m, 1H), 8.79-9.08 (m, 3H), 8.17 (s, 1H), 7.98-8.11 (m, 2H), 6.20 (s, 1H), 3.63-3.89 (m, 6H), 3.24-3.30 (m, 3H), 2.65 (td, J = 7.3, 3.9 Hz, 1H), 2.35-2.45 (m, 3H), 0.56-0.71 (m, 2H), 0.30-0.49 (m, 2H) | 0.74 M 503.9 | 39 |
| 184 | 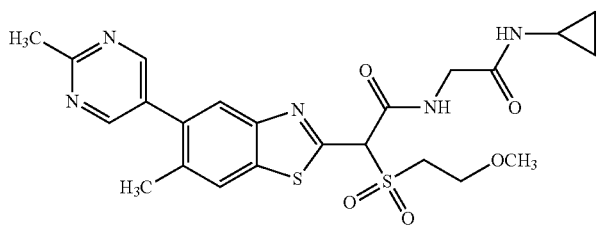 [SMILES: COCCS(=O)(=O)C(C(=O)NCC(=O)NC1CC1)c1nc2cc(-c3cnc(C)nc3)c(C)cc2s1] | N-[(cyclopropyl-carbamoyl)methyl]-2-(2-methoxyethane-sulfonyl)-2-[6-methyl-5-(2-methylpyrimidin-5-yl)-1,3-benzothiazol-2-yl]acetamide | 9.00 (t, J = 5.2 Hz, 1H), 8.71-8.89 (m, 2H), 8.15 (s, 1H), 7.78-8.07 (m, 2H), 6.20 (s, 1H), 3.64-3.89 (m, 6H), 3.28 (s, 3H), 2.68-2.79 (m, 3H), 2.60-2.67 (m, 1H), 2.39 (s, 3H), 0.64 (d, J = 6.9 Hz, 2H), 0.41 (br. s., 2H) | 0.71 M 518.3 | 29 |
| 185 | 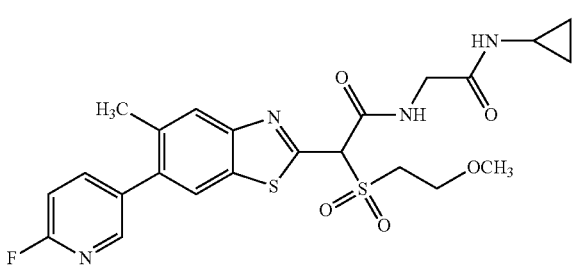 [SMILES: COCCS(=O)(=O)C(C(=O)NCC(=O)NC1CC1)c1nc2cc(C)c(-c3ccc(F)nc3)cc2s1] | N-[(cyclopropyl-carbamoyl)methyl]-2-[6-(6-fluoropyridin-3-yl)-5-methyl-1,3-benzothiazol-2-yl]-2-(2-methoxyethane-sulfonyl)acetamide | 8.99 (t, J = 5.5 Hz, 1H), 8.19-8.37 (m, 1H), 7.93-8.15 (m, 4H), 7.32 (dd, J = 8.4, 2.6 Hz, 1H), 6.20 (s, 1H), 3.65-3.90 (m, 6H), 3.28 (s, 3H), 2.64 (td, J = 7.4, 3.7 Hz, 1H), 2.37 (s, 3H), 0.58-0.70 (m, 2H), 0.32-0.48 (m, 2H) | 0.83 M 521.3 | 4 |
| 186 | 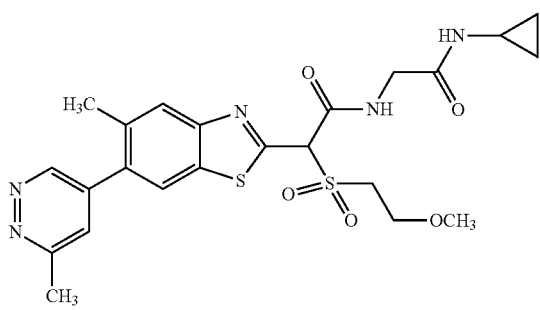 [SMILES: COCCS(=O)(=O)C(C(=O)NCC(=O)NC1CC1)c1nc2cc(C)c(-c3cnnc(C)c3)cc2s1] | N-[(cyclopropyl-carbamoyl)methyl]-2-(2-methoxyethane-sulfonyl)-2-[5-methyl-6-(6-methylpyridazin-4-yl)-1,3-benzothiazol-2-yl]acetamide | 9.14-9.32 (m, 1H), 9.03 (t, J = 5.2 Hz, 1H), 7.90-8.24 (m, 3H), 7.67-7.85 (m, 1H), 6.21 (s, 1H), 3.65-4.01 (m, 6H), 2.91 (s, 3H), 2.69-2.81 (m, 3H), 2.65 (m, 2H), 2.43 (s, 3H), 0.65 (d, J = 5.8 Hz, 3H), 0.41 (br. s., 3H) | 0.98 O 518.2 | 40 |
| 187 | 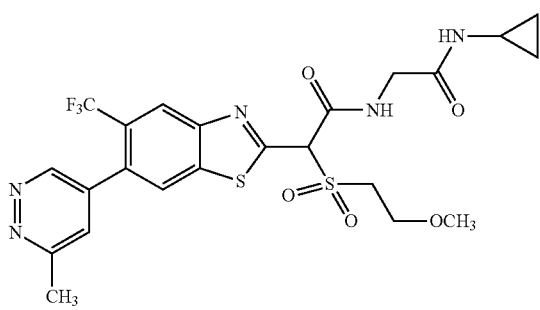 [SMILES: COCCS(=O)(=O)C(C(=O)NCC(=O)NC1CC1)c1nc2cc(C(F)(F)F)c(-c3cnnc(C)c3)cc2s1] | N-[(cyclopropyl-carbamoyl)methyl]-2-(2-methoxyethane-sulfonyl)-2-[6-(6-methylpyridazin-4-yl)-5-(trifluoromethyl)-1,3-benzothiazol-2-yl]acetamide | 6.31-9.15 (m, 7H), 3.73-3.89 (m, 11H), 3.29 (s, 2H), 2.68-2.76 (m, 3H), 2.64 (td, J = 7.2, 3.4 Hz, 1H), 0.57-0.72 (m, 2H), 0.34-0.49 (m, 2H) | 0.71 M 572.2 | 229 |

-continued

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 188 | 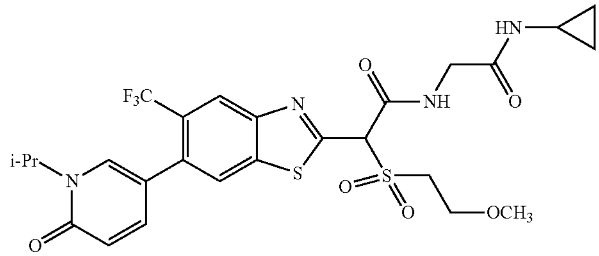 [SMILES: COCCS(=O)(=O)C(C(=O)NCC(=O)NC1CC1)c1nc2cc(C(F)(F)F)c(-c3ccc(=O)n(C(C)C)c3)cc2s1] | N-[(cyclopropyl-carbamoyl)methyl]-2-(2-methoxyethane-sulfonyl)-2-{6-[6-oxo-1-(propan-2-yl)-1,6-dihydropyridin-3-yl]-5-(trifluoromethyl)-1,3-benzothiazol-2-yl}acetamide | 7.87-9.24 (m, 4H), 7.63-7.82 (m, 1H), 7.31-7.51 (m, 1H), 6.38-6.59 (m, 1H), 6.27 (s, 1H), 5.12 (quin, J = 6.9 Hz, 1H), 3.71-3.87 (m, 6H), 3.23-3.35 (m, 3H), 2.64 (m, 1H), 1.17-1.43 (m, 6H), 0.57-0.74 (m, 2H), 0.28-0.47 (m, 2H) | 0.79 M 615.3 | 37 |
| 189 | 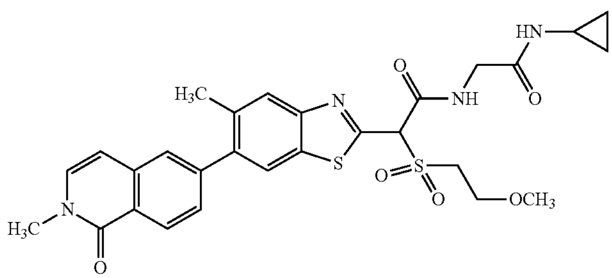 [SMILES: COCCS(=O)(=O)C(C(=O)NCC(=O)NC1CC1)c1nc2cc(C)c(-c3ccc4c(=O)n(C)ccc4c3)cc2s1] | N-[(cyclopropyl-carbamoyl)methyl]-2-(2-methoxyethane-sulfonyl)-2-[5-methyl-6-(2-methyl-1-oxo-1,2-dihydro-isoquinolin-6-yl)-1,3-benzothiazol-2-yl]acetamide | 8.84-9.20 (m, 1H), 8.22-8.52 (m, 1H), 7.88-8.15 (m, 3H), 7.63-7.79 (m, 1H) 7.54 (m, 2H), 6.59-6.82 (m, 1H), 6.20 (s, 1H), 3.65-3.96 (m, 5H), 3.56 (m, 1H), 3.24-3.49 (m, 3H), 2.91 (s, 3H), 2.65 (m, 1H), 2.39 (s, 3H), 0.65 (d, J = 5.5 Hz, 2H), 0.42 (br. s., 2H) | 1.73 O 583.2 | 4 |
| 190 | 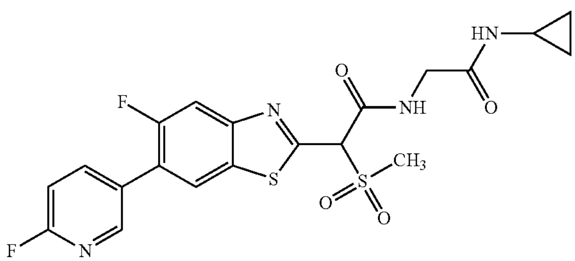 [SMILES: CS(=O)(=O)C(C(=O)NCC(=O)NC1CC1)c1nc2cc(F)c(-c3ccc(F)nc3)cc2s1] | N-[(cyclopropyl-carbamoyl)methyl]-2-[5-fluoro-6-(6-fluoropyridin-3-yl)-1,3-benzothiazol-2-yl]-2-methanesulfonyl-acetamide | 9.08 (t, J = 5.3 Hz, 1H), 8.49 (br. s., 1H), 8.42 (d, J = 7.3 Hz, 1H), 8.26 (t, J = 8.1 Hz, 1H), 8.12 (d, J = 11.0 Hz, 1H), 8.06 (d, J = 3.4 Hz, 1H), 7.36 (d, J = 6.1 Hz, 1H), 6.22 (s, 1H), 3.71-3.95 (m, 2H), 3.28 (s, 3H), 2.64 (m, 1H), 0.64 (d, J = 6.4 Hz, 2H), 0.40 (br. s., 2H) | 0.77 M 481.2 | 16 |
| 191 | 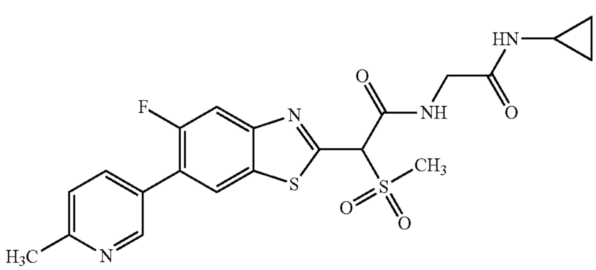 [SMILES: Cc1ccc(-c2cc3sc(C(C(=O)NCC(=O)NC4CC4)S(C)(=O)=O)nc3cc2F)cn1] | N-[(cyclopropyl-carbamoyl)methyl]-2-[5-fluoro-6-(6-methylpyridin-3-yl)-1,3-benzothiazol-2-yl]-2-methanesulfonyl-acetamide | 9.01-9.22 (m, 1H), 8.85 (br. s., 1H), 8.45 (d, J = 7.3 Hz, 1H), 8.29 (d, J = 7.9 Hz, 1H), 8.14 (s, 1H), 8.06 (d, J = 2.7 Hz, 1H), 7.70 (d, J = 7.9 Hz, 1H), 6.22 (s, 1H), 3.53-3.94 (m, 2H), 3.28 (s, 3H), 2.66 (M + s, 4H), 0.64 (d, J = 6.7 Hz, 2H), 0.40 (br. s., 2H) | 0.61 M 476.9 | 9 |
| 192 | 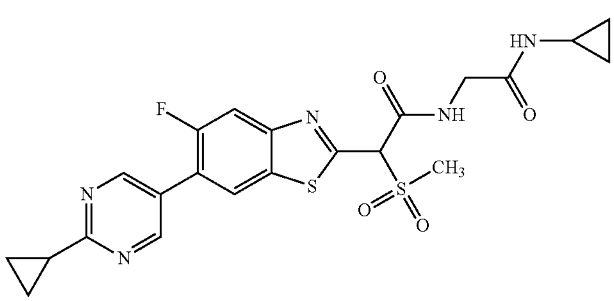 [SMILES: CS(=O)(=O)C(C(=O)NCC(=O)NC1CC1)c1nc2cc(F)c(-c3cnc(C4CC4)nc3)cc2s1] | N-[(cyclopropyl-carbamoyl)methyl]-2-[6-(2-cyclopropyl-pyrimidin-5-yl)-5-fluoro-1,3-benzothiazol-2-yl]-2-methanesulfonyl-acetamide | 9.07 (t, J = 5.2 Hz, 1H), 8.89 (s, 2H), 8.46 (d, J = 7.3 Hz, 1H), 8.13 (d, J = 11.3 Hz, 1H), 8.06 (d, J = 3.1 Hz, 1H), 6.22 (s, 1H), 3.84 (m, 1H), 3.46-3.57 (m, 1H), 3.28 (s, 3H), 2.64 (m, 1H), 2.29 (m, 1H), 0.98-1.19 (m, 5H), 0.64 (d, J = 6.7 Hz, 2H), 0.40 (br. s., 2H) | 1.45 N 504.1 | 25 |

| Ex. No. | Structure | Name | $^{1}$H NMR δ (500 MHz, DMSO-$d_6$, unless otherwise indicated) | LC/MS RT (min) ethod M + H | EL IC$_{50}$ (nM) |
|---|---|---|---|---|---|
| 193 | 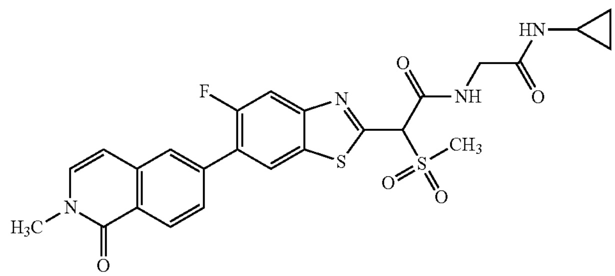 [SMILES: Cn1ccc2cc(-c3cc4sc(C(C(=O)NCC(=O)NC5CC5)S(C)(=O)=O)nc4cc3F)ccc2c1=O] | N-[(cyclopropyl-carbamoyl)methyl]-2-[5-fluoro-6-(2-methyl-1-oxo-1,2-dihydro-isoquinolin-6-yl)-1,3-benzothiazol-2-yl]-2-methanesulfonyl-acetamide | 9.16 (m, 1H), 8.50 (d, J = 7.0 Hz, 1H), 8.40 (d, J = 8.2 Hz, 1H), 8.06-8.24 (m, 2H), 7.98 (br. s., 1H), 7.81 (d, J = 8.2 Hz, 1H), 7.58 (d, J = 7.3 Hz, 1H), 6.80 (d, J = 7.0 Hz, 1H), 6.27 (s, 1H), 3.90 (m, 1H), 3.77 (m, 1H), 3.36 (s, 3H), 2.70 (m, 1H), 0.71 (d, J = 6.4 Hz, 2H), 0.47 (br. s., 2H) | 0.73 M 543.2 | 5 |
| 194 | 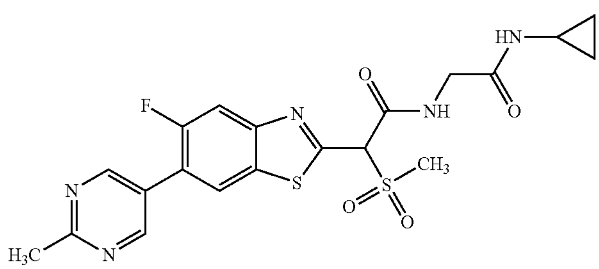 | N-[(cyclopropyl-carbamoyl)methyl]-2-[5-fluoro-6-(2-methylpyrimidin-5-yl)-1,3-benzothiazol-2-yl]-2-methanesulfonyl-acetamide | 5.75-9.78 (m, 7H), 3.52-3.93 (m, 2H), 2.73 (s, 3H), 2.59-2.65 (m, 1H), 0.59-0.69 (m, 2H), 0.40 (br. s., 2H) | 0.66 M 478.2 | 34 |
| 195 | 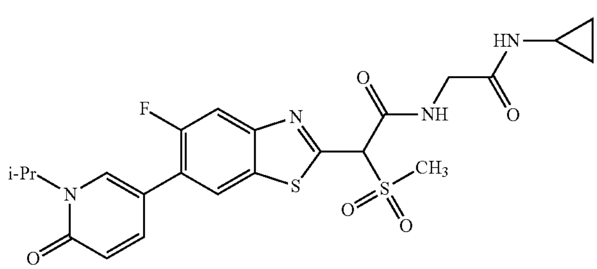 [SMILES: CC(C)n1cc(-c2cc3sc(C(C(=O)NCC(=O)NC4CC4)S(C)(=O)=O)nc3cc2F)ccc1=O] | N-[(cyclopropyl-carbamoyl)methyl]-2-{5-fluoro-6-[6-oxo-1-(propan-2-yl)-1,6-dihydropyridin-3-yl]-1,3-benzothiazol-2-yl}-2-methanesulfonyl-acetamide | 9.04 (t, J = 5.2 Hz, 1H), 8.26 (d, J = 7.3 Hz, 1H), 7.86-8.08 (m, 3H), 7.65 (d, J = 9.2 Hz, 1H), 6.50 (d, J = 9.5 Hz, 1H), 6.12 (s, 1H), 5.06 (dt, J = 13.4, (m, 1H), 3.24 (s, 3H), 2.58 (d, J = 3.7 Hz, 1H), 1.31 (d, J = 6.7 Hz, 6H), 0.59 (d, J = 7.0 Hz, 2H), 0.35 (br. s., 2H) | 0.70 M 521.1 | 23 |
| 196 | 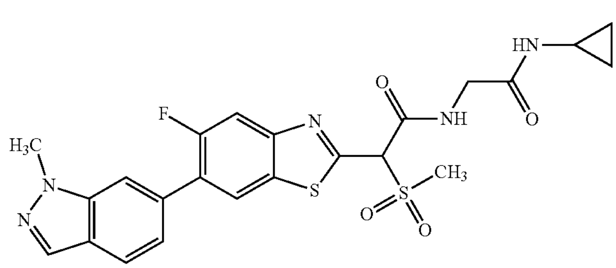 [SMILES: Cn1ncc2ccc(-c3cc4sc(C(C(=O)NCC(=O)NC5CC5)S(C)(=O)=O)nc4cc3F)cc21] | N-[(cyclopropyl-carbamoyl)methyl]-2-[5-fluoro-6-(1-methyl-1H-indazol-6-yl)-1,3-benzothiazol-2-yl]-2-methanesulfonyl-acetamide | 8.97-9.11 (m, 1H), 8.36 (d, J = 7.3 Hz, 1H), 7.71-8.14 (m, 6H), 7.31 (d, J = 8.2 Hz, 1H), 6.16 (s, 1H), 4.04 (s, 3H), 3.56-3.86 (m, 2H), 3.26 (s, 3H), 2.58 (d, J = 3.7 Hz, 1H), 0.52-0.64 (m, 2H), 0.34 (br. s., 2H) | 0.79 M 516.2 | 1 |
| 197 | 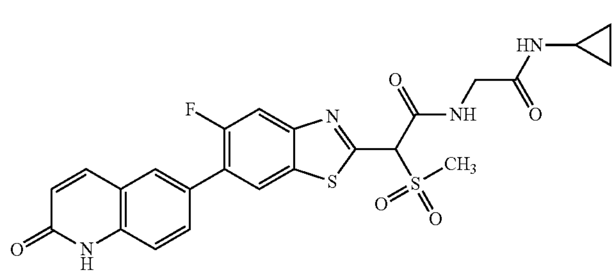 [SMILES: CS(=O)(=O)C(C(=O)NCC(=O)NC1CC1)c1nc2cc(F)c(-c3ccc4[nH]c(=O)ccc4c3)cc2s1] | N-[(cyclopropyl-carbamoyl)methyl]-2-[5-fluoro-6-(2-oxo-1,2-dihydroquinolin-6-yl)-1,3-benzothiazol-2-yl]-2-methanesulfonyl-acetamide | 11.79 (br. s., 1H), 9.01 (m, 1H), 8.12-8.38 (m, 1H), 7.91-8.04 (m, 1H), 7.82-7.90 (m, 1H), 7.73 (dd, J = 15.5, 8.1 Hz, 2H), 7.38 (s, 1H), 7.21 (d, J = 12.1 Hz, 1H), 6.32-6.67 (m, 1H), 3.66-3.84 (m, 4H), 3.20 (br. s., 3H), 2.57-2.75 (m, 1H), 0.53-0.71 (m, 2H), 0.29-0.49 (m, 2H) | 0.66 M 529.2 | 3 |

-continued

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 198 | 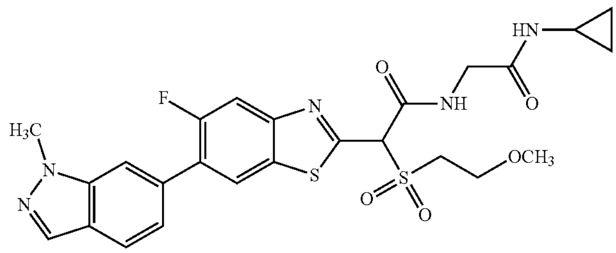 [SMILES: COCCS(=O)(=O)C(C(=O)NCC(=O)NC1CC1)c1nc2cc(F)c(-c3ccc4cnn(C)c4c3)cc2s1] | N-[(cyclopropylcarbamoyl)methyl]-2-[5-fluoro-6-(1-methyl-1H-indazol-6-yl)-1,3-benzothiazol-2-yl]-2-(2-methoxyethanesulfonyl)acetamide | 6.04-9.32 (m, 9H), 4.08 (br. s., 3H), 3.52-3.87 (m, 6H), 3.22 (s, 3H), 2.64 (m, 1H), 0.64 (d, J = 6.1 Hz, 2H), 0.41 (br. s., 2H) | 0.83 M 560.2 | 5 |
| 199 | 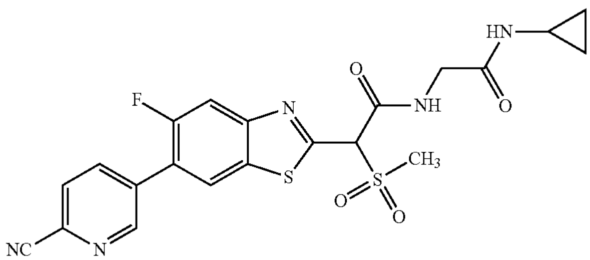 [SMILES: CS(=O)(=O)C(C(=O)NCC(=O)NC1CC1)c1nc2cc(F)c(-c3ccc(C#N)nc3)cc2s1] | 2-[6-(6-cyanopyridin-3-yl)-5-fluoro-1,3-benzothiazol-2-yl]-N-[(cyclopropylcarbamoyl)methyl]-2-methanesulfonylacetamide | 7.85-9.46 (m, 7H), 7.26 (d, J = 12.4 Hz, 1H), 3.68-3.87 (m, 2H), 3.12-3.22 (m, 3H), 2.64 (tq, J = 7.3, 3.7 Hz, 1H), 0.55-0.70 (m, 2H), 0.27-0.50 (m, 2H) | 1.32 O 488.1 | 24 |
| 200 | 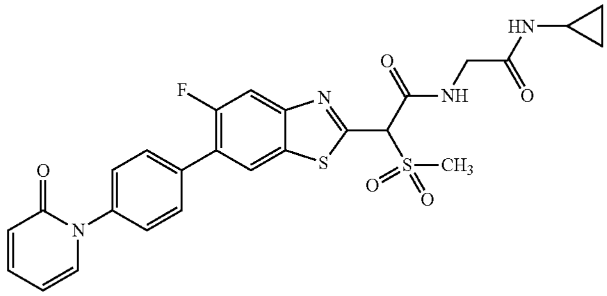 [SMILES: CS(=O)(=O)C(C(=O)NCC(=O)NC1CC1)c1nc2cc(F)c(-c3ccc(-n4ccccc4=O)cc3)cc2s1] | N-[(cyclopropylcarbamoyl)methyl]-2-{5-fluoro-6-[4-(2-oxo-1,2-dihydropyridin-1-yl)phenyl]-1,3-benzothiazol-2-yl}-2-methanesulfonylacetamide | 9.05 (t, J = 5.5 Hz, 1H), 8.38 (d, J = 7.6 Hz, 1H), 8.00-8.15 (m, 2H), 7.92 (s, 1H), 7.63-7.81 (m, 3H), 7.54 (d, J = 8.5 Hz, 2H), 6.52 (d, J = 9.2 Hz, 1H), 6.37 (t, J = 6.3 Hz, 1H), 6.19 (s, 1H), 3.71-3.89 (m, 2H), 3.41-3.64 (m, 3H), 2.62 (m, 1H), 0.62 (d, J = 7.0 Hz, 2H), 0.38 (br. s., 2H) | 1.28 O 555.1 | 8 |
| 201 | 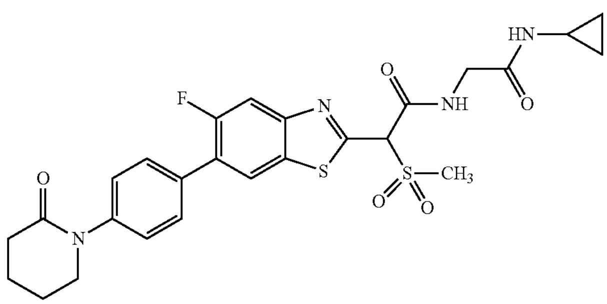 [SMILES: CS(=O)(=O)C(C(=O)NCC(=O)NC1CC1)c1nc2cc(F)c(-c3ccc(N4CCCCC4=O)cc3)cc2s1] | N-[(cyclopropylcarbamoyl)methyl]-2-{5-fluoro-6-[4-(2-oxopiperidin-1-yl)phenyl]-1,3-benzothiazol-2-yl}-2-methanesulfonylacetamide | 9.04 (t, J = 5.5 Hz, 1H), 8.33 (d, J = 7.3 Hz, 1H), 7.99-8.10 (m, 2H), 7.61 (d, J = 7.3 Hz, 2H), 7.41 (d, J = 8.5 Hz, 2H), 6.18 (s, 1H), 3.82 (d, J = 5.5 Hz, 2H), 3.61-3.71 (m, 1H), 3.53 (s, 1H), 3.35 (s, 3H), 2.62 (m, 1H), 2.41 (t, J = 6.4 Hz, 2H), 1.67-1.96 (m, 4H), 0.55-0.69 (m, 2H), 0.39 (d, J = 2.1 Hz, 2H) | 0.77 M 559.5 | 10 |
| 202 | 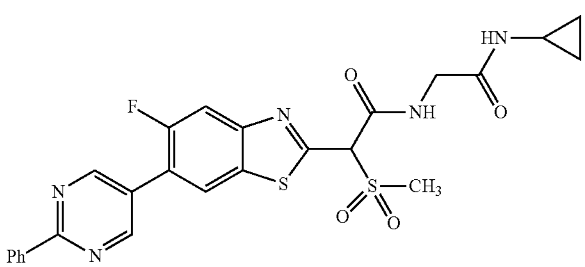 | N-[(cyclopropylcarbamoyl)methyl]-2-[5-fluoro-6-(2-phenylpyrimidin-5-yl)-1,3-benzothiazol-2-yl]-2-methanesulfonylacetamide | (chloroform-d/MeOD): 8.75-9.15 (m, 2H), 8.37 (br. s., 2H), 7.56-8.13 (m, 2H), 7.45 (br. s., 3H), 4.00-4.21 (m, 1H), 3.87 (m, 1H), 2.99-3.20 (m, 3H), 2.66 (m, 1H), 0.68 (br. s., 2H), 0.47 (br. s., 2H) | 0.92 M 540.5 | 5 |

-continued

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 203 | 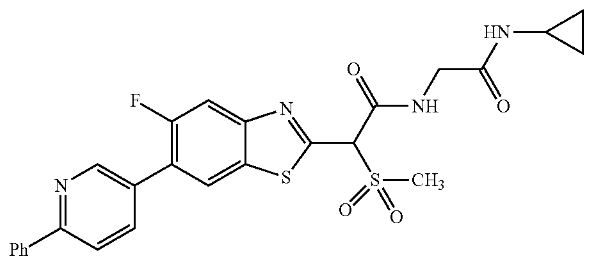 [SMILES: CS(=O)(=O)C(C(=O)NCC(=O)NC1CC1)c1nc2cc(F)c(-c3ccc(-c4ccccc4)nc3)cc2s1] | N-[(cyclopropyl-carbamoyl)methyl]-2-[5-fluoro-6-(6-phenylpyridin-3-yl)-1,3-benzothiazol-2-yl]-2-methanesulfonyl-acetamide | (chloroform-d/MeOD): 8.60-9.03 (m, 1H), 7.62-8.23 (m, 6H), 7.41-7.58 (m, 3H), 3.70-4.29 (m, 2H), 3.09-3.32 (m, 3H), 2.44-2.88 (m, 1H), 0.71-0.91 (m, 2H), 0.38-0.67 (m, 2H) | 0.82 M 539.4 | 3 |
| 204 | 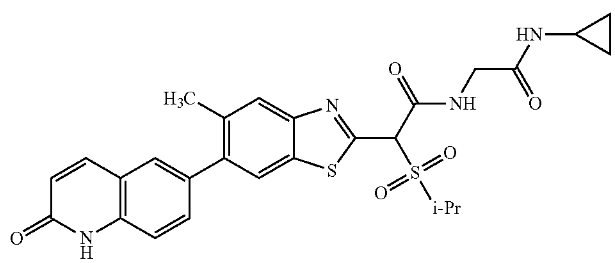 [SMILES: Cc1cc2nc(C(C(=O)NCC(=O)NC3CC3)S(=O)(=O)C(C)C)sc2cc1-c1ccc2[nH]c(=O)ccc2c1] | N-[(cyclopropyl-carbamoyl)methyl]-2-[5-methyl-6-(2-oxo-1,2-dihydroquinolin-6-yl)-1,3-benzothiazol-2-yl]-2-(propane-2-sulfonyl)acetamide | 9.11 (br. s., 1H), 8.03 (d, J = 4.88 Hz, 2H), 7.97 (s, 2H), 7.66-7.75 (m, 1H), 7.51-7.60 (m, 1H), 7.37-7.44 (m, 1H), 6.53-6.59 (m, 1H), 3.76-3.92 (m, 2H), 2.63-2.69 (m, 1H), 2.26-2.42 (m, 3H), 1.33-1.42 (m, 2H), 1.23-1.31 (m, 4H), 0.65 (d, J = 6.71 Hz, 2H), 0.42 (br. s., 2H) | 0.75 O 553.3 | 2 |
| 205 | 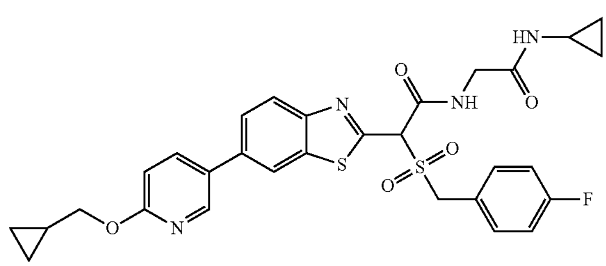 [SMILES: O=C(CNC(=O)C(c1nc2ccc(-c3ccc(OCC4CC4)nc3)cc2s1)S(=O)(=O)Cc1ccc(F)cc1)NC1CC1] | N-[(cyclopropyl-carbamoyl)methyl]-2-{6-[6-(cyclopropyl-methoxy)pyridin-3-yl]-1,3-benzothiazol-2-yl}-2-[(4-fluorophenyl)methanesulfonyl]acetamide | 9.07 (t, J = 5.36 Hz, 1H), 8.44-8.49 (m, 1H), 8.01-8.19 (m, 3H), 7.59-7.91 (m, 2H), 7.43-7.50 (m, 1H), 7.38 (t, J = 6.33 Hz, 1H), 7.19-7.29 (m, 1H), 6.88-7.02 (m, 1H), 6.24 (s, 1H), 4.78 (s, 1H), 4.62-4.74 (m, 1H), 4.11-4.18 (m, 2H), 3.75-3.86 (m, 2H), 2.64 (dd, J = 3.71, 7.29 Hz, 1H), 1.22-1.32 (m, 1H), 0.60-0.66 (m, 2H), 0.51-0.60 (m, 2H), 0.37-0.45 (m, 2H), 0.32-0.37 (m, 2H) | 1.08 O 609.9 | 8 |
| 206 | 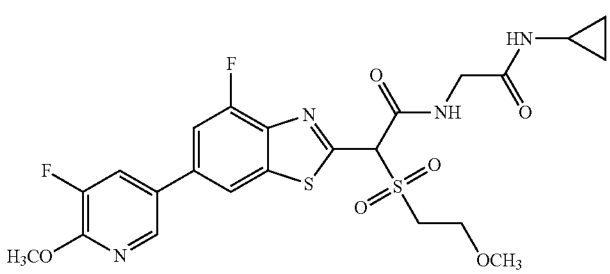 [SMILES: COCCS(=O)(=O)C(C(=O)NCC(=O)NC1CC1)c1nc2c(F)cc(-c3cnc(OC)c(F)c3)cc2s1] | N-[(cyclopropyl-carbamoyl)methyl]-2-[4-fluoro-6-(5-fluoro-6-methoxypyridin-3-yl)-1,3-benzothiazol-2-yl]-2-(2-methoxyethane-sulfonyl)acetamide | 9.02 (t, J = 5.50 Hz, 1H), 8.47 (d, J = 2.20 Hz, 1H), 8.39 (d, J = 1.65 Hz, 1H), 8.19 (dd, J = 1.93, 11.83 Hz, 1H), 8.02 (d, J = 3.85 Hz, 1H), 7.85 (dd, J = 1.38, 12.10 Hz, 1H), 6.24 (s, 1H), 3.30 (m, 3H), 2.63 (dt, J = 3.71, 7.36 Hz, 1H), 0.58-0.66 (m, 2H), 0.35-0.46 (m, 2H) | 0.88 O 555.2 | 9 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 207 | 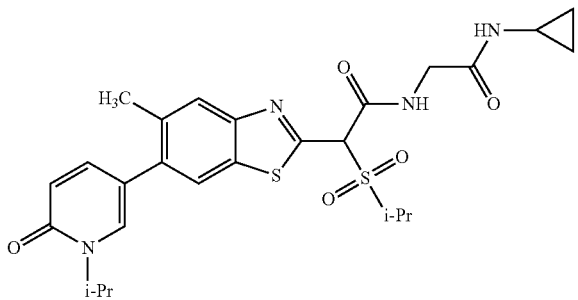 [SMILES: Cc1cc2nc(C(C(=O)NCC(=O)NC3CC3)S(=O)(=O)C(C)C)sc2cc1-c1ccc(=O)n(C(C)C)c1] | N-[(cyclopropyl-carbamoyl)methyl]-2-{5-methyl-6-[6-oxo-1-(propan-2-yl)-1,6-dihydropyridin-3-yl]-1,3-benzothiazol-2-yl}-2-(propane-2-sulfonyl)acetamide | 9.08 (t, J = 5.19 Hz, 1H), 7.99 (d, J = 6.71 Hz, 1H), 7.94 (s, 1H), 7.63-7.76 (m, 1H), 7.41-7.53 (m, 1H), 6.40-6.48 (m, 1H), 5.08-5.14 (m, 1H), 3.74-3.90 (m, 2H), 2.63 (dt, J = 3.66, 7.17 Hz, 1H), 2.25-2.41 (m, 3H), 1.30-1.38 (m, 9H), 1.22-1.27 (m, 2H), 1.19 (d, J = 5.80 Hz, 3H), 0.62 (d, J = 6.71 Hz, 2H), 0.39 (br. s., 2H) | 0.78 O 545.3 | 10 |
| 208 | 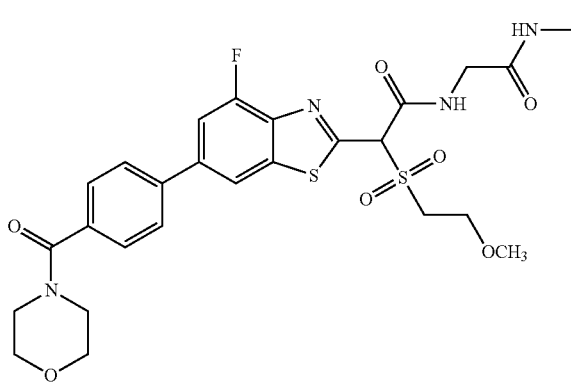 | N-[(cyclopropyl-carbamoyl)methyl]-2-{4-fluoro-6-[4-(morpholine-4-carbonyl)phenyl]-1,3-benzothiazol-2-yl}-2-(2-methoxyethane-sulfonyl)acetamide | 9.01 (t, J = 5.36 Hz, 1H), 8.40 (s, 1H), 8.01 (d, J = 3.58 Hz, 1H), 7.87 (d, J = 7.98 Hz, 2H), 7.81 (d, J = 11.83 Hz, 1H), 7.55 (d, J = 7.98 Hz, 2H), 6.25 (s, 1H), 3.90 (s, 2H), 3.82 (t, J = 6.05 Hz, 2H), 3.76-3.80 (m, 2H), 3.70-3.74 (m, 2H), 3.62 (br. s., 6H), 3.28 (s, 3H), 2.63 (dt, J = 3.71, 7.08 Hz, 1H), 0.62 (d, J = 7.15 Hz, 2H), 0.39 (br. s., 2H) | 0.82 O 619.9 | 11 |
| 209 | 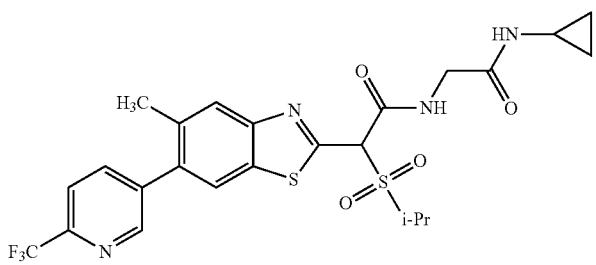 [SMILES: Cc1cc2nc(C(C(=O)NCC(=O)NC3CC3)S(=O)(=O)C(C)C)sc2cc1-c1ccc(C(F)(F)F)nc1] | N-[(cyclopropyl-carbamoyl)methyl]-2-{5-methyl-6-[6-(trifluoromethyl)pyridin-3-yl]-1,3-benzothiazol-2-yl}-2-(propane-2-sulfonyl)acetamide | 9.09 (t, J = 5.19 Hz, 1H), 8.75-8.88 (m, 1H), 8.18 (d, J = 6.41 Hz, 1H), 8.08 (s, 1H), 8.02 (d, J = 7.93 Hz, 1H), 7.94 (s, 1H), 6.36 (s, 1H), 3.74-3.90 (m, 2H), 3.38 (d, J = 7.93 Hz, 1H), 2.60-2.66 (m, 1H), 2.37 (s, 2H), 2.28 (s, 1H), 1.37 (d, J = 6.71 Hz, 2H), 1.26 (d, J = 6.71 Hz, 4H), 0.62 (d, J = 5.49 Hz, 2H), 0.39 (d, J = 2.14 Hz, 2H) | 0.95 O 555.3 | 11 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 210 | 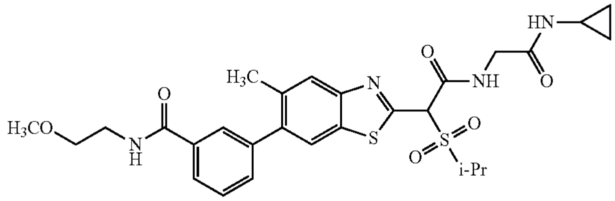 [SMILES: COCCNC(=O)c1cccc(-c2cc3sc(C(C(=O)NCC(=O)NC4CC4)S(=O)(=O)C(C)C)nc3cc2C)c1] | 3-[2-({[(cyclopropyl-carbamoyl)methyl]carbamoyl}(propane-2-sulfonyl)methyl)-5-methyl-1,3-benzothiazol-6-yl]-N-(2-methoxyethyl)benzamide | 8.02 (d, J = 6.71 Hz, 2H), 7.95 (s, 1H), 7.85-7.91 (m, 2H), 7.56 (d, J = 4.58 Hz, 2H), 6.35 (s, 1H), 3.75-3.89 (m, 2H), 3.53-3.62 (m, 1H), 3.46 (d, J = 3.66 Hz, 2H), 3.34 (d, J = 5.49 Hz, 2H), 3.24-3.28 (m, 3H), 2.54-2.66 (m, 1H), 2.35 (s, 3H), 1.37 (d, J = 6.71 Hz, 2H), 1.27 (d, J = 7.02 Hz, 4H), 0.60-0.67 (m, 2H), 0.39 (br. s., 2H) | 0.81 O 587.3 | 12 |
| 211 | 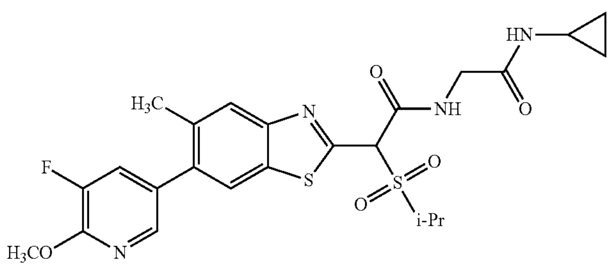 [SMILES: COc1ncc(-c2cc3sc(C(C(=O)NCC(=O)NC4CC4)S(=O)(=O)C(C)C)nc3cc2C)cc1F] | N-[(cyclopropyl-carbamoyl)methyl]-2-[6-(5-fluoro-6-methoxypyridin-3-yl)-5-methyl-1,3-benzothiazol-2-yl]-2-(propane-2-sulfonyl)acetamide | 9.11 (t, J = 5.34 Hz, 1H), 8.03-8.08 (m, 2H), 7.97 (s, 1H), 7.88 (d, J = 11.60 Hz, 1H), 6.37 (s, 1H), 4.02 (s, 3H), 3.77-3.94 (m, 2H), 3.38 (br. s., 1H), 2.61-2.71 (m, 1H), 2.26-2.43 (m, 3H), 1.39 (d, J = 6.71 Hz, 2H), 1.29 (d, J = 6.71 Hz, 4H), 0.65 (d, J = 5.49 Hz, 2H), 0.42 (d, J = 2.44 Hz, 2H) | 0.95 O 535.3 | 14 |
| 212 | 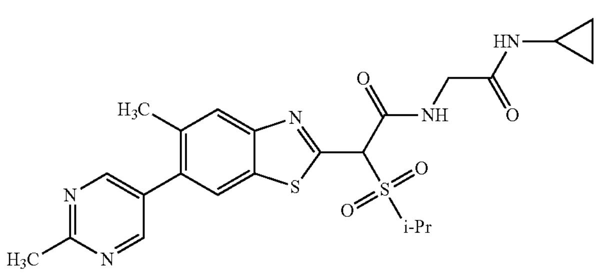 [SMILES: Cc1ncc(-c2cc3sc(C(C(=O)NCC(=O)NC4CC4)S(=O)(=O)C(C)C)nc3cc2C)cn1] | N-[(cyclopropyl-carbamoyl)methyl]-2-[5-methyl-6-(2-methylpyrimidin-5-yl)-1,3-benzothiazol-2-yl]-2-(propane-2-sulfonyl)acetamide | 9.09 (t, J = 5.36 Hz, 1H), 8.74 (s, 2H), 8.08 (d, J = 13.48 Hz, 1H), 7.73-8.03 (m, 1H), 6.37 (s, 1H), 3.75-3.90 (m, 2H), 3.51-3.59 (m, 2H), 2.68-2.72 (m, 3H), 2.64 (dt, J = 3.71, 7.22 Hz, 1H), 2.28-2.40 (m, 3H), 1.38 (d, J = 6.88 Hz, 2H), 1.25-1.30 (m, 4H), 0.62-0.65 (m, 1H), 0.39-0.42 (m, 1H) | 0.75 O 502.3 | 15 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 213 | 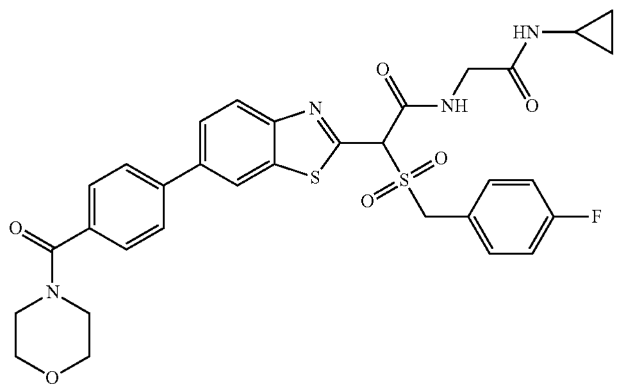 [SMILES: O=C(CNC(=O)C(c1nc2ccc(-c3ccc(C(=O)N4CCOCC4)cc3)cc2s1)S(=O)(=O)Cc1ccc(F)cc1)NC1CC1] | N-[(cyclopropylcarbamoyl)methyl]-2-[(4-fluorophenyl)methanesulfonyl]-2-{6-[4-(morpholine-4-carbonyl)phenyl]-1,3-benzothiazol-2-yl}acetamide | 9.04-9.13 (m, 1H), 8.53 (s, 1H), 8.20 (d, J = 8.53 Hz, 1H), 8.02 (d, J = 13.76 Hz, 1H), 7.90-7.97 (m, 1H), 7.85 (d, J = 7.43 Hz, 1H), 7.74 (d, J = 6.60 Hz, 1H), 7.55 (d, J = 7.98 Hz, 1H), 7.43-7.50 (m, 2H), 7.23 (t, J = 8.25 Hz, 1H), 7.06 (br. s., 1H), 6.25 (s, 1H), 4.79 (br. s., 1H), 4.70 (br. s., 1H), 3.83 (d, J = 4.95 Hz, 1H), 3.62 (br. s., 5H), 2.89 (s, 1H), 2.69-2.78 (m, 1H), 2.64 (br. s., 1H), 2.59 (d, J = 4.68 Hz, 1H), 0.63 (d, J = 6.60 Hz, 2H), 0.40 (br. s., 2H) | 0.83 O 651.3 | 15 |
| 214 | 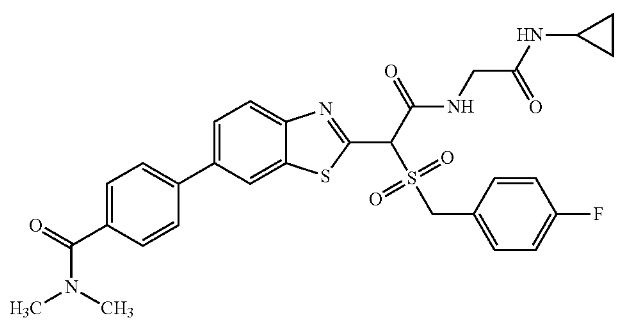 [SMILES: CN(C)C(=O)c1ccc(-c2ccc3nc(C(C(=O)NCC(=O)NC4CC4)S(=O)(=O)Cc4ccc(F)cc4)sc3c2)cc1] | 4-[2-({[(cyclopropylcarbamoyl)methyl]carbamoyl}(4-fluorophenyl)methanesulfonylmethyl)-1,3-benzothiazol-6-yl]-N,N-dimethylbenzamide | 9.08 (t, J = 5.36 Hz, 1H), 8.54 (s, 1H), 8.20 (d, J = 8.53 Hz, 1H), 8.01-8.13 (m, 1H), 7.92 (d, J = 8.53 Hz, 1H), 7.84 (d, J = 7.70 Hz, 2H), 7.54 (d, J = 7.98 Hz, 1H), 7.45-7.51 (m, 2H), 7.38 (t, J = 6.05 Hz, 1H), 7.23 (t, J = 8.53 Hz, 1H), 7.03-7.12 (m, 1H), 6.25 (s, 1H), 4.79 (d, J = 3.58 Hz, 1H), 4.63-4.72 (m, 1H), 3.75-3.84 (m, 2H), 2.98 (br. s., 6H), 2.64 (dd, J = 3.58, 7.15 Hz, 1H), 0.60-0.66 (m, 2H), 0.41 (d, J = 13.48 Hz, 2H) | 0.92 O 609.9 | 18 |
| 215 | 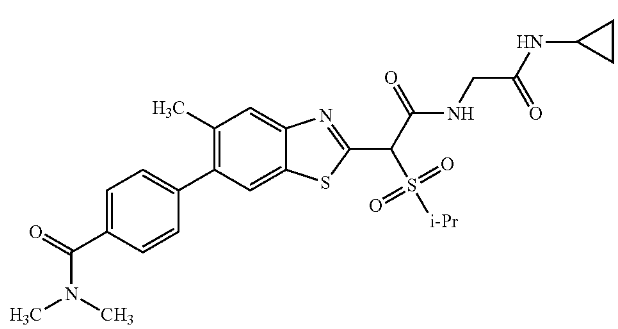 [SMILES: Cc1cc2nc(C(C(=O)NCC(=O)NC3CC3)S(=O)(=O)C(C)C)sc2cc1-c1ccc(C(=O)N(C)C)cc1] | 4-[2-({[(cyclopropylcarbamoyl)methyl]carbamoyl}(propane-2-sulfonyl)methyl)-5-methyl-1,3-benzothiazol-6-yl]-N,N-dimethylbenzamide | 9.08 (t, J = 5.19 Hz, 1H), 8.01 (d, J = 7.32 Hz, 2H), 7.95 (s, 1H), 7.44-7.52 (m, 4H), 6.35 (s, 1H), 3.73-3.89 (m, 2H), 2.89 (s, 3H), 2.73 (s, 3H), 2.63 (d, J = 3.66 Hz, 1H), 2.36 (s, 3H), 2.27 (s, 1H), 1.38 (d, J = 6.71 Hz, 2H), 1.26 (d, J = 7.02 Hz, 4H), 0.62 (d, J = 5.19 Hz, 2H), 0.39 (br. s., 2H) | 0.86 O 557.3 | 19 |

-continued

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 216 | 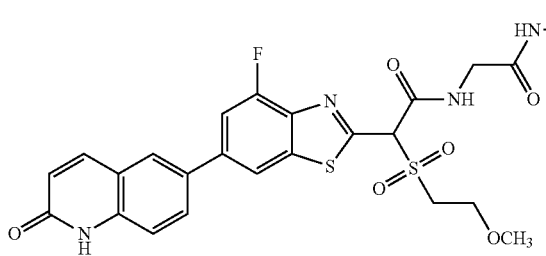 | N-[(cyclopropyl-carbamoyl)methyl]-2-[4-fluoro-6-(2-oxo-1,2-dihydroquinolin-6-yl)-1,3-benzothiazol-2-yl]-2-(2-methoxyethane-sulfonyl)acetamide | 9.01 (t, J = 5.36 Hz, 1H), 8.37 (d, J = 1.65 Hz, 1H), 8.15 (d, J = 2.20 Hz, 1H), 8.02 (d, J = 3.85 Hz, 1H), 7.93-7.98 (m, 2H), 7.81 (dd, J = 1.51, 12.24 Hz, 1H), 7.42 (d, J = 8.53 Hz, 1H), 6.57 (dd, J = 1.93, 9.35 Hz, 1H), 6.24 (s, 1H), 3.81-3.84 (m, 2H), 3.76-3.80 (m, 2H), 3.70-3.74 (m, 2H), 3.28 (s, 3H), 2.63 (dt, J = 3.58, 7.29 Hz, 1H), 0.60-0.65 (m, 2H), 0.37-0.41 (m, 2H) | 0.69 O 573.3 | 19 |
| 217 | 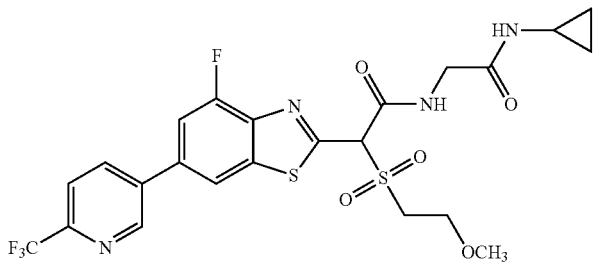 [SMILES: COCCS(=O)(=O)C(C(=O)NCC(=O)NC1CC1)c1nc2c(F)cc(-c3ccc(C(F)(F)F)nc3)cc2s1] | N-[(cyclopropyl-carbamoyl)methyl]-2-{4-fluoro-6-[6-(trifluoromethyl)pyridin-3-yl]-1,3-benzothiazol-2-yl}-2-(2-methoxyethane-sulfonyl)acetamide | 9.21 (d, J = 2.20 Hz, 1H), 9.02 (t, J = 5.64 Hz, 1H), 8.54 (d, J = 1.38 Hz, 1H), 8.50 (dd, J = 2.06, 8.12 Hz, 1H), 8.06 (d, J = 8.25 Hz, 1H), 8.02 (d, J = 3.85 Hz, 1H), 7.98 (dd, J = 1.38, 11.83 Hz, 1H), 6.27 (s, 1H), 3.81-3.85 (m, 2H), 3.76-3.81 (m, 2H), 3.71-3.74 (m, 2H), 3.28 (s, 3H), 2.63 (dt, J = 3.85, 7.29 Hz, 1H), 0.59-0.67 (m, 2H), 0.35-0.44 (m, 2H) | 0.89 O 575.2 | 26 |
| 218 | 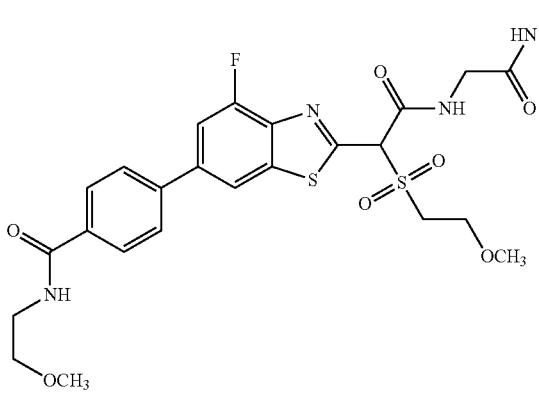 | 4-[2-({[(cyclopropyl-carbamoyl)methyl]carbamoyl}(2-methoxyethane-sulfonyl)methyl)-4-fluoro-1,3-benzothiazol-6-yl]-N-(2-methoxyethyl)benzamide | 9.01 (t, J = 5.36 Hz, 1H), 8.68-8.72 (m, 1H), 8.41 (s, 1H), 8.24 (s, 1H), 8.02 (d, J = 3.58 Hz, 1H), 7.95 (d, J = 7.43 Hz, 1H), 7.86-7.91 (m, 2H), 7.61 (t, J = 7.70 Hz, 1H), 6.25 (s, 1H), 3.82 (t, J = 5.78 Hz, 2H), 3.76-3.79 (m, 2H), 3.71-3.74 (m, 2H), 3.47-3.49 (m, 4H), 3.28 (d, J = 4.40 Hz, 6H), 2.63 (dd, J = 3.44, 7.01 Hz, 1H), 0.62 (d, J = 7.15 Hz, 2H), 0.40 (br. s., 2H) | 0.83 O 607.9 | 28 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 219 | 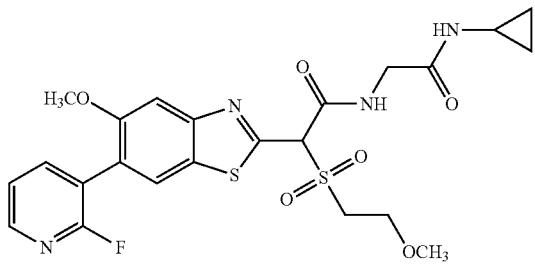 [SMILES: COCCS(=O)(=O)C(C(=O)NCC(=O)NC1CC1)c1nc2cc(OC)c(-c3cccnc3F)cc2s1] | N-[(cyclopropyl-carbamoyl) methyl]-2-[6-(2-fluoropyridin-3-yl)-5-methoxy-1,3-benzothiazol-2-yl]-2-(2-methoxyethane-sulfonyl) acetamide | 8.98 (t, J = 5.50 Hz, 1H), 8.38 (d, J = 2.20 Hz, 1H), 8.14-8.18 (m, 2H), 8.01 (d, J = 3.85 Hz, 1H), 7.80 (s, 1H), 7.28 (dd, J = 2.61, 8.39 Hz, 1H), 6.18 (s, 1H), 3.90 (s, 3H), 3.79-3.83 (m, 2H), 3.74-3.79 (m, 2H), 3.70-3.74 (m, 2H), 3.28 (s, 3H), 2.63 (qd, J = 3.71, 7.01 Hz, 1H), 1.21-1.28 (m, 2H), 0.60-0.65 (m, 2H), 0.37-0.42 (m, 2H) | 3.19 A 537.2 | 39 |
| 220 | 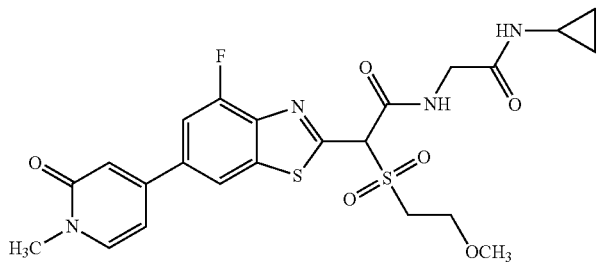 [SMILES: COCCS(=O)(=O)C(C(=O)NCC(=O)NC1CC1)c1nc2c(F)cc(-c3ccn(C)c(=O)c3)cc2s1] | N-[(cyclopropyl-carbamoyl) methyl]-2-[4-fluoro-6-(1-methyl-2-oxo-1,2-dihydropyridin-4-yl)-1,3-benzothiazol-2-yl]-2-(2-methoxyethane-sulfonyl) acetamide | 9.01 (t, J = 5.50 Hz, 1H), 8.45 (d, J = 1.38 Hz, 1H), 8.01 (d, J = 3.85 Hz, 1H), 7.83 (s, 1H), 7.80-7.83 (m, 1H), 6.83 (d, J = 2.20 Hz, 1H), 6.68 (dd, J = 2.20, 7.15 Hz, 1H), 6.25 (s, 1H), 3.82 (t, J = 5.91 Hz, 2H), 3.75-3.80 (m, 2H), 3.69-3.73 (m, 2H), 3.47 (s, 3H), 3.27 (s, 3H), 2.63 (dt, J = 3.85, 7.29 Hz, 1H), 0.59-0.65 (m, 2H), 0.36-0.42 (m, 2H) | 0.65 O 537 | 60 |
| 221 | 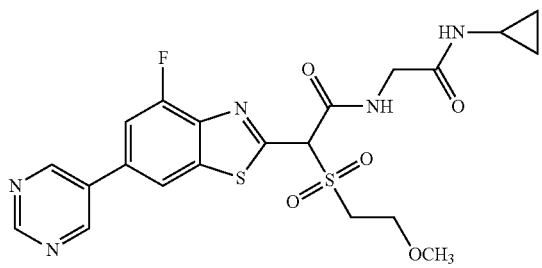 [SMILES: COCCS(=O)(=O)C(C(=O)NCC(=O)NC1CC1)c1nc2c(F)cc(-c3cncnc3)cc2s1] | N-[(cyclopropyl-carbamoyl) methyl]-2-[4-fluoro-6-(pyrimidin-5-yl)-1,3-benzothiazol-2-yl]-2-(2-methoxyethane-sulfonyl) acetamide | 9.26 (s, 2H), 9.24 (s, 1H), 9.02 (t, J = 5.36 Hz, 1H), 8.52 (s, 1H), 8.02 (d, J = 3.58 Hz, 1H), 7.99 (d, J = 11.83 Hz, 1H), 6.27 (s, 1H), 3.90 (s, 1H), 3.82 (t, J = 6.19 Hz, 2H), 3.76-3.81 (m, 2H), 3.70-3.75 (m, 2H), 3.27 (s, 3H), 2.63 (dd, J = 3.44, 7.02 Hz, 1H), 0.62 (d, J = 6.88 Hz, 2H), 0.39 (br. s., 2H) | 0.76 O 508.8 | 61 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 222 | 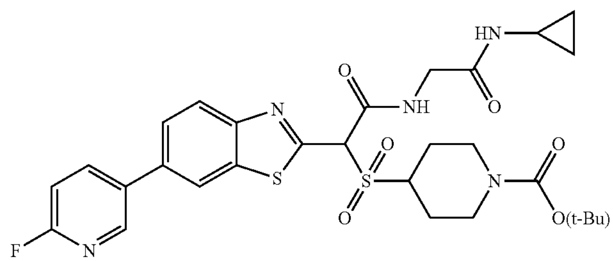 | tert-butyl 4-({[(cyclopropyl-carbamoyl)methyl]carbamoyl}[6-(6-fluoropyridin-3-yl)-1,3-benzothiazol-2-yl]methanesulfonyl)piperidine-1-carboxylate | 9.09 (t, J = 5.36 Hz, 1H), 8.55 (s, 1H), 8.26-8.42 (m, 1H), 8.14-8.22 (m, 1H), 8.01-8.12 (m, 1H), 7.91 (d, J = 8.80 Hz, 1H), 7.27-7.38 (m, 1H), 6.37 (s, 1H), 4.04 (br. s., 2H), 3.79-3.88 (m, 2H), 3.65-3.73 (m, 1H), 2.60-2.67 (m, 1H), 2.02-2.20 (m, 2H), 1.97 (d, J = 11.83Hz, 2H), 1.46-1.58 (m, 2H), 1.39 (d, J = 8.80 Hz, 9H), 0.63 (d, J = 6.88 Hz, 2H), 0.40 (br. s., 2H) | 0.95 O 632.3 | 78 |
| 223 | 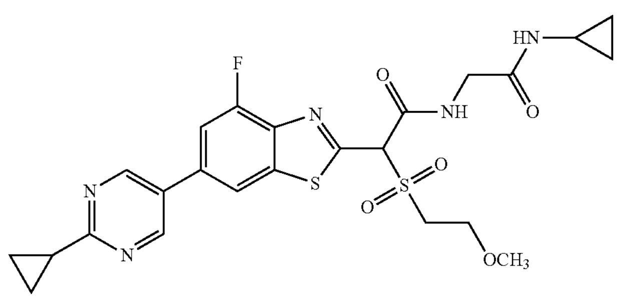 [SMILES: COCCS(=O)(=O)C(C(=O)NCC(=O)NC1CC1)c1nc2c(F)cc(-c3cnc(C4CC4)nc3)cc2s1] | N-[(cyclopropyl-carbamoyl)methyl]-2-[6-(2-cyclopropyl-pyrimidin-5-yl)-4-fluoro-1,3-benzothiazol-2-yl]-2-(2-methoxyethane-sulfonyl)acetamide | 9.06 (s, 2H), 9.02 (t, J = 5.50 Hz, 1H), 8.45 (d, J = 1.38 Hz, 1H), 8.02 (d, J = 4.13 Hz, 1H), 7.91 (dd, J = 1.51, 11.97 Hz, 1H), 6.25 (s, 1H), 3.82 (t, J = 5.78 Hz, 2H), 3.75-3.80 (m, 2H), 3.69-3.73 (m, 2H), 3.25-3.29 (m, 3H), 2.63 (dt, J = 3.71, 7.36 Hz, 1H), 2.23-2.31 (m, 1H), 1.08-1.14 (m, 2H), 1.03-1.08 (m, 2H), 0.59-0.66 (m, 2H), 0.35-0.43 (m, 2H) | 0.81 O 548.3 | 80 |
| 224 | 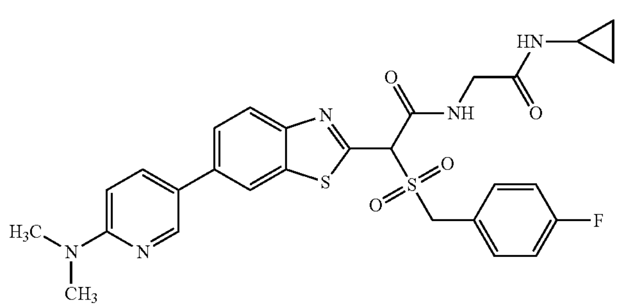 [SMILES: CN(C)c1ccc(-c2ccc3nc(C(C(=O)NCC(=O)NC4CC4)S(=O)(=O)Cc4ccc(F)cc4)sc3c2)cn1] | N-[(cyclopropyl-carbamoyl)methyl]-2-{6-[6-(dimethylamino)pyridin-3-yl]-1,3-benzothiazol-2-yl}-2-[(4-fluorophenyl)methanesulfonyl]acetamide | 9.10 (t, J = 5.36 Hz, 1H), 8.47 (br. s., 1H), 8.09-8.21 (m, 2H), 8.06 (d, J = 3.30 Hz, 1H), 7.88 (d, J = 8.80 Hz, 1H), 7.44-7.52 (m, 1H), 7.40 (br. s., 1H), 7.22-7.29 (m, 1H), 7.00-7.17 (m, 2H), 6.26 (s, 1H), 4.80 (br. s., 1H), 4.64-4.76 (m, 1H), 3.78-3.86 (m, 2H), 3.18 (s, 6H), 2.66 (dd, J = 3.30, 7.15 Hz, 1H), 0.62-0.69 (m, 2H), 0.38-0.47 (m, 2H) | 0.7 O 582.3 | 86 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 225 | 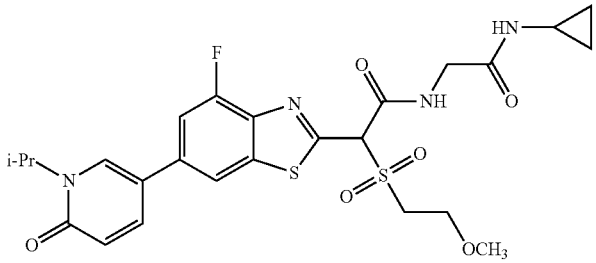 [SMILES: COCCS(=O)(=O)C(C(=O)NCC(=O)NC1CC1)c1nc2c(F)cc(-c3ccc(=O)n(C(C)C)c3)cc2s1] | N-[(cyclopropylcarbamoyl)methyl]-2-{4-fluoro-6-[6-oxo-1-(propan-2-yl)-1,6-dihydropyridin-3-yl]-1,3-benzothiazol-2-yl}-2-(2-methoxyethanesulfonyl)acetamide | 9.00 (t, J = 5.50 Hz, 1H), 8.27 (d, J = 1.38 Hz, 1H), 8.15 (d, J = 2.48 Hz, 1H), 8.02 (d, J = 4.13 Hz, 1H), 7.89 (dd, J = 2.75, 9.63 Hz, 1H), 7.79 (dd, J = 1.38, 12.38 Hz, 1H), 6.52 (d, J = 9.63 Hz, 1H), 6.22 (s, 1H), 5.12 (quin, J = 6.88 Hz, 1H), 3.80-3.83 (m, 2H), 3.75-3.78 (m, 2H), 3.69-3.73 (m, 2H), 3.27 (s, 3H), 2.63 (dt, J = 3.85, 7.29 Hz, 1H), 1.39 (dd, J = 1.79, 6.74 Hz, 6H), 0.58-0.66 (m, 2H), 0.35-0.42 (m, 2H) | 0.73 O 565.3 | 88 |
| 226 | 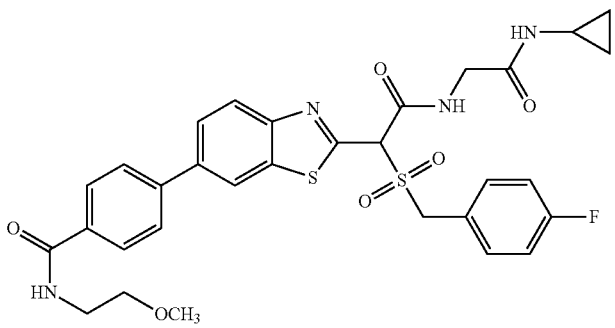 [SMILES: COCCNC(=O)c1ccc(-c2ccc3nc(C(C(=O)NCC(=O)NC4CC4)S(=O)(=O)Cc4ccc(F)cc4)sc3c2)cc1] | 4-[2-({[(cyclopropylcarbamoyl)methyl]carbamoyl}(4-fluorophenyl)methanesulfonylmethyl)-1,3-benzothiazol-6-yl]-N-(2-methoxyethyl)benzamide | 9.08 (t, J = 5.36 Hz, 1H), 8.62-8.72 (m, 1H), 8.55 (s, 1H), 8.20-8.26 (m, 1H), 8.11-8.16 (m, 1H), 7.94 (dd, J = 8.25, 15.41 Hz, 2H), 7.88 (d, J = 7.70 Hz, 1H), 7.83 (d, J = 7.70 Hz, 1H), 7.52-7.62 (m, 1H), 7.45-7.50 (m, 1H), 7.39 (t, J = 6.46 Hz, 1H), 7.24 (t, J = 8.53 Hz, 1H), 7.04-7.13 (m, 1H), 6.26 (s, 1H), 4.76-4.83 (m, 1H), 4.64-4.74 (m, 1H), 3.76-3.86 (m, 2H), 3.48 (d, J = 4.13 Hz, 5H), 3.28 (s, 3H), 2.65 (dd, J = 3.58, 7.15 Hz, 1H), 0.60-0.66 (m, 2H), 0.38-0.46 (m, 2H) | 0.84 O 639.1 | 91 |
| 227 | 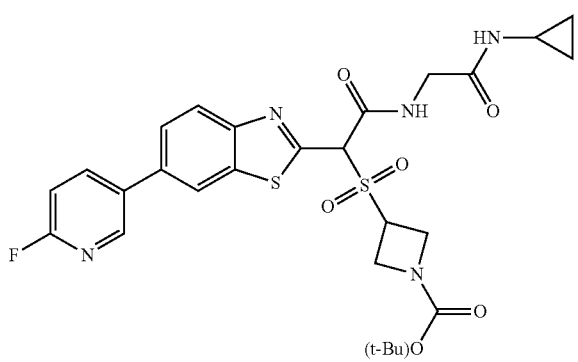 | tert-butyl 3-({[(cyclopropylcarbamoyl)methyl]carbamoyl}[6-(6-fluoropyridin-3-yl)-1,3-benzothiazol-2-yl]methanesulfonyl)azetidine-1-carboxylate | 9.10 (t, J = 5.09 Hz, 1H), 8.65 (s, 1H), 8.56 (s, 1H), 8.35-8.41 (m, 1H), 8.20 (d, J = 8.53 Hz, 1H), 8.08 (d, J = 3.30 Hz, 1H), 7.93 (d, J = 8.53 Hz, 1H), 7.31-7.37 (m, 1H), 6.25-6.30 (m, 1H), 4.63 (br. s., 1H), 3.99-4.32 (m, 4H), 3.83 (t, J = 4.95 Hz, 2H), 2.61-2.67 (m, 1H), 1.35-1.39 (m, 10H), 0.63 (d, J = 7.15 Hz, 2H), 0.40 (d, J = 2.20 Hz, 2H) | 0.90 O 604.1 | 103 |

-continued

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 228 | 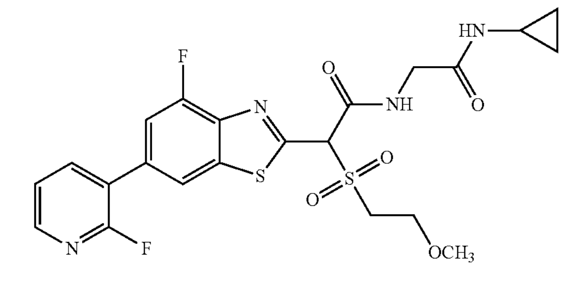 [SMILES: COCCS(=O)(=O)C(C(=O)NCC(=O)NC1CC1)c1nc2c(F)cc(-c3cccnc3F)cc2s1] | N-[(cyclopropyl-carbamoyl)methyl]-2-[4-fluoro-6-(2-fluoropyridin-3-yl)-1,3-benzothiazol-2-yl]-2-(2-methoxyethane-sulfonyl)acetamide | 9.01 (t, J = 5.50 Hz, 1H), 8.28-8.35 (m, 2H), 8.23 (t, J = 8.67 Hz, 1H), 8.01 (d, J = 3.85 Hz, 1H), 7.72 (d, J = 11.55 Hz, 1H), 7.51-7.58 (m, 1H), 6.26 (s, 1H), 3.83 (br. s., 6H), 2.59-2.66 (m, 1H), 0.62 (d, J = 6.60 Hz, 2H), 0.39 (br. s., 2H) | 0.87 O 525.9 | 106 |
| 229 | 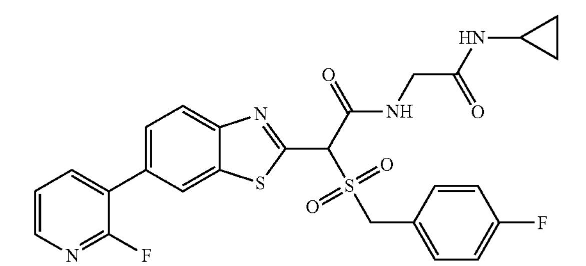 [SMILES: O=C(CNC(=O)C(c1nc2ccc(-c3cccnc3F)cc2s1)S(=O)(=O)Cc1ccc(F)cc1)NC1CC1] | N-[(cyclopropyl-carbamoyl)methyl]-2-[(4-fluorophenyl)methanesulfonyl]-2-[6-(2-fluoropyridin-3-yl)-1,3-benzothiazol-2-yl]acetamide | 9.09 (t, J = 5.50 Hz, 1H), 8.46 (s, 1H), 8.30 (d, J = 4.40 Hz, 1H), 8.18-8.27 (m, 2H), 7.99-8.07 (m, 1H), 7.82 (d, J = 8.53 Hz, 1H), 7.42-7.51 (m, 2H), 7.24 (t, J = 8.94 Hz, 1H), 6.27 (s, 1H), 4.64-4.84 (m, 2H), 3.84 (d, J = 6.05 Hz, 2H), 2.62-2.68 (m, 1H), 0.58-0.66 (m, 2H), 0.36-0.47 (m, 2H) | 0.89 O 557.1 | 150 |
| 230 | 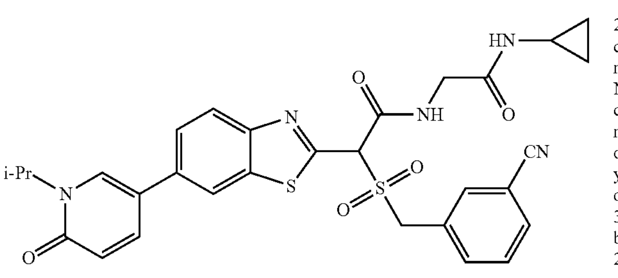 | 2-[(3-cyanophenyl)methanesulfonyl]-N-[(cyclopropyl-carbamoyl)methyl]-2-{6-[6-oxo-1-(propan-2-yl)-1,6-dihydropyridin-3-yl]-1,3-benzothiazol-2-yl}acetamide | 9.06 (t, J = 5.50 Hz, 1H), 8.41 (d, J = 1.65 Hz, 1H), 8.09-8.16 (m, 2H), 7.99-8.07 (m, 1H), 7.82-7.90 (m, 1H), 7.80 (s, 1H), 7.76 (d, J = 7.98 Hz, 1H), 7.58-7.67 (m, 1H), 6.46-6.55 (m, 1H), 5.07-5.18 (m, 1H), 4.73-4.93 (m, 2H), 3.74-3.87 (m, 2H), 2.64 (tt, J = 3.68, 7.32 Hz, 1H), 1.35-1.42 (m, 6H), 0.59-0.67 (m, 2H), 0.37-0.46 (m, 2H) | 0.79 O 604.1 | 46 |
| 231 | 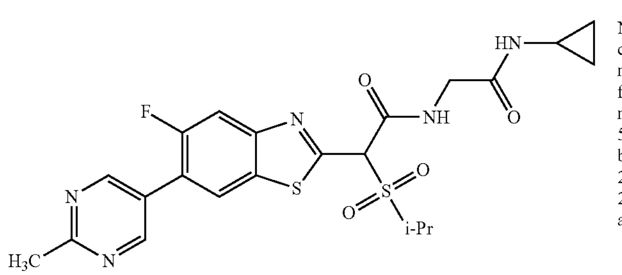 | N-[(cyclopropyl-carbamoyl)methyl]-2-[5-fluoro-6-(2-methylpyrimidin-5-yl)-1,3-benzothiazol-2-yl]-2-(propane-2-sulfonyl)acetamide | 9.12 (t, J = 5.19 Hz, 1H), 8.96 (s, 1H), 8.48 (d, J = 7.63 Hz, 1H), 8.00-8.14 (m, 2H), 6.38 (s, 1H), 3.75-3.91 (m, 2H), 3.51-3.63 (m, 1H), 2.66-2.73 (m, 3H), 2.63 (d, J = 3.36 Hz, 1H), 1.38 (d, J = 6.71 Hz, 2H), 1.25-1.30 (m, 4H), 0.62 (d, J = 6.10 Hz, 2H), 0.40 (br. s., 2H) | 0.76 O 506.3 | 11 |

| Ex. No. | Structure | Name | ¹H NMR δ (500 MHz, DMSO-d₆, unless otherwise indicated) | LC/MS RT (min) ethod M + H | EL IC₅₀ (nM) |
|---|---|---|---|---|---|
| 232 | 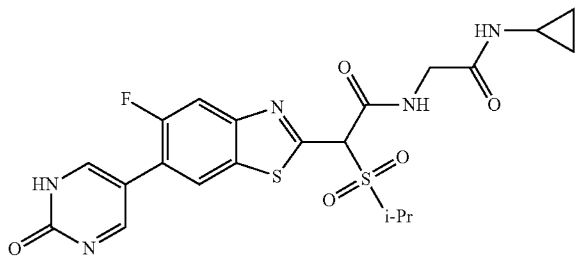 [SMILES: CC(C)S(=O)(=O)C(C(=O)NCC(=O)NC1CC1)c1nc2cc(F)c(-c3cnc(=O)[nH]c3)cc2s1] | N-[(cyclopropyl-carbamoyl)methyl]-2-[5-fluoro-6-(2-oxo-1,2-dihydropyrimidin-5-yl)-1,3-benzothiazol-2-yl]-2-(propane-2-sulfonyl)acetamide | 9.11 (br. s., 1H), 8.29-8.39 (m, 1H), 7.94-8.07 (m, 2H), 7.77 (d, J = 10.38 Hz, 1H), 6.34 (d, J = 4.58 Hz, 1H), 3.73-3.92 (m, 2H), 2.62 (br. s., 1H), 1.36 (d, J = 6.41 Hz, 2H), 1.26 (d, J = 4.58 Hz, 4H), 0.62 (d, J = 5.80 Hz, 2H), 0.39 (br. s., 2H) | 0.61 O 508.3 | 122 |
| 233 | 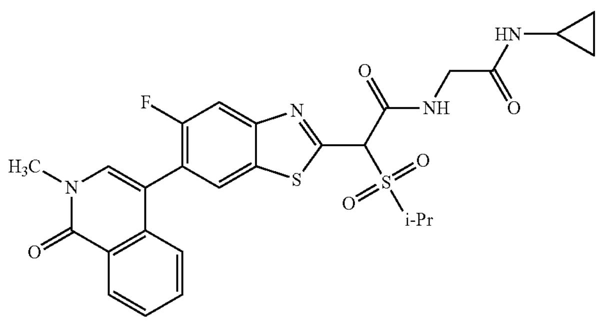 [SMILES: CC(C)S(=O)(=O)C(C(=O)NCC(=O)NC1CC1)c1nc2cc(F)c(-c3cn(C)c(=O)c4ccccc34)cc2s1] | N-[(cyclopropyl-carbamoyl)methyl]-2-[5-fluoro-6-(2-methyl-1-oxo-1,2-dihydro-isoquinolin-4-yl)-1,3-benzothiazol-2-yl]-2-(propane-2-sulfonyl)acetamide | 9.19 (br. s., 1H), 8.29-8.41 (m, 2H), 8.04-8.17 (m, 2H), 7.72 (d, J = 11.90 Hz, 1H), 7.61 (d, J = 6.10 Hz, 1H), 7.29 (br. s., 1H), 6.43 (br. s., 1H), 3.79-3.98 (m, 2H), 3.57-3.66 (m, 1H), 3.42 (S,3H), 2.69 (br. s., 1H), 1.44 (br. s., 2H), 1.34 (d, J = 4.58 Hz, 4H), 0.67 (br. s., 2H), 0.45 (br. s., 2H) | 0.82 O 571.3 | 26 |
| 234 | 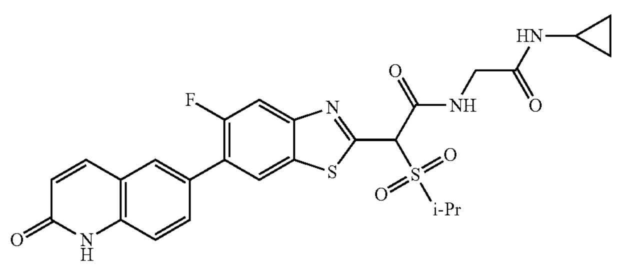 [SMILES: CC(C)S(=O)(=O)C(C(=O)NCC(=O)NC1CC1)c1nc2cc(F)c(-c3ccc4[nH]c(=O)ccc4c3)cc2s1] | N-[(cyclopropyl-carbamoyl)methyl]-2-[5-fluoro-6-(2-oxo-1,2-dihydroquinolin-6-yl)-1,3-benzothiazol-2-yl]-2-(propane-2-sulfonyl)acetamide | 9.12 (br. s., 1H), 8.36 (d, J = 7.63 Hz, 1H), 8.05 (d, J = 11.29 Hz, 1H), 7.92-8.03 (m, 3H), 7.73-7.82 (m, 1H), 7.38-7.46 (m, 1H), 6.53-6.59 (m, 1H), 6.36 (s, 1H), 3.74-3.92 (m, 2H), 2.63 (d, J = 3.66 Hz, 1H), 1.38 (d, J = 6.71 Hz, 2H), 1.27 (d, J = 6.71 Hz, 4H), 0.62 (d, J = 5.49 Hz, 2H), 0.39 (br. s., 2H) | 1.36 O 557.15 | 6 |
| 235 | 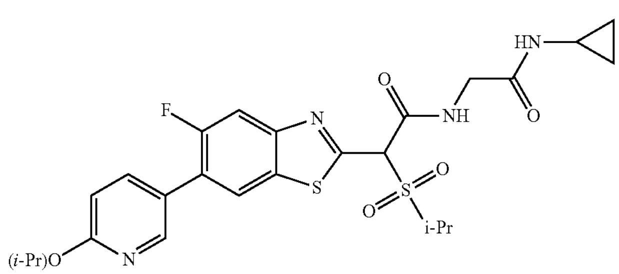 | N-[(cyclopropyl-carbamoyl)methyl]-2-{5-fluoro-6-[6-(propan-2-yloxy)pyridin-3-yl]-1,3-benzothiazol-2-yl}-2-(propane-2-sulfonyl)acetamide | 9.09-9.14 (m, 1H), 8.37 (br. s., 1H), 8.34 (d, J = 7.63 Hz, 1H), 8.04 (d, J = 10.99 Hz, 1H), 7.92 (d, J = 8.54 Hz, 1H), 6.82-6.90 (m, 1H),6.35 (s, 1H), 5.24-5.37 (m, 1H), 3.73-3.86 (m, 2H), 3.48-3.63 (m, 1H), 2.63 (d, J = 3.36 Hz, 1H), 1.37 (d, J = 6.71 Hz, 2H), 1.30-1.33 (m, 6H), 1.26 (d, J = 6.41 Hz, 4H), 0.62 (d, J = 6.41 Hz, 2H), 0.39 (br. s., 2H) | 0.98 O 549.3 | 6 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 236 | 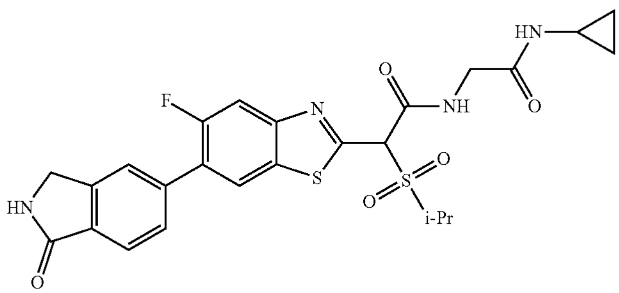 [SMILES: CC(C)S(=O)(=O)C(C(=O)NCC(=O)NC1CC1)c1nc2cc(F)c(-c3ccc4c(c3)CNC4=O)cc2s1] | N-[(cyclopropyl-carbamoyl)methyl]-2-[5-fluoro-6-(1-oxo-2,3-dihydro-1H-isoindol-5-yl)-1,3-benzothiazol-2-yl]-2-(propane-2-sulfonyl)acetamide | 9.12 (t, J = 5.19 Hz, 1H), 8.60-8.66 (m, 1H), 8.39 (d, J = 7.63 Hz, 1H), 8.08 (d, J = 10.99 Hz, 1H), 7.80 (d, J = 7.63 Hz, 1H), 7.69-7.73 (m, 1H), 6.38 (s, 1H), 4.40-4.51 (m, 2H), 3.76-3.86 (m, 2H), 3.48-3.63 (m, 1H), 2.63 (dd, J = 3.51, 7.17 Hz, 1H), 1.39 (d, J = 6.71 Hz, 2H), 1.24-1.30 (m, 4H), 0.56-0.65 (m, 2H), 0.40 (d, J = 2.44 Hz, 2H) | 0.72 O 545.3 | 16 |
| 237 | 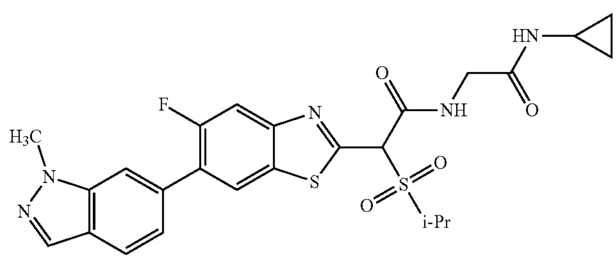 [SMILES: CC(C)S(=O)(=O)C(C(=O)NCC(=O)NC1CC1)c1nc2cc(F)c(-c3ccc4cnn(C)c4c3)cc2s1] | N-[(cyclopropyl-carbamoyl)methyl]-2-[5-fluoro-6-(1-methyl-1H-indazol-6-yl)-1,3-benzothiazol-2-yl]-2-(propane-2-sulfonyl)acetamide | 9.12 (br. s., 1H), 8.36 (d, J = 7.63 Hz, 1H), 8.10-8.15 (m, 1H), 7.98-8.05 (m, 2H), 7.71-7.80 (m, 1H), 7.63 (d, J = 8.85 Hz, 1H), 6.36 (s, 1H), 4.06-4.12 (m, 3H), 3.75-3.87 (m, 2H), 3.58 (t, J = 6.71 Hz, 1H), 2.63 (d, J = 3.36 Hz, 1H), 1.38 (d, J = 6.71 Hz, 2H), 1.27 (d, J = 6.71 Hz, 4H), 0.62 (d, J = 6.71 Hz, 2H), 0.39 (br. s., 2H) | 0.87 O 544.3 | 5 |
| 238 | 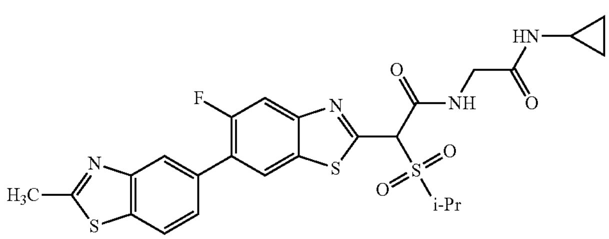 [SMILES: Cc1nc2cc(-c3cc4sc(C(C(=O)NCC(=O)NC5CC5)S(=O)(=O)C(C)C)nc4cc3F)ccc2s1] | N-[(cyclopropyl-carbamoyl)methyl]-2-[5-fluoro-6-(2-methyl-1,3-benzothiazol-5-yl)-1,3-benzothiazol-2-yl]-2-(propane-2-sulfonyl)acetamide | 9.12 (t, J = 5.34 Hz, 1H), 8.40 (d, J = 7.63 Hz, 1H), 8.29 (s, 1H), 7.97-8.05 (m, 2H), 7.68-7.85 (m, 1H), 3.74-3.86 (m, 2H), 3.58 (t, J = 6.71 Hz, 1H), 2.80-2.86 (m, 3H), 2.63 (d, J = 3.97 Hz, 1H), 1.39 (d, J = 6.71 Hz, 2H), 1.24-1.31 (m, 4H), 0.62 (d, J = 5.80 Hz, 2H), 0.40 (br. s., 2H) | 0.91 O 561.3 | 5 |
| 239 | 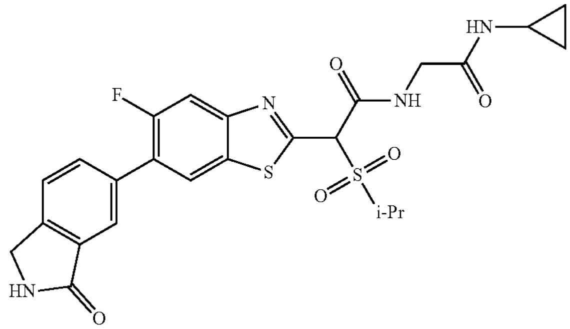 [SMILES: CC(C)S(=O)(=O)C(C(=O)NCC(=O)NC1CC1)c1nc2cc(F)c(-c3ccc4c(c3)C(=O)NC4)cc2s1] | N-[(cyclopropyl-carbamoyl)methyl]-2-[5-fluoro-6-(3-oxo-2,3-dihydro-1H-isoindol-5-yl)-1,3-benzothiazol-2-yl]-2-(propane-2-sulfonyl)acetamide | 9.12 (br. s., 1H), 8.64-8.68 (m, 1H), 8.41 (d, J = 7.63 Hz, 1H), 8.06 (d, J = 11.29 Hz, 1H), 7.81-7.87 (m, 1H), 7.67-7.74 (m, 1H), 6.37 (s, 1H), 4.41-4.49 (m, 3H), 3.77-3.87 (m, 2H), 3.58 (t, J = 6.71 Hz, 1H), 2.63 (d, J = 3.66 Hz, 1H), 1.38 (d, J = 6.41 Hz, 2H), 1.27 (d, J = 6.41 Hz, 4H), 0.62 (d, J = 6.41 Hz, 2H), 0.39 (br. s., 2H) | 0.74 O 545.3 | 16 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 240 | 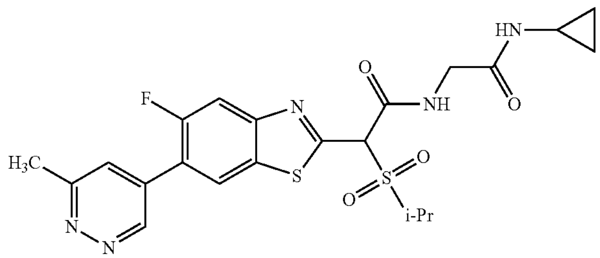 [SMILES: Cc1cc(-c2cc3sc(C(C(=O)NCC(=O)NC4CC4)S(=O)(=O)C(C)C)nc3cc2F)cnn1] | N-[(cyclopropyl carbamoyl) methyl]-2-[5-fluoro-6-(6-methylpyridazin-4-yl)-1,3-benzothiazol-2-yl]-2-(propane-2-sulfonyl) acetamide | 9.30-9.39 (m, 1H), 9.13 (br. s., 1H), 8.58 (d, J = 7.02 Hz, 1H), 8.12-8.23 (m, 1H), 7.87 (d, J = 11.29 Hz, 1H), 6.39 (s, 1H), 3.82 (dd, J = 5.34, 18.46 Hz, 2H), 3.59 (d, J = 6.41 Hz, 1H), 2.72 (d, J = 11.60 Hz, 3H), 2.63 (d, J = 3.66 Hz, 1H), 1.38 (d, J = 6.71 Hz, 2H), 1.27 (d, J = 6.71 Hz, 4H), 0.62 (d, J = 6.10 Hz, 2H), 0.40 (br. s., 2H) | 0.67 O 506.3 | 192 |
| 241 | 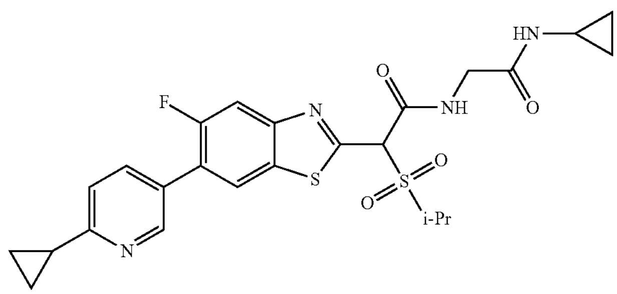 [SMILES: CC(C)S(=O)(=O)C(C(=O)NCC(=O)NC1CC1)c1nc2cc(F)c(-c3ccc(C4CC4)nc3)cc2s1] | N-[(cyclopropyl-carbamoyl) methyl]-2-[6-(6-cyclopropyl-pyridin-3-yl)-5-fluoro-1,3-benzothiazol-2-yl]-2-(propane-2-sulfonyl) acetamide | 9.11 (s, 1H), 8.52-8.64 (m, 1H), 8.36 (d, J = 5.49 Hz, 1H), 8.06 (d, J = 11.29 Hz, 1H), 7.77-7.91 (m, 1H), 7.35-7.44 (m, 1H), 6.35 (d, J = 2.75 Hz, 1H), 3.78-3.88 (m, 2H), 3.54 (br. s., 1H), 2.63 (br. s., 1H), 1.37 (d, J = 6.71 Hz, 2H), 1.26 (d, J = 5.49 Hz, 4H), 0.92-1.02 (m, 4H), 0.62 (d, J = 6.71 Hz, 2H), 0.39 (br. s., 2H) | 0.86 O 531.5 | 17 |
| 242 | 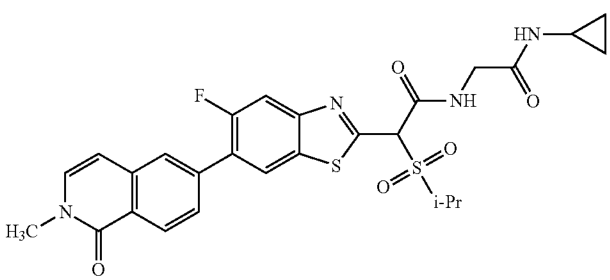 [SMILES: CC(C)S(=O)(=O)C(C(=O)NCC(=O)NC1CC1)c1nc2cc(F)c(-c3ccc4c(=O)n(C)ccc4c3)cc2s1] | N-[(cyclopropyl-carbamoyl) methyl]-2-[5-fluoro-6-(2-methyl-1-oxo-1,2-dihydro-isoquinolin-6-yl)-1,3-benzothiazol-2-yl]-2-(propane-2-sulfonyl) acetamide | 9.14 (br. s., 1H), 8.44 (d, J = 7.32 Hz, 1H), 8.25-8.35 (m, 1H), 8.09 (s, 1H), 7.87-7.95 (m, 1H), 7.62-7.74 (m, 1H), 7.49-7.55 (m, 1H), 6.64-6.74 (m, 1H), 6.38 (s, 1H), 3.72-3.90 (m, 2H), 3.54-3.64 (m, 1H), 2.63 (d, J = 3.36 Hz, 1H), 1.38 (d, J = 6.71 Hz, 2H), 1.28 (d, J = 6.71 Hz, 4H), 0.62 (d, J = 6.10 Hz, 2H), 0.40 (br. s., 2H) | 0.81 O 571.3 | 4 |
| 243 | 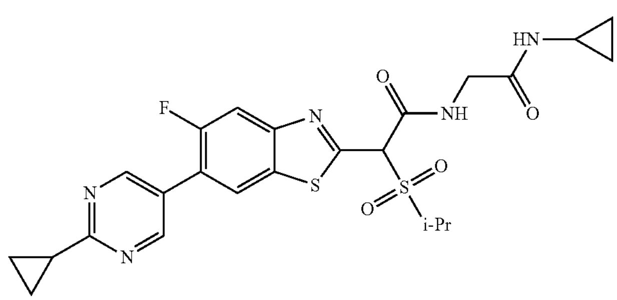 [SMILES: CC(C)S(=O)(=O)C(C(=O)NCC(=O)NC1CC1)c1nc2cc(F)c(-c3cnc(C4CC4)nc3)cc2s1] | N-[(cyclopropyl-carbamoyl) methyl]-2-[6-(2-cyclopropyl-pyrimidin-5-yl)-5-fluoro-1,3-benzothiazol-2-yl]-2-(propane-2-sulfonyl) acetamide | 9.13 (br. s., 1H), 8.78-8.90 (m, 2H), 8.44 (d, J = 7.02 Hz, 1H), 8.10 (d, J = 10.99 Hz, 1H), 6.37 (s, 1H), 3.74-3.91 (m, 2H), 3.50-3.63 (m, 2H), 2.63 (br. s., 1H), 2.28 (br. s., 1H), 1.37 (d, J = 6.41 Hz, 2H), 1.20-1.31 (m, 4H), 1.01-1.14 (m, 4H), 0.62 (d, J = 6.10 Hz, 2H), 0.39 (br. s., 2H) | 0.85 O 532.3 | 33 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 244 | 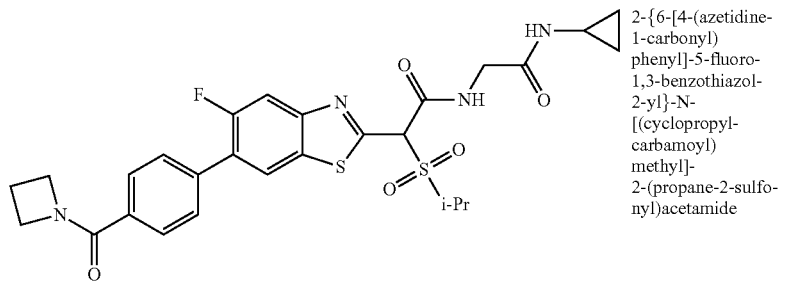 | 2-{6-[4-(azetidine-1-carbonyl)phenyl]-5-fluoro-1,3-benzothiazol-2-yl}-N-[(cyclopropylcarbamoyl)methyl]-2-(propane-2-sulfonyl)acetamide | 9.13 (t, J = 5.19 Hz, 1H), 8.35 (d, J = 7.32 Hz, 1H), 8.03 (d, J = 11.29 Hz, 1H), 8.00 (d, J = 3.97 Hz, 1H), 7.74 (d, J = 7.93 Hz, 1H), 7.66-7.70 (m,1H), 7.61 (d, J = 5.80 Hz, 1H), 6.33 (s, 1H), 4.33 (d, J = 7.32 Hz, 2H), 4.06 (br. s., 2H), 3.72-3.88 (m, 2H), 3.53-3.67 (m, 1H), 2.61 (d, J = 3.66 Hz, 1H), 2.21-2.34 (m, 2H), 1.37 (d, J = 6.71 Hz, 2H), 1.26 (d, J = 6.71 Hz, 4H), 0.62 (d, J = 6.10 Hz, 2H), 0.38 (br. s., 2H) | 0.82 O 573.3 | 7 |
| 245 | 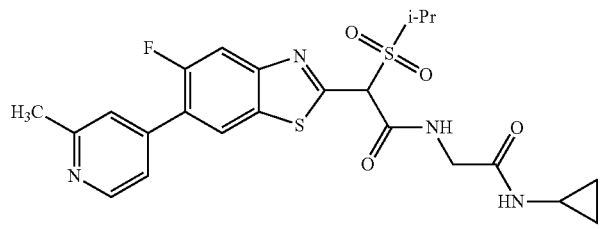 [SMILES: Cc1cc(-c2cc3sc(C(C(=O)NCC(=O)NC4CC4)S(=O)(=O)C(C)C)nc3cc2F)ccn1] | N-[(cyclopropylcarbamoyl)methyl]-2-[5-fluoro-6-(2-methylpyridin-4-yl)-1,3-benzothiazol-2-yl]-2-(propane-2-sulfonyl)acetamide | 9.15 (br. s., 1H), 8.75 (dd, J = 5.65, 11.75 Hz, 1H), 8.56 (d, J = 7.32 Hz, 1H), 8.14-8.21 (m, 1H), 7.94-8.03 (m, 1H), 7.83-7.91 (m, 1H), 6.38 (s, 1H), 3.76-3.90 (m, 2H), 3.49 (br. s., 1H), 2.67-2.73 (m, 3H), 2.63 (br. s., 1H), 1.38 (d, J = 6.71 Hz, 2H), 1.27 (d, J = 6.41 Hz, 4H), 0.62 (d, J = 6.41 Hz, 2H), 0.39 (br. s., 2H) | 0.62 O 505.3 | 12 |
| 246 | 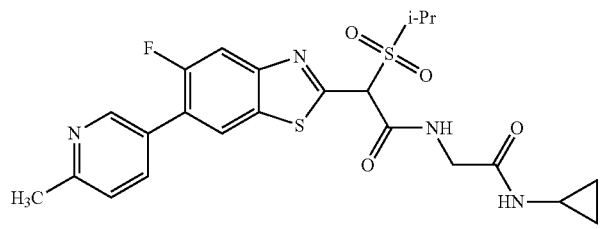 [SMILES: Cc1ccc(-c2cc3sc(C(C(=O)NCC(=O)NC4CC4)S(=O)(=O)C(C)C)nc3cc2F)cn1] | N-[(cyclopropylcarbamoyl)methyl]-2-[5-fluoro-6-(6-methylpyridin-3-yl)-1,3-benzothiazol-2-yl]-2-(propane-2-sulfonyl)acetamide | 9.13 (t, J = 4.88 Hz, 1H), 8.43 (d, J = 7.32 Hz,1H), 8.24 (d, J = 7.93 Hz, 1H), 8.11 (d, J = 10.99 Hz, 1H), 8.01-8.06 (m, 1H), 7.67 (d, J = 7.93 Hz, 1H), 6.36 (s, 1H), 3.72-3.89 (m, 2H), 2.63 (br. s., 4H), 1.37 (d, J = 6.41 Hz, 2H), 1.27 (d, J = 6.41 Hz, 5H), 0.62 (d, J = 6.41 Hz, 2H), 0.39 (br. s., 2H) | 0.62 O 505.3 | 12 |

-continued

| Ex. No. | Structure | Name | ¹H NMR δ (500 MHz, DMSO-d₆, unless otherwise indicated) | LC/MS RT (min) ethod M + H | EL IC$_{50}$ (nM) |
|---|---|---|---|---|---|
| 247 | 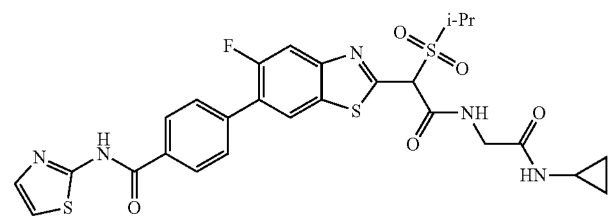 [SMILES: CC(C)S(=O)(=O)C(C(=O)NCC(=O)NC1CC1)c1nc2cc(F)c(-c3ccc(C(=O)Nc4nccs4)cc3)cc2s1] | 4-[2-({[(cyclopropyl-carbamoyl)methyl] carbamoyl} (propane-2-sulfonyl)methyl)-5-fluoro-1,3-benzothiazol-6-yl]-N-(1,3-thiazol-2-yl) benzamide | 9.13 (br. s., 1H), 8.45 (d, J = 7.02 Hz, 1H), 8.26-8.40 (m, 1H), 8.07-8.17 (m, 2H), 7.85-8.06 (m, 1H), 7.64-7.85 (m, 1H), 7.57 (br. s., 1H), 7.30 (br. s., 1H), 6.37 (s, 1H), 3.75-3.89 (m, 2H), 3.46 (br. s., 1H), 2.63 (br. s., 1H), 1.38 (d, J = 6.41 Hz, 2H), 1.28 (d, J = 6.41 Hz, 4H), 0.62 (d, J = 5.49 Hz, 2H), 0.39 (br. s., 2H) | 0.87 O 616.3 | 11 |
| 248 | 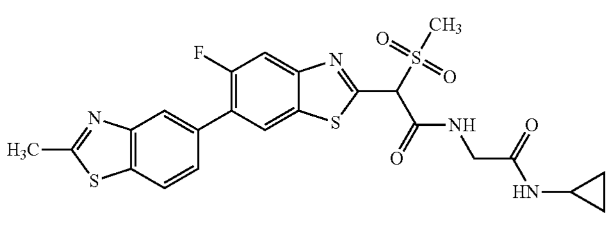 [SMILES: Cc1nc2cc(-c3cc4sc(C(C(=O)NCC(=O)NC5CC5)S(C)(=O)=O)nc4cc3F)ccc2s1] | N-[(cyclopropyl-carbamoyl) methyl]-2-[5-fluoro-6-(2-methyl-1,3-benzothiazol-5-yl)-1,3-benzothiazol-2-yl]-2-methanesulfonyl-acetamide | 8.45 (br. s., 1H), 7.90 (br. s., 1H), 7.83 (d, J = 5.78 Hz, 1H), 7.46 (br. s., 1H), 7.38 (br. s., 1H), 7.21 (d, J = 13.48 Hz, 1H), 3.75 (br. s., 1H), 3.25 (s, 3H), 3.15-3.21 (m, 3H), 2.62 (qt, J = 3.90, 7.36 Hz, 1H), 0.58-0.66 (m, 2H), 0.36-0.44 (m, 2H) | 0.82 O 533.3 | 1 |
| 249 | 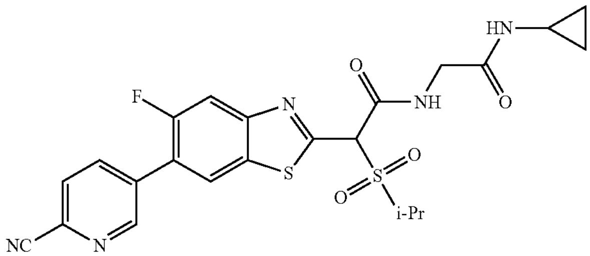 [SMILES: CC(C)S(=O)(=O)C(C(=O)NCC(=O)NC1CC1)c1nc2cc(F)c(-c3ccc(C#N)nc3)cc2s1] | 2-[6-(6-cyanopyridin-3-yl)-5-fluoro-1,3-benzothiazol-2-yl]-N-[(cyclopropyl-carbamoyl) methyl]-2-(propane-2-sulfonyl)acetamide | 9.08-9.14 (m, 1H), 8.45 (d, J = 7.32 Hz, 1H), 8.27 (d, J = 7.93 Hz, 1H), 8.12-8.20 (m, 1H), 8.05-8.09 (m, 1H), 7.87-7.99 (m, 1H), 6.33 (s, 1H), 3.77 (dd, J = 5.19, 15.56 Hz, 2H), 2.54-2.62 (m, 1H), 2.45 (br. s., 3H), 1.33 (d, J = 6.71 Hz, 2H), 1.22 (d, J = 6.71 Hz, 4H), 0.57 (d, J = 6.41 Hz, 2H), 0.34 (br. s., 2H) | 0.83 O 516.3 | 29 |
| 250 | 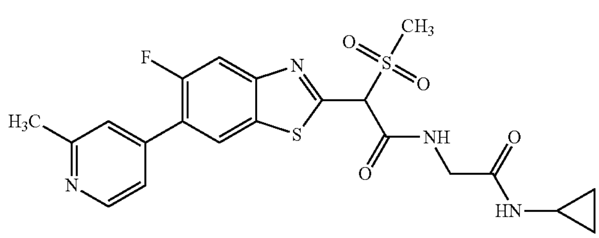 [SMILES: Cc1cc(-c2cc3sc(C(C(=O)NCC(=O)NC4CC4)S(C)(=O)=O)nc3cc2F)ccn1] | N-[(cyclopropyl-carbamoyl) methyl]-2-[5-fluoro-6-(2-methylpyridin-4-yl)-1,3-benzothiazol-2-yl]-2-methanesulfonyl-acetamide | 8.45 (br. s., 1H), 7.90 (br. s., 1H), 7.83 (d, J = 5.78 Hz, 1H), 7.46 (br. s., 1H), 7.38 (br. s., 1H), 7.21 (d, J = 13.48 Hz, 1H), 3.75 (br. s., 2H), 3.58 (s, 3H), 3.15-3.21 (m, 3H), 2.62 (qt, J = 3.90, 7.36 Hz, 1H), 0.58-0.66 (m, 2H), 0.36-0.44 (m, 2H) | 0.54 O 477.3 | 11 |

-continued

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 251 | 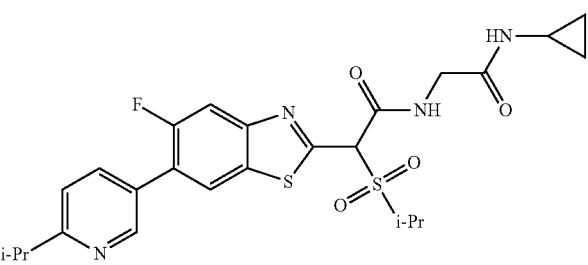 [SMILES: CC(C)c1ccc(-c2cc3sc(C(C(=O)NCC(=O)NC4CC4)S(=O)(=O)C(C)C)nc3cc2F)cn1] | N-[(cyclopropyl-carbamoyl)methyl]-2-{5-fluoro-6-[6-(propan-2-yl)pyridin-3-yl]-1,3-benzothiazol-2-yl}-2-(propane-2-sulfonyl)acetamide | 9.13 (br. s., 1H), 8.71-8.81 (m, 1H), 8.42 (d, J = 7.32 Hz, 1H), 8.14 (d, J = 8.24 Hz, 1H), 8.10 (d, J = 10.99 Hz, 1H), 7.59 (d, J = 7.93 Hz, 1H), 6.36 (s, 1H), 3.74-3.91 (m, 2H), 3.54 (br. s., 1H), 3.06-3.22 (m, 1H), 2.63 (br. s., 1H), 1.26-1.38 (m, 12H), 0.62 (d, J = 5.80 Hz, 2H), 0.39 (br. s., 2H) | 0.67 O 533.3 | 8 |
| 252 | 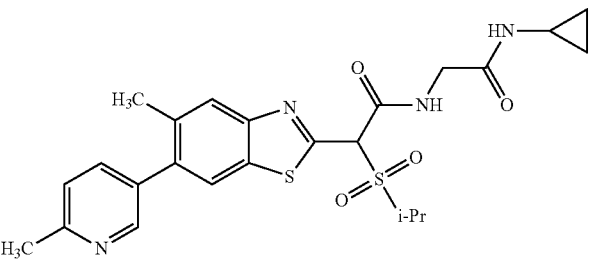 | N-[(cyclopropyl-carbamoyl)methyl]-2-[5-methyl-6-(6-methylpyridin-3-yl)-1,3-benzothiazol-2-yl]-2-(propane-2-sulfonyl)acetamide | 9.14 (t, J = 5.22 Hz, 1H), 8.71-8.78 (m, 1H), 8.29 (d, J = 6.73 Hz, 1H), 8.08 (d, J = 8.08 Hz, 1H), 7.96-8.05 (m, 1H), 7.79 (d, J = 6.73 Hz, 1H), 6.35 (s, 1H), 3.74-3.90 (m, 2H), 3.49-3.64 (m, 1H), 2.70 (s, 3H), 2.62 (d, J = 3.70 Hz, 1H), 2.25-2.40 (m, 3H), 1.37 (d, J = 6.73 Hz, 2H), 1.26 (d, J = 6.73 Hz, 4H), 0.62 (d, J = 5.72 Hz, 2H), 0.38 (d, J = 2.02 Hz, 2H) | 0.62 O 501.4 | 15 |
| 253 | 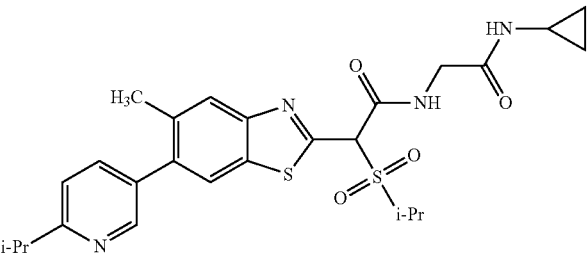 [SMILES: Cc1cc2nc(C(C(=O)NCC(=O)NC3CC3)S(=O)(=O)C(C)C)sc2cc1-c1ccc(C(C)C)nc1] | N-[(cyclopropyl-carbamoyl)methyl]-2-{5-methyl-6-[6-(propan-2-yl)pyridin-3-yl]-1,3-benzothiazol-2-yl}-2-(propane-2-sulfonyl)acetamide | 10.30 (t, J = 5.39 Hz, 1H), 9.83-9.91 (m, 1H), 9.38 (d, J = 7.74 Hz, 1H), 9.24 (d, J = 7.41 Hz, 1H), 9.13-9.21 (m, 1H), 8.91 (d, J = 8.08 Hz, 1H), 7.52 (s, 1H), 4.91-5.05 (m, 2H), 4.61-4.78 (m, 1H), 4.41 (td, J = 6.86, 13.55 Hz, 1H), 3.76-3.84 (m, 1H), 3.43-3.56 (m, 3H), 2.49-2.55 (m, 8H), 2.44 (br. s., 4H), 1.79 (d, J = 5.72 Hz, 2H), 1.55 (d, J = 2.36 Hz, 2H) | 0.69 O 529.3 | 7 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 254 | 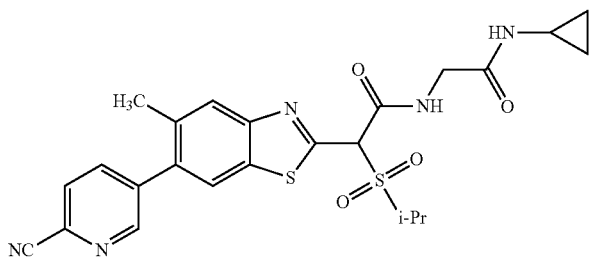 [SMILES: Cc1cc2nc(C(C(=O)NCC(=O)NC3CC3)S(=O)(=O)C(C)C)sc2cc1-c1ccc(C#N)nc1] | 2-[6-(6-cyanopyridin-3-yl)-5-methyl-1,3-benzothiazol-2-yl]-N-[(cyclopropyl-carbamoyl)methyl]-2-(propane-2-sulfonyl)acetamide | 9.24 (t, J = 5.39 Hz, 1H), 8.90-8.99 (m, 1H), 8.19-8.27 (m, 2H), 8.09-8.18 (m, 1H), 7.87-7.94 (m, 1H), 6.50 (s, 1H), 3.86-4.06 (m, 2H), 3.59-3.75 (m, 1H), 2.75 (td, J = 3.53, 7.07 Hz, 1H), 2.35-2.54 (m, 3H), 1.50 (d, J = 6.73 Hz, 2H), 1.32-1.44 (m, 4H), 0.75 (d, J = 5.72 Hz, 2H), 0.52 (d, J = 2.36 Hz, 2H) | 0.83 O 512.3 | 9 |
| 255 | 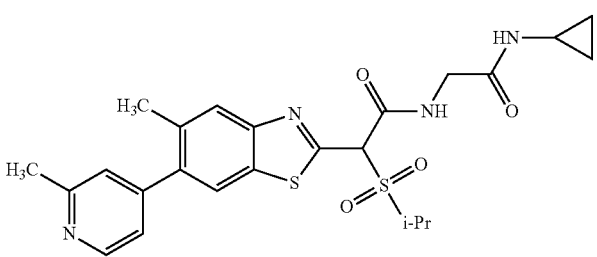 [SMILES: Cc1cc(-c2cc3sc(C(C(=O)NCC(=O)NC4CC4)S(=O)(=O)C(C)C)nc3cc2C)ccn1] | N-[(cyclopropyl-carbamoyl)methyl]-2-[5-methyl-6-(2-methylpyridin-4-yl)-1,3-benzothiazol-2-yl]-2-(propane-2-sulfonyl)acetamide | 9.14 (t, J = 5.39 Hz, 1H), 8.74-8.79 (m, 1H), 8.08-8.15 (m, 2H), 7.76-7.83 (m, 2H), 6.37 (s, 1H), 3.76-3.89 (m, 2H), 2.71 (s, 3H), 2.57-2.66 (m, 1H), 2.30-2.45 (m, 3H), 1.37 (d, J = 6.73 Hz, 2H), 1.23-1.29 (m, 4H), 1.07 (d, J = 6.73 Hz, 1H), 0.62 (d, J = 5.72 Hz, 2H), 0.39 (d, J = 2.02 Hz, 2H) | 2.39 A 501.3 | 5 |
| 256 | 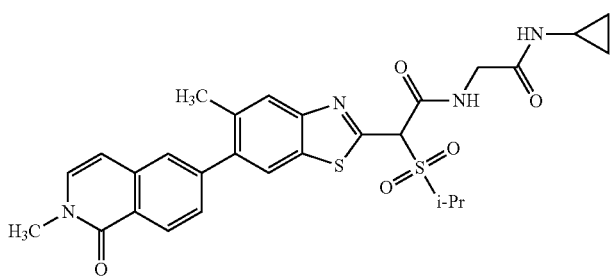 | N-[(cyclopropyl-carbamoyl)methyl]-2-[5-methyl-6-(2-methyl-1-oxo-1,2-dihydro-isoquinolin-6-yl)-1,3-benzothiazol-2-yl]-2-(propane-2-sulfonyl)acetamide | 9.12 (t, J = 5.39 Hz, 1H), 8.23-8.33 (m, 1H), 7.84-8.06 (m, 2H), 7.65-7.74 (m, 1H), 7.45-7.55 (m, 2H), 6.61-6.70 (m, 1H), 6.35 (s, 1H), 3.74-3.90 (m, 2H), 3.48-3.61 (m, 1H), 2.57-2.69 (m, 1H), 2.23-2.37 (m, 3H), 1.33-1.39 (m, 2H), 1.20-1.30 (m, 4H), 0.58-0.66 (m, 2H), 0.39 (d, J = 2.36 Hz, 2H) | 3.52 A 567.3 | 3 |
| 257 | 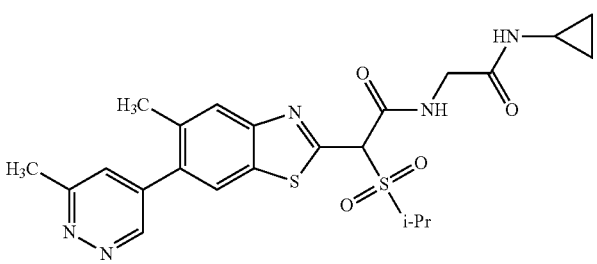 [SMILES: Cc1cc(-c2cc3sc(C(C(=O)NCC(=O)NC4CC4)S(=O)(=O)C(C)C)nc3cc2C)cnn1] | N-[(cyclopropyl-carbamoyl)methyl]-2-[5-methyl-6-(6-methylpyridazin-4-yl)-1,3-benzothiazol-2-yl]-2-(propane-2-sulfonyl)acetamide | 9.17-9.24 (m, 1H), 9.10 (t, J = 5.36 Hz, 1H), 8.09 (s, 1H), 8.01 (d, J = 3.85 Hz, 1H), 7.76-7.80 (m, 1H), 6.38 (s, 1H), 3.84-3.90 (m, 2H), 3.51-3.60 (m, 1H), 2.69-2.72 (m, 3H), 2.63 (dt, J = 3.85, 7.29 Hz, 1H), 2.29-2.44 (m, 3H), 1.37 (d, J = 6.88 Hz, 2H), 1.23-1.30 (m, 4H), 0.60-0.66 (m, 2H), 0.34-0.47 (m, 2H) | 2.6 A 502.3 | 11 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 258 | 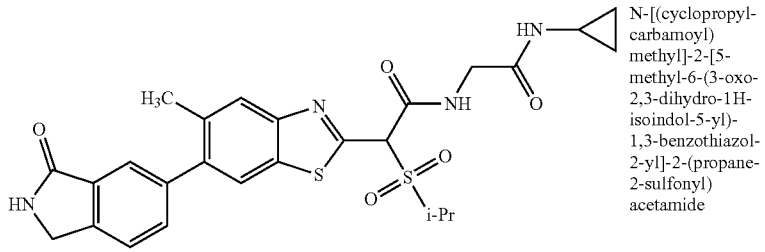 | N-[(cyclopropyl-carbamoyl)methyl]-2-[5-methyl-6-(3-oxo-2,3-dihydro-1H-isoindol-5-yl)-1,3-benzothiazol-2-yl]-2-(propane-2-sulfonyl)acetamide | 9.11 (t, J = 5.22 Hz, 1H), 8.65-8.68 (m, 1H), 7.93-8.01 (m, 1H), 7.65-7.70 (m, 1H), 7.55-7.65 (m, 2H), 6.34 (s, 1H), 4.41-4.49 (m, 2H), 3.74-3.91 (m, 2H), 3.46-3.60 (m, 1H), 2.62 (dd, J = 3.37, 7.07 Hz, 1H), 2.22-2.36 (m, 3H), 1.38 (d, J = 6.73 Hz, 2H), 1.21-1.28 (m, 4H), 0.62 (d, J = 5.39 Hz, 2H), 0.39 (d, J = 2.02 Hz, 2H) | 0.75 O 541.3 | 19 |
| 259 | 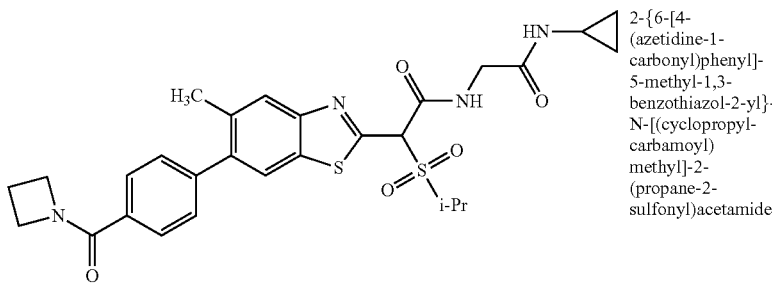 | 2-{6-[4-(azetidine-1-carbonyl)phenyl]-5-methyl-1,3-benzothiazol-2-yl}-N-[(cyclopropyl-carbamoyl)methyl]-2-(propane-2-sulfonyl)acetamide | 9.10 (t, J = 5.22 Hz, 1H), 8.02 (br. s., 2H), 7.67-7.73 (m, 2H), 7.41-7.50 (m, 2H), 6.36 (s, 1H), 4.36 (d, J = 6.73 Hz, 2H), 4.07 (br. s., 2H), 3.73-3.90 (m, 2H), 3.48-3.60 (m, 1H), 2.57-2.67 (m, 1H), 2.23-2.38 (m, 5H), 1.38 (d, J = 6.40 Hz, 2H), 1.24-1.29 (m, 4H), 0.62 (d, J = 5.72 Hz, 2H), 0.39 (d, J = 2.36 Hz, 2H) | 0.78 O 569.3 | 3 |
| 260 | 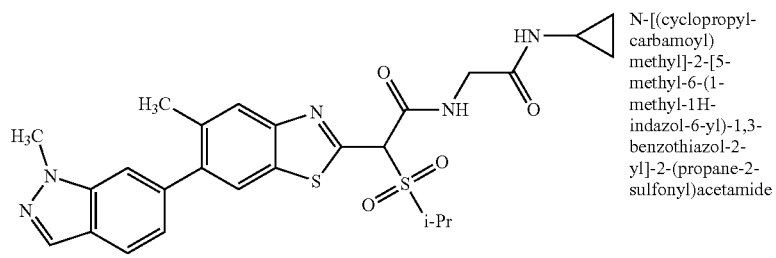 | N-[(cyclopropyl-carbamoyl)methyl]-2-[5-methyl-6-(1-methyl-1H-indazol-6-yl)-1,3-benzothiazol-2-yl]-2-(propane-2-sulfonyl)acetamide | 9.11 (t, J = 5.05 Hz, 1H), 8.07-8.12 (m, 1H), 8.04 (d, J = 6.06 Hz, 2H), 7.79-7.84 (m, 1H), 7.59-7.67 (m, 1H), 7.09-7.18 (m, 1H), 6.36 (s, 1H), 4.03-4.10 (m, 3H), 3.75-3.91 (m, 2H), 3.51-3.61 (m, 1H), 2.63 (d, J = 3.70 Hz, 1H), 2.25-2.39 (m, 3H), 1.38 (d, J = 6.73 Hz, 2H), 1.25-1.29 (m, 4H), 0.63 (d, J = 5.72 Hz, 2H), 0.39 (br. s., 2H) | 0.89 O 540.3 | 7 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 261 | 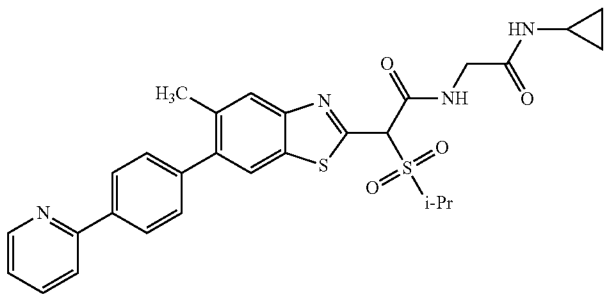 [SMILES: Cc1cc2nc(C(C(=O)NCC(=O)NC3CC3)S(=O)(=O)C(C)C)sc2cc1-c1ccc(-c2ccccn2)cc1] | N-[(cyclopropyl-carbamoyl)methyl]-2-{5-methyl-6-[4-(pyridin-2-yl)phenyl]-1,3-benzothiazol-2-yl}-2-(propane-2-sulfonyl)acetamide | 9.11 (t, J = 5.19 Hz, 1H), 8.70 (br. s., 1H), 8.12-8.18 (m, 2H), 8.06 (t, J = 7.02 Hz, 1H), 7.96-8.03 (m, 3H), 7.54 (d, J = 7.63 Hz, 1H), 7.49 (d, J = 7.93 Hz, 1H), 7.44 (br. s., 1H), 6.33 (s, 1H), 3.74-3.89 (m, 2H), 3.56 (br. s., 1H), 2.63 (br. s., 1H), 2.28-2.41 (m, 3H), 1.37 (d, J = 6.71 Hz, 2H), 1.26 (d, J = 6.41 Hz, 4H), 0.62 (d, J = 6.41 Hz, 2H), 0.39 (br. s., 2H) | 0.75 O 563.4 | 4 |
| 262 | 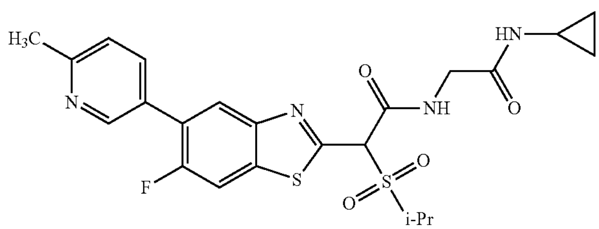 [SMILES: Cc1ccc(-c2cc3nc(C(C(=O)NCC(=O)NC4CC4)S(=O)(=O)C(C)C)sc3cc2F)cn1] | N-[(cyclopropyl-carbamoyl)methyl]-2-[6-fluoro-5-(6-methylpyridin-3-yl)-1,3-benzothiazol-2-yl]-2-(propane-2-sulfonyl)acetamide | 9.12 (br. s., 1H), 8.32 (dd, J = 7.48, 16.02 Hz, 2H), 8.23 (d, J = 10.07 Hz, 1H), 7.94 (s, 1H), 7.70 (d, J = 7.63 Hz, 1H), 6.34 (s, 1H), 3.73-3.88 (m, 2H), 3.58 (t, J = 6.71 Hz, 1H), 2.57-2.67 (m, 4H), 1.37 (d, J = 6.71 Hz, 2H), 1.27 (d, J = 6.71 Hz, 4H), 0.62 (d, J = 6.41 Hz, 2H), 0.39 (br. s., 2H) | 0.61 O 505.3 | 10 |
| 263 | 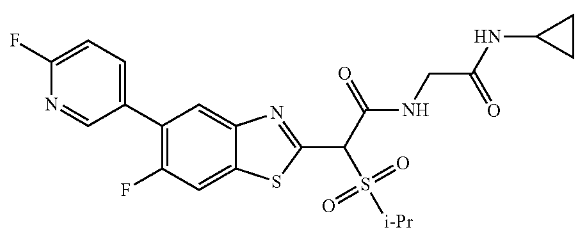 [SMILES: CC(C)S(=O)(=O)C(C(=O)NCC(=O)NC1CC1)c1nc2cc(-c3ccc(F)nc3)c(F)cc2s1] | N-[(cyclopropyl-carbamoyl)methyl]-2-[6-fluoro-5-(6-fluoropyridin-3-yl)-1,3-benzothiazol-2-yl]-2-(propane-2-sulfonyl)acetamide | 9.20 (br. s., 1H), 8.58 (br. s., 1H), 8.36 (t, J = 7.48 Hz, 1H), 8.29 (d, J = 10.07 Hz, 1H), 8.02 (br. s., 1H), 7.42 (d, J = 8.55 Hz, 1H), 6.42 (s, 1H), 3.83-3.96 (m, 2H), 3.66 (s, 1H), 2.70 (br. s., 1H), 1.45 (d, J = 6.41 Hz, 2H), 1.35 (d, J = 6.41 Hz, 4H), 0.70 (d, J = 6.71 Hz, 2H), 0.47 (br. s., 2H) | 0.85 O 509.7 | 13 |
| 264 | 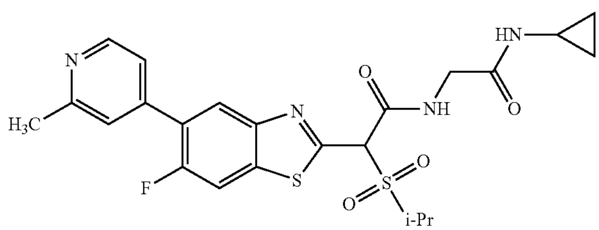 [SMILES: Cc1cc(-c2cc3nc(C(C(=O)NCC(=O)NC4CC4)S(=O)(=O)C(C)C)sc3cc2F)ccn1] | N-[(cyclopropyl-carbamoyl)methyl]-2-[6-fluoro-5-(2-methylpyridin-4-yl)-1,3-benzothiazol-2-yl]-2-(propane-2-sulfonyl)acetamide | 9.10-9.16 (m, 1H), 8.70-8.77 (m, 1H), 8.44 (d, J = 6.71 Hz, 1H), 8.28 (d, J = 10.68 Hz, 1H), 7.82-7.95 (m, 2H), 6.35 (s, 1H), 3.76-3.89 (m, 2H), 3.50-3.56 (m, 1H), 2.67-2.70 (m, 3H), 2.62 (d, J = 3.36 Hz, 1H), 1.37 (d, J = 6.71 Hz, 2H), 1.27 (d, J = 6.71 Hz, 4H), 0.62 (d, J = 6.71 Hz, 2H), 0.39 (br. s., 2H) | 0.61 O 505.3 | 7 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 265 | 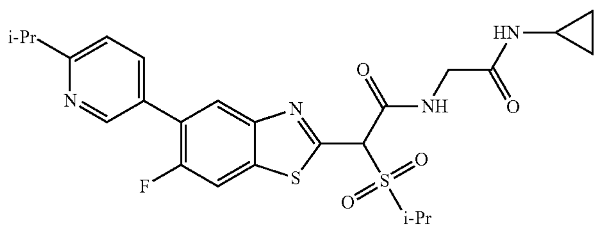 [SMILES: CC(C)c1ccc(-c2cc3nc(C(C(=O)NCC(=O)NC4CC4)S(=O)(=O)C(C)C)sc3cc2F)cn1] | N-[(cyclopropylcarbamoyl)methyl]-2-{6-fluoro-5-[6-(propan-2-yl)pyridin-3-yl]-1,3-benzothiazol-2-yl}-2-(propane-2-sulfonyl)acetamide | 9.13 (br. s., 1H), 8.85 (br. s., 1H), 8.32 (d, J = 6.41 Hz, 1H), 8.19-8.28 (m, 2H), 7.58-7.71 (m, 1H), 6.34 (s, 1H), 3.73-3.90 (m, 2H), 3.52 (br. s., 1H), 3.11-3.23 (m, 1H), 2.63 (br. s., 1H), 1.24-1.37 (m, 12H), 0.62 (d, J = 6.71 Hz, 2H), 0.39 (br. s., 2H) | 0.69 O 533.3 | 4 |
| 266 | 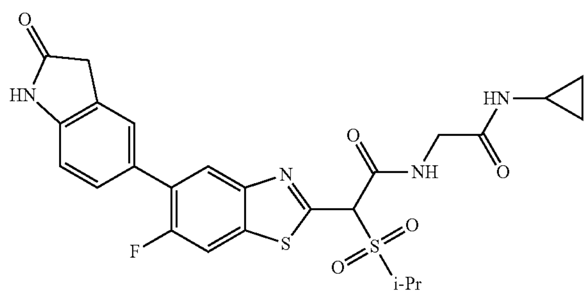 [SMILES: CC(C)S(=O)(=O)C(C(=O)NCC(=O)NC1CC1)c1nc2cc(-c3ccc4c(c3)CC(=O)N4)c(F)cc2s1] | N-[(cyclopropylcarbamoyl)methyl]-2-[6-fluoro-5-(2-oxo-2,3-dihydro-1H-indol-5-yl)-1,3-benzothiazol-2-yl]-2-(propane-2-sulfonyl)acetamide | 10.49 (s, 1H), 9.12 (br. s., 1H), 8.12 (d, J = 7.32 Hz, 1H), 8.01 (br. s., 1H), 7.30-7.36 (m, 1H), 7.17 (d, J = 7.63 Hz, 1H), 7.03 (s, 1H), 6.33 (s, 1H), 3.72-3.88 (m, 2H), 3.51-3.60 (m, 1H), 2.62 (br. s., 1H), 1.37 (d, J = 6.71 Hz, 2H), 1.19-1.29 (m, 4H), 0.62 (d, J = 6.41 Hz, 2H), 0.39 (br. s., 2H) | 0.76 O 545.2 | 38 |
| 267 | 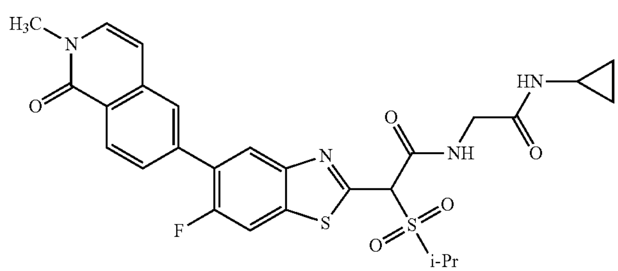 [SMILES: CC(C)S(=O)(=O)C(C(=O)NCC(=O)NC1CC1)c1nc2cc(-c3ccc4c(=O)n(C)ccc4c3)c(F)cc2s1] | N-[(cyclopropylcarbamoyl)methyl]-2-[6-fluoro-5-(2-methyl-1-oxo-1,2-dihydroisoquinolin-6-yl)-1,3-benzothiazol-2-yl]-2-(propane-2-sulfonyl)acetamide | 9.12 (br. s., 1H), 8.30 (dd, J = 7.32, 17.09 Hz, 2H), 8.21 (d, J = 10.07 Hz, 1H), 7.75 (d, J = 8.24 Hz, 1H), 7.51 (d, J = 7.02 Hz, 1H), 6.71 (d, J = 7.02 Hz, 1H), 6.35 (s, 1H), 3.81 (dd, J = 5.04, 16.94 Hz, 2H), 3.52 (br. s., 1H), 2.63 (br. s., 1H), 1.37 (d, J = 6.41 Hz, 2H), 1.27 (d, J = 6.10 Hz, 4H), 0.62 (d, J = 6.10 Hz, 2H), 0.39 (br. s., 2H) | 0.81 O 571.2 | 5 |
| 268 | 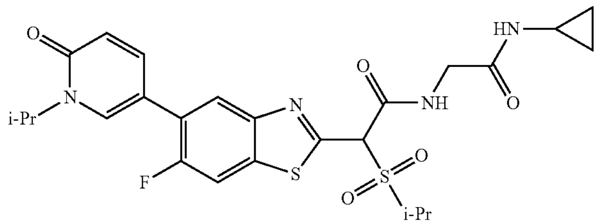 [SMILES: CC(C)n1cc(-c2cc3nc(C(C(=O)NCC(=O)NC4CC4)S(=O)(=O)C(C)C)sc3cc2F)ccc1=O] | N-[(cyclopropylcarbamoyl)methyl]-2-{6-fluoro-5-[6-oxo-1-(propan-2-yl)-1,6-dihydropyridin-3-yl]-1,3-benzothiazol-2-yl}-2-(propane-2-sulfonyl)acetamide | 9.11 (br. s., 1H), 8.21 (d, J = 6.71 Hz, 1H), 8.13 (d, J = 10.38 Hz, 1H), 7.99 (br. s., 1H), 7.69 (d, J = 8.85 Hz, 1H), 6.51 (d, J = 9.16 Hz, 1H), 6.32 (s, 1H), 5.02-5.14 (m, 1H), 3.73-3.89 (m, 2H), 3.46-3.63 (m, 1H), 2.62 (br. s., 1H), 1.24-1.39 (m, 12H), 0.62 (d, J = 6.10 Hz, 2H), 0.39 (br. s., 2H) | 0.77 O 549.7 | 11 |

| Ex. No. | Structure | Name | ¹H NMR δ (500 MHz, DMSO-d₆, unless otherwise indicated) | LC/MS RT (min) Method M + H | EL IC$_{50}$ (nM) |
|---|---|---|---|---|---|
| 269 | 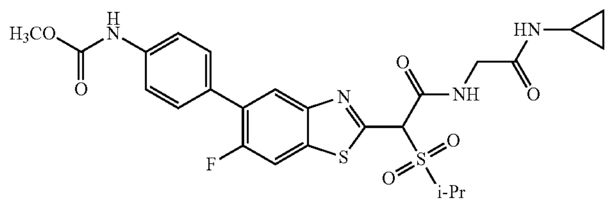 [SMILES: COC(=O)Nc1ccc(-c2cc3nc(C(C(=O)NCC(=O)NC4CC4)S(=O)(=O)C(C)C)sc3cc2F)cc1] | methyl N-{4-[2-({[(cyclopropyl-carbamoyl)methyl]carbamoyl}(propane-2-sulfonyl)methyl)-6-fluoro-1,3-benzothiazol-5-yl]phenyl}carbamate | 9.81 (br. s., 1H), 9.11 (br. s., 1H), 8.12 (d, J = 8.55 Hz, 2H), 7.53-7.60 (m, 4H), 6.32 (s, 1H), 3.74-3.88 (m, 2H), 3.65 (s, 3H), 3.44-3.50 (m, 2H), 2.62 (br. s., 1H), 1.36 (d, J = 6.41 Hz, 2H), 1.26 (d, J = 6.41 Hz, 4H), 0.62 (d, J = 6.71 Hz, 2H), 0.39 (br. s., 2H) | 0.84 O 563.3 | 6 |
| 270 | 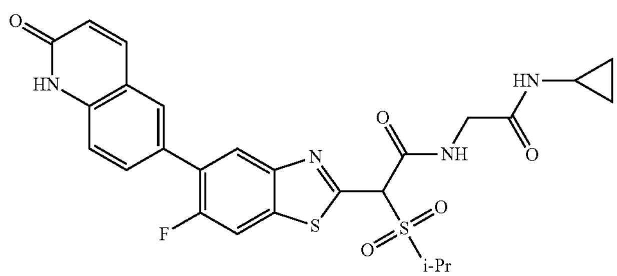 [SMILES: CC(C)S(=O)(=O)C(C(=O)NCC(=O)NC1CC1)c1nc2cc(-c3ccc4[nH]c(=O)ccc4c3)c(F)cc2s1] | N-[(cyclopropyl-carbamoyl)methyl]-2-[6-fluoro-5-(2-oxo-1,2-dihydroquinolin-6-yl)-1,3-benzothiazol-2-yl]-2-(propane-2-sulfonyl)acetamide | 11.89 (br. s., 1H), 9.12 (t, J = 4.88 Hz, 1H), 8.22 (d, J = 7.02 Hz, 1H), 8.17 (d, J = 10.38 Hz, 1H), 7.97 (d, J = 10.99 Hz, 2H), 7.78 (d, J = 8.55 Hz, 1H), 7.43 (d, J = 8.24 Hz, 1H), 6.56 (d, J = 9.46 Hz, 1H), 6.34 (s, 1H), 3.76-3.89 (m, 2H), 3.54-3.62 (m, 1H), 2.62 (br. s., 1H), 1.37 (d, J = 6.41 Hz, 2H), 1.27 (d, J = 6.41 Hz, 4H), 0.62 (d, J = 6.71 Hz, 2H), 0.39 (br. s., 2H) | 0.73 O 557.3 | 9 |
| 271 | 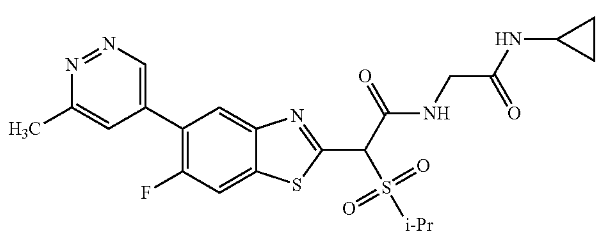 | N-[(cyclopropyl-carbamoyl)methyl]-2-[6-fluoro-5-(6-methylpyridazin-4-yl)-1,3-benzothiazol-2-yl]-2-(propane-2-sulfonyl)acetamide | 9.38 (br. s., 1H), 9.13 (br. s., 1H), 8.45 (d, J = 6.10 Hz, 1H), 8.27 (d, J = 10.38 Hz, 1H), 7.92 (br. s., 1H), 6.36 (s, 1H), 3.72-3.90 (m, 2H), 3.48-3.60 (m, 1H), 2.71 (s, 3H), 2.62 (br. s., 1H), 1.37 (d, J = 6.41 Hz, 2H), 1.27 (d, J = 6.41 Hz, 4H), 0.62 (d, J = 6.41 Hz, 2H), 0.39 (br. s., 2H) | 0.66 O 506.3 | 45 |
| 272 | 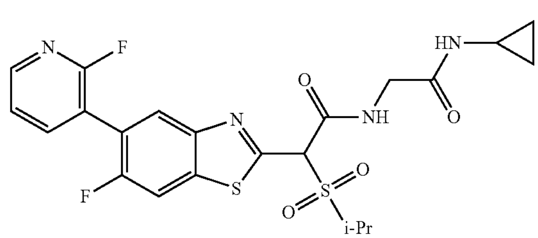 [SMILES: CC(C)S(=O)(=O)C(C(=O)NCC(=O)NC1CC1)c1nc2cc(-c3cccnc3F)c(F)cc2s1] | N-[(cyclopropyl-carbamoyl)methyl]-2-[6-fluoro-5-(2-fluoropyridin-3-yl)-1,3-benzothiazol-2-yl]-2-(propane-2-sulfonyl)acetamide | 9.12 (br. s., 1H), 8.34 (d, J = 3.66 Hz, 1H), 8.20-8.25 (m, 1H), 8.15 (t, J = 8.39 Hz, 1H), 7.92-8.03 (m, 1H), 7.53 (br. s., 1H), 6.34 (s, 1H), 3.75-3.90 (m, 2H), 3.47-3.55 (m, 1H), 2.62 (d, J = 3.36 Hz, 1H), 1.37 (d, J = 6.41 Hz, 2H), 1.27 (d, J = 6.41 Hz, 4H), 0.62 (d, J = 6.10 Hz, 2H), 0.39 (br. s., 2H) | 0.82 O 509.7 | 29 |

-continued

| Ex. No. | Structure | Name | $^1$H NMR δ (500 MHz, DMSO-$d_6$, unless otherwise indicated) | LC/MS RT (min) ethod M + H | EL IC$_{50}$ (nM) |
|---|---|---|---|---|---|
| 273 | 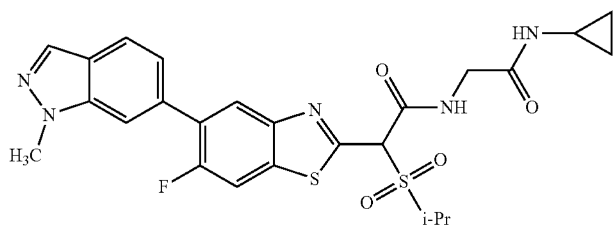 [SMILES: CC(C)S(=O)(=O)C(C(=O)NCC(=O)NC1CC1)c1nc2cc(-c3ccc4cnn(C)c4c3)c(F)cc2s1] | N-[(cyclopropyl-carbamoyl)methyl]-2-[6-fluoro-5-(1-methyl-1H-indazol-6-yl)-1,3-benzothiazol-2-yl]-2-(propane-2-sulfonyl)acetamide | 9.15 (t, J = 5.19 Hz, 1H), 8.23 (d, J = 6.71 Hz, 1H), 8.13 (d, J = 10.07 Hz, 1H), 8.09 (s, 1H), 7.99 (br. s., 1H), 7.83-7.86 (m, 1H), 7.35 (d, J = 8.24 Hz, 1H), 6.28 (s, 1H), 4.02-4.09 (m, 3H), 3.58 (td, J = 6.64, 13.58 Hz, 1H), 2.60 (br. s., 1H), 1.36 (d, J = 6.41 Hz, 3H), 1.26 (d, J = 6.71 Hz, 4H), 0.62 (d, J = 6.71 Hz, 2H), 0.38 (br. s., 2H) | 0.86 O 544.2 | 9 |
| 274 | 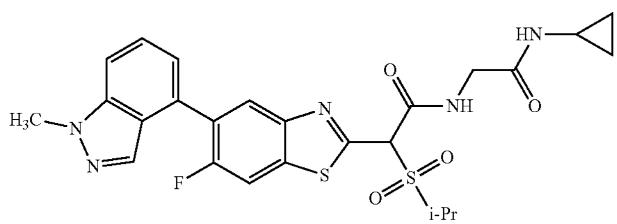 [SMILES: CC(C)S(=O)(=O)C(C(=O)NCC(=O)NC1CC1)c1nc2cc(-c3cccc4c3cnn4C)c(F)cc2s1] | N-[(cyclopropyl-carbamoyl)methyl]-2-[6-fluoro-5-(1-methyl-1H-indazol-4-yl)-1,3-benzothiazol-2-yl]-2-(propane-2-sulfonyl)acetamide | 9.15 (br. s., 1H), 8.18-8.23 (m, 1H), 7.97-8.03 (m, 1H), 7.84-7.93 (m, 1H), 7.66-7.74 (m, 1H), 7.49-7.56 (m, 1H), 7.23-7.30 (m, 1H), 6.30 (s, 1H), 4.07 (br. s., 3H), 3.76-3.84 (m, 1H), 2.61 (br. s., 1H), 1.37 (d, J = 6.41 Hz, 2H), 1.26 (d, J = 6.41 Hz, 4H), 0.62 (d, J = 6.41 Hz, 2H), 0.38 (br. s., 2H) | 0.82 O 544.2 | 3 |
| 275 | 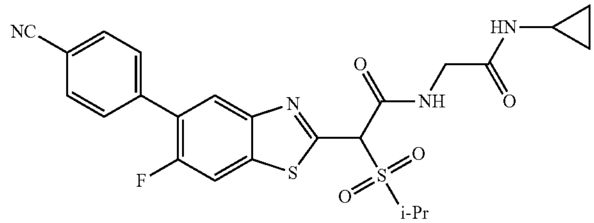 [SMILES: CC(C)S(=O)(=O)C(C(=O)NCC(=O)NC1CC1)c1nc2cc(-c3ccc(C#N)cc3)c(F)cc2s1] | 2-[5-(4-cyanophenyl)-6-fluoro-1,3-benzothiazol-2-yl]-N-[(cyclopropyl-carbamoyl)methyl]-2-(propane-2-sulfonyl)acetamide | 9.13 (br. s., 1H), 8.37 (d, J = 6.41 Hz, 1H), 8.33 (d, J = 7.93 Hz, 1H), 8.25 (d, J = 9.77 Hz, 1H), 8.16 (d, J = 7.32 Hz, 1H), 8.01 (br. s., 1H), 7.84-7.94 (m, 1H), 6.33 (s, 1H), 3.73-3.89 (m, 2H), 3.58 (s, 1H), 2.62 (br. s., 1H), 1.36 (d, J = 5.80 Hz, 2H), 1.26 (d, J = 5.80 Hz, 4H), 0.62 (d, J = 6.41 Hz, 2H), 0.38 (br. s., 2H) | 0.83 O 515.5 | 40 |
| 276 | 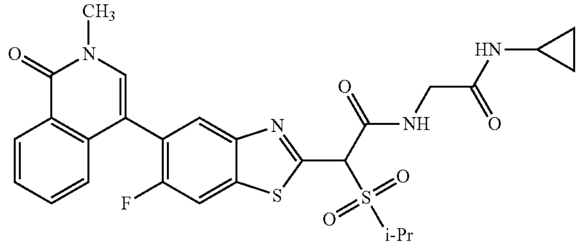 [SMILES: CC(C)S(=O)(=O)C(C(=O)NCC(=O)NC1CC1)c1nc2cc(-c3cn(C)c(=O)c4ccccc34)c(F)cc2s1] | N-[(cyclopropyl-carbamoyl)methyl]-2-[6-fluoro-5-(2-methyl-1-oxo-1,2-dihydro-isoquinolin-4-yl)-1,3-benzothiazol-2-yl]-2-(propane-2-sulfonyl)acetamide | 8.21 (d, J = 9.16 Hz, 1H), 8.15 (d, J = 6.10 Hz, 1H), 7.94 (s, 1H), 7.69 (t, J = 7.32 Hz, 1H), 7.62-7.67 (m, 2H), 7.57 (d, J = 7.02 Hz, 1H), 6.35 (s, 1H), 3.77-3.89 (m, 2H), 3.18 (s., 3H), 2.63 (br. s., 1H), 1.39 (d, J = 6.41 Hz, 2H), 1.29 (d, J = 6.10 Hz, 4H), 0.64 (d, J = 6.41 Hz, 2H), 0.40 (br. s., 2H) | 0.78 O 571.3 | 8 |

| Ex. No. | Structure | Name | $^1$H NMR δ (500 MHz, DMSO-$d_6$, unless otherwise indicated) | LC/MS RT (min) ethod M + H | EL IC$_{50}$ (nM) |
|---|---|---|---|---|---|
| 277 | 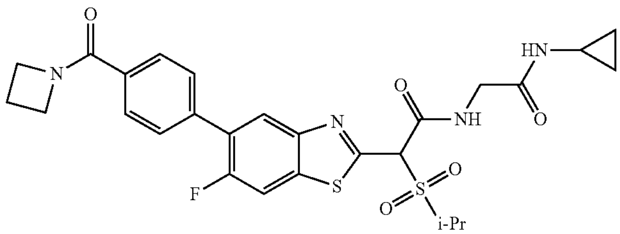 [SMILES: CC(C)S(=O)(=O)C(C(=O)NCC(=O)NC1CC1)c1nc2cc(-c3ccc(C(=O)N4CCC4)cc3)c(F)cc2s1] | 2-{5-[4-(azetidine-1-carbonyl)phenyl]-6-fluoro-1,3-benzothiazol-2-yl}-N-[(cyclopropyl-carbamoyl)methyl]-2-(propane-2-sulfonyl)acetamide | 9.14 (br. s., 1H), 8.16-8.23 (m, 1H), 8.04 (br. s., 1H), 7.73 (d, J = 10.10 Hz, 3H), 6.35 (s, 1H), 4.36 (br. s., 2H), 4.21 (br. s., 2H), 3.75-3.87 (m, 2H), 3.51-3.62 (m, 1H), 2.62 (br. s., 1H), 2.28 (br. s., 2H), 1.37 (d, J = 6.40 Hz, 2H), 1.27 (d, J = 6.06 Hz, 4H), 0.62 (d, J = 6.06 Hz, 2H), 0.39 (br. s., 2H) | 0.8 O 573.3 | 13 |
| 278 | 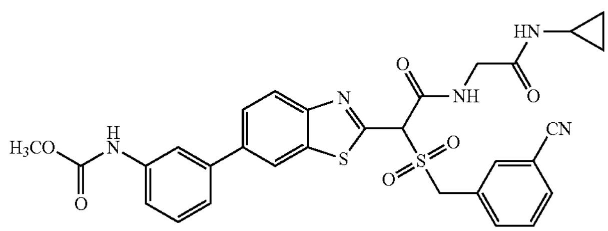 [SMILES: COC(=O)Nc1cccc(-c2ccc3nc(C(C(=O)NCC(=O)NC4CC4)S(=O)(=O)Cc4cccc(C#N)c4)sc3c2)c1] | methyl N-(3-{2-[(3-cyanophenyl)methanesulfonyl({[(cyclopropyl-carbamoyl)methyl]carbamoyl})methyl]-1,3-benzothiazol-6-yl}phenyl)carbamate | 9.09 (br. s., 1H), 8.03-8.23 (m, 1H), 7.96 (br. s., 1H), 7.74-7.89 (m, 3H), 7.51-7.65 (m, 3H), 7.28-7.46 (m, 3H), 6.25 (s, 1H), 4.83-4.95 (m, 1H), 4.78 (br. s., 1H), 3.51 (d, J = 8.08 Hz, 2H), 2.63 (br. s., 1H), 1.55 (d, J = 6.06 Hz, 3H), 0.62 (d, J = 5.39 Hz, 2H), 0.40 (d, J = 15.15 Hz, 2H) | 0.88 O 618.3 | 9 |
| 279 | 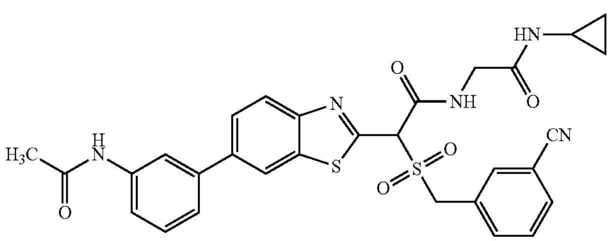 [SMILES: CC(=O)Nc1cccc(-c2ccc3nc(C(C(=O)NCC(=O)NC4CC4)S(=O)(=O)Cc4cccc(C#N)c4)sc3c2)c1] | 2-[(3-cyanophenyl)methanesulfonyl]-N-[(cyclopropyl-carbamoyl)methyl]-benzothiazol-2-yl]acetamide | 9.09 (br. s., 1H), 8.03-8.23 (m, 1H), 7.96 (br. s., 1H), 7.74-7.89 (m, 3H), 7.51-7.65 (m, 3H), 7.28-7.46 (m, 3H), 6.25 (s, 1H), 4.83-4.95 (m, 1H), 4.78 (br. s., 1H), 3.51 (d, J = 8.08 Hz, 2H), 2.63 (br. s., 1H), 2.07 (d, J = 6.06 Hz, 3H), 0.62 (d, J = 5.39 Hz, 2H), 0.40 (d, J = 15.15 Hz, 2H) | 0.8 O 602.6 | 89 |
| 280 | 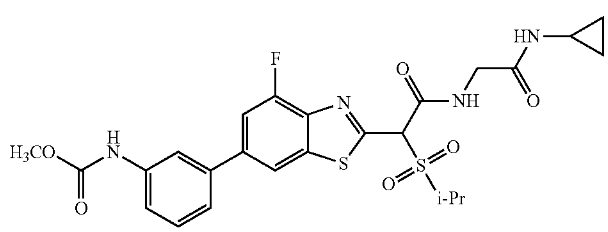 [SMILES: COC(=O)Nc1cccc(-c2cc(F)c3nc(C(C(=O)NCC(=O)NC4CC4)S(=O)(=O)C(C)C)sc3c2)c1] | methyl N-{3-[2-({[(cyclopropyl-carbamoyl)methyl]carbamoyl}(propane-2-sulfonyl)methyl)-4-fluoro-1,3-benzothiazol-6-yl]phenyl}carbamate | 9.76 (br. s., 1H), 9.12 (t, J = 5.49 Hz, 1H), 7.80 (br. s., 1H), 7.44-7.65 (m, 1H), 7.33-7.46 (m, 2H), 6.36 (s, 1H), 3.75-3.89 (m, 1H), 3.63-3.72 (m, 1H), 3.62 (br. s., 4H), 2.61 (dd, J = 3.66, 7.32 Hz, 1H), 1.37 (d, J = 6.71 Hz, 2H), 1.27 (d, J = 7.02 Hz, 2H), 1.06 (d, J = 6.71 Hz, 2H), 0.62 (d, J = 5.49 Hz, 2H), 0.37 (d, J = 6.41 Hz, 2H) | 0.85 U 563.5 | 6 |

-continued

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 281 | 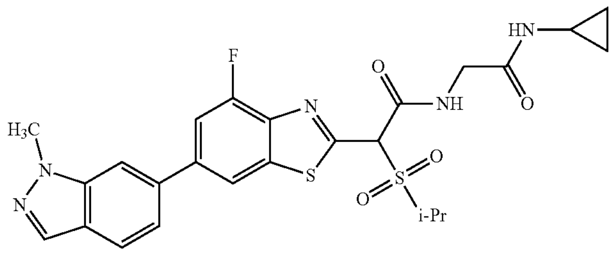 [SMILES: CC(C)S(=O)(=O)C(C(=O)NCC(=O)NC1CC1)c1nc2c(F)cc(-c3ccc4cnn(C)c4c3)cc2s1] | N-[(cyclopropyl-carbamoyl)methyl]-2-[4-fluoro-6-(1-methyl-1H-indazol-6-yl)-1,3-benzothiazol-2-yl]-2-(propane-2-sulfonyl)acetamide | 9.10-9.18 (m, 1H), 8.37-8.44 (m, 1H), 8.06 (d, J = 13.43 Hz, 2H), 7.83-7.90 (m, 2H), 7.56 (d, J = 8.24 Hz, 1H), 6.37 (s, 1H), 4.10 (s, 3H), 3.78-3.90 (m, 1H), 3.60-3.72 (m, 1H), 2.62 (d, J = 3.97 Hz, 1H), 1.38 (d, J = 6.71 Hz, 2H), 1.28 (d, J = 7.02 Hz, 2H), 1.06 (d, J = 6.71 Hz, 2H), 0.62 (d, J = 6.41 Hz, 2H), 0.38 (d, J = 3.97 Hz, 2H) | 0.86 U 544.5 | 9 |
| 282 | 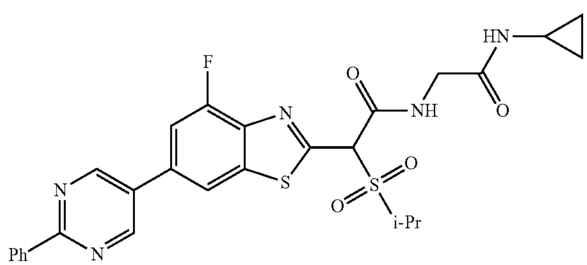 [SMILES: CC(C)S(=O)(=O)C(C(=O)NCC(=O)NC1CC1)c1nc2c(F)cc(-c3cnc(-c4ccccc4)nc3)cc2s1] | N-[(cyclopropyl-carbamoyl)methyl]-2-[4-fluoro-6-(2-phenylpyrimidin-5-yl)-1,3-benzothiazol-2-yl]-2-(propane-2-sulfonyl)acetamide | 9.14 (t, J = 5.34 Hz, 1H), 8.52 (s, 1H), 8.41-8.46 (m, 2H), 7.95-8.04 (m, 2H), 7.52-7.59 (m, 4H), 6.40 (s, 1H), 3.74-3.90 (m, 2H), 2.62 (td, J = 3.55, 7.25 Hz, 1H), 1.38 (d, J = 6.71 Hz, 3H), 1.28 (d, J = 7.02 Hz, 3H), 1.06 (d, J = 6.71 Hz, 1H), 0.62 (d, J = 5.49 Hz, 2H), 0.38 (br. s., 2H) | 0.98 U 568.5 | 22 |
| 283 | 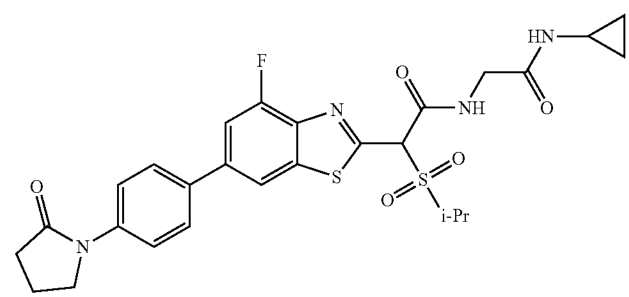 [SMILES: CC(C)S(=O)(=O)C(C(=O)NCC(=O)NC1CC1)c1nc2c(F)cc(-c3ccc(N4CCCC4=O)cc3)cc2s1] | N-[(cyclopropyl-carbamoyl)methyl]-2-{4-fluoro-6-[4-(2-oxopyrrolidin-1-yl)phenyl]-1,3-benzothiazol-2-yl}-2-(propane-2-sulfonyl)acetamide | 9.12 (t, J = 5.34 Hz, 1H), 8.31 (s, 1H), 7.75-7.81 (m, 4H), 7.73 (d, J = 12.51 Hz, 1H), 6.36 (s, 1H), 3.72-3.92 (m, 4H), 3.57 (br. s., 1H), 2.61 (td, J = 3.74, 7.17 Hz, 1H), 2.53 (br. s., 2H), 2.08 (quin, J = 7.48 Hz, 2H), 1.37 (d, J = 6.71 Hz, 3H), 1.27 (d, J = 6.71 Hz, 3H), 0.62 (d, J = 5.49 Hz, 2H), 0.38 (br. s., 2H) | 1.83 M 573.1 | 10 |
| 284 | 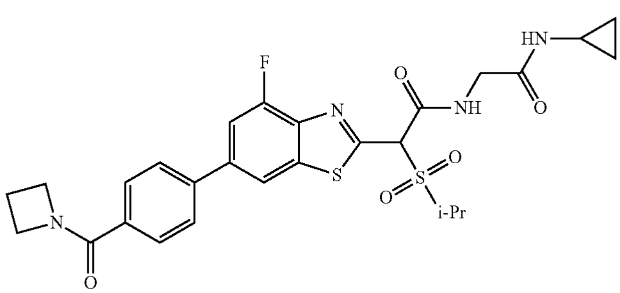 [SMILES: CC(C)S(=O)(=O)C(C(=O)NCC(=O)NC1CC1)c1nc2c(F)cc(-c3ccc(C(=O)N4CCC4)cc3)cc2s1] | 2-{6-[4-(azetidine-1-carbonyl)phenyl]-4-fluoro-1,3-benzothiazol-2-yl}-N-[(cyclopropyl-carbamoyl)methyl]-2-(propane-2-sulfonyl)acetamide | 8.29-8.36 (m, 1H), 7.88-7.94 (m, 1H), 7.86 (d, J = 8.24 Hz, 2H), 7.70-7.78 (m, 3H), 4.27-4.39 (m, 2H), 4.06 (t, J = 7.32 Hz, 2H), 3.62-3.90 (m, 2H), 2.56-2.64 (m, 1H), 2.27 (quin, J = 7.71 Hz, 2H), 1.22-1.40 (m, 1H), 1.07 (d, J = 6.71 Hz, 6H), 0.56-0.67 (m, 2H), 0.30-0.43 (m, 2H) | 0.79 U 573.1 | 12 |

-continued

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 285 | 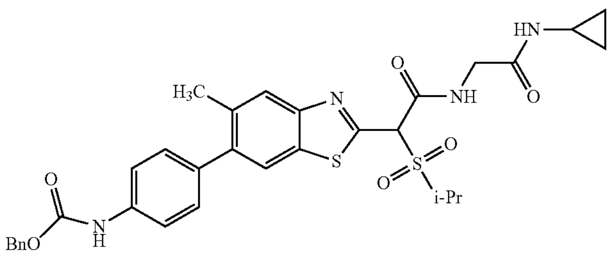 [SMILES: Cc1cc2nc(C(C(=O)NCC(=O)NC3CC3)S(=O)(=O)C(C)C)sc2cc1-c1ccc(NC(=O)OCc2ccccc2)cc1] | benzyl N-{4-[2-({[(cyclopropyl-carbamoyl)methyl] carbamoyl} (propane-2-sulfonyl)methyl)-5-methyl-1,3-benzothiazol-6-yl] phenyl}carbamate | 9.82-9.91 (m, 1H), 9.08 (t, J = 5.34 Hz, 1H), 7.89-7.95 (m, 2H), 7.50-7.58 (m, 2H), 7.37-7.46 (m, 4H), 7.29-7.37 (m, 3H), 6.31 (s, 1H), 5.17 (s, 2H), 3.71-3.90 (m, 2H), 3.53 (s, 1H), 2.57-2.66 (m, 2H), 2.34 (s, 3H), 1.36 (d, J = 6.71 Hz, 3H), 1.25 (d, J = 6.71 Hz, 3H), 0.58-0.67 (m, 2H), 0.39 (d, J = 2.14 Hz, 2H) | 0.99 U 635.4 | 12 |
| 286 | 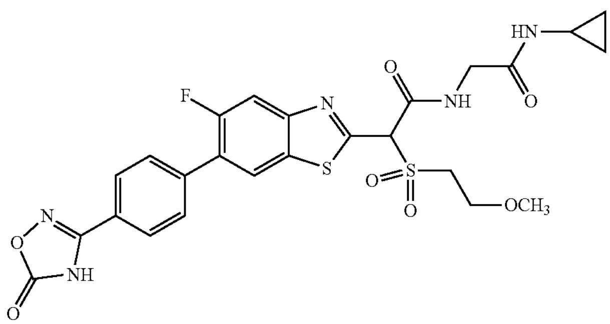 [SMILES: COCCS(=O)(=O)C(C(=O)NCC(=O)NC1CC1)c1nc2cc(F)c(-c3ccc(-c4noc(=O)[nH]4)cc3)cc2s1] | N-[(cyclopropyl-carbamoyl) methyl]-2-{5-fluoro-6-[4-(5-oxo-4,5-dihydro-1,2,4-oxadiazol-3-yl)phenyl]-1,3-benzothiazol-2-yl}-2-(2-methoxyethane-sulfonyl)acetamide | 9.05-8.96 (m, 1H), 8.42 (d, J = 7.6 Hz, 1H), 8.10 (d, J = 11.3 Hz, 1H), 8.02 (d, J = 3.7 Hz, 1H), 7.97-7.93 (m, 2H), 7.83 (m, 2H), 3.83-3.68 (m, 4H), 3.45 (s, 3H), 3.42-3.45 (m, 2H), 2.63 (m, 1H), 0.62 (m, 2H), 0.39 (m, 2H) | 1.10 N 590.1 | 8 |
| 288 | 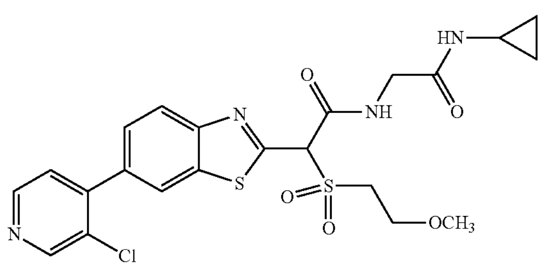 [SMILES: COCCS(=O)(=O)C(C(=O)NCC(=O)NC1CC1)c1nc2ccc(-c3ccncc3Cl)cc2s1] | 2-[6-(3-chloropyridin-4-yl)-1,3-benzothiazol-2-yl]-N-[(cyclopropyl-carbamoyl) methyl]-2-(2-methoxyethane-sulfonyl)acetamide | 9.02 (br. s., 1H), 8.79 (s, 1H), 8.64 (d, J = 4.6 Hz, 1H), 8.37 (s, 1H), 8.22 (d, J = 8.5 Hz, 1H), 8.04 (br. s., 1H), 7.71 (d, J = 8.5 Hz, 1H), 7.59 (d, J = 4.9 Hz, 1H), 6.24 (s, 1H), 3.87-3.70 (m, 6H), 3.28 (s, 3H), 2.64 (br. s., 1H), 0.63 (d, J = 5.8 Hz, 2H), 0.41 (br. s., 2H) | 1.32 S 523.2 | 15 |
| 289 | 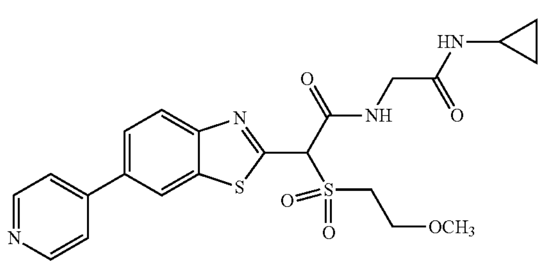 [SMILES: COCCS(=O)(=O)C(C(=O)NCC(=O)NC1CC1)c1nc2ccc(-c3ccncc3)cc2s1] | N-[(cyclopropyl-carbamoyl) methyl]-2-(2-methoxyethane-sulfonyl)-2-[6-(pyridin-4-yl)-1,3-benzothiazol-2-yl] acetamide | 9.02 (br. s., 1H), 8.76-8.56 (m, 3H), 8.22 (d, J = 8.9 Hz, 1H), 8.09-7.93 (m, 2H), 7.82 (br. s., 2H), 6.22 (br. s., 1H), 3.90-3.69 (m, 6H), 3.28 (br. s., 3H), 2.64 (d, J = 3.7 Hz, 1H), 0.64 (d, J = 4.9 Hz, 2H), 0.40 (br. s., 2H) | 1.11 S 489.3 | 23 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 290 | 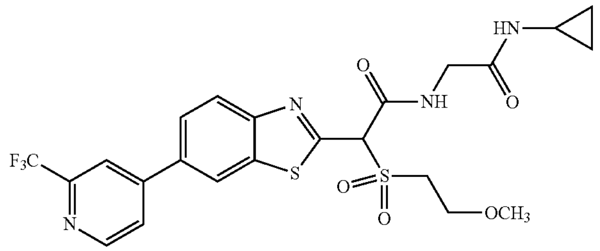 [SMILES: COCCS(=O)(=O)C(C(=O)NCC(=O)NC1CC1)c1nc2ccc(-c3ccnc(C(F)(F)F)c3)cc2s1] | N-[(cyclopropyl-carbamoyl)methyl]-2-(2-methoxyethane-sulfonyl)-2-{6-[2-(trifluoromethyl)pyridin-4-yl]-1,3-benzothiazol-2-yl}acetamide | 8.98 (t, J = 5.4 Hz, 1H), 8.87 (d, J = 5.1 Hz, 1H), 8.80 (br. s., 1H), 8.30 (s, 1H), 8.24 (d, J = 8.6 Hz, 1H), 8.15 (d, J = 4.6 Hz, 1H), 8.11 (d, J = 8.6 Hz, 1H), 7.98 (d, J = 3.7 Hz, 1H), 6.23 (s, 1H), 3.86-3.71 (m, 6H), 3.28 (s, 3H), 2.65 (td, J = 7.1, 3.6 Hz, 1H), 0.64 (dd, J = 7.1, 1.4 Hz, 2H), 0.41 (d, J = 2.0 Hz, 2H) | 1.6 S 557.1 | 23 |
| 291 | 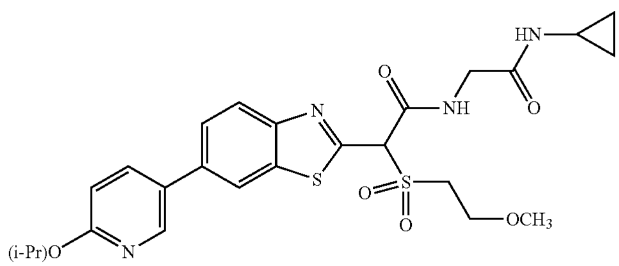 | N-[(cyclopropyl-carbamoyl)methyl]-2-(2-methoxyethane-sulfonyl)-2-{6-[6-(propan-2-yloxy)pyridin-3-yl]-1,3-benzothiazol-2-yl}acetamide | 9.01 (br. s., 1H), 8.57 (br. s., 1H), 8.47 (br. s., 1H), 8.20-7.96 (m, 3H), 7.86 (d, J = 8.5 Hz, 1H), 6.88 (d, J = 7.9 Hz, 1H), 6.19 (br. s., 1H), 5.31 (d, J = 6.1 Hz, 1H), 3.87-3.58 (m, 6H), 3.27 (s, 3H), 2.64 (br. s., 1H), 1.33 (d, J = 6.1 Hz, 6H), 0.63 (br. s., 2H), 0.40 (br. s., 2H) | 2.03 S 547.3 | 29 |
| 292 | 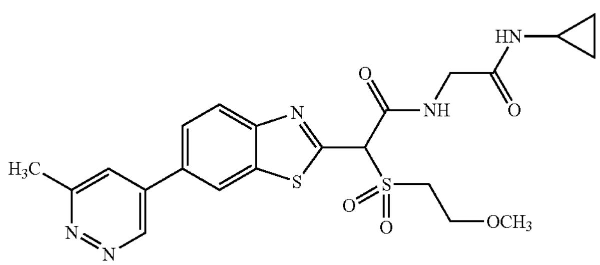 [SMILES: COCCS(=O)(=O)C(C(=O)NCC(=O)NC1CC1)c1nc2ccc(-c3cnnc(C)c3)cc2s1] | N-[(cyclopropyl-carbamoyl)methyl]-2-(2-methoxyethane-sulfonyl)-2-[6-(6-methylpyridazin-4-yl)-1,3-benzothiazol-2-yl]acetamide | 9.57 (br. s., 1H), 9.03 (br. s., 1H), 8.79 (s, 1H), 8.26 (d, J = 8.5 Hz, 1H), 8.11 (d, J = 8.2 Hz, 1H), 8.07-7.99 (m, 2H), 6.24 (s, 1H), 3.88-3.61 (m, 6H), 3.28 (s, 3H), 2.72 (s, 3H), 2.65 (br. s., 1H), 0.63 (d, J = 6.7 Hz, 2H), 0.41 (br. s., 2H) | 1.81 T 504.3 | 31 |
| 293 | 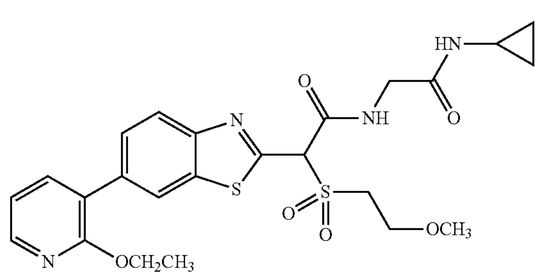 [SMILES: CCOc1ncccc1-c1ccc2nc(C(C(=O)NCC(=O)NC3CC3)S(=O)(=O)CCOC)sc2c1] | N-[(cyclopropyl-carbamoyl)methyl]-2-[6-(2-ethoxypyridin-3-yl)-1,3-benzothiazol-2-yl]-2-(2-methoxyethane-sulfonyl)acetamide | 9.01 (br. s., 1H), 8.35 (s, 1H), 8.20 (br. s., 1H), 8.13 (d, J = 8.5 Hz, 1H), 7.84 J = 6.7 Hz, 1H), 7.77 (d, J = 8.5 Hz, 1H), 7.13 (t, J = 6.0 Hz, 1H), 6.21 (s, 1H), 4.45-4.33 (m, 2H), 3.88-3.59 (m, 6H), 3.29 (s, 3H), 2.64 (br. s., 1H), 1.31 (t, J = 6.9 Hz, 3H), 0.63 (br. s., 2H), 0.41 (br. s., 2H) | 1.79 S 533.3 | 33 |

-continued

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 294 | 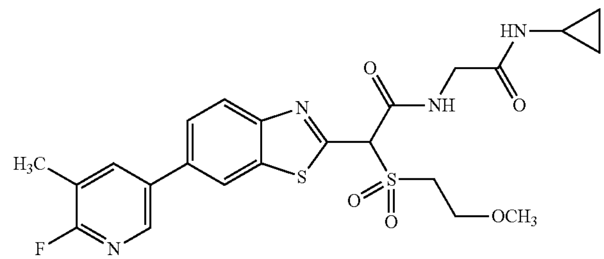 [SMILES: COCCS(=O)(=O)C(C(=O)NCC(=O)NC1CC1)c1nc2ccc(-c3cnc(F)c(C)c3)cc2s1] | N-[(cyclopropyl-carbamoyl)methyl]-2-[6-(6-fluoro-5-methylpyridin-3-yl)-1,3-benzothiazol-2-yl]-2-(2-methoxyethane-sulfonyl)acetamide | 9.02 (br. s., 1H), 8.54 (s, 1H), 8.45 (br. s., 1H), 8.28 (d, J = 9.2 Hz, 1H), 8.19 (d, J = 8.5 Hz, 1H), 8.03 (br. s., 1H), 7.92 (d, J = 8.5 Hz, 1H), 6.21 (s, 1H), 3.86-3.69 (m, 6H), 3.28 (s, 3H), 2.64 (d, J = 3.7 Hz, 1H), 2.35 (s, 3H), 0.63 (d, J = 5.5 Hz, 2H), 0.40 (br. s., 2H) | 1.49 S 521.3 | 36 |
| 295 | 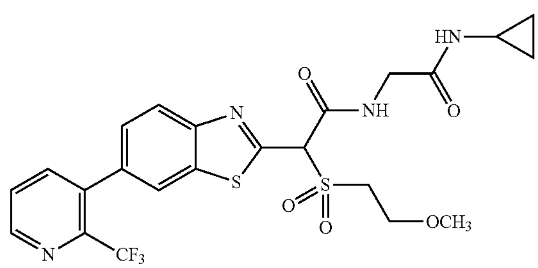 [SMILES: COCCS(=O)(=O)C(C(=O)NCC(=O)NC1CC1)c1nc2ccc(-c3cccnc3C(F)(F)F)cc2s1] | N-[(cyclopropyl-carbamoyl)methyl]-2-(2-methoxyethane-sulfonyl)-2-{6-[2-(trifluoromethyl)pyridin-3-yl]-1,3-benzothiazol-2-yl}acetamide | 9.02-8.96 (m, 1H), 8.94 (s, 1H), 8.40 (d, J = 8.1 Hz, 1H), 8.34 (d, J = 8.6 Hz, 1H), 8.26-8.20 (m, 2H), 7.98 (d, J = 3.3 Hz, 1H), 7.90 (d, J = 7.7 Hz, 1H), 6.23 (s, 1H), 3.88-3.70 (m, 6H), 3.28 (s, 3H), 2.65 (td, J = 7.1, 3.7 Hz, 1H), 0.64 (d, J = 5.9 Hz, 2H), 0.41 (br. s., 2H) | 1.88 S 556.1 | 37 |
| 296 | 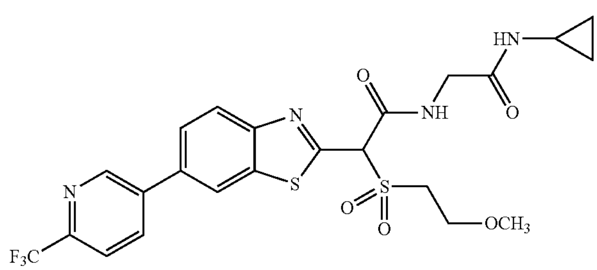 [SMILES: COCCS(=O)(=O)C(C(=O)NCC(=O)NC1CC1)c1nc2ccc(-c3ccc(C(F)(F)F)nc3)cc2s1] | N-[(cyclopropyl-carbamoyl)methyl]-2-(2-methoxyethane-sulfonyl)-2-{6-[6-(trifluoromethyl)pyridin-3-yl]-1,3-benzothiazol-2-yl}acetamide | 9.19 (s, 1H), 8.98 (t, J = 5.3 Hz, 1H), 8.67 (s, 1H), 8.47 (d, J = 8.3 Hz, 1H), 8.24 (d, J = 8.6 Hz, 1H), 8.07-7.97 (m, 3H), 6.23 (s, 1H), 3.86-3.70 (m, 7H), 3.28 (s, 3H), 2.65 (td, J = 7.2, 3.6 Hz, 1H), 0.67-0.60 (m, 2H), 0.41 (d, J = 2.0 Hz, 2H) | 1.85 S 557.2 | 69 |
| 297 | 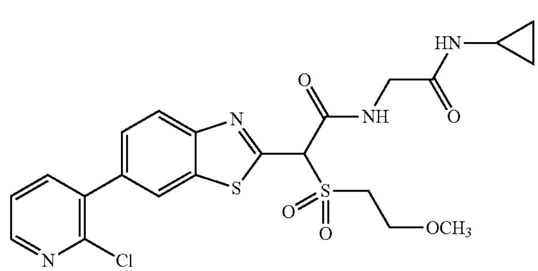 [SMILES: COCCS(=O)(=O)C(C(=O)NCC(=O)NC1CC1)c1nc2ccc(-c3cccnc3Cl)cc2s1] | 2-[6-(2-chloropyridin-3-yl)-1,3-benzothiazol-2-yl]-N-2-(2-methoxyethane-sulfonyl)acetamide | 8.39 (br. s., 1H), 7.91 (br. s., 1H), 7.87 (br. s., 1H), 7.73 (br. s., 1H), 7.50 (br. s., 1H), 7.44 (br. s., 1H), 7.28 (br. s., 1H), 3.80-3.56 (m, 6H), 3.18 (br. s., 3H), 2.64 (br. s., 1H), 0.62 (br. s., 2H), 0.41 (br. s., 2H) | 1.32 S 523.2 | 85 |

| Ex. No. | Structure | Name | $^1$H NMR δ (500 MHz, DMSO-$d_6$, unless otherwise indicated) | LC/MS RT (min) Method | EL $IC_{50}$ (nM) M + H |
|---|---|---|---|---|---|
| 298 | 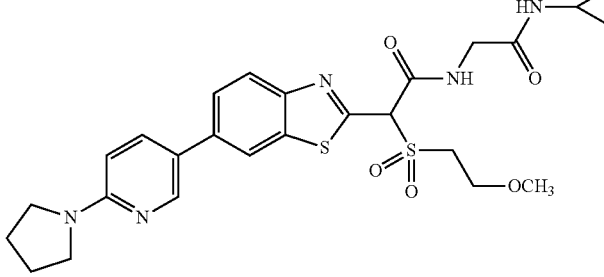 | N-[(cyclopropylcarbamoyl)methyl]-2-(2-methoxyethanesulfonyl)-2-{6-[6-(pyaolidin-1-yl)pyridin-3-yl]-1,3-benzothiazol-2-yl}acetamide | 9.00 (br. s., 1H), 8.52 (br. s., 1H), 8.39 (br. s., 1H), 8.10 (d, J = 8.2 Hz, 1H), 8.03 (br. s., 1H), 7.92 (d, J = 8.9 Hz, 1H), 7.81 (d, J = 8.2 Hz, 1H), 6.57 (d, J = 8.5 Hz, 1H), 6.18 (s, 1H), 3.86-3.68 (m, 6H), 3.48-3.40 (m, 4H), 3.28 (s, 3H), 2.64 (br. s., 1H), 1.97 (br. s., 4H), 0.63 (br. s., 2H), 0.40 (br. s., 2H) | 1.59 S | 118 557.2 |
| 299 | 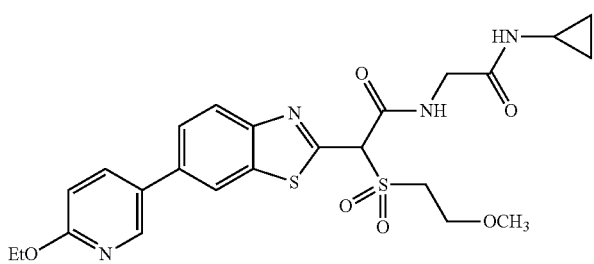 [SMILES: CCOc1ccc(-c2ccc3nc(C(C(=O)NCC(=O)NC4CC4)S(=O)(=O)CCOC)sc3c2)cn1] | N-[(cyclopropylcarbamoyl)methyl]-2-[6-(6-ethoxypyridin-3-yl)-1,3-benzothiazol-2-yl]-2-(2-methoxyethanesulfonyl)acetamide | 9.01 (br. s., 1H), 8.57 (br. s., 1H), 8.48 (s, 1H), 8.15 (d, J = 8.5 Hz, 1H), 8.11 (d, J = 8.9 Hz, 1H), 8.03 (br. s., 1H), 7.87 (d, J = 8.5 Hz, 1H), 6.93 (d, J = 8.2 Hz, 1H), 6.20 (s, 1H), 4.45-4.26 (m, 2H), 3.88-3.68 (m, 6H), 3.28 (s, 3H), 2.64 (br. s., 1H), 1.45-1.23 (m, 3H), 0.63 (d, J = 6.1 Hz, 2H), 0.41 (br. s., 2H) | 1.74 S | 118 533.2 |
| 300 | 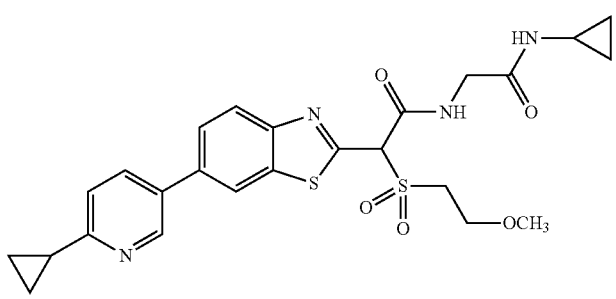 [SMILES: COCCS(=O)(=O)C(C(=O)NCC(=O)NC1CC1)c1nc2ccc(-c3ccc(C4CC4)nc3)cc2s1] | N-[(cyclopropylcarbamoyl)methyl]-2-[6-(6-cyclopropylpyridin-3-yl)-1,3-benzothiazol-2-yl]-2-(2-methoxyethanesulfonyl)acetamide | 9.01 (br. s., 1H), 8.81 (br. s., 1H), 8.51 (s, 1H), 8.17 (d, J = 8.5 Hz, 1H), 8.03 (d, J = 4.6 Hz, 2H), 7.89 (d, J = 8.5 Hz, 1H), 7.43 (d, J = 7.9 Hz, 1H), 6.20 (s, 1H), 3.87-3.67 (m, 6H), 3.28 (s, 3H), 2.64 (br. s., 1H), 2.17 (br. s., 1H), 1.06-0.91 (m, 4H), 0.63 (d, J = 6.1 Hz, 2H), 0.41 (br. s., 2H) | 1.72 S | 125 529.3 |
| 301 | 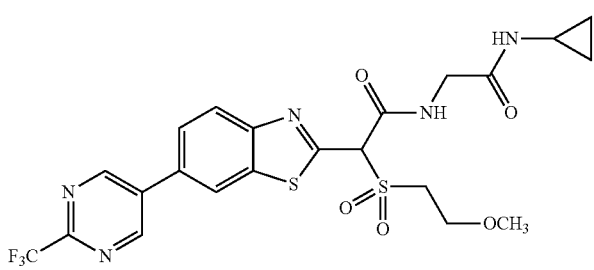 | N-[(cyclopropylcarbamoyl)methyl]-2-(2-methoxyethanesulfonyl)-2-{6-[2-(trifluoromethyl)pyrimidin-5-yl]-1,3-benzothiazol-2-yl}acetamide | 9.49 (s, 2H), 8.99 (t, J = 5.4 Hz, 1H), 8.75 (s, 1H), 8.28 (d, J = 8.4 Hz, 1H), 8.09 (d, J = 8.6 Hz, 1H), 7.98 (d, J = 3.7 Hz, 1H), 6.23 (s, 1H), 3.87-3.70 (m, 6H), 3.28 (s, 3H), 2.64 (td, J = 7.2, 3.6 Hz, 1H), 0.67-0.59 (m, 2H), 0.41 (d, J = 2.0 Hz, 2H) | 1.71 S | 155 558.3 |

-continued

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 302 | 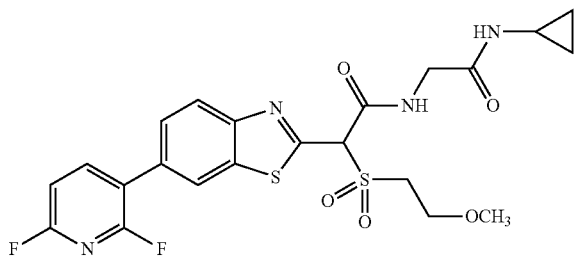 [SMILES: COCCS(=O)(=O)C(C(=O)NCC(=O)NC1CC1)c1nc2ccc(-c3ccc(F)nc3F)cc2s1] | N-[(cyclopropylcarbamoyl)methyl]-2-[6-(2,6-difluoropyridin-3-yl)-1,3-benzothiazol-2-yl]-2-(2-methoxyethanesulfonyl)acetamide | 9.02 (br. s., 1H), 8.49-8.38 (m, 1H), 8.36-8.15 (m, 1H), 8.09-7.72 (m, 2H), 7.42-7.22 (m, 1H), 7.10 (br. s., 1H), 6.22 (br. s., 1H), 3.88-3.58 (m, 6H), 3.28 (br. s., 3H), 2.64 (br. s., 1H), 0.63 (br. s., 2H), 0.41 (br. s., 2H) | 1.51 S 525.3 | 160 |
| 303 | 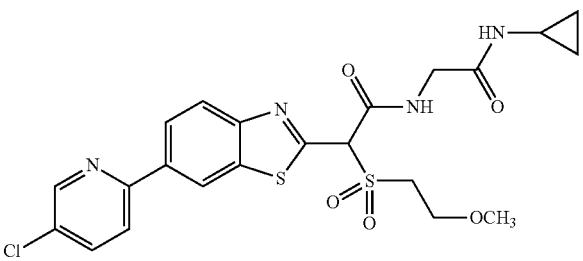 [SMILES: COCCS(=O)(=O)C(C(=O)NCC(=O)NC1CC1)c1nc2ccc(-c3ccc(Cl)cn3)cc2s1] | 2-[6-(5-chloropyridin-2-yl)-1,3-benzothiazol-2-yl]-N-[(cyclopropylcarbamoyl)methyl]-2-(2-methoxyethanesulfonyl)acetamide | 9.05-8.87 (m, 1H), 8.79-8.62 (m, 1H), 8.43-8.41 (m, 1H), 8.41-7.88 (m, 5H), 6.22 (s, 1H), 3.86-3.64 (m, 6H), 3.34 (br. s., 3H), 2.64 (br. s., 1H), 0.63 (br. s., 2H), 0.41 (br. s., 2H) | 1.84 S 523.2 | 247 |
| 304 | 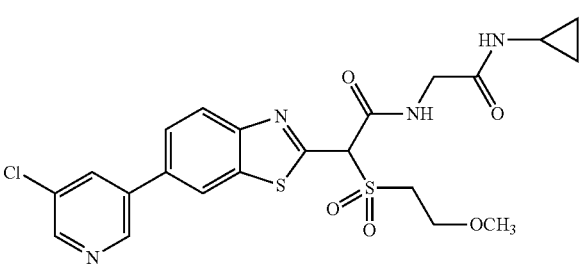 [SMILES: COCCS(=O)(=O)C(C(=O)NCC(=O)NC1CC1)c1nc2ccc(-c3cncc(Cl)c3)cc2s1] | 2-[6-(5-chloropyridin-3-yl)-1,3-benzothiazol-2-yl]-N-(cyclopropylcarbamoyl)methyl]-2-(2-methoxyethanesulfonyl)acetamide | 9.05-9.01 (m, 1H), 8.98 (d, J = 1.8 Hz, 1H), 8.67 (d, J = 2.2 Hz, 1H), 8.64 (s, 1H), 8.37 (d, J = 1.8 Hz, 1H), 8.21 (d, J = 8.6 Hz, 1H), 8.03 (d, J = 3.7 Hz, 1H), 8.00 (dd, J = 8.6, 1.7 Hz, 1H), 6.22 (s, 1H), 3.85-3.71 (m, 6H), 3.28 (s, 3H), 2.64 (td, J = 7.2, 3.6 Hz, 1H), 0.67-0.60 (m, 2H), 0.41 (dd, J = 4.1, 2.7 Hz, 2H) | 1.67 S 523.2 | 52 |
| 305 | 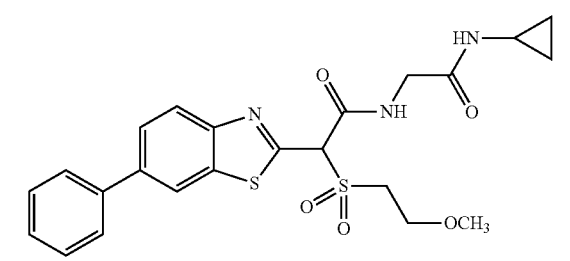 [SMILES: COCCS(=O)(=O)C(C(=O)NCC(=O)NC1CC1)c1nc2ccc(-c3ccccc3)cc2s1] | N-[(cyclopropylcarbamoyl)methyl]-2-(2-methoxyethanesulfonyl)-2-(6-phenyl-1,3-benzothiazol-2-yl)acetamide | 9.03 (t, J = 5.2 Hz, 1H), 8.50 (s, 1H), 8.17 (d, J = 8.5 Hz, 1H), 8.06 (d, J = 2.8 Hz, 1H), 7.89 (d, J = 8.8 Hz, 1H), 7.79 (d, J = 7.4 Hz, 2H), 7.53 (t, J = 7.4 Hz, 2H), 7.46-7.41 (m, 1H), 6.21 (s, 1H), 3.86-3.82 (m, 2H), 3.81-3.76 (m, 2H), 3.74 (d, J = 5.0 Hz, 2H), 3.29 (s, 3H), 2.68-2.62 (m, 1H), 0.64 (d, J = 6.6 Hz, 2H), 0.44-0.39 (m, 2H) | 1.69 O 488.2 | 7 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 306 | 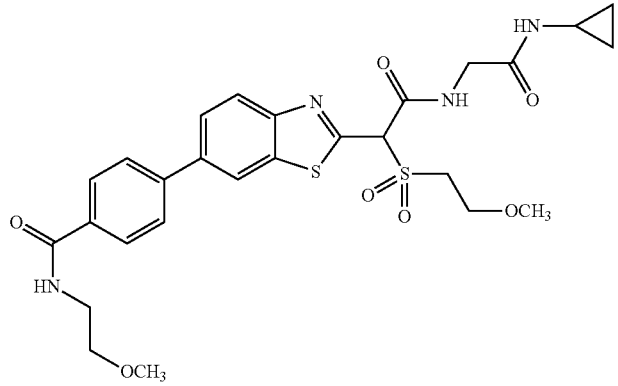 [SMILES: COCCNC(=O)c1ccc(-c2ccc3nc(C(C(=O)NCC(=O)NC4CC4)S(=O)(=O)CCOC)sc3c2)cc1] | 4-[2-({[(cyclopropyl-carbamoyl)methyl]carbamoyl}(2-methoxyethane-sulfonyl)methyl)-1,3-benzothiazol-6-yl]-N-(2-methoxyethyl)benzamide | (400 MHz, DMSO-$d_6$) 9.00 (t, J = 5.4 Hz, 1H), 8.63-8.59 (m, 1H), 8.57 (d, J = 1.5 Hz, 1H), 8.18 (d, J = 8.4 Hz, 1H), 8.00 (d, J = 8.6 Hz, 2H), 7.94 (dd, J = 8.6, 1.8 Hz, 1H), 7.88 (d, J = 8.6 Hz, 2H), 6.21 (s, 1H), 3.86-3.81 (m, 2H), 3.80-3.76 (m, 2H), 3.75-3.71 (m, 2H), 3.52-3.44 (m, 4H), 3.30 (s, 3H), 3.28 (s, 3H), 2.70-2.61 (m, 1H), 0.69-0.60 (m, 2H), 0.46-0.38 (m, 2H) | 1.29 O 589.2 | 13 |
| 307 | 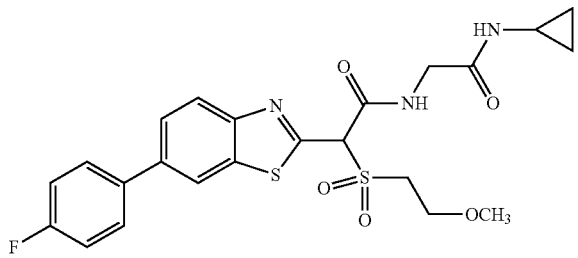 [SMILES: COCCS(=O)(=O)C(C(=O)NCC(=O)NC1CC1)c1nc2ccc(-c3ccc(F)cc3)cc2s1] | N-[(cyclopropyl-carbamoyl)methyl]-2-[6-(4-fluorophenyl)-1,3-benzothiazol-2-yl]-2-(2-methoxyethane-sulfonyl)acetamide | 9.03 (t, J = 5.4 Hz, 1H), 8.48 (s, 1H), 8.16 (d, J = 8.5 Hz, 1H), 8.06 (d, J = 3.3 Hz, 1H), 7.87 (d, J = 8.5 Hz, 1H), 7.83 (dd, J = 7.8, 5.6 Hz, 2H), 7.36 (t, J = 8.7 Hz, 2H), 6.21 (s, 1H), 3.86-3.82 (m, 2H), 3.81-3.76 (m, 2H), 3.74 (d, J = 5.0 Hz, 2H), 3.29 (s, 3H), 2.65 (td, J = 7.0, 3.6 Hz, 1H), 0.64 (d, J = 6.9 Hz, 2H), 0.44-0.37 (m, 2H) | 1.72 O 506.2 | 15 |
| 308 | 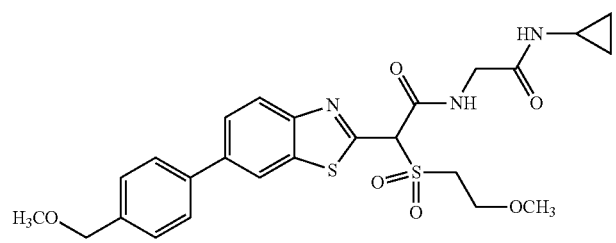 [SMILES: COCCS(=O)(=O)C(C(=O)NCC(=O)NC1CC1)c1nc2ccc(-c3ccc(COC)cc3)cc2s1] | N-[(cyclopropyl-carbamoyl)methyl]-2-(2-methoxyethane-sulfonyl)-2-{6-[4-(methoxymethyl)phenyl]-1,3-benzothiazol-2-yl}acetamide | 9.03 (br. s., 1H), 8.50 (s, 1H), 8.16 (d, J = 8.5 Hz, 1H), 8.06 (br. s., 1H), 7.89 (d, J = 8.5 Hz, 1H), 7.78 (d, J = 7.7 Hz, 2H), 7.47 (d, J = 7.7 Hz, 2H), 6.21 (s, 1H), 4.49 (s, 2H), 3.84 (d, J = 6.3 Hz, 2H), 3.78 (d, J = 5.5 Hz, 2H), 3.74 (d, J = 5.5 Hz, 2H), 3.34 (s, 3H), 3.29 (s, 3H), 2.65 (br. s., 1H), 0.64 (d, J = 6.6 Hz, 2H), 0.41 (br. s., 2H) | 1.62 O 532.2 | 27 |

| Ex. No. | Structure | Name | $^1$H NMR δ (500 MHz, DMSO-$d_6$, unless otherwise indicated) | LC/MS RT (min) EL ethod M + H | IC$_{50}$ (nM) |
|---|---|---|---|---|---|
| 309 | 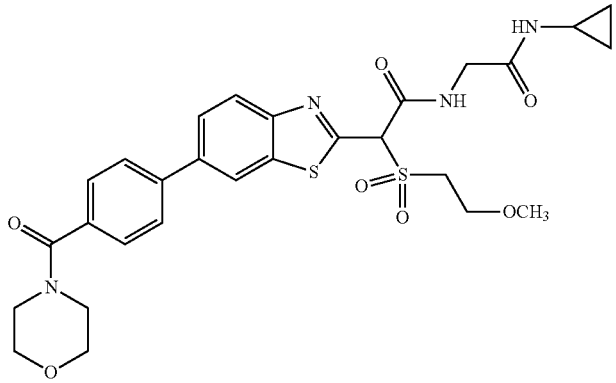 [SMILES: COCCS(=O)(=O)C(C(=O)NCC(=O)NC1CC1)c1nc2ccc(-c3ccc(C(=O)N4CCOCC4)cc3)cc2s1] | N-[(cyclopropylcarbamoyl)methyl]-2-(2-methoxyethanesulfonyl)-2-{6-[4-(morpholine-4-arbonyl)phenyl]-1,3-benzothiazol-2-yl}acetamide | 9.07-9.00 (m, 1H), 8.55 (s, 1H), 8.19 (d, J = 8.5 Hz, 1H), 8.06 (br. s., 1H), 7.92 (d, J = 8.5 Hz, 1H), 7.86 (d, J = 7.7 Hz, 2H), 7.57 (d, J = 7.4 Hz, 2H), 6.22 (s, 1H), 3.87-3.82 (m, 2H), 3.81-3.76 (m, 2H), 3.74 (d, J = 6.1 Hz, 2H), 3.66 (m, 8H), 3.29 (s, 3H), 0.66-0.62 (m, 2H), 0.44-0.39 (m, 2H) | 1.3 N 601.2 | 50 |
| 310 | 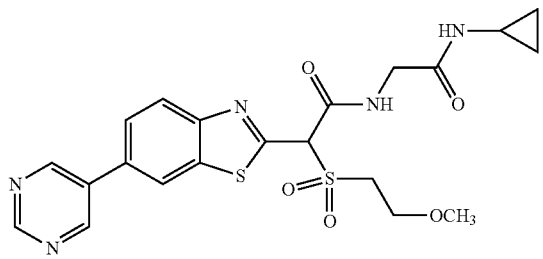 [SMILES: COCCS(=O)(=O)C(C(=O)NCC(=O)NC1CC1)c1nc2ccc(-c3cncnc3)cc2s1] | N-[(cyclopropylcarbamoyl)methyl]-2-(2-methoxyethanesulfonyl)-2-[6-(pyrimidin-5-yl)-1,3-benzothiazol-2-yl]acetamide | (400 MHz, DMSO-$d_6$) 9.28-9.22 (m, 3H), 9.01 (t, J = 5.4 Hz, 1H), 8.67 (d, J = 1.5 Hz, 1H), 8.24 (d, J = 8.6 Hz, 1H), 8.06-7.99 (m, 2H), 6.23 (s, 1H), 3.83 (t, J = 5.0 Hz, 2H), 3.80-3.75 (m, 2H), 3.75-3.70 (m, 2H), 3.28 (s, 3H), 2.73-2.61 (m, 1H), 0.68-0.60 (m, 2H), 0.44-0.38 (m, 2H) | 1.56 B 490.1 | 93 |
| 311 | 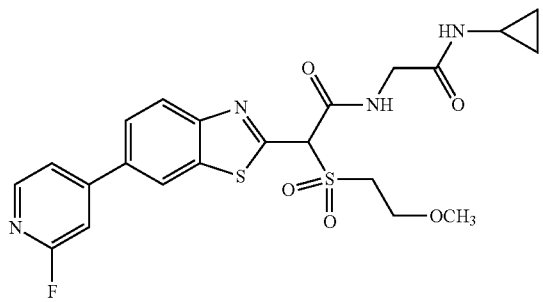 [SMILES: COCCS(=O)(=O)C(C(=O)NCC(=O)NC1CC1)c1nc2ccc(-c3ccnc(F)c3)cc2s1] | N-[(cyclopropylcarbamoyl)methyl]-2-[6-(2-fluoropyridin-4-yl)-1,3-benzothiazol-2-yl]-2-(2-methoxyethanesulfonyl)acetamide | (400 MHz, DMSO-$d_6$) 9.01 (t, J = 5.5 Hz, 1H), 8.74 (d, J = 1.3 Hz, 1H), 8.37 (d, J = 5.3 Hz, 1H), 8.23 (d, J = 8.6 Hz, 1H), 8.06 (dd, J = 8.6, 2.0 Hz, 1H), 8.03 (d, J = 3.7 Hz, 1H), 7.82 (dt, J = 5.3, 1.7 Hz, 1H), 7.65 (s, 1H), 6.24 (s, 1H), 3.87-3.82 (m, 2H), 3.77 (dd, J = 4.5, 3.2 Hz, 2H), 3.74-3.70 (m, 2H), 3.28 (s, 3H), 2.64 (td, J = 7.3, 3.7 Hz, 1H), 0.67-0.60 (m, 2H), 0.43-0.37 (m, 2H) | 1.66 B 507.1 | 94 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 312 | 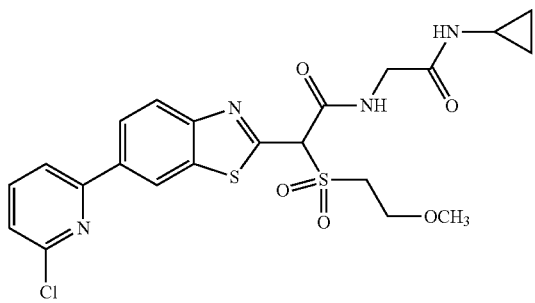 [SMILES: COCCS(=O)(=O)C(C(=O)NCC(=O)NC1CC1)c1nc2ccc(-c3cccc(Cl)n3)cc2s1] | 2-[6-(6-chloropyridin-2-yl)-1,3-benzothiazol-2-yl]-N-[(cyclopropyl-carbamoyl)methyl]-2-(2-methoxyethane-sulfonyl)acetamide | 9.05 (br. s., 1H), 8.91 (br. s., 1H), 8.32-8.26 (m, 1H), 8.21 (d, J = 8.5 Hz, 1H), 8.14 (d, J = 8.0 Hz, 1H), 8.06 (br. s., 1H), 8.04-8.00 (m, 1H), 7.54 (d, J = 7.7 Hz, 1H), 6.24 (s, 1H), 3.87-3.82 (m, 2H), 3.81-3.77 (m, 2H), 3.76-3.73 (m, 2H), 3.28 (s, 3H), 2.65 (d, J = 3.3 Hz, 1H), 0.67-0.62 (m, 2H), 0.44-0.38 (m, 2H) | 1.65 O 523.1 | 188 |
| 313 | 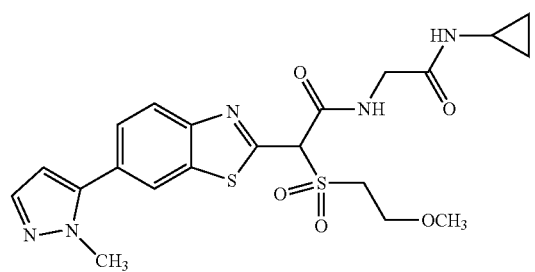 [SMILES: COCCS(=O)(=O)C(C(=O)NCC(=O)NC1CC1)c1nc2ccc(-c3ccnn3C)cc2s1] | N-[(cyclopropyl-carbamoyl)methyl]-2-(2-methoxyethane-sulfonyl)-2-[6-(1-methyl-1H-pyrazol-5-yl)-1,3-benzothiazol-2-yl]acetamide | 9.04 (br. s., 1H), 8.39 (br. s., 1H), 8.20 (d, J = 8.5 Hz, 1H), 8.06 (br. s., 1H), 7.73 (d, J = 8.0 Hz, 1H), 7.53 (br. s., 1H), 6.52 (s, 1H), 6.23 (s, 1H), 3.92 (s, 3H), 3.86-3.81 (m, 2H), 3.81-3.77 (m, 2H), 3.76-3.70 (m, 2H), 3.29 (s, 3H), 2.68-2.62 (m, 1H), 0.67-0.61 (m, 2H), 0.44-0.38 (m, 2H) | 1.23 N 492.2 | 313 |
| 314 | 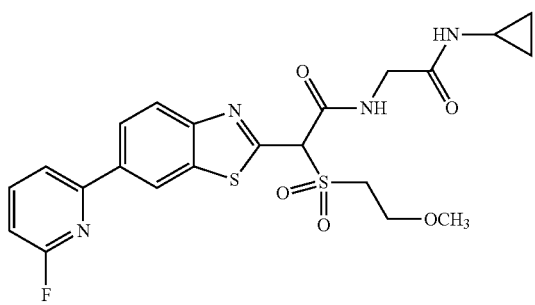 [SMILES: COCCS(=O)(=O)C(C(=O)NCC(=O)NC1CC1)c1nc2ccc(-c3cccc(F)n3)cc2s1] | N-[(cyclopropyl-carbamoyl)methyl]-2-[6-(6-fluoropyridin-2-yl)-1,3-benzothiazol-2-yl]-2-(2-methoxyethane-sulfonyl)acetamide | 9.07-9.01 (m, 1H), 8.92 (br. s., 1H), 8.29 (d, J = 8.5 Hz, 1H), 8.21 (d, J = 8.3 Hz, 1H), 8.15 (d, J = 7.2 Hz, 1H), 8.11-8.04 (m, 2H), 7.21 (d, J = 7.7 Hz, 1H), 6.23 (s, 1H), 3.87-3.82 (m, 2H), 3.81-3.77 (m, 2H), 3.76-3.73 (m, 2H), 3.28 (s, 3H), 2.68-2.61 (m, 1H), 0.64 (d, J = 6.1 Hz, 2H), 0.44-0.38 (m, 2H) | 1.53 N 507.2 | 150 |
| 315 | 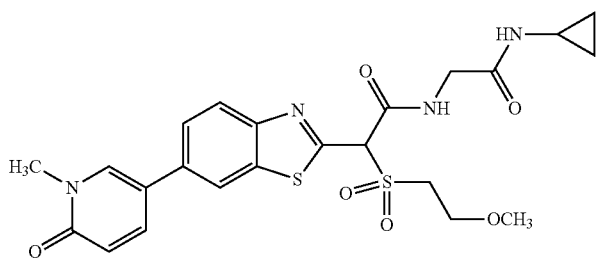 [SMILES: COCCS(=O)(=O)C(C(=O)NCC(=O)NC1CC1)c1nc2ccc(-c3ccc(=O)n(C)c3)cc2s1] | N-[(cyclopropyl-carbamoyl)methyl]-2-(2-methoxyethane-sulfonyl)-2-[6-(1-methyl-6-oxo-1,6-dihydropyridin-3-yl)-1,3-benzothiazol-2-yl]acetamide | 9.04 (t, J = 5.4 Hz, 1H), 8.38 (s, 1H), 8.13 (d, J = 8.5 Hz, 1H), 8.06 (d, J = 3.6 Hz, 1H), 7.99-7.92 (m, 2H), 7.80 (d, J = 8.8 Hz, 1H), 6.55 (d, J = 9.4 Hz, 1H), 6.20 (s, 1H), 3.86-3.81 (m, 2H), 3.80-3.75 (m, 2H), 3.73 (d, J = 5.5 Hz, 2H), 3.55 (s, 3H), 3.28 (s, 3H), 2.68-2.61 (m, 1H), 0.66-0.61 (m, 2H), 0.44-0.39 (m, 2H) | 1.07 O 519.2 | 12 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 316 | 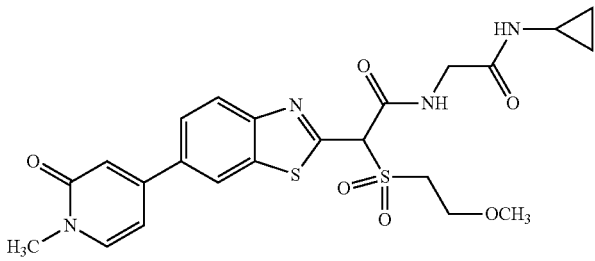 [SMILES: COCCS(=O)(=O)C(C(=O)NCC(=O)NC1CC1)c1nc2ccc(-c3ccn(C)c(=O)c3)cc2s1] | N-[(cyclopropyl-carbamoyl)methyl]-2-(2-methoxyethane-sulfonyl)-2-[6-(1-methyl-2-oxo-1,2-dihydropyridin-4-yl)-1,3-benzothiazol-2-yl]acetamide | 9.03 (t, J = 5.2 Hz, 1H), 8.60 (s, 1H), 8.17 (d, J = 8.5 Hz, 1H), 8.06 (d, J = 3.6 Hz, 1H), 7.97 (s, 1H), 7.92 (d, J = 8.5 Hz, 1H), 7.85 (d, J = 7.2 Hz, 1H), 6.80 (s, 1H), 6.69 (d, J = 7.2 Hz, 1H), 3.86-3.81 (m, 2H), 3.77 (t, J = 5.6 Hz, 2H), 3.73 (d, J = 5.2 Hz, 2H), 3.48 (s, 3H), 3.28 (s, 3H), 2.68-2.61 (m, 1H), 0.66-0.62 (m, 2H), 0.44-0.38 (m, 2H) | 1.07 O 519.2 | 13 |
| 317 | 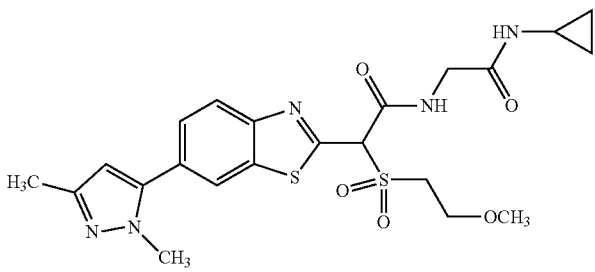 [SMILES: COCCS(=O)(=O)C(C(=O)NCC(=O)NC1CC1)c1nc2ccc(-c3cc(C)nn3C)cc2s1] | N-[(cyclopropyl-carbamoyl)methyl]-2-[6-(1,3-dimethyl-1H-pyrazol-5-yl)-1,3-benzothiazol-2-yl]-2-(2-methoxyethane-sulfonyl)acetamide | 9.03 (br. s., 1H), 8.35 (s, 1H), 8.18 (d, J = 8.0 Hz, 1H), 8.06 (br. s., 1H), 7.69 (d, J = 8.3 Hz, 1H), 6.29 (s, 1H), 6.22 (s, 1H), 3.86-3.81 (m, 4H), 3.80-3.76 (m, 2H), 3.75-3.70 (m, 2H), 3.29 (s, 3H), 2.65 (br. s., 1H), 2.20 (s, 3H), 0.64 (d, J = 6.1 Hz, 2H), 0.45-0.37 (m, 2H) | 1.89 O 506.2 | 4 |
| 318 | 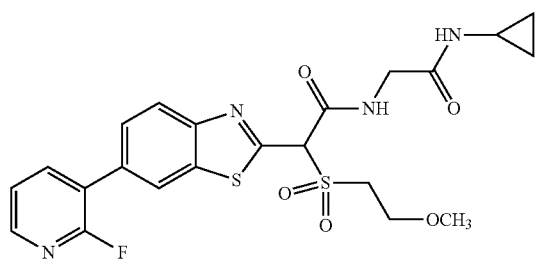 [SMILES: COCCS(=O)(=O)C(C(=O)NCC(=O)NC1CC1)c1nc2ccc(-c3cccnc3F)cc2s1] | N-[(cyclopropyl-carbamoyl)methyl]-2-[6-(2-fluoropyridin-3-yl)-1,3-benzothiazol-2-yl]-2-(2-methoxyethane-sulfonyl)acetamide | 9.04 (br. s., 1H), 8.47 (br. s., 1H), 8.31 (br. s., 1H), 8.23 (br. s., 1H), 8.21 (br. s., 1H), 8.06 (br. s., 1H), 7.82 (d, J = 8.5 Hz, 1H), 7.55 (br. s., 1H), 6.24 (s, 1H), 3.87-3.82 (m, 2H), 3.81-3.76 (m, 2H), 3.76-3.71 (m, 2H), 3.29 (s, 3H), 2.69-2.61 (m, 1H), 0.64 (d, J = 6.1 Hz, 2H), 0.45-0.38 (m, 2H) | 1.38 N 507.2 | 7 |
| 319 | 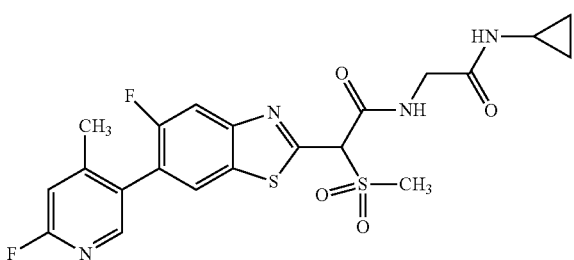 [SMILES: Cc1cc(F)ncc1-c1cc2sc(C(C(=O)NCC(=O)NC3CC3)S(C)(=O)=O)nc2cc1F] | N-[(cyclopropyl-carbamoyl)methyl]-2-[5-fluoro-6-(6-fluoro-4-methylpyridin-3-yl)-1,3-benzothiazol-2-yl]-2-methanesulfonyl-acetamide | 8.83 (t, J = 5.2 Hz, 1H), 8.00 (d, J = 7.1 Hz, 1H), 7.91 (s, 1H), 7.88 (d, J = 10.4 Hz, 1H), 7.84 (d, J = 3.4 Hz, 1H), 7.02 (s, 1H), 6.00 (s, 1H), 3.59 (d, J = 5.4 Hz, 2H), 3.05 (s, 3H), 2.39 (dd, J = 7.1, 3.4 Hz, 1H), 2.00 (s, 3H), 0.39 (d, J = 5.7 Hz, 2H), 0.15 (br. s., 2H) | 1.41 N 495.1 | 15 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 320 | 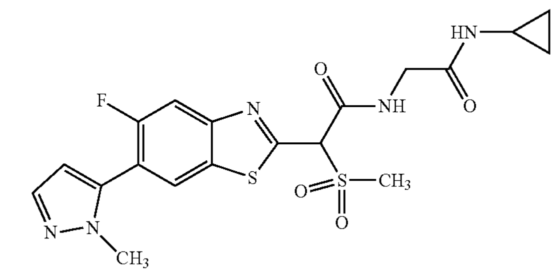 [SMILES: Cn1nccc1-c1cc2sc(C(C(=O)NCC(=O)NC3CC3)S(C)(=O)=O)nc2cc1F] | N-[(cyclopropyl-carbamoyl)methyl]-2-[5-fluoro-6-(1-methyl-1H-pyrazol-5-yl)-1,3-benzothiazol-2-yl]-2-methanesulfonyl-acetamide | 9.07 (t, J = 5.4 Hz, 1H), 8.35 (d, J = 7.1 Hz, 1H), 8.15 (d, J = 10.4 Hz, 1H), 8.08 (d, J = 3.7 Hz, 1H), 7.57 (s, 1H), 6.49 (s, 1H), 6.24 (s, 1H), 3.84 (d, J = 5.4 Hz, 2H), 3.78 (s, 3H), 3.29 (s, 3H), 2.64 (td, J = 7.1, 3.7 Hz, 1H), 0.63 (d, J = 5.7 Hz, 2H), 0.40 (br. s., 2H) | 1.15 O 463.9 | 26 |
| 321 | 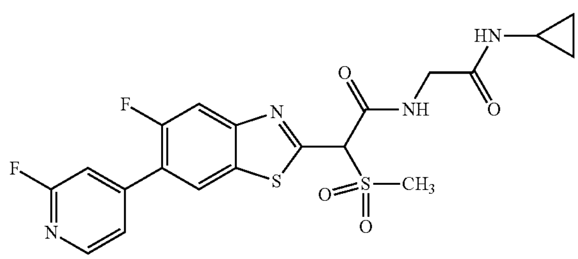 [SMILES: CS(=O)(=O)C(C(=O)NCC(=O)NC1CC1)c1nc2cc(F)c(-c3ccnc(F)c3)cc2s1] | N-[(cyclopropyl-carbamoyl)methyl]-2-[5-fluoro-6-(2-fluoropyridin-4-yl)-1,3-benzothiazol-2-yl]-2-methanesulfonyl-acetamide | 8.84 (t, J = 5.2 Hz, 1H), 8.31 (d, J = 7.4 Hz, 1H), 8.16 (d, J = 5.0 Hz, 1H), 7.93 (d, J = 11.1 Hz, 1H), 7.84 (d, J = 3.4 Hz, 1H), 7.41 (d, J = 4.0 Hz, 1H), 7.25 (s, 1H), 6.01 (s, 1H), 3.60 (d, J = 5.0 Hz, 2H), 3.05 (s, 3H), 2.40 (d, J = 4.0 Hz, 1H), 0.40 (d, J = 6.1 Hz, 2H), 0.16 (br. s., 2H) | 1.35 O 481.1 | 14 |
| 322 | 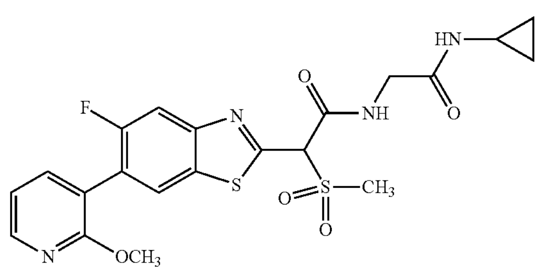 [SMILES: COc1ncccc1-c1cc2sc(C(C(=O)NCC(=O)NC3CC3)S(C)(=O)=O)nc2cc1F] | N-[(cyclopropyl-carbamoyl)methyl]-2-[5-fluoro-6-(2-methoxypyridin-3-yl)-1,3-benzothiazol-2-yl]-2-methanesulfonyl-acetamide | 8.81 (t, J = 5.4 Hz, 1H), 8.04 (d, J = 3.4 Hz, 1H), 7.98 (d, J = 6.7 Hz, 1H), 7.82 (d, J = 3.4 Hz, 1H), 7.79 (d, J = 10.4 Hz, 1H), 7.54 (d, J = 7.1 Hz, 1H), 6.91 (dd, J = 7.1, 5.0 Hz, 1H), 5.98 (s, 1H), 3.61 (s, 3H), 3.59 (d, J = 5.7 Hz, 2H), 3.04 (s, 3H), 2.39 (dd, J = 7.1, 3.4 Hz, 1H), 0.39 (d, J = 6.1 Hz, 2H), 0.15 (br. s., 2H) | 1.4 O 493.1 | 5 |
| 323 | 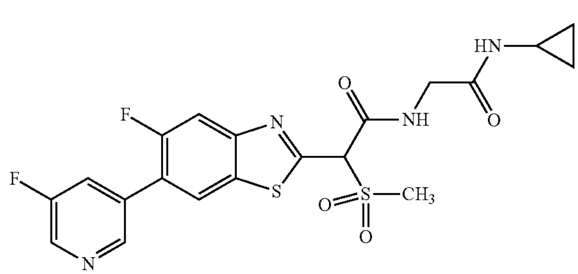 [SMILES: CS(=O)(=O)C(C(=O)NCC(=O)NC1CC1)c1nc2cc(F)c(-c3cncc(F)c3)cc2s1] | N-[(cyclopropyl-carbamoyl)methyl]-2-[5-fluoro-6-(5-fluoropyridin-3-yl)-1,3-benzothiazol-2-yl]-2-methanesulfonyl-acetamide | 8.84 (t, J = 5.2 Hz, 1H), 8.52-8.40 (m, 2H), 8.24 (d, J = 7.4 Hz, 1H), 7.90 (d, J = 11.4 Hz, 1H), 7.86-7.76 (m, 2H), 5.98 (s, 1H), 3.59 (d, J = 5.4 Hz, 2H), 3.04 (s, 3H), 2.39 (dd, J = 7.2, 3.5 Hz, 1H), 0.39 (d, J = 6.1 Hz, 2H), 0.15 (br. s., 2H) | 1.25 O 481.1 | 23 |

-continued

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 324 | 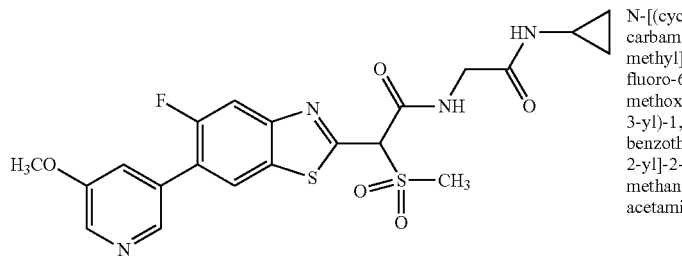 | N-[(cyclopropyl-carbamoyl)methyl]-2-[5-fluoro-6-(5-methoxypyridin-3-yl)-1,3-benzothiazol-2-yl]-2-methanesulfonyl-acetamide | 8.83 (br. s., 1H), 8.21 (d, J = 7.4 Hz, 1H), 8.17 (d, J = 18.5 Hz, 2H), 7.88 (d, J = 11.1 Hz, 1H), 7.83 (br. s., 1H), 7.41 (br. s., 1H), 5.98 (s, 1H), 3.67 (s, 3H), 3.59 (d, J = 5.0 Hz, 2H), 3.04 (s, 3H), 2.39 (d, J = 3.4 Hz, 1H), 0.39 (d, J = 6.4 Hz, 2H), 0.15 (br. s., 2H) | 0.98 O 493.1 | 15 |
| 325 | 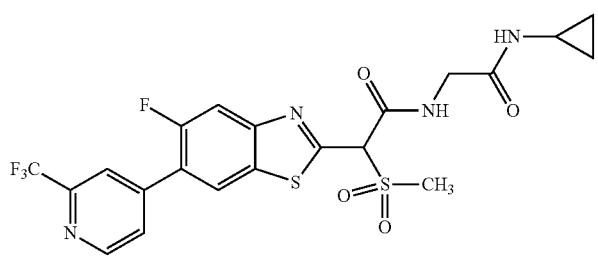 [SMILES: CS(=O)(=O)C(C(=O)NCC(=O)NC1CC1)c1nc2cc(F)c(-c3ccnc(C(F)(F)F)c3)cc2s1] | N-[(cyclopropyl-carbamoyl)methyl]-2-{5-fluoro-6-[2-(trifluoromethyl)pyridin-4-yl]-1,3-benzothiazol-2-yl}-2-methanesulfonyl-acetamide | 9.09 (br. s., 1H), 8.90 (d, J = 4.9 Hz, 1H), 8.55 (d, J = 7.0 Hz, 1H), 8.17-8.10 (m, 2H), 8.06 (d, J = 3.1 Hz, 1H), 7.99 (d, J = 4.3 Hz, 1H), 6.21 (s, 1H), 3.83 (d, J = 5.2 Hz, 2H), 3.69 (br. s., 3H), 2.63 (br. s., 1H), 0.64 (d, J = 6.7 Hz, 2H), 0.40 (br. s., 2H) | 1.6 O 530.6 | 15 |
| 326 | 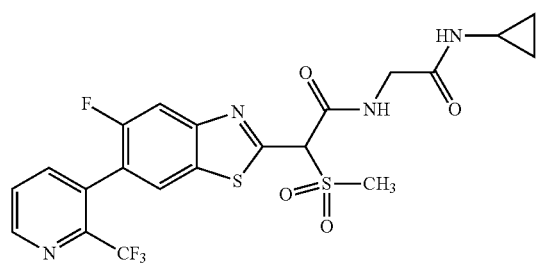 | N-[(cyclopropyl-carbamoyl)methyl]-2-{5-fluoro-6-[2-(trifluoromethyl)pyridin-3-yl]-1,3-benzothiazol-2-yl}-2-methanesulfonyl-acetamide | 9.14 (br. s., 1H), 8.75 (d, J = 6.7 Hz, 1H), 8.33 (br. s., 1H), 8.26-8.17 (m, 2H), 8.13 (br. s., 1H), 8.04 (d, J = 7.0 Hz, 1H), 6.29 (br. s., 1H), 3.91 (br. s., 2H), 3.61 (s, 3H), 2.70 (br. s., 1H), 0.70 (d, J = 6.4 Hz, 2H), 0.47 (br. s., 2H) | 1.69 O 531.1 | 65 |
| 327 | 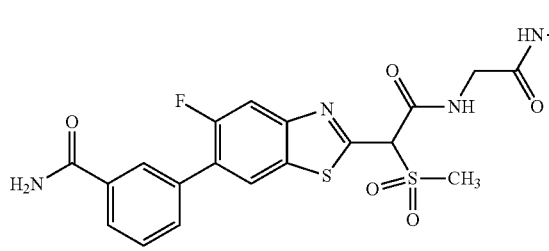 | 3-[2-({[(cyclopropyl-carbamoyl)methyl]carbamoyl}(methanesulfonyl)methyl)-5-fluoro-1,3-benzothiazol-6-yl]benzamide | 9.07 (br. s., 1H), 8.40 (d, J = 7.0 Hz, 1H), 8.16-8.07 (m, 2H), 8.06 (br. s., 1H), 7.95 (br. s., 2H), 7.78 (d, J = 7.3 Hz, 1H), 7.62 (t, J = 7.3 Hz, 1H), 7.46 (br. s., 1H), 6.21 (s, 1H), 3.84 (d, J = 4.9 Hz, 2H), 3.52 (br. s., 3H), 2.64 (br. s., 1H), 0.64 (d, J = 7.0 Hz, 2H), 0.41 (br. s., 2H) | 1.10 O 505.1 | 19 |

| Ex. No. | Structure | Name | ¹H NMR δ (500 MHz, DMSO-d₆, unless otherwise indicated) | LC/MS RT (min) Method M + H | EL IC$_{50}$ (nM) |
|---|---|---|---|---|---|
| 328 | 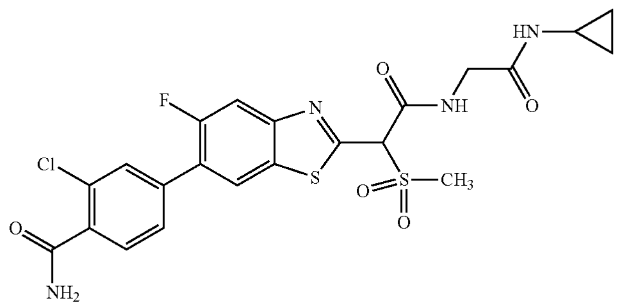 [SMILES: CS(=O)(=O)C(C(=O)NCC(=O)NC1CC1)c1nc2cc(F)c(-c3ccc(C(N)=O)c(Cl)c3)cc2s1] | 2-chloro-4-[2-({[(cyclopropyl-carbamoyl)methyl]carbamoyl}(methanesulfonyl)methyl)-5-fluoro-1,3-benzothiazol-6-yl]benzamide | 9.13 (br. s., 1H), 8.47 (d, J = 7.3 Hz, 1H), 8.16 (d, J = 11.0 Hz, 1H), 8.12 (br. s., 1H), 8.07 (br. s., 1H), 7.80 (s, 1H), 7.74 (br. s., 1H), 7.72-7.68 (m, 1H), 7.67-7.63 (m, 1H), 6.28 (s, 1H), 3.90 (d, J = 4.9 Hz, 2H), 3.59 (br. s., 3H), 2.70 (br. s., 1H), 0.70 (d, J = 6.7 Hz, 2H), 0.47 (br. s., 2H) | 1.14 O 539.1 | 22 |
| 329 | 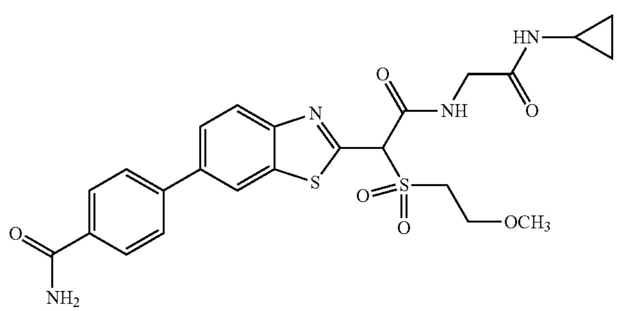 [SMILES: COCCS(=O)(=O)C(C(=O)NCC(=O)NC1CC1)c1nc2ccc(-c3ccc(C(N)=O)cc3)cc2s1] | 4-[2-({[(cyclopropyl-carbamoyl)methyl]carbamoyl}(2-methoxyethane-sulfonyl)methyl)-1,3-benzothiazol-6-yl]benzamide | 9.09 (br. s., 1H), 8.56 (s, 1H), 8.43 (br. s., 1H), 8.25 (d, J = 7.9 Hz, 1H), 8.15 (d, J = 8.5 Hz, 1H), 8.10-7.90 (m, 6H), 6.23 (s, 1H), 3.86-3.75 (m, 4H), 3.63 (t, J = 7.3 Hz, 2H), 3.28 (s, 3H), 2.83 (t, J = 7.5 Hz, 1H), 2.69 (br. s., 1H), 0.72 (dd, J = 12.8, 7.0 Hz, 2H), 0.47 (br. s., 2H) | 1.18 N 531.1 | 46 |
| 330 | 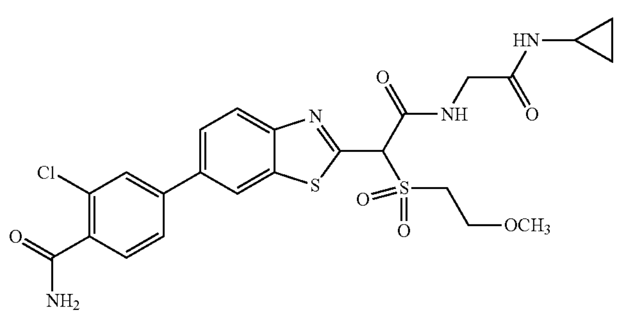 [SMILES: COCCS(=O)(=O)C(C(=O)NCC(=O)NC1CC1)c1nc2ccc(-c3ccc(C(N)=O)c(Cl)c3)cc2s1] | 2-chloro-4-[2-({[(cyclopropyl-carbamoyl)methyl]carbamoyl}(2-methoxyethane-sulfonyl)methyl)-1,3-benzothiazol-6-yl]benzamide | 9.02 (br. s., 1H), 8.55 (br. s., 1H), 8.18 (d, J = 8.2 Hz, 1H), 8.02 (br. s., 1H), 7.97 (br. s., 1H), 7.95-7.90 (m, 1H), 7.89 (br. s., 1H), 7.79 (d, J = 7.9 Hz, 1H), 7.65 (br. s., 1H), 7.58 (d, J = 7.3 Hz, 1H), 6.19 (s, 1H), 3.84-3.69 (m, 4H), 3.57 (br. s., 2H), 3.28 (s, 3H), 2.64 (br. s., 1H), 0.64 (d, J = 6.1 Hz, 2H), 0.40 (br. s., 2H) | 1.2 O 566.4 | 33 |
| 331 | 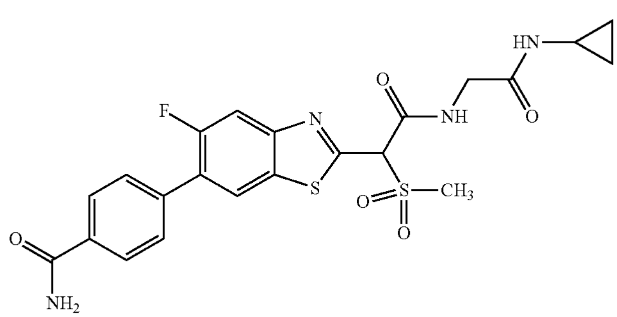 [SMILES: CS(=O)(=O)C(C(=O)NCC(=O)NC1CC1)c1nc2cc(F)c(-c3ccc(C(N)=O)cc3)cc2s1] | 4-[2-({[(cyclopropyl-carbamoyl)methyl]carbamoyl}(methanesulfonyl)methyl)-5-fluoro-1,3-benzothiazol-6-yl]benzamide | 8.83 (br. s., 1H), 8.14 (d, J = 7.1 Hz, 1H), 7.86 (d, J = 10.8 Hz, 2H), 7.82 (br. s., 1H), 7.76 (d, J = 8.1 Hz, 2H), 7.46 (d, J = 7.4 Hz, 2H), 7.22 (br. s., 1H), 5.96 (s, 1H), 3.58 (d, J = 5.0 Hz, 2H), 3.03 (s, 3H), 2.38 (d, J = 3.7 Hz, 1H), 0.38 (d, J = 6.1 Hz, 2H), 0.15 (br. s., 2H) | 1.11 N 505.1 | 4 |

-continued

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 332 | 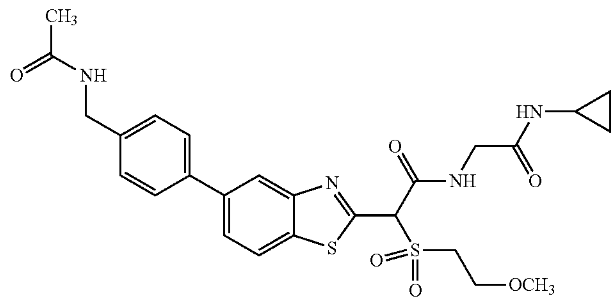 [SMILES: COCCS(=O)(=O)C(C(=O)NCC(=O)NC1CC1)c1nc2cc(-c3ccc(CNC(C)=O)cc3)ccc2s1] | N-[(cyclopropylcarbamoyl)methyl]-2-{5-[4-(acetamidomethyl)phenyl]-1,3-benzothiazol-2-yl}-2-(2-methoxyethanesulfonyl)acetamide | 9.03 (br. s., 1H), 8.43 (br. s., 1H), 8.25 (d, J = 8.0 Hz, 1H), 8.06 (br. s., 1H), 7.88-7.73 (m, 3H), 7.39 (d, J = 7.2 Hz, 2H), 6.22 (s, 1H), 4.32 (br. s., 2H), 3.87-3.71 (m, 5H), 3.29 (s, 3H), 3.13 (d, J = 15.4 Hz, 1H), 2.65 (br. s., 1H), 1.91 (s, 3H), 0.64 (d, J = 6.1 Hz, 2H), 0.41 (br. s., 2H) | 0.7 M 559.1 | 10 |
| 333 | 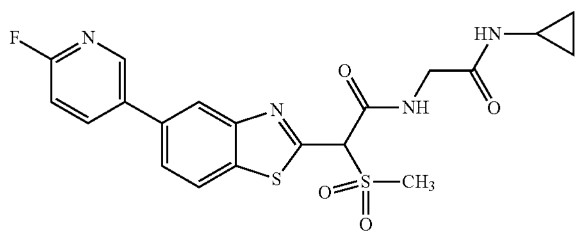 [SMILES: CS(=O)(=O)C(C(=O)NCC(=O)NC1CC1)c1nc2cc(-c3ccc(F)nc3)ccc2s1] | N-[(cyclopropylcarbamoyl)methyl]-2-[5-(6-fluoropyridin-3-yl)-1,3-benzothiazol-2-yl]-2-methanesulfonylacetamide | 9.02 (t, J = 5.4 Hz, 1H), 8.69 (s, 1H), 8.51-8.39 (m, 2H), 8.28 (d, J = 8.5 Hz, 1H), 8.04 (d, J = 3.6 Hz, 1H), 7.88 (d, J = 8.5 Hz, 1H), 7.33 (dd, J = 8.5, 2.5 Hz, 1H), 6.22 (s, 1H), 3.83 (d, J = 5.5 Hz, 2H), 3.28 (s, 3H), 2.68-2.59 (m, 1H), 0.62 (d, J = 6.9 Hz, 2H), 0.40 (d, J = 2.2 Hz, 2H) | 1.77 B 463 | 13 |
| 334 | 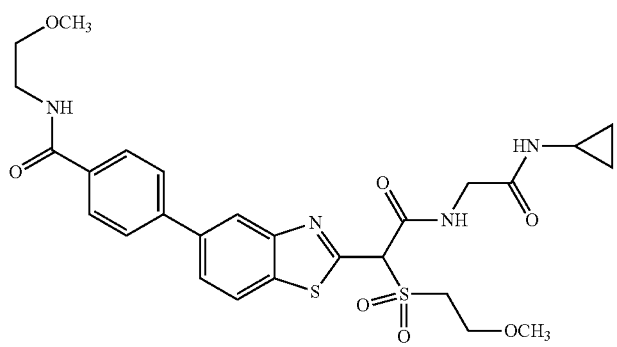 [SMILES: COCCNC(=O)c1ccc(-c2ccc3sc(C(C(=O)NCC(=O)NC4CC4)S(=O)(=O)CCOC)nc3c2)cc1] | 4-[2-({[(cyclopropylcarbamoyl)methyl]carbamoyl}(2-methoxyethanesulfonyl)methyl)-1,3-benzothiazol-5-yl]-N-(2-methoxyethyl)benzamide | 9.04 (br. s., 1H), 8.64 (br. s., 1H), 8.46 (br. s., 1H), 8.29 (d, J = 8.5 Hz, 1H), 8.09-7.90 (m, 6H), 6.23 (br. s., 1H), 3.92-3.70 (m, 6H), 3.30 (br. s., 6H), 3.13 (d, J = 16.8 Hz, 1H), 2.91 (s, 1H), 2.75 (s, 1H), 2.65 (br. s., 1H), 2.56 (br. s., 1H), 0.64 (d, J = 6.1 Hz, 2H), 0.41 (br. s., 2H) | 0.72 M 589.1 | 15 |
| 335 | 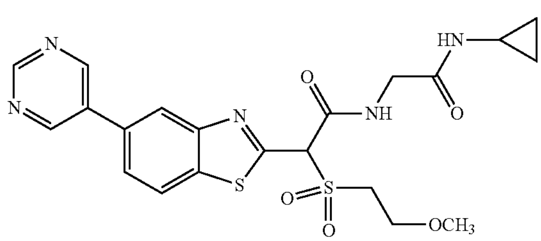 | N-[(cyclopropylcarbamoyl)methyl]-2-(2-methoxyethanesulfonyl)-2-[5-(pyrimidin-5-yl)-1,3-benzothiazol-2-yl]acetamide | 9.35-9.14 (m, 3H), 9.04 (br. s., 1H), 8.60 (s, 1H), 8.36 (d, J = 8.3 Hz, 1H), 8.10-7.95 (m, 2H), 6.25 (s, 1H), 3.97-3.69 (m, 6H), 3.29 (s, 3H), 2.65 (br. s., 1H), 0.64 (d, J = 6.3 Hz, 2H), 0.41 (br. s., 2H) | 0.64 M 490.1 | 16 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 336 | 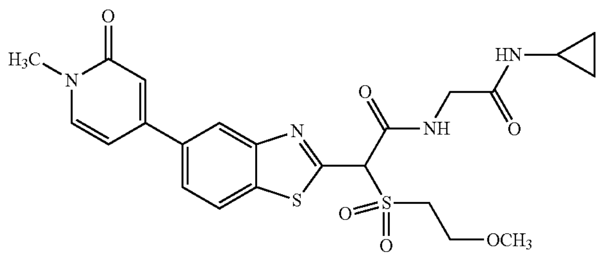 [SMILES: COCCS(=O)(=O)C(C(=O)NCC(=O)NC1CC1)c1nc2cc(-c3ccn(C)c(=O)c3)ccc2s1] | N-[(cyclopropylcarbamoyl)methyl]-2-(2-methoxyethanesulfonyl)-2-[5-(1-methyl-2-oxo-1,2-dihydropyridin-4-yl)-1,3-benzothiazol-2-yl]acetamide | 9.03 (br. s., 1H), 8.44 (s, 1H), 8.28 (d, J = 8.5 Hz, 1H), 8.06 (br. s., 1H), 7.91-7.80 (m, 2H), 6.84 (br. s., 1H), 6.75 (d, J = 6.6 Hz, 1H), 6.23 (s, 1H), 3.92-3.70 (m, 6H), 3.52-3.44 (m, 3H), 3.29 (s, 3H), 2.65 (d, J = 3.0 Hz, 1H), 0.64 (d, J = 6.3 Hz, 2H), 0.41 (br. s., 2H) | 0.63 M 519.1 | 21 |
| 337 | 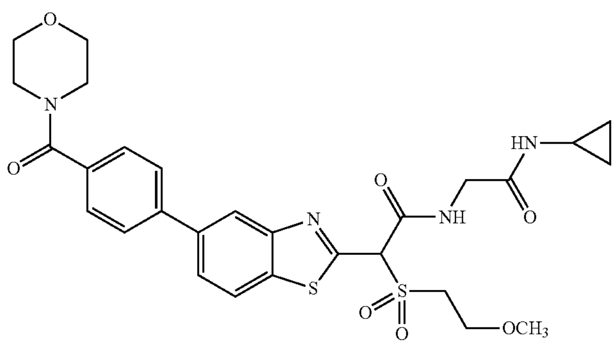 [SMILES: COCCS(=O)(=O)C(C(=O)NCC(=O)NC1CC1)c1nc2cc(-c3ccc(C(=O)N4CCOCC4)cc3)ccc2s1] | N-[(cyclopropylcarbamoyl)methyl]-2-(2-methoxyethanesulfonyl)-2-{5-[4-(morpholine-4-arbonyl)phenyl]-1,3-benzothiazol-2-yl}acetamide | 9.04 (br. s., 1H), 8.52-8.24 (m, 1H), 7.99-7.89 (m, 2H), 7.79 (d, J = 7.7 Hz, 2H), 7.62-7.51 (m, 2H), 6.23 (br. s., 1H), 3.89-3.57 (m, 9H), 3.29 (br. s., 2H), 3.17 (br. s., 2H), 2.91 (s, 1H), 2.75 (s, 1H), 2.65 (d, J = 3.0 Hz, 1H), 1.93 (s, 3H), 0.64 (br. s., 2H), 0.42 (br. s., 2H) | 0.72 M 601.1 | 38 |
| 338 | 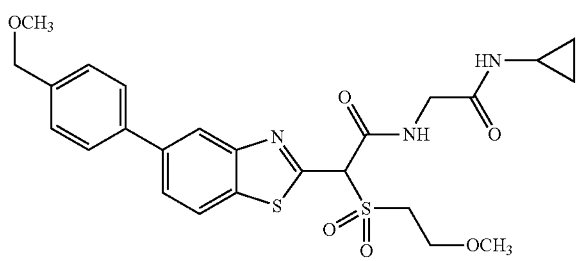 [SMILES: COCCS(=O)(=O)C(C(=O)NCC(=O)NC1CC1)c1nc2cc(-c3ccc(COC)cc3)ccc2s1] | N-[(cyclopropylcarbamoyl)methyl]-2-(2-methoxyethanesulfonyl)-2-{5-[4-(methoxymethyl)phenyl]-1,3-benzothiazol-2-yl}acetamide | 9.03 (br. s., 1H), 8.38 (s, 1H), 8.26 (d, J = 8.3 Hz, 1H), 8.06 (br. s., 1H), 7.88-7.79 (m, 3H), 7.46 (d, J = 7.2 Hz, 2H), 6.22 (s, 1H), 4.49 (br. s., 2H), 3.89-3.70 (m, 6H), 3.34 (br. s., 3H), 3.29 (s, 3H), 2.65 (d, J = 3.0 Hz, 1H), 0.64 (d, J = 6.3 Hz, 2H), 0.41 (br. s., 2H) | 0.85 M 532.1 | 42 |
| 339 | 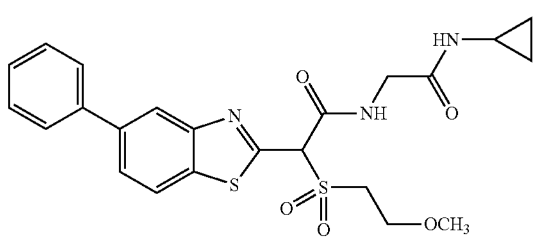 [SMILES: COCCS(=O)(=O)C(C(=O)NCC(=O)NC1CC1)c1nc2cc(-c3ccccc3)ccc2s1] | N-[(cyclopropylcarbamoyl)methyl]-2-(2-methoxyethanesulfonyl)-2-(5-phenyl-1,3-benzothiazol-2-yl)acetamide | 9.04 (br. s., 1H), 8.37 (br. s., 1H), 8.26 (d, J = 8.0 Hz, 1H), 8.06 (br. s., 1H), 7.89-7.77 (m, 3H), 7.57-7.48 (m, 2H), 7.43 (t, J = 7.4 Hz, 1H), 6.22 (s, 1H), 3.90-3.70 (m, 6H), 3.29 (s, 3H), 2.65 (br. s., 1H), 0.64 (d, J = 6.1 Hz, 2H), 0.41 (br. s., 2H) | 0.88 M 488.1 | 215 |

-continued

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 340 | 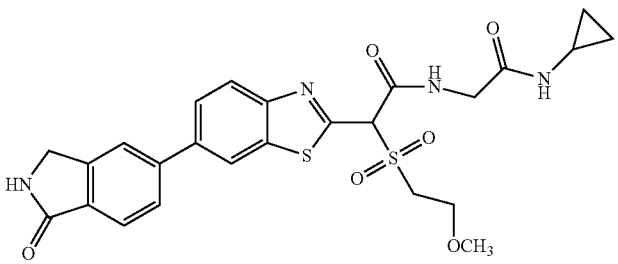 [SMILES: COCCS(=O)(=O)C(C(=O)NCC(=O)NC1CC1)c1nc2ccc(-c3ccc4c(c3)CNC4=O)cc2s1] | N-[(cyclopropyl-carbamoyl)methyl]-2-(2-methoxyethane-sulfonyl)-2-[6-(1-oxo-2,3-dihydro-1H-isoindol-5-yl)-1,3-benzothiazol-2-yl]acetamide | 9.07-8.97 (m, 1H), 8.65-8.60 (m, 1H), 8.58-8.54 (m, 1H), 8.22-8.18 (m, 1H), 8.06-8.01 (m, 1H), 7.99-7.92 (m, 3H), 7.90-7.85 (m, 1H), 7.82-7.78 (m, 1H), 6.22 (s, 1H), 4.52-4.42 (m, 2H), 3.86-3.72 (m, 5H), 3.29 (s, 3H), 2.68-2.62 (m, 1H), 0.67-0.62 (m, 2H), 0.44-0.39 (m, 2H) | 1.13 O 543.2 | 9 |
| 341 | 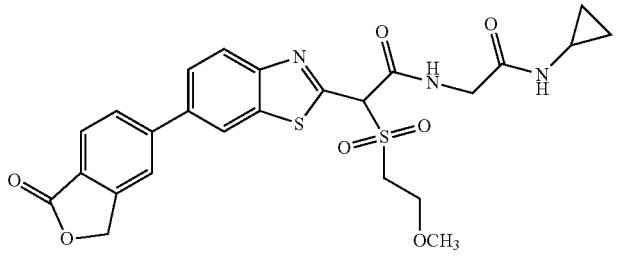 [SMILES: COCCS(=O)(=O)C(C(=O)NCC(=O)NC1CC1)c1nc2ccc(-c3ccc4c(c3)COC4=O)cc2s1] | N-[(cyclopropyl-carbamoyl)methyl]-2-(2-methoxyethane-sulfonyl)-2-[6-(1-oxo-1,3-dihydro-2-benzofuran-5-yl)-1,3-benzothiazol-2-yl]acetamide | (400 MHz, DMSO-$d_6$) 9.03-8.92 (m, 1H), 8.66-8.56 (m, 1H), 8.26-8.17 (m, 1H), 8.11-8.06 (m, 1H), 8.05-7.90 (m, 4H), 6.31-6.17 (m, 1H), 5.54-5.50 (m, 2H), 4.00-3.90 (m, 2H), 3.87-3.69 (m, 5H), 3.29 (s, 3H), 0.67-0.60 (m, 2H), 0.44-0.38 (m, 2H) | 0.81 M 544.2 | 11 |
| 342 | 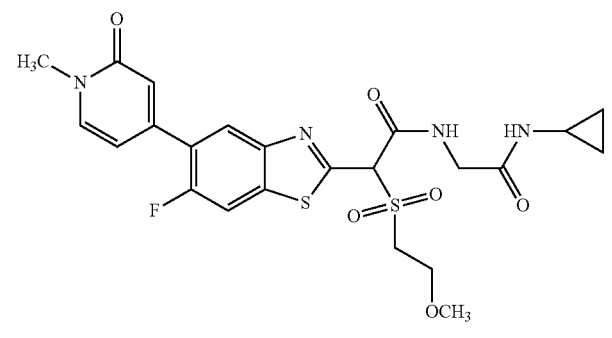 [SMILES: COCCS(=O)(=O)C(C(=O)NCC(=O)NC1CC1)c1nc2cc(-c3ccn(C)c(=O)c3)c(F)cc2s1] | N-[(cyclopropyl-carbamoyl)methyl]-2-[6-fluoro-5-(1-methyl-2-oxo-1,2-dihydropyridin-4-yl)-1,3-benzothiazol-2-yl]-2-(2-methoxyethane-sulfonyl)acetamide | 9.01 (t, J = 5.5 Hz, 1H), 8.34-8.17 (m, 2H), 8.06-7.99 (m, 1H), 7.86-7.77 (m, 1H), 6.72-6.63 (m, 1H), 6.55-6.48 (m, 1H), 6.28-6.16 (m, 1H), 3.95-3.89 (m, 1H), 3.85-3.71 (m, 5H), 3.50 (s, 3H), 3.29 (s, 3H), 2.69-2.58 (m, 1H), 0.67-0.60 (m, 2H), 0.43-0.37 (m, 2H) | 1.13 S 537.2 | 23 |
| 343 | 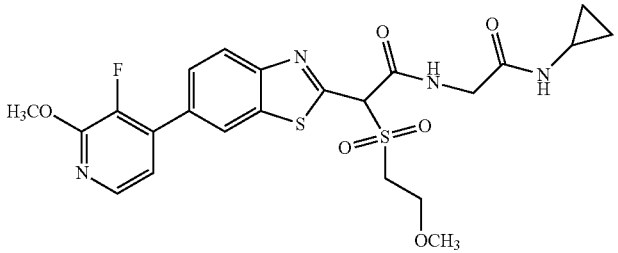 [SMILES: COCCS(=O)(=O)C(C(=O)NCC(=O)NC1CC1)c1nc2ccc(-c3ccnc(OC)c3F)cc2s1] | N-[(cyclopropyl-carbamoyl)methyl]-2-[6-(3-fluoro-2-methoxypyridin-4-yl)-1,3-benzothiazol-2-yl]-2-(2-methoxyethane-sulfonyl)acetamide | 9.15-8.97 (m, 1H), 8.54-8.47 (m, 1H), 8.27-8.20 (m, 1H), 8.11-8.07 (m, 1H), 8.05-8.00 (m, 1H), 7.86-7.79 (m, 1H), 7.32-7.25 (m, 1H), 6.23 (s, 1H), 4.02 (s, 3H), 3.86-3.71 (m, 5H), 3.29 (s, 3H), 3.16-3.07 (m, 1H), 2.68-2.62 (m, 1H), 0.65 (s, 2H), 0.42 (br. s., 2H). | 1.54 O 537.1 | 48 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 344 | 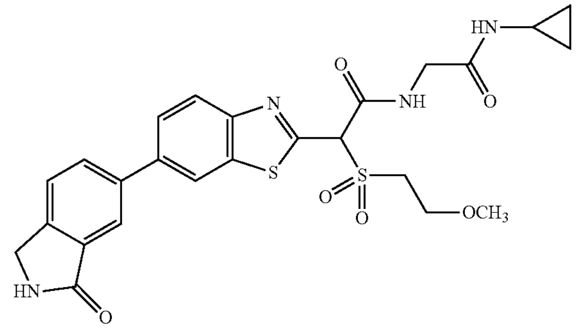 [SMILES: COCCS(=O)(=O)C(C(=O)NCC(=O)NC1CC1)c1nc2ccc(-c3ccc4c(c3)C(=O)NC4)cc2s1] | N-[(cyclopropyl-carbamoyl)methyl]-2-(2-methoxyethane-sulfonyl)-2-[6-(3-oxo-2,3-dihydro-1H-isoindol-5-yl)-1,3-benzothiazol-2-yl]acetamide | 9.05-8.97 (m, 1H), 8.67-8.63 (m, 1H), 8.60-8.56 (m, 1H), 8.21-8.17 (m, 1H), 8.07-7.99 (m, 3H), 7.98-7.92 (m, 2H), 7.75-7.71 (m, 1H), 6.26-6.15 (m, 1H), 4.51-4.45 (m, 2H), 3.86-3.71 (m, 5H), 3.29 (s, 3H), 2.69-2.63 (m, 1H), 0.67-0.59 (m, 2H), 0.47-0.38 (m, 2H) | 1.18 O 543.1 | 98 |
| 345 | 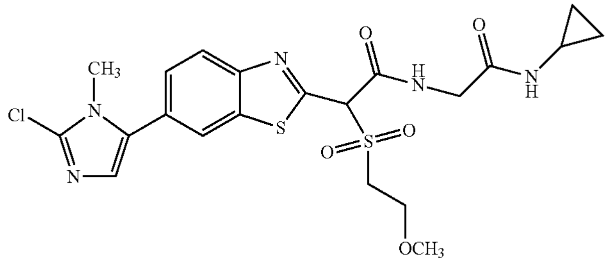 [SMILES: COCCS(=O)(=O)C(C(=O)NCC(=O)NC1CC1)c1nc2ccc(-c3cnc(Cl)n3C)cc2s1] | 2-[6-(2-chloro-1-methyl-1H-imidazol-5-yl)-1,3-benzothiazol-2-yl]-N-[(cyclopropyl-carbamoyl)methyl]-2-(2-methoxyethane-sulfonyl)acetamide | 9.07-8.97 (m, 1H), 8.33 (s, 1H), 8.18 (d, J = 8.5 Hz, 1H), 8.05-7.99 (m, 1H), 7.73-7.65 (m, 1H), 7.16 (s, 1H), 6.22 (s, 1H), 3.85-3.70 (m, 5H), 3.66 (s, 3H), 3.62-3.58 (m, 1H), 3.29 (s, 3H), 2.65 (td, J = 7.3, 3.6 Hz, 1H), 0.68-0.60 (m, 2H), 0.44-0.39 (m, 2H) | 1.09 O 526.1 | 135 |
| 346 | 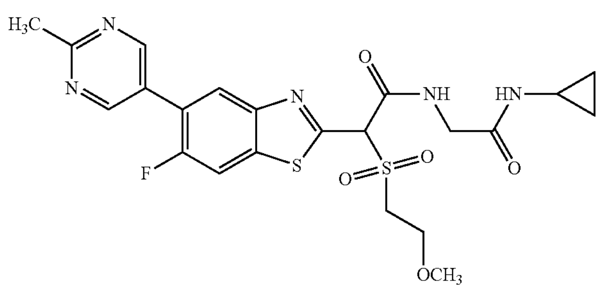 [SMILES: COCCS(=O)(=O)C(C(=O)NCC(=O)NC1CC1)c1nc2cc(-c3cnc(C)nc3)c(F)cc2s1] | N-[(cyclopropyl-carbamoyl)methyl]-2-[6-fluoro-5-(2-methylpyrimidin-5-yl)-1,3-benzothiazol-2-yl]-2-(2-methoxyethane-sulfonyl)acetamide | 9.08-8.96 (m, 3H), 8.48-8.36 (m, 1H), 8.30-8.25 (m, 1H), 8.07-8.00 (m, 1H), 6.28-6.09 (m, 1H), 3.87-3.71 (m, 6H), 3.29 (s, 3H), 2.72 (s, 3H), 2.68-2.62 (m, 1H), 0.71-0.59 (m, 2H), 0.49-0.35 (m, 2H) | 1.23 O 522 | 6 |
| 347 | 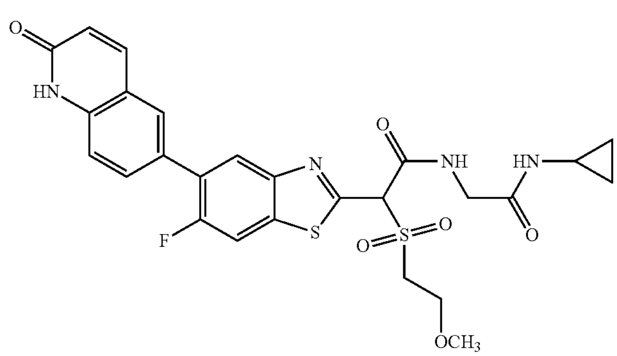 [SMILES: COCCS(=O)(=O)C(C(=O)NCC(=O)NC1CC1)c1nc2cc(-c3ccc4[nH]c(=O)ccc4c3)c(F)cc2s1] | N-[(cyclopropyl-carbamoyl)methyl]-2-[6-fluoro-5-(2-oxo-1,2-dihydroquinolin-6-yl)-1,3-benzothiazol-2-yl]-2-(2-methoxyethane-sulfonyl)acetamide | 11.90 (br. s., 1H), 9.12-8.96 (m, 1H), 8.27 (d, J = 6.5 Hz, 1H), 8.21 (d, J = 10.6 Hz, 1H), 8.00 (br. s., 3H), 7.81 (d, J = 9.0 Hz, 1H), 7.45 (d, J = 8.0 Hz, 1H), 6.58 (d, J = 9.8 Hz, 1H), 6.21 (s, 1H), 3.86-3.71 (m, 6H), 3.29 (s, 3H), 2.69-2.62 (m, 1H), 0.64 (d, J = 6.5 Hz, 2H), 0.41 (br. s., 2H) | 1.29 O 573.1 | 18 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 348 | 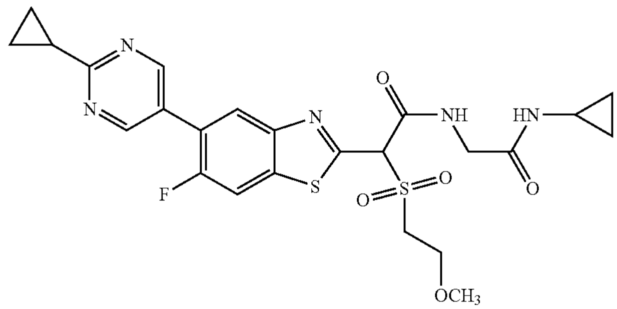 [SMILES: COCCS(=O)(=O)C(C(=O)NCC(=O)NC1CC1)c1nc2cc(-c3cnc(C4CC4)nc3)c(F)cc2s1] | N-[(cyclopropyl-carbamoyl)methyl]-2-[5-(2-cyclopropyl-pyrimidin-5-yl)-6-fluoro-1,3-benzothiazol-2-yl]-2-(2-methoxyethane-sulfonyl)acetamide | 9.05-8.98 (m, 1H), 8.93 (s, 2H), 8.46-8.38 (m, 1H), 8.31-8.23 (m, 1H), 8.07-8.01 (m, 1H), 6.29-6.14 (m, 1H), 3.87-3.69 (m, 6H), 3.29 (s, 3H), 2.68-2.61 (m, 1H), 2.34-2.25 (m, 1H), 1.17-1.06 (m, 4H), 0.67-0.61 (m, 2H), 0.41 (br. s., 2H) | 1.53 O 548.2 | 10 |
| 349 | 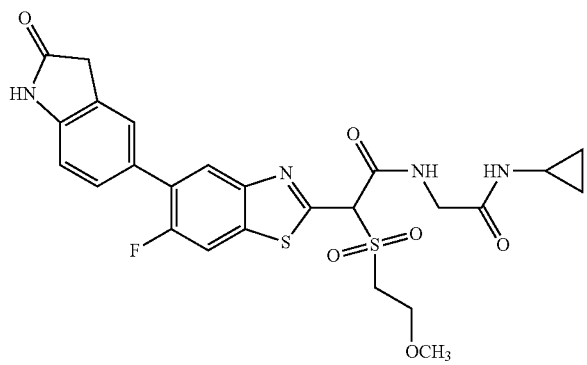 [SMILES: COCCS(=O)(=O)C(C(=O)NCC(=O)NC1CC1)c1nc2cc(-c3ccc4c(c3)CC(=O)N4)c(F)cc2s1] | N-[(cyclopropyl-carbamoyl)methyl]-2-[6-fluoro-5-(2-oxo-2,3-dihydro-1H-indol-5-yl)-1,3-benzothiazol-2-yl]-2-(2-methoxyethane-sulfonyl)acetamide | 10.62-10.45 (m, 1H), 9.05-8.95 (m, 1H), 8.20-8.08 (m, 2H), 8.05-7.96 (m, 1H), 7.54-7.40 (m, 2H), 7.02-6.82 (m, 1H), 6.20-6.12 (m, 1H), 3.84-3.65 (m, 6H), 3.56 (br. s., 2H), 3.26 (s, 3H), 2.66-2.57 (m, 1H), 0.62 (d, J = 6.1 Hz, 2H), 0.39 (br. s., 2H) | 1.37 S 561.2 | 42 |
| 350 | 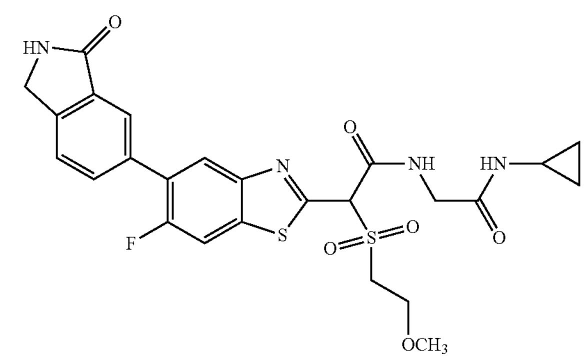 [SMILES: COCCS(=O)(=O)C(C(=O)NCC(=O)NC1CC1)c1nc2cc(-c3ccc4c(c3)C(=O)NC4)c(F)cc2s1] | N-[(cyclopropyl-carbamoyl)methyl]-2-[6-fluoro-5-(3-oxo-2,3-dihydro-1H-isoindol-5-yl)-1,3-benzothiazol-2-yl]-2-(2-methoxyethane-sulfonyl)acetamide | 9.08-8.98 (m, 1H), 8.75-8.65 (m, 1H), 8.28 (d, J = 7.0 Hz, 1H), 8.23 (d, J = 10.1 Hz, 1H), 8.04 (br. s., 1H), 7.92-7.85 (m, 2H), 7.75 (d, J = 7.9 Hz, 1H), 6.23 (s, 1H), 4.48 (s, 2H), 3.92 (s, 3H), 3.87-3.71 (m, 6H), 2.66 (d, J = 3.7 Hz, 1H), 0.65 (d, J = 6.7 Hz, 2H), 0.42 (br. s., 2H) | 1.36 S 561.2 | 18 |
| 351 | 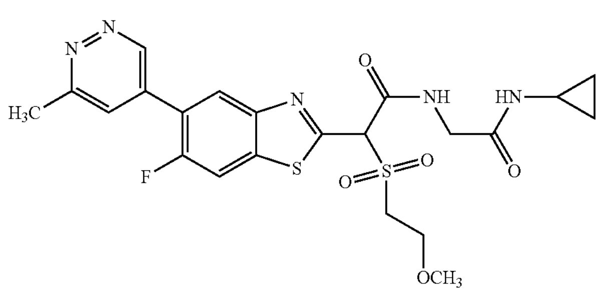 [SMILES: COCCS(=O)(=O)C(C(=O)NCC(=O)NC1CC1)c1nc2cc(-c3cnnc(C)c3)c(F)cc2s1] | N-[(cyclopropyl-carbamoyl)methyl]-2-[6-fluoro-5-(6-methylpyridazin-4-yl)-1,3-benzothiazol-2-yl]-2-(2-methoxyethane-sulfonyl)acetamide | 9.48-9.37 (m, 1H), 9.10-8.98 (m, 1H), 8.55-8.45 (m, 1H), 8.38-8.27 (m, 1H), 8.09-8.00 (m, 1H), 7.92 (s, 1H), 6.24 (s, 1H), 3.98-3.70 (m, 6H), 3.51-3.44 (m, 2H), 3.19 (s, 1H), 2.74 (s, 3H), 2.66 (d, J = 4.0 Hz, 1H), 0.65 (d, J = 5.5 Hz, 2H), 0.42 (br. s., 2H) | 1.04 O 522.1 | 36 |

| Ex. No. | Structure | Name | $^1$H NMR δ (500 MHz, DMSO-$d_6$, unless otherwise indicated) | LC/MS RT (min) ethod M + H | EL IC$_{50}$ (nM) |
|---|---|---|---|---|---|
| 352 | 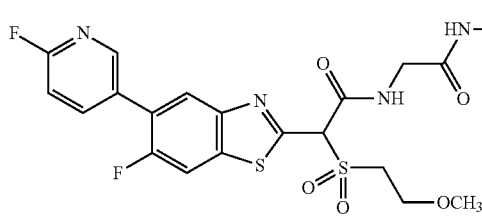 | 2-[6-fluoro-5-(6-fluoropyridin-3-yl)-1,3-benzothiazol-2-yl]-2-(2-methoxyethane-sulfonyl)-N-({[2-(propan-2-yloxy)ethyl]carbamoyl}methyl)acetamide | 9.01 (t, J = 5.3 Hz, 1H), 8.50 (s, 1H), 8.34-8.13 (m, 3H), 7.97 (t, J = 5.3 Hz, 1H), 7.36-7.28 (m, 1H), 6.17 (s, 1H), 3.96-3.65 (m, 6H), 3.52 (br. s., 1H), 3.38-3.32 (m, 2H), 3.22-3.14 (m, 3H), 1.03 (d, J = 6.1 Hz, 6H) | 1.59 O 571.1 | 14 |
| 353 | 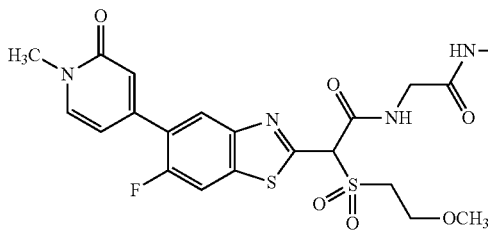 | 2-[6-fluoro-5-(1-methyl-2-oxo-1,2-dihydropyridin-4-yl)-1,3-benzothiazol-2-yl]-2-(2-methoxyethane-sulfonyl)-N-({[2-(propan-2-yloxy)ethyl]carbamoyl}methyl)acetamide | 9.02 (br. s., 1H), 8.22 (d, J = 6.4 Hz, 1H), 8.16 (d, J = 10.4 Hz, 1H), 7.95 (br. s., 2H), 7.77 (d, J = 6.7 Hz, 1H), 6.64 (br. s., 1H), 6.51 (d, J = 6.1 Hz, 1H), 6.15 (s, 1H), 3.93-3.55 (m, 6H), 3.47 (br. s., 3H), 3.34 (br. s., 3H), 3.22-3.12 (m, 3H), 3.07 (br. s., 1H), 1.08-0.95 (m, 6H) | 1.24 O 583.1 | 34 |
| 354 | 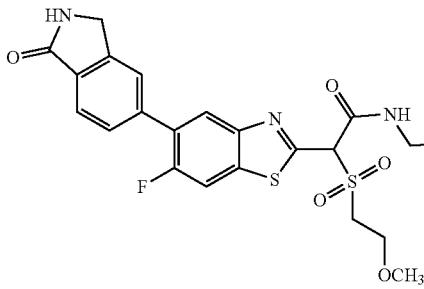 | 2-[6-fluoro-5-(1-oxo-2,3-dihydro-1H-isoindol-5-yl)-1,3-benzothiazol-2-yl]-2-(2-methoxyethane-sulfonyl)-N-({[2-(propan-2-yloxy)ethyl]carbamoyl}methyl)acetamide | 9.02 (br. s., 1H), 8.63 (br. s., 1H), 8.26-8.12 (m, 2H), 7.83 (br. s., 5H), 6.17 (br. s., 1H), 4.46 (br. s., 2H), 3.94-3.68 (m, 5H), 3.35 (br. s., 2H), 3.26 (br. s., 3H), 3.23-3.14 (m, 3H), 1.04 (d, J = 4.6 Hz, 6H) | 1.39 O 607.1 | 24 |
| 355 | 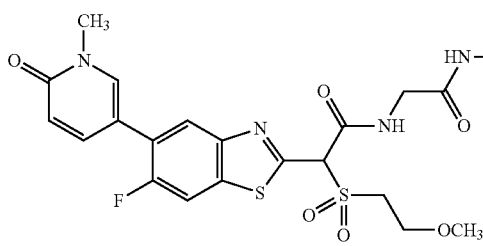 | 2-[6-fluoro-5-(1-methyl-6-oxo-1,6-dihydropyridin-3-yl)-1,3-benzothiazol-2-yl]-2-(2-methoxyethane-sulfonyl)-N-({[2-(propan-2-yloxy)ethyl]carbamoyl}methyl)acetamide | 9.00 (br. s., 1H), 8.21-8.04 (m, 3H), 7.96 (br. s., 1H), 7.74 (d, J = 9.2 Hz, 1H), 6.52 (d, J = 9.2 Hz, 1H), 6.14 (s, 1H), 3.99-3.65 (m, 5H), 3.57 (br. s., 3H), 3.53-3.44 (m, 3H), 3.34 (d, J = 5.5 Hz, 3H), 3.22-3.13 (m, 3H), 1.03 (d, J = 5.5 Hz, 6H) | 1.25 O 583.1 | 36 |
| 356 | 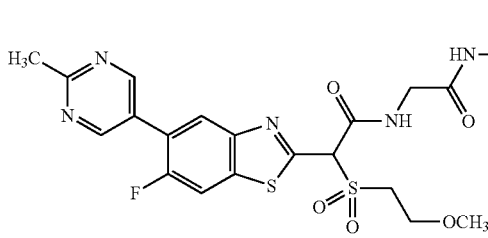 | 2-[6-fluoro-5-(2-methylpyrimidin-5-yl)-1,3-benzothiazol-2-yl]-2-(2-methoxyethane-sulfonyl)-N-({[2-(propan-2-yloxy)ethyl]carbamoyl}methyl)acetamide | 1H NMR (500 MHz, DMSO-$d_6$) d 9.05-9.00 (m, 1H), 8.96 (s, 2H), 8.37-8.31 (m, 1H), 8.24-8.18 (m, 1H), 7.96 (br. s., 1H), 6.16 (s, 1H), 3.95-3.45 (m, 6H), 3.40-3.30 (m, 2H), 3.25 (s, 3H), 3.22-3.15 (m, 3H), 2.68 (s, 3H), 1.03 (d, J = 6.1 Hz, 6H) | 1.32 O 568.1 | 55 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 357 | 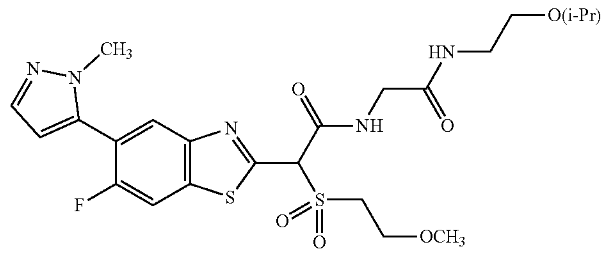 | 2-[6-fluoro-5-(1-methyl-1H-pyrazol-5-yl)-1,3-benzothiazol-2-yl]-2-(2-methoxyethane-sulfonyl)-N-({[2-(propan-2-yloxy)ethyl]carbamoyl}methyl)acetamide | 9.02 (br. s., 1H), 8.29-8.09 (m, 2H), 8.01-7.81 (m, 2H), 7.54 (s, 1H), 6.47 (s, 1H), 6.14 (s, 1H), 3.93-3.82 (m, 2H), 3.79-3.62 (m, 5H), 3.53-3.45 (m, 1H), 3.34 (br. s., 2H), 3.25 (s, 3H), 3.21-3.13 (m, 3H), 1.02 (d, J = 5.2 Hz, 6H) | 1.38 O 556.1 | 49 |
| 358 | 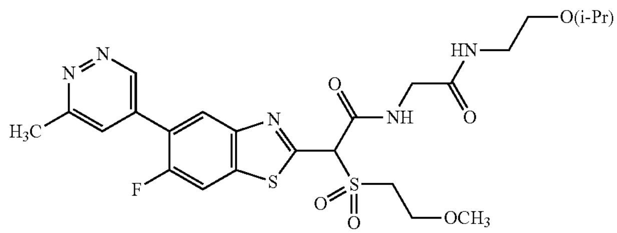 | 2-[6-fluoro-5-(6-methylpyridazin-4-yl)-1,3-benzothiazol-2-yl]-2-(2-methoxyethane-sulfonyl)-N-({[2-(propan-2-yloxy)ethyl]carbamoyl}methyl)acetamide | 9.46-9.35 (m, 1H), 9.02 (t, J = 5.2 Hz, 1H), 8.46 (d, J = 6.7 Hz, 1H), 8.26 (d, J = 10.4 Hz, 1H), 8.01-7.92 (m, 2H), 6.18 (s, 1H), 3.93-3.68 (m, 3H), 3.65-3.56 (m, 1H), 3.53-3.44 (m, 1H), 3.38-3.31 (m, 2H), 3.26 (s, 3H), 3.22-3.14 (m, 3H), 2.77-2.65 (m, 4H), 1.03 (d, J = 5.8 Hz, 6H) | 1.14 O 568.1 | 60 |
| 359 | 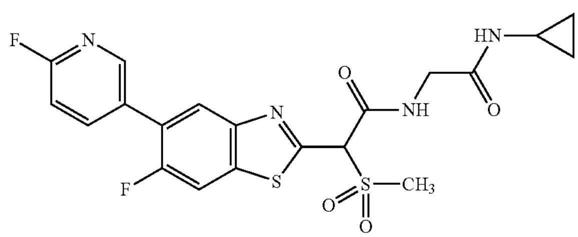 [SMILES: CS(=O)(=O)C(C(=O)NCC(=O)NC1CC1)c1nc2cc(-c3ccc(F)nc3)c(F)cc2s1] | N-[(cyclopropylcarbamoyl)methyl]-2-[6-fluoro-5-(6-fluoropyridin-3-yl)-1,3-benzothiazol-2-yl]-2-methanesulfonyl-acetamide | 9.10-9.01 (m, 1H), 8.51 (br. s., 1H), 8.32-8.18 (m, 3H), 8.04 (d, J = 3.1 Hz, 1H), 7.34 (d, J = 6.7 Hz, 1H), 6.20 (s, 1H), 3.82 (d, J = 5.2 Hz, 1H), 3.47-3.38 (m, 1H), 3.27 (s, 3H), 2.63 (d, J = 3.7 Hz, 1H), 0.62 (d, J = 6.7 Hz, 2H), 0.39 (br. s., 2H) | 1.33 S 481.1 | 7 |
| 360 | 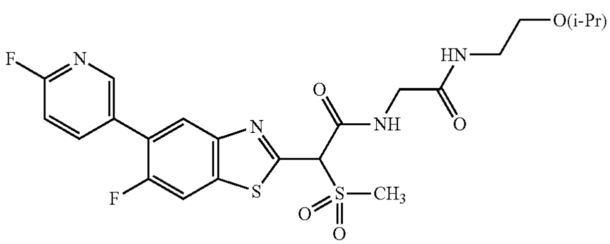 | 2-[6-fluoro-5-(6-fluoropyridin-3-yl)-1,3-benzothiazol-2-yl]-2-methanesulfonyl-N-({[2-(propan-2-yloxy)ethyl]carbamoyl}methyl)acetamide | 9.05 (br. s., 1H), 8.50 (br. s., 1H), 8.33-8.16 (m, 3H), 8.01 (br. s., 1H), 7.34 (d, J = 6.7 Hz, 1H), 6.18 (s, 1H), 3.88 (br. s., 2H), 3.50-3.43 (m, 1H), 3.39-3.31 (m, 2H), 3.26 (s, 3H), 3.23-3.15 (m, 2H), 1.04 (d, J = 5.8 Hz, 6H) | 1.53 O 527.1 | 21 |
| 361 | 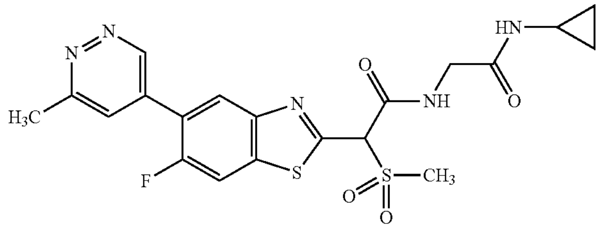 [SMILES: Cc1cc(-c2cc3nc(C(C(=O)NCC(=O)NC4CC4)S(C)(=O)=O)sc3cc2F)cnn1] | N-[(cyclopropylcarbamoyl)methyl]-2-[6-fluoro-5-(6-methylpyridazin-4-yl)-1,3-benzothiazol-2-yl]-2-methanesulfonyl-acetamide | 9.49-9.40 (m, 1H), 9.12-9.02 (m, 1H), 8.48 (d, J = 6.4 Hz, 1H), 8.27 (d, J = 10.4 Hz, 1H), 8.09-7.97 (m, 2H), 6.20 (s, 1H), 3.85-3.79 (m, 1H), 3.70-3.61 (m, 1H), 3.27 (s, 2H), 2.73 (br. s., 3H), 2.62 (d, J = 3.1 Hz, 1H), 0.62 (d, J = 6.4 Hz, 2H), 0.38 (br. s., 2H) | 0.96 O 478.1 | 26 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 362 | 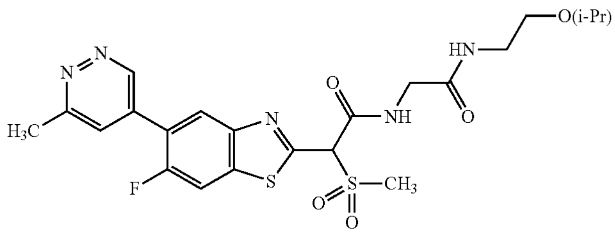 | 2-[6-fluoro-5-(6-methylpyridazin-4-yl)-1,3-benzothiazol-2-yl]-2-methanesulfonyl-N-({[2-(propan-2-yloxy)ethyl]carbamoyl}methyl)acetamide | 9.42 (br. s., 1H), 9.06 (br. s., 1H), 8.48 (d, J = 6.7 Hz, 1H), 8.28 (d, J = 10.4 Hz, 1H), 8.08-7.96 (m, 2H), 6.21 (s, 1H), 3.88 (d, J = 4.0 Hz, 2H), 3.35 (br. s., 2H), 3.27 (s, 3H), 3.23-3.16 (m, 2H), 2.73 (s, 4H), 1.04 (d, J = 5.8 Hz, 6H) | 1.15 S 524.1 | 25 |
| 363 | 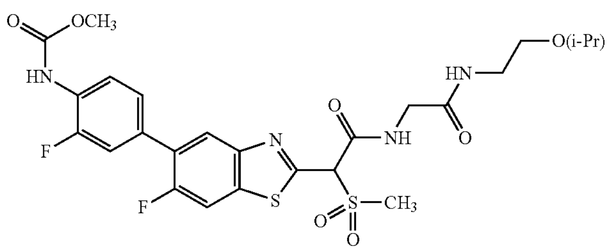 | methyl N-[2-fluoro-4-(6-fluoro-2-{methanesulfonyl[({[2-(propan-2-yloxy)ethyl]carbamoyl}methyl)carbamoyl]methyl}-1,3-benzothiazol-5-yl)phenyl]carbamate | 9.58-9.48 (m, 1H), 9.14-8.96 (m, 1H), 8.27-8.22 (m, 1H), 8.20-8.12 (m, 1H), 8.07-7.98 (m, 1H), 7.84-7.75 (m, 1H), 7.57-7.50 (m, 1H), 7.48-7.39 (m, 1H), 6.18 (s, 1H), 3.92-3.84 (m, 2H), 3.69 (s, 3H), 3.52-3.44 (m, 1H), 3.39-3.32 (m, 2H), 3.26 (s, 3H), 3.22-3.14 (m, 2H), 1.04 (d, J = 6.1 Hz, 6H) | 1.59 S 599.1 | 11 |
| 364 | 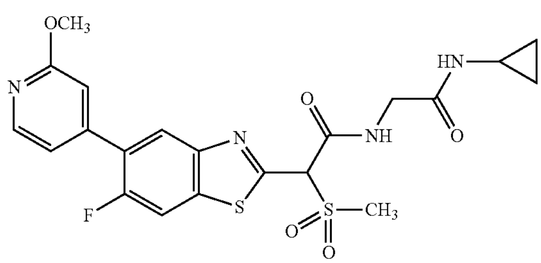 [SMILES: COc1cc(-c2cc3nc(C(C(=O)NCC(=O)NC4CC4)S(C)(=O)=O)sc3cc2F)ccn1] | N-[(cyclopropylcarbamoyl)methyl]-2-[6-fluoro-5-(2-methoxypyridin-4-yl)-1,3-benzothiazol-2-yl]-2-methanesulfonyl-acetamide | 9.11-9.03 (m, 1H), 8.26 (d, J = 5.8 Hz, 2H), 8.20-8.13 (m, 1H), 8.06-7.99 (m, 1H), 7.26-7.20 (m, 1H), 7.07-7.02 (m, 1H), 6.19-6.12 (m, 1H), 3.89 (s, 5H), 3.25 (s, 3H), 2.64-2.56 (m, 1H), 0.64-0.57 (m, 2H), 0.43-0.31 (m, 2H) | 1.28 O 493.1 | 12 |
| 365 | 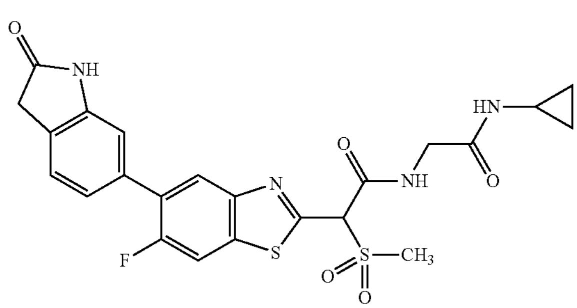 [SMILES: CS(=O)(=O)C(C(=O)NCC(=O)NC1CC1)c1nc2cc(-c3ccc4c(c3)NC(=O)C4)c(F)cc2s1] | N-[(cyclopropylcarbamoyl)methyl]-2-[6-fluoro-5-(2-oxo-2,3-dihydro-1H-indol-6-yl)-1,3-benzothiazol-2-yl]-2-methanesulfonyl-acetamide | 10.60-10.39 (m, 1H), 9.04 (br. s., 1H), 8.13 (d, J = 5.5 Hz, 2H), 8.05-7.97 (m, 1H), 7.38-7.31 (m, 1H), 7.20-7.15 (m, 1H), 7.08-7.03 (m, 1H), 6.16 (s, 1H), 3.85-3.77 (m, 2H), 3.60-3.48 (m, 2H), 3.26 (s, 3H), 2.62 (d, J = 3.1 Hz, 1H), 0.67-0.58 (m, 2H), 0.43-0.28 (m, 2H) | 1.23 O 517.1 | 36 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 366 | 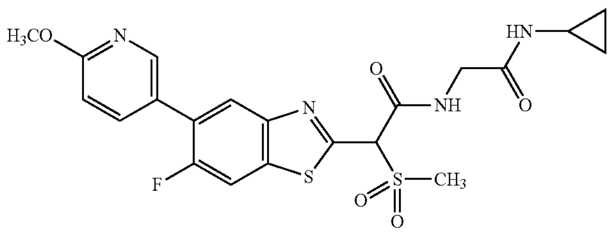 [SMILES: COc1ccc(-c2cc3nc(C(C(=O)NCC(=O)NC4CC4)S(C)(=O)=O)sc3cc2F)cn1] | N-[(cyclopropylcarbamoyl)methyl]-2-[6-fluoro-5-(6-methoxypyridin-3-yl)-1,3-benzothiazol-2-yl]-2-methanesulfonylacetamide | 9.10-9.04 (m, 1H), 8.48-8.41 (m, 1H), 8.26-8.22 (m, 1H), 8.21-8.16 (m, 1H), 8.05 (br. s., 1H), 8.00 (d, J = 8.5 Hz, 1H), 6.98 (d, J = 8.5 Hz, 1H), 6.18 (s, 1H), 3.93 (s, 3H), 3.85-3.80 (m, 2H), 3.28 (s, 3H), 2.68-2.59 (m, 1H), 0.64 (d, J = 6.7 Hz, 2H), 0.40 (br. s., 2H) | 1.54 S 493.1 | 30 |
| 367 | 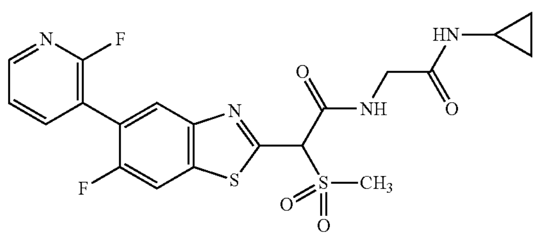 [SMILES: CS(=O)(=O)C(C(=O)NCC(=O)NC1CC1)c1nc2cc(-c3cccnc3F)c(F)cc2s1] | N-[(cyclopropylcarbamoyl)methyl]-2-[6-fluoro-5-(2-fluoropyridin-3-yl)-1,3-benzothiazol-2-yl]-2-methanesulfonylacetamide | 9.10-9.00 (m, 1H), 8.38-8.30 (m, 1H), 8.27-8.17 (m, 2H), 8.14 (t, J = 8.5 Hz, 1H), 8.03 (br. s., 1H), 7.53 (t, J = 5.8 Hz, 1H), 6.16 (s, 1H), 3.81 (d, J = 5.2 Hz, 2H), 3.26 (s, 3H), 2.61 (br. s., 1H), 0.62 (d, J = 6.7 Hz, 2H), 0.38 (br. s., 2H) | 1.35 O 481 | 25 |
| 368 | 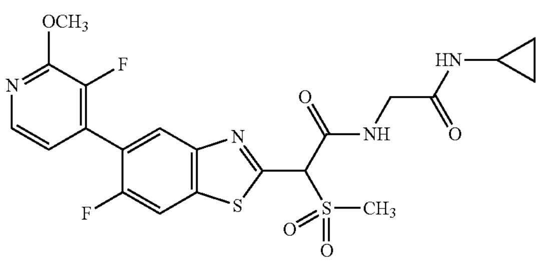 [SMILES: COc1nccc(-c2cc3nc(C(C(=O)NCC(=O)NC4CC4)S(C)(=O)=O)sc3cc2F)c1F] | N-[(cyclopropylcarbamoyl)methyl]-2-[6-fluoro-5-(3-fluoro-2-methoxypyridin-4-yl)-1,3-benzothiazol-2-yl]-2-methanesulfonylacetamide | 9.08-9.00 (m, 1H), 8.29-8.20 (m, 2H), 8.13-8.07 (m, 1H), 8.03 (br. s., 1H), 7.19 (br. s., 1H), 6.18 (s, 1H), 4.00 (s, 3H), 3.81 (d, J = 4.9 Hz, 2H), 3.53 (br. s., 3H), 2.66-2.58 (m, 1H), 0.62 (d, J = 6.7 Hz, 2H), 0.38 (br. s., 2H) | 1.57 S 511.1 | 17 |
| 369 | 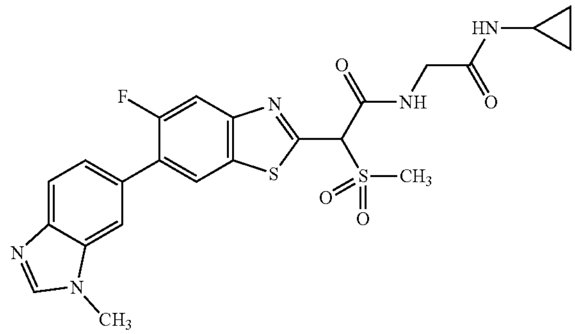 [SMILES: Cn1cnc2ccc(-c3cc4sc(C(C(=O)NCC(=O)NC5CC5)S(C)(=O)=O)nc4cc3F)cc21] | N-[(cyclopropylcarbamoyl)methyl]-2-[5-fluoro-6-(1-methyl-1H-1,3-benzodiazol-6-yl)-1,3-benzothiazol-2-yl]-2-methanesulfonylacetamide | 9.20 (s, 1H), 9.07 (t, J = 5.5 Hz, 1H), 8.40 (d, J = 7.6 Hz, 1H), 8.09 (d, J = 11.3 Hz, 1H), 8.06-7.90 (m, 4H), 7.77 (d, J = 8.5 Hz, 1H), 6.19 (s, 1H), 4.04 (s, 3H), 3.82 (d, J = 5.8 Hz, 1H), 3.27 (s, 3H), 2.62 (td, J = 7.2, 3.5 Hz, 1H), 0.67-0.58 (m, 2H), 0.39 (d, J = 2.1 Hz, 2H) | 0.97 O 516.1 | 16 |

| Ex. No. | Structure | Name | $^1$H NMR δ (500 MHz, DMSO-d$_6$, unless otherwise indicated) | LC/MS RT (min) Method M + H | EL IC$_{50}$ (nM) |
|---|---|---|---|---|---|
| 370 | 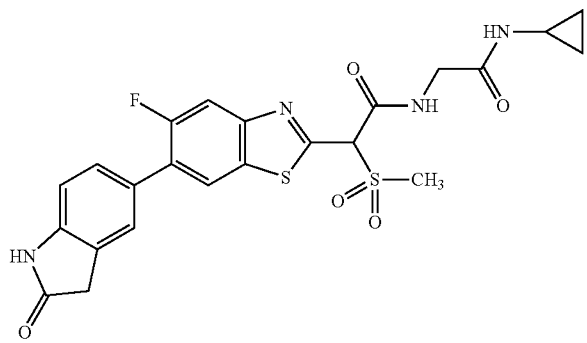 [SMILES: CS(=O)(=O)C(C(=O)NCC(=O)NC1CC1)c1nc2cc(F)c(-c3ccc4c(c3)CC(=O)N4)cc2s1] | N-[(cyclopropyl-carbamoyl)methyl]-2-[5-fluoro-6-(2-oxo-2,3-dihydro-1H-indol-5-yl)-1,3-benzothiazol-2-yl]-2-methanesulfonyl-acetamide | 10.54 (s, 1H), 9.04 (t, J = 5.5 Hz, 1H), 8.24 (d, J = 7.6 Hz, 1H), 8.07-7.96 (m, 1H), 7.50-7.39 (m, 2H), 6.96 (d, J = 8.2 Hz, 1H), 6.16 (s, 1H), 3.81 (d, J = 5.5 Hz, 1H), 3.55 (br. s., 3H), 3.25 (s, 3H), 2.62 (dd, J = 7.3, 3.4 Hz, 1H), 0.65-0.58 (m, 2H), 0.38 (d, J = 2.1 Hz, 2H) | 1.15 U 517.1 | 5 |
| 371 | 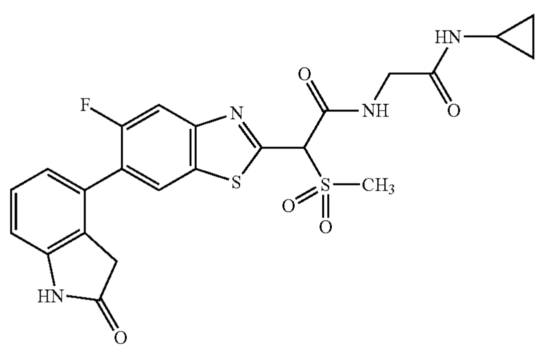 [SMILES: CS(=O)(=O)C(C(=O)NCC(=O)NC1CC1)c1nc2cc(F)c(-c3cccc4c3CC(=O)N4)cc2s1] | N-[(cyclopropyl-carbamoyl)methyl]-2-[5-fluoro-6-(2-oxo-2,3-dihydro-1H-indol-4-yl)-1,3-benzothiazol-2-yl]-2-methanesulfonyl-acetamide | 10.56 (s, 1H), 9.04 (t, J = 5.5 Hz, 1H), 8.29 (d, J = 7.0 Hz, 1H), 8.10-7.99 (m, 2H), 7.95-7.89 (m, 1H), 7.39-7.23 (m, 1H), 7.01 (d, J = 7.6 Hz, 1H), 6.92 (d, J = 7.9 Hz, 1H), 6.18 (s, 1H), 3.81 (d, J = 5.5 Hz, 1H), 3.55 (br. s., 2H), 3.27 (s, 3H), 2.66-2.57 (m, 1H), 0.66-0.56 (m, 2H), 0.38 (d, J = 2.1 Hz, 2H) | 1.2 U 517.1 | 5 |
| 372 | 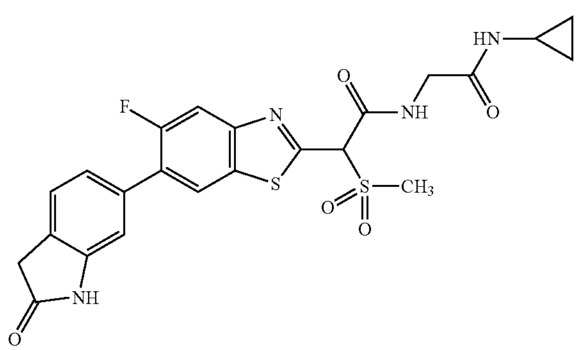 [SMILES: CS(=O)(=O)C(C(=O)NCC(=O)NC1CC1)c1nc2cc(F)c(-c3ccc4c(c3)NC(=O)C4)cc2s1] | N-[(cyclopropyl-carbamoyl)methyl]-2-[5-fluoro-6-(2-oxo-2,3-dihydro-1H-indol-6-yl)-1,3-benzothiazol-2-yl]-2-methanesulfonyl-acetamide | 10.61-10.47 (m, 1H), 9.09-8.97 (m, 1H), 8.30 (d, J = 7.3 Hz, 1H), 8.08-8.01 (m, 2H), 7.94 (s, 2H), 7.34 (d, J = 7.6 Hz, 1H), 7.15 (d, J = 7.3 Hz, 1H), 7.02 (s, 1H), 6.19 (s, 1H), 3.82 (d, J = 5.2 Hz, 2H), 3.54 (s, 1H), 3.26 (s, 2H), 2.67-2.60 (m, 1H), 0.62 (d, J = 5.8 Hz, 2H), 0.39 (br. s., 2H) | 1.21 U 517 | 6 |
| 373 | 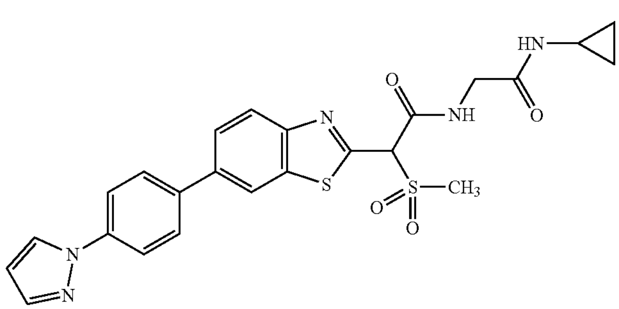 [SMILES: CS(=O)(=O)C(C(=O)NCC(=O)NC1CC1)c1nc2ccc(-c3ccc(-n4cccn4)cc3)cc2s1] | N-[(cyclopropyl-carbamoyl)methyl]-2-methanesulfonyl-2-{6-[4-(1H-pyrazol-1-yl)phenyl]-1,3-benzothiazol-2-yl}acetamide | 9.04 (t, J = 5.3 Hz, 1H), 8.62-8.49 (m, 2H), 8.16 (d, J = 8.5 Hz, 1H), 8.05-8.01 (m, 1H), 7.99-7.88 (m, 6H), 7.78 (s, 1H), 6.58 (s, 1H), 6.19 (s, 1H), 3.83 (d, J = 5.5 Hz, 1H), 3.27 (s, 3H), 2.66-2.59 (m, 1H), 0.65-0.59 (m, 2H), 0.39 (br. s., 2H) | 1.53 U 510 | 2 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 374 | 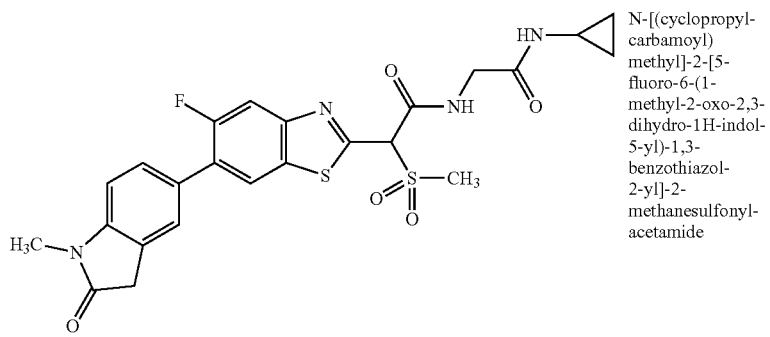 | N-[(cyclopropylcarbamoyl)methyl]-2-[5-fluoro-6-(1-methyl-2-oxo-2,3-dihydro-1H-indol-5-yl)-1,3-benzothiazol-2-yl]-2-methanesulfonylacetamide | 9.04 (t, J = 5.5 Hz, 1H), 8.26 (d, J = 7.6 Hz, 1H), 8.06-7.90 (m, 2H), 7.55-7.47 (m, 2H), 7.10 (d, J = 7.9 Hz, 1H), 6.16 (s, 1H), 3.81 (d, J = 5.5 Hz, 2H), 3.57 (s, 2H), 3.25 (s, 3H), 3.15 (s, 3H), 2.62 (d, J = 3.7 Hz, 1H), 0.68-0.59 (m, 2H), 0.38 (d, J = 2.1 Hz, 2H) | 1.31 U 531 | 9 |
| 375 | 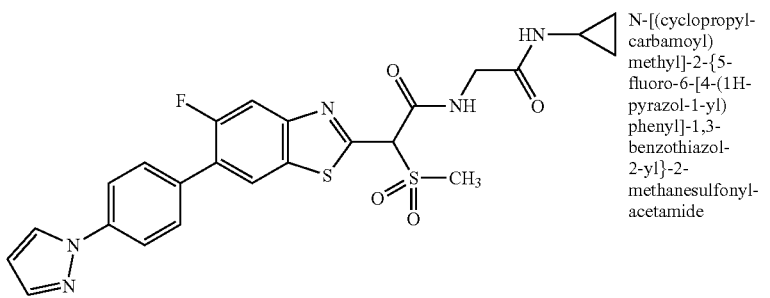 | N-[(cyclopropylcarbamoyl)methyl]-2-{5-fluoro-6-[4-(1H-pyrazol-1-yl)phenyl]-1,3-benzothiazol-2-yl}-2-methanesulfonylacetamide | 9.06 (t, J = 5.5 Hz, 1H), 8.50 (d, J = 2.1 Hz, 1H), 8.36 (d, J = 7.6 Hz, 1H), 8.12-8.00 (m, 2H), 7.98-7.92 (m, 2H), 7.79-7.70 (m, 3H), 6.57 (s, 1H), 6.16 (s, 1H), 3.81 (d, J = 5.5 Hz, 1H), 3.67 (s, 4H), 2.65-2.56 (m, 1H), 0.66-0.55 (m, 2H), 0.38 (br. s., 2H) | 1.59 U 528.1 | 2 |
| 377 | 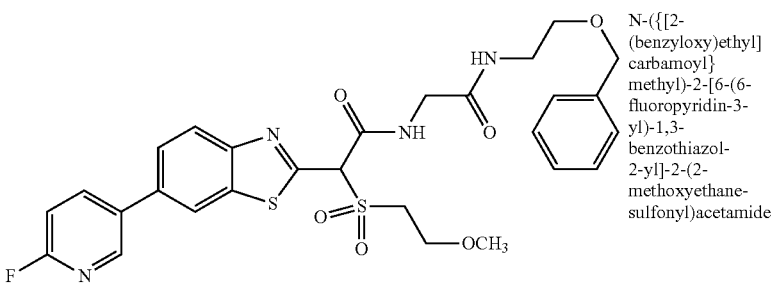 | N-({[2-(benzyloxy)ethyl]carbamoyl}methyl)-2-[6-(6-fluoropyridin-3-yl)-1,3-benzothiazol-2-yl]-2-(2-methoxyethanesulfonyl)acetamide | 8.94 (br. s., 1H), 8.58 (br. s., 1H), 8.48 (s, 1H), 8.31 (t, J = 8.0 Hz, 1H), 8.12 (d, J = 8.3 Hz, 1H), 8.03 (br. s., 1H), 7.84 (d, J = 8.3 Hz, 1H), 7.32-7.23 (m, 5H), 7.21-7.14 (m, 1H), 6.14 (s, 1H), 4.40 (s, 2H), 3.92-3.75 (m, 2H), 3.73-3.59 (m, 5H), 3.38 (m., 3H), 3.19 (s, 3H) | 1.65 O 601.2 | 1 |
| 378 | 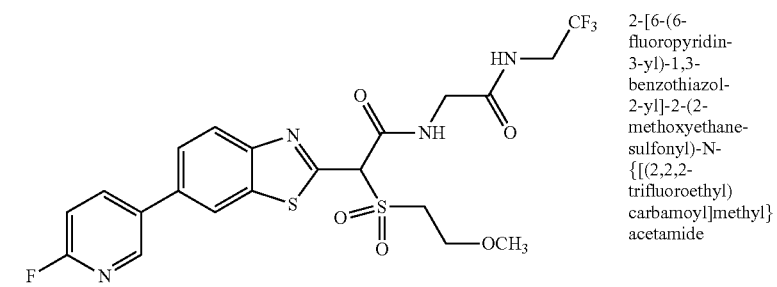 | 2-[6-(6-fluoropyridin-3-yl)-1,3-benzothiazol-2-yl]-2-(2-methoxyethanesulfonyl)-N-{[(2,2,2-trifluoroethyl)carbamoyl]methyl}acetamide | 9.11 (t, J = 5.6 Hz, 1H), 8.72 (t, J = 6.2 Hz, 1H), 8.67 (d, J = 2.5 Hz, 1H), 8.57 (d, J = 1.7 Hz, 1H), 8.41 (td, J = 8.2, 2.6 Hz, 1H), 8.21 (d, J = 8.5 Hz, 1H), 7.94 (dd, J = 8.5, 1.7 Hz, 1H), 7.36 (dd, J = 8.5, 2.8 Hz, 1H), 6.21 (s, 1H), 4.10-3.88 (m, 4H), 3.77 (t, J = 5.5 Hz, 2H), 3.76-3.70 (m, 2H), 3.28 (s, 3H) | 1.56 O 549.2 | 198 |

-continued

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 379 | 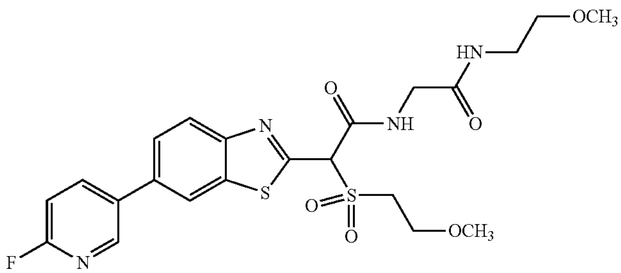 [SMILES: COCCNC(=O)CNC(=O)C(c1nc2ccc(-c3ccc(F)nc3)cc2s1)S(=O)(=O)CCOC] | 2-[6-(6-fluoropyridin-3-yl)-1,3-benzothiazol-2-yl]-2-(2-methoxyethane-sulfonyl)-N-{[(2-methoxyethyl)carbamoyl]methyl}acetamide | 9.02 (br. s., 1H), 8.67 (s, 1H), 8.57 (s, 1H), 8.41 (t, J = 8.1 Hz, 1H), 8.21 (d, J = 8.3 Hz, 1H), 8.07 (br. s., 1H), 7.94 (d, J = 8.3 Hz, 1H), 7.36 (d, J = 8.5 Hz, 1H), 6.22 (s, 1H), 3.99-3.83 (m, 2H), 3.82-3.68 (m, 4H), 3.36 (t, J = 5.2 Hz, 2H), 3.29 (s, 3H), 3.27 (br. s., 2H), 3.25 (s, 3H) | 1.31 O 525.2 | 108 |
| 380 | 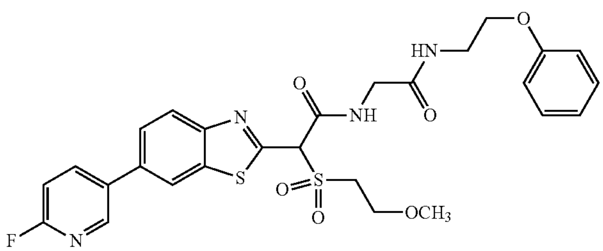 [SMILES: COCCS(=O)(=O)C(C(=O)NCC(=O)NCCOc1ccccc1)c1nc2ccc(-c3ccc(F)nc3)cc2s1] | 2-[6-(6-fluoropyridin-3-yl)-1,3-benzothiazol-2-yl]-2-(2-methoxyethane-sulfonyl)-N-{[(2-phenoxyethyl)carbamoyl]methyl}acetamide | 9.05 (br. s., 1H), 8.67 (s, 1H), 8.56 (s, 1H), 8.40 (t, J = 8.1 Hz, 1H), 8.27 (br. s., 1H), 8.21 (d, J = 8.3 Hz, 1H), 7.93 (d, J = 8.3 Hz, 1H), 7.36 (d, J = 8.5 Hz, 1H), 7.33-7.23 (m, 2H), 6.94 (d, J = 8.3 Hz, 3H), 6.22 (s, 1H), 4.05-3.99 (m, 2H), 3.93 (dd, J = 18.6, 4.5 Hz, 2H), 3.83-3.75 (m, 2H), 3.80-3.72 (m, 2H), 3.48 (d, J = 5.2 Hz, 2H), 3.28 (s, 3H) | 1.65 N 587.3 | 1 |
| 381 | 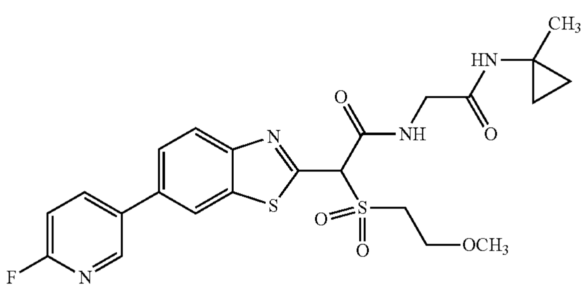 [SMILES: COCCS(=O)(=O)C(C(=O)NCC(=O)NC1(C)CC1)c1nc2ccc(-c3ccc(F)nc3)cc2s1] | 2-[6-(6-fluoropyridin-3-yl)-1,3-benzothiazol-2-yl]-2-(2-methoxyethane-sulfonyl)-N-{[(1-methylcyclopropyl)carbamoyl]methyl}acetamide | 9.00 (t, J = 5.4 Hz, 1H), 8.67 (d, J = 2.5 Hz, 1H), 8.57 (d, J = 1.7 Hz, 1H), 8.41 (td, J = 8.2, 2.6 Hz, 1H), 8.23-8.17 (m, 2H), 7.94 (dd, J = 8.5, 1.7 Hz, 1H), 7.36 (dd, J = 8.5, 2.8 Hz, 1H), 6.22 (s, 1H), 3.83-3.68 (m, 6H), 3.28 (s, 3H), 1.27 (s, 3H), 0.64-0.58 (m, 2H), 0.56-0.53 (m, 2H) | 1.5 O 521.2 | 15 |
| 382 | 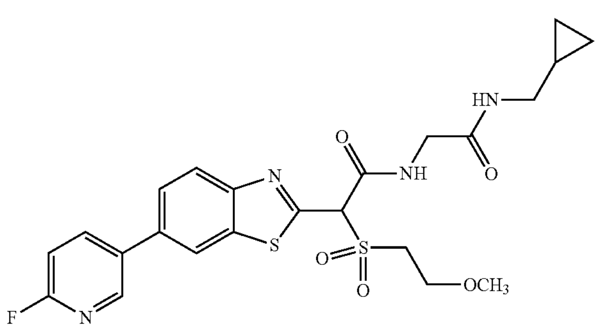 [SMILES: COCCS(=O)(=O)C(C(=O)NCC(=O)NCC1CC1)c1nc2ccc(-c3ccc(F)nc3)cc2s1] | N-{[(cyclopropyl-methyl)carbamoyl]methyl}-2-[6-(6-fluoropyridin-3-yl)-1,3-benzothiazol-2-yl]-2-(2-methoxyethane-sulfonyl)acetamide | 8.89 (t, J = 5.5 Hz, 1H), 8.50 (d, J = 2.5 Hz, 1H), 8.40 (d, J = 1.4 Hz, 1H), 8.24 (td, J = 8.2, 2.6 Hz, 1H), 8.04 (d, J = 8.5 Hz, 1H), 7.91 (t, J = 5.5 Hz, 1H), 7.77 (dd, J = 8.7, 1.8 Hz, 1H), 7.19 (dd, J = 8.5, 2.8 Hz, 1H), 6.06 (s, 1H), 3.81-3.67 (m, 2H), 3.65-3.52 (m, 4H), 3.11 (s, 3H), 2.85-2.75 (m, 2H), 0.83-0.63 (m, 1H), 0.31-0.16 (m, 2H), 0.06-0.07 (m, 2H) | 1.53 O 521.2 | 22 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 383 | 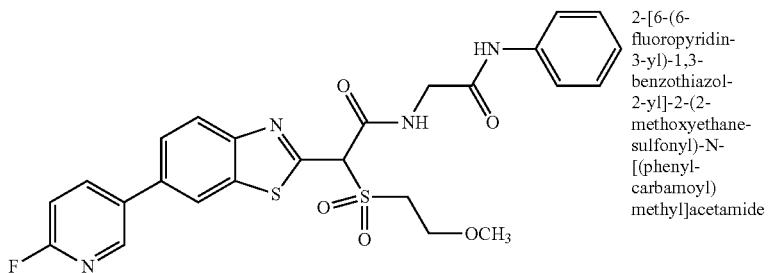 | 2-[6-(6-fluoropyridin-3-yl)-1,3-benzothiazol-2-yl]-2-(2-methoxyethane-sulfonyl)-N-[(phenyl-carbamoyl)methyl]acetamide | 8.66-8.50 (m, 2H), 8.38 (br. s., 1H), 8.19 (d, J = 8.8 Hz, 1H), 7.91 (br. s., 1H), 7.56 (d, J = 6.1 Hz, 2H), 7.31 (br. s., 4H), 7.06 (br. s., 1H), 6.25 (br. s., 1H), 4.17-4.01 (m, 2H), 3.81-3.70 (m, 4H), 3.28 (br. s., 3H) | 0.89 M 543.2 | 3 |
| 384 | 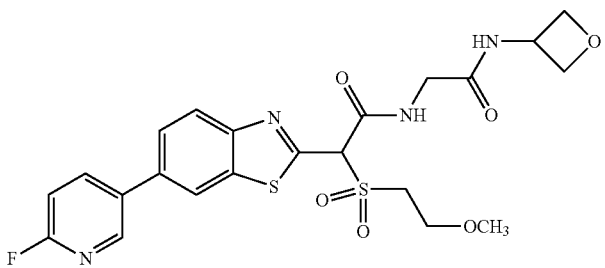 [SMILES: COCCS(=O)(=O)C(C(=O)NCC(=O)NC1COC1)c1nc2ccc(-c3ccc(F)nc3)cc2s1] | 2-[6-(6-fluoropyridin-3-yl)-1,3-benzothiazol-2-yl]-2-(2-methoxyethane-sulfonyl)-N-{[(oxetan-3-yl)carbamoyl]methyl}acetamide | 9.04 (br. s., 1H), 8.65 (br. s., 2H), 8.55 (br. s., 1H), 8.39 (br. s., 1H), 8.19 (d, J = 8.3 Hz, 1H), 7.92 (d, J = 8.3 Hz, 1H), 7.34 (d, J = 8.3 Hz, 1H), 6.20 (br. s., 1H), 4.81 (br. s., 1H), 4.71 (br. s., 2H), 4.46-4.36 (m, 2H), 3.98-3.85 (m, 2H), 3.81-3.68 (m, 4H), 3.27 (br. s., 3H) | 1.64 B 523.1 | 13 |
| 385 | 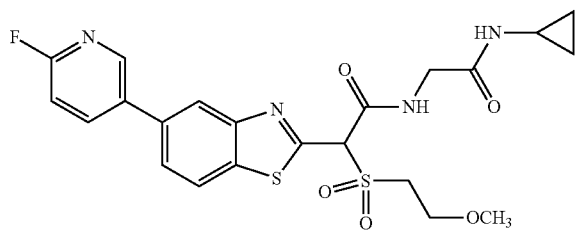 [SMILES: COCCS(=O)(=O)C(C(=O)NCC(=O)NC1CC1)c1nc2cc(-c3ccc(F)nc3)ccc2s1] | N-[(cyclopropyl-carbamoyl)methyl]-2-[5-(6-fluoropyridin-3-yl)-1,3-benzothiazol-2-yl]-2-(2-methoxyethane-sulfonyl)acetamide | 9.03 (br. s., 1H), 8.71 (br. s., 1H), 8.51-8.41 (m, 2H), 8.31 (d, J = 8.3 Hz, 1H), 8.06 (br. s., 1H), 7.90 (d, J = 8.3 Hz, 1H), 7.35 (d, J = 8.5 Hz, 1H), 6.24 (s, 1H), 3.99-3.69 (m, 6H), 3.29 (s, 3H), 2.65 (br. s., 1H), 0.64 (d, J = 6.6 Hz, 2H), 0.41 (br. s., 2H) | 0.77 M 507.1 | 13 |
| 386 | 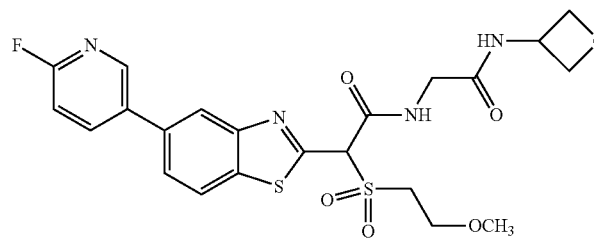 | 2-[5-(6-fluoropyridin-3-yl)-1,3-benzothiazol-2-yl]-2-(2-methoxyethane-sulfonyl)-N-{[(oxetan-3-yl)carbamoyl]methyl}acetamide | 9.05 (t, J = 5.5 Hz, 1H), 8.78-8.69 (m, 2H), 8.49-8.42 (m, 2H), 8.30 (d, J = 8.3 Hz, 1H), 7.90 (d, J = 8.5 Hz, 1H), 7.34 (dd, J = 8.4, 2.6 Hz, 1H), 6.23 (s, 1H), 4.89-4.79 (m, 1H), 4.76-4.68 (m, 2H), 4.48-4.38 (m, 2H), 3.99-3.86 (m, 2H), 3.84-3.70 (m, 4H), 3.29 (s, 3H) | 1.78 B 523.1 | 25 |

-continued

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 387 | 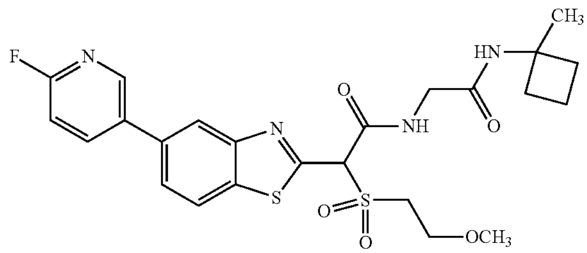 [SMILES: COCCS(=O)(=O)C(C(=O)NCC(=O)NC1(C)CCC1)c1nc2cc(-c3ccc(F)nc3)ccc2s1] | 2-[5-(6-fluoropyridin-3-yl)-1,3-benzothiazol-2-yl]-2-(2-methoxyethane-sulfonyl)-N-{[(1-methylcyclobutyl)carbamoyl]methyl}acetamide | 9.00 (br. s., 1H), 8.71 (s, 1H), 8.53-8.42 (m, 2H), 8.31 (d, J = 8.3 Hz, 1H), 8.04-7.87 (m, 2H), 7.35 (d, J = 8.5 Hz, 1H), 6.25 (s, 1H), 3.96-3.67 (m, 6H), 3.28 (s, 3H), 3.13 (d, J = 10.7 Hz, 1H), 2.25 (quin, J = 9.0 Hz, 2H), 1.90 (d, J = 5.5 Hz, 2H), 1.82-1.65 (m, 2H), 1.46-1.31 (m, 3H) | 0.86 M 535.2 | 28 |
| 388 | 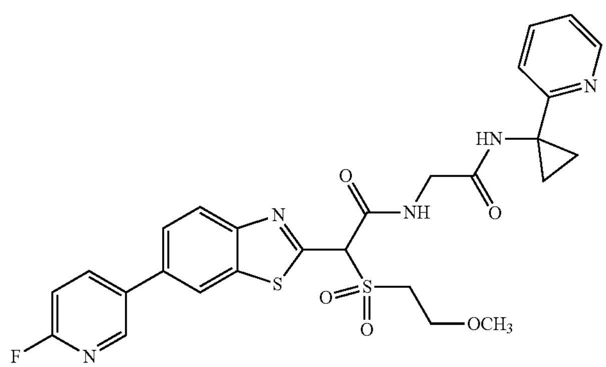 [SMILES: COCCS(=O)(=O)C(C(=O)NCC(=O)NC1(c2ccccn2)CC1)c1nc2ccc(-c3ccc(F)nc3)cc2s1] | 2-[6-(6-fluoropyridin-3-yl)-1,3-benzothiazol-2-yl]-2-(2-methoxyethane-sulfonyl)-N-({[1-(pyridin-2-yl)cyclopropyl]carbamoyl}methyl)acetamide | 9.11 (t, J = 5.0 Hz, 1H), 8.79 (s, 1H), 8.68-8.54 (m, 2H), 8.46-8.33 (m, 2H), 8.24-8.15 (m, 1H), 7.96-7.87 (m, 1H), 7.79-7.67 (m, 1H), 7.48-7.29 (m, 2H), 7.23-7.11 (m, 1H), 6.22 (s, 1H), 4.05-3.87 (m, 2H), 3.80-3.67 (m, 4H), 3.26 (s, 3H), 3.13-3.00 (m, 1H), 1.55-1.40 (m, 2H), 1.21-1.11 (m, 2H) | 1.23 O 584.2 | 48 |
| 389 | 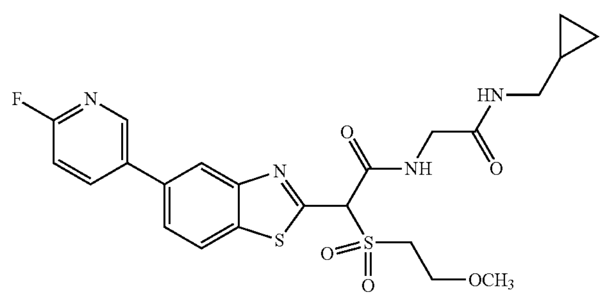 [SMILES: COCCS(=O)(=O)C(C(=O)NCC(=O)NCC1CC1)c1nc2cc(-c3ccc(F)nc3)ccc2s1] | N-{[(cyclopropylmethyl)carbamoyl]methyl}-2-[5-(6-fluoropyridin-3-yl)-1,3-benzothiazol-2-yl]-2-(2-methoxyethane-sulfonyl)acetamide | 8.88 (br. s., 1H), 8.55 (br. s., 1H), 8.33-8.24 (m, 1H), 8.14 (d, J = 8.0 Hz, 1H), 7.91 (br. s., 1H), 7.74 (d, J = 8.3 Hz, 1H), 7.18 (d, J = 8.3 Hz, 1H), 6.07 (s, 1H), 3.80-3.54 (m, 6H), 3.12 (s, 3H), 2.82 (br. s., 2H), 0.73 (br. s., 1H), 0.25 (d, J = 6.6 Hz, 2H), 0.00 (br. s., 2H) | 0.81 M 521.2 | 59 |
| 390 | 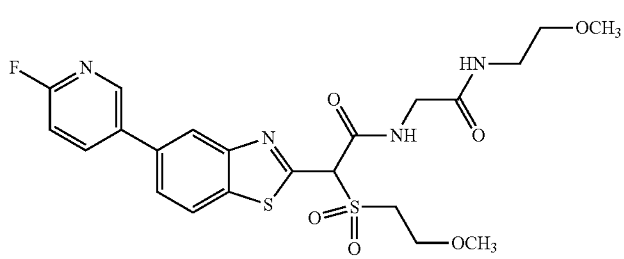 [SMILES: COCCNC(=O)CNC(=O)C(c1nc2cc(-c3ccc(F)nc3)ccc2s1)S(=O)(=O)CCOC] | 2-[5-(6-fluoropyridin-3-yl)-1,3-benzothiazol-2-yl]-2-(2-methoxyethane-sulfonyl)-N-{[(2-methoxyethyl)carbamoyl]methyl}acetamide | 9.02 (br. s., 1H), 8.71 (br. s., 1H), 8.52-8.42 (m, 2H), 8.30 (d, J = 7.2 Hz, 1H), 8.07 (br. s., 1H), 7.90 (d, J = 8.0 Hz, 1H), 7.34 (d, J = 7.7 Hz, 1H), 6.23 (br. s., 1H), 4.00-3.69 (m, 7H), 3.31-3.21 (m, 9H). | 0.75 M 525.1 | 102 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 391 | 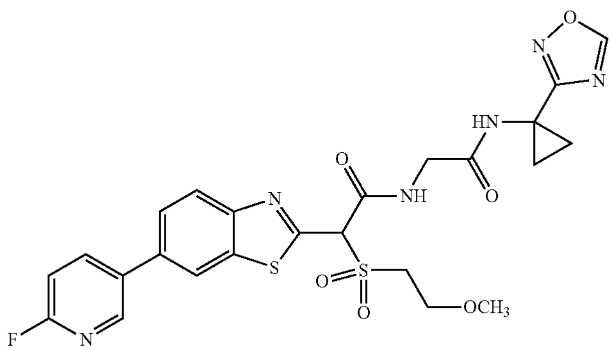 [SMILES: COCCS(=O)(=O)C(C(=O)NCC(=O)NC1(c2ncon2)CC1)c1nc2ccc(-c3ccc(F)nc3)cc2s1] | 2-[6-(6-fluoropyridin-3-yl)-1,3-benzothiazol-2-yl]-2-(2-methoxyethane-sulfonyl)-N-({[1-(1,2,4-oxadiazol-3-yl)cyclopropyl]carbamoyl}methyl)acetamide | 9.48-9.39 (m, 1H), 9.05 (t, J = 5.1 Hz, 1H), 8.95 (s, 1H), 8.67 (s, 1H), 8.61-8.56 (m, 1H), 8.40 (t, J = 8.1 Hz, 1H), 8.20 (d, J = 8.5 Hz, 1H), 7.93 (d, J = 8.5 Hz, 1H), 7.36 (d, J = 8.5 Hz, 1H), 6.22 (s, 1H), 4.01-3.87 (m, 2H), 3.81-3.67 (m, 4H), 3.28 (s, 3H), 3.13 (br. s., 1H), 1.41 (br. s., 2H), 1.29-1.18 (m, 2H) | 1.71 B 575.2 | 68 |
| 392 | 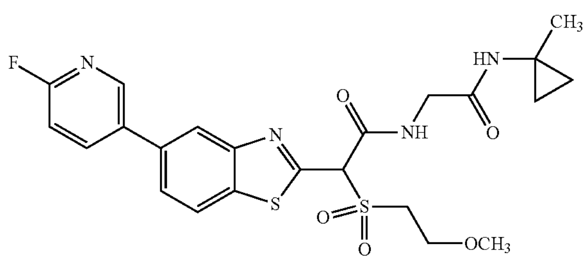 [SMILES: COCCS(=O)(=O)C(C(=O)NCC(=O)NC1(C)CC1)c1nc2cc(-c3ccc(F)nc3)ccc2s1] | 2-[5-(6-fluoropyridin-3-yl)-1,3-benzothiazol-2-yl]-2-(2-methoxyethane-sulfonyl)-N-{[(1-methylcyclopropyl)carbamoyl]methyl}acetamide | 8.98 (br. s., 1H), 8.70 (s, 1H), 8.48-8.41 (m, 2H), 8.33-8.15 (m, 2H), 7.88 (d, J = 8.5 Hz, 1H), 7.33 (d, J = 8.5 Hz, 1H), 6.22 (s, 1H), 3.95-3.62 (m, 7H), 3.27 (s, 3H), 1.34-1.20 (m, 3H), 0.65-0.46 (m, 4H) | 0.81 M 521.1 | 14 |
| 394 | 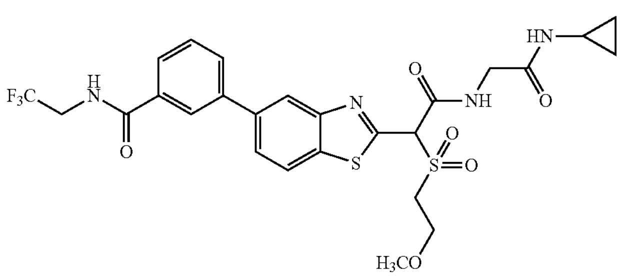 [SMILES: COCCS(=O)(=O)C(C(=O)NCC(=O)NC1CC1)c1nc2cc(-c3cccc(C(=O)NCC(F)(F)F)c3)ccc2s1] | 3-[2-({[(cyclopropylcarbamoyl)methyl]carbamoyl}(2-methoxyethane-sulfonyl)methyl)-1,3-benzothiazol-5-yl]-N-(2,2,2-trifluoroethyl)benzamide | 9.28 (t, J = 6.1 Hz, 1H), 9.01 (t, J = 5.2 Hz, 1H), 8.52 (s, 1H), 8.38-8.28 (m, 2H), 8.08-8.01 (m, 2H), 7.97-7.91 (m, 2H), 7.66 (t, J = 7.7 Hz, 1H), 6.24 (s, 1H), 4.22-4.12 (m, 2H), 3.95-3.72 (m, 6H), 3.29 (s, 3H), 2.69-2.61 (m, 1H), 0.64 (d, J = 6.3 Hz, 2H), 0.42 (d, J = 2.2 Hz, 2H) | 0.84 M 613.2 | 4 |
| 395 | 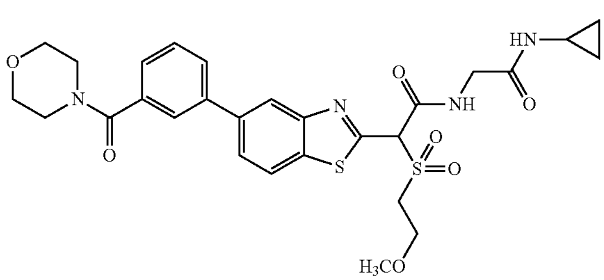 [SMILES: COCCS(=O)(=O)C(C(=O)NCC(=O)NC1CC1)c1nc2cc(-c3cccc(C(=O)N4CCOCC4)c3)ccc2s1] | N-[(cyclopropylcarbamoyl)methyl]-2-(2-methoxyethane-sulfonyl)-2-{5-[3-(morpholine-4-carbonyl)phenyl]-1,3-benzothiazol-2-yl}acetamide | 9.01 (t, J = 5.2 Hz, 1H), 8.42 (s, 1H), 8.28 (d, J = 8.3 Hz, 1H), 8.03 (d, J = 3.6 Hz, 1H), 7.90 (dd, J = 13.6, 8.1 Hz, 2H), 7.83 (s, 1H), 7.60 (t, J = 7.7 Hz, 1H), 7.45 (d, J = 7.4 Hz, 1H), 6.23 (s, 1H), 3.92 (s, 1H), 3.87-3.54 (m, 13H), 3.29 (s, 3H), 2.65 (d, J = 2.8 Hz, 1H), 0.64 (d, J = 6.9 Hz, 2H), 0.42 (br. s., 2H) | 0.76 M 601.2 | 4 |

| Ex. No. | Structure | Name | $^1$H NMR δ (500 MHz, DMSO-d$_6$, unless otherwise indicated) | LC/MS RT (min) Method M + H | EL IC$_{50}$ (nM) |
|---|---|---|---|---|---|
| 396 | 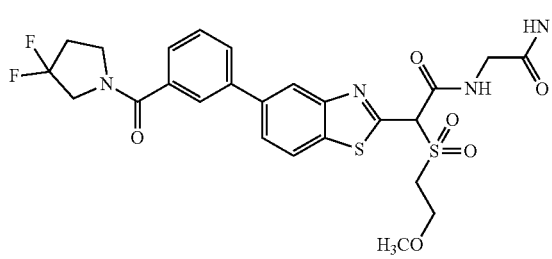 | N-[(cyclopropyl-carbamoyl)methyl]-2-{5-[3-(3,3-difluoro-pyrrolidine-1-carbonyl)phenyl]-1,3-benzothiazol-2-yl}-2-(2-methoxyethane-sulfonyl)acetamide | 9.01 (t, J = 5.2 Hz, 1H), 8.44 (s, 1H), 8.28 (d, J = 8.3 Hz, 1H), 8.03 (d, J = 3.6 Hz, 1H), 7.95 (d, J = 6.6 Hz, 2H), 7.90 (d, J = 8.5 Hz, 1H), 7.65-7.55 (m, 1H), 6.23 (s, 1H), 4.03-3.89 (m, 4H), 3.86-3.70 (m, 8H), 3.29 (s, 3H), 2.65 (d, J = 3.6 Hz, 1H), 0.64 (d, J = 7.2 Hz, 2H), 0.42 (br. s., 2H) | 0.83 M 621.3 | 8 |
| 397 | 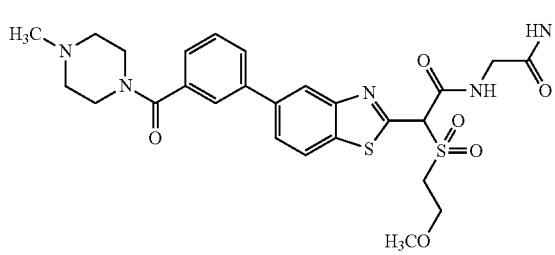 | N-[(cyclopropyl-carbamoyl)methyl]-2-(2-methoxyethane-sulfonyl)-2-{5-[3-(4-methylpiperazine-1-carbonyl)phenyl]-1,3-benzothiazol-2-yl}acetamide | 9.02 (br. s., 1H), 8.43 (s, 1H), 8.30 (d, J = 8.3 Hz, 1H), 8.04 (br. s., 1H), 7.96 (d, J = 7.7 Hz, 1H), 7.91-7.85 (m, 2H), 7.69-7.60 (m, 1H), 7.50 (d, J = 7.2 Hz, 1H), 6.23 (s, 1H), 3.95-3.72 (m, 6H), 3.29 (s, 3H), 3.14 (d, J = 15.4 Hz, 2H), 2.85 (br. s., 3H), 2.65 (br. s., 1H), 0.64 (d, J = 6.9 Hz, 2H), 0.42 (br. s., 2H) | 0.63 M 614.5 | 19 |
| 398 | 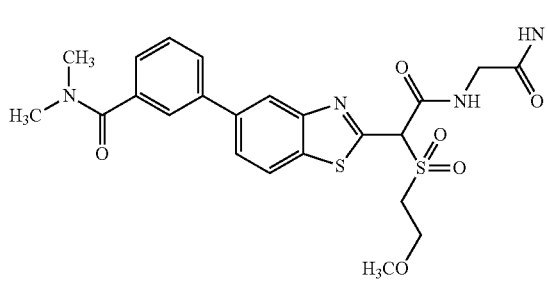 | 3-[2-({[(cyclopropyl-carbamoyl)methyl]carbamoyl}(2-methoxyethane-sulfonyl)methyl)-1,3-benzothiazol-5-yl]-N,N-dimethyl-benzamide | 9.03-8.98 (m, 1H), 8.41 (s, 1H), 8.27 (d, J = 8.5 Hz, 1H), 8.03 (d, J = 3.6 Hz, 1H), 7.92-7.87 (m, 2H), 7.81 (s, 1H), 7.59 (t, J = 7.7 Hz, 1H), 7.44 (d, J = 7.2 Hz, 1H), 6.23 (s, 1H), 3.92 (s, 2H), 3.88-3.73 (m, 4H), 3.29 (s, 3H), 3.07-2.95 (m, 6H), 2.65 (d, J = 2.5 Hz, 1H), 1.93 (s, 1H), 0.64 (d, J = 7.2 Hz, 2H), 0.42 (br. s., 2H) | 1.72 B 559.2 | 38 |
| 399 | 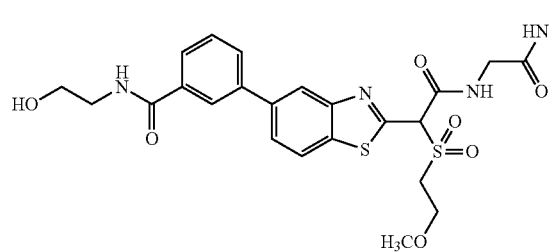 | 3-[2-({[(cyclopropyl-carbamoyl)methyl]carbamoyl}(2-methoxyethane-sulfonyl)methyl)-1,3-benzothiazol-5-yl]-N-(2-hydroxyethyl)benzamide | 9.01 (t, J = 5.4 Hz, 1H), 8.65 (t, J = 5.4 Hz, 1H), 8.51 (s, 1H), 8.34-8.26 (m, 2H), 8.06-7.86 (m, 4H), 7.61 (t, J = 7.6 Hz, 1H), 6.24 (s, 1H), 3.94-3.73 (m, 8H), 3.60-3.54 (m, 2H), 3.29 (s, 3H), 2.65 (d, J = 3.0 Hz, 1H), 0.64 (d, J = 7.2 Hz, 2H), 0.42 (br. s., 2H) | 0.69 M 575.2 | 63 |

| Ex. No. | Structure | Name | $^1$H NMR δ (500 MHz, DMSO-$d_6$, unless otherwise indicated) | LC/MS RT (min) Method M+H | EL IC$_{50}$ (nM) |
|---|---|---|---|---|---|
| 400 | 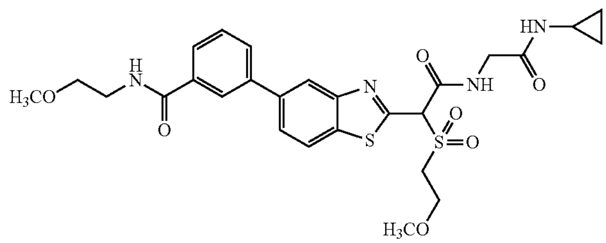 [SMILES: COCCNC(=O)c1cccc(-c2ccc3sc(C(C(=O)NCC(=O)NC4CC4)S(=O)(=O)CCOC)nc3c2)c1] | 3-[2-({[(cyclopropyl-carbamoyl)methyl]carbamoyl}(2-methoxyethane-sulfonyl)methyl)-1,3-benzothiazol-5-yl]-N-(2-methoxyethyl)benzamide | 9.01 (t, J = 5.4 Hz, 1H), 8.74 (br. s., 1H), 8.51 (s, 1H), 8.29 (d, J = 5.8 Hz, 2H), 8.07-7.81 (m, 4H), 7.61 (t, J = 7.6 Hz, 1H), 6.24 1H), 3.93-3.74 (m, 6H), 3.50 (d, J = 4.1 Hz, 4H), 3.30 (d, J = 7.2 Hz, 6H), 2.68-2.62 (m, H), 0.64 (d, J = 6.1 Hz, 2H), 0.42 (br. s., 2H) | 0.72 M 589.1 | 9 |
| 401 | 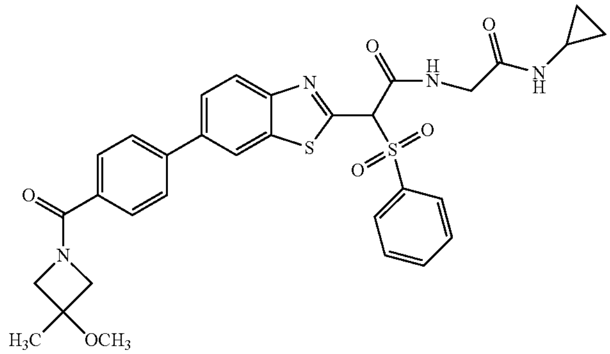 [SMILES: COC1(C)CN(C(=O)c2ccc(-c3ccc4nc(C(C(=O)NCC(=O)NC5CC5)S(=O)(=O)c5ccccc5)sc4c3)cc2)C1] | 2-(benzenesulfonyl)-N-[(cyclopropyl-carbamoyl)methyl]-2-{6-[4-(3-methoxy-3-methylazetidine-1-carbonyl)phenyl]-1,3-benzothiazol-2-yl}acetamide | 9.07 (t, J = 5.4 Hz, 1H), 8.51 (s, 1H), 8.08-7.99 (m, 2H), 7.84 (s, 2H), 7.79 (d, J = 8.3 Hz, 3H), 7.72-7.68 (m, 1H), 7.64-7.57 (m, 2H), 6.41 (s, 1H), 4.30 (d, J = 8.5 Hz, 1H), 4.19-4.11 (m, 1H), 4.05-3.97 (m, 1H), 3.94-3.79 (m, 4H), 3.75-3.65 (m, 1H), 3.21 (s, 3H), 2.67-2.60 (m, 1H), 1.45 (s, 3H), 0.68-0.61 (m, 2H), 0.45-0.38 (m, 2H) | 1.55 O 633.2 | 5 |
| 402 | 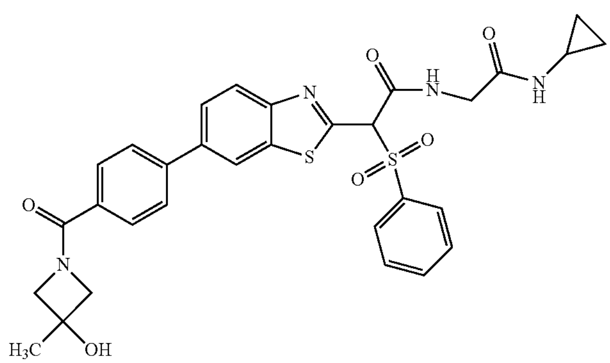 [SMILES: CC1(O)CN(C(=O)c2ccc(-c3ccc4nc(C(C(=O)NCC(=O)NC5CC5)S(=O)(=O)c5ccccc5)sc4c3)cc2)C1] | 2-(benzenesulfonyl)-N-[(cyclopropyl-carbamoyl)methyl]-2-{6-[4-(3-hydroxy-3-methylazetidine-1-carbonyl)phenyl]-1,3-benzothiazol-2-yl}acetamide | 9.11-9.04 (m, 1H), 8.58-8.43 (m, 1H), 8.09-8.01 (m, 2H), 7.90-7.83 (m, 2H), 7.80-7.75 (m, 3H), 7.71-7.68 (m, 1H), 7.64-7.58 (m, 2H), 6.40 (s, 1H), 5.86-5.61 (m, 1H), 4.26-4.15 (m, 2H), 3.92 (s, 3H), 3.89-3.82 (m, 1H), 3.73-3.66 (m, 1H), 2.66-2.59 (m, 1H), 1.42 (s, 3H), 0.64 (d, J = 7.4 Hz, 2H), 0.45-0.38 (m, 2H) | 133 O 619.2 | 6 |
| 403 | 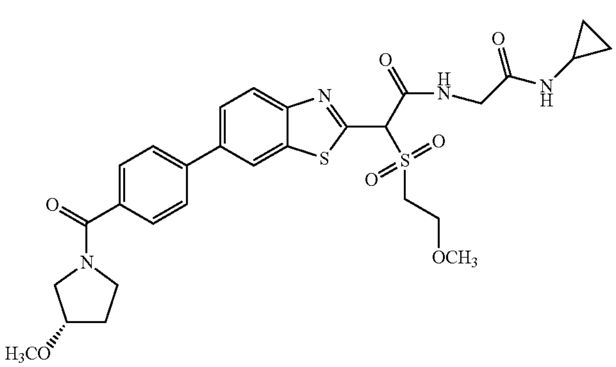 [SMILES: COCCS(=O)(=O)C(C(=O)NCC(=O)NC1CC1)c1nc2ccc(-c3ccc(C(=O)N4CC[C@H](OC)C4)cc3)cc2s1] | N-[(cyclopropyl-carbamoyl)methyl]-2-(2-methoxyethane-sulfonyl)-2-(6-{4-[(3S)-3-methoxy-pyrrolidine-1-carbonyl]phenyl}-1,3-benzothiazol-2-yl)acetamide | 9.07-8.96 (m, 1H), 8.56 (s, 1H), 8.23-8.17 (m, 1H), 8.04-8.00 (m, 1H), 7.95-7.90 (m, 1H), 7.88-7.83 (m, 2H), 7.70-7.65 (m, 2H), 6.22 (s, 1H), 4.07-3.94 (m, 1H), 3.92 (s, 3H), 3.86-3.71 (m, 6H), 3.32-3.26 (m, 4H), 3.19 (s, 2H), 2.68-2.61 (m, 1H), 2.07-1.94 (m, 2H), 0.64 (dd, J = 7.2, 1.9 Hz, 2H), 0.41 (dd, J = 4.1, 2.5 Hz, 2H). | 1.31 S 15.3 | 8 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 404 | 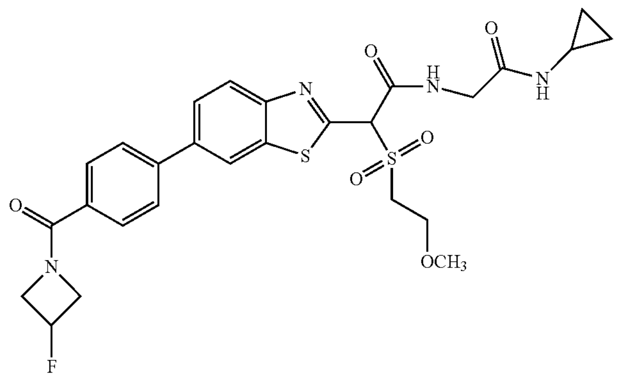 [SMILES: COCCS(=O)(=O)C(C(=O)NCC(=O)NC1CC1)c1nc2ccc(-c3ccc(C(=O)N4CC(F)C4)cc3)cc2s1] | N-[(cyclopropyl-carbamoyl)methyl]-2-{6-[4-3-fluoroazetidine-1-carbonyl)phenyl]-1,3-benzothiazol-2-yl}-2-(2-methoxyethane-sulfonyl)acetamide | 9.02 (br. s., 1H), 8.57 (br. s., 1H), 8.23-7.73 (m, 7H), 6.22 (br. s., 1H), 5.58-5.10 (m, 1H), 4.74-4.03 (m, 4H), 3.96-3.71 (m, 5H), 3.29 (br. s., 3H), 2.70-2.61 (m, 1H), 2.56 (br. s., 1H), 0.64 (br. s., 2H), 0.42 (br. s., 2H) | 1.31 S 589.2 | 10 |
| 405 | 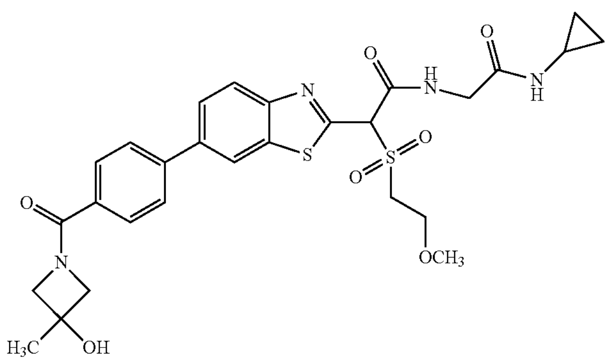 [SMILES: COCCS(=O)(=O)C(C(=O)NCC(=O)NC1CC1)c1nc2ccc(-c3ccc(C(=O)N4CC(C)(O)C4)cc3)cc2s1] | N-[(cyclopropyl-carbamoyl)methyl]-2-{6-[4-(3-hydroxy-3-methylazetidine-1-carbonyl)phenyl]-1,3-benzothiazol-2-yl}-2-(2-methoxyethane-sulfonyl)acetamide | 9.01 (t, J = 5.4 Hz, 1H), 8.56 (d, J = 1.7 Hz, 1H), 8.19 (d, J = 8.5 Hz, 1H), 8.05-8.00 (m, 1H), 7.94-7.90 (m, 1H), 7.89-7.84 (m, 2H), 7.80-7.76 (m, 2H), 6.22 (s, 1H), 4.29-4.12 (m, 3H), 4.00-3.90 (m, 3H), 3.87-3.70 (m, 5H), 3.29 (s, 3H), 2.70-2.60 (m, 1H), 1.42 (s, 3H), 0.68-0.61 (m, 2H), 0.45-0.38 (m, 2H). | 1.17 S 601.2 | 12 |
| 406 | 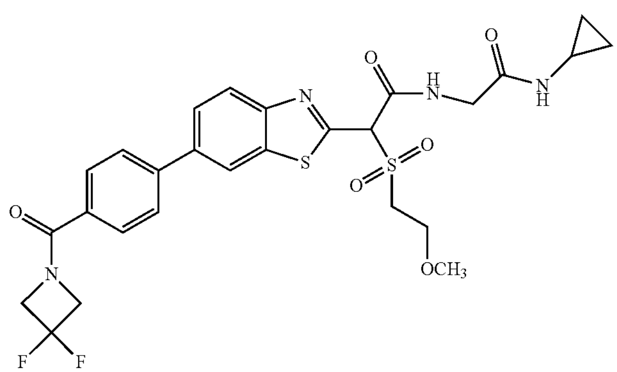 [SMILES: COCCS(=O)(=O)C(C(=O)NCC(=O)NC1CC1)c1nc2ccc(-c3ccc(C(=O)N4CC(F)(F)C4)cc3)cc2s1] | N-[(cyclopropyl-carbamoyl)methyl]-2-{6-[4-(3,3-difluoroazetidine-1-carbonyl)phenyl]-1,3-benzothiazol-2-yl}-2-(2-methoxyethane-sulfonyl)acetamide | 9.01 (t, J = 5.5 Hz, 1H), 8.64-8.55 (m, 1H), 8.21-8.17 (m, 1H), 8.05-8.01 (m, 1H), 7.96-7.93 (m, 1H), 7.90-7.88 (m, 2H), 7.86-7.79 (m, 2H), 6.22 (s, 1H), 5.06-4.39 (m, 4H), 3.91 (s, 1H), 3.86-3.71 (m, 5H), 3.29 (s, 3H), 2.68-2.61 (m, 1H), 0.67-0.60 (m, 2H), 0.45-0.38 (m, 2H) | 1.45 O 607.2 | 13 |
| 407 | 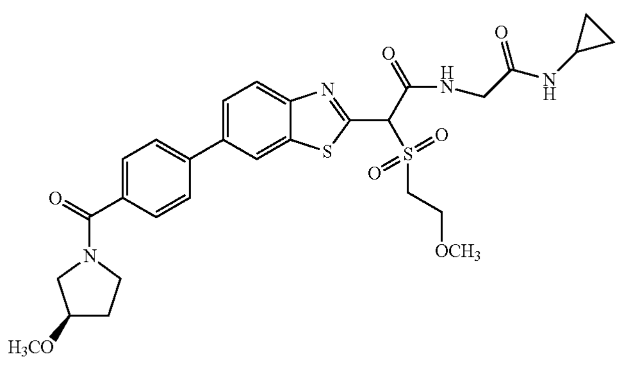 [SMILES: COCCS(=O)(=O)C(C(=O)NCC(=O)NC1CC1)c1nc2ccc(-c3ccc(C(=O)N4CC[C@@H](OC)C4)cc3)cc2s1] | N-[(cyclopropyl-carbamoyl)methyl]-2-(2-methoxyethane-sulfonyl)-2-(6-{4-[(3R)-3-methoxy-pyrrolidine-1-carbonyl]phenyl}-1,3-benzothiazol-2-yl)acetamide | 9.07-8.96 (m, 1H), 8.56 (s, 1H), 8.23-8.17 (m, 1H), 8.04-8.00 (m, 1H), 7.95-7.90 (m, 1H), 7.88-7.83 (m, 2H), 7.70-7.65 (m, 2H), 6.22 (s, 1H), 4.07-3.94 (m, 1H), 3.92 (s, 3H), 3.86-3.71 (m, 6H), 3.32-3.26 (m, 4H), 3.19 (s, 2H), 2.68-2.61 (m, 1H), 2.07-1.94 (m, 2H), 0.64 (dd, J = 7.2, 1.9 Hz, 2H), 0.41 (dd, J = 4.1, 2.5 Hz, 2H). | 1.31 O 615.3 | 24 |

-continued

| Ex. No. | Structure | Name | $^1$H NMR δ (500 MHz, DMSO-d$_6$, unless otherwise indicated) | LC/MS RT (min) Method M + H | EL IC$_{50}$ (nM) |
|---|---|---|---|---|---|
| 408 | 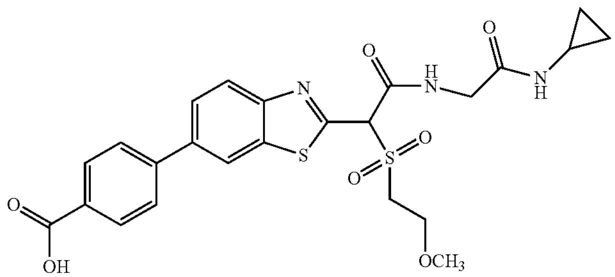 [SMILES: COCCS(=O)(=O)C(C(=O)NCC(=O)NC1CC1)c1nc2ccc(-c3ccc(C(=O)O)cc3)cc2s1] | 4-[2-({[(cyclopropyl-carbamoyl)methyl] carbamoyl}(2-methoxyethane-sulfonyl)methyl)-1,3-benzothiazol-6-yl]benzoic acid | 13.01 (br. s., 1H), 9.09-8.96 (m, 1H), 8.59 (d, J = 1.7 Hz, 1H), 8.22-8.17 (m, 1H), 8.07 (s, 2H), 8.05-8.01 (m, 1H), 7.97-7.91 (m, 3H), 7.88-7.75 (m, 1H), 6.23 (s, 1H), 3.88-3.69 (m, 5H), 3.29 (s, 3H), 2.69-2.62 (m, 1H), 0.69-0.60 (m, 2H), 0.47-0.32 (m, 2H). | 1.26 O 532.1 | 48 |
| 409 | 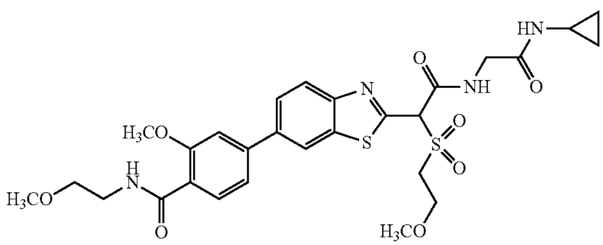 [SMILES: COCCNC(=O)c1ccc(-c2ccc3nc(C(C(=O)NCC(=O)NC4CC4)S(=O)(=O)CCOC)sc3c2)cc1OC] | 4-[2-({[(cyclopropyl-carbamoyl)methyl] carbamoyl}(2-methoxyethane-sulfonyl)methyl)-1,3-benzothiazol-6-yl]-2-methoxy-N-(2-methoxyethyl) benzamide | 8.64-8.56 (m, 1H), 8.32-8.25 (m, 1H), 8.20-8.16 (m, 1H), 8.04-7.90 (m, 3H), 7.74-7.69 (m, 1H), 7.58-7.40 (m, 3H), 4.03 (s, 3H), 3.85-3.70 (m, 6H), 3.48 (d, J = 2.5 Hz, 4H), 3.31-3.30 (m, 3H), 3.27 (s, 3H), 2.68-2.60 (m, 1H), 0.68-0.59 (m, 2H), 0.47-0.33 (m, 2H) | 1.33 N 619.2 | 23 |
| 410 | 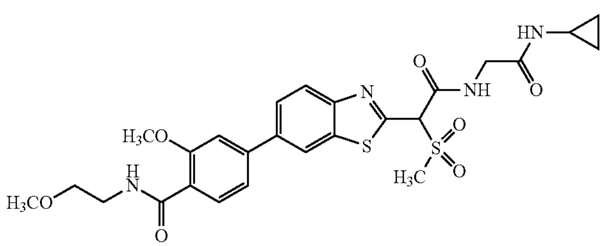 [SMILES: COCCNC(=O)c1ccc(-c2ccc3nc(C(C(=O)NCC(=O)NC4CC4)S(C)(=O)=O)sc3c2)cc1OC] | 4-[2-({[(cyclopropyl-carbamoyl)methyl] carbamoyl}(methanesulfonyl)methyl)-1,3-benzothiazol-6-yl]-2-methoxy-N-(2-methoxyethyl) benzamide | 9.13-8.99 (m, 1H), 8.67-8.57 (m, 1H), 8.36-8.29 (m, 2H), 8.25-8.16 (m, 1H), 8.10-8.03 (m, 1H), 8.01-7.89 (m, 2H), 7.58-7.36 (m, 2H), 4.04 (s, 3H), 3.91-3.70 (m, 2H), 3.49 (d, J = 2.5 Hz, 4H), 3.28 (s, 3H), 3.17 (s, 3H), 2.75-2.59 (m, 1H), 1.34-1.21 (m, 2H), 1.18-1.11 (m, 2H) | 0.78 N 574.9 | 53 |
| 412 | 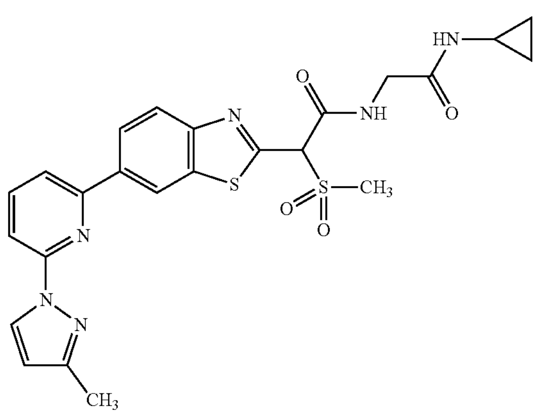 [SMILES: Cc1ccn(-c2cccc(-c3ccc4nc(C(C(=O)NCC(=O)NC5CC5)S(C)(=O)=O)sc4c3)n2)n1] | N-[(cyclopropyl-carbamoyl) methyl]-2-methanesulfonyl-2-{6-[6-(3-methyl-1H-pyrazol-1-yl) pyridin-2-yl]-1,3-benzothiazol-2-yl}acetamide | 9.11-9.02 (m, 2H), 8.82 (d, J = 2.1 Hz, 1H), 8.40 (d, J = 8.5 Hz, 1H), 8.19 (d, J = 8.5 Hz, 1H), 8.10-7.96 (m, 3H), 7.82 (d, J = 7.9 Hz, 1H), 6.43 (d, J = 1.8 Hz, 1H), 6.20 (s, 1H), 3.83 (d, J = 5.2 Hz, 2H), 3.44 (br. s., 1H), 3.28 (s, 2H), 2.63 (d, J = 3.7 Hz, 1H), 2.41-2.25 (m, 3H), 0.62 (d, J = 6.4 Hz, 2H), 0.39 (br. s., 2H) | 1.69 S 525.1 | 14 |

| Ex. No. | Structure | Name | $^1$H NMR δ (500 MHz, DMSO-d$_6$, unless otherwise indicated) | LC/MS RT (min) ethod M + H | EL IC$_{50}$ (nM) |
|---|---|---|---|---|---|
| 413 | 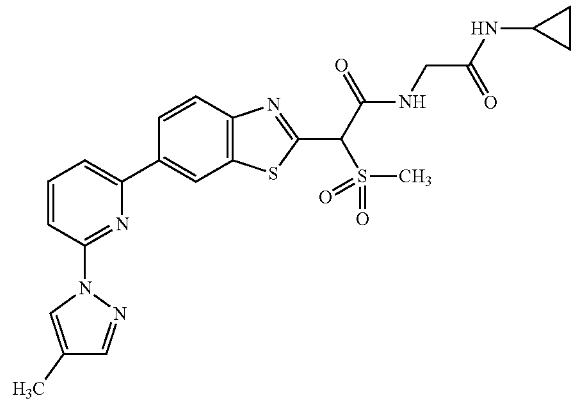 [SMILES: Cc1cnn(-c2cccc(-c3ccc4nc(C(C(=O)NCC(=O)NC5CC5)S(C)(=O)=O)sc4c3)n2)c1] | N-[(cyclopropylcarbamoyl)methyl]-2-methanesulfonyl-2-{6-[6-(4-methyl-1H-pyrazol-1-yl)pyridin-2-yl]-1,3-benzothiazol-2-yl}acetamide | 9.11-9.01 (m, 1H), 8.72 (s, 1H), 8.41 (d, J = 8.8 Hz, 1H), 8.19 (d, J = 8.5 Hz, 1H), 8.12-7.97 (m, 4H), 7.84 (d, J = 7.9 Hz, 1H), 7.67 (s, 1H), 6.21 (s, 1H), 3.83 (d, J = 5.5 Hz, 2H), 3.43 (br. s., 1H), 3.29 (s, 2H), 2.68-2.59 (m, 1H), 2.16 (s, 3H), 0.62 (d, J = 7.0 Hz, 2H), 0.39 (br. s., 2H) | 1.7 U 525.1 | 7 |
| 414 | 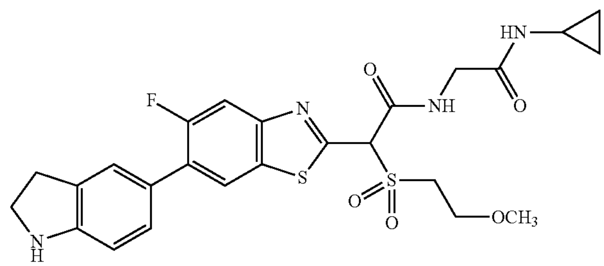 [SMILES: COCCS(=O)(=O)C(C(=O)NCC(=O)NC1CC1)c1nc2cc(F)c(-c3ccc4c(c3)CCN4)cc2s1] | N-[(cyclopropylcarbamoyl)methyl]-2-[6-(2,3-dihydro-1H-indol-5-yl)-5-fluoro-1,3-benzothiazol-2-yl]-2-(2-methoxyethanesulfonyl)acetamide | 9.06 (t, J = 5.2 Hz, 1H), 8.26 (d, J = 7.6 Hz, 1H), 8.08 (d, J = 3.4 Hz, 1H), 8.04-7.99 (m, 1H), 7.35 (s, 1H), 7.30-7.23 (m, 1H), 6.67 (d, J = 7.9 Hz, 1H), 6.23 (s, 1H), 3.88 (br. s., 6H), 3.54 (br. s., 1H), 3.34 (s, 3H), 3.05 (s, 3H), 2.73-2.65 (m, 1H), 0.70 (d, J = 7.0 Hz, 2H), 0.47 (br. s., 2H) | 1.02 U 548.1 | 3 |
| 415 | 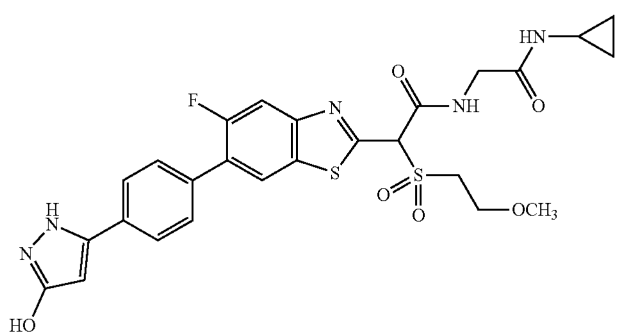 [SMILES: COCCS(=O)(=O)C(C(=O)NCC(=O)NC1CC1)c1nc2cc(F)c(-c3ccc(-c4cc(O)n[nH]4)cc3)cc2s1] | N-[(cyclopropylcarbamoyl)methyl]-2-{5-fluoro-6-[4-(3-hydroxy-1H-pyrazol-5-yl)phenyl]-1,3-benzothiazol-2-yl}-2-(2-methoxyethanesulfonyl)acetamide | 8.96 (t, J = 5.3 Hz, 1H), 8.33 (d, J = 7.6 Hz, 1H), 8.10-7.94 (m, 2H), 7.80-7.69 (m, 2H), 7.65-7.49 (m, 2H), 6.15 (s, 1H), 5.97-5.87 (m, 1H), 3.79-3.62 (m, 6H), 3.22 (s, 3H), 2.63-2.52 (m, 1H), 0.57 (d, J = 5.2 Hz, 2H), 0.34 (d, J = 2.7 Hz, 2H) | 1.16 U 588.1 | 49 |
| 416 | 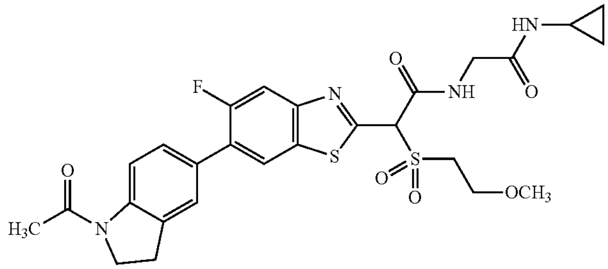 [SMILES: COCCS(=O)(=O)C(C(=O)NCC(=O)NC1CC1)c1nc2cc(F)c(-c3ccc4c(c3)CCN4C(C)=O)cc2s1] | 2-[6-(1-acetyl-2,3-dihydro-1H-indol-5-yl)-5-fluoro-1,3-benzothiazol-2-yl]-N-[(cyclopropylcarbamoyl)methyl]-2-(2-methoxyethanesulfonyl)acetamide | 8.99 (t, J = 5.3 Hz, 1H), 8.29 (d, J = 7.3 Hz, 1H), 8.13 (d, J = 8.2 Hz, 1H), 8.05-7.98 (m, 2H), 7.96-7.90 (m, 1H), 7.49-7.45 (m, 1H), 7.42-7.37 (m, 1H), 6.25-6.10 (m, 1H), 4.19-4.10 (m, 2H), 3.84-3.67 (m, 4H), 3.41 (s, 1H), 3.26 (s, 2H), 3.24-3.09 (m, 3H), 2.67-2.59 (m, 1H), 2.23-2.16 (m, 3H), 0.62 (d, J = 7.0 Hz, 2H), 0.39 (d, J = 2.4 Hz, 2H) | 1.44 S 589.1 | 11 |

| Ex. No. | Structure | Name | ¹H NMR δ (500 MHz, DMSO-d₆, unless otherwise indicated) | LC/MS RT (min) Method M + H | EL IC$_{50}$ (nM) |
|---|---|---|---|---|---|
| 417 | 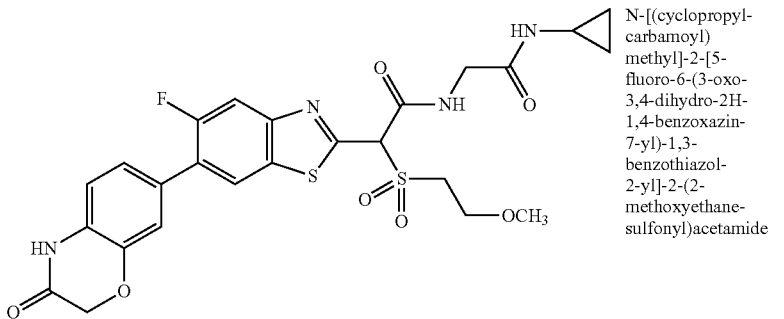 | N-[(cyclopropyl-carbamoyl)methyl]-2-[5-fluoro-6-(3-oxo-3,4-dihydro-2H-1,4-benzoxazin-7-yl)-1,3-benzothiazol-2-yl]-2-(2-methoxyethane-sulfonyl)acetamide | 10.83 (s, 1H), 8.99 (s, 1H), 8.27 (d, J = 7.6 Hz, 1H), 8.09-7.92 (m, 2H), 7.30-6.97 (m, 4H), 6.19 (s, 1H), 4.74-4.55 (m, 2H), 3.81 (s, 5H), 3.27 (s, 3H), 2.66-2.57 (m, 1H), 0.66-0.57 (m, 2H), 0.39 (br. s., 2H) | 1.41 U 577.1 | 35 |
| 418 | 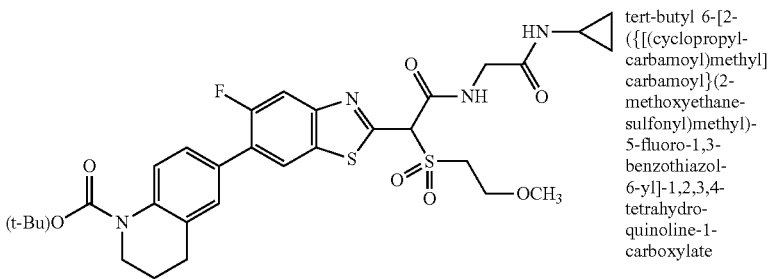 | tert-butyl 6-[2-({[(cyclopropyl-carbamoyl)methyl]carbamoyl}(2-methoxyethane-sulfonyl)methyl)-5-fluoro-1,3-benzothiazol-6-yl]-1,2,3,4-tetrahydro-quinoline-1-carboxylate | 8.99 (t, J = 5.3 Hz, 1H), 8.30 (d, J = 7.6 Hz, 1H), 8.08-7.92 (m, 2H), 7.72 (d, J = 9.2 Hz, 1H), 7.36 (s, 2H), 6.19 (s, 1H), 3.83-3.64 (m, 8H), 3.27 (s, 3H), 2.82-2.76 (m, 2H), 2.67-2.59 (m, 1H), 1.94-1.81 (m, 2H), 1.48 (s, 9H), 0.62 (d, J = 5.8 Hz, 2H), 0.39 (d, J = 2.4 Hz, 2H) | 2.16 U 661.1 | 9 |
| 419 | 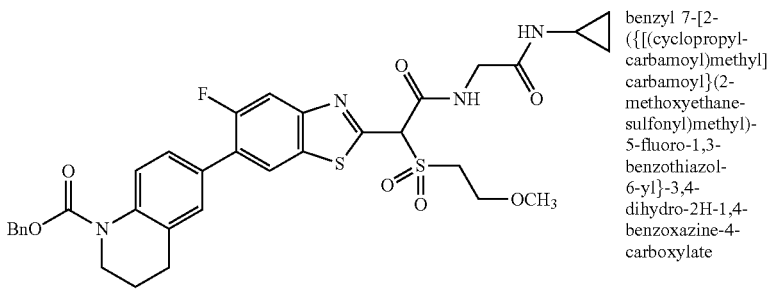 | benzyl 7-[2-({[(cyclopropyl-carbamoyl)methyl]carbamoyl}(2-methoxyethane-sulfonyl)methyl)-5-fluoro-1,3-benzothiazol-6-yl}-3,4-dihydro-2H-1,4-benzoxazine-4-carboxylate | 8.93 (s, 1H), 8.26 (d, J = 7.3 Hz, 1H), 8.02-7.87 (m, 3H), 7.43-7.25 (m, 6H), 7.13-7.04 (m, 2H), 6.12 (s, 1H), 5.19 (s, 2H), 4.32-4.13 (m, 2H), 3.94-3.59 (m, 7H), 3.38-3.32 (m, 1H), 3.21 (s, 2H), 2.57 (dd, J = 7.2, 3.5 Hz, 1H), 0.61-0.52 (m, 2H), 0.33 (d, J = 2.4 Hz, 2H) | 2.01 O 697 | 9 |
| 420 | 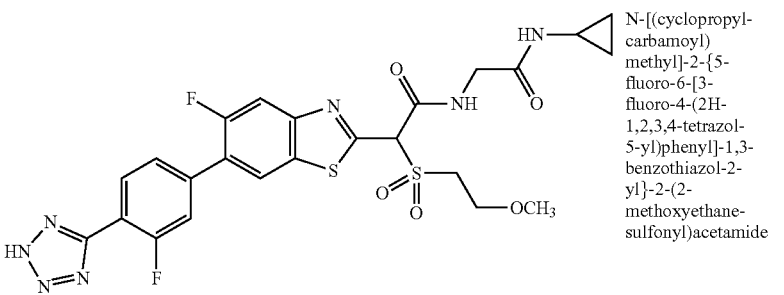 | N-[(cyclopropyl-carbamoyl)methyl]-2-{5-fluoro-6-[3-fluoro-4-(2H-1,2,3,4-tetrazol-5-yl)phenyl]-1,3-benzothiazol-2-yl}-2-(2-methoxyethane-sulfonyl)acetamide | 9.01 (t, J = 5.4 Hz, 1H), 8.49 (d, J = 7.4 Hz, 1H), 8.25-8.09 (m, 2H), 8.02 (d, J = 3.9 Hz, 1H), 7.74-7.62 (m, 2H), 6.23 (s, 1H), 3.90 (s, 1H), 3.85-3.69 (m, 6H), 3.28 (s, 3H), 2.68-2.60 (m, 1H), 0.63 (d, J = 7.2 Hz, 2H), 0.46-0.36 (m, 2H) | 1.34 U 592 | 11 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 422 | 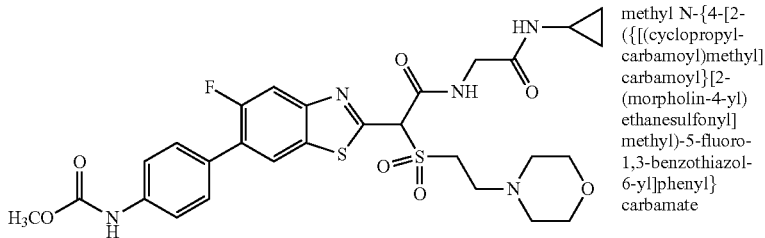 | methyl N-{4-[2-({[(cyclopropylcarbamoyl)methyl]carbamoyl}[2-(morpholin-4-yl)ethanesulfonyl]methyl)-5-fluoro-1,3-benzothiazol-6-yl]phenyl}carbamate | 9.82 (s, 1H), 8.85 (br. s., 1H, NH of glycine amide), 8.24 (d, J = 5.9 Hz, 1H), 8.03 (br. s., 1H), 7.98 (d, J = 11.4 Hz, 1H), 7.63-7.57 (m, 2H), 7.57-7.51 (m, 2H), 3.83 (d, J = 5.3 Hz, 2H), 3.70 (s, 3H), 3.62 (t, J = 7.0 Hz, 2H), 3.54 (br. s., 4H), 2.80 (br. s., 2H), 2.64 (td, J = 7.3, 3.7 Hz, 1H), 2.42 (br. s., 4H), 0.70-0.56 (m, 2H), 0.45-0.35 (m, 2H) | 1.59 B 634.3 | 3 |
| 423 | 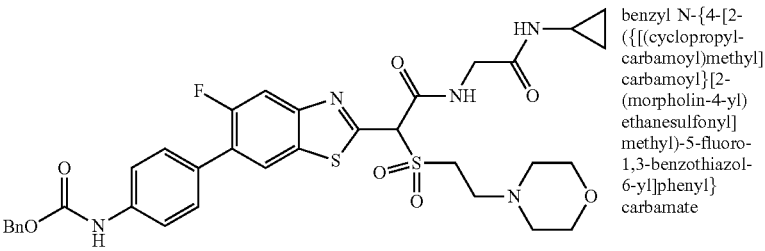 | benzyl N-{4-[2-({[(cyclopropylcarbamoyl)methyl]carbamoyl}[2-(morpholin-4-yl)ethanesulfonyl]methyl)-5-fluoro-1,3-benzothiazol-6-yl]phenyl}carbamate | 9.95 (br. s., 1H), 8.85 (br. s., 1H), 8.25 (d, J = 5.9 Hz, 1H), 8.03 (br. s., 1H), 7.98 (d, J = 10.8 Hz, 1H), 7.66-7.59 (m, 2H), 7.58-7.50 (m, 2H), 7.49-7.33 (m, 5H), 5.19 (s, 2H), 3.83 (d, J = 5.1 Hz, 2H), 3.61 (t, J = 7.0 Hz, 2H), 3.54 (br. s., 4H), 2.80 (br. s., 2H), 2.64 (td, J = 7.3, 3.9 Hz, 1H), 2.42 (br. s., 4H), 0.68-0.57 (m, 2H), 0.44-0.36 (m, 2H) | 0.82 M 710.6 | 1 |
| 424 | 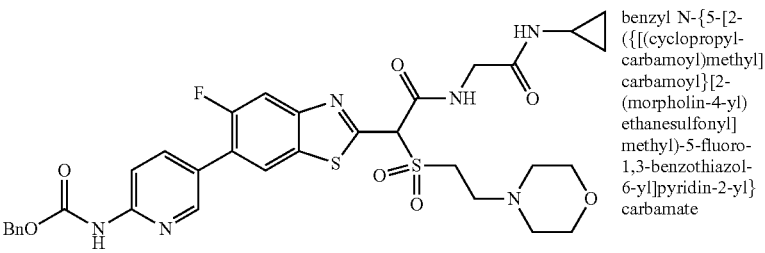 | benzyl N-{5-[2-({[(cyclopropylcarbamoyl)methyl]carbamoyl}[2-(morpholin-4-yl)ethanesulfonyl]methyl)-5-fluoro-1,3-benzothiazol-6-yl]pyridin-2-yl}carbamate | 10.48 (s, 1H), 8.85 (br. s., 1H), 8.52 (s, 1H), 8.32 (br. s., 1H), 8.09-7.93 (m, 4H), 7.49-7.39 (m, 4H), 7.38-7.32 (m, 1H), 5.22 (s, 2H), 3.83 (d, J = 5.1 Hz, 2H), 3.62 (t, J = 6.7 Hz, 2H), 3.54 (br. s., 4H), 2.81 (br. s., 2H), 2.64 (ddt, J = 11.1, 7.4, 4.0 Hz, 1H), 2.43 (br. s., 4H), 0.69-0.58 (m, 2H), 0.45-0.34 (m, 2H) | 1.77 B 711.3 | 15 |

-continued

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 426 | 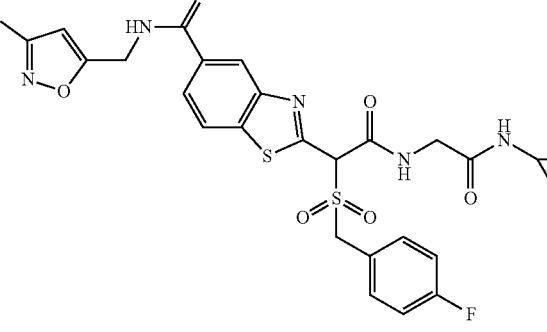 | 2-({[(cyclopropyl-carbamoyl)methyl] carbamoyl}(4-fluorophenyl) methanesulfonyl-methyl)-N-{[3-(propan-2-yl)-1,2-oxazol-5-yl] methyl}-1,3-benzothiazole-5-carboxamide | 9.38 (t, J = 5.5 Hz, 1H), 9.11 (t, J = 5.3 Hz, 1H), 8.67 (s, 1H), 8.29 (d, J = 8.5 Hz, 1H), 8.09-7.98 (m, 1H), 7.55-7.44 (m, 2H), 7.42-7.35 (m, 1H), 7.25 (t, J = 8.9 Hz, 2H), 7.07 (br. s., 1H), 6.37 (s, 1H), 4.82 (q, J = 13.7 Hz, 2H), 4.68-4.53 (m, 3H), 3.89-3.74 (m, 2H), 2.99 (dt, J = 13.7, 6.9 Hz, 1H), 2.66 (dt, J = 7.0, 3.5 Hz, 1H), 1.22 (d, J = 7.0 Hz, 6H), 0.65 (d, J = 5.8 Hz, 2H), 0.49-0.33 (m, 2H). | 1.55 N 628 | 62 |
| 427 | 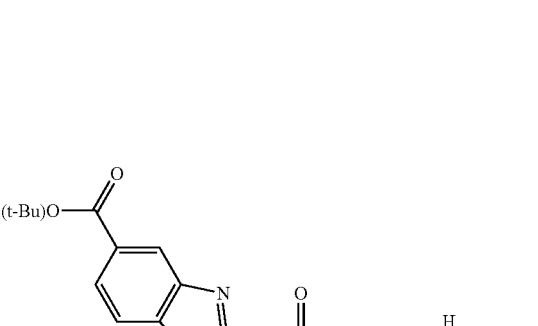 | tert-butyl 2-({[(cyclopropyl-carbamoyl)methyl] carbamoyl}(2-methoxyethane-sulfonyl)methyl)-1,3-benzothiazole-5-carboxylate | (400 MHz, DMSO-$d_6$) 9.09-8.95 (m, 1H), 8.60-8.50 (m, 1H), 8.30 (d, J = 8.6 Hz, 1H), 8.07-7.96 (m, 2H), 6.23 (s, 1H), 3.95-3.64 (m, 4H), 3.27 (s, 3H), 2.71-2.58 (m, 1H), 1.64-1.49 (m, 9H), 1.25 (br. s., 2H), 0.64 (dd, J = 7.2, 1.9 Hz, 2H), 0.45-0.29 (m, 2H). | 1.92 B 512 | 66 |
| 428 | 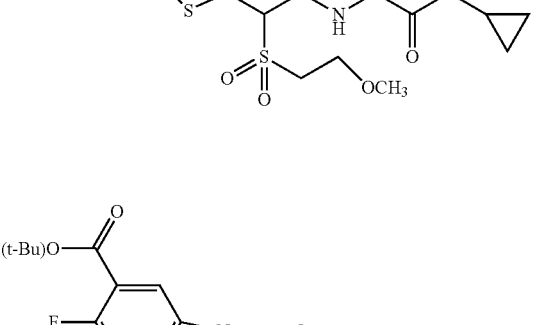 | tert-butyl 2-({[(cyclopropyl-carbamoyl)methyl] carbamoyl}(2-methoxyethane-sulfonyl)methyl)-6-fluoro-1,3-benzothiazole-5-carboxylate | (400 MHz, DMSO-$d_6$) 9.06-8.94 (m, 1H), 8.51-8.44 (m, 1H), 8.23-8.15 (m, 1H), 8.07-7.94 (m, 1H), 6.21 (s, 1H), 3.85-3.67 (m, 5H), 3.28-3.25 (m, 3H), 2.90-2.89 (m, 1H), 2.67-2.58 (m, 1H), 1.61-1.53 (m, 9H), 0.66-0.59 (m, 2H), 0.44-0.28 (m, 2H) | 0.92 M 530.2 | 12 |
| 429 | 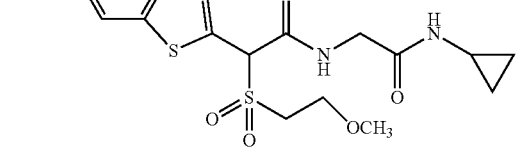 | N-[(cyclopropyl-carbamoyl) methyl]-2-[6-fluoro-5-(3-methoxy-3-methylazetidine-1-carbonyl)-1,3-benzothiazol-2-yl]-2-(2-methoxyethane-sulfonyl)acetamide | 9.22-8.97 (m, 1H), 8.29-8.13 (m, 2H), 8.08-7.98 (m, 1H), 6.27-6.07 (m, 1H), 4.03-3.95 (m, 2H), 3.93-3.69 (m, 8H), 3.30-3.25 (m, 3H), 3.19-3.16 (m, 3H), 2.68-2.60 (m, 1H), 1.44 (s, 3H), 0.68-0.61 (m, 2H), 0.46-0.36 (m, 2H). | 1.18 O 557.2 | 69 |

| Ex. No. | Structure | Name | ¹H NMR δ (500 MHz, DMSO-d₆, unless otherwise indicated) | LC/MS RT (min) Method M+H | EL IC₅₀ (nM) |
|---|---|---|---|---|---|
| 431 | 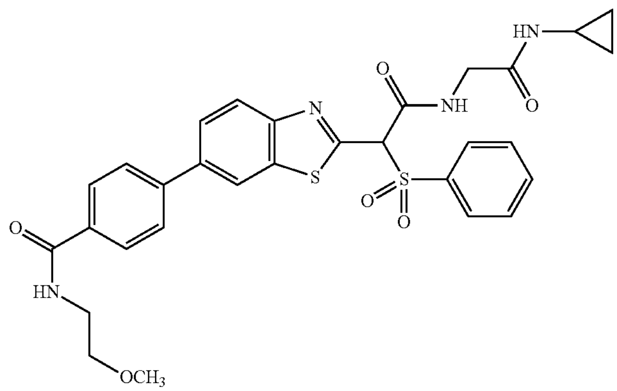 [SMILES: COCCNC(=O)c1ccc(-c2ccc3nc(C(C(=O)NCC(=O)NC4CC4)S(=O)(=O)c4ccccc4)sc3c2)cc1] | 4-{2-[(benzenesulfonyl)({[(cyclopropyl-carbamoyl)methyl]carbamoyl})methyl]-1,3-benzothiazol-6-yl}-N-(2-methoxyethyl)benzamide | 9.07 (t, J = 5.2 Hz, 1H), 8.61 (t, J = 5.2 Hz, 1H), 8.52 (d, J = 1.4 Hz, 1H), 8.07-8.03 (m, 2H), 7.99 (d, J = 8.5 Hz, 2H), 7.91-7.84 (m, 2H), 7.78 (d, J = 7.2 Hz, 1H), 7.69 (d, J = 7.7 Hz, 2H), 7.63-7.57 (m, 2H), 6.40 (s, 1H), 3.86 (dd, J = 16.5, 5.8 Hz, 1H), 3.70 (dd, J = 16.5, 5.0 Hz, 1H), 3.51-3.45 (m, 4H), 3.30 (s, 3H), 2.64 (dt, J = 7.3, 3.5 Hz, 1H), 0.67-0.60 (m, 2H), 0.43-0.38 (m, 2H) | 1.43 O 607.3 | 3 |
| 432 | 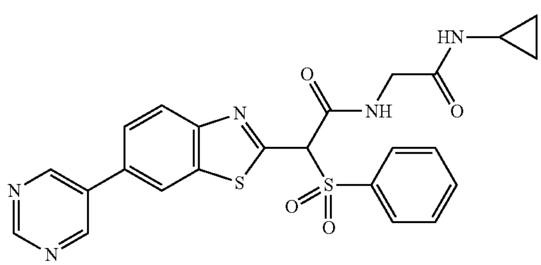 [SMILES: O=C(CNC(=O)C(c1nc2ccc(-c3cncnc3)cc2s1)S(=O)(=O)c1ccccc1)NC1CC1] | 2-(benzenesulfonyl)-N-[(cyclopropyl-carbamoyl)methyl]-2-[6-(pyrimidin-5-yl)-1,3-benzothiazol-2-yl]acetamide | 9.26-9.21 (m, 2H), 9.09 (t, J = 5.4 Hz, 1H), 8.63 (s, 1H), 8.10 (d, J = 8.5 Hz, 1H), 8.04 (d, J = 3.6 Hz, 1H), 7.98-7.94 (m, 1H), 7.81-7.75 (m, 1H), 7.69 (d, J = 7.7 Hz, 2H), 7.64-7.56 (m, 2H), 6.42 (s, 1H), 3.86 (dd, J = 16.8, 5.8 Hz, 1H), 3.74-3.67 (m, 1H), 2.69-2.60 (m, 1H), 0.69-0.58 (m, 2H), 0.41 (br. s., 2H) | 1.26 O 508.2 | 61 |
| 433 | 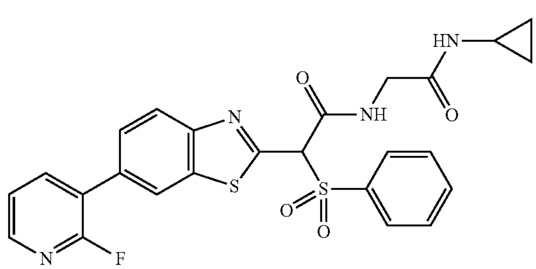 [SMILES: O=C(CNC(=O)C(c1nc2ccc(-c3cccnc3F)cc2s1)S(=O)(=O)c1ccccc1)NC1CC1] | 2-(benzenesulfonyl)-N-[(cyclopropyl-carbamoyl)methyl]-2-[6-(2-fluoropyridin-3-yl)-1,3-benzothiazol-2-yl]acetamide | 9.08 (t, J = 5.5 Hz, 1H), 8.41 (s, 1H), 8.30 (d, J = 5.0 Hz, 1H), 8.24-8.19 (m, 1H), 8.07 (d, J = 8.5 Hz, 1H), 8.04 (d, J = 3.9 Hz, 1H), 7.82-7.73 (m, 2H), 7.70 (d, J = 7.4 Hz, 2H), 7.64-7.58 (m, 2H), 7.56-7.50 (m, 1H), 6.42 (s, 1H), 3.86 (dd, J = 16.5, 5.8 Hz, 1H), 3.70 (dd, J = 16.6, 5.1 Hz, 1H), 2.64 (dt, J = 7.4, 3.6 Hz, 1H), 0.67-0.60 (m, 2H), 0.44-0.37 (m, 2H) | 1.53 O 523.2 | 102 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 434 | 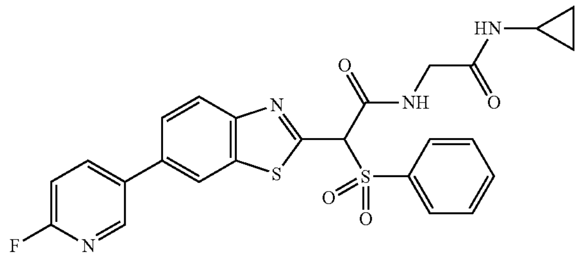 [SMILES: O=C(CNC(=O)C(c1nc2ccc(-c3ccc(F)nc3)cc2s1)S(=O)(=O)c1ccccc1)NC1CC1] | 2-(benzenesulfonyl)-N-[(cyclopropyl-carbamoyl)methyl]-2-[6-(6-fluoropyridin-3-yl)-1,3-benzothiazol-2-yl]acetamide | (400 MHz, DMSO-d₆) 9.07 (t, J = 5.2 Hz, 1H), 8.65 (d, J = 2.6 Hz, 1H), 8.51 (d, J = 1.3 Hz, 1H), 8.38 (td, J = 8.1, 2.6 Hz, 1H), 8.05 (d, J = 8.6 Hz, 1H), 8.04-8.01 (m, 1H), 7.87 (dd, J = 8.6, 2.0 Hz, 1H), 7.81-7.73 (m, 1H), 7.71-7.66 (m, 2H), 7.62-7.57 (m, 2H), 7.34 (dd, J = 8.7, 2.5 Hz, 1H), 6.40 (s, 1H), 3.90-3.80 (m, 1H), 3.73-3.65 (m, 1H), 2.63 (td, J = 7.4, 3.4 Hz, 1H), 0.68-0.57 (m, 2H), 0.45-0.35 (m, 2H) | 1.81 B 525.1 | 14 |
| 435 | 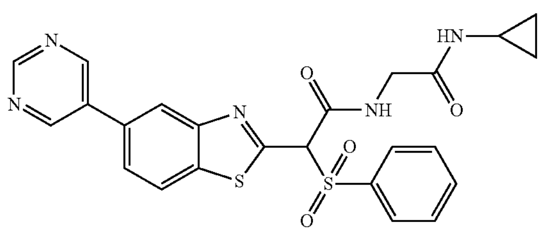 [SMILES: O=C(CNC(=O)C(c1nc2cc(-c3cncnc3)ccc2s1)S(=O)(=O)c1ccccc1)NC1CC1] | 2-(benzenesulfonyl)-N-[(cyclopropyl-carbamoyl)methyl]-2-[5-(pyrimidin-5-yl)-1,3-benzothiazol-2-yl]acetamide | 9.07 (t, J = 5.4 Hz, 1H), 8.47 (d, J = 1.4 Hz, 1H), 8.28 (d, J = 8.5 Hz, 1H), 8.03 (d, J = 4.1 Hz, 1H), 7.93 (dd, J = 8.4, 1.8 Hz, 1H), 7.79-7.74 (m, 1H), 7.71-7.66 (m, 2H), 7.64-7.55 (m, 3H), 6.42 (s, 1H), 3.84 (dd, J = 16.8, 5.8 Hz, 1H), 3.73-3.65 (m, 1H), 2.63 (td, J = 7.4, 3.6 Hz, 1H), 0.66-0.59 (m, 2H), 0.44-0.36 (m, 2H) | 1.81 B 508.1 | 12 |
| 436 | 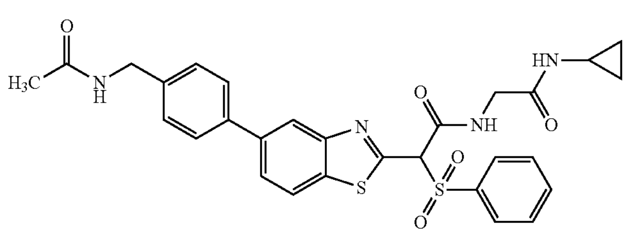 [SMILES: CC(=O)NCc1ccc(-c2ccc3sc(C(C(=O)NCC(=O)NC4CC4)S(=O)(=O)c4ccccc4)nc3c2)cc1] | 2-(benzenesulfonyl)-N-[(cyclopropyl-carbamoyl)methyl]-2-{5-[4-(acetamidomethyl)phenyl]-1,3-benzothiazol-2-yl}acetamide | 9.06 (t, J = 5.4 Hz, 1H), 8.38 (t, J = 5.8 Hz, 1H), 8.24-8.14 (m, 2H), 8.02 (d, J = 3.9 Hz, 1H), 7.80-7.66 (m, 5H), 7.62-7.56 (m, 2H), 7.37 (d, J = 8.3 Hz, 2H), 6.40 (s, 1H), 4.31 (d, J = 6.1 Hz, 2H), 3.84 (dd, J = 16.5, 5.8 Hz, 1H), 3.73-3.63 (m, 1H), 2.65-2.61 (m, 1H), 1.90 (s, 3H), 0.67-0.56 (m, 2H), 0.44-0.36 (m, 2H) | 1.94 B 577.2 | 13 |

| Ex. No. | Structure | Name | $^1$H NMR δ (500 MHz, DMSO-d$_6$, unless otherwise indicated) | LC/MS RT (min) Method M + H | EL IC$_{50}$ (nM) |
|---|---|---|---|---|---|
| 437 | 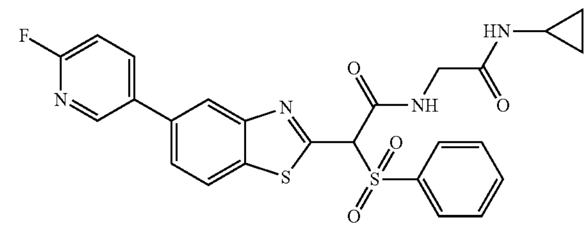 [SMILES: O=C(CNC(=O)C(c1nc2cc(-c3ccc(F)nc3)ccc2s1)S(=O)(=O)c1ccccc1)NC1CC1] | 2-(benzenesulfonyl)-N-[(cyclopropyl-carbamoyl)methyl]-2-[5-(6-fluoropyridin-3-yl)-1,3-benzothiazol-2-yl]acetamide | 9.07 (t, J = 5.2 Hz, 1H), 8.68 (d, J = 1.9 Hz, 1H), 8.42 (td, J = 8.1, 2.5 Hz, 2H), 8.25 (d, J = 8.5 Hz, 1H), 8.03 (d, J = 3.9 Hz, 1H), 7.86 (d, J = 8.5 Hz, 1H), 7.81-7.76 (m, 1H), 7.69 (d, J = 8.0 Hz, 2H), 7.64-7.58 (m, 2H), 7.33 (dd, J = 8.5, 2.5 Hz, 1H), 6.43 (s, 1H), 3.85 (dd, J = 16.5, 5.8 Hz, 1H), 3.74-3.65 (m, 1H), 2.64 (td, J = 7.3, 3.6 Hz, 1H), 0.64 (d, J = 7.2 Hz, 2H), 0.47-0.34 (m, 2H) | 1.98 B 525.1 | 13 |
| 438 | 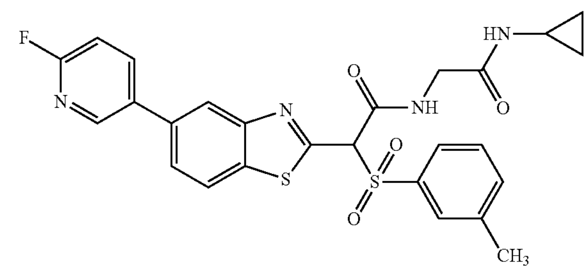 [SMILES: Cc1cccc(S(=O)(=O)C(C(=O)NCC(=O)NC2CC2)c2nc3cc(-c4ccc(F)nc4)ccc3s2)c1] | N-[(cyclopropyl-carbamoyl)methyl]-2-[5-(6-fluoropyridin-3-yl)-1,3-benzothiazol-2-yl]-2-(3-methylbenzene-sulfonyl)acetamide | 9.04 (t, J = 5.4 Hz, 1H), 8.68 (d, J = 2.2 Hz, 1H), 8.47-8.35 (m, 2H), 8.25 (d, J = 8.5 Hz, 1H), 8.03 (d, J = 3.9 Hz, 1H), 7.86 (d, J = 8.5 Hz, 1H), 7.58 (d, J = 6.1 Hz, 1H), 7.52-7.45 (m, 3H), 7.33 (dd, J = 8.5, 2.8 Hz, 1H), 6.38 (s, 1H), 3.84 (dd, J = 16.8, 5.8 Hz, 1H), 3.69 (dd, J = 16.5, 5.0 Hz, 1H), 2.64 (td, J = 7.3, 3.6 Hz, 1H), 2.33 (s, 3H), 0.75-0.61 (m, 2H), 0.46-0.31 (m, 2H) | 2.05 B 539.1 | 33 |
| 439 | 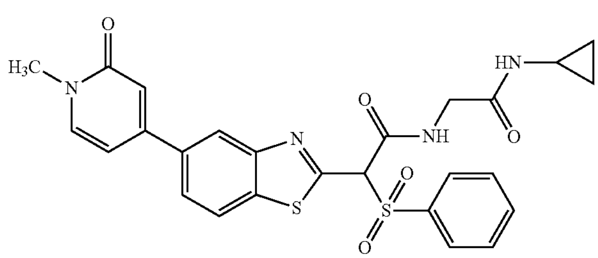 [SMILES: Cn1ccc(-c2ccc3sc(C(C(=O)NCC(=O)NC4CC4)S(=O)(=O)c4ccccc4)nc3c2)cc1=O] | 2-(benzenesulfonyl)-N-[(cyclopropyl-carbamoyl)methyl]-2-[5-(1-methyl-2-oxo-1,2-dihydropyridin-4-yl)-1,3-benzothiazol-2-yl]acetamide | 8.29 (d, J = 1.4 Hz, 1H), 8.21 (d, J = 8.5 Hz, 1H), 8.02 (d, J = 3.9 Hz, 1H), 7.86-7.74 (m, 3H), 7.70-7.65 (m, 2H), 7.62-7.56 (m, 3H), 6.79 (d, J = 1.9 Hz, 1H), 6.69 (dd, J = 7.0, 2.1 Hz, 1H), 6.40 (s, 1H), 3.83 (dd, J = 16.6, 5.9 Hz, 1H), 3.72-3.63 (m, 1H), 3.47 (s, 3H), 2.63 (tt, J = 7.4, 3.8 Hz, 1H), 0.67-0.58 (m, 2H), 0.46-0.35 (m, 2H) | 1.79 B 537.2 | 48 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 440 | 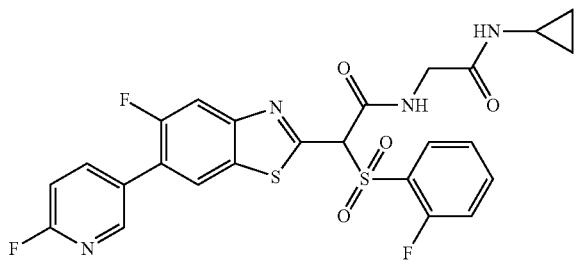 [SMILES: O=C(CNC(=O)C(c1nc2cc(F)c(-c3ccc(F)nc3)cc2s1)S(=O)(=O)c1ccccc1F)NC1CC1] | N-[(cyclopropyl-carbamoyl)methyl]-2-[5-fluoro-6-(6-fluoropyridin-3-yl)-1,3-benzothiazol-2-yl]-2-(2-fluorobenzene-sulfonyl)acetamide | 9.28 (br. s., 1H), 8.52-7.82 (m, 6H), 7.68-7.58 (m, 1H), 7.53-7.28 (m, 3H), 6.41 (s, 1H), 3.89-3.64 (m, 1H), 3.54-3.33 (m, 1H), 2.62 (d, J = 3.4 Hz, 1H), 0.62 (d, J = 6.4 Hz, 2H), 0.39 (br. s., 2H). | 1.93 B 531.1 | 58 |
| 441 | 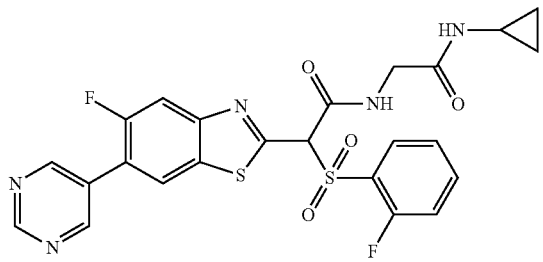 [SMILES: O=C(CNC(=O)C(c1nc2cc(F)c(-c3cncnc3)cc2s1)S(=O)(=O)c1ccccc1F)NC1CC1] | N-[(cyclopropyl-carbamoyl)methyl]-2-[5-fluoro-6-(pyrimidin-5-yl)-1,3-benzothiazol-2-yl]-2-(2-fluorobenzene-sulfonyl)acetamide | 9.20-8.74 (m, 3H), 8.25 (d, J = 7.1 Hz, 1H), 7.98-7.69 (m, 3H), 7.62-7.31 (m, 1H), 7.25-7.07 (m, 2H), 6.17 (s, 1H), 3.63-3.40 (m, 2H), 3.21 (d, J = 11.4 Hz, 1H), 2.37 (d, J = 3.7 Hz, 1H), 0.37 (d, J = 5.7 Hz, 2H), 0.14 (br. s., 2H) | 1.75 B 544.1 | 87 |
| 442 | 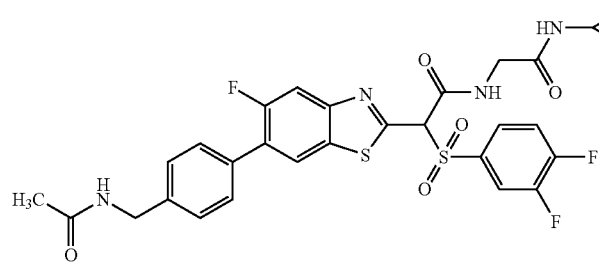 | N-[(cyclopropyl-carbamoyl)methyl]-2-(3,4-difluorobenzene-sulfonyl)-2-{6-[4-(acetamidomethyl)phenyl]-5-fluoro-1,3-benzothiazol-2-yl}acetamide | 8.84-8.76 (m, 1H), 8.20 (t, J = 5.9 Hz, 1H), 8.09-7.98 (m, 1H), 7.84 (d, J = 3.4 Hz, 1H), 7.76-7.67 (m, 1H), 7.63-7.55 (m, 1H), 7.50-7.42 (m, 1H), 7.31 (d, J = 7.1 Hz, 2H), 7.18-7.08 (m, 2H), 6.19 (s, 1H), 4.11-4.03 (m, 2H), 3.66-3.43 (m, 2H), 2.37 (d, J = 3.7 Hz, 1H), 1.69-1.60 (m, 3H), 0.43-0.30 (m, 2H), 0.15 (d, J = 3.7 Hz, 2H) | 0.84 M 631.6 | 10 |
| 443 | 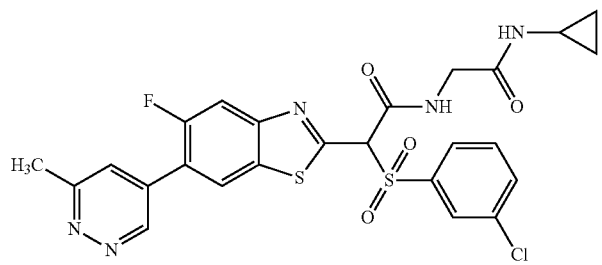 [SMILES: Cc1cc(-c2cc3sc(C(C(=O)NCC(=O)NC4CC4)S(=O)(=O)c4cccc(Cl)c4)nc3cc2F)cnn1] | 2-(3-chlorobenzene-sulfonyl)-N-[(cyclopropyl-carbamoyl)methyl]-2-[5-fluoro-6-(6-methylpyridazin-4-yl)-1,3-benzothiazol-2-yl}acetamide | 9.18-9.07 (m, 1H), 8.89 (br. s., 1H), 8.36-8.28 (m, 1H), 7.93-7.82 (m, 2H), 7.77-7.66 (m, 1H), 7.59-7.50 (m, 1H), 7.45-7.29 (m, 2H), 7.17 (br. s., 1H), 6.26 (s, 1H), 3.71-3.47 (m, 2H), 2.41 (d, J = 3.0 Hz, 1H), 2.29 (br. s., 3H), 0.41 (d, J = 7.4 Hz, 2H), 0.18 (br. s., 2H) | 1.79 B 574.2 | 37 |

| Ex. No. | Structure | Name | ¹H NMR δ (500 MHz, DMSO-d₆, unless otherwise indicated) | LC/MS RT (min) Method M+H | EL IC$_{50}$ (nM) |
|---|---|---|---|---|---|
| 444 | 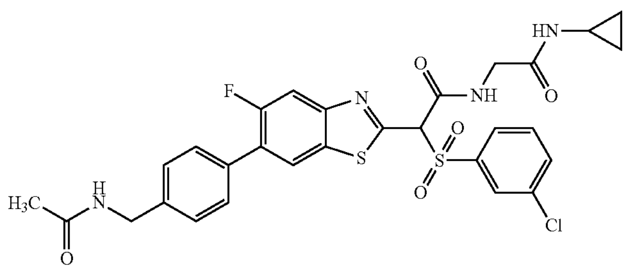 [SMILES: CC(=O)NCc1ccc(-c2cc3sc(C(C(=O)NCC(=O)NC4CC4)S(=O)(=O)c4cccc(Cl)c4)nc3cc2F)cc1] | 2-(3-chlorobenzene-sulfonyl)-N-[(cyclopropyl-carbamoyl)methyl]-2-{6-[4-(acetamidomethyl)phenyl]-5-fluoro-1,3-benzothiazol-2-yl}acetamide | 8.21 (t, J = 6.2 Hz, 1H), 8.08-8.01 (m, 1H), 7.85 (d, J = 3.4 Hz, 1H), 7.73-7.62 (m, 2H), 7.50 (s, 1H), 7.42-7.30 (m, 4H), 7.19-7.10 (m, 3H), 6.21 (s, 1H), 4.15-4.01 (m, 2H), 3.65-3.56 (m, 1H), 3.48 (dd, J = 12.1, 4.7 Hz, 1H), 2.40 (dt, J = 7.2, 3.8 Hz, 1H), 2.28 (br. s., 3H), 0.46-0.35 (m, 2H), 0.23-0.11 (m, 2H) | 1.95 B 629.2 | 5 |
| 445 | 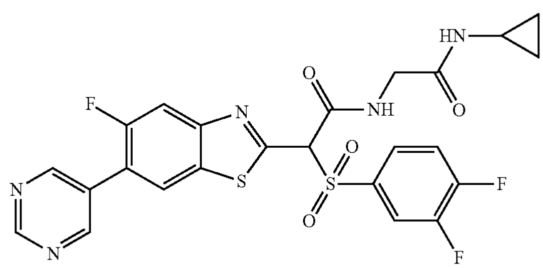 [SMILES: O=C(CNC(=O)C(c1nc2cc(F)c(-c3cncnc3)cc2s1)S(=O)(=O)c1ccc(F)c(F)c1)NC1CC1] | N-[(cyclopropyl-carbamoyl)methyl]-2-(3,4-difluorobenzene-sulfonyl)-2-[5-fluoro-6-(pyrimidin-5-yl)-1,3-benzothiazol-2-yl]acetamide | 9.32-9.22 (m, 1H), 9.17-9.01 (m, 2H), 8.56-8.46 (m, 1H), 8.19-8.03 (m, 2H), 7.98-7.83 (m, 1H), 7.72 (d, J = 8.4 Hz, 1H), 7.60-7.48 (m, 1H), 6.47 (s, 1H), 3.96-3.67 (m, 2H), 2.62 (br. s., 1H), 0.63 (d, J = 7.7 Hz, 2H), 0.39 (br. s., 2H) | 0.81 M 562.4 | 59 |
| 446 | 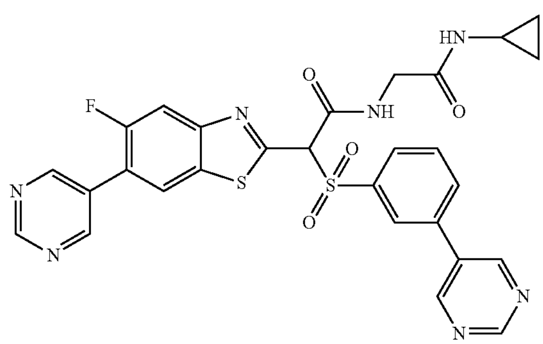 [SMILES: O=C(CNC(=O)C(c1nc2cc(F)c(-c3cncnc3)cc2s1)S(=O)(=O)c1cccc(-c2cncnc2)c1)NC1CC1] | N-[(cyclopropyl-carbamoyl)methyl]-2-[5-fluoro-6-(pyrimidin-5-yl)-1,3-benzothiazol-2-yl]-2-[3-(pyrimidin-5-yl)benzenesulfonyl]acetamide | 9.29-9.18 (m, 3H), 9.12-9.00 (m, 3H), 8.95 (s, 1H), 8.46 (d, J = 7.1 Hz, 1H), 8.22-7.99 (m, 3H), 7.87 (s, 1H), 7.81-7.74 (m, 2H), 6.46 (s, 1H), 3.94-3.81 (m, 1H), 3.71 (dd, J = 16.5, 5.0 Hz, 1H), 2.68-2.56 (m, 1H), 0.68-0.57 (m, 2H), 0.38 (br. s., 2H) | 1.66 B 604.2 | 78 |
| 447 | 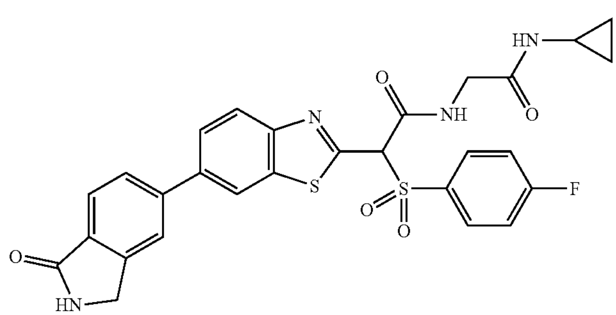 [SMILES: O=C(CNC(=O)C(c1nc2ccc(-c3ccc4c(c3)CNC4=O)cc2s1)S(=O)(=O)c1ccc(F)cc1)NC1CC1] | N-[(cyclopropyl-carbamoyl)methyl]-2-(4-fluorobenzene-sulfonyl)-2-[6-(1-oxo-2,3-dihydro-1H-isoindol-5-yl)-1,3-benzothiazol-2-yl}acetamide | 9.13-9.02 (m, 1H), 8.64-8.57 (m, 1H), 8.52 (s, 1H), 8.11-8.04 (m, 2H), 7.98-7.94 (m, 1H), 7.91-7.84 (m, 2H), 7.82-7.73 (m, 3H), 7.53-7.42 (m, 2H), 6.46-6.34 (m, 1H), 4.47 (s, 2H), 3.92-3.62 (m, 2H), 2.67-2.61 (m, 1H), 0.69-0.61 (m, 2H), 0.41 (br. s., 2H) | 143 O 579.1 | 9 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 448 | 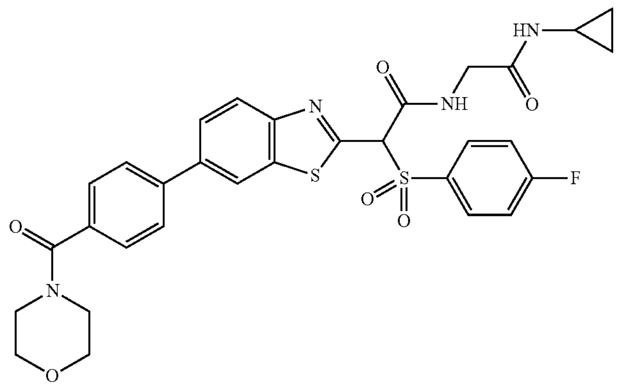 [SMILES: O=C(CNC(=O)C(c1nc2ccc(-c3ccc(C(=O)N4CCOCC4)cc3)cc2s1)S(=O)(=O)c1ccc(F)cc1)NC1CC1] | N-[(cyclopropyl-carbamoyl)methyl]-2-(4-fluorobenzene-sulfonyl)-2-{6-[4-(morpholine-4-carbonyl)phenyl]-1,3-benzothiazol-2-yl}acetamide | 9.12-9.02 (m, 1H), 8.50 (s, 1H), 8.11-8.02 (m, 2H), 7.90-7.84 (m, 2H), 7.80-7.71 (m, 3H), 7.56 (d, J = 7.7 Hz, 2H), 7.47 (s, 2H), 6.42 (s, 1H), 3.89-3.68 (m, 2H), 3.68-3.53 (m, 8H), 2.67-2.59 (m, 1H), 0.68-0.60 (m, 2H), 0.45-0.36 (m, 2H) | 1.49 O 637.1 | 10 |
| 449 | 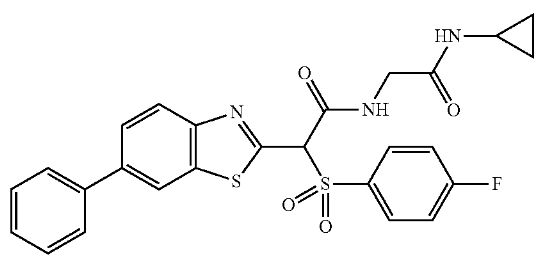 [SMILES: O=C(CNC(=O)C(c1nc2ccc(-c3ccccc3)cc2s1)S(=O)(=O)c1ccc(F)cc1)NC1CC1] | N-[(cyclopropyl-carbamoyl)methyl]-2-(4-fluorobenzene-sulfonyl)-2-(6-phenyl-1,3-benzothiazol-2-yl)acetamide | 9.15-9.00 (m, 1H), 8.49-8.40 (m, 1H), 8.08-8.01 (m, 2H), 7.88-7.82 (m, 1H), 7.76 (s, 3H), 7.56-7.40 (m, 5H), 6.45-6.29 (m, 1H), 3.89-3.68 (m, 2H), 2.68-2.58 (m, 1H), 0.67-0.62 (m, 2H), 0.41 (br. s., 2H) | 1.96 O 524 | 16 |
| 450 | 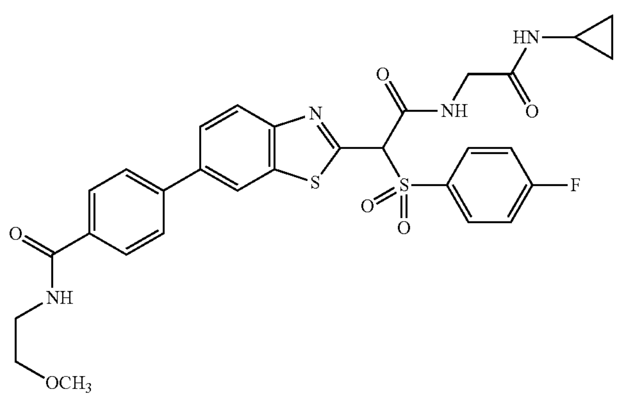 [SMILES: COCCNC(=O)c1ccc(-c2ccc3nc(C(C(=O)NCC(=O)NC4CC4)S(=O)(=O)c4ccc(F)cc4)sc3c2)cc1] | 4-[2-({[(cyclopropyl-carbamoyl)methyl]carbamoyl}(4-fluorobenzene-sulfonyl)methyl)-1,3-benzothiazol-6-yl]-N-(2-methoxyethyl)benzamide | 9.13-9.01 (m, 1H), 8.64-8.57 (m, 1H), 8.54-8.51 (m, 1H), 8.09-8.03 (m, 2H), 8.00-7.97 (m, 2H), 7.88-7.85 (m, 2H), 7.76-7.72 (m, 2H), 7.49-7.43 (m, 2H), 6.41 (s, 1H), 3.87-3.68 (m, 3H), 3.48 (br. s., 5H), 3.31-3.25 (m, 6H), 2.65-2.60 (m, 1H) | 1.49 O 625.1 | 19 |
| 451 | 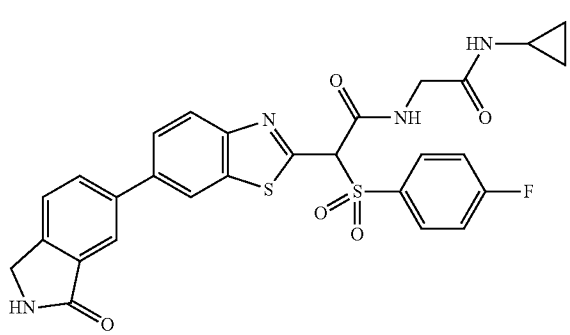 [SMILES: O=C(CNC(=O)C(c1nc2ccc(-c3ccc4c(c3)C(=O)NC4)cc2s1)S(=O)(=O)c1ccc(F)cc1)NC1CC1] | N-[(cyclopropyl-carbamoyl)methyl]-2-(4-fluorobenzene-sulfonyl)-2-[6-(3-oxo-2,3-dihydro-1H-isoindol-5-yl)-1,3-benzothiazol-2-yl]acetamide | 9.14-9.02 (m, 1H), 8.67-8.63 (m, 1H), 8.58-8.50 (m, 1H), 8.05-8.02 (m, 1H), 8.01-7.98 (m, 2H), 7.91-7.88 (m, 1H), 7.77-7.73 (m, 1H), 7.49-7.44 (m, 2H), 6.41 (s, 1H), 4.48-4.44 (m, 2H), 3.91 (s, 1H), 3.87-3.66 (m, 2H), 2.66-2.59 (m, 1H), 2.55 (s, 2H), 0.64-0.62 (m, 2H), 0.41-0.39 (m, 2H). | 1.39 O 579.1 | 39 |

-continued

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 452 | 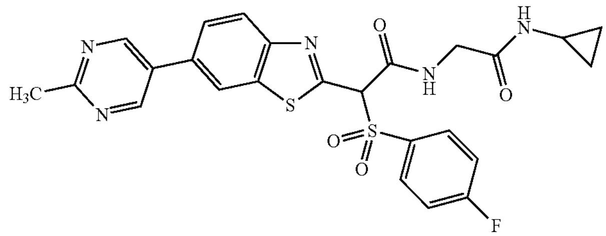 [SMILES: Cc1ncc(-c2ccc3nc(C(C(=O)NCC(=O)NC4CC4)S(=O)(=O)c4ccc(F)cc4)sc3c2)cn1] | N-[(cyclopropyl-carbamoyl)methyl]-2-(4-fluorobenzene-sulfonyl)-2-[6-(2-methylpyrimidin-5-yl)-1,3-benzothiazol-2-yl]acetamide | 9.12 (s, 1H), 9.07 (d, J = 15.6 Hz, 1H), 8.60 (s, 1H), 8.64-8.47 (m, 1H), 8.15-8.09 (m, 1H), 8.06 (br. s., 1H), 7.94 (s, 1H), 7.96 (s, 1H), 7.76 (dd, J = 8.7, 5.0 Hz, 1H), 7.48 (t, J = 8.7 Hz, 2H), 6.43 (s, 1H), 3.90-3.69 (m, 2H), 2.71 (s, 3H), 2.68-2.61 (m, 1H), 0.65 (d, J = 7.3 Hz, 2H), 0.42 (br. s., 2H) | 1.93 O 540.1 | 39 |
| 453 | 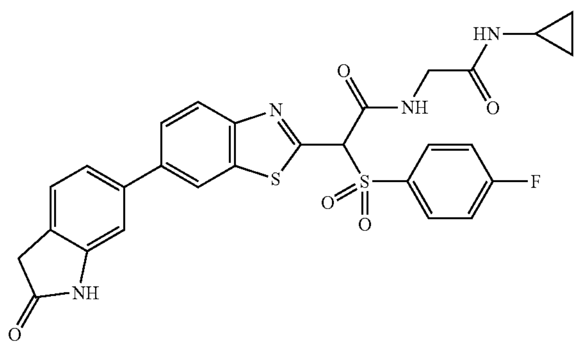 [SMILES: O=C1Cc2ccc(-c3ccc4nc(C(C(=O)NCC(=O)NC5CC5)S(=O)(=O)c5ccc(F)cc5)sc4c3)cc2N1] | N-[(cyclopropyl-carbamoyl)methyl]-2-(4-fluorobenzene-sulfonyl)-2-[6-(2-oxo-2,3-dihydro-1H-indol-6-yl)-1,3-benzothiazol-2-yl]acetamide | 10.53 (s, 1H), 9.09-9.01 (m, 1H), 8.40 (s, 1H), 8.07-7.94 (m, 2H), 7.83-7.71 (m, 3H), 7.47 (t, J = 8.5 Hz, 2H), 7.37-7.29 (m, 2H), 7.12 (s, 1H), 6.41 (s, 1H), 3.88-3.68 (m, 2H), 3.56-3.51 (m, 2H), 2.67-2.60 (m, 1H), 0.65 (s, 2H), 0.41 (br. s., 2H) | 1.45 O 579.1 | 67 |
| 454 | 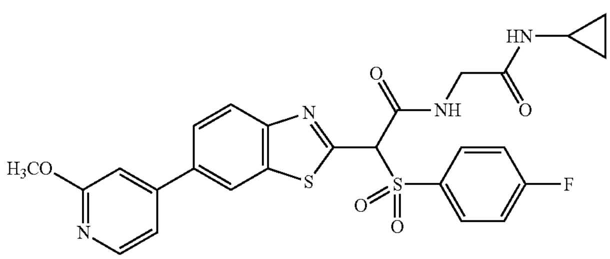 [SMILES: COc1cc(-c2ccc3nc(C(C(=O)NCC(=O)NC4CC4)S(=O)(=O)c4ccc(F)cc4)sc3c2)ccn1] | N-[(cyclopropyl-carbamoyl)methyl]-2-(4-fluorobenzene-sulfonyl)-2-[6-(2-methoxypyridin-4-yl)-1,3-benzothiazol-2-yl]acetamide | 9.16-9.01 (m, 1H), 8.65-8.56 (m, 1H), 8.31-8.27 (m, 1H), 8.10-(m, 2H), 7.97-7.92 (m, 1H), 7.79-7.71 (m, 2H), 7.50-7.39 (m, 4H), 7.24-7.20 (m, 1H), 6.47-6.36 (m, 1H), 3.94-3.93 (m, 2H), 3.88-3.69 (m, 2H), 2.66-2.60 (m, 1H), 0.70-0.61 (m, 2H), 0.46-0.36 (m, 2H) | 1.48 O 555.1 | 73 |
| 455 | 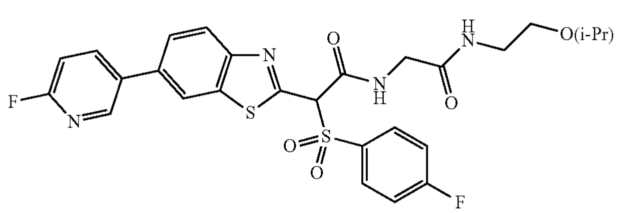 | 2-(4-fluorobenzene-sulfonyl)-2-[6-(6-fluoropyridin-3-yl)-1,3-benzothiazol-2-yl]-N-({[2-(propan-2-yloxy)ethyl]carbamoyl}methyl)acetamide | 9.17-9.03 (m, 1H), 8.67-8.63 (m, 1H), 8.52 (d, J = 1.4 Hz, 1H), 8.38 (td, J = 8.2, 2.6 Hz, 1H), 8.08 (d, J = 8.5 Hz, 1H), 8.02 (t, J = 5.6 Hz, 1H), 7.88 (dd, J = 8.5, 1.9 Hz, 1H), 7.76-7.71 (m, 2H), 7.49-7.43 (m, 2H), 7.34 (dd, J = 8.5, 2.8 Hz, 1H), 6.40 (s, 1H), 3.96-3.71 (m, 2H), 3.52 (dt, J = 12.1, 6.1 Hz, 1H), 3.38-3.34 (m, 2H), 3.22-3.18 (m, 2H), 1.07-1.06 (m, 3H), 1.06-1.05 (m, 3H). | 2.53 O 589.1 | 100 |

-continued

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 456 | 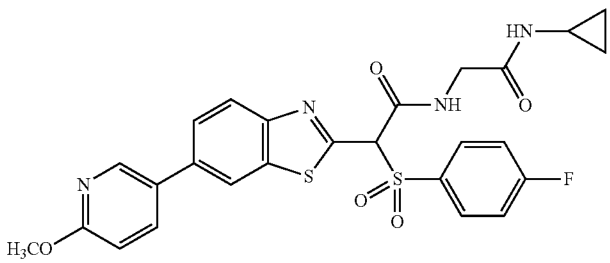 [SMILES: COc1ccc(-c2ccc3nc(C(C(=O)NCC(=O)NC4CC4)S(=O)(=O)c4ccc(F)cc4)sc3c2)cn1] | N-[(cyclopropyl-carbamoyl)methyl]-2-(4-fluorobenzene-sulfonyl)-2-[6-(6-methoxypyridin-3-yl)-1,3-benzothiazol-2-yl]acetamide | 9.11-9.01 (m, 1H), 8.62-8.56 (m, 1H), 8.48-8.40 (m, 1H), 8.15-8.10 (m, 1H), 8.07-8.02 (m, 2H), 7.87-7.80 (m, 1H), 7.78-7.72 (m, 2H), 7.53-7.43 (m, 2H), 7.00-6.94 (m, 1H), 6.48-6.19 (m, 1H), 3.93 (s, 3H), 3.88-3.69 (m, 2H), 2.66-2.61 (m, 1H), 0.66-0.62 (m, 2H), 0.43-0.39 (m, 2H) | 1.66 O 555.1 | 109 |
| 457 | 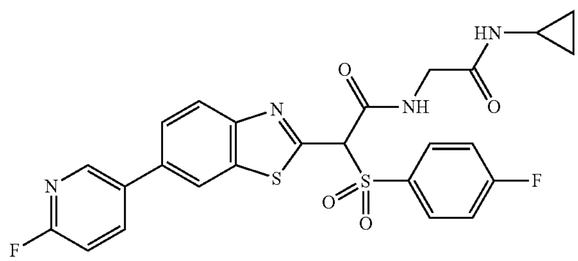 [SMILES: O=C(CNC(=O)C(c1nc2ccc(-c3ccc(F)nc3)cc2s1)S(=O)(=O)c1ccc(F)cc1)NC1CC1] | N-[(cyclopropyl-carbamoyl)methyl]-2-(4-fluorobenzene-sulfonyl)-2-[6-(6-fluoropyridin-3-yl)-1,3-benzothiazol-2-yl]acetamide | 9.07 (t, J = 5.1 Hz, 1H), 8.70-8.64 (m, 1H), 8.53 (s, 1H), 8.43-8.36 (m, 1H), 8.13-8.03 (m, 2H), 7.92-7.87 (m, 1H), 7.81-7.71 (m, 2H), 7.54-7.43 (m, 2H), 7.37-7.31 (m, 1H), 6.52-6.29 (m, 1H), 3.88-3.68 (m, 2H), 2.67-2.60 (m, 1H), 0.64 (d, J = 7.4 Hz, 2H), 0.41 (br. s., 2H) | 1.63 O 543.1 | 24 |
| 458 | 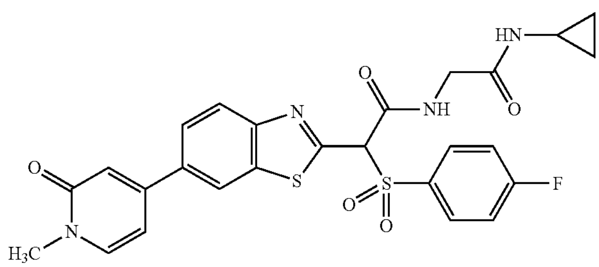 [SMILES: Cn1ccc(-c2ccc3nc(C(C(=O)NCC(=O)NC4CC4)S(=O)(=O)c4ccc(F)cc4)sc3c2)cc1=O] | N-[(cyclopropyl-carbamoyl)methyl]-2-(4-fluorobenzene-sulfonyl)-2-[6-(1-methyl-2-oxo-1,2-dihydropyridin-4-yl)-1,3-benzothiazol-2-yl]acetamide | 9.11-9.02 (m, 1H), 8.59-8.52 (m, 1H), 8.07-8.02 (m, 2H), 7.89-7.80 (m, 2H), 7.77-7.72 (m, 2H), 7.52-7.41 (m, 2H), 6.83-6.75 (m, 1H), 6.69-6.63 (m, 1H), 6.46-6.34 (m, 1H), 3.89-3.68 (m, 2H), 3.48 (s, 3H), 2.67-2.58 (m, 1H), 0.65-0.62 (m, 2H), 0.42-0.38 (m, 2H) | 1.28 O 555.1 | 32 |
| 459 | 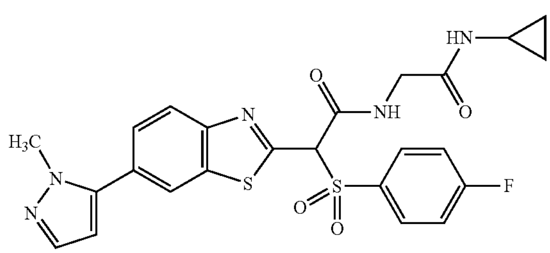 [SMILES: Cn1nccc1-c1ccc2nc(C(C(=O)NCC(=O)NC3CC3)S(=O)(=O)c3ccc(F)cc3)sc2c1] | N-[(cyclopropyl-carbamoyl)methyl]-2-(4-fluorobenzene-sulfonyl)-2-[6-(1-methyl-1H-pyrazol-5-yl)-1,3-benzothiazol-2-yl]acetamide | 9.05 (s, 1H), 8.35 (s, 1H), 8.11-8.02 (m, 2H), 7.80-7.74 (m, 2H), 7.72-7.66 (m, 1H), 7.54-7.45 (m, 3H), 6.51 (s, 1H), 6.43 (s, 1H), 3.91 (s, 3H), 3.87-3.66 (m, 2H), 2.66-2.59 (m, 1H), 0.68-0.61 (m, 2H), 0.44-0.37 (m, 2H) | 1.41 O 528.1 | 18 |
| 460 | 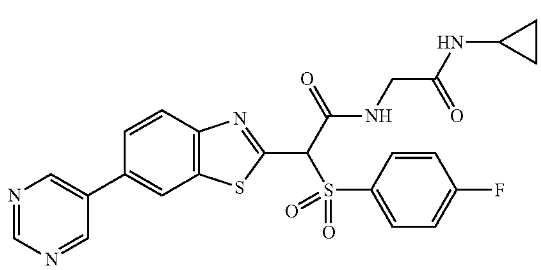 [SMILES: O=C(CNC(=O)C(c1nc2ccc(-c3cncnc3)cc2s1)S(=O)(=O)c1ccc(F)cc1)NC1CC1] | N-[(cyclopropyl-carbamoyl)methyl]-2-(4-fluorobenzene-sulfonyl)-2-[6-(pyrimidin-5-yl)-1,3-benzothiazol-2-yl]acetamide | 9.28-9.16 (m, 3H), 9.12-9.04 (m, 1H), 8.72-8.59 (m, 1H), 8.17-8.11 (m, 1H), 8.07-8.04 (m, 1H), 8.01-7.96 (m, 1H), 7.79-7.73 (m, 2H), 7.50-7.42 (m, 2H), 6.43 (s, 1H), 3.89-3.67 (m, 2H), 2.68-2.59 (m, 1H), 0.68-0.62 (m, 2H), 0.46-0.38 (m, 2H) | 1.36 O 525.9 | 47 |

| Ex. No. | Structure | Name | ¹H NMR δ (500 MHz, DMSO-d$_6$, unless otherwise indicated) | LC/MS RT (min) Method M + H | EL IC$_{50}$ (nM) |
|---|---|---|---|---|---|
| 461 | 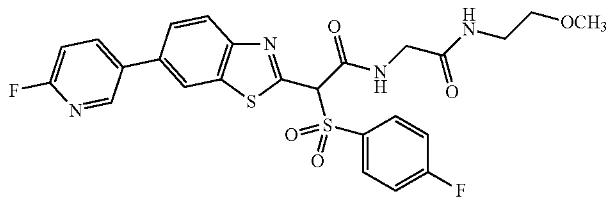 [SMILES: COCCNC(=O)CNC(=O)C(c1nc2ccc(-c3ccc(F)nc3)cc2s1)S(=O)(=O)c1ccc(F)cc1] | 2-(4-fluorobenzene-sulfonyl)-2-[6-(6-fluoropyridin-3-yl)-1,3-benzothiazol-2-yl]-N-{[(2-methoxyethyl)carbamoyl]methyl}acetamide | 9.12-9.02 (m, 1H), 8.67-8.61 (m, 1H), 8.55-8.47 (m, 1H), 8.42-8.35 (m, 1H), 8.11-8.04 (m, 2H), 7.91-7.85 (m, 1H), 7.77-7.71 (m, 2H), 7.48-7.43 (m, 2H), 7.37-7.31 (m, 1H), 6.45-6.36 (m, 1H), 3.98-3.69 (m, 2H), 3.36-3.31 (m, 2H), 3.27-3.22 (m, 5H). | 2.3 O 561.1 | 150 |
| 462 | 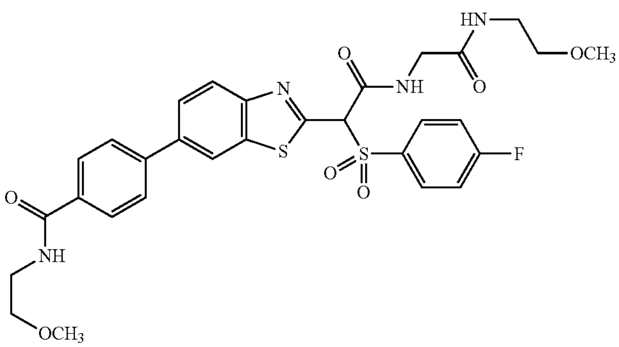 [SMILES: COCCNC(=O)CNC(=O)C(c1nc2ccc(-c3ccc(C(=O)NCCOC)cc3)cc2s1)S(=O)(=O)c1ccc(F)cc1] | 4-{2-[(4-fluorobenzene-sulfonyl)({[(2-methoxyethyl)carbamoyl]methyl}carbamoyl)methyl]-1,3-benzothiazol-6-yl}-N-(2-methoxyethyl)benzamide | 9.11-8.99 (m, 1H), 8.65-8.57 (m, 1H), 8.54-8.47 (m, 1H), 8.10-8.03 (m, 2H), 7.97 (s, 2H), 7.92-7.83 (m, 3H), 7.49-7.39 (m, 2H), 6.40 (s, 1H), 3.94-3.86 (m, 1H), 3.80-3.73 (m, 1H), 3.49-3.45 (m, 2H), 3.29 (s, 3H), 3.24-3.23 (m, 3H), 2.53-2.49 (m, 8H) | 2.06 O 643.1 | 4 |
| 463 | 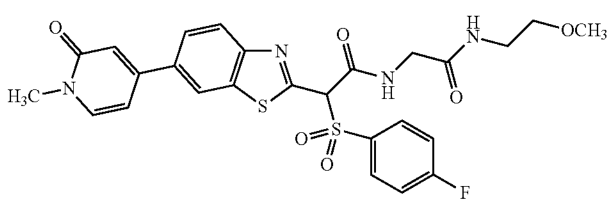 [SMILES: COCCNC(=O)CNC(=O)C(c1nc2ccc(-c3ccn(C)c(=O)c3)cc2s1)S(=O)(=O)c1ccc(F)cc1] | 2-(4-fluorobenze-nesulfonyl)-N-{[(2-methoxyethyl)carbamoyl]methyl}-2-[6-(1-methyl-2-oxo-1,2-dihydropyridin-4-yl)-1,3-benzothiazol-2-yl]acetamide | 9.06 (t, J = 5.4 Hz, 1H), 8.54 (d, J = 1.7 Hz, 1H), 8.11-8.02 (m, 2H), 7.88-7.80 (m, 2H), 7.75-7.72 (m, 2H), 7.45 (s, 3H), 6.78 (d, J = 1.9 Hz, 1H), 6.67-6.65 (m, 1H), 6.40 (s, 1H), 3.98-3.72 (m, 3H), 3.47 (s, 3H), 3.40-3.31 (m, 2H), 3.23 (s, 3H) | 1.8 O 573.1 | 24 |
| 464 | 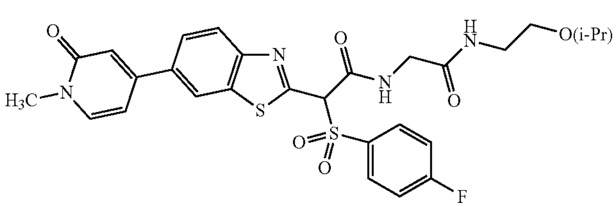 | 2-(4-fluorobenzene-sulfonyl)-2-[6-(1-methyl-2-oxo-1,2-dihydropyridin-4-yl)-1,3-benzothiazol-2-yl]-N-({[2-(propan-2-yloxy)ethyl]carbamoyl}methyl)acetamide | 9.13-9.03 (m, 1H), 8.58-8.50 (m, 1H), 8.07-7.99 (m, 2H), 7.89-7.80 (m, 2H), 7.76-7.72 (m, 2H), 7.48-7.43 (m, 2H), 6.78 (d, J = 1.9 Hz, 1H), 6.67-6.64 (m, 1H), 6.40 (s, 1H), 3.95-3.86 (m, 2H), 3.76 (dd, J = 16.8, 5.0 Hz, 1H), 3.45 (br. s., 3H), 3.37-3.34 (m, 2H), 3.20 (dd, J = 5.8, 1.4 Hz, 2H), 1.06 (d, J = 1.1 Hz, 3H), 1.05 (d, J = 1.1 Hz, 3H). | 2.04 O 601.1 | 45 |

-continued

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 465 | 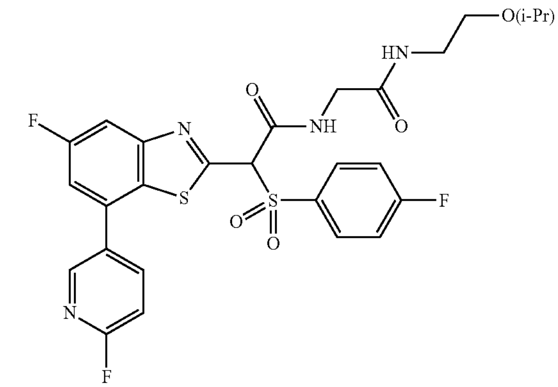 | 2-[5-fluoro-7-(6-fluoropyridin-3-yl)-1,3-benzothiazol-2-yl]-2-(4-fluorobenzene-sulfonyl)-N-({[2-(propan-2-yloxy)ethyl]carbamoyl}methyl)acetamide | 9.10 (br. s., 1H), 8.61-8.25 (m, 2H), 8.02 (br. s., 2H), 7.80-7.62 (m, 2H), 7.53-7.42 (m, 2H), 6.49-6.33 (m, 1H), 5.42-5.30 (m, 1H), 3.94-3.67 (m, 1H), 3.46-3.13 (m, 2H), 2.07-1.89 (m, 4H), 1.49 (d, J = 6.4 Hz, 1H), 1.13-0.98 (m, 6H) | 1.84 O 607.1 | 53 |
| 466 | 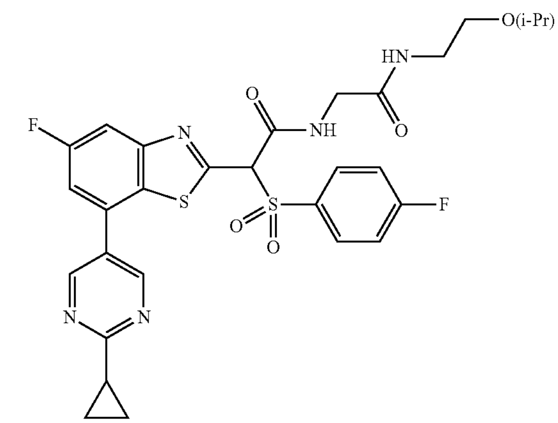 | 2-[7-(2-cyclopropyl-pyrimidin-5-yl)-5-fluoro-1,3-benzothiazol-2-yl]-2-(4-fluorobenzene-sulfonyl)-N-({[2-(propan-2-yloxy)ethyl]carbamoyl}methyl)acetamide | 9.14-9.06 (m, 1H), 8.95 (s, 1H), 8.05-7.90 (m, 2H), 7.80-7.62 (m, 3H), 7.46 (t, J = 8.5 Hz, 2H), 6.39 (s, 1H), 3.96-3.67 (m, 2H), 3.44-3.11 (m, 4H), 2.33 (d, J = 4.6 Hz, 1H), 1.92 (s, 1H), 1.20-0.98 (m, 10H) | 1.86 O 630.1 | 157 |
| 467 | 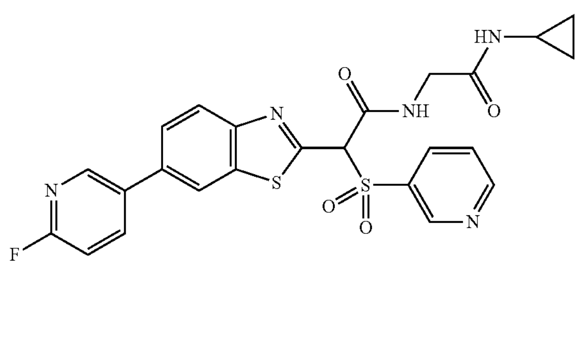 [SMILES: O=C(CNC(=O)C(c1nc2ccc(-c3ccc(F)nc3)cc2s1)S(=O)(=O)c1cccnc1)NC1CC1] | N-[(cyclopropyl-carbamoyl)methyl]-2-[6-(6-fluoropyridin-3-yl)-1,3-benzothiazol-2-yl]-2-(pyridine-3-sulfonyl)acetamide | 9.15-9.05 (m, 1H), 8.93-8.83 (m, 1H), 8.71 (s, 1H), 8.60 (br. s., 1H), 8.47 (s, 1H), 8.37-8.31 (m, 1H), 8.05 (d, J = 8.2 Hz, 2H), 7.86 (d, J = 7.6 Hz, 1H), 7.68-7.57 (m, 1H), 7.38-7.19 (m, 1H), 6.45 (s, 1H), 3.61-3.50 (m, 1H), 3.87 (s, 2H), 2.67-2.54 (m, 1H), 0.68-0.57 (m, 2H), 0.45-0.27 (m, 2H) | 1.41 O 526.1 | 193 |
| 468 | 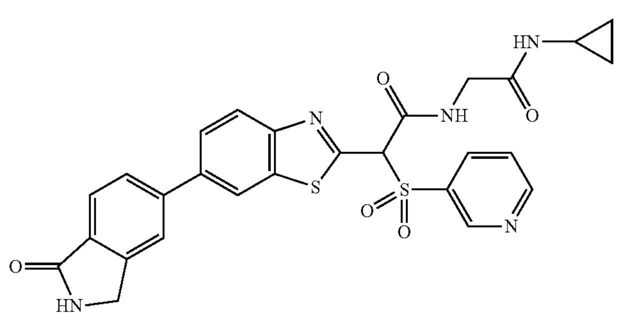 [SMILES: O=C(CNC(=O)C(c1nc2ccc(-c3ccc4c(c3)CNC4=O)cc2s1)S(=O)(=O)c1cccnc1)NC1CC1] | N-[(cyclopropyl-carbamoyl)methyl]-2-[6-(1-oxo-2,3-dihydro-1H-isoindol-5-yl)-1,3-benzothiazol-2-yl]-2-(pyridine-3-sulfonyl)acetamide | 9.12-9.05 (m, 1H), 8.93-8.87 (m, 1H), 8.76-8.70 (m, 1H), 8.62-8.58 (m, 1H), 8.54-8.47 (m, 1H), 8.06 (br. s., 2H), 7.96-7.82 (m, 3H), 7.80-7.59 (m, 2H), 6.47 (s, 1H), 4.54-4.41 (m, 2H), 3.89-3.67 (m, 2H), 3.47-3.37 (m, 1H), 2.65-2.57 (m, 1H), 0.67-0.57 (m, 2H), 0.45-0.36 (m, 2H) | 1.16 O 562.1 | 6 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 469 | 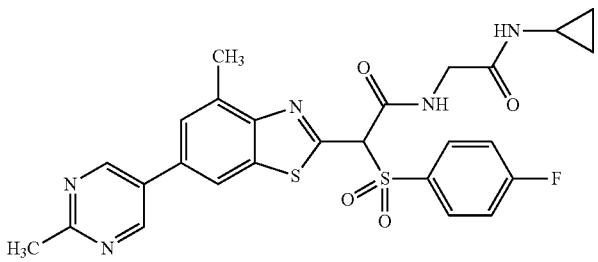 [SMILES: Cc1ncc(-c2cc(C)c3nc(C(C(=O)NCC(=O)NC4CC4)S(=O)(=O)c4ccc(F)cc4)sc3c2)cn1] | N-[(cyclopropylcarbamoyl)methyl]-2-(4-fluorobenzenesulfonyl)-2-[4-methyl-6-(2-methylpyrimidin-5-yl)-1,3-benzothiazol-2-yl]acetamide | 9.10 (s, 2H), 9.04 (m, 1H), 8.40 (s, 1H), 7.99-8.12 (m, 1H), 7.69-7.86 (m, 2H), 7.49 (t, J = 8.3 Hz, 2H), 6.94-7.32 (m, 1H), 6.45 (s, 1H), 3.89 (dd, J = 16.9, 6.2 Hz, 1H), 3.81-3.95 (m, 1H), 3.67-3.77 (m, 1H), 3.73 (dd, J = 16.5, 4.1 Hz, 1H), 2.68-2.73 (m, 3H), 2.70 (s, 3H), 2.64 (d, J = 3.3 Hz, 1H), 2.58 (s, 3H), 0.64 (d, J = 7.2 Hz, 2H), 0.41 (br. s., 2H) | 0.81 M 554.2 | 41 |
| 470 | 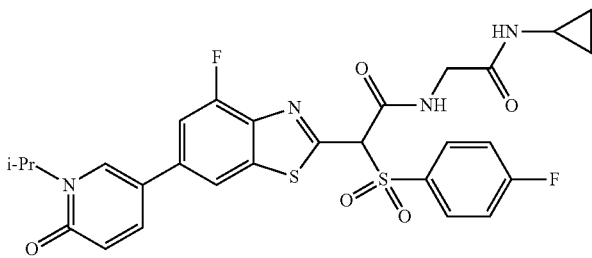 | N-[(cyclopropylcarbamoyl)methyl]-2-{4-fluoro-6-[6-oxo-1-(propan-2-yl)-1,6-dihydropyridin-3-yl]-1,3-benzothiazol-2-yl}-2-(4-fluorobenzenesulfonyl)acetamide | 9.04 (t, J = 5.4 Hz, 1H), 8.23 (d, J = 1.4 Hz, 1H), 8.14 (d, J = 2.5 Hz, 1H), 8.04 (d, J = 3.9 Hz, 1H), 7.89 (dd, J = 9.6, 2.8 Hz, 1H), 7.68-7.82 (m, 3H), 7.47 (t, J = 8.8 Hz, 2H), 6.52 (d, J = 9.4 Hz, 1H), 6.32-6.48 (m, 1H), 5.12 (quin, J = 6.9 Hz, 1H), 3.62-3.89 (m, 2H), 2.62 (td, J = 7.3, 3.9 Hz, 1H), 1.33-1.53 (m, 6H), 0.55-0.67 (m, 2H), 0.32-0.45 (m, 2H) | 0.89 M 600.9 | 16 |
| 471 | 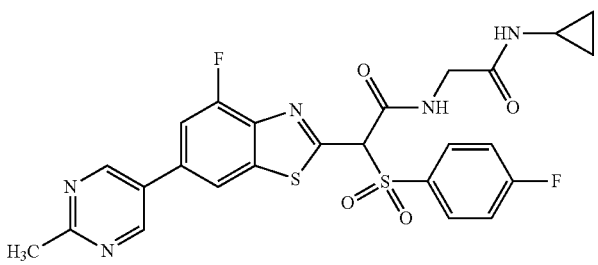 [SMILES: Cc1ncc(-c2cc(F)c3nc(C(C(=O)NCC(=O)NC4CC4)S(=O)(=O)c4ccc(F)cc4)sc3c2)cn1] | N-[(cyclopropylcarbamoyl)methyl]-2-[4-fluoro-6-(2-methylpyrimidin-5-yl)-1,3-benzothiazol-2-yl]-2-(4-fluorobenzenesulfonyl)acetamide | 9.13 (s, 2H), 9.07 (t, J = 5.4 Hz, 1H), 8.45 (d, J = 1.4 Hz, 1H), 8.04 (d, J = 3.9 Hz, 1H), 7.91 (dd, J = 11.8, 1.1 Hz, 1H), 7.69-7.81 (m, 2H), 7.47 (t, J = 8.8 Hz, 2H), 6.44 (s, 1H), 3.78-3.90 (m, 1H), 3.60-3.77 (m, 1H), 2.70 (s, 3H), 2.63 (td, J = 7.4, 3.4 Hz, 1H), 0.56-0.67 (m, 2H), 0.40 (m, 2H) | 0.78 M 558.3 | 23 |
| 472 | 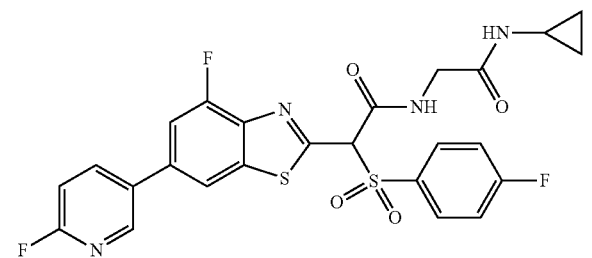 [SMILES: O=C(CNC(=O)C(c1nc2c(F)cc(-c3ccc(F)nc3)cc2s1)S(=O)(=O)c1ccc(F)cc1)NC1CC1] | N-[(cyclopropylcarbamoyl)methyl]-2-[4-fluoro-6-(6-fluoropyridin-3-yl)-1,3-benzothiazol-2-yl]-2-(4-fluorobenzenesulfonyl)acetamide | 9.08 (m, 1H), 8.66 (br. s., 1H), 8.26-8.47 (m, 2H), 8.05 (br. s., 1H), 7.65-7.90 (m, 3H), 7.47 (t, J = 8.2 Hz, 2H), 7.33 (d, J = 7.9 Hz, 1H), 6.42 (s, 1H), 3.69-3.96 (m, 2H), 2.62 (d, J = 3.4 Hz, 1H), 0.63 (d, J = 7.0 Hz, 2H), 0.40 (br. s., 2H) | 0.96 M 560.8 | 23 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 473 | 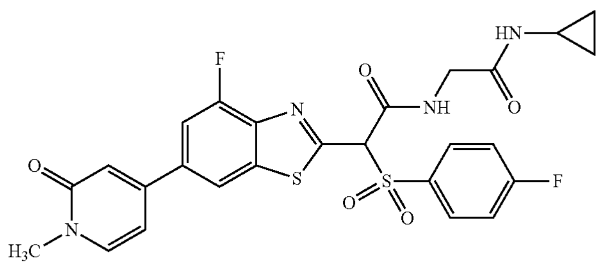 [SMILES: Cn1ccc(-c2cc(F)c3nc(C(C(=O)NCC(=O)NC4CC4)S(=O)(=O)c4ccc(F)cc4)sc3c2)cc1=O] | N-[(cyclopropylcarbamoyl)methyl]-2-[4-fluoro-6-(1-methyl-2-oxo-1,2-dihydropyridin-4-yl)-1,3-benzothiazol-2-yl]-2-(4-fluorobenzenesulfonyl)acetamide | 9.06 (t, J = 5.4 Hz, 1H), 8.42 (d, J = 1.4 Hz, 1H), 8.04 (d, J = 3.9 Hz, 1H), 7.68-7.91 (m, 4H), 7.47 (t, J = 8.8 Hz, 2H), 6.83 (d, J = 1.9 Hz, 1H), 6.59-6.72 (m, 1H), 6.43 (s, 1H), 3.79-3.88 (m, 1H), 3.63-3.79 (m, 1H), 3.44-3.52 (m, 3H), 2.62 (td, J = 7.3, 3.9 Hz, 1H), 0.57-0.68 (m, 2H), 0.31-0.47 (m, 2H) | 0.81 M 572.9 | 77 |
| 474 | 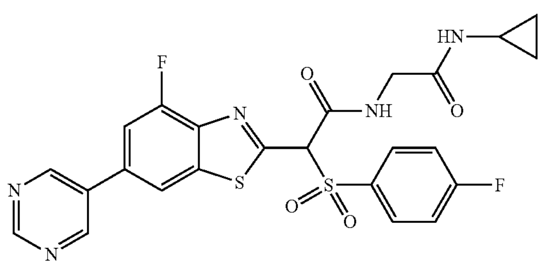 [SMILES: O=C(CNC(=O)C(c1nc2c(F)cc(-c3cncnc3)cc2s1)S(=O)(=O)c1ccc(F)cc1)NC1CC1] | N-[(cyclopropylcarbamoyl)methyl]-2-[4-fluoro-6-(pyrimidin-5-yl)-1,3-benzothiazol-2-yl]-2-(4-fluorobenzenesulfonyl)acetamide | 9.25 (s, 3H), 9.07 (t, J = 5.4 Hz, 1H), 8.49 (d, J = 1.7 Hz, 1H), 8.05 (d, J = 4.1 Hz, 1H), 7.95 (dd, J = 11.8, 1.7 Hz, 1H), 7.68-7.84 (m, 2H), 7.42-7.56 (m, 2H), 6.45 (s, 1H), 3.80-3.89 (m, 1H), 3.66-3.78 (m, 1H), 2.63 (td, J = 7.4, 3.7 Hz, 1H), 0.57-0.68 (m, 2H), 0.40 (m, 2H) | 0.84 M 543.9 | 116 |
| 475 | 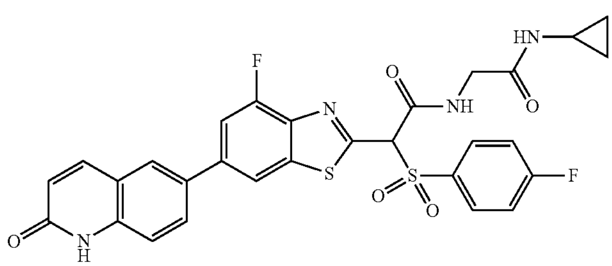 [SMILES: O=C(CNC(=O)C(c1nc2c(F)cc(-c3ccc4[nH]c(=O)ccc4c3)cc2s1)S(=O)(=O)c1ccc(F)cc1)NC1CC1] | N-[(cyclopropylcarbamoyl)methyl]-2-[4-fluoro-6-(2-oxo-1,2-dihydroquinolin-6-yl)-1,3-benzothiazol-2-yl]-2-(4-fluorobenzenesulfonyl)acetamide | 11.94 (br. s., 1H), 9.12 (m, 1H), 8.39 (s, 1H), 8.20 (s, 1H), 8.10 (m, 1H), 8.03 (m, 2H), 7.74-7.90 (m, 3H), 7.50-7.57 (m, 2H), 7.45-7.50 (m, 1H), 6.64 (d, J = 9.5 Hz, 1H), 6.48 (s, 1H), 3.90 (dd, J = 16.5, 5.8 Hz, 1H), 3.68-3.82 (m, 1H), 2.68 (d, J = 3.4 Hz, 1H), 0.69 (d, J = 7.0 Hz, 2H), 0.46 (br. s., 2H) | 0.76 M 609.2 | 7 |
| 476 | 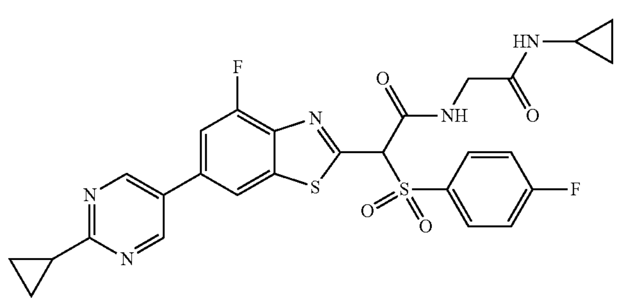 [SMILES: O=C(CNC(=O)C(c1nc2c(F)cc(-c3cnc(C4CC4)nc3)cc2s1)S(=O)(=O)c1ccc(F)cc1)NC1CC1] | N-[(cyclopropylcarbamoyl)methyl]-2-[6-(2-cyclopropylpyrimidin-5-yl)-4-fluoro-1,3-benzothiazol-2-yl]-2-(4-fluorobenzenesulfonyl)acetamide | 9.05-9.22 (m, 3H), 8.47 (s, 1H), 8.11 (br. s., 1H), 7.92 (d, J = 11.6 Hz, 1H), 7.81 (m, 2H), 7.53 (t, J = 8.2 Hz, 2H), 6.49 (s, 1H), 3.90 (dd, J = 16.5, 5.5 Hz, 1H), 3.65-3.84 (m, 1H), 2.69 (m, 1H), 2.34 (m, 1H), 1.05-1.25 (m, 4H), 0.69 (d, J = 7.0 Hz, 2H), 0.45 (br. s., 2H) | 0.88 M 584.3 | 51 |

| Ex. No. | Structure | Name | $^1$H NMR δ (500 MHz, DMSO-d$_6$, unless otherwise indicated) | LC/MS RT (min) Method M + H | EL IC$_{50}$ (nM) |
|---|---|---|---|---|---|
| 477 | 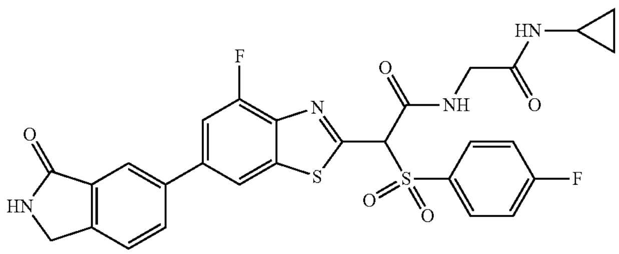 [SMILES: O=C(CNC(=O)C(c1nc2c(F)cc(-c3ccc4c(c3)C(=O)NC4)cc2s1)S(=O)(=O)c1ccc(F)cc1)NC1CC1] | N-[(cyclopropyl-carbamoyl)methyl]-2-[4-fluoro-6-(3-oxo-2,3-dihydro-1H-isoindol-5-yl)-1,3-benzothiazol-2-yl]-2-(4-fluorobenzene-sulfonyl)acetamide | 9.08 (t, J = 5.3 Hz, 1H), 8.68 (s, 1H), 8.41 (s, 1H), 8.00-8.10 (m, 3H), 7.68-7.85 (m, 4H), 7.48 (t, J = 8.8 Hz, 2H), 6.43 (s, 1H), 4.46 (s, 2H), 3.41-3.93 (m, 2H), 2.58-2.68 (m, 1H), 0.60-0.71 (m, 2H), 0.41 (m, 2H) | 1.55 O 597.1 | 68 |
| 478 | 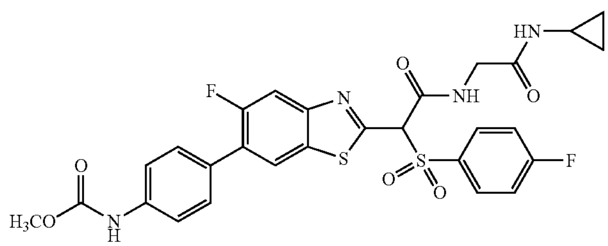 [SMILES: COC(=O)Nc1ccc(-c2cc3sc(C(C(=O)NCC(=O)NC4CC4)S(=O)(=O)c4ccc(F)cc4)nc3cc2F)cc1] | methyl N-{4-[2-({[(cyclopropyl-carbamoyl)methyl]carbamoyl}(4-fluorobenzene-sulfonyl)methyl)-5-fluoro-1,3-benzothiazol-6-yl]phenyl}carbamate | 9.81 (s, 1H), 9.05 (t, J = 5.3 Hz, 1H), 8.25 (s, 1H), 8.03 (d, J = 3.7 Hz, 1H), 7.89 (d, J = 11.3 Hz, 1H), 7.73 (dd, J = 8.5, 5.2 Hz, 2H), 7.49-7.63 (m, 4H), 7.44 (m, 2H), 6.34 (s, 1H), 3.75-3.92 (m, 1H), 3.63-3.73 (m, 4H), 2.61 (m, 1H), 0.61 (d, J = 6.4 Hz, 2H), 0.38 (br. s., 2H) | 1.70 U 615.1 | 2 |
| 479 | 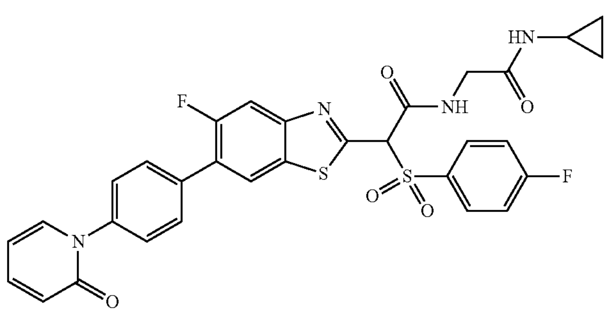 [SMILES: O=C(CNC(=O)C(c1nc2cc(F)c(-c3ccc(-n4ccccc4=O)cc3)cc2s1)S(=O)(=O)c1ccc(F)cc1)NC1CC1] | N-[(cyclopropyl-carbamoyl)methyl]-2-{5-fluoro-6-[4-(2-oxo-1,2-dihydropyridin-1-yl)phenyl]-1,3-benzothiazol-2-yl}-2-(4-fluorobenzene-sulfonyl)acetamide | 8.84-9.32 (m, 1H), 8.21-8.45 (m, 1H), 7.85-8.18 (m, 3H), 7.62-7.82 (m, 5H), 7.48-7.59 (m, 3H), 7.44 (t, J = 8.7 Hz, 2H), 6.52 (d, J = 9.2 Hz, 1H), 6.34-6.43 (m, 2H), 3.65-3.85 (m, 1H), 3.61-3.41 (m, 1H), 2.61 (dt, J = 7.2, 3.7 Hz, 1H), 0.54-0.67 (m, 2H), 0.38 (br. s., 2H) | 0.83 M 635.5 | 9 |
| 481 | 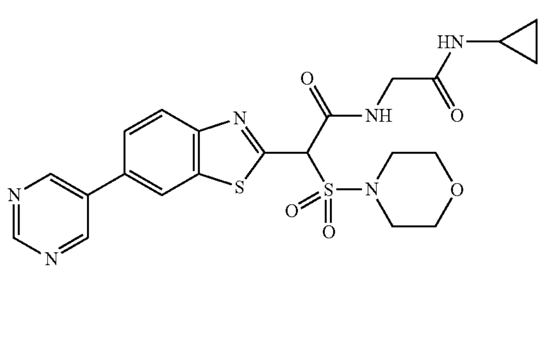 [SMILES: O=C(CNC(=O)C(c1nc2ccc(-c3cncnc3)cc2s1)S(=O)(=O)N1CCOCC1)NC1CC1] | N-[(cyclopropyl-carbamoyl)methyl]-2-(morpholine-4-sulfonyl)-2-[6-(pyrimidin-5-yl)-1,3-benzothiazol-2-yl]acetamide | 9.28-9.23 (m, 3H), 9.08 (t, J = 5.4 Hz, 1H), 8.67 (s, 1H), 8.25 (d, J = 8.5 Hz, 1H), 8.05 (d, J = 3.6 Hz, 1H), 8.02 (d, J = 8.5 Hz, 1H), 6.33 (s, 1H), 3.90-3.84 (m, 1H), 3.83-3.76 (m, 1H), 3.66-3.51 (m, 4H), 3.25-3.05 (m, 4H), 2.68-2.60 (m, 1H), 0.68-0.59 (m, 2H), 0.45-0.36 (m, 2H) | 1.09 O 517.2 | 99 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 482 | 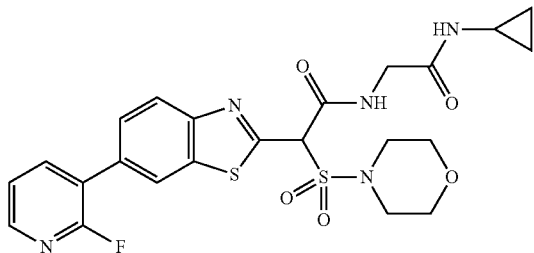 [SMILES: O=C(CNC(=O)C(c1nc2ccc(-c3cccnc3F)cc2s1)S(=O)(=O)N1CCOCC1)NC1CC1] | N-[(cyclopropyl-carbamoyl) methyl]-2-[6-(2-fluoropyridin-3-yl)-1,3-benzothiazol-2-yl]-2-(morpholine-4-sulfonyl)acetamide | 9.07 (t, J = 5.5 Hz, 1H), 8.46 (s, 1H), 8.31 (d, J = 5.0 Hz, 1H), 8.26-8.19 (m, 2H), 8.05 (d, J = 3.9 Hz, 1H), 7.81 (d, J = 8.5 Hz, 1H), 7.54 (t, J = 5.5 Hz, 1H), 6.33 (s, 1H), 3.91-3.84 (m, 1H), 3.83-3.75 (m, 1H), 3.64-3.53 (m, 4H), 3.27-3.08 (m, 4H), 2.69-2.60 (m, 1H), 0.67-0.60 (m, 2H), 0.45-0.37 (m, 2H) | 1.34 O 534.2 | 173 |
| 483 | 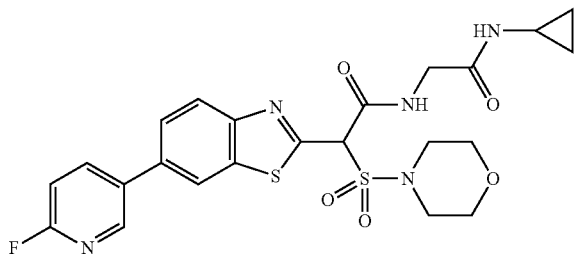 [SMILES: O=C(CNC(=O)C(c1nc2ccc(-c3ccc(F)nc3)cc2s1)S(=O)(=O)N1CCOCC1)NC1CC1] | N-[(cyclopropyl-carbamoyl) methyl]-2-[6-(6-fluoropyridin-3-yl)-1,3-benzothiazol-2-yl]-2-(morpholine-4-sulfonyl)acetamide | 9.07 (t, J = 5.4 Hz, 1H), 8.67 (d, J = 2.2 Hz, 1H), 8.56 (d, J = 1.1 Hz, 1H), 8.40 (td, J = 8.1, 2.5 Hz, 1H), 8.21 (d, J = 8.5 Hz, 1H), 8.04 (d, J = 3.9 Hz, 1H), 7.92 (dd, J = 8.5, 1.4 Hz, 1H), 7.35 (dd, J = 8.5, 2.8 Hz, 1H), 6.32 (s, 1H), 3.90-3.75 (m, 2H), 3.62-3.51 (m, 4H), 3.25-3.07 (m, 4H), 2.64 (tq, J = 7.3, 3.7 Hz, 1H), 0.68-0.60 (m, 2H), 0.45-0.35 (m, 2H) | 1.38 O 534.2 | 299 |
| 484 | 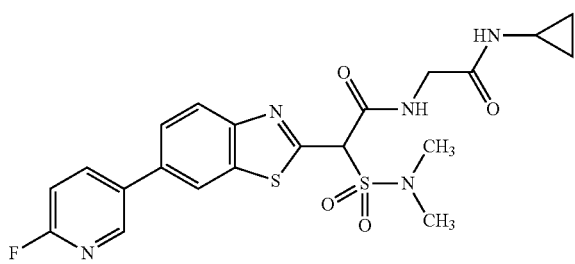 [SMILES: CN(C)S(=O)(=O)C(C(=O)NCC(=O)NC1CC1)c1nc2ccc(-c3ccc(F)nc3)cc2s1] | N-[(cyclopropyl-carbamoyl) methyl]-2-(dimethyl-sulfamoyl)-2-[6-(6-fluoropyridin-3-yl)-1,3-benzothiazol-2-yl]acetamide | (400 MHz, DMSO-$d_6$) 9.07 (t, J = 5.4 Hz, 1H), 8.66 (d, J = 2.6 Hz, 1H), 8.55 (d, J = 1.5 Hz, 1H), 8.39 (td, J = 8.1, 2.6 Hz, 1H), 8.18 (d, J = 8.6 Hz, 1H), 8.03 (d, J = 3.7 Hz, 1H), 7.91 (dd, J = 8.6, 2.0 Hz, 1H), 7.34 (dd, J = 8.6, 2.9 Hz, 1H), 6.30 (s, 1H), 3.92-3.75 (m, 2H), 2.78 (s, 6H), 2.64 (ddt, J = 11.1, 7.5, 3.9 Hz, 1H), 0.68-0.58 (m, 2H), 0.45-0.35 (m, 2H) | 1.69 B 492.1 | 7 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 485 | 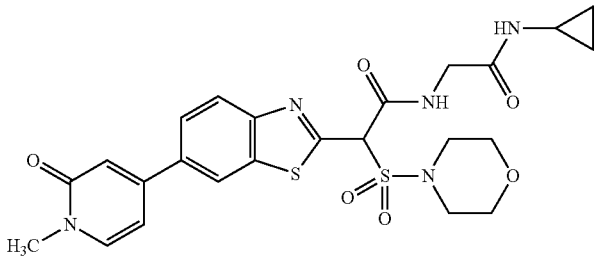 [SMILES: Cn1ccc(-c2ccc3nc(C(C(=O)NCC(=O)NC4CC4)S(=O)(=O)N4CCOCC4)sc3c2)cc1=O] | N-[(cyclopropylcarbamoyl)methyl]-2-[6-(1-methyl-2-oxo-1,2-dihydropyridin-4-yl)-1,3-benzothiazol-2-yl]-2-(morpholine-4-sulfonyl)acetamide | 9.07 (t, J = 5.4 Hz, 1H), 8.59 (s, 1H), 8.17 (d, J = 8.5 Hz, 1H), 8.04 (d, J = 3.6 Hz, 1H), 7.91 (d, J = 8.8 Hz, 1H), 7.83 (d, J = 7.2 Hz, 1H), 6.80 (s, 1H), 6.69 (d, J = 7.2 Hz, 1H), 6.32 (s, 1H), 3.90-3.83 (m, 1H), 3.82-3.76 (m, 1H), 3.62-3.51 (m, 4H), 3.49 (s, 3H), 3.25-3.07 (m, 4H), 2.64 (td, J = 7.2, 3.4 Hz, 1H), 0.64 (d, J = 6.1 Hz, 2H), 0.46-0.35 (m, 2H) | 1.07 O 546.3 | 57 |
| 486 | 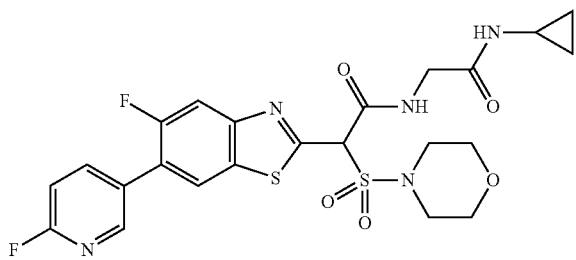 [SMILES: O=C(CNC(=O)C(c1nc2cc(F)c(-c3ccc(F)nc3)cc2s1)S(=O)(=O)N1CCOCC1)NC1CC1] | N-[(cyclopropylcarbamoyl)methyl]-2-[5-fluoro-6-(6-fluoropyridin-3-yl)-1,3-benzothiazol-2-yl]-2-(morpholine-4-sulfonyl)acetamide | 9.03 (br. s., 1H), 8.44 (br. s., 1H), 8.37 (d, J = 7.3 Hz, 1H), 8.21 (t, J = 7.6 Hz, 1H), 8.07 (d, J = 11.0 Hz, 1H), 7.98 (br. s., 1H), 7.89 (s, 1H), 7.31 (d, 1.46 J = 7.0 Hz, 1H), 6.25 (s, 1H), 3.89-3.66 (m, 2H), 3.58-3.46 (m, 4H), 3.22-3.06 (m, 4H), 2.57 (d, J = 3.7 Hz, 1H), 0.57 (d, J = 6.4 Hz, 2H), 0.33 (br. s., 2H) | 1.46 N 552.1 | 48 |
| 487 | 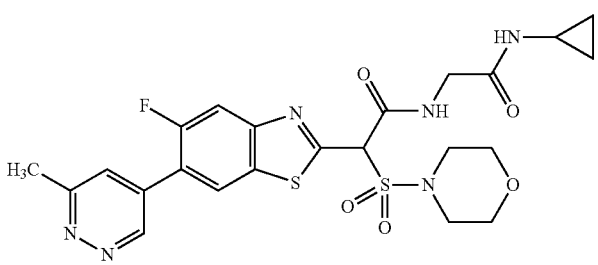 [SMILES: Cc1cc(-c2cc3sc(C(C(=O)NCC(=O)NC4CC4)S(=O)(=O)N4CCOCC4)nc3cc2F)cnn1] | N-[(cyclopropylcarbamoyl)methyl]-2-[5-fluoro-6-(6-methylpyridazin-4-yl)-1,3-benzothiazol-2-yl]-2-(morpholine-4-sulfonyl)acetamide | 9.31 (br. s., 1H), 9.04 (br. s., 1H), 8.52 (d, J = 7.0 Hz, 1H), 8.14 (d, J = 11.3 Hz, 1H), 7.99 (br. s., 1H), 7.83 (s, 1H), 6.26 (s, 1H), 3.86-3.67 (m, 2H), 3.56-3.45 (m, 4H), 3.18-3.07 (m, 4H), 2.66 (s, 3H), 2.57 (d, J = 3.4 Hz, 1H), 0.57 (d, J = 6.7 Hz, 2H), 0.33 (br. s., 2H) | 1.15 N 549.2 | 93 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 488 | 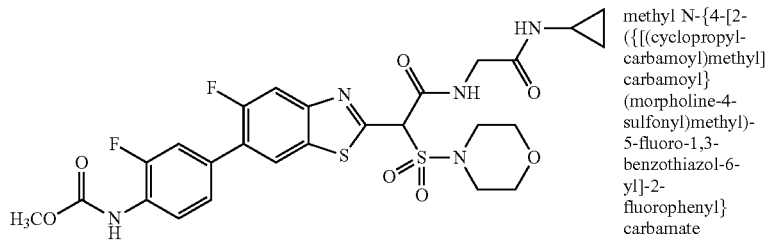 | methyl N-{4-[2-({[(cyclopropyl-carbamoyl)methyl]carbamoyl}(morpholine-4-sulfonyl)methyl)-5-fluoro-1,3-benzothiazol-6-yl]-2-fluorophenyl}carbamate | (400 MHz, DMSO-$d_6$) 9.52 (s, 1H), 9.07 (t, J = 5.6 Hz, 1H), 8.38 (d, J = 7.7 Hz, 1H), 8.09 (d, J = 11.2 Hz, 1H), 8.04 (d, J = 3.7 Hz, 1H), 7.82 (t, J = 8.6 Hz, 1H), 7.53 (d, J = 11.9 Hz, 1H), 7.44 (d, J = 8.6 Hz, 1H), 6.31 (s, 1H), 3.82 (qd, J = 16.8, 5.4 Hz, 2H), 3.71 (s, 3H), 3.60-3.55 (m, 4H), 3.21-3.13 (m, 4H), 2.64 (td, J = 7.3, 3.6 Hz, 1H), 0.63 (dd, J = 7.2, 1.9 Hz, 2H), 0.44-0.35 (m, 2H) | 1.22 O 624.5 | 13 |
| 489 | 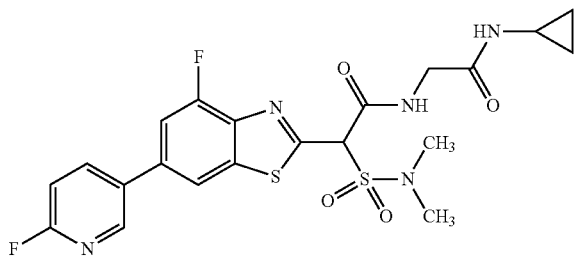 [SMILES: CN(C)S(=O)(=O)C(C(=O)NCC(=O)NC1CC1)c1nc2c(F)cc(-c3ccc(F)nc3)cc2s1] | N-[(cyclopropyl-carbamoyl)methyl]-2-(dimethyl-sulfamoyl)-2-[4-fluoro-6-(6-fluoropyridin-3-yl)-1,3-benzothiazol-2-yl]acetamide | 9.12 (m, 1H), 8.67 (br. s., 1H), 8.29-8.48 (m, 2H), 8.04 (d, J = 2.7 Hz, 1H), 7.83 (d, J = 11.9 Hz, 1H), 7.33 (d, J = 6.7 Hz, 1H), 6.30 (s, 1H), 3.73-3.96 (m, 1H), 3.45-3.62 (m, 1H), 2.80 (br. s, 6H), 2.63 (m, 1H), 0.63 (d, J = 6.1 Hz, 2H), 0.39 (br. s., 2H) | 0.82 M 510.2 | 165 |
| 490 | 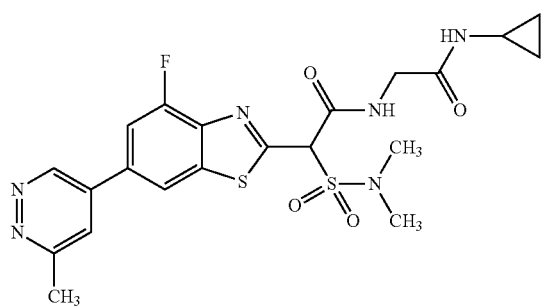 [SMILES: Cc1cc(-c2cc(F)c3nc(C(C(=O)NCC(=O)NC4CC4)S(=O)(=O)N(C)C)sc3c2)cnn1] | N-[(cyclopropyl-carbamoyl)methyl]-2-(dimethyl-sulfamoyl)-2-[4-fluoro-6-(6-methypyridazin-4-yl)-1,3-benzothiazol-2-yl]acetamide | 9.59 (s, 1H), 9.13 (t, J = 5.2 Hz, 1H), 8.64 (s, 1H), 7.94-8.15 (m, 3H), 6.33 (s, 1H), 3.83 (m, 1H), 3.54 (m, 1H), 2.76-2.90 (m, 6H), 2.73 (s, 3H), 2.63 (m, 1H), 0.63 (d, J = 6.4 Hz, 2H), 0.40 (br. s., 2H) | 0.63 M 507.2 | 207 |
| 491 | 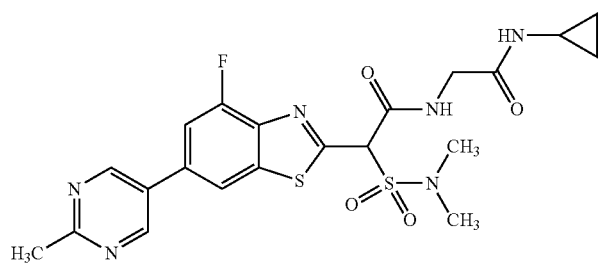 [SMILES: Cc1ncc(-c2cc(F)c3nc(C(C(=O)NCC(=O)NC4CC4)S(=O)(=O)N(C)C)sc3c2)cn1] | N-[(cyclopropyl-carbamoyl)methyl]-2-(dimethyl-sulfamoyl)-2-[4-fluoro-6-(2-methylpyrimidin-5-yl)-1,3-benzothiazol-2-yl]acetamide | 8.86-9.23 (m, 3H), 8.45 (m, 1H), 6.17-8.22 (m, 3H), 3.50-3.88 (m, 2H), 2.72-2.84 (m, 6H), 2.67-2.70 (m, 3H), 2.59-2.66 (m, 1H), 0.63 (d, J = 6.4 Hz, 2H), 0.40 (br. s., 2H) | 0.70 M 507.3 | 82 |

| Ex. No. | Structure | Name | ¹H NMR δ (500 MHz, DMSO-d₆, unless otherwise indicated) | LC/MS RT (min) Method M + H | EL IC$_{50}$ (nM) |
|---|---|---|---|---|---|
| 492 | 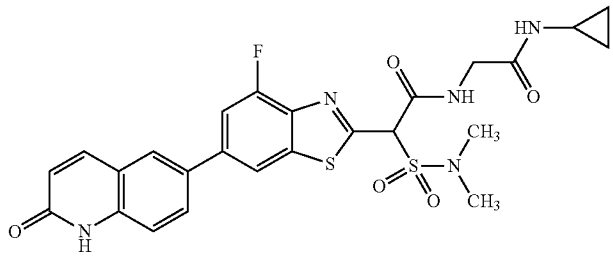 [SMILES: CN(C)S(=O)(=O)C(C(=O)NCC(=O)NC1CC1)c1nc2c(F)cc(-c3ccc4[nH]c(=O)ccc4c3)cc2s1] | N-[(cyclopropyl-carbamoyl)methyl]-2-(dimethyl-sulfamoyl)-2-[4-fluoro-6-(2-oxo-1,2-dihydroquinolin-6-yl)-1,3-benzothiazol-2-yl]acetamide | 11.84 (br. s., 1H), 9.04 (m, 1H), 8.29 (br. s., 1H), 8.08 (br. s., 1H), 7.85-8.03 (m, 3H), 7.73 (d, J = 11.9 Hz, 1H), 7.38 (d, J = 8.2 Hz, 1H), 6.52 (d, J = 9.2 Hz, 1H), 6.24 (br. s., 1H), 3.67-3.88 (m, 2H), 2.65-2.80 (m, 6H), 2.57 (m, 1H), 0.57 (m, 2H), 0.33 (br. s., 2H) | 0.71 M 558.2 | 5 |
| 493 | 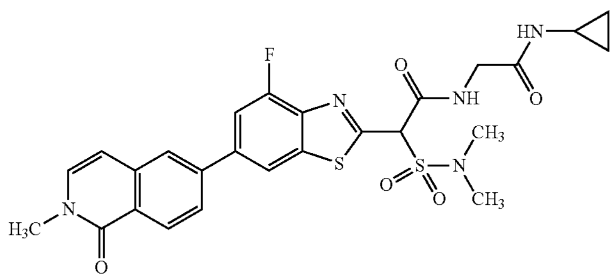 [SMILES: CN(C)S(=O)(=O)C(C(=O)NCC(=O)NC1CC1)c1nc2c(F)cc(-c3ccc4c(=O)n(C)ccc4c3)cc2s1] | N-[(cyclopropyl-carbamoyl)methyl]-2-(dimethyl-sulfamoyl)-2-[4-fluoro-6-(2-methyl-1-oxo-1,2-dihydro-isoquinolin-6-yl)-1,3-benzothiazol-2-yl]acetamide | 9.10 (t, J = 5.4 Hz, 1H), 8.49 (s, 1H), 8.31 (d, J = 8.3 Hz, 1H), 8.11 (d, J = 1.7 Hz, 1H), 8.04 (d, J = 3.9 Hz, 1H), 7.73-7.99 (m, 2H), 7.53 (d, J = 7.4 Hz, 1H), 6.69 (d, J = 7.4 Hz, 1H), 6.34 (s, 1H), 3.72-3.89 (m, 2H), 3.54 (s, 3H), 2.82 (br. s., 6H), 2.64 (td, J = 7.3, 3.6 Hz, 1H), 0.52-0.76 (m, 2H), 0.22-0.46 (m, 2H) | 0.78 M 572.2 | 1 |
| 494 | 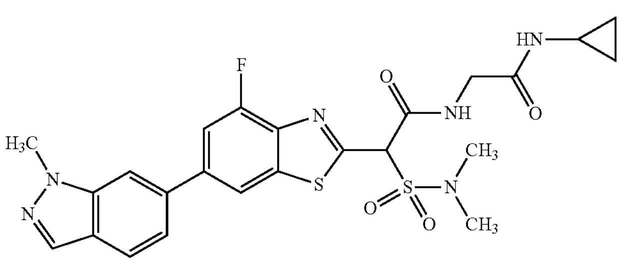 [SMILES: CN(C)S(=O)(=O)C(C(=O)NCC(=O)NC1CC1)c1nc2c(F)cc(-c3ccc4cnn(C)c4c3)cc2s1] | N-[(cyclopropyl-carbamoyl)methyl]-2-(dimethyl-sulfamoyl)-2-[4-fluoro-6-(1-methyl-1H-indazol-6-yl)-1,3-benzothiazol-2-yl]acetamide | 7.06-9.43 (m, 9H), 3.28-4.45 (m, 5H), 2.75 (s, 6H), 2.64 (tq, J = 7.3, 3.9 Hz, 1H), 0.53-0.70 (m, 2H), 0.34-0.47 (m, 2H) | 0.86 M 545.2 | 44 |
| 495 | 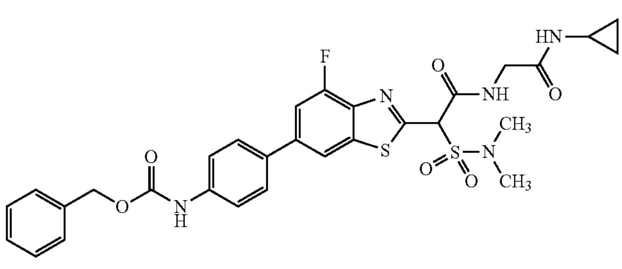 [SMILES: CN(C)S(=O)(=O)C(C(=O)NCC(=O)NC1CC1)c1nc2c(F)cc(-c3ccc(NC(=O)OCc4ccccc4)cc3)cc2s1] | benzyl N-{4-[2-({[(cyclopropyl-carbamoyl)methyl]carbamoyl}(dimethyl-sulfamoyl)methyl)-4-fluoro-1,3-benzothiazol-6-yl]phenyl}carbamate | 9.92 (br. s., 1H), 9.07 (t, J = 5.3 Hz, 1H), 8.25 (s, 1H), 8.01 (d, J = 3.7 Hz, 1H), 7.64-7.82 (m, 3H), 7.58 (d, J = 8.2 Hz, 2H), 7.16-7.49 (m, 5H), 6.25 (s, 1H), 5.16 (s, 2H), 3.72-4.04 (m, 1H), 3.60 (d, J = 5.2 Hz, 1H), 2.74 (s, 6H), 2.56-2.67 (m, 1H), 0.61 (d, J = 6.1 Hz, 2H), 0.37 (br. s., 2H) | 0.94 M 640.5 | 2 |

-continued

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 496 | 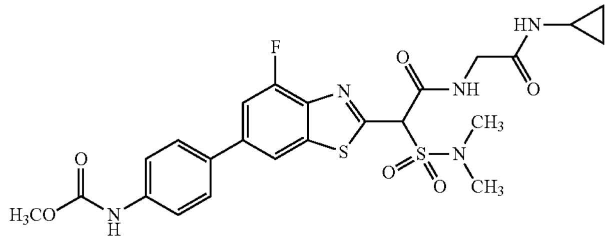 [SMILES: COC(=O)Nc1ccc(-c2cc(F)c3nc(C(C(=O)NCC(=O)NC4CC4)S(=O)(=O)N(C)C)sc3c2)cc1] | methyl N-{4-[2-({[(cyclopropyl-carbamoyl)methyl]carbamoyl}(dimethyl-sulfamoyl)methyl)-4-fluoro-1,3-benzothiazol-6-yl]phenyl}carbamate | 9.77 (s, 1H), 9.04 (t, J = 5.3 Hz, 1H), 8.22 (s, 1H), 7.98 (m, 1H), 7.94-8.09 (m, 1H), 7.61-7.75 (m, 2H), 7.53 (d, J = 8.2 Hz, 2H), 6.22 (s, 1H), 3.76 (dd, J = 9.9, 5.6 Hz, 2H), 3.58 (s, 3H), 2.74 (s, 6H), 2.58 (dt, J = 7.2, 3.4 Hz, 1H), 0.58 (d, J = 5.8 Hz, 2H), 0.34 (br. s., 2H) | 0.81 M 564.5 | 2 |
| 497 | 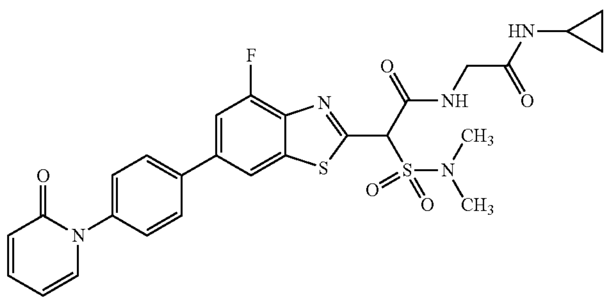 [SMILES: CN(C)S(=O)(=O)C(C(=O)NCC(=O)NC1CC1)c1nc2c(F)cc(-c3ccc(-n4ccccc4=O)cc3)cc2s1] | N-[(cyclopropyl-carbamoyl)methyl]-2-(dimethyl-sulfamoyl)-2-{4-fluoro-6-[4-(2-oxo-1,2-dihydropyridin-1-yl)phenyl]-1,3-benzothiazol-2-yl}acetamide | 9.09 (t, J = 5.3 Hz, 1H), 8.37 (s, 1H), 8.02 (d, J = 3.4 Hz, 1H), 7.91 (d, J = 8.9 Hz, 2H), 7.79 (d, J = 11.9 Hz, 1H), 7.68 (d, J = 6.1 Hz, 1H), 7.44-7.61 (m, 3H), 6.51 (d, J = 9.2 Hz, 1H), 6.37 (t, J = 6.6 Hz, 1H), 6.28 (s, 1H), 3.80 (dd, J = 10.5, 5.6 Hz, 2H), 2.74-2.82 (m, 6H), 2.61 (m, 1H), 0.61 (d, J = 6.1 Hz, 2H), 0.37 (br. s., 2H) | 0.76 M 584.5 | 3 |
| 498 | 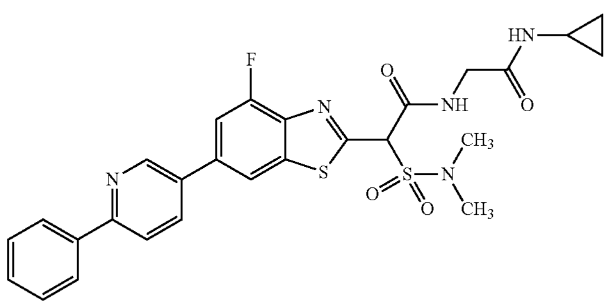 [SMILES: CN(C)S(=O)(=O)C(C(=O)NCC(=O)NC1CC1)c1nc2c(F)cc(-c3ccc(-c4ccccc4)nc3)cc2s1] | N-[(cyclopropyl-carbamoyl)methyl]-2-(dimethyl-sulfamoyl)-2-[4-fluoro-6-(6-phenylpyridin-3-yl)-1,3-benzothiazol-2-yl]acetamide | 8.95-9.21 (m, 2H), 8.48 (s, 1H), 8.31 (d, J = 8.2 Hz, 1H), 8.16-8.16 (m, 1H), 8.08-8.22 (m, 2H), 8.03 (br. s., 1H), 7.82-7.99 (m, 1H), 7.38-7.62 (m, 3H), 6.31 (s, 1H), 3.68-4.02 (m, 2H), 2.80 (s, 6H), 2.63 (m, 1H), 0.63 (d, J = 7.0 Hz, 2H), 0.39 (br. s., 2H) | 0.84 M 568.5 | 3 |
| 499 | 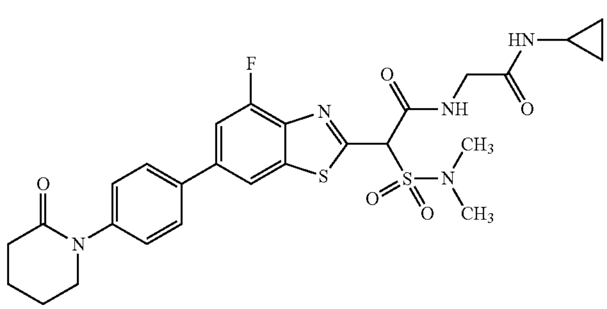 [SMILES: CN(C)S(=O)(=O)C(C(=O)NCC(=O)NC1CC1)c1nc2c(F)cc(-c3ccc(N4CCCCC4=O)cc3)cc2s1] | N-[(cyclopropyl-carbamoyl)methyl]-2-(dimethyl-sulfamoyl)-2-{4-fluoro-6-[4-(2-oxopiperidin-1-yl)phenyl]-1,3-benzothiazol-2-yl}acetamide | 9.09 (t, J = 5.2 Hz, 1H), 8.34 (s, 1H), 8.04 (m, 1H), 7.96 (s, 1H), 7.63-7.67 (m, 1H), 7.43 (d, J = 8.2 Hz, 2H), 7.33-7.36 (m, 1H), 6.31 (s, 1H), 3.76-3.91 (m, 2H), 3.57-3.73 (m, 2H), 2.80 (s, 6H), 2.64 (m, 1H), 2.32-2.48 (m, 2H), 1.71-2.00 (m, 4H), 0.64 (d, J = 6.7 Hz, 2H), 0.40 (br. s., 2H) | 0.79 M 588.5 | 4 |

-continued

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 500 | 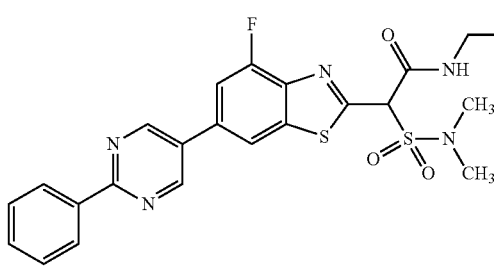 | N-[(cyclopropylcarbamoyl)methyl]-2-(dimethylsulfamoyl)-2-[4-fluoro-6-(2-phenylpyrimidin-5-yl)-1,3-benzothiazol-2-yl]acetamide | 9.35 (s, 2H), 9.12 (t, J = 5.5 Hz, 1H), 8.55 (s, 1H), 8.47 (m, 2H), 7.78-8.10 (m, 3H), 7.58 (m, 2H), 6.33 (s, 1H), 3.84 (dd, J = 11.4, 5.3 Hz, 2H), 2.81 (s, 6H), 2.64 (m, 1H), 0.64 (d, J = 5.8 Hz, 2H), 0.40 (br. s., 2H) | 0.94 M 569.5 | 8 |
| 501 | 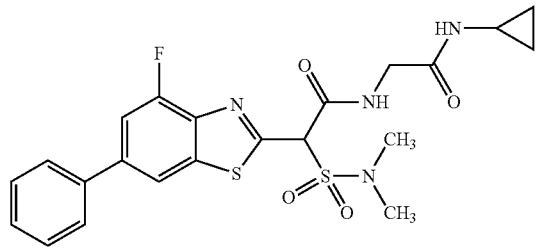 [SMILES: CN(C)S(=O)(=O)C(C(=O)NCC(=O)NC1CC1)c1nc2c(F)cc(-c3ccccc3)cc2s1] | N-[(cyclopropylcarbamoyl)methyl]-2-(dimethylsulfamoyl)-2-(4-fluoro-6-phenyl-1,3-benzothiazol-2-yl)acetamide | 9.07 (m, 1H), 8.32 (s, 1H), 8.02 (br. s., 1H), 7.78 (d, J = 7.6 Hz, 2H), 7.73 (d, J = 12.2 Hz, 1H), 7.48-7.55 (m, 2H), 7.34-7.46 (m, 1H), 6.30 (s, 1H), 3.68-3.90 (m, 2H), 2.78 (s, 6H), 2.62 (m, 1H), 0.62 (d, J = 6.7 Hz, 2H), 0.38 (br. s., 2H) | 0.91 M 491.5 | 8 |
| 502 | 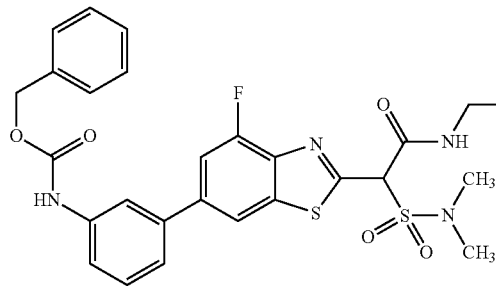 | benzyl N-{3-[2-({[(cyclopropylcarbamoyl)methyl]carbamoyl}(dimethylsulfamoyl)methyl)-4-fluoro-1,3-benzothiazol-6-yl]phenyl}carbamate | 9.90 (br. s., 1H), 9.08 (t, J = 5.3 Hz, 1H), 8.22 (s, 1H), 8.02 (d, J = 3.7 Hz, 1H), 7.85 (br. s., 1H), 7.60 (d, J = 11.9 Hz, 1H), 7.21-7.53 (m, 8H), 6.29 (s, 1H), 5.17 (s, 2H), 3.60-3.93 (m, 2H), 2.71-2.87 (m, 6H), 2.55-2.67 (m, 1H), 0.62 (d, J = 6.1 Hz, 2H), 0.38 (br. s., 2H) | 0.95 M 640.6 | 2 |
| 503 | 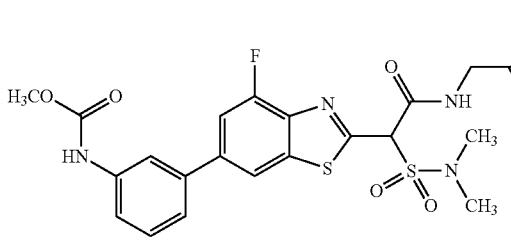 | methyl N-{3-[2-({[(cyclopropylcarbamoyl)methyl]carbamoyl}(dimethylsulfamoyl)methyl)-4-fluoro-1,3-benzothiazol-6-yl]phenyl}carbamate | 9.84 (s, 1H), 9.14 (t, J = 5.3 Hz, 1H), 8.30 (s, 1H), 8.09 (d, J = 3.4 Hz, 1H), 7.91 (s, 1H), 7.68 (d, J = 11.9 Hz, 1H), 7.56 (d, J = 7.3 Hz, 1H), 7.39-7.52 (m, 2H), 6.38 (s, 1H), 3.80-3.98 (m, 2H), 3.75 (s, 3H), 2.86 (s, 6H), 2.70 (dt, J = 7.2, 3.5 Hz, 1H), 0.69 (d, J = 6.1 Hz, 2H), 0.45 (br. s., 2H) | 0.82 M 564.5 | 21 |

-continued

| Ex. No. | Structure | Name | ¹H NMR δ (500 MHz, DMSO-d₆, unless otherwise indicated) | LC/MS RT (min) ethod M + H | EL IC$_{50}$ (nM) |
|---|---|---|---|---|---|
| 504 | 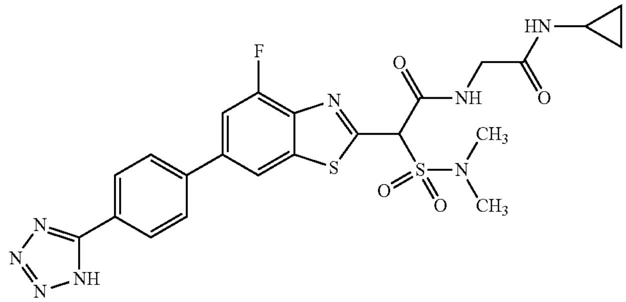 [SMILES: CN(C)S(=O)(=O)C(C(=O)NCC(=O)NC1CC1)c1nc2c(F)cc(-c3ccc(-c4nnn[nH]4)cc3)cc2s1] | N-[(cyclopropyl-carbamoyl)methyl]-2-(dimethyl-sulfamoyl)-2-{4-fluoro-6-[4-(1H-1,2,3,4-tetrazol-5-yl)phenyl]-1,3-benzothiazol-2-yl}acetamide | 9.09 (t, J = 5.3 Hz, 1H), 8.45 (s, 1H), 8.17 (d, J = 8.2 Hz, 2H), 7.97-8.09 (m, 3H), 7.86 (d, J = 11.9 Hz, 1H), 6.32 (s, 1H), 3.50-3.99 (m, 2H), 2.72-2.85 (m, 6H), 2.63 (td, J = 7.2, 3.7 Hz, 1H), 0.53-0.72 (m, 2H), 0.39 (d, J = 2.1 Hz, 2H) | 1.33 O 559.1 | 10 |
| 505 | 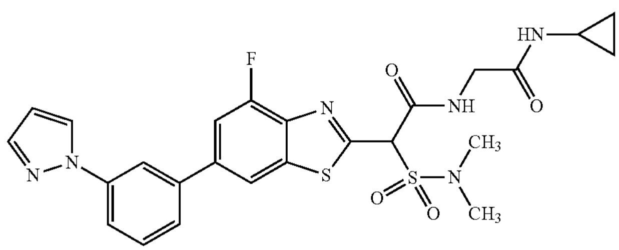 [SMILES: CN(C)S(=O)(=O)C(C(=O)NCC(=O)NC1CC1)c1nc2c(F)cc(-c3cccc(-n4cccn4)c3)cc2s1] | N-[(cyclopropyl-carbamoyl)methyl]-2-(dimethyl-sulfamoyl)-2-{4-fluoro-6-[3-(1H-pyrazol-1-yl)phenyl]-1,3-benzothiazol-2-yl}acetamide | 9.09 (t, J = 5.5 Hz, 1H), 8.66 (d, J = 2.1 Hz, 1H), 8.44 (s, 1H), 8.20 (s, 1H), 8.03 (d, J = 3.4 Hz, 1H), 7.83-7.96 (m, 2H), 7.78 (s, 1H), 7.73 (d, J = 7.6 Hz, 1H), 7.54-7.66 (m, 1H), 6.59 (s, 1H), 6.31 (s, 1H), 3.65-3.94 (m, 2H), 2.79 (s, 6H), 2.62 (td, J = 7.2, 3.5 Hz, 1H), 0.62 (d, J = 5.8 Hz, 2H), 0.39 (br. s., 2H) | 1.73 O 557.1 | 130 |
| 506 | 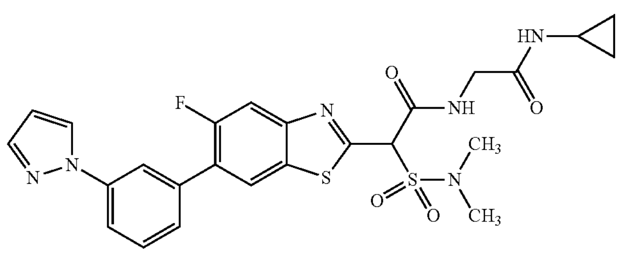 [SMILES: CN(C)S(=O)(=O)C(C(=O)NCC(=O)NC1CC1)c1nc2cc(F)c(-c3cccc(-n4cccn4)c3)cc2s1] | N-[(cyclopropyl-carbamoyl)methyl]-2-(dimethyl-sulfamoyl)-2-{5-fluoro-6-[3-(1H-pyrazol-1-yl)phenyl]-1,3-benzothiazol-2-yl}acetamide | 8.99-9.15 (m, 1H), 8.57 (s, 1H), 8.42 (d, J = 7.6 Hz, 1H), 7.97-8.14 (m, 3H), 7.87-7.96 (m, 1H), 7.77 (s, 1H), 7.60-7.70 (m, 1H), 7.54 (d, J = 7.6 Hz, 1H), 6.57 (s, 1H), 6.27 (s, 1H), 3.70-3.93 (m, 2H), 2.77 (s, 6H), 2.57-2.67 (m, 1H), 0.62 (d, J = 6.1 Hz, 2H), 0.38 (br. s., 2H) | 1.74 O 557.1 | 52 |
| 507 | 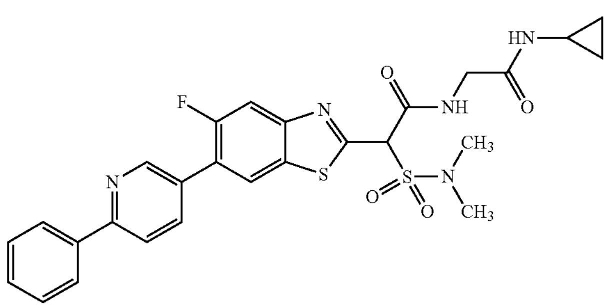 | N-[(cyclopropyl-carbamoyl)methyl]-2-(dimethyl-sulfamoyl)-2-[5-fluoro-6-(6-phenylpyridin-3-yl)-1,3-benzothiazol-2-yl]acetamide | 9.10 (t, J = 5.3 Hz, 1H), 8.91 (s, 1H), 8.47 (d, J = 7.3 Hz, 1H), 7.97-8.22 (m, 6H), 7.36-7.66 (m, 3H), 6.27 (s, 1H), 3.63-3.96 (m, 2H), 2.78 (s, 6H), 2.62 (dt, J = 7.3, 3.7 Hz, 1H), 0.56-0.72 (m, 2H), 0.21-0.49 (m, 2H) | 1.44 O 568.1 | 16 |

-continued

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 508 | 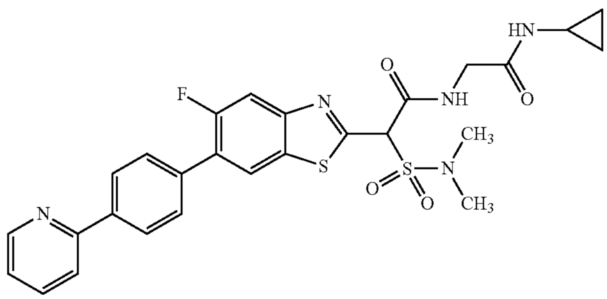 [SMILES: CN(C)S(=O)(=O)C(C(=O)NCC(=O)NC1CC1)c1nc2cc(F)c(-c3ccc(-c4ccccn4)cc3)cc2s1] | N-[(cyclopropylcarbamoyl)methyl]-2-(dimethylsulfamoyl)-2-{5-fluoro-6-[4-(pyridin-2-yl)phenyl]-1,3-benzothiazol-2-yl}acetamide | 9.09 (t, J = 5.3 Hz, 1H), 8.72 (d, J = 4.3 Hz, 1H), 8.40 (d, J = 7.6 Hz, 1H), 8.20 (d, J = 8.2 Hz, 2H), 7.96-8.12 (m, 4H), 7.77 (d, J = 7.6 Hz, 2H), 7.38-7.54 (m, 1H), 6.26 (s, 1H), 3.81 (dd, J = 9.8, 5.5 Hz, 2H), 2.78 (s, 6H), 2.62 (dd, J = 7.2, 3.5 Hz, 1H), 0.62 (d, J = 5.5 Hz, 2H), 0.38 (br. s., 2H) | 1.21 O 568.2 | 15 |
| 511 | 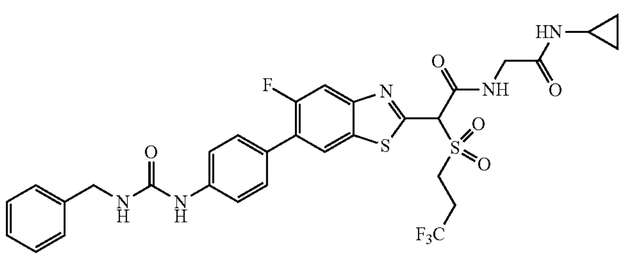 [SMILES: O=C(CNC(=O)C(c1nc2cc(F)c(-c3ccc(NC(=O)NCc4ccccc4)cc3)cc2s1)S(=O)(=O)CCC(F)(F)F)NC1CC1] | 2-(6-{4-[(benzylcarbamoyl)amino]phenyl}-5-fluoro-1,3-benzothiazol-2-yl)-N-[(cyclopropylcarbamoyl)methyl]-2-(3,3,3-trifluoropropanesulfonyl)acetamide | 8.78 (s, 1H), 8.30 (d, J = 7.6 Hz, 1H), 8.07 (br. s., 1H), 8.01 (d, J = 11.0 Hz, 1H), 7.94 (s, 1H), 7.55 (d, J = 8.5 Hz, 2H), 7.49 (d, J = 8.2 Hz, 2H), 7.42 (d, J = 7.9 Hz, 1H), 7.38-7.29 (m, 4H), 7.25 (d, J = 6.7 Hz, 1H), 6.81-6.59 (m, 1H), 4.32 (d, J = 5.5 Hz, 2H), 3.88-3.35 (m, 4H), 2.86-2.78 (m, 1H), 2.68-2.56 (m, 2H), 0.62 (d, J = 5.5 Hz, 2H), 0.39 (br. s., 2H) | 1.73 N 692.2 | 1 |
| 512 | 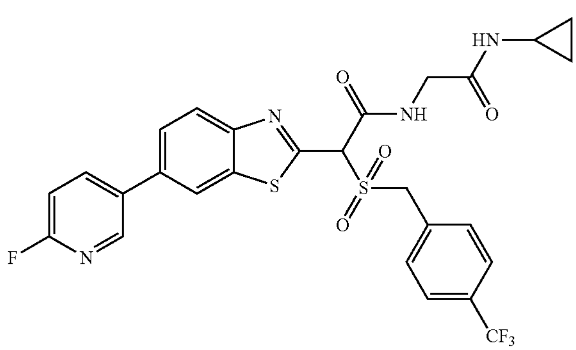 [SMILES: O=C(CNC(=O)C(c1nc2ccc(-c3ccc(F)nc3)cc2s1)S(=O)(=O)Cc1ccc(C(F)(F)F)cc1)NC1CC1] | N-[(cyclopropylcarbamoyl)methyl]-2-[6-(6-fluoropyridin-3-yl)-1,3-benzothiazol-2-yl]-2-{[4-(trifluoromethyl)phenyl]methanesulfonyl}acetamide | 9.08 (t, J = 5.23 Hz, 1H), 8.65 (s, 1H), 8.55 (s, 1H), 8.39 (t, J = 6.74 Hz, 1H), 8.19-8.29 (m, 1H), 8.04-8.14 (m, 1H), 7.93 (d, J = 8.53 Hz, 1H), 7.75 (d, J = 8.25 Hz, 1H), 7.64 (d, J = 8.25 Hz, 1H), 7.57 (br. s., 1H), 7.28-7.36 (m, 1H), 6.30 (s, 1H), 4.93 (d, J = 4.13 Hz, 1H), 4.77-4.86 (m, 1H), 3.82-3.85 (m, 1H), 3.76 (d, J = 13.75 Hz, 1H), 2.61-2.66 (m, 1H), 0.62 (d, J = 6.60 Hz, 2H), 0.37-0.44 (m, 2H) | 0.96 O 607.3 | 16 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 513 | 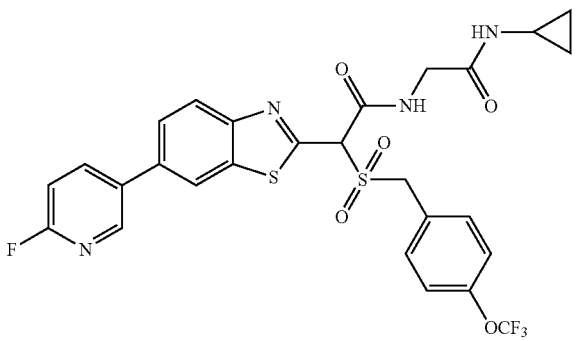 | N-[(cyclopropyl-carbamoyl)methyl]-2-[6-(6-fluoropyridin-3-yl)-1,3-benzothiazol-2-yl]-2-{[4-(trifluoromethoxy)phenyl]methanesulfonyl}acetamide | 9.09 (t, J = 5.36 Hz, 1H), 8.54-8.67 (m, 1H), 8.37-8.42 (m, 1H), 8.22 (d, J = 8.53 Hz, 1H), 8.03-8.14 (m, 1H), 7.93 (d, J = 8.53 Hz, 1H), 7.67-7.85 (m, 1H), 7.55 (d, J = 8.25 Hz, 1H), 7.47 (d, J = 6.33 Hz, 1H), 7.39 (d, J = 8.25 Hz, 1H), 7.27-7.36 (m, 1H), 7.23 (dd, J = 7.57, 14.99 Hz, 1H), 6.30 (s, 1H), 4.86 (d, J = 3.30 Hz, 1H), 4.69-4.79 (m, 1H), 3.84 (d, J = 5.50 Hz, 1H), 3.79 (d, J = 19.81 Hz, 1H), 2.59-2.69 (m, 1H), 0.62 (d, J = 6.60 Hz, 2H), 0.38-0.45 (m, 2H) | 0.97 O 623.2 | 20 |
| 514 | 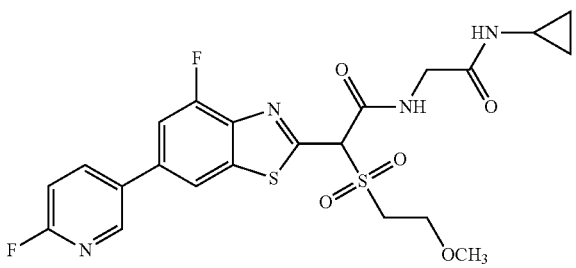 [SMILES: COCCS(=O)(=O)C(C(=O)NCC(=O)NC1CC1)c1nc2c(F)cc(-c3ccc(F)nc3)cc2s1] | N-[(cyclopropyl-carbamoyl)methyl]-2-[4-fluoro-6-(6-fluoropyridin-3-yl)-1,3-benzothiazol-2-yl]-2-(2-methoxyethane-sulfonyl)acetamide | 9.01 (t, J = 5.36 Hz, 1H), 8.68 (s, 1H), 8.39-8.43 (m, 2H), 8.01 (d, J = 3.58 Hz, 1H), 7.88 (d, J = 11.83 Hz, 1H), 7.35 (d, J = 8.53 Hz, 1H), 6.25 (s, 1H), 3.90 (s, 1H), 3.82 (t, J = 6.05 Hz, 2H), 3.76-3.80 (m, 2H), 3.70-3.73 (m, 2H), 3.27 (s, 3H), 2.63 (dd, J = 3.44, 7.02 Hz, 1H), 0.62 (d, J = 6.88 Hz, 2H), 0.39 (d, J = 1.38 Hz, 2H) | 0.89 O 524.8 | 43 |
| 515 | 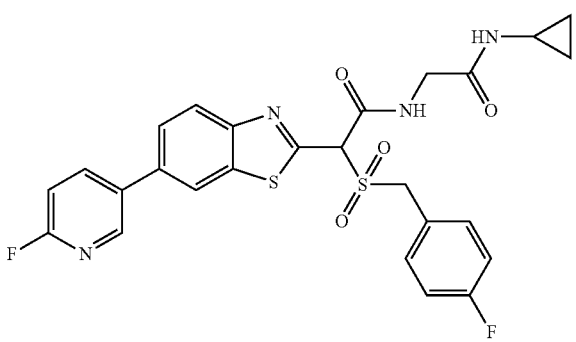 [SMILES: O=C(CNC(=O)C(c1nc2ccc(-c3ccc(F)nc3)cc2s1)S(=O)(=O)Cc1ccc(F)cc1)NC1CC1] | N-[(cyclopropyl-carbamoyl)methyl]-2-[(4-fluorophenyl)methanesulfonyl]-2-[6-(6-fluoropyridin-3-yl)-1,3-benzothiazol-2-yl]acetamide | 9.08 (t, J = 5.36 Hz, 1H), 8.52-8.59 (m, 1H), 8.39 (t, J = 8.12 Hz, 1H), 8.18-8.34 (m, 1H), 8.02-8.15 (m, 1H), 7.93 (d, J = 8.53 Hz, 1H), 7.67-7.87 (m, 1H), 7.44-7.50 (m, 1H), 7.20-7.32 (m, 2H), 7.03-7.12 (m, 1H), 6.26 (s, 1H), 4.77-4.84 (m, 1H), 4.64-4.75 (m, 1H), 3.75-3.86 (m, 2H), 2.60-2.68 (m, 1H), 0.62 (d, J = 6.88 Hz, 2H), 0.41 (d, J = 12.93 Hz, 2H) | 0.91 O 557.1 | 48 |

-continued

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 516 | 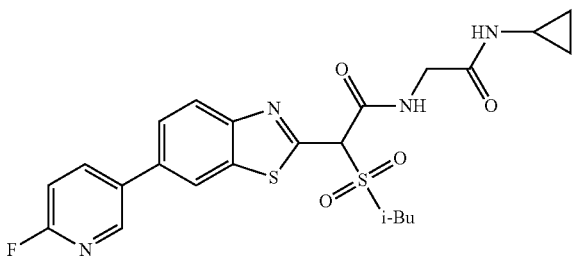 | N-[(cyclopropyl-carbamoyl)methyl]-2-[6-(6-fluoropyridin-3-yl)-1,3-benzothiazol-2-yl]-2-(2-methylpropane-sulfonyl)acetamide | 9.05 (t, J = 5.23 Hz, 1H), 8.55 (s, 1H), 8.34-8.42 (m, 1H), 8.19 (d, J = 8.53 Hz, 1H), 8.01 (d, J = 3.58 Hz, 1H), 7.91 (d, J = 8.53 Hz, 1H), 7.31-7.37 (m, 1H), 6.21 (s, 1H), 3.90 (s, 1H), 3.82 (d, J = 5.50 Hz, 2H), 3.34-3.39 (m, 1H), 2.61-2.66 (m, 1H), 2.21-2.30 (m, 1H), 1.03 (d, J = 6.60 Hz, 6H), 0.62 (d, J = 6.88 Hz, 2H), 0.39 (dd, J = 1.93, 3.58 Hz, 2H) | 0.88 O 505.2 | 57 |
| 517 | 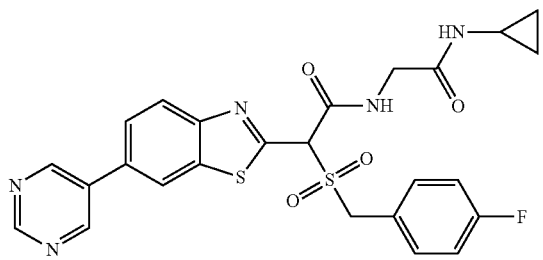 [SMILES: O=C(CNC(=O)C(c1nc2ccc(-c3cncnc3)cc2s1)S(=O)(=O)Cc1ccc(F)cc1)NC1CC1] | N-[(cyclopropyl-carbamoyl)methyl]-2-[(4-fluorophenyl)methanesulfonyl]-2-[6-(pyrimidin-5-yl)-1,3-benzothiazol-2-yl]acetamide | 9.23-9.27 (m, 2H), 9.06-9.19 (m, 2H), 8.21-8.29 (m, 1H), 8.01-8.05 (m, 1H), 7.46 (t, J = 6.19 Hz, 1H), 7.39 (br. s., 1H), 7.24 (t, J = 8.39 Hz, 1H), 7.08 (t, J = 8.67 Hz, 1H), 6.27 (s, 1H), 4.80 (br. s., 1H), 4.65-4.75 (m, 1H), 3.76-3.86 (m, 2H), 2.64 (br. s., 1H), 0.63 (d, J = 6.60 Hz, 2H), 0.41 (d, J = 12.93 Hz, 2H) | 0.78 O 540.1 | 117 |
| 518 | 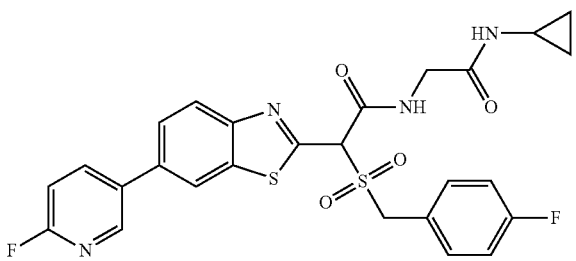 [SMILES: O=C(CNC(=O)C(c1nc2ccc(-c3ccc(F)nc3)cc2s1)S(=O)(=O)Cc1ccc(F)cc1)NC1CC1] | N-[(cyclopropyl-carbamoyl)methyl]-2-[(3-fluorophenyl)methanesulfonyl]-2-[6-(6-fluoropyridin-3-yl)-1,3-benzothiazol-2-yl]acetamide | 9.09 (t, J = 5.50 Hz, 1H), 8.53-8.58 (m, 1H), 8.40 (dt, J = 2.34, 8.18 Hz, 1H), 8.22 (d, J = 8.53 Hz, 1H), 8.04 (d, J = 3.58 Hz, 1H), 7.93 (d, J = 8.53 Hz, 1H), 7.66-7.88 (m, 1H), 7.32-7.49 (m, 1H), 7.25-7.32 (m, 2H), 7.17-7.25 (m, 2H), 6.96-7.12 (m, 1H), 6.28 (s, 1H), 4.83 (d, J = 4.68 Hz, 1H), 4.70-4.80 (m, 1H), 3.76-3.86 (m, 2H), 2.62-2.70 (m, 1H), 0.60-0.66 (m, 2H), 0.37-0.47 (m, 2H) | 0.9 O 557.2 | 124 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 519 | 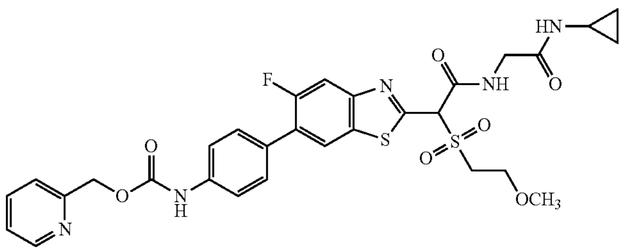 | pyridin-2-ylmethyl N-{4-[2-({[(cyclopropyl-carbamoyl)methyl]carbamoyl}(2-methoxyethane-sulfonyl)methyl)-5-fluoro-1,3-benzothiazol-6-yl]phenyl}carbamate | 10.19-9.91 (m, 1H), 9.00 (t, J = 5.2 Hz, 1H), 8.61 (d, J = 4.3 Hz, 1H), 8.29 (d, J = 7.6 Hz, 1H), 8.04-7.89 (m, 3H), 7.64-7.41 (m, 5H), 6.17 (s, 1H), 5.27 (s, 2H), 3.86-3.66 (m, 3H), 3.56 (d, J = 5.5 Hz, 1H), 3.32-3.21 (m, 2H), 3.10 (d, J = 18.3 Hz, 1H), 2.62 (d, J = 3.7 Hz, 1H), 0.62 (d, J = 6.1 Hz, 2H), 0.38 (br. s., 2H) | 1.50 N 656.2 | 2 |
| 520 | 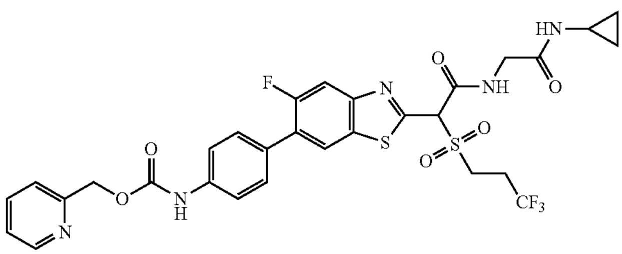 [SMILES: O=C(CNC(=O)C(c1nc2cc(F)c(-c3ccc(NC(=O)OCc4ccccn4)cc3)cc2s1)S(=O)(=O)CCC(F)(F)F)NC1CC1] | pyridin-2-ylmethyl N-{4-[2-({[(cyclopropyl-carbamoyl)methyl]carbamoyl}(3,3,3-trifluoropropane-sulfonyl)methyl)-5-fluoro-1,3-benzothiazol-6-yl]phenyl}carbamate | 9.02 (s, 1H), 8.56 (d, J = 4.6 Hz, 1H), 8.31 (d, J = 7.3 Hz, 1H), 8.14-7.99 (m, 2H), 7.93 (s, 1H), 7.85 (t, J = 7.6 Hz, 1H), 7.67-7.52 (m, 3H), 7.47 (d, J = 7.9 Hz, 2H), 7.35 (t, J = 6.0 Hz, 1H), 5.23 (br. s., 2H), 3.91-3.68 (m, 2H), 3.52 (s, 2H), 2.87-2.78 (m, 2H), 2.62 (d, J = 4.0 Hz, 1H), 0.62 (d, J = 6.7 Hz, 2H), 0.39 (br. s., 2H) | 1.45 O 694.1 | 2 |
| 521 | 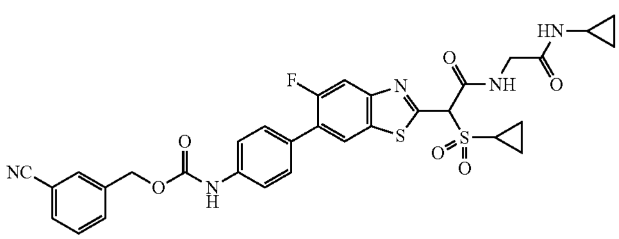 [SMILES: N#Cc1cccc(COC(=O)Nc2ccc(-c3cc4sc(C(C(=O)NCC(=O)NC5CC5)S(=O)(=O)C5CC5)nc4cc3F)cc2)c1] | (3-cyanophenyl)methyl N-(4-{2-[(cyclopropane-sulfonyl)({[(cyclopropyl-carbamoyl)methyl]carbamoyl}methyl]-5-fluoro-1,3-benzothiazol-6-yl}phenyl)carbamate | 10.01 (br. s., 1H), 9.11 (br. s., 1H), 8.28 (d, J = 7.6 Hz, 1H), 8.08-7.97 (m, 2H), 7.90 (s, 1H), 7.80 (dd, J = 15.1, 7.8 Hz, 2H), 7.71-7.39 (m, 6H), 5.22 (s, 2H), 3.99-3.73 (m, 2H), 3.54-3.41 (m, 1H), 2.62 (d, J = 3.4 Hz, 1H), 1.08 (d, J = 7.6 Hz, 2H), 0.95 (d, J = 10.4 Hz, 2H), 0.62 (d, J = 6.1 Hz, 2H), 0.38 (br. s., 2H) | 1.74 N 662.1 | 3 |
| 522 | 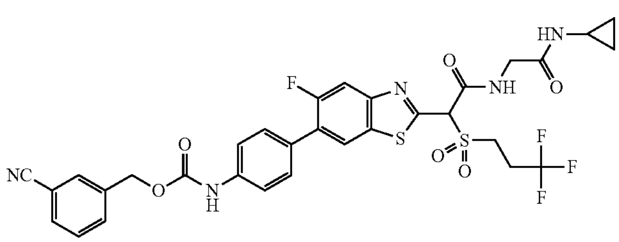 [SMILES: N#Cc1cccc(COC(=O)Nc2ccc(-c3cc4sc(C(C(=O)NCC(=O)NC5CC5)S(=O)(=O)CCC(F)(F)F)nc4cc3F)cc2)c1] | (3-cyanophenyl)methyl N-{4-[2-({[(cyclopropyl-carbamoyl)methyl]carbamoyl}(3,3,3-trifluoropropane-sulfonyl)methyl)-5-fluoro-1,3-benzothiazol-6-yl]phenyl}carbamate | 10.21-9.83 (m, 1H), 9.03 (t, J = 5.2 Hz, 1H), 8.31 (d, J = 7.6 Hz, 1H), 8.15-7.89 (m, 3H), 7.80 (dd, J = 15.3, 7.6 Hz, 2H), 7.72-7.42 (m, 5H), 5.40-5.07 (m, 2H), 3.96-3.61 (m, 4H), 2.95-2.82 (m, 2H), 2.68-2.57 (m, 1H), 0.62 (d, J = 7.0 Hz, 2H), 0.39 (br. s., 2H) | 1.76 N 718.1 | 1 |

| Ex. No. | Structure | Name | $^1$H NMR δ (500 MHz, DMSO-$d_6$, unless otherwise indicated) | LC/MS RT (min) ELethod M + H | IC$_{50}$ (nM) |
|---|---|---|---|---|---|
| 523 | 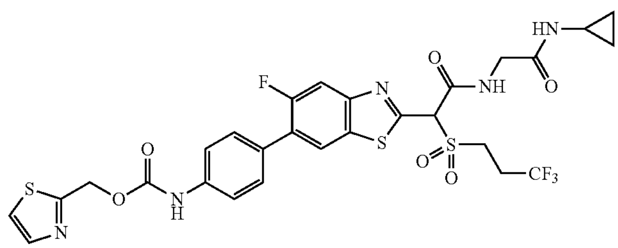 [SMILES: O=C(CNC(=O)C(c1nc2cc(F)c(-c3ccc(NC(=O)OCc4nccs4)cc3)cc2s1)S(=O)(=O)CCC(F)(F)F)NC1CC1] | 1,3-thiazol-2-ylmethyl N-{4-[2-({[(cyclopropyl-carbamoyl)methyl]carbamoyl}(3,3,3-trifluoropropane-sulfonyl)methyl)-5-fluoro-1,3-benzothiazol-6-yl]phenyl} carbamate | 10.32-9.95 (m, 1H), 9.03 (br. s., 1H), 8.31 (d, J = 7.3 Hz, 1H), 8.12-7.92 (m, 2H), 7.89-7.76 (m, 2H), 7.68-7.40 (m, 4H), 5.46 (br. s., 2H), 3.95-3.71 (m, 3H), 3.55-3.39 (m, 1H), 2.87-2.79 (m, 2H), 2.62 (d, J = 3.7 Hz, 1H), 0.62 (d, J = 6.4 Hz, 2H), 0.39 (br. s., 2H) | 1.69 N 700.1 | 6 |
| 524 | 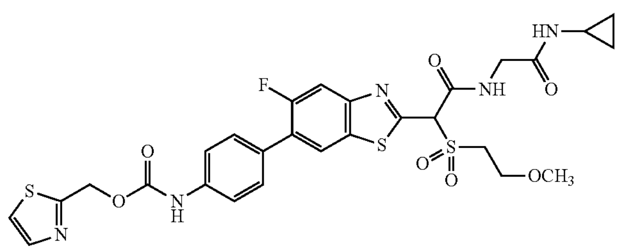 [SMILES: COCCS(=O)(=O)C(C(=O)NCC(=O)NC1CC1)c1nc2cc(F)c(-c3ccc(NC(=O)OCc4nccs4)cc3)cc2s1] | 1,3-thiazol-2-ylmethyl N-{4-[2-({[(cyclopropyl-carbamoyl)methyl]carbamoyl}(2-methoxyethane-sulfonyl)methyl)-5-fluoro-1,3-benzothiazol-6-yl]phenyl} carbamate | 10.13 (br. s., 1H), 8.99 (t, J = 5.3 Hz, 1H), 8.30 (d, J = 7.6 Hz, 1H), 8.07-7.90 (m, 2H), 7.87-7.73 (m, 2H), 7.67-7.42 (m, 4H), 5.57-5.31 (m, 2H), 3.98-3.63 (m, 5H), 3.53-3.32 (m, 2H), 3.26 (s, 2H), 2.62 (dd, J = 7.0, 3.4 Hz, 1H), 0.62 (d, J = 6.7 Hz, 2H), 0.39 (d, J = 2.4 Hz, 2H) | 1.56 N 662.1 | 13 |
| 526 | 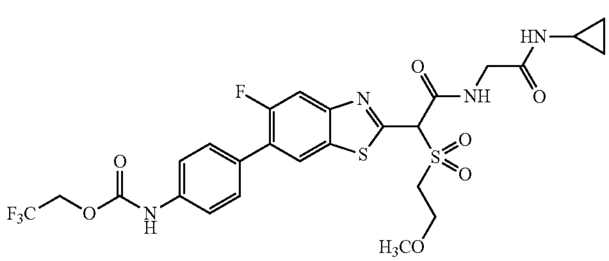 [SMILES: COCCS(=O)(=O)C(C(=O)NCC(=O)NC1CC1)c1nc2cc(F)c(-c3ccc(NC(=O)OCC(F)(F)F)cc3)cc2s1] | 2,2,2-trifluoroethyl N-{4-[2-({[(cyclopropyl-carbamoyl)methyl]carbamoyl}(2-methoxyethane-sulfonyl)methyl)-5-fluoro-1,3-benzothiazol-6-yl]phenyl} carbamate | 10.26 (br. s., 1H), 8.99 (br. s., 1H), 8.27 (d, J = 7.3 Hz, 1H), 7.99 (d, J = 9.5 Hz, 2H), 7.91 (br. s., 1H), 7.57 (d, J = 5.2 Hz, 3H), 7.50 (br. s., 1H), 6.14 (s, 1H), 4.78 (d, J = 8.8 Hz, 2H), 3.90-3.72 (m, 2H), 3.66 (br. s., 4H), 3.34-2.99 (m, 3H), 2.61 (br. s., 1H), 0.61 (d, J = 6.4 Hz, 2H), 0.37 (br. s., 2H) | 1.75 N 647.1 | 1 |
| 527 | 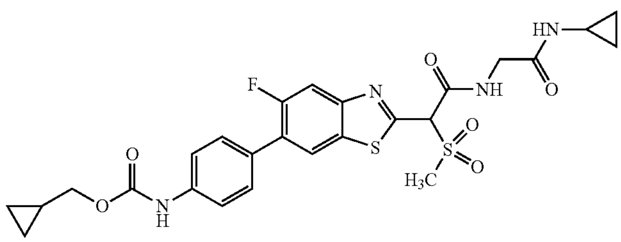 [SMILES: CS(=O)(=O)C(C(=O)NCC(=O)NC1CC1)c1nc2cc(F)c(-c3ccc(NC(=O)OCC4CC4)cc3)cc2s1] | cyclopropylmethyl N-{4-[2-({[(cyclopropyl-carbamoyl)methyl]carbamoyl})(methanesulfonyl)methyl)-5-fluoro-1,3-benzothiazol-6-yl]phenyl} carbamate | 9.89 (s, 1H), 8.43-8.24 (m, 1H), 8.07 (d, J = 3.7 Hz, 1H), 7.81 (d, J = 7.6 Hz, 1H), 7.74-7.59 (m, 3H), 7.54 (d, J = 7.9 Hz, 2H), 6.68 (s, 1H), 3.91 (m, 3H), 3.79 (d, J = 5.8 Hz, 2H), 3.52 (br. s., 1H), 2.69 (dd, J = 7.2, 3.5 Hz, 1H), 1.42-1.07 (m, 2H), 0.69 (d, J = 5.5 Hz, 2H), 0.62 (d, J = 7.6 Hz, 2H), 0.51-0.43 (m, 2H), 0.38 (d, J = 4.3 Hz, 2H) | 1.79 N 575.1 | 9 |

| Ex. No. | Structure | Name | ¹H NMR δ (500 MHz, DMSO-d₆, unless otherwise indicated) | LC/MS RT (min) Method M + H | EL IC$_{50}$ (nM) |
|---|---|---|---|---|---|
| 528 | 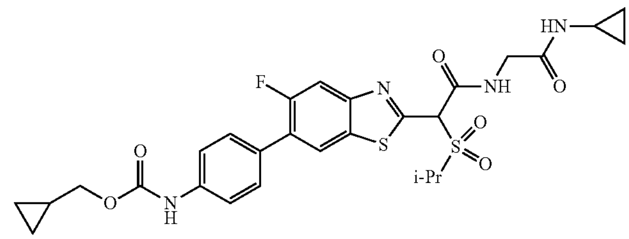 [SMILES: CC(C)S(=O)(=O)C(C(=O)NCC(=O)NC1CC1)c1nc2cc(F)c(-c3ccc(NC(=O)OCC4CC4)cc3)cc2s1] | cyclopropylmethyl N-{4-[2-[(cyclopropyl-carbamoyl)methyl]carbamoyl}(propane-2-sulfonyl)methyl]-5-fluoro-1,3-benzothiazol-6-yl]phenyl}carbamate | 9.92 (br. s., 1H), 9.18 (br. s., 1H), 8.35 (d, J = 7.3 Hz, 1H), 8.16-8.04 (m, 1H), 8.01 (s, 1H), 7.74-7.64 (m, 1H), 7.64-7.56 (m, 2H), 7.52 (d, J = 7.9 Hz, 1H), 6.42 (s, 1H), 4.08-3.93 (m, 2H), 3.93-3.75 (m, 2H), 2.70 (d, J = 3.7 Hz, 1H), 1.44 (d, J = 6.7 Hz, 2H), 1.39-1.26 (m, 4H), 1.23 (br. s., 1H), 0.69 (d, J = 7.0 Hz, 2H), 0.62 (d, J = 7.6 Hz, 2H), 0.46 (br. s., 2H), 0.43-0.23 (m, 2H) | 1.82 N 603.2 | 1 |
| 529 | 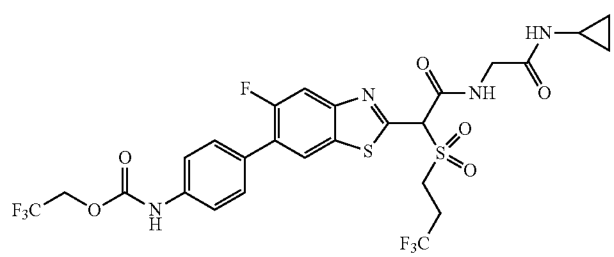 [SMILES: O=C(CNC(=O)C(c1nc2cc(F)c(-c3ccc(NC(=O)OCC(F)(F)F)cc3)cc2s1)S(=O)(=O)CCC(F)(F)F)NC1CC1] | 2,2,2-trifluoroethyl N-{4-[2-({[(cyclopropyl-carbamoyl)methyl]carbamoyl}(3,3,3-trifluoropropane-sulfonyl)methyl)-5-fluoro-1,3-benzothiazol-6-yl]phenyl}carbamate | 10.25 (br. s., 1H), 8.97 (t, J = 5.2 Hz, 1H), 8.27 (d, J = 7.6 Hz, 1H), 8.08-7.90 (m, 2H), 7.63-7.48 (m, 3H), 7.45 (d, J = 8.9 Hz, 1H), 6.33 (s, 1H), 4.80-4.71 (m, 2H), 3.84-3.63 (m, 4H), 3.32 (s, 2H), 2.89-2.73 (m, 1H), 2.65-2.51 (m, 1H), 0.57 (d, J = 7.0 Hz, 2H), 0.40-0.30 (m, 2H) | 1.83 N 685.1 | 2 |
| 530 | 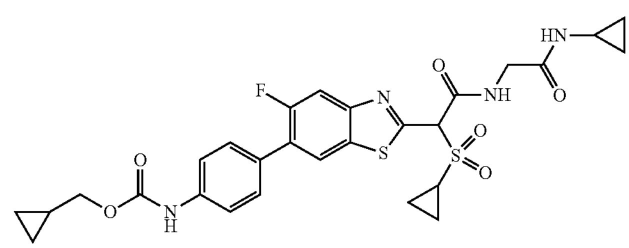 [SMILES: O=C(CNC(=O)C(c1nc2cc(F)c(-c3ccc(NC(=O)OCC4CC4)cc3)cc2s1)S(=O)(=O)C1CC1)NC1CC1] | cyclopropylmethyl N-(4-{2-[(cyclopropane-sulfonyl)({[(cyclopropyl-carbamoyl)methyl]carbamoyl})methyl]-5-fluoro-1,3-benzothiazol-6-yl}phenyl)carbamate | 9.92 (br. s., 1H), 9.18 (br. s., 1H), 8.36 (d, J = 7.6 Hz, 1H), 8.15-8.04 (m, 1H), 8.01 (s, 1H), 7.76-7.64 (m, 2H), 7.61 (d, J = 7.9 Hz, 2H), 7.52 (d, J = 8.2 Hz, 1H), 4.01 (d, J = 7.0 Hz, 2H), 3.97-3.74 (m, 2H), 3.55-3.14 (m, 1H), 2.69 (d, J = 3.7 Hz, 1H), 1.22 (br. s., 1H), 1.15 (d, J = 7.9 Hz, 2H), 1.01 (d, J = 16.5 Hz, 2H), 0.69 (d, J = 6.7 Hz, 2H), 0.62 (d, J = 7.3 Hz, 2H), 0.46 (br. s., 2H), 0.39 (d, J = 4.6 Hz, 2H) | 1.74 N 601.2 | 3 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 531 | 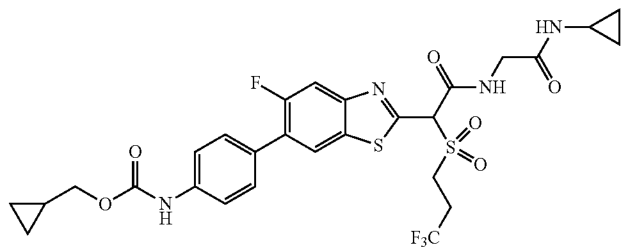 [SMILES: O=C(CNC(=O)C(c1nc2cc(F)c(-c3ccc(NC(=O)OCC4CC4)cc3)cc2s1)S(=O)(=O)CCC(F)(F)F)NC1CC1] | cyclopropylmethyl N-{4-[2-({[(cyclopropyl-carbamoyl)methyl] carbamoyl}(3,3,3-trifluoropropane-sulfonyl)methyl)-5-fluoro-1,3-benzothiazol-6-yl]phenyl} carbamate | 9.93 (s, 1H), 9.17-8.96 (m, 1H), 8.38 (d, J = 7.6 Hz, 1H), 8.19-7.97 (m, 2H), 7.77-7.57 (m, 4H), 6.44 (s, 1H), 4.01 (d, J = 7.3 Hz, 2H), 3.95-3.55 (m, 4H), 2.98-2.77 (m, 2H), 2.70 (d, J = 3.4 Hz, 1H), 1.23 (br. s., 1H), 0.69 (d, J = 6.7 Hz, 2H), 0.62 (d, J = 7.3 Hz, 2H), 0.46 (br. s., 2H), 0.39 (d, J = 4.3 Hz, 2H) | 1.85 N 657.2 | 1 |
| 533 | 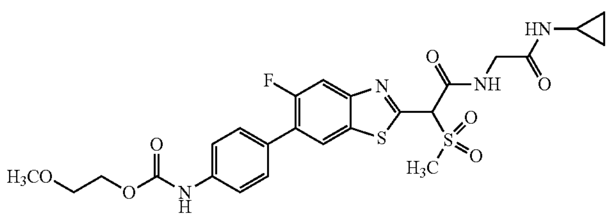 [SMILES: COCCOC(=O)Nc1ccc(-c2cc3sc(C(C(=O)NCC(=O)NC4CC4)S(C)(=O)=O)nc3cc2F)cc1] | 2-methoxyethyl N-{4-[2-({[(cyclopropyl-carbamoyl)methyl] carbamoyl}(methanesulfonyl)methyl)-5-fluoro-1,3-benzothiazol-6-yl]phenyl} carbamate | 9.93 (s, 1H), 9.03 (t, J = 5.4 Hz, 1H), 8.31 (d, J = 7.7 Hz, 1H), 8.12-7.95 (m, 2H), 7.62 (d, J = 8.5 Hz, 2H), 7.55 (d, J = 8.0 Hz, 2H), 7.47 (d, J = 7.7 Hz, 1H), 6.20 (s, 1H), 4.29-4.17 (m, 3H), 3.83 (d, J = 5.5 Hz, 2H), 3.76 (br. s., 1H), 3.64-3.54 (m, 3H), 3.27 (s, 3H), 3.19 (br. s., 2H), 2.64 (td, J = 7.4, 3.7 Hz, 1H), 0.63 (d, J = 6.1 Hz, 3H), 0.51-0.31 (m, 2H) | 1.42 N 579.2 | 3 |
| 534 | 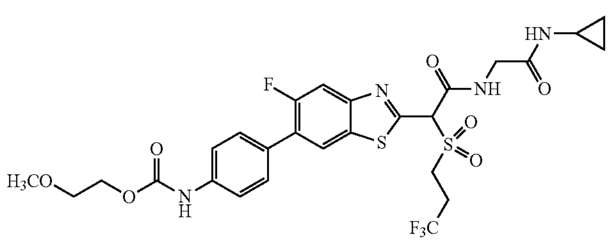 [SMILES: COCCOC(=O)Nc1ccc(-c2cc3sc(C(C(=O)NCC(=O)NC4CC4)S(=O)(=O)CCC(F)(F)F)nc3cc2F)cc1] | 2-methoxyethyl N-{4-[2-({[(cyclopropyl-carbamoyl)methyl] carbamoyl}(3,3,3-trifluoropropane-sulfonyl)methyl)-5-fluoro-1,3-benzothiazol-6-yl]phenyl} carbamate | 9.95-9.77 (m, 1H), 9.04 (t, J = 5.3 Hz, 1H), 8.29 (d, J = 7.3 Hz, 1H), 8.06 (d, J = 3.7 Hz, 1H), 8.00 (d, J = 11.0 Hz, 1H), 7.96-7.83 (m, 1H), 7.65-7.49 (m, 3H), 4.30-4.12 (m, 2H), 3.88-3.66 (m, 3H), 3.66-3.48 (m, 3H), 2.86-2.77 (m, 2H), 2.66-2.52 (m, 2H), 0.72-0.50 (m, 2H), 0.38 (d, J = 2.7 Hz, 2H) | 1.63 N 661.1 | 2 |
| 535 | 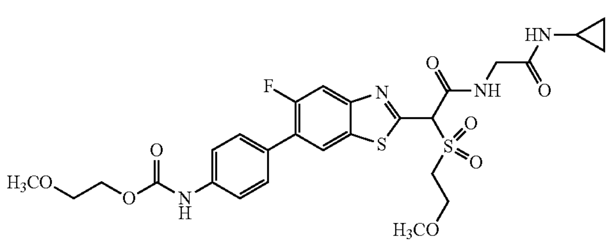 [SMILES: COCCOC(=O)Nc1ccc(-c2cc3sc(C(C(=O)NCC(=O)NC4CC4)S(=O)(=O)CCOC)nc3cc2F)cc1] | 2-methoxyethyl N-{4-[2-({[(cyclopropyl-carbamoyl)methyl] carbamoyl}(2-methoxyethane-sulfonyl)methyl)-5-fluoro-1,3-benzothiazol-6-yl]phenyl} carbamate | 9.89 (s, 1H), 8.99 (t, J = 5.5 Hz, 1H), 8.28 (d, J = 7.6 Hz, 1H), 8.09-7.96 (m, 2H), 7.66-7.48 (m, 4H), 6.16 (s, 1H), 4.31-4.15 (m, 2H), 3.84-3.62 (m, 5H), 3.60-3.53 (m, 1H), 3.50 (s, 1H), 3.26 (s, 6H), 3.10 (br. s., 1H), 2.62 (dt, J = 7.2, 3.5 Hz, 1H), 0.72-0.51 (m, 2H), 0.38 (d, J = 2.4 Hz, 2H) | 1.46 N 623.2 | 4 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 536 | 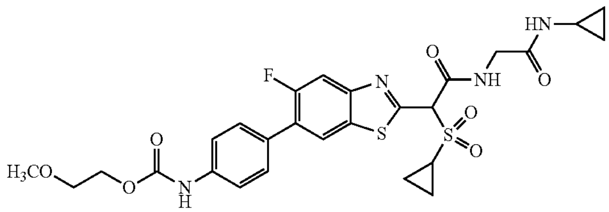 [SMILES: COCCOC(=O)Nc1ccc(-c2cc3sc(C(C(=O)NCC(=O)NC4CC4)S(=O)(=O)C4CC4)nc3cc2F)cc1] | 2-methoxyethyl N-(4-{2-[(cyclopropane-sulfonyl)({[(cyclopropyl-carbamoyl)methyl]carbamoyl})methyl]-5-fluoro-1,3-benzothiazol-6-yl}phenyl) carbamate | 9.97 (s, 1H), 9.19 (t, J = 5.5 Hz, 1H), 8.35 (d, J = 7.6 Hz, 1H), 8.17-8.03 (m, 1H), 8.01 (s, 1H), 7.72-7.50 (m, 4H), 6.31 (s, 1H), 4.39-4.20 (m, 2H), 3.89 (dd, J = 11.1, 5.6 Hz, 2H), 3.62 (s, 2H), 2.95-2.89 (m, 1H), 2.70 (dt, J = 7.3, 3.7 Hz, 1H), 1.16 (d, J = 7.6 Hz, 2H), 1.09-0.90 (m, 2H), 0.80-0.56 (m, 2H), 0.55-0.33 (m, 2H) | 1.49 N 605.2 | 2 |
| 537 | 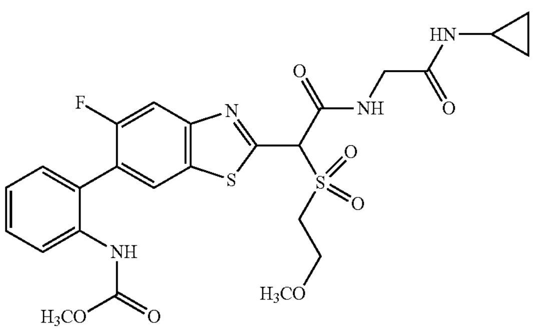 [SMILES: COCCS(=O)(=O)C(C(=O)NCC(=O)NC1CC1)c1nc2cc(F)c(-c3ccccc3NC(=O)OC)cc2s1] | methyl N-{2-[2-({[(cyclopropyl-carbamoyl)methyl]carbamoyl}(2-methoxyethane-sulfonyl)methyl)-5-fluoro-1,3-benzothiazol-6-yl]phenyl} carbamate | 9.00 (t, J = 5.5 Hz, 1H), 8.74 (s, 1H), 8.20-7.88 (m, 3H), 7.63-7.22 (m, 4H), 6.17 (s, 1H), 3.90-3.68 (m, 6H), 3.63-3.42 (m, 3H), 3.27 (s, 3H), 2.61 (dd, J = 7.2, 3.5 Hz, 1H), 0.62 (d, J = 5.5 Hz, 2H), 0.38 (d, J = 2.4 Hz, 2H) | 1.48 N 579.1 | 92 |
| 539 | 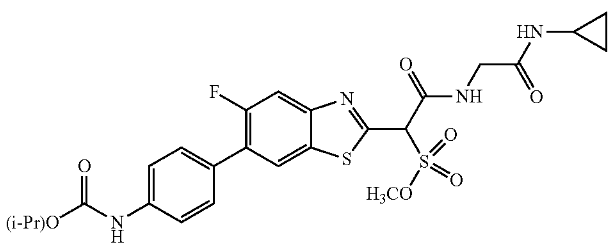 | propan-2-yl N-{4-[2-({[(cyclopropyl-carbamoyl)methyl]carbamoyl}(methanesulfonyl)methyl)-5-fluoro-1,3-benzothiazol-6-yl]phenyl} carbamate | 9.71 (s, 1H), 9.04 (t, J = 5.3 Hz, 1H), 8.28 (d, J = 7.6 Hz, 1H), 8.09-7.87 (m, 2H), 7.58 (d, J = 8.2 Hz, 2H), 7.52 (d, J = 7.9 Hz, 2H), 6.17 (s, 1H), 5.00-4.78 (m, 1H), 3.81 (d, J = 5.5 Hz, 2H), 3.51 (br. s., 1H), 3.25 (s, 2H), 2.62 (d, J = 4.0 Hz, 1H), 1.35-1.17 (m, 6H), 0.62 (d, J = 6.1 Hz, 2H), 0.38 (br. s., 2H) | 1.63 N 563.1 | 1 |
| 540 | 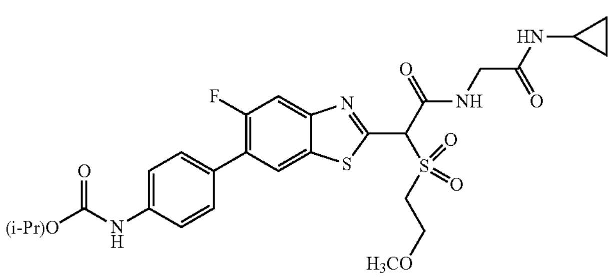 | propan-2-yl N-{4-[2-({[(cyclopropyl-carbamoyl)methyl]carbamoyl}(2-methoxyethane-sulfonyl)methyl)-5-fluoro-1,3-benzothiazol-6-yl]phenyl} carbamate | 9.70 (s, 1H), 8.99 (t, J = 5.5 Hz, 1H), 8.28 (d, J = 7.6 Hz, 1H), 8.05-7.96 (m, 1H), 7.93 (s, 1H), 7.64-7.48 (m, 4H), 6.16 (s, 1H), 5.01-4.78 (m, 1H), 3.96-3.56 (m, 4H), 3.53 (s, 1H), 3.28-3.03 (m, 3H), 2.66-2.54 (11, 1H), 1.26 (d, J = 6.1 Hz, 6H), 1.23-1.14 (m, 1H), 0.62 (d, J = 5.8 Hz, 2H), 0.38 (br. s., 2H) | 1.70 N 607.2 | 2 |

| Ex. No. | Structure | Name | $^1$H NMR δ (500 MHz, DMSO-d$_6$, unless otherwise indicated) | LC/MS RT (min) Method M + H | EL IC$_{50}$ (nM) |
|---|---|---|---|---|---|
| 541 | 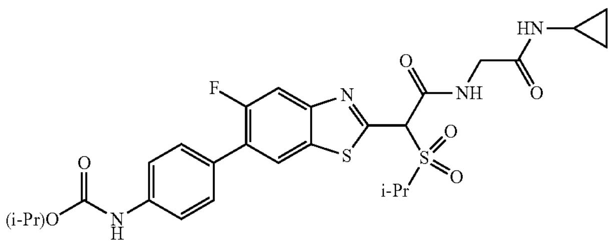 | propan-2-yl N-{4-[2-({[(cyclopropyl-carbamoyl)methyl]carbamoyl}(propane-2-sulfonyl)methyl)-5-fluoro-1,3-benzothiazol-6-yl]phenyl}carbamate | 9.79-9.61 (m, 1H), 9.11 (br. s., 1H), 8.27 (d, J = 7.3 Hz, 1H), 7.99 (s, 1H), 7.93 (s, 1H), 7.65-7.48 (m, 3H), 7.45 (br. s., 1H), 6.32 (s, 1H), 4.94-4.85 (m, 1H), 3.88-3.74 (m, 2H), 3.55 (s, 1H), 2.62 (d, J = 3.7 Hz, 1H), 1.36 (d, J = 6.7 Hz, 2H), 1.31-1.16 (m, 10H), 0.62 (d, J = 6.4 Hz, 2H), 0.38 (br. s., 2H) | 1.81 N 591.2 | 2 |
| 542 | 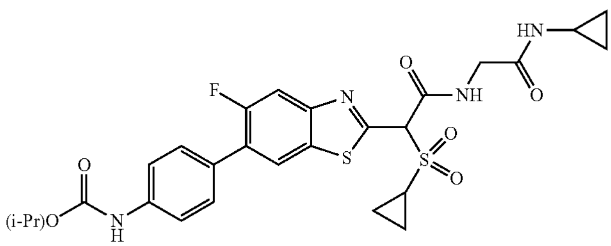 | propan-2-yl N-(4-{2-[(cyclopropane-sulfonyl)({[(cyclopropyl-carbamoyl)methyl]carbamoyl})methyl]-5-fluoro-1,3-benzothiazol-6-yl}phenyl)carbamate | 9.73 (s, 1H), 9.10 (t, J = 5.5 Hz, 1H), 8.30 (d, J = 7.7 Hz, 1H), 8.08-7.96 (m, 2H), 7.66-7.57 (m, 2H), 7.57-7.50 (m, 2H), 6.27 (s, 1H), 5.01-4.85 (m, 1H), 3.95-3.72 (m, 2H), 2.91-2.82 (m, 1H), 2.70-2.56 (m, 1H), 1.37-1.17 (m, 6H), 1.16-1.03 (m, 2H), 1.03-0.84 (m, 2H), 0.63 (dd, J = 7.3, 1.8 Hz, 2H), 0.48-0.27 (m, 2H) | 1.72 N 589.2 | 2 |
| 543 | 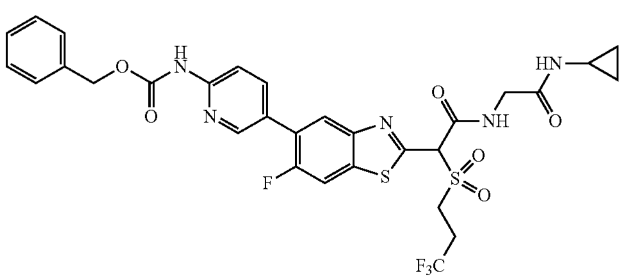 | benzyl N-{5-[2-({[(cyclopropyl-carbamoyl)methyl]carbamoyl}(3,3,3-trifluoropropane-sulfonyl)methyl)-6-fluoro-1,3-benzothiazol-5-yl]pyridin-2-yl}carbamate | 10.45 (s, 1H), 9.04 (t, J = 5.2 Hz, 1H), 8.53 (s, 1H), 8.26 (d, J = 7.0 Hz, 1H), 8.20 (d, J = 10.1 Hz, 1H), 8.07 (d, J = 8.8 Hz, 2H), 7.96 (d, J = 8.5 Hz, 2H), 7.46-7.28 (m, 5H), 6.36 (s, 1H), 5.20 (s, 2H), 3.88-3.67 (m, 3H), 3.50 (br. s., 1H), 2.97-2.78 (m, 2H), 2.69-2.57 (m, 1H), 0.62 (d, J = 7.0 Hz, 2H), 0.39 (br. s., 2H) | 1.95 N 694.1 | 6 |
| 544 | 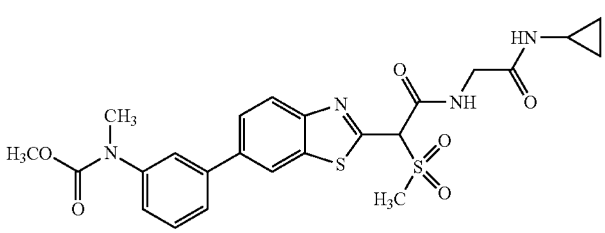 [SMILES: COC(=O)N(C)c1cccc(-c2ccc3nc(C(C(=O)NCC(=O)NC4CC4)S(C)(=O)=O)sc3c2)c1] | methyl N-{3-[2-({[(cyclopropyl-carbamoyl)methyl]carbamoyl}(methanesulfonyl)methyl)-1,3-benzothiazol-6-yl]phenyl}-N-methylcarbamate | 9.03 (br. s., 1H), 8.48 (s, 1H), 8.15 (d, J = 8.2 Hz, 1H), 8.03 (br. s., 1H), 7.87 (d, J = 8.5 Hz, 1H), 7.69 (br. s., 1H), 7.62 (d, J = 7.6 Hz, 1H), 7.50 (t, J = 7.6 Hz, 1H), 7.33 (d, J = 7.6 Hz, 1H), 6.18 (s, 1H), 3.82 (d, J = 4.9 Hz, 3H), 3.62 (s, 1H), 3.52-3.44 (m, 1H), 3.29 (s, 3H), 3.29-3.22 (m, 3H), 2.62 (br. s., 1H), 0.62 (d, J = 7.0 Hz, 2H), 0.39 (br. s., 2H) | 1.44 N 531.1 | 19 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 545 | 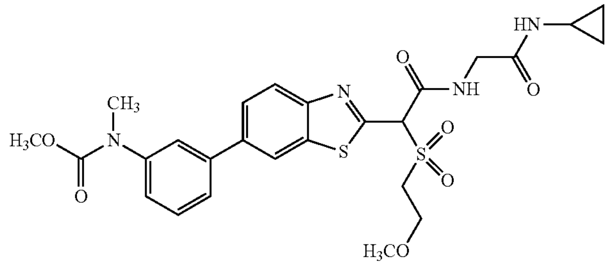 [SMILES: COCCS(=O)(=O)C(C(=O)NCC(=O)NC1CC1)c1nc2ccc(-c3cccc(N(C)C(=O)OC)c3)cc2s1] | methyl N-{3-[2-({[(cyclopropyl-carbamoyl)methyl]carbamoyl}(2-methoxyethane-sulfonyl)methyl)-1,3-benzothiazol-6-yl]phenyl}-N-methylcarbamate | 8.99 (br. s., 1H), 8.47 (s, 1H), 8.14 (d, J = 8.5 Hz, 1H), 8.00 (br. s., 1H), 7.87 (d, J = 8.5 Hz, 1H), 7.68 (br. s., 1H), 7.62 (d, J = 7.6 Hz, 1H), 7.55-7.43 (m, 1H), 7.41-7.26 (m, 1H), 6.17 (s, 1H), 3.93-3.66 (m, 5H), 3.62 (br. s., 1H), 3.55-3.45 (m, 3H), 3.27 (d, J = 10.7 Hz, 6H), 2.62 (br. s., 1H), 0.62 (d, J = 6.7 Hz, 2H), 0.39 (br. s., 2H) | 1.52 N 576.2 | 13 |
| 546 | 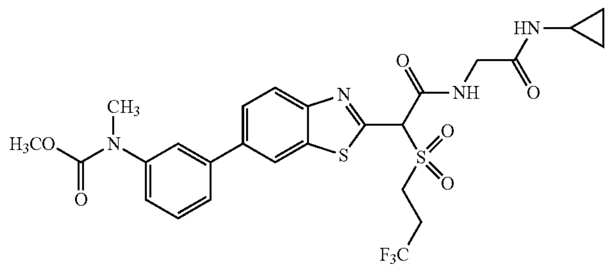 [SMILES: COC(=O)N(C)c1cccc(-c2ccc3nc(C(C(=O)NCC(=O)NC4CC4)S(=O)(=O)CCC(F)(F)F)sc3c2)c1] | methyl N-{3-[2-({[(cyclopropyl-carbamoyl)methyl]carbamoyl}(3,3,3-trifluoropropane-sulfonyl)methyl)-1,3-benzothiazol-6-yl]phenyl}-N-methylcarbamate | 8.65-8.40 (m, 1H), 8.32 (br. s., 1H), 8.19-7.96 (m, 2H), 7.94-7.77 (m, 1H), 7.77-7.59 (m, 2H), 7.58-7.43 (m, 1H), 7.41-7.21 (m, 1H), 4.02-3.65 (m, 2H), 3.66-3.47 (m, 2H), 3.28 (s, 3H), 2.97-2.77 (m, 1H), 2.71-2.54 (m, 2H), 2.50 (br. s., 3H), 0.78-0.58 (m, 2H), 0.49-0.23 (m, 2H) | 1.78 N 613.1 | 7 |
| 547 | 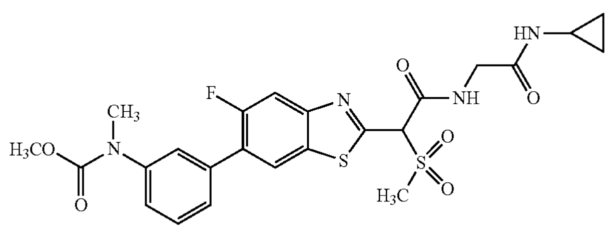 [SMILES: COC(=O)N(C)c1cccc(-c2cc3sc(C(C(=O)NCC(=O)NC4CC4)S(C)(=O)=O)nc3cc2F)c1] | methyl N-{3-[2-({[(cyclopropyl-carbamoyl)methyl]carbamoyl}(methanesulfonyl)methyl)-5-fluoro-1,3-benzothiazol-6-yl]phenyl}-N-methylcarbamate | 9.06 (br. s., 1H), 8.35 (d, J = 7.4 Hz, 1H), 8.08-7.99 (m, 2H), 7.94 (s, 1H), 7.62-7.30 (m, 4H), 6.20 (s, 1H), 3.99-3.79 (m, 3H), 3.62 (s, 3H), 3.54-3.40 (m, 2H), 2.62 (d, J = 3.4 Hz, 1H), 2.50 (br. s., 3H), 0.62 (d, J = 6.1 Hz, 2H), 0.39 (br. s., 2H) | 1.46 N 549.1 | 8 |
| 548 | 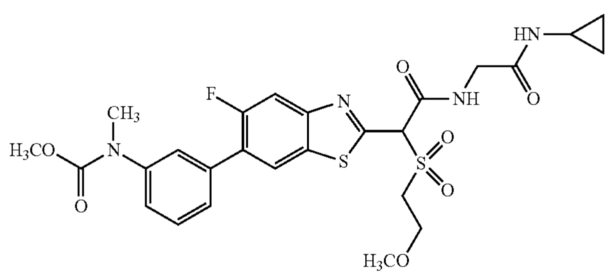 [SMILES: COCCS(=O)(=O)C(C(=O)NCC(=O)NC1CC1)c1nc2cc(F)c(-c3cccc(N(C)C(=O)OC)c3)cc2s1] | methyl N-{3-[2-({[(cyclopropyl-carbamoyl)methyl]carbamoyl}(2-methoxyethane-sulfonyl)methyl)-5-fluoro-1,3-benzothiazol-6-yl]phenyl}-N-methylcarbamate | 8.79 (t, J = 5.2 Hz, 1H), 8.13 (d, J = 7.4 Hz, 1H), 7.92-7.78 (m, 2H), 7.72 (s, 1H), 7.44-7.18 (m, 3H), 7.21-6.89 (m, 1H), 5.98 (s, 1H), 3.75-3.45 (m, 6H), 3.40 (s, 3H), 3.05 (d, J = 4.0 Hz, 3H), 2.40 (dd, J = 7.1, 3.4 Hz, 1H), 2.28 (br. s., 3H), 0.40 (d, J = 6.1 Hz, 2H), 0.17 (d, J = 2.0 Hz, 2H) | 1.52 N 593.2 | 12 |

-continued

| Ex. No. | Structure | Name | $^1$H NMR δ (500 MHz, DMSO-d$_6$, unless otherwise indicated) | LC/MS RT (min) Method M + H | EL IC$_{50}$ (nM) |
|---|---|---|---|---|---|
| 549 | 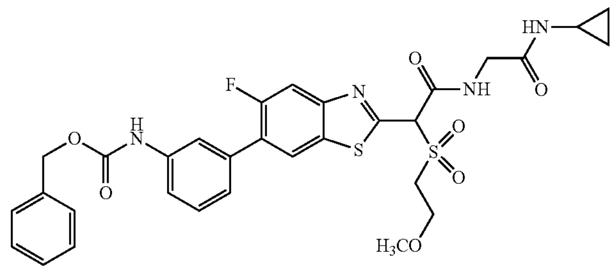 [SMILES: COCCS(=O)(=O)C(C(=O)NCC(=O)NC1CC1)c1nc2cc(F)c(-c3cccc(NC(=O)OCc4ccccc4)c3)cc2s1] | benzyl N-{3-[2-({[(cyclopropyl-carbamoyl)methyl]carbamoyl}(2-methoxyethane-sulfonyl)methyl)-5-fluoro-1,3-benzothiazol-6-yl]phenyl} carbamate | 10.03-9.75 (m, 1H), 9.00 (t, J = 5.5 Hz, 1H), 8.28 (d, J = 7.3 Hz, 1H), 8.12-7.88 (m, 2H), 7.78-7.62 (m, 1H), 7.56-7.06 (m, 8H), 6.18 (s, 1H), 5.16 (s, 2H), 3.94-3.65 (m, 4H), 3.56-3.36 (m, 2H), 3.26 (s, 3H), 2.62 (td, J = 7.2, 3.7 Hz, 1H), 0.68-0.57 (m, 2H), 0.43-0.33 (m, 2H) | 1.86 N 655.2 | 4 |
| 550 | 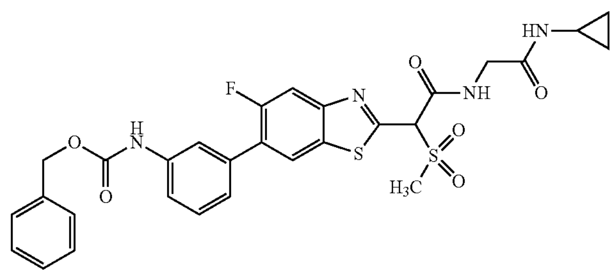 [SMILES: CS(=O)(=O)C(C(=O)NCC(=O)NC1CC1)c1nc2cc(F)c(-c3cccc(NC(=O)OCc4ccccc4)c3)cc2s1] | benzyl N-{3-[2-({[(cyclopropyl-carbamoyl)methyl]carbamoyl}(methanesulfonyl)methyl)-5-fluoro-1,3-benzothiazol-6-yl]phenyl} carbamate | 9.91 (br. s., 1H), 9.27-8.93 (m, 1H), 8.27 (d, J = 7.3 Hz, 1H), 8.13-7.96 (m, 2H), 7.82-7.60 (m, 1H), 7.56-7.09 (m, 7H), 6.18 (s, 1H), 5.15 (s, 2H), 4.02-3.71 (m, 2H), 3.58 (d, J = 5.2 Hz, 3H), 2.62 (dd, J = 7.2, 3.5 Hz, 1H), 0.74-0.56 (m, 2H), 0.39 (br. s., 2H) | 1.82 N 611.1 | 1 |
| 551 | 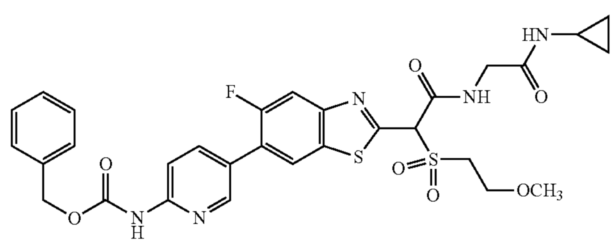 [SMILES: COCCS(=O)(=O)C(C(=O)NCC(=O)NC1CC1)c1nc2cc(F)c(-c3ccc(NC(=O)OCc4ccccc4)nc3)cc2s1] | benzyl N-{5-[2-({[(cyclopropyl-carbamoyl)methyl]carbamoyl}(2-methoxyethane-sulfonyl)methyl)-5-fluoro-1,3-benzothiazol-6-yl]pyridin-2-yl} carbamate | 9.00 (br. s., 1H), 8.49 (br. s., 1H), 8.35 (d, J = 7.6 Hz, 1H), 8.15-7.87 (m, 5H), 7.50-7.26 (m, 5H), 6.15 (s, 1H), 5.19 (s, 2H), 3.89-3.74 (m, 2H), 3.69 (br. s., 4H), 3.32-3.17 (m, 3H), 2.66-2.56 (m, 1H), 0.62 (d, J = 5.8 Hz, 2H), 0.38 (br. s., 2H) | 1.77 N 656.2 | 1 |
| 552 | 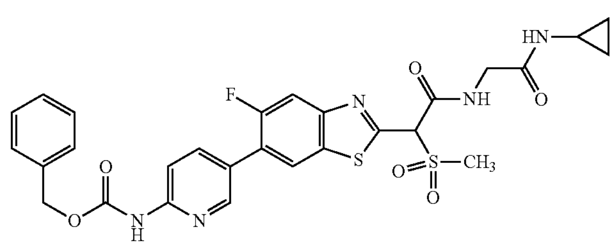 [SMILES: CS(=O)(=O)C(C(=O)NCC(=O)NC1CC1)c1nc2cc(F)c(-c3ccc(NC(=O)OCc4ccccc4)nc3)cc2s1] | benzyl N-{5-[2-({[(cyclopropyl-carbamoyl)methyl]carbamoyl}(methanesulfonyl)methyl)-5-fluoro-1,3-benzothiazol-6-yl]pyridin-2-yl}carbamate | 9.06 (t, J = 5.2 Hz, 1H), 8.49 (br. s., 1H), 8.35 (d, J = 7.3 Hz, 1H), 8.14-7.85 (m, 4H), 7.51-7.16 (m, 5H), 6.16 (s, 1H), 5.32-5.06 (m, 2H), 3.88-3.76 (m, 1H), 3.71-3.60 (m, 1H), 3.32-3.15 (m, 3H), 2.66-2.58 (m, 1H), 0.62 (d, J = 6.1 Hz, 2H), 0.38 (br. s., 2H) | 1.75 N 612.1 | 1 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 553 | 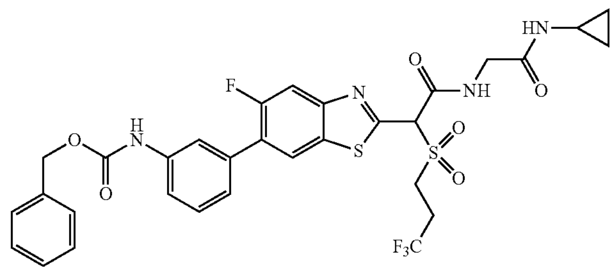 [SMILES: O=C(CNC(=O)C(c1nc2cc(F)c(-c3cccc(NC(=O)OCc4ccccc4)c3)cc2s1)S(=O)(=O)CCC(F)(F)F)NC1CC1] | benzyl N-{3-[2-({[(cyclopropyl-carbamoyl)methyl]carbamoyl}(3,3,3-trifluoropropane-sulfonyl)methyl)-5-fluoro-1,3-benzothiazol-6-yl]phenyl} carbamate | 10.08-9.82 (m, 1H), 9.03 (t, J = 5.0 Hz, 1H), 8.30 (d, J = 7.6 Hz, 1H), 8.16-7.98 (m, 2H), 7.81-7.64 (m, 1H), 7.57-7.10 (m, 8H), 6.38 (s, 1H), 5.16 (s, 2H), 3.92-3.68 (m, 3H), 3.51-3.37 (m, 1H), 2.96-2.70 (m, 2H), 2.63 (d, J = 3.4 Hz, 1H), 0.62 (d, J = 7.0 Hz, 2H), 0.39 (br. s., 2H) | 2.0 N 693.2 | 1 |
| 554 | 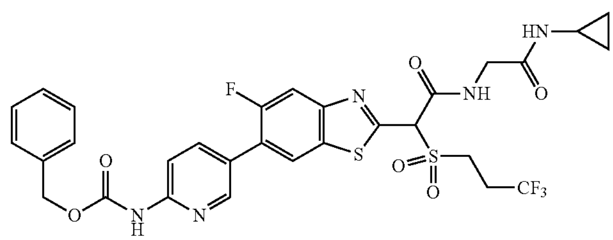 [SMILES: O=C(CNC(=O)C(c1nc2cc(F)c(-c3ccc(NC(=O)OCc4ccccc4)nc3)cc2s1)S(=O)(=O)CCC(F)(F)F)NC1CC1] | benzyl N-{5-[2-({[(cyclopropyl-carbamoyl)methyl]carbamoyl}(3,3,3-trifluoropropane-sulfonyl)methyl)-5-fluoro-1,3-benzothiazol-6-yl]pyridin-2-yl} carbamate | 10.58-10.27 (m, 1H), 9.04 (t, J = 5.2 Hz, 1H), 8.59-8.31 (m, 2H), 8.13-7.86 (m, 4H), 7.47-7.25 (m, 6H), 5.20 (s, 2H), 3.91-3.66 (m, 3H), 3.55 (br. s., 1H), 2.91-2.78 (m, 2H), 2.66-2.56 (m, 1H), 0.62 (d, J = 6.4 Hz, 2H), 0.39 (br. s., 2H) | 1.93 N 694.1 | 3 |
| 555 | 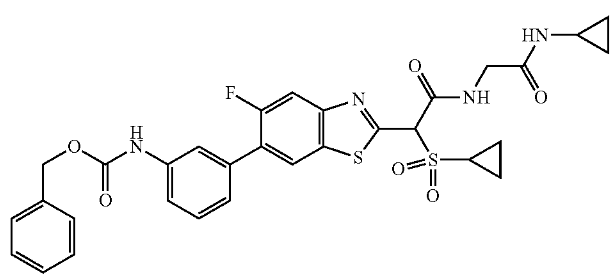 [SMILES: O=C(CNC(=O)C(c1nc2cc(F)c(-c3cccc(NC(=O)OCc4ccccc4)c3)cc2s1)S(=O)(=O)C1CC1)NC1CC1] | benzyl N-(3-{2-[(cyclopropane-sulfonyl)({[(cyclopropyl-carbamoyl)methyl]carbamoyl})methyl]-5-fluoro-1,3-benzothiazol-6-yl}phenyl) carbamate | 9.91 (br. s., 1H), 9.12 (t, J = 5.3 Hz, 1H), 8.27 (d, J = 7.6 Hz, 1H), 8.12-7.92 (m, 2H), 7.59-7.22 (m, 10H), 5.25-5.12 (m, 2H), 4.01-3.69 (m, 2H), 3.00-2.81 (m, 1H), 2.71-2.55 (m, 1H), 1.28-1.03 (m, 2H), 0.95 (d, J = 11.0 Hz, 2H), 0.62 (d, J = 6.1 Hz, 2H), 0.38 (br. s., 2H) | 1.88 N 637.2 | 1 |
| 556 | 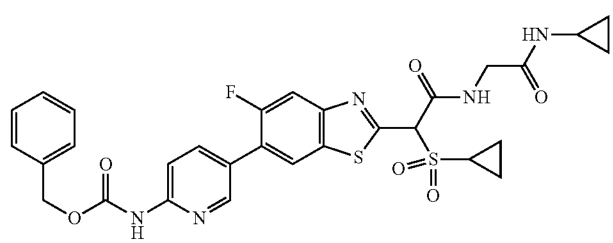 [SMILES: O=C(CNC(=O)C(c1nc2cc(F)c(-c3ccc(NC(=O)OCc4ccccc4)nc3)cc2s1)S(=O)(=O)C1CC1)NC1CC1] | benzyl N-(5-{2-[(cyclopropane-sulfonyl)({[(cyclopropyl-carbamoyl)methyl]carbamoyl)methyl]-5-fluoro-1,3-benzothiazol-6-yl}pyridin-2-yl) carbamate | 10.47 (s, 1H), 9.25-9.08 (m, 1H), 8.51 (br. s., 1H), 8.38 (d, J = 7.6 Hz, 1H), 8.11-7.87 (m, 5H), 7.56-7.21 (m, 6H), 5.21 (s, 2H), 3.93-3.69 (m, 2H), 2.91-2.82 (m, 1H), 2.62 (d, J = 3.7 Hz, 1H), 2.54 (t, J = 5.5 Hz, 2H), 1.08 (d, J = 7.9 Hz, 2H), 0.95 (d, J = 10.1 Hz, 2H), 0.62 (d, J = 6.1 Hz, 2H), 0.38 (br. s., 2H) | 1.82 N 638.1 | 15 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 557 | 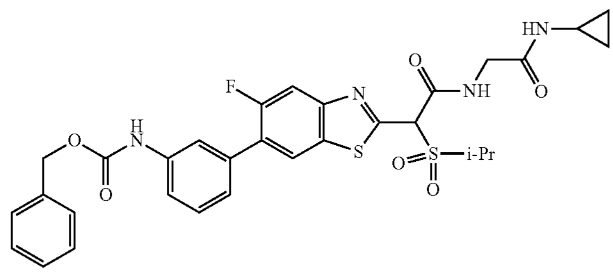 [SMILES: CC(C)S(=O)(=O)C(C(=O)NCC(=O)NC1CC1)c1nc2cc(F)c(-c3cccc(NC(=O)OCc4ccccc4)c3)cc2s1] | benzyl N-{3-[2-({[(cyclopropyl-carbamoyl)methyl]carbamoyl}(propane-2-sulfonyl)methyl)-5-fluoro-1,3-benzothiazol-6-yl]phenyl}carbamate | 9.93 (br. s., 1H), 9.11 (br. s., 1H), 8.28 (d, J = 7.2 Hz, 1H), 8.15-7.99 (m, 2H), 7.78-7.66 (m, 1H), 7.58-6.99 (m, 9H), 5.17 (br. s., 2H), 3.91-3.74 (m, 2H), 3.61-3.49 (m, 1H), 2.64 (br. s., 1H), 1.43-1.20 (m, 6H), 0.62 (d, J = 5.2 Hz, 2H), 0.40 (br. s., 2H) | 1.84 N 639.2 | 7 |
| 560 | 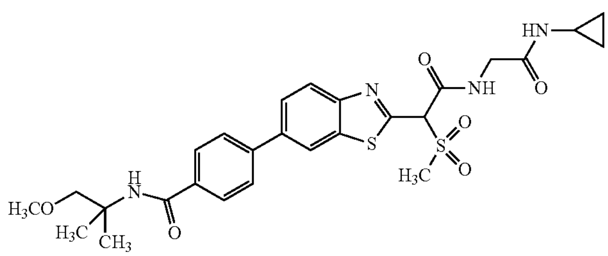 [SMILES: COCC(C)(C)NC(=O)c1ccc(-c2ccc3nc(C(C(=O)NCC(=O)NC4CC4)S(C)(=O)=O)sc3c2)cc1] | 4-[2-({[(cyclopropyl-carbamoyl)methyl]carbamoyl}(methanesulfonyl)methyl)-1,3-benzothiazol-6-yl]-N-(1-methoxy-2-methylpropan-2-yl)benzamide | 9.05 (t, J = 5.4 Hz, 1H), 8.57 (s, 1H), 8.19 (d, J = 8.5 Hz, 1H), 8.05 (d, J = 3.6 Hz, 1H), 8.02-7.89 (m, 3H), 7.86 (d, J = 8.3 Hz, 2H), 7.72 (s, 1H), 6.22 (s, 1H), 3.85 (d, J = 5.5 Hz, 2H), 3.57 (s, 2H), 3.30 (d, J = 9.1 Hz, 6H), 2.69-2.60 (m, 1H), 1.38 (s, 6H), 0.69-0.58 (m, 2H), 0.47-0.33 (m, 2H) | 1.47 N 573.2 | 2 |
| 561 | 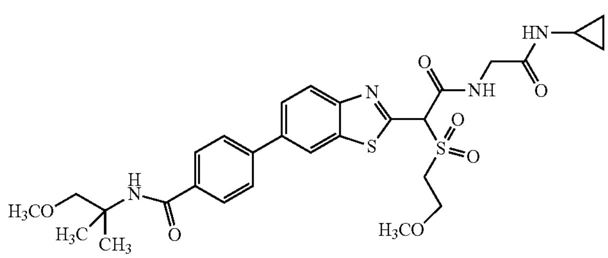 [SMILES: COCCS(=O)(=O)C(C(=O)NCC(=O)NC1CC1)c1nc2ccc(-c3ccc(C(=O)NC(C)(C)COC)cc3)cc2s1] | 4-[2-({[(cyclopropyl-carbamoyl)methyl]carbamoyl}(2-methoxyethane-sulfonyl)methyl)-1,3-benzothiazol-6-yl]-N-(1-methoxy-2-methylpropan-2-yl)benzamide | 9.02 (d, J = 5.5 Hz, 1H), 8.57 (d, J = 4.1 Hz, 1H), 8.25-8.14 (m, 1H), 8.03 (br. s., 1H), 7.99-7.88 (m, 3H), 7.88-7.82 (m, 2H), 7.78 (br. s., 1H), 7.72 (d, J = 5.5 Hz, 1H), 6.22 (d, J = 5.8 Hz, 1H), 3.93-3.70 (m, 8H), 3.57 (d, J = 5.5 Hz, 3H), 3.34-3.25 (m, 3H), 2.66 (br. s., 1H), 1.38 (d, J = 5.8 Hz, 6H), 0.75-0.58 (m, 2H), 0.42 (br. s., 2H) | 1.28 N 617.2 | 3 |
| 562 | 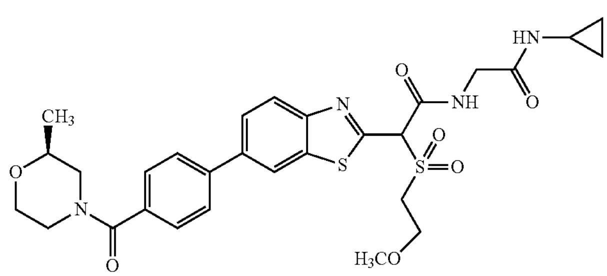 [SMILES: COCCS(=O)(=O)C(C(=O)NCC(=O)NC1CC1)c1nc2ccc(-c3ccc(C(=O)N4CCO[C@@H](C)C4)cc3)cc2s1] | N-[(cyclopropyl-carbamoyl)methyl]-2-(2-methoxyethane-sulfonyl)-2-(6-{4-[(2S)-2-methyl-morpholine-4-carbonyl]phenyl}-1,3-benzothiazol-2-yl)acetamide | 9.06-8.95 (m, 1H), 8.55 (s, 1H), 8.19 (d, J = 8.5 Hz, 1H), 8.03 (d, J = 3.9 Hz, 1H), 7.92 (d, J = 8.5 Hz, 1H), 7.89-7.82 (m, J = 7.7 Hz, 2H), 7.59-7.46 (m, J = 8.0 Hz, 2H), 6.22 (s, 1H), 3.88-3.69 (m, 8H), 3.68-3.55 (m, 4H), 3.29 (s, 3H), 2.73-2.60 (m, 1H), 1.29 (d, J = 6.6 Hz, 3H), 0.64 (d, J = 6.9 Hz, 2H), 0.47-0.31 (m, 2H) | 1.36 N 615.3 | 11 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 563 | 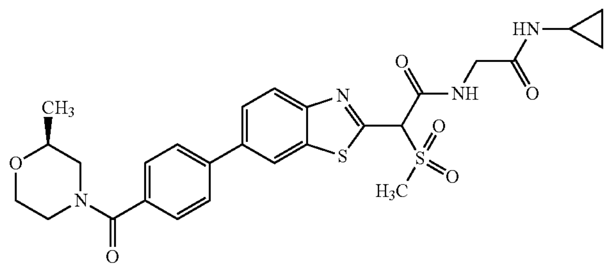 [SMILES: C[C@H]1CN(C(=O)c2ccc(-c3ccc4nc(C(C(=O)NCC(=O)NC5CC5)S(C)(=O)=O)sc4c3)cc2)CCO1] | N-[(cyclopropyl-carbamoyl)methyl]-2-methanesulfonyl-2-(6-{4-[(2S)-2-methyl-morpholine-4-carbonyl]phenyl}-1,3-benzothiazol-2-yl)acetamide | 9.05 (s, 1H), 8.59-8.49 (m, 1H), 8.18 (d, J = 8.5 Hz, 1H), 8.05 (d, J = 4.1 Hz, 1H), 7.92 (dd, J = 8.5, 1.7 Hz, 1H), 7.88-7.81 (m, J = 8.3 Hz, 2H), 7.58-7.48 (m, J = 8.0 Hz, 2H), 6.21 (s, 1H), 3.91 (s, 3H), 3.84 (d, J = 5.5 Hz, 3H), 3.69-3.54 (m, 3H), 3.29 (s, 4H), 2.65 (d, J = 3.6 Hz, 1H), 1.29 (d, J = 6.9 Hz, 3H), 0.72-0.57 (m, 2H), 0.41 (dd, J = 3.7, 2.1 Hz, 2H) | 1.29 N 570.3 | 31 |
| 564 | 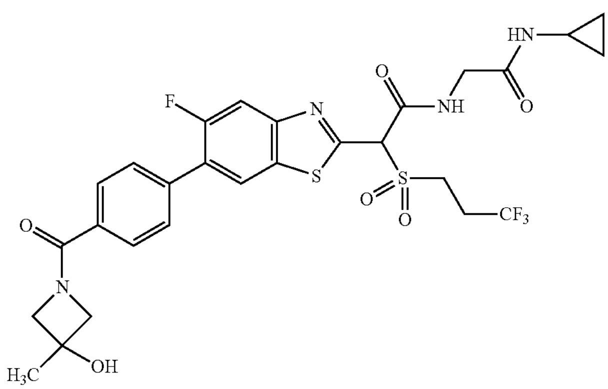 [SMILES: CC1(O)CN(C(=O)c2ccc(-c3cc4sc(C(C(=O)NCC(=O)NC5CC5)S(=O)(=O)CCC(F)(F)F)nc4cc3F)cc2)C1] | N-[(cyclopropyl-carbamoyl)methyl]-2-{5-fluoro-6-[4-(3-hydroxy-3-methylazetidine-1-carbonyl)phenyl]-1,3-benzothiazol-2-yl}-2-[3,3,3-trifluoropropane-sulfonyl)acetamide | 9.09-9.00 (m, 1H), 8.41-8.35 (m, 1H), 8.07 (br. s., 1H), 7.78-7.67 (m, 4H), 6.36 (s, 1H), 4.28-4.10 (m, 2H), 3.98-3.71 (m, 5H), 3.54 (br. s., 3H), 2.90-2.79 (m, 2H), 2.68-2.55 (m, 1H), 1.40 (s, 3H), 0.62 (d, J = 7.0 Hz, 2H), 0.38 (d, J = 2.4 Hz, 2H). | 1.55 U 657.1 | 5 |
| 565 | 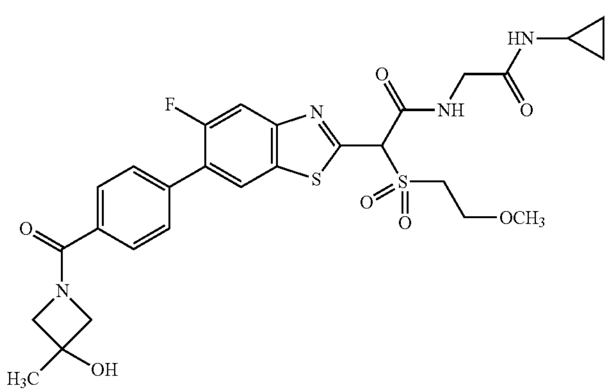 [SMILES: COCCS(=O)(=O)C(C(=O)NCC(=O)NC1CC1)c1nc2cc(F)c(-c3ccc(C(=O)N4CC(C)(O)C4)cc3)cc2s1] | N-[(cyclopropyl-carbamoyl)methyl]-2-{5-fluoro-6-[4-(3-hydroxy-3-methylazetidine-1-carbonyl)phenyl]-1,3-benzothiazol-2-yl}-2-(2-methoxyethane-sulfonyl)acetamide | 9.06-8.95 (m, 1H), 8.39 (d, J = 7.6 Hz, 1H), 8.13-8.05 (m, 1H), 8.04-7.99 (m, 1H), 7.81-7.57 (m, 4H), 6.20 (s, 1H), 4.24-4.12 (m, 2H), 3.92 (br. s., 2H), 3.85-3.67 (m, 5H), 3.39 (br. s., 2H), 3.27 (s, 2H), 2.67-2.56 (m, 1H), 1.40 (s, 3H), 0.62 (d, J = 5.5 Hz, 2H), 0.39 (d, J = 2.4 Hz, 2H) | 1.26 U 619.1 | 3 |
| 566 | 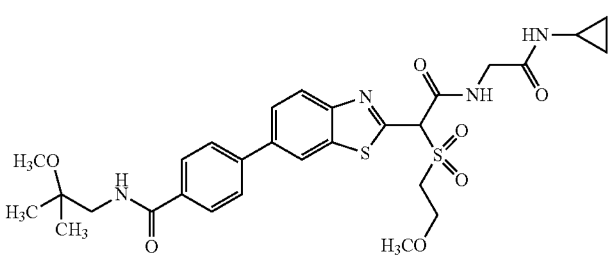 [SMILES: COCCS(=O)(=O)C(C(=O)NCC(=O)NC1CC1)c1nc2ccc(-c3ccc(C(=O)NCC(C)(C)OC)cc3)cc2s1] | 4-[2-({[[(cyclopropyl-carbamoyl)methyl]carbamoyl}(2-methoxyethane-sulfonyl)methyl)-1,3-benzothiazol-6-yl]-N-(2-methoxy-2-methylpropyl)benzamide | 9.10-8.92 (m, 1H), 8.65-8.52 (m, 1H), 8.40-8.28 (m, 1H), 8.23-8.11 (m, 1H), 8.07-7.75 (m, 6H), 3.93-3.60 (m, 6H), 3.40-3.35 (m, 2H), 3.27 (s, 3H), 3.17 (s, 3H), 2.70-2.60 (m, 1H), 1.22-1.07 (m, 6H), 0.68-0.60 (m, 2H), 0.47-0.34 (m, 2H) | 1.46 N 617.2 | 4 |

-continued

| Ex. No. | Structure | Name | $^1$H NMR δ (500 MHz, DMSO-d$_6$, unless otherwise indicated) | LC/MS RT (min) Method M + H | EL IC$_{50}$ (nM) |
|---|---|---|---|---|---|
| 567 | 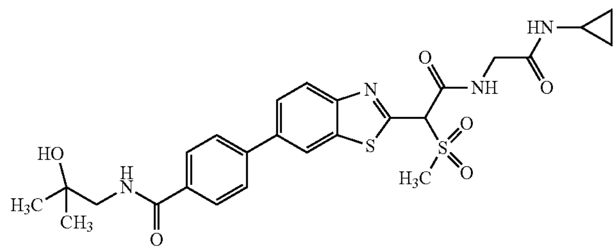 [SMILES: CC(C)(O)CNC(=O)c1ccc(-c2ccc3nc(C(C(=O)NCC(=O)NC4CC4)S(C)(=O)=O)sc3c2)cc1] | 4-[2-({[(cyclopropyl-carbamoyl)methyl]carbamoyl}(methanesulfonyl)methyl)-1,3-benzothiazol-6-yl]-N-(2-hydroxy-2-methylpropyl)benzamide | 8.32 (t, J = 6.0 Hz, 1H), 8.17 (d, J = 8.5 Hz, 1H), 8.10-7.80 (m, 7H), 7.33-6.87 (m, 2H), 3.83 (d, J = 5.5 Hz, 2H), 3.35-3.23 (m, 2H), 2.96-2.82 (m, 3H), 2.63 (td, J = 7.2, 3.7 Hz, 1H), 0.76-0.56 (m, 2H), 0.40 (d, J = 1.8 Hz, 2H) | 1.12 N 559.2 | 4 |
| 568 | 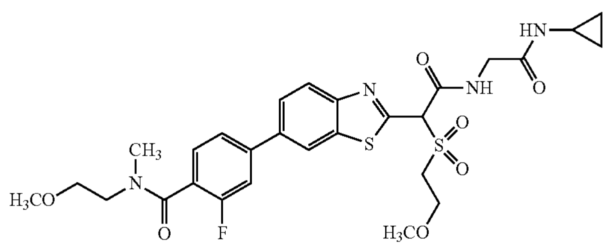 [SMILES: COCCN(C)C(=O)c1ccc(-c2ccc3nc(C(C(=O)NCC(=O)NC4CC4)S(=O)(=O)CCOC)sc3c2)cc1F] | 4-[2-({[(cyclopropyl-carbamoyl)methyl]carbamoyl}(2-methoxyethane-sulfonyl)methyl)-1,3-benzothiazol-6-yl]-2-fluoro-N-(2-methoxyethyl)-N-methylbenzamide | 8.40 (s, 1H), 8.18 (d, J = 8.5 Hz, 1H), 8.06-7.93 (m, 2H), 7.76 (d, J = 8.5 Hz, 1H), 7.67 (br. s., 1H), 7.45-7.32 (m, 2H), 4.03-3.48 (m, 8H), 3.42-3.11 (m, 2H), 2.99 (br. s., 2H), 2.89 (s, 3H), 2.73 (s, 3H), 2.63 (td, J = 7.2, 3.7 Hz, 1H), 0.76-0.61 (m, 2H), 0.39 (d, J = 2.7 Hz, 2H) | 1.35 N 621.2 | 9 |
| 569 | 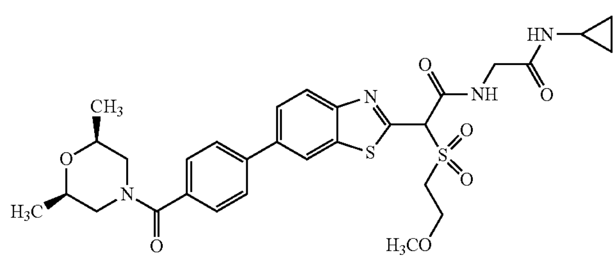 [SMILES: COCCS(=O)(=O)C(C(=O)NCC(=O)NC1CC1)c1nc2ccc(-c3ccc(C(=O)N4C[C@@H](C)O[C@@H](C)C4)cc3)cc2s1] | N-[(cyclopropyl-carbamoyl)methyl]-2-(6-{4-[(2R,6S)-2,6-dimethyl-morpholine-4-carbonyl]phenyl}-1,3-benzothiazol-2-yl)-2-(2-methoxyethane-sulfonyl)acetamide | (500 MHz, METHANOL-d$_4$) 8.51-8.33 (m, 1H), 8.24-8.14 (m, 1H), 8.08-7.99 (m, 1H), 7.94-7.82 (m, 2H), 7.80-7.75 (m, 1H), 7.73-7.62 (m, 1H), 7.61-7.45 (m, 2H), 4.64-4.44 (m, 1H), 4.16-3.51 (m, 9H), 3.31 (s, 3H), 3.02-2.87 (m, 1H), 2.79-2.65 (m, 1H), 2.64-2.54 (m, 1H), 1.28-1.19 (m, 3H), 1.17-1.00 (m, 3H), 0.78-0.69 (m, 2H), 0.60-0.50 (m, 2H) | 0.86 M 629.1 | 20 |
| 570 | 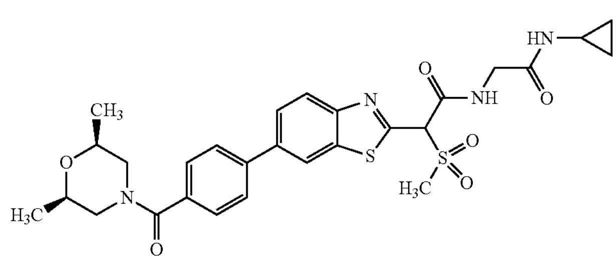 [SMILES: C[C@@H]1CN(C(=O)c2ccc(-c3ccc4nc(C(C(=O)NCC(=O)NC5CC5)S(C)(=O)=O)sc4c3)cc2)C[C@H](C)O1] | N-[(cyclopropyl-carbamoyl)methyl]-2-(6-{4-[(2R,6S)-2,6-dimethyl-morpholine-4-carbonyl]phenyl}-1,3-benzothiazol-2-yl)-2-methanesulfonyl-acetamide | 9.11-8.91 (m, 1H), 8.62-8.47 (m, 1H), 8.22-8.11 (m, 1H), 8.09-7.98 (m, 1H), 7.94-7.73 (m, 3H), 7.63-7.32 (m, 3H), 4.53-4.22 (m, 1H), 3.90 (s, 1H), 3.86-3.80 (m, 1H), 3.77-3.71 (m, 1H), 3.63-3.47 (m, 4H), 3.28 (br. s., 3H), 3.19 (br. s., 3H), 2.69-2.59 (m, 1H), 1.30-0.93 (m, 6H), 0.69-0.56 (m, 2H), 0.48-0.35 (m, 2H) | 1.96 N 585.2 | 4 |

| Ex. No. | Structure | Name | $^1$H NMR δ (500 MHz, DMSO-d$_6$, unless otherwise indicated) | LC/MS RT (min) Method M + H | EL IC$_{50}$ (nM) |
|---|---|---|---|---|---|
| 571 | 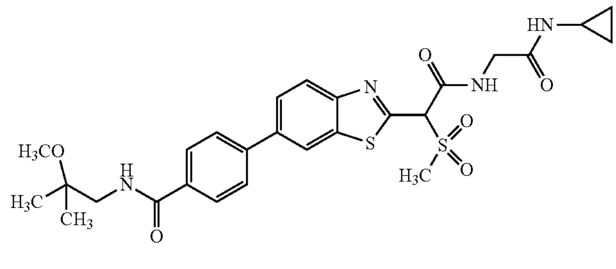 [SMILES: COC(C)(C)CNC(=O)c1ccc(-c2ccc3nc(C(C(=O)NCC(=O)NC4CC4)S(C)(=O)=O)sc3c2)cc1] | 4-[2-({[(cyclopropyl-carbamoyl)methyl]carbamoyl}(methanesulfonyl)methyl)-1,3-benzothiazol-6-yl]-N-(2-methoxy-2-methylpropyl)benzamide | 9.16-8.95 (m, 1H), 8.62-8.52 (m, 1H), 8.36-8.28 (m, 1H), 8.22-8.15 (m, 1H), 8.09-7.84 (m, 7H), 3.89-3.81 (m, 2H), 3.38-3.33 (m, 2H), 3.29-3.26 (m, 3H), 3.17 (s, 3H), 2.67-2.60 (m, 1H), 1.13 (s, 6H), 0.72-0.58 (m, 2H), 0.51-0.30 (m, 2H) | 1.32 N 573.2 | 12 |
| 573 | 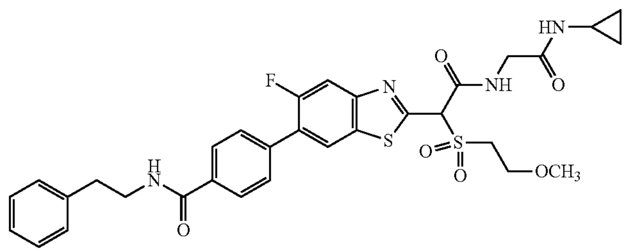 [SMILES: COCCS(=O)(=O)C(C(=O)NCC(=O)NC1CC1)c1nc2cc(F)c(-c3ccc(C(=O)NCCc4ccccc4)cc3)cc2s1] | 4-[2-({[(cyclopropyl-carbamoyl)methyl]carbamoyl}(2-methoxyethane-sulfonyl)methyl)-5-fluoro-1,3-benzothiazol-6-yl]-N-(2-phenylethyl)benzamide | 9.00 (t, J = 5.3 Hz, 1H), 8.78-8.56 (m, 1H), 8.37 (d, J = 7.3 Hz, 1H), 8.15-7.86 (m, 4H), 7.74-7.56 (m, 2H), 7.35-7.14 (m, 5H), 6.18 (s, 1H), 3.99-3.64 (m, 5H), 3.59-3.43 (m, 2H), 3.26 (s, 2H), 3.09 (br. s., 1H), 2.95-2.77 (m, 3H), 2.68-2.59 (m, 1H), 0.62 (d, J = 5.5 Hz, 2H), 0.39 (d, J = 2.7 Hz, 2H) | 1.68 N 653.2 | 3 |
| 574 | 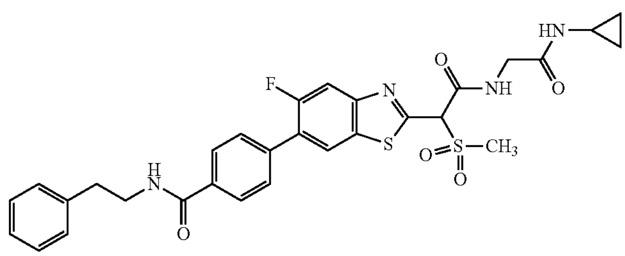 [SMILES: CS(=O)(=O)C(C(=O)NCC(=O)NC1CC1)c1nc2cc(F)c(-c3ccc(C(=O)NCCc4ccccc4)cc3)cc2s1] | 4-[2-({[(cyclopropyl-carbamoyl)methyl]carbamoyl}(methanesulfonyl)methyl)-5-fluoro-1,3-benzothiazol-6-yl]-N-(2-phenylethyl)benzamide | 9.06 (t, J = 5.2 Hz, 1H), 8.76-8.64 (m, 1H), 8.36 (d, J = 7.6 Hz, 1H), 8.13-8.01 (m, 2H), 7.96-7.87 (m, 2H), 7.75-7.59 (m, 2H), 7.39-7.03 (m, 5H), 6.18 (s, 1H), 3.81 (d, J = 5.2 Hz, 1H), 3.67-3.58 (m, 2H), 3.55-3.44 (m, 1H), 3.32-3.12 (m, 3H), 2.86 (t, J = 7.5 Hz, 2H), 2.62 (d, J = 3.7 Hz, 1H), 0.62 (d, J = 6.4 Hz, 2H), 0.38 (br. s., 2H) | 1.62 N 611.1 | 1 |
| 576 | 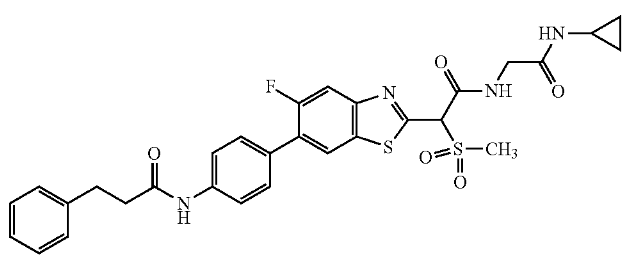 [SMILES: CS(=O)(=O)C(C(=O)NCC(=O)NC1CC1)c1nc2cc(F)c(-c3ccc(NC(=O)CCc4ccccc4)cc3)cc2s1] | N-{4-[2-({[(cyclopropyl-carbamoyl)methyl]carbamoyl}(methanesulfonyl)methyl)-5-fluoro-1,3-benzothiazol-6-yl]phenyl}-3-phenyl-propanamide | 10.12 (s, 1H), 9.05 (br. s., 1H), 8.28 (d, J = 7.3 Hz, 1H), 8.09-7.88 (m, 2H), 7.69 (d, J = 8.2 Hz, 2H), 7.54 (d, J = 7.6 Hz, 2H), 7.38-6.96 (m, 5H), 6.16 (s, 1H), 3.81 (d, J = 5.5 Hz, 2H), 3.25 (s, 3H), 3.00-2.85 (m, 2H), 2.71-2.56 (m, 3H), 0.62 (d, J = 5.8 Hz, 2H), 0.38 (br. s., 2H) | 1.73 N 609.2 | 1 |

| Ex. No. | Structure | Name | ¹H NMR δ (500 MHz, DMSO-d₆, unless otherwise indicated) | LC/MS RT (min) ethod M + H | EL IC₅₀ (nM) |
|---|---|---|---|---|---|
| 577 | 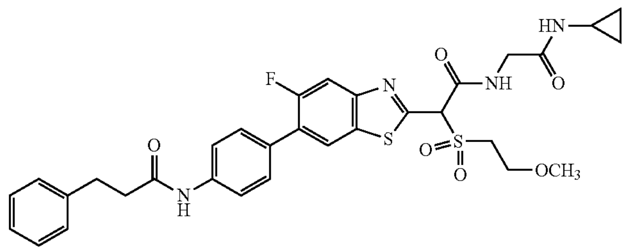 [SMILES: COCCS(=O)(=O)C(C(=O)NCC(=O)NC1CC1)c1nc2cc(F)c(-c3ccc(NC(=O)CCc4ccccc4)cc3)cc2s1] | N-{4-[2-({[(cyclopropyl-carbamoyl)methyl]carbamoyl}(2-methoxyethane-sulfonyl)methyl)-5-fluoro-1,3-benzothiazol-6-yl]phenyl}-3-phenyl-propanamide | 10.57-9.84 (m, 1H), 9.00 (t, J = 5.5 Hz, 1H), 8.27 (d, J = 7.6 Hz, 1H), 8.04-7.93 (m, 2H), 7.74-7.62 (m, 2H), 7.57-7.46 (m, 2H), 7.34-7.07 (m, 5H), 6.15 (s, 1H), 3.91-3.67 (m, 3H), 3.64-3.52 (m, 3H), 3.31-3.17 (m, 3H), 2.99-2.84 (m, 2H), 2.69-2.57 (m, 3H), 0.62 (d, J = 6.1 Hz, 2H), 0.38 (d, J = 2.7 Hz, 2H) | 1.78 N 653.2 | 1 |
| 578 | 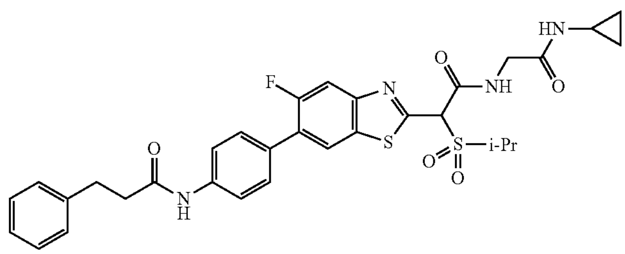 [SMILES: CC(C)S(=O)(=O)C(C(=O)NCC(=O)NC1CC1)c1nc2cc(F)c(-c3ccc(NC(=O)CCc4ccccc4)cc3)cc2s1] | N-{4-[2-({[(cyclopropyl-carbamoyl)methyl]carbamoyl}(propane-2-sulfonyl)methyl)-5-fluoro-1,3-benzothiazol-6-yl]phenyl}-3-phenyl-propanamide | 10.54-9.96 (m, 1H), 9.12 (t, J = 5.3 Hz, 1H), 8.26 (d, J = 7.6 Hz, 1H), 8.05-7.86 (m, 2H), 7.78-7.62 (m, 2H), 7.59-7.40 (m, 2H), 7.36-7.07 (m, 5H), 6.31 (s, 1H), 3.97-3.72 (m, 1H), 3.69-3.34 (m, 2H), 2.98-2.79 (m, 2H), 2.69-2.56 (m, 3H), 1.50-1.15 (m, 6H), 0.62 (d, J = 6.4 Hz, 2H), 0.38 (br. s., 2H) | 1.89 N 637.2 | 4 |
| 580 | 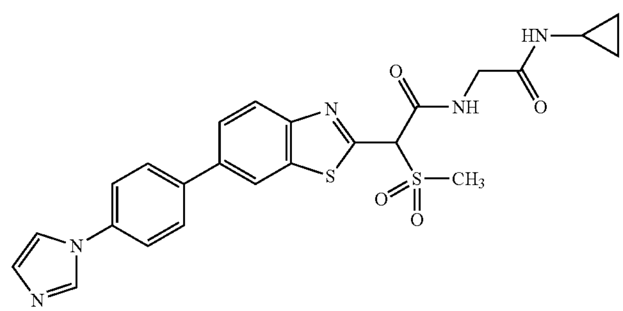 [SMILES: CS(=O)(=O)C(C(=O)NCC(=O)NC1CC1)c1nc2ccc(-c3ccc(-n4ccnc4)cc3)cc2s1] | N-[(cyclopropyl-carbamoyl)methyl]-2-{6-[4-(1H-imidazol-1-yl)phenyl]-1,3-benzothiazol-2-yl}-2-methanesulfonyl-acetamide | 9.05 (d, J = 5.2 Hz, 1H), 8.53 (s, 1H), 8.34 (br. s., 1H), 8.19-8.12 (m, 1H), 8.03 (br. s., 1H), 7.91 (d, J = 8.5 Hz, 3H), 7.84-7.75 (m, 3H), 7.14 (br. s., 1H), 3.92-3.79 (m, 2H), 3.46 (br. s., 1H), 3.27 (s, 2H), 3.19 (d, J = 14.0 Hz, 1H), 2.63 (dd, J = 7.0, 3.4 Hz, 1H), 0.62 (d, J = 7.0 Hz, 2H), 0.39 (br. s., 2H) | 0.99 U 510.1 | 12 |
| 581 | 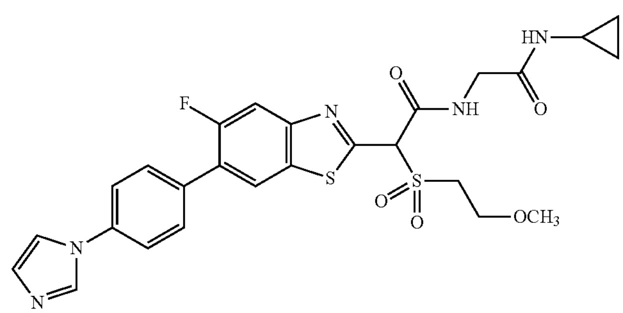 [SMILES: COCCS(=O)(=O)C(C(=O)NCC(=O)NC1CC1)c1nc2cc(F)c(-c3ccc(-n4ccnc4)cc3)cc2s1] | N-[(cyclopropyl-carbamoyl)methyl]-2-{5-fluoro-6-[4-(1H-imidazol-1-yl)phenyl]-1,3-benzothiazol-2-yl}-2-(2-methoxyethane-sulfonyl)acetamide | 9.02 (br. s., 1H), 8.38 (br. s., 2H), 8.18-7.65 (m, 6H), 6.22 (br. s., 1H), 3.86-3.68 (m, 6H), 2.87 (s, 3H), 2.71 (s, 2H), 2.63 (br. s., 1H), 0.61 (d, J = 6.6 Hz, 2H), 0.52-0.28 (m, 2H) | 1.09 U 572.1 | 36 |

| Ex. No. | Structure | Name | ¹H NMR δ (500 MHz, DMSO-d₆, unless otherwise indicated) | LC/MS RT (min) Method M + H | EL IC₅₀ (nM) |
|---|---|---|---|---|---|
| 582 | 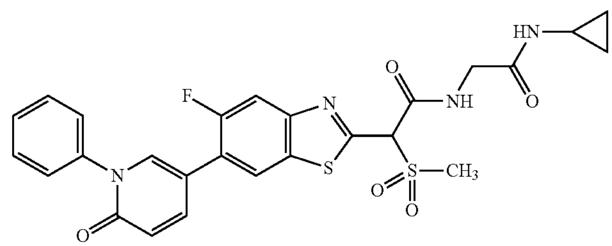 [SMILES: CS(=O)(=O)C(C(=O)NCC(=O)NC1CC1)c1nc2cc(F)c(-c3ccc(=O)n(-c4ccccc4)c3)cc2s1] | N-[(cyclopropyl-carbamoyl)methyl]-2-[5-fluoro-6-(6-oxo-1-phenyl-1,6-dihydropyridin-3-yl)-1,3-benzothiazol-2-yl]-2-methanesulfonyl-acetamide | 9.07-8.98 (m, 1H), 8.41-8.32 (m, 1H), 8.03 (br. s., 2H), 7.92 (br. s., 3H), 7.57-7.45 (m, 4H), 6.73-6.60 (m, H), 6.19-6.09 (m, 1H), 3.88-3.75 (m, 2H), 3.24 (s, 3H), 2.66-2.56 (m, 1H), 0.66-0.57 (m, 2H), 0.37 (br. s., 2H) | 1.29 U 554.3 | 6 |
| 583 | 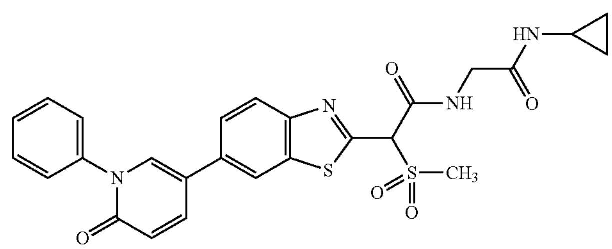 [SMILES: CS(=O)(=O)C(C(=O)NCC(=O)NC1CC1)c1nc2ccc(-c3ccc(=O)n(-c4ccccc4)c3)cc2s1] | N-[(cyclopropyl-carbamoyl)methyl]-2-methanesulfonyl-2-[6-(6-oxo-1-phenyl-1,6-dihydropyridin-3-yl)-1,3-benzothiazol-2-yl]acetamide | 9.03 (t, J = 5.3 Hz, 1H), 8.43 (s, 2H), 8.15-8.00 (m, 7H), 7.89-7.80 (m, 2H), 7.59-7.44 (m, 9H), 6.65 (d, J = 9.5 Hz, 2H), 6.15 (s, 1H), 3.81 (d, J = 5.5 Hz, 3H), 3.48 (br. s., 3H), 2.66-2.55 (m, 2H), 0.65-0.55 (m, 3H), 0.38 (d, J = 2.1 Hz, 3H) | 1.22 U 537.1 | 20 |
| 584 | 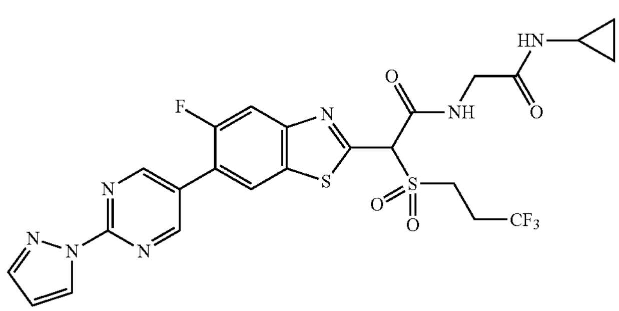 [SMILES: O=C(CNC(=O)C(c1nc2cc(F)c(-c3cnc(-n4cccn4)nc3)cc2s1)S(=O)(=O)CCC(F)(F)F)NC1CC1] | N-[(cyclopropyl-carbamoyl)methyl]-2-{5-fluoro-6-[2-(1H-pyrazol-1-yl)pyrimidin-5-yl]-1,3-benzothiazol-2-yl}-2-(3,3,3-trifluoropropane-sulfonyl)acetamide | 9.12 (s, 2H), 9.08-9.00 (m, 1H), 8.78-8.67 (m, 1H), 8.55 (d, J = 7.6 Hz, 1H), 8.15 (d, J = 11.0 Hz, 1H), 8.10-8.05 (m, 1H), 7.93-7.88 (m, 1H), 6.65 (br. s., 1H), 6.39 (s, 1H), 3.91-3.68 (m, 3H), 3.54 (br. s., 1H), 2.89-2.80 (m, 1H), 2.65-2.59 (m, 1H), 2.56-2.52 (m, 1H), 0.62 (d, J = 5.8 Hz, 2H), 0.39 (d, J = 2.4 Hz, 2H) | 1.6 U 612.1 | 64 |
| 585 | 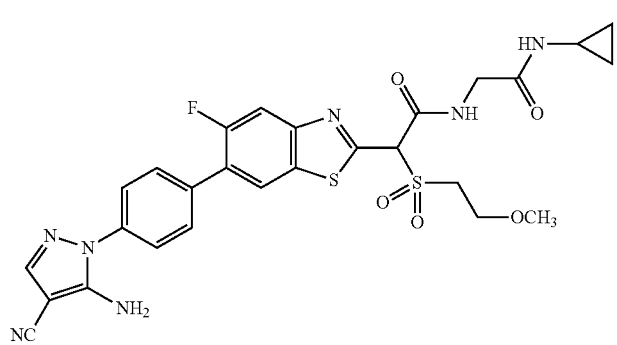 [SMILES: COCCS(=O)(=O)C(C(=O)NCC(=O)NC1CC1)c1nc2cc(F)c(-c3ccc(-n4ncc(C#N)c4N)cc3)cc2s1] | 2-{6-[4-(5-amino-4-cyano-1H-pyrazol-1-yl)phenyl]-5-fluoro-1,3-benzothiazol-2-yl}-N-[(cyclopropyl-carbamoyl)methyl]-2-(2-methoxyethane-sulfonyl)acetamide | 9.16-9.04 (m, 1H), 8.53-8.43 (m, 1H), 8.18-8.13 (m, 1H), 8.11-8.07 (m, 1H), 7.93-7.55 (m, 5H), 6.97-6.77 (m, 2H), 6.28 (s, 1H), 3.93-3.74 (m, 6H), 3.34 (s, 3H), 2.70 (d, J = 3.7 Hz, 1H), 0.69 (d, J = 6.1 Hz, 2H), 0.46 (br. s., 2H) | 1.46 U 612 | 1 |

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 586 | 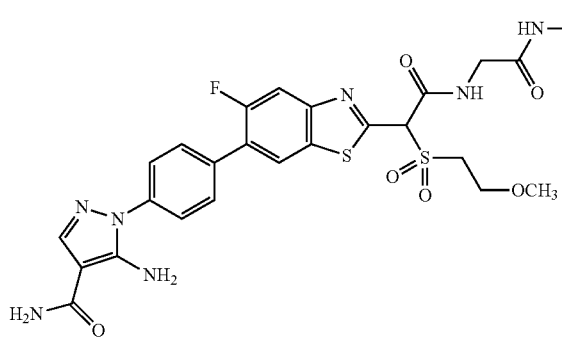 | 5-amino-1-{4-[2-({[(cyclopropyl-carbamoyl)methyl]carbamoyl}(2-methoxyethane-sulfonyl)methyl)-5-fluoro-1,3-benzothiazol-6-yl]phenyl}-1H-pyrazole-4-carboxamide | 9.01 (t, J = 5.2 Hz, 1H), 8.38 (d, J = 7.3 Hz, 1H), 8.08 (d, J = 11.3 Hz, 1H), 8.02 (d, J = 3.7 Hz, 1H), 7.96-7.91 (m, 1H), 7.81-7.66 (m, 4H), 7.45 (br. s., 2H), 6.85 (br. s., 2H), 6.57-6.38 (m, 1H), 6.19 (s, 1H), 3.94-3.67 (m, 5H), 3.27 (s, 3H), 2.68-2.55 (m, 1H), 0.62 (d, J = 6.7 Hz, 2H), 0.39 (d, J = 2.1 Hz, 2H) | 1.21 U 630.1 | 1 |
| 587 | 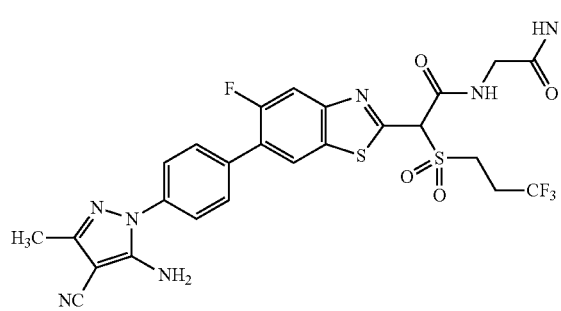 | 2-{6-[4-(5-amino-4-cyano-3-methyl-1H-pyrazol-1-yl)phenyl]-5-fluoro-1,3-benzothiazol-2-yl}-N-[(cyclopropyl-carbamoyl)methyl]-2-(3,3,3-trifluoropropane-sulfonyl)acetamide | 9.03 (t, J = 5.2 Hz, 1H), 8.46 (d, J = 7.3 Hz, 1H), 8.12-8.05 (m, 2H), 7.75-7.47 (m, 4H), 6.79-6.68 (m, 2H), 6.39 (s, 1H), 3.93-3.70 (m, 4H), 2.93-2.81 (m, 2H), 2.63 (d, J = 3.7 Hz, 1H), 2.17 (s, 3H), 0.62 (d, J = 7.0 Hz, 2H), 0.40 (br. s., 2H) | 1.73 U 664.1 | 3 |
| 588 | 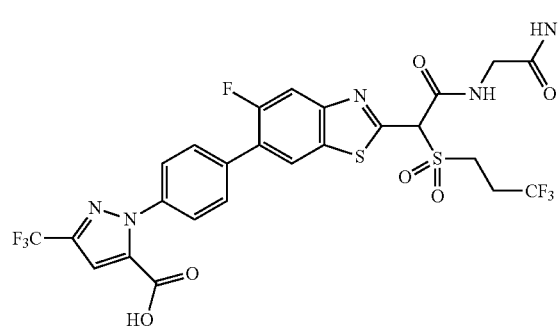 | 1-{4-[2-({[(cyclopropyl-carbamoyl)methyl]carbamoyl}(3,3,3-trifluoropropane-sulfonyl)methyl)-5-fluoro-1,3-benzothiazol-6-yl]phenyl}-3-(trifluoromethyl)-1H-pyrazole-5-carboxylic acid | 9.05 (br. s., 1H), 8.42 (d, J = 6.7 Hz, 1H), 8.15-7.91 (m, 3H), 7.83-7.51 (m, 5H), 7.42 (s, 1H), 3.88-3.73 (m, 3H), 2.63 (br. s., 1H), 2.56-2.52 (m, 1H), 0.62 (d, J = 6.7 Hz, 2H), 0.39 (br. s., 2H) | 1.39 S 722 | 6 |
| 589 | 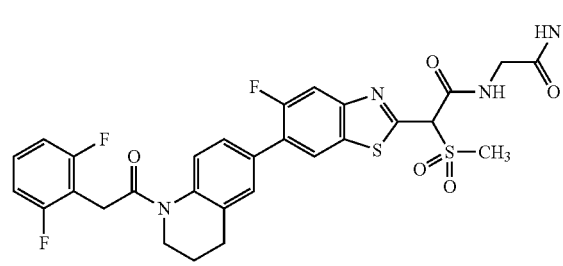 | N-[(cyclopropyl-carbamoyl)methyl]-2-(6-{1-[2-(2,6-difluorophenyl)acetyl]-1,2,3,4-tetrahydroquinolin-6-yl}-5-fluoro-1,3-benzothiazol-2-yl)-2-methanesulfonyl-acetamide | 8.96 (t, J = 5.3 Hz, 1H), 8.23-8.06 (m, 2H), 7.97 (br. s., 1H), 7.74-7.57 (m, 1H), 7.43 (br. s., 4H), 7.00 (t, J = 7.6 Hz, 2H), 3.93 (s, 2H), 3.76 (d, J = 5.5 Hz, 4H), 3.21 (s, 2H), 2.78-2.70 (m, 2H), 2.62-2.51 (m, 1H), 1.95-1.73 (m, 2H), 0.56 (d, J = 7.3 Hz, 2H), 0.33 (br. s., 2H) | 1.88 U 571.1 | 7 |

| Ex. No. | Structure | Name | $^1$H NMR δ (500 MHz, DMSO-d$_6$, unless otherwise indicated) | LC/MS RT (min) Method M + H | EL IC$_{50}$ (nM) |
|---|---|---|---|---|---|
| 590 | 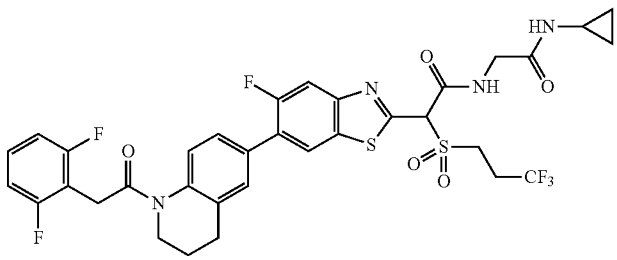 [SMILES: O=C(CNC(=O)C(c1nc2cc(F)c(-c3ccc4c(c3)CCCN4C(=O)Cc3c(F)cccc3F)cc2s1)S(=O)(=O)CCC(F)(F)F)NC1CC1] | N-[(cyclopropyl-carbamoyl) methyl]-2-(6-{1-[2-(2,6-difluorophenyl) acetyl]-1,2,3,4-tetrahydroquinolin-6-yl}-5-fluoro-1,3-benzothiazol-2-yl)-2-(3,3,3-trifluoropropane-sulfonyl)acetamide | 9.10-9.00 (m, 1H), 8.34 (d, J = 7.6 Hz, 1H), 8.14-8.00 (m, 2H), 7.94 (s, 2H), 7.78-7.69 (m, 1H), 7.54-7.28 (m, 3H), 7.05 (t, J = 7.5 Hz, 2H), 6.37 (s, 1H), 4.07-3.92 (m, 2H), 3.88-3.70 (m, 4H), 3.51-3.38 (m, 2H), 2.86-2.75 (m, 2H), 2.65-2.56 (m, 1H), 2.00-1.83 (m, 2H), 0.62 (d, J = 6.7 Hz, 2H), 0.39 (br. s., 2H) | 2.14 U 753 | 8 |
| 592 | 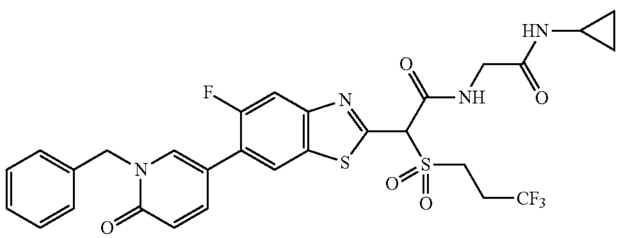 [SMILES: O=C(CNC(=O)C(c1nc2cc(F)c(-c3ccc(=O)n(Cc4ccccc4)c3)cc2s1)S(=O)(=O)CCC(F)(F)F)NC1CC1] | 2-[6-(1-benzyl-6-oxo-1,6-dihydropyridin-3-yl)-5-fluoro-1,3-benzothiazol-2-yl]-N-[(cyclopropyl-carbamoyl) methyl]-2-(3,3,3-trifluoropropane-sulfonyl)acetamide | 9.07-9.00 (m, 1H), 8.33-8.25 (m, 1H), 8.19-8.14 (m, 1H), 8.09-8.04 (m, 2H), 8.03-7.98 (m, 1H), 7.78-7.72 (m, 1H), 7.38-7.32 (m, 5H), 7.30-7.25 (m, 1H), 6.60-6.56 (m, 1H), 6.33 (s, 1H), 5.18 (s, 1H), 3.85-3.68 (m, 3H), 2.89-2.79 (m, 2H), 2.66-2.56 (m, 1H), 0.61 (d, J = 6.1 Hz, 2H), 0.38 (d, J = 2.4 Hz, 2H) | 1.69 U 651.1 | 5 |
| 593 | 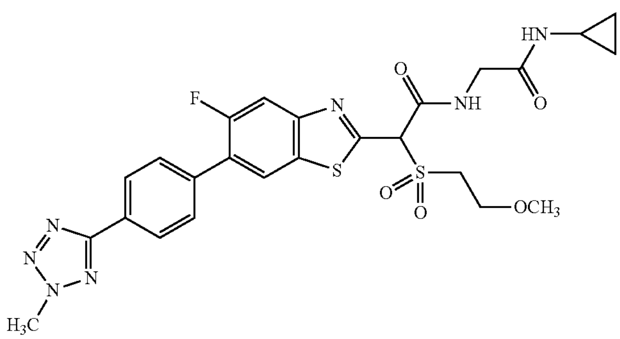 [SMILES: COCCS(=O)(=O)C(C(=O)NCC(=O)NC1CC1)c1nc2cc(F)c(-c3ccc(-c4nnn(C)n4)cc3)cc2s1] | N-[(cyclopropyl-carbamoyl) methyl]-2-{5-fluoro-6-[4-(2-methyl-2H-1,2,3,4-tetrazol-5-yl) phenyl]-1,3-benzothiazol-2-yl}-2-(2-methoxyethane-sulfonyl)acetamide | 9.01 (t, J = 5.3 Hz, 1H), 8.42 (d, J = 7.6 Hz, 1H), 8.24-7.98 (m, 4H), 7.82 (d, J = 7.6 Hz, 2H), 6.20 (s, 1H), 4.49-4.41 (m, 3H), 3.85-3.68 (m, 5H), 3.42 (br. s., 2H), 3.27 (s, 2H), 2.68-2.58 (m, 1H), 0.62 (d, J = 5.8 Hz, 2H), 0.39 (d, J = 2.7 Hz, 2H) | 1.57 U 588 | 9 |
| 594 | 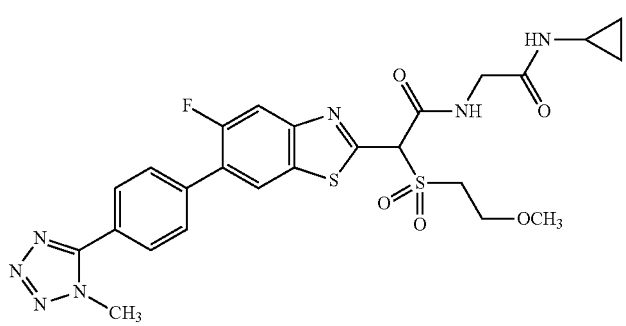 [SMILES: COCCS(=O)(=O)C(C(=O)NCC(=O)NC1CC1)c1nc2cc(F)c(-c3ccc(-c4nnnn4C)cc3)cc2s1] | N-[(cyclopropyl-carbamoyl) methyl]-2-{5-fluoro-6-[4-(1-methyl-1H-1,2,3,4-tetrazol-5-yl) phenyl]-1,3-benzothiazol-2-yl}-2-(2-methoxyethane-sulfonyl)acetamide | 9.01 (t, J = 5.2 Hz, 1H), 8.45 (d, J = 7.3 Hz, 1H), 8.15-7.96 (m, 3H), 7.91-7.77 (m, 2H), 6.21 (s, 1H), 4.25-4.20 (m, 4H), 3.84-3.67 (m, 6H), 3.27 (s, 3H), 2.68-2.60 (m, 1H), 0.62 (d, J = 5.8 Hz, 2H), 0.43-0.34 (m, 2H) | 1.4 U 588 | 67 |

| Ex. No. | Structure | Name | $^1$H NMR δ (500 MHz, DMSO-$d_6$, unless otherwise indicated) | LC/MS RT (min) EL ethod M + H | IC$_{50}$ (nM) |
|---|---|---|---|---|---|
| 596 | 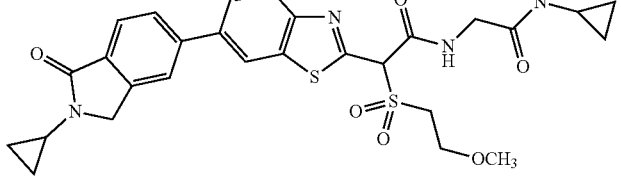 | 2-[6-(2-cyclopropyl-1-oxo-2,3-dihydro-1H-isoindol-5-yl)-1,3-benzothiazol-2-yl]-N-[(cyclopropyl-carbamoyl)methyl]-2-(2-ethoxyethane-sulfonyl)acetamide | 9.01 (t, J = 5.4 Hz, 1H), 8.55 (d, J = 1.7 Hz, 1H), 8.21-8.16 (m, 1H), 8.04-8.00 (m, 1H), 7.93 (s, 2H), 7.86-7.82 (m, 1H), 7.74-7.71 (m, 1H), 6.21 (s, 1H), 5.53-5.49 (m, 2H), 3.91 (s, 1H), 3.85-3.80 (m, 2H), 3.80-3.76 (m, 2H), 3.75-3.71 (m, 2H), 3.29-3.25 (m, 3H), 2.67-2.61 (m, 1H), 0.83-0.76 (m, 2H), 0.66-0.60 (m, 4H), 0.45-0.37 (m, 2H). | 1.66 O 582.6 | 2 |
| 597 | 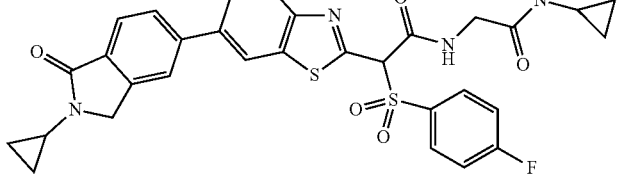 | 2-[6-(2-cyclopropyl-1-oxo-2,3-dihydro-1H-isoindol-5-yl)-1,3-benzothiazol-2-yl]-N-[(cyclopropyl-carbamoyl)methyl]-2-(4-fluorobenzene-sulfonyl)acetamide | 9.14-9.00 (m, 1H), 8.10-8.01 (m, 3H), 7.94-7.80 (m, 2H), 7.77-7.67 (m, 3H), 7.66-7.54 (m, 1H), 7.46 (s, 2H), 6.41 (s, 1H), 5.50 (s, 2H), 3.87-3.66 (m, 2H), 2.70-2.56 (m, 1H), 0.83-0.74 (m, 2H), 0.69-0.57 (m, 4H), 0.39 (d, J = 3.6 Hz, 2H) | 1.94 O 619.1 | 7 |
| 599 | 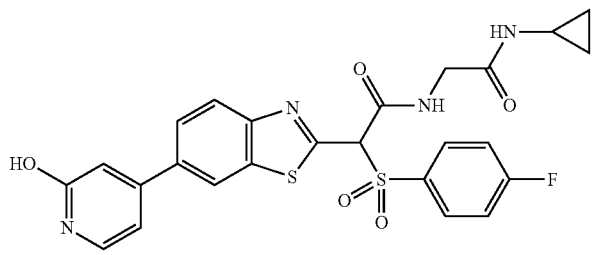 [SMILES: O=C(CNC(=O)C(c1nc2ccc(-c3ccnc(O)c3)cc2s1)S(=O)(=O)c1ccc(F)cc1)NC1CC1] | N-[(cyclopropyl-carbamoyl)methyl]-2-(4-fluorobenzene-sulfonyl)-2-[6-(2-hydroxypyridin-4-yl)-1,3-benzothiazol-2-yl]acetamide | 9.11-9.01 (m, 1H), 8.58-8.49 (m, 1H), 8.07-8.01 (m, 2H), 7.88-7.81 (m, 1H), 7.76-7.69 (m, 2H), 7.52-7.41 (m, 3H), 6.74-6.66 (m, 1H), 6.61-6.56 (m, 1H), 6.43-6.37 (m, 1H), 3.89-3.67 (m, 2H), 3.00 (s, 1H), 2.66-2.59 (m, 1H), 0.64-0.60 (m, 2H), 0.41-0.36 (m, 2H). | 1.21 O 541.1 | 27 |
| 600 | 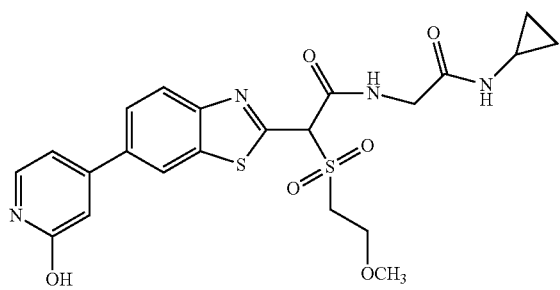 [SMILES: COCCS(=O)(=O)C(C(=O)NCC(=O)NC1CC1)c1nc2ccc(-c3ccnc(O)c3)cc2s1] | N-[(cyclopropyl-carbamoyl)methyl]-2-[6-(2-hydroxypyridin-4-yl)-1,3-benzothiazol-2-yl]-2-(2-methoxyethane-sulfonyl)acetamide | 9.07-8.97 (m, 1H), 8.57 (s, 1H), 8.20-8.13 (m, 1H), 8.05-8.00 (m, 1H), 7.94-7.85 (m, 1H), 7.55-7.48 (m, 1H), 6.72-6.68 (m, 1H), 6.66-6.58 (m, 1H), 6.22 (s, 1H), 3.87-3.70 (m, 6H), 3.28 (s, 3H), 2.68-2.62 (m, 1H), 0.64 (d, J = 5.5 Hz, 2H), 0.46-0.36 (m, 2H). | 0.99 O 505.3 | 14 |

| Ex. No. | Structure | Name | $^1$H NMR δ (500 MHz, DMSO-d$_6$, unless otherwise indicated) | LC/MS RT (min) ethod M + H | EL IC$_{50}$ (nM) |
|---|---|---|---|---|---|
| 602 | 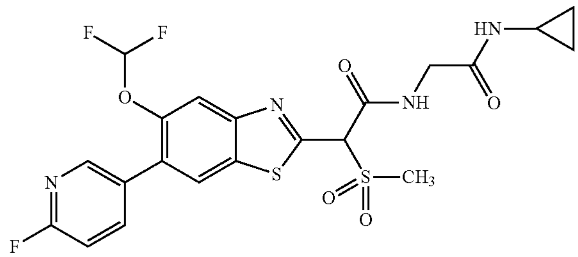 [SMILES: CS(=O)(=O)C(C(=O)NCC(=O)NC1CC1)c1nc2cc(OC(F)F)c(-c3ccc(F)nc3)cc2s1] | N-[(cyclopropyl-carbamoyl)methyl]-2-[5-(difluoromethoxy)-6-(6-fluoropyridin-3-yl)-1,3-benzothiazol-2-yl]-2-methanesulfonyl-acetamide | 9.12 (m, 1H), 8.51-8.39 (m, 2H), 8.29-8.18 (m, 1H), 8.14-8.07 (m, 2H), 7.45-7.33 (m, 2H), 6.29 (s, 1H), 3.90 (m, 2H), 3.56 (m, 3H), 2.70 (m, 1H), 0.70 (m, 2H), 0.46 (m, 2H) | 1.44 N 529.1 | 18 |
| 603 | 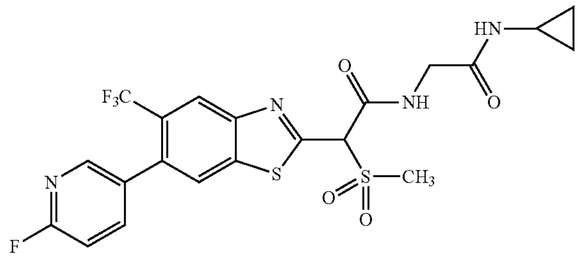 [SMILES: CS(=O)(=O)C(C(=O)NCC(=O)NC1CC1)c1nc2cc(C(F)(F)F)c(-c3ccc(F)nc3)cc2s1] | N-[(cyclopropyl-carbamoyl)methyl]-2-[6-(6-fluoropyridin-3-yl)-5-(trifluoromethoxy)-1,3-benzothiazol-2-yl]-2-methanesulfonyl-acetamide | 9.02 (m, 1H), 8.37 (m, 2H), 8.21 (s, 1H), 8.13 (m, 1H), 7.31 (m, 1H), 6.19 (s, 1H), 3.77 (m, 2H), 3.46 (s, 3H), 3.45 (s, 3H), 2.57 (m, 1H), 0.57 (m, 2H), 0.34 (m, 2H) | 1.57 N 546.5 | 7 |
| 604 | 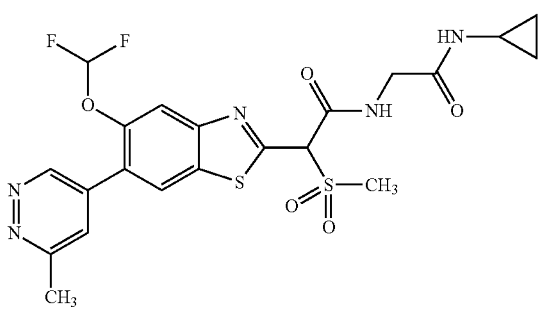 [SMILES: Cc1cc(-c2cc3sc(C(C(=O)NCC(=O)NC4CC4)S(C)(=O)=O)nc3cc2OC(F)F)cnn1] | N-[(cyclopropyl-carbamoyl)methyl]-2-[5-(difluoromethoxy)-6-(6-methylpyridazin-4-yl)-1,3-benzothiazol-2-yl]-2-methanesulfonyl-acetamide | 9.05 (m, 1H), 8.47 (s, 1H), 8.12-8.02 (m, 2H), 7.79 (s, 1H), 7.56-7.19 (m, 1.12 1H), 3.84 (m, 2H), 3.29 (s, 3H), 2.71 (s, 3H), 2.64 (m, 1H), 0.63 (m, 2H), 0.40 (m, 2H) | 1.12 N 526.1 | 27 |
| 605 | 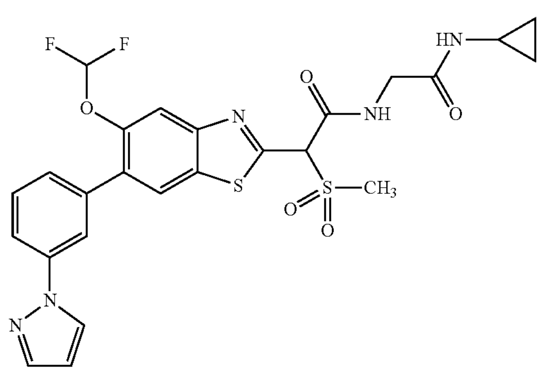 [SMILES: CS(=O)(=O)C(C(=O)NCC(=O)NC1CC1)c1nc2cc(OC(F)F)c(-c3cccc(-n4cccn4)c3)cc2s1] | N-[(cyclopropyl-carbamoyl)methyl]-2-[5-(difluoromethoxy)-6-[3-(1H-pyrazol-1-yl)phenyl]-1,3-benzothiazol-2-yl]-2-methanesulfonyl-acetamide | 9.12 (m, 1H), 8.60 (d, J = 1.8 Hz, 1H), 8.42 (s, 1H), 8.17-7.92 (m, 5H), 7.84 (s, 1H), 7.68 (m, 1H), 7.53 (d, J = 8.2 Hz, 1H), 3.90 (m, 2H), 3.55 (s, 3H), 2.70 (m, 1H), 0.70 (m, 2H), 0.46 (m, 2H) | 1.67 N 576.1 | 3 |
| 606 | 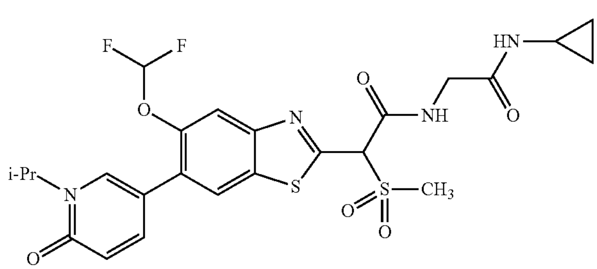 | N-[(cyclopropyl-carbamoyl)methyl]-2-[5-(difluoromethoxy)-6-[6-oxo-1-propan-2-yl]-1,6-dihydropyridin-3-yl]-1,3-benzothiazol-2-yl]-2-methanesulfonyl-acetamide | 9.02 (s, 1H), 8.29 (s, 1H), 8.04 (d, J = 3.9 Hz, 1H), 7.92 (d, J = 2.5 Hz, 1H), 7.61 (m, 1H), 7.50-7.17 (m, 1H), 6.50 (m, 1H), 6.22 (m, 1H), 5.12 (m, 1H), 3.83 (m, 2H), 3.27 (s, 3H), 2.64 (m, 1H), 1.35 (m, 6H), 0.63 (m, 2H), 0.40 (m, 2H) | 1.30 N 569.2 | 4 |

-continued

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 607 | 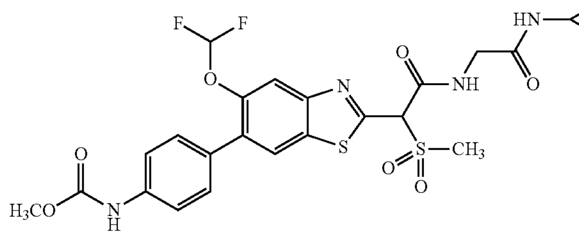 | methyl N-{4-[2-({[(cyclopropyl-carbamoyl)methyl]carbamoyl}(methanesulfonyl)methyl)-5-(difluoromethoxy)-1,3-benzothiazol-6-yl]phenyl} carbamate | 9.03 (m, 1H), 8.22 (s, 1H), 8.03 (m, 1H), 7.57-7.53 (m, 4H), 7.52-7.48 (m, 2H), 7.45 (m, 2H), 3.82 (m, 2H), 3.68 (s, 3H), 3.66 (s, 3H), 2.63 (m, 1H), 0.62 (m, 2H), 0.39 (m, 2H) | 1.50 N 583.1 | 5 |
| 608 | 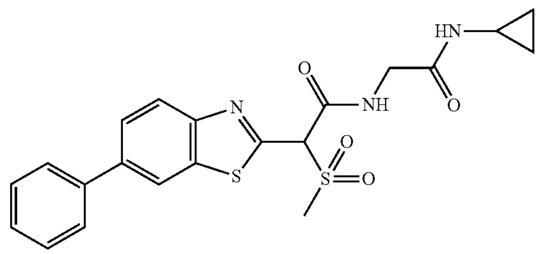 [SMILES: CS(=O)(=O)C(C(=O)NCC(=O)NC1CC1)c1nc2ccc(-c3ccccc3)cc2s1] | N-[(cyclopropyl-carbamoyl)methyl]-2-methanesulfonyl-2-(6-phenyl-1,3-benzothiazol-2-yl)acetamide | 9.07 (t, J = 5.3 Hz, 1H), 8.30-8.20 (m, 2H), 8.08 (br. s., 1H), 7.70 (d, J = 7.3 Hz, 2H), 7.63-7.55 (m, 2H), 7.55-7.48 (m, 1H), 6.25 (s, 1H), 3.79 (d, J = 5.8 Hz, 2H), 3.34 (s, 3H), 2.70 (d, J = 3.7 Hz, 1H), 0.70 (d, J = 6.1 Hz, 2H), 0.46 (br. s., 2H) | 1.65 N 444.1 | 152 |
| 609 | 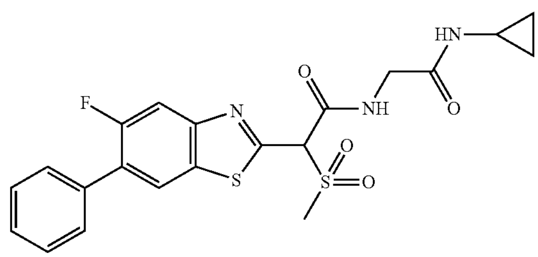 [SMILES: CS(=O)(=O)C(C(=O)NCC(=O)NC1CC1)c1nc2cc(F)c(-c3ccccc3)cc2s1] | N-[(cyclopropyl-carbamoyl)methyl]-2-(5-fluoro-6-phenyl-1,3-benzothiazol-2-yl)-2-methanesulfonyl-acetamide | 9.07 (t, J = 5.4 Hz, 1H), 8.34 (d, J = 7.7 Hz, 1H), 8.08 (br. s., 1H), 7.61 (d, J = 7.7 Hz, 2H), 7.53 (t, J = 7.4 Hz, 2H), 7.48-7.42 (m, 1H), 6.20 (s, 1H), 3.83 (d, J = 5.4 Hz, 2H), 3.28 (s, 3H), 2.63 (dd, J = 7.2, 3.5 Hz, 1H), 0.63 (d, J = 5.7 Hz, 2H), 0.40 (br. s., 2H) | 1.68 N 462.1 | 2 |
| 610 | 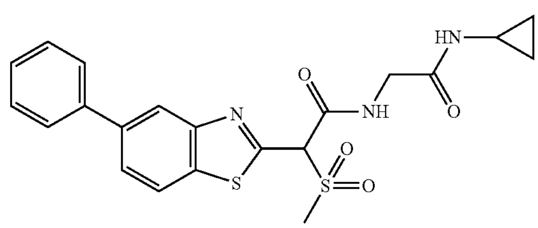 [SMILES: CS(=O)(=O)C(C(=O)NCC(=O)NC1CC1)c1nc2cc(-c3ccccc3)ccc2s1] | N-[(cyclopropyl-carbamoyl)methyl]-2-methanesulfonyl-2-(5-phenyl-1,3-benzothiazol-2-yl)acetamide | 9.10 (t, J = 5.4 Hz, 1H), 8.32 (s, 1H), 8.21 (d, J = 8.4 Hz, 1H), 8.05 (d, J = 3.4 Hz, 1H), 7.82 (d, J = 8.4 Hz, 1H), 7.76 (d, J = 7.4 Hz, 2H), 7.51 (t, J = 7.6 Hz, 2H), 7.44-7.37 (m, 1H), 6.13 (s, 1H), 3.89 (d, J = 4.7 Hz, 2H), 3.26 (s, 3H), 2.66-2.57 (m, 1H), 0.63 (d, J = 5.7 Hz, 2H), 0.38 (br. s., 2H) | 1.65 O 444.1 | 40 |
| 611 | 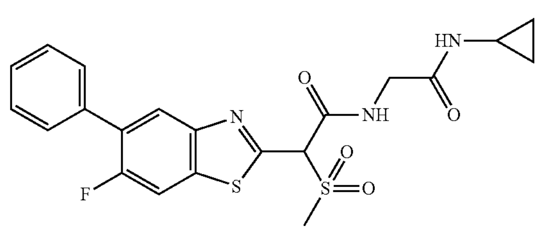 [SMILES: CS(=O)(=O)C(C(=O)NCC(=O)NC1CC1)c1nc2cc(-c3ccccc3)c(F)cc2s1] | N-[(cyclopropyl-carbamoyl)methyl]-2-(6-fluoro-5-phenyl-1,3-benzothiazol-2-yl)-2-methanesulfonyl-acetamide | 9.06 (br. s., 1H), 8.24-8.16 (m, 2H), 8.05 (br. s., 1H), 7.65 (d, J = 7.3 Hz, 2H), 7.57-7.50 (m, 2H), 7.49-7.43 (m, 1H), 6.20 (s, 1H), 3.84 (d, J = 5.2 Hz, 2H), 3.29 (s, 3H), 2.65 (d, J = 3.7 Hz, 1H), 0.64 (d, J = 7.0 Hz, 2H), 0.41 (br. s., 2H) | 1.68 N 461.5 | 4 |

-continued

| Ex. No. | Structure | Name | $^1$H NMR δ (500 MHz, DMSO-$d_6$, unless otherwise indicated) | LC/MS RT (min) Method M + H | EL IC$_{50}$ (nM) |
|---|---|---|---|---|---|
| 612 | 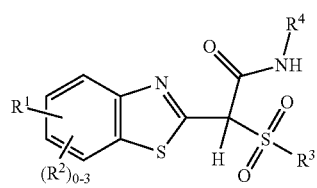 | N-[(cyclopropyl-carbamoyl)methyl]-2-(6-fluoro-5-phenyl-1,3-benzothiazol-2-yl)-2-(2-methoxyethane-sulfonyl)acetamide | 9.08 (t, J = 5.3 Hz, 1H), 8.28-8.20 (m, 2H), 8.08 (d, J = 3.7 Hz, 1H), 7.70 (d, J = 7.6 Hz, 2H), 7.64-7.55 (m, 2H), 7.55-7.49 (m, 1H), 6.24 (s, 1H), 3.79 (d, J = 5.5 Hz, 2H), 3.65-3.57 (m, 5H), 3.34 (s, 2H), 2.70 (dd, J = 7.3, 3.4 Hz, 1H), 0.70 (d, J = 5.5 Hz, 2H), 0.46 (br. s., 2H) | 1.74 N 505.6 | 3 |

What is claimed is:

1. A compound of Formula (I):

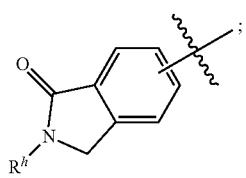

or a stereoisomer, a tautomer, or a pharmaceutically acceptable salt, wherein:

$R^1$ is

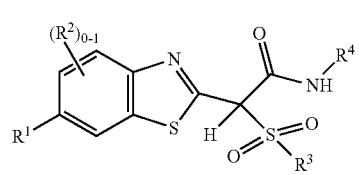

$R^2$ is, independently at each occurrence, selected from: halogen, OH, $C_{1-4}$ alkyl, $C_{1-4}$ alkoxy, $C_{1-4}$ haloalkyl, $C_{1-4}$ haloalkoxy, CN, $NH_2$, $NO_2$, $NH(C_{1-4}$ alkyl), $N(C_{1-4}$ alkyl)$_2$, $CO_2H$, $CO_2(C_{1-4}$ alkyl), and $CONH_2$;

$R^3$ is independently selected from: $C_{1-6}$ alkyl substituted with 0-1 $R^7$, $C_{2-6}$ alkenyl, $C_{1-6}$ haloalkyl, $N(C_{1-4}$ alkyl)$_2$, and —X—($C_{3-6}$ carbocycle substituted with 0-3 $R^b$);

X is —(CH$_2$)$_m$—, or —(CH$_2$)$_s$—(O)$_n$—;

$R^4$ is independently —(CH$_2$)$_s$—CONHR$^5$;

$R^5$ is independently selected from: $C_{1-6}$ alkyl substituted with $R^6$ and —(CH$_2$)$_m$—($C_{3-6}$ carbocycle substituted with 0-2 $R^8$);

$R^6$ is independently selected from: OH, $C_{1-4}$ alkoxy, $C_{1-4}$ haloalkyl, $C_{1-4}$ haloalkoxy, OPh, and OBn;

$R^7$ is independently selected from: OH, halogen, CN, $C_{1-4}$ alkoxy, $C_{1-4}$ haloalkyl, $C_{1-4}$ haloalkoxy, $NH_2$, $CO_2H$, $CO_2(C_{1-4}$ alkyl), $SO_3H$, CONHR$^d$, NHCONHR$^d$, and NHCO$_2$R$^d$;

$R^8$ is, independently at each occurrence, selected from: OH, halogen, $C_{1-6}$ alkyl, $C_{1-4}$ alkoxy, $C_{1-4}$ haloalkyl, $C_{1-4}$ haloalkoxy, $NH_2$, OPh, OBn, and Ph;

$R^b$ is, independently at each occurrence, selected from: halogen, $C_{1-6}$ alkyl, $C_{1-4}$ alkoxy, $C_{1-4}$ haloalkyl, $C_{1-4}$ haloalkoxy, OH, CN, $NH_2$, $NO_2$, $NH(C_{1-4}$ alkyl), $N(C_{1-4}$ alkyl)2, $CO_2H$, $CO_2(C_{1-4}$ alkyl), $SO_2(C_{1-4}$ alkyl), $CONH_2$, and CONH($C_{1-4}$ alkyl);

$R^d$ is, independently at each occurrence, selected from: $C_{1-6}$ alkyl and —(CH$_2$)$_t$-(phenyl substituted with 0-2 $R^e$);

$R^e$ and $R^f$ are, independently at each occurrence, selected from: OH, halogen, CN, $C_{1-4}$ alkyl, $C_{1-4}$ haloalkyl, $C_{1-4}$ alkoxy, $C_{1-4}$ haloalkoxy, $CO_2H$, $NH_2$, $CONH_2$, and NHCO($C_{1-4}$ alkyl);

$R^g$ is, independently at each occurrence, selected from: H and $C_{1-4}$ alkyl;

$R^h$ is, independently at each occurrence, selected from: H, $C_{1-6}$ haloalkyl, $C_{1-6}$ alkyl substituted with 0-1 $R^f$, and —(CH$_2$)$_t$—($C_{3-6}$ carbocycle substituted with 0-1 $R^f$);

m and t are, independently at each occurrence, selected from 0, 1, 2, and 3;

n is, independently at each occurrence, selected from 0 and 1;

p is, independently at each occurrence, selected from 0, 1, and 2; and s is, independently at each occurrence, selected from 1, 2, and 3.

2. A compound according to claim 1, wherein the compound is of Formula (IIa) or (IIb):

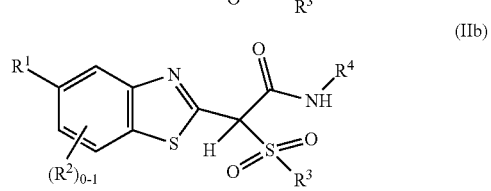

or a stereoisomer, a tautomer, or a pharmaceutically acceptable salt; wherein:

$R^2$ is, independently at each occurrence, selected from: halogen, $C_{1-4}$ alkyl, $C_{1-4}$ alkoxy, $C_{1-4}$ haloalkyl, and $C_{1-4}$ haloalkoxy.

3. A compound according to claim 2 wherein the compound is of Formula (I), (IIa) or (IIb), or a stereoisomer, a tautomer, or a pharmaceutically acceptable salt, wherein:
$R^1$ is

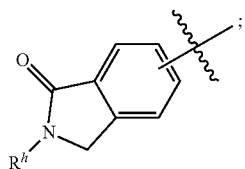

$R^3$ is independently selected from: $C_{1-6}$ alkyl substituted with 0-1 $R^7$, $C_{2-4}$ alkenyl, —X—($C_{3-6}$ carbocycle substituted with 0-1 $R^b$) and $N(C_{1-4}$ alkyl$)_2$;
$R^4$ is independently —$CH_2CONHR^5$;
$R^5$ is independently selected from: $C_{1-6}$ alkyl substituted with $R^6$, —$(CH_2)_{0-1}$—($C_{3-6}$ cycloalkyl substituted with 0-1 $R^8$), and Ph;
$R^6$ is independently selected from: OH, $C_{1-4}$ alkoxy, $C_{1-4}$ haloalkyl, $C_{1-4}$ haloalkoxy, OPh, and OBn;
$R^7$ is independently selected from: OH, halogen, CN, $C_{1-4}$ alkoxy, $C_{1-4}$ haloalkyl, $C_{1-4}$ haloalkoxy, $NH_2$, and $NHCO_2Bn$;
$R^8$ is $C_{1-4}$ alkyl;
$R_b$ is, independently at each occurrence, selected from: halogen, CN, $C_{1-4}$ alkyl, $C_{1-4}$ alkoxy, $C_{1-4}$ haloalkyl, and $C_{1-4}$ haloalkoxy;
$R^f$ is, independently at each occurrence, selected from: OH, halogen, CN, $C_{1-4}$ alkyl, $C_{1-4}$ haloalkyl, $C_{1-4}$ alkoxy, $C_{1-4}$ haloalkoxy, $CO_2H$, $NH_2$, $CONH_2$, and $NHCO(C_{1-4}$ alkyl);
$R^h$ is, independently at each occurrence, selected from: H, $C_{1-6}$ haloalkyl, $C_{1-6}$ alkyl substituted with 0-1 $R^f$, and —$(CH_2)_t$—($C_{3-6}$ carbocycle substituted with 0-1 $R^f$); and
$R^g$ is independently selected from: H and $C_1$-4 alkyl.

4. A compound according to claim 3, wherein the compound is of Formula (I), (IIa) or (IIb), or a stereoisomer, a tautomer, or a pharmaceutically acceptable salt, wherein:
$R^1$ is

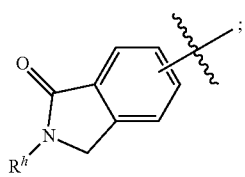

$R^3$ is independently selected from: $C_{1-6}$ alkyl substituted with 0-1, $R^7$, $C_{2-4}$ alkenyl, —$(CH_2)_{0-3}$—$(O)_{0-3}$—$(C_{3-6}$ carbocycle substituted with 0-1 $R^b$);
$R^6$ is independently selected from: OH, $C_{1-4}$ alkoxy, $C_{1-4}$ haloalkyl, OPh, and OBn; and
$R^8$ is $C_{1-4}$ alkyl.

5. A compound according to claim 4, wherein the compound is of Formula (I), (IIa) or (IIb), or a stereoisomer, a tautomer, or a pharmaceutically acceptable salt, wherein:
$R^1$ is

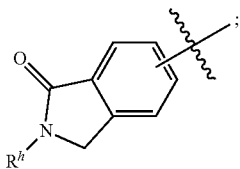

$R^2$ is, independently at each occurrence, selected from: halogen, $C_{1-4}$ alkyl, $C_{1-4}$ alkoxy, $C_{1-4}$ haloalkyl, and $C_{1-4}$ haloalkoxy;
$R^3$ is independently selected from: $C_{1-6}$ alkyl substituted with 0-1 $R^7$, —$(CH2)_{0-1}$—($C3$-$6$ carbocycle substituted with 0-1 $R^b$), and $N(C_{1-4}$ alkyl$)_2$;
$R^4$ is independently —$CH_2CONH(C_{3-6}$ cycloalkyl substituted with 0-1 $R^8$);
$R^7$ is independently selected from: halogen, CN, $C_{1-4}$ alkoxy, $C_{1-4}$ haloalkyl, and $C_{1-4}$ haloalkoxy.

6. A compound according to claim 5, wherein the compound is of Formula (I), (IIa) or (IIb), or a stereoisomer, a tautomer, or a pharmaceutically acceptable salt, wherein:
$R^1$ is

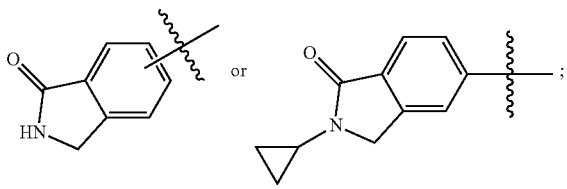

$R^2$ is independently selected from: F, Cl, Me, OMe, $OCF_2$, and $CF_3$;
$R^3$ is independently selected from: Me, Et, Pr, i-Pr, n-Bu, i-Bu, —$CH_2CN$, —$(CH_2)_2OMe$, —$(CH_2)_2CF_3$, —$(CH_2)_{0-1}$-(cyclopropyl), —$CH_2$-(cyclohexyl), $N(Me)_2$, Ph, 4-F-Ph, 4-F-Bn, and 3-CN-Bn; and
$R^4$ is independently selected from: —$CH_2CONH$(cyclopropyl) and

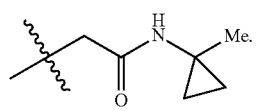

7. A compound according to claim 1, wherein the compound is selected from

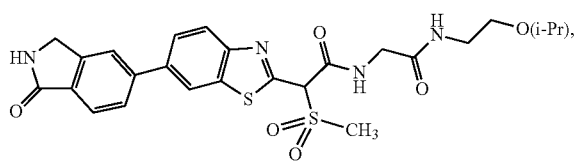

407
-continued
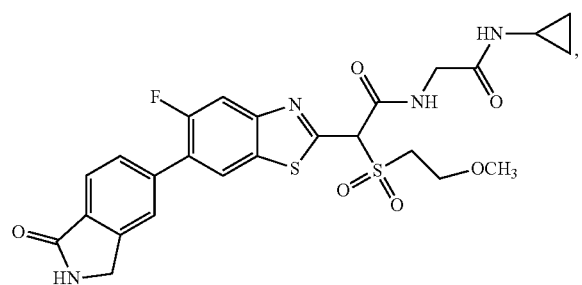
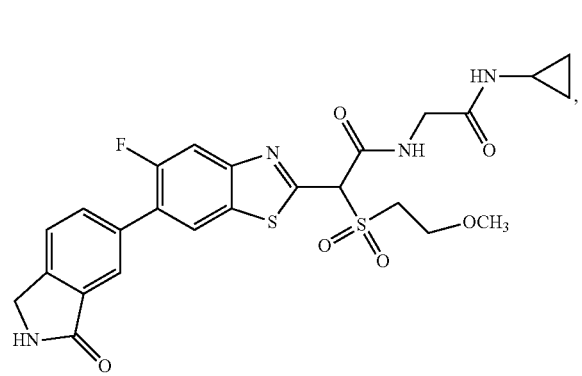
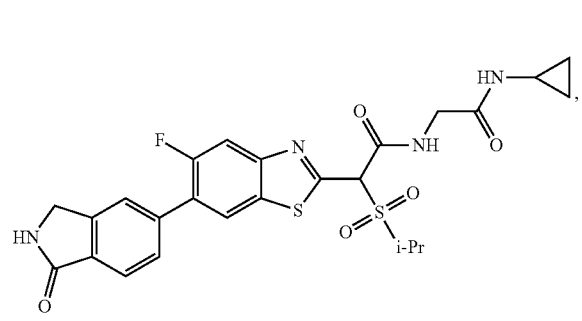
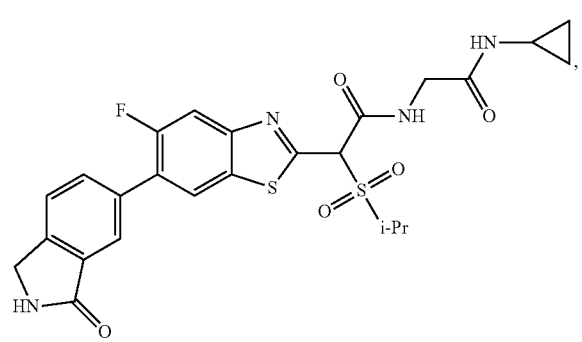
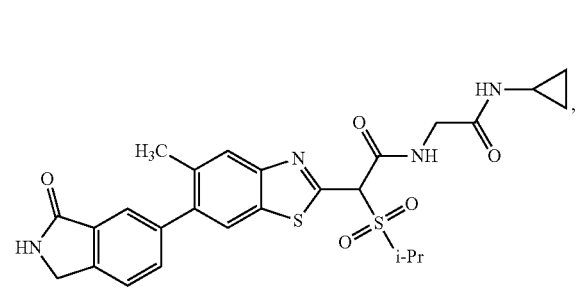
408
-continued
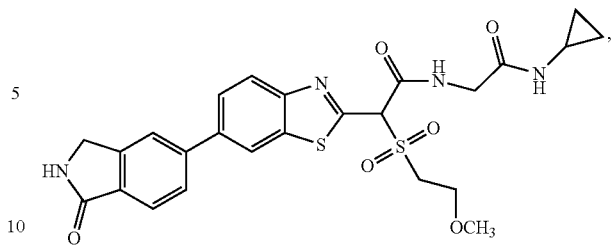
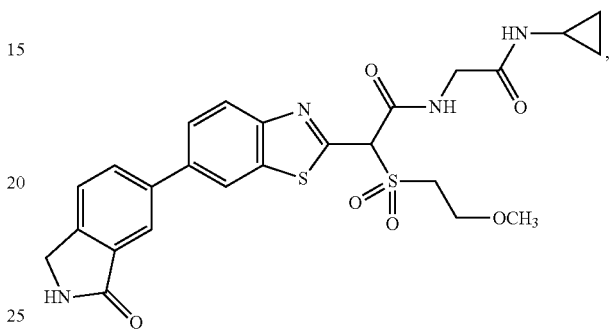
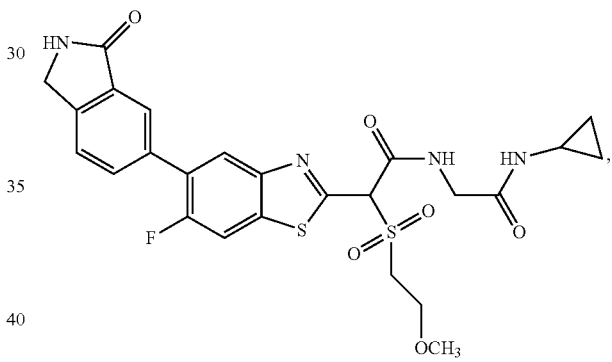
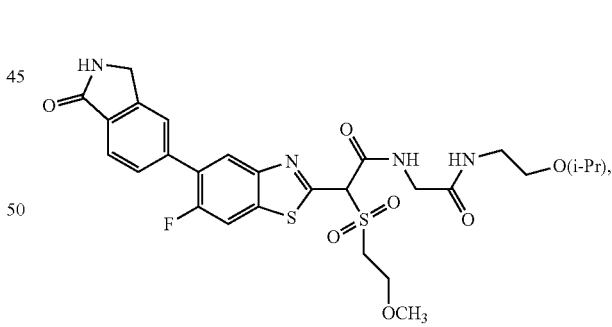
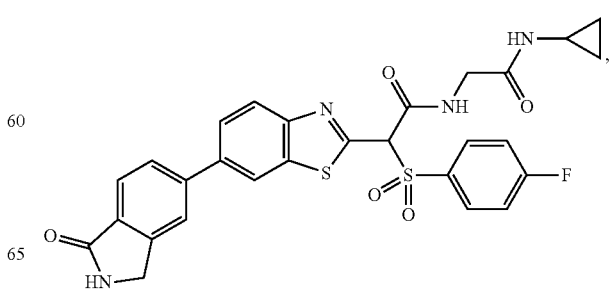

409
-continued
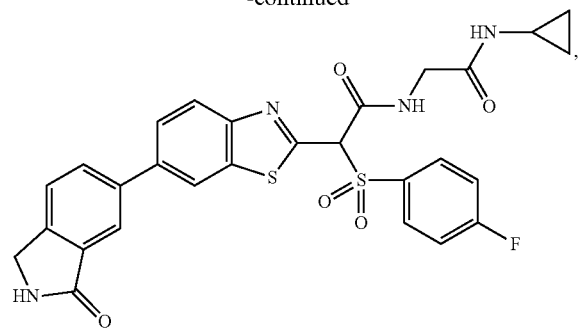
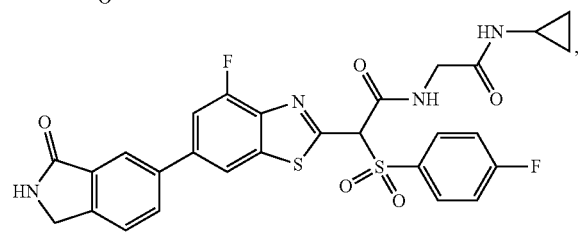
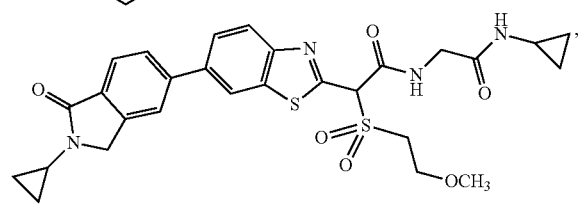
410
-continued
or a stereoisomer, a tautomer, or a pharmaceutically acceptable salt thereof.
8. A pharmaceutical composition, comprising a pharmaceutically acceptable carrier and a compound according to claim 1, or a stereoisomer, a tautomer, or a pharmaceutically acceptable salt thereof.
* * * * *